United States Patent
Hudkins et al.

(10) Patent No.: US 11,046,707 B2
(45) Date of Patent: Jun. 29, 2021

(54) SPIROPIPERIDINE DERIVATIVES

(71) Applicant: 89BIO LTD, Herzliya (IL)

(72) Inventors: Robert L. Hudkins, Chester Springs, PA (US); David B. Whitman, Phoenixville, PA (US); Craig A. Zificsak, Downingtown, PA (US); Allison L. Zulli, Chesterbrook, PA (US); Melody McWherter, Boyertown, PA (US)

(73) Assignee: 89BIO LTD, Herzliya (IL)

( * ) Notice: Subject to any disclaimer, the term of this patent is extended or adjusted under 35 U.S.C. 154(b) by 0 days.

(21) Appl. No.: 16/469,840

(22) PCT Filed: Dec. 14, 2017

(86) PCT No.: PCT/US2017/066422
§ 371 (c)(1),
(2) Date: Jun. 14, 2019

(87) PCT Pub. No.: WO2018/112204
PCT Pub. Date: Jun. 21, 2018

(65) Prior Publication Data
US 2020/0031840 A1    Jan. 30, 2020

Related U.S. Application Data

(60) Provisional application No. 62/434,167, filed on Dec. 14, 2016.

(51) Int. Cl.
*C07D 491/107* (2006.01)
*C07D 491/113* (2006.01)

(52) U.S. Cl.
CPC ...... *C07D 491/107* (2013.01); *C07D 491/113* (2013.01)

(58) Field of Classification Search
CPC ...... A61P 11/06; A61P 17/00; C07D 491/107; C07D 491/113; C07D 519/00
See application file for complete search history.

(56) References Cited

U.S. PATENT DOCUMENTS

| | | |
|---|---|---|
| 2007/0117823 A1 | 5/2007 | Antel et al. |
| 2011/0071131 A1 | 3/2011 | Bacon et al. |

FOREIGN PATENT DOCUMENTS

| | | | |
|---|---|---|---|
| CN | 103304571 * | 9/2013 | ......... C07D 491/107 |
| WO | 94/18204 A1 | 8/1994 | |
| WO | 2007/054580 A1 | 5/2007 | |
| WO | 2012/161119 A1 | 11/2012 | |

OTHER PUBLICATIONS

Berod et al., De Novo Fatty Add Synthesis Controls the Fate Between Regulatory T and T Helper 17 Cells, Nature Medicine, Nov. 2014, 20(11), 1327-1333.
Chung et al., A Fluorescence-Based Thiol Quantification Assay for Ultra-High-Throughput Screening for Inhibitors of Coenzyme A Production, Assay and Drug Development Technologies, 2008, vol. 6, No. 3: 361-374
Everts et al., TLR-Driven Early Glycolytic Reprogramming Via the Kinases TBK1-IKK? supports the anabolic Demands of Dendritic Cell Activation, Nature Immunology, 2014, 15, 323-332
Hunt et al., mRNA Stability and Overexpression of Fatty Acid Synthase in Human Breast Cancer Cell Lines, Anticancer Research 27, 2007, 27-34.
Kuhajda, F.P., Fatty Acid Synthase and Cancer: New Application of an Old Pathway, Cancer Research, Jun. 2006, 66 (12), 5977-5980.
Kuhajda, F.P., Fatty-acid Synthase and Human Cancer: New Perspectives on its Role in Tumor Biology, Nutrition, 2000, vol. 16, Issue 3, 202-208.
Menendez et al., Fatty Acid Synthase and the Lipogenic Phenotype in Cancer Pathogenesis, Nature Reviews Cancer, Oct. 2007, 7, 763-777.
Munger et al, Systems-Level Metabolic Flux Profiling Identifies Fatty Acide Synthesis as a Target for Antiviral Therapy, Nature Biotechnology, 2008, 26, 1179-1186.
Nasheri et al., Modulation of Fatty Acid Synthase Enzyme Activity and Expression During Hepatitis C Virus Replication, Chemistry and Biology, Apr. 18, 2013, 20: 570-582.
Pollak, M., Targeting Oxidative Phosphorylation: Why, When and How, Cancer Cell, Mar. 18, 2013, 23(3): 263-264.

(Continued)

*Primary Examiner* — Erich A Leeser
(74) *Attorney, Agent, or Firm* — BakerHostetler

(57) ABSTRACT

Described herein are spiropiperidine compounds according to Formula I that have demonstrated activity as fatty acid synthase inhibitors. Also described herein are pharmaceutical compositions containing the described spiropiperidine compounds, and methods of treating diseases mediated by fatty acid synthase, by administering one or more of the compounds or pharmaceutical formulations described herein. Also described herein are methods of synthesizing the compounds described, including the described spiropiperidine compounds and synthetic intermediates that are useful in those syntheses.

I

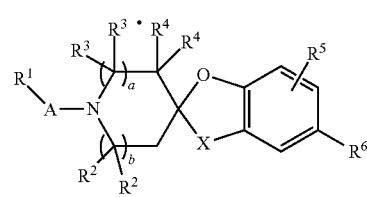

16 Claims, No Drawings

(56) References Cited

OTHER PUBLICATIONS

Shen et at. "Discovery of spirocyclic secondary amine-derived tertiary ureas as highly potent selective and bioavailable soluble epoxide hydrolase inhibitors", Bioorganic & Medicinal Chemistry Letters. 2009. vol. 19, p. 3398-3404.
Sounni, NE et al., Blocking Lipid Synthesis Overcomes Tumor Regrowth and Metastasis After Angiogenic Therapy Withdrawal; (Aug. 5, 2014) Cell Metabolism 20(2), 280-294.

* cited by examiner

SPIROPIPERIDINE DERIVATIVES

CROSS-REFERENCE TO RELATED APPLICATIONS

This application is the U.S. National Stage Application of International Patent Application No. PCT/US2017/066422, filed Dec. 14, 2017 which claims priority to U.S. Provisional Patent Application Ser. No. 62/434,167, filed Dec. 14, 2016. The content of each of these applications is herein incorporated by reference in its entirety.

FIELD OF THE INVENTION

The present invention relates to compounds according to Formula I, as well as to pharmaceutical compositions containing these compounds and to methods of treatment of FASN-mediated disorders such as cancers, viral disorders (wherein FASN inhibition correlates inhibition of viral replication), obesity related disorders, eating disorders, metabolic diseases (e.g., fatty liver disease, non-alcoholic hepatic steatosis and Type 2 diabetes), drug induced body weight gain; e.g. treatment of weight gain associated with drug therapy with atypical antipsychotic drugs, these methods comprising administering a therapeutically effective dose of one or more of the compounds of Formula I, or a pharmaceutical composition comprising one or more of the compounds of Formula I, to a patient in need of such therapy.

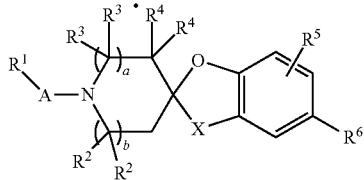

I

BACKGROUND

Fatty acid synthase (FASN) is a multi-enzyme protein complex that catalyzes the synthesis of fatty acids involved in energy production and storage, cellular structure and formation of intermediates in the biosynthesis of hormones and other biologically significant molecules (Nature Reviews Cancer, 2007, 7, 763-777). FASN is composed of two identical 272 kDa multifunctional polypeptides. As its main function, it catalyzes the synthesis of palmitate from acetyl-CoA and malonyl-CoA, in the presence of nicotinamide adenine dinucleotide phosphate (NADPH). In normal human tissues (with the exception of liver and adipose tissue), fatty acids are preferentially acquired from the diet, and expression of FASN levels are low. In contrast, FASN expression and activity is highly elevated in several pathological states including cancer, inflammatory and metabolic diseases. In particular, evidence shows that increased endogenous fatty acid synthesis is critical for tumorigenesis.

Cancer is a disease of accelerated cell growth and proliferation. Cancer cells adapt metabolically to increase levels of lipids to support their anabolic requirements. Increased synthesis of fatty acids represents a fundamental metabolic adaptation of cancer cells and is facilitated by high levels of FASN expression. Increased expression of FASN is an early event in tumorigenesis and is found in numerous tumor types, often correlating with a poor prognosis (Nature Reviews Cancer, 2007, 7, 763-777). FASN gene amplification and protein overexpression was observed in human breast, ovarian, prostate, colon, lung, bladder, stomach and kidney cancers suggesting FASN as a potential drug target and marker of poor prognosis (Nature Reviews Cancer, 2007, 7, 763-777; Anticancer Res. 2007, 27, 27-34; Cancer Res., 2006, 66, 5977-5980, Nutrition, 2000, 16, 202-208).

In addition to tumor cells, immune cells metabolically adapt, proliferate and differentiate into distinct functional classes in response to immunogenic stimuli. Studies have demonstrated that lipogenesis plays a critical role in immune responses and metabolic adaptation of activated immune cells. Inhibition of fatty acid synthesis during T-cell differentiation result in a switch from Th17 to Treg cells, suggesting a novel approach to treat autoimmune diseases, such as multiple sclerosis, and to modulate immune responses (Nature Medicine, 2014, 20, 1327-1333). Similarly, de novo fatty acid synthesis is critical for CD8+T cell expansion and dendritic cell activation (Nature Immunology, 2014, 15, 323-332). These results demonstrate that modulation of the fatty acid synthesis pathway might represent a strategy to control immune responses and to treat a wide range of autoimmune diseases.

FASN has been implicated as an important enzyme promoting a life cycle of multiple viruses and microorganisms. De novo lipid biosynthesis has been shown to be necessary for replication of the Flaviviridae family including Hepatitis C Virus, Dengue virus, yellow fever virus, West Nile virus and others (Chemistry and Biology, 2013, 570-582). Inhibition of FASN by small molecule inhibitors such as Cerulenin and Orlistat resulted in a strong inhibition of viral replication. Other viruses also depend on FASN activity including human cytomegalo virus (HCMV) influenza A, Epstein-Barr virus (EBV) and coxsackievirus B3 (CVB3). Numerous genome wide screens identified multiple host genes involved in lipid metabolism which are crucial for replication of viruses and increased expression FASN is often required for efficient viral replication (Nature Biotechnology, 2008, 26, 179-186). Taken together, these results provide a strong rationale for targeting FASN for antiviral therapy.

Fatty acid accumulation is associated with variety of metabolic diseases and has been shown to contribute to their pathogenesis. The non-alcoholic hepatic steatosis (NASH), also called fatty liver disease, encompasses a spectrum of liver diseases (steatosis, steatosis with inflammation, cirrhosis) characterized by a fatty acid accumulation in hepatocytes. Currently, NASH is the most common liver disease in developed countries and is associated with obesity, insulin resistance and type 2 diabetes. Studies in animal models demonstrated that pharmacological inhibition of FASN improved hepatic function and decreased liver fat accumulation (PloS One, 2013, 9, 1-8).

FASN is highly expressed in tissues with high metabolic activity (liver, adipose tissue and brain), and is a critical enzyme for endogenous lipogenesis and modulation of key intermediates of lipid and carbohydrate cellular metabolism. A FASN inhibitor has been proposed for treatment of obesity, and inhibition of FASN in the hypothalamus may result in reduced food intake. The non-specific irreversible FASN inhibitors cerulenin and C-75 have been reported to decrease brain levels of orexigenic neuropeptides and decrease food intake.

Therefore, FASN inhibition represents a therapeutic target in a wide spectrum of pathologies including cancer, antiviral, liver and cardiovascular diseases and treatment of obesity, diabetes and drug-induced body weight gain; e.g. antipsychotics.

Recent advances in the treatment and management of cancer show that many anti-cancer therapies lead to profound changes in tumor metabolism. Inhibition of BRAF signaling by vemurafenib and inhibition of BCR-ABL by imatinib led to increased oxidative phosphorylation [Pollak M, (2013) Targeting Oxidative Phosphorylation: Why, When and How; *Cancer Cell* 18, 263-63]. Such a drug-induced reprogramming of cellular metabolism from glycolysis to oxidative phosphorylation might create a dependency on lipids which could be exploited therapeutically by use of FASN inhibitors. In yet another example, it was demonstrated that cessation of the anti-angiogenic therapy by sunitinib and sorafenib resulted in a rapid regrowth of tumors and increased metastasis which were mediated by a rapid metabolic switch of tumor and stromal cells to de novo lipogenesis. Pharmacological inhibition of FASN was sufficient to reverse tumor regrowth and metastatic dissemination further confirming the role of lipid metabolism in tumor adaptation to anti-cancer therapies (Sounni N E, Cimino J, Blacher S, Primac I, Truong A, Mazucchelli G, Paye A, calligaris D, Debois D, mari B, de pauw E, Noel A (2014) Blocking Lipid Synthesis Overcomes Tumor Regrowth and Metastasis after Angiogenic Therapy Withdrawal; *Cell Metabolism* 20, 1-15) and providing a rationale for combinatorial treatments using FASN inhibitors.

SUMMARY

This application relates to compounds according to Formula I:

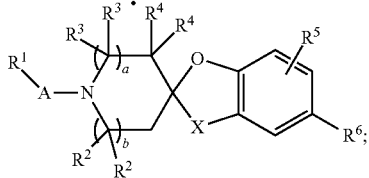

I including all stereoisomeric forms, and mixtures of stereoisomeric forms of these compounds. The application further relates to salts of compounds according to Formula I, e.g., pharmaceutically acceptable salts, and to compositions, e.g., pharmaceutical compositions, that contain compounds according to Formula I, or salts thereof. The application further relates to compounds according to Formula I that are isotopically enriched at one or more positions.

The compounds of Formula I and/or their pharmaceutically acceptable salts are useful for treating conditions, disorders and diseases that are directed or indirectly controlled, mediated, affected or influenced by FASN expression. Compounds of Formula I are FASN inhibitors and are therefore useful in the treatment of various conditions, disorders or diseases mediated by FASN expression, including conditions related to cancer, metabolic disorders, and the central nervous system (CNS).

DETAILED DESCRIPTION

The following provides additional non-limiting details of the compounds of Formulae I, IA, IB, IC, ID, and IE, as well as various species and more specific embodiments of the same, intermediates, and synthesis processes.

One aspect of this application is directed to compounds of Formula I:

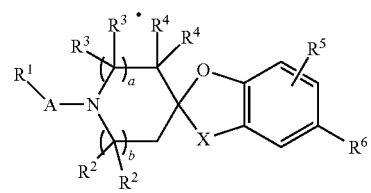

I and salts thereof, e.g., pharmaceutically acceptable salts thereof, wherein:

A is selected from —C(=O)— and —SO$_2$—;
$R^1$ is selected from —(C$_1$-C$_7$) hydrocarbyl, substituted —(C$_1$-C$_7$) hydrocarbyl, 3-7 membered heterocyclyl, —C(=O)(C$_1$-C$_7$) hydrocarbyl, —NR$^7$R$^8$, —OR$^7$, —SR$^7$, —NR$^7$(OR$^8$) and —NR$^7$(SR$^8$);
a and b are independently selected from 0 and 1;
each $R^2$ is independently selected from —H and —(C$_1$-C$_4$) alkyl;
each $R^3$ is independently selected from —H and —(C$_1$-C$_4$) alkyl
each $R^4$ is independently selected from —H, —(C$_1$-C$_6$) alkyl, —OH, —O(C$_1$-C$_6$) alkyl, halogen, —CN, or the two geminal $R^4$ groups may together form a carbonyl group;
wherein one of the $R^3$ groups can optionally be structurally connected to one of the $R^2$ groups to form an alkylene bridge to produce a bicyclic ring; or
one of the $R^3$ groups can optionally be structurally connected to the $R^1$ group to form a 5 to 7 membered heterocyclyl ring fused to the 1-2 face of the piperidine ring; or
one of the $R^3$ groups can optionally be structurally connected to the $R^4$ group to form a 5-7 membered carbocyclic or heterocyclic ring fused to the 2-3 face of the piperidine ring;
X is selected from —O(CH$_2$)$_q$(CR$^9$R$^{9a}$)$_{p1}$—, —S(CH$_2$)$_q$(CR$^9$R$^{9a}$)$_{p2}$—, —(CH$_2$)$_q$(CR$^9$R$^{9a}$)$_{p3}$— and —CH=CH—;
p1 is an integer selected from 0 and 1;
p2 is an integer selected from 0 and 1;
p3 is an integer selected from 1 and 2;
q is an integer selected from 0 and 1;
$R^5$ is selected from —H, —C$_1$-C$_7$ hydrocarbyl, halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, substituted 5-6 membered heteroaryl; wherein n is an integer selected from 2, 3 and 4;
$R^6$ is selected from naphthyl, substituted naphthyl, 6-membered heteroaryl, substituted 6-membered heteroaryl, 9-10 membered bicyclic heteroaryl and substituted 9-10 membered bicyclic heteroaryl;
$R^7$ is selected from —H, —(C$_1$-C$_7$) hydrocarbyl, substituted —(C$_1$-C$_7$) hydrocarbyl, —C(=O)R$^{8b}$, —(C$_1$-C$_6$) heteroalkyl, 6 membered aryl, 5-6 membered heteroaryl and 5-6 membered heterocyclyl, wherein R$^{8b}$ is selected from —H and —(C$_1$-C$_6$) alkyl;

$R^8$ is selected from —H and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^{8b}$ and —($C_1$-$C_6$) heteroalkyl, wherein $R^{8b}$ is selected from —H and —($C_1$-$C_6$) alkyl;

$R^{8a}$ is selected from —H and —($C_1$-$C_6$) alkyl, wherein $R^{7a}$ can optionally be structurally connected to $R^{8a}$ to form a 5 to 7 membered heterocyclyl ring;

each $R^9$ is independently selected from —H, —OH, —($C_1$-$C_7$) hydrocarbyl, —O($C_1$-$C_7$) hydrocarbyl and halogen; and each $R^{9a}$ is —H, or a geminal $R^9$ and $R^{9a}$ may together form a carbonyl group.

According to some embodiments of compounds according to Formula I, A is —C(=O)—. According to other embodiments, A is —$SO_2$—.

According to some embodiments, $R^1$ is selected from —($C_1$-$C_7$) hydrocarbyl, substituted —($C_1$-$C_7$) hydrocarbyl, 3-7 membered heterocyclyl, —$NR^7R^8$, —$SR^7$, —$NR^7(OR^8)$ and —$NR^7(SR^8)$.

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, benzyl, substituted benzyl, 5-6 membered heterocyclyl, —C(=O)($C_1$-$C_6$) alkyl, —$SR^7$, —$NR^7R^8$ and —$NR^7(OR^8)$.

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, benzyl, substituted benzyl, —$SR^7$, —$NR^7R^8$ and —$NR^7(OR^8)$. According to some embodiments, $R^1$ is selected from —$NR^7R^8$ and —$NR^7(OR^8)$. According to some embodiments, $R^1$ is —$NR^7R^8$. According to some embodiments, $R^1$ is —$NR^7(OR^8)$.

According to other embodiments, $R^1$ is selected from —$CH_3$, —$CH_2CH_3$, —$(CH_2)_2CH_3$, —$(CH_2)_3CH_3$, —$(CH_2)_4CH_3$, —$CH(CH_3)_2$, —$C(CH_3)_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH($CH_3$)$_2$, —NH—$OCH_2CH_3$, —NHS$CH_3$, —NHS$CH_2CH_3$, —S$CH_3$, —S$CH_2CH_3$, —SCH($CH_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —$(CH_2)_2$—$OCH_3$ and —$(CH_2)_3$—$OCH_3$.

According to other embodiments, $R^1$ is selected from —$CH_3$, —$CH_2CH_3$, —$(CH_2)_2CH_3$, —$(CH_2)_3CH_3$, —$(CH_2)_4CH_3$, —$CH(CH_3)_2$, —$C(CH_3)_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH($CH_3$)$_2$, —NH—$OCH_2CH_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —$(CH_2)_2$—$OCH_3$ and —$(CH_2)_3$—$OCH_3$.

According to some embodiments, when $R^1$ is substituted cyclopropyl, the cyclopropyl ring may be substituted with 1 or two substituents selected from —OH, —$CH_2OH$, —C(=O)$NH_2$, —$NH_2$, —$CH_3$, —CN and —$CF_3$.

According to some embodiments, when $R^1$ is tetrahydrofuranyl, it is tetrahydrofuran-2-yl or tetrahydrofuran-3-yl. According to some embodiments, when $R^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when $R^1$ is furanyl, it is 2-furanyl or 3-furanyl. According to some embodiments, when $R^1$ is substituted furanyl, it is 2-methylfuran-2-yl, 5-methylfuran-2-yl, or 2,5-dimethylfuran-2-yl.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetra-hydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is furanyl, it is 2-furanyl or 3-furanyl. According to some embodiments, when $R^1$ is thiophenyl, it is 2-thiophenyl or 2-thiophenyl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl. According to some embodiments, when $R^1$ is oxazolyl, it is oxazol-1-yl, oxazol-2-one-1-yl oxazol-2-yl or oxazol-5-yl. According to some embodiments, when $R^1$ is isoxazolyl, it is isoxazol-1-yl, isoxazol-3-yl or isoxazol-5-yl. According to some embodiments, when $R^1$ is imidazolyl, it is imidazol-2-yl or imidazol-5-yl. According to some embodiments, when $R^1$ is thiazolyl, it is thiazol-2-yl or thiazol-5-yl. According to some embodiments, when $R^1$ is isothiazolyl, it is isothiazol-3-yl or isothiazol-5-yl. According to some embodiments, when $R^1$ is pyridyl, it is 2-pyridyl, 3-pyridyl, or 4-pyridyl. According to some embodiments, when $R^1$ is substituted quinolyl, it is quinolin-1-yl, quinolin-2-yl or quinolin-3-yl. According to some embodiments, when $R^1$ is substituted phenyl, it is 2-methylphenyl, 3-methylphenyl, 4-methylphenyl, or 2,5-dimethylphenyl. According to some embodiments, $R^1$ is selected from the moieties depicted in Table 1 and Table 1a below.

TABLE 1

A selection of some suitable $R^1$ moieties.

—$CH_3$
—$CH_2CH_3$
—$CH_2CH(CH_3)_2$
—$CH(CH_3)_2$
—$OCH_3$
—$OCH_2CH_3$
—$OCH_2CH(CH_3)_2$
—$OCH_2CH=CH_2$
—$(CH_2)_3$—$CH_3$
—$CH(CH_3)CH_2CH_3$

TABLE 1-continued

A selection of some suitable R¹ moieties.

—C(CH₃)₃
—CH₂OCH(CH3)₂

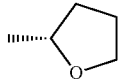

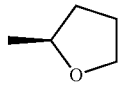

—NH₂
—NHCH₂CH(CH₃)₂
—NHCH₂CH₃
—NHCH(CH₃)₂
—NHCH₃
—NH(CH₂)₂CH₃

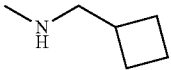

—NH—OH
—NH(CH₂)₂CH(CH₃)₂

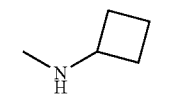

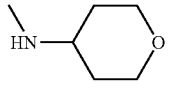

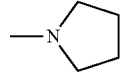

—N(CH₃)₂
—NH—OCH₂CH₃
—NH—OCH₃
—NHO(CH₂)₂CH₃
—NHOCH(CH₃)₂
—NHOCH₂CH(CH₃)₂
—N(CH₃)—OCH₃

—CH₂—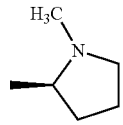

—NHOCH₃
—NH—OCH₂CH₃

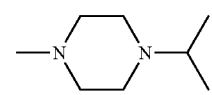

—CH₂OH
—OC(CH3)₃
—CH₂OC(=O)CH₃
—CF₃
—CH₂OCH₃
—NH—SCH₂CH₃
—NH—SCH₃

TABLE 1-continued

A selection of some suitable R¹ moieties.

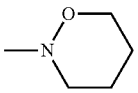

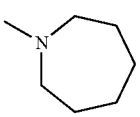

—SCH(CH₃)₂

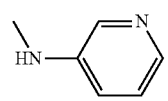

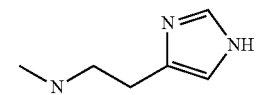

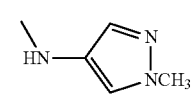

TABLE 1A

A selection of some additional suitable R¹ moieties.

—CF₂CH₃
—CH₂SO₂CH₃
—O(CH₂)₂OCH₃
—(CH₂)₂—NH₂
—CH₂—CN
—C(=O)CH₃
—NH(CH₂)₂OCH₃
—CH(CH₃)—OCH₃
—NHCH₂CF₃
—CF₂CF₃

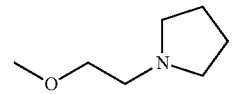

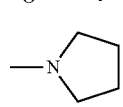

TABLE 1A-continued
A selection of some additional suitable R¹ moieties.
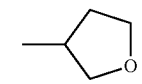
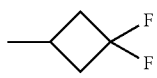
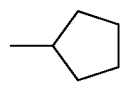
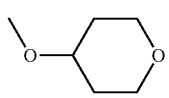
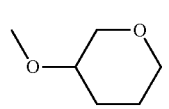
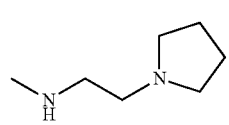
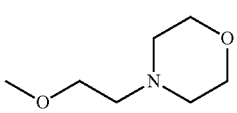
—NH(CH₂)₂N(CH₃)₂
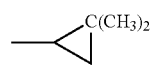
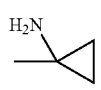
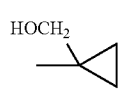
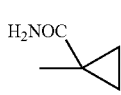
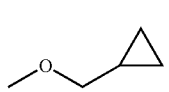
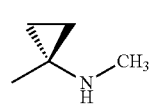
TABLE 1A-continued
A selection of some additional suitable R¹ moieties.
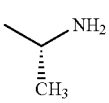
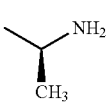
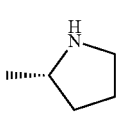
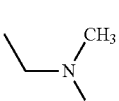
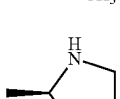
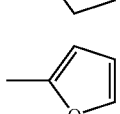
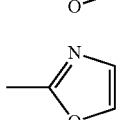
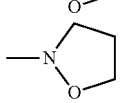
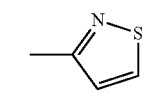
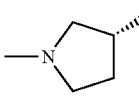
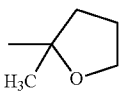
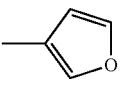
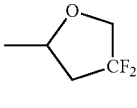
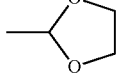

TABLE 1A-continued
A selection of some additional suitable R¹ moieties.
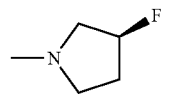
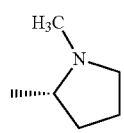
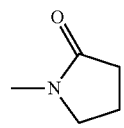
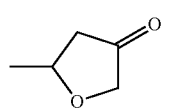
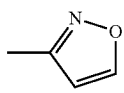
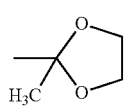
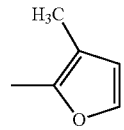
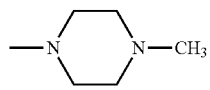
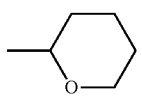
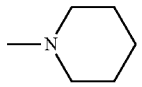
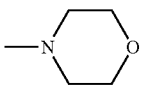
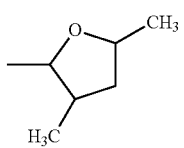
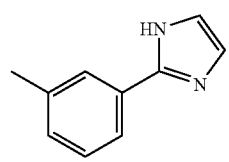
TABLE 1A-continued
A selection of some additional suitable R¹ moieties.
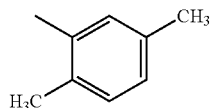
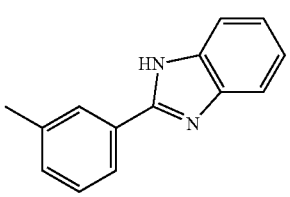 [SMILES: Cc1cccc(-c2nc3ccccc3[nH]2)c1]
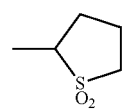
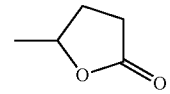
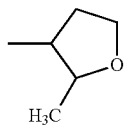
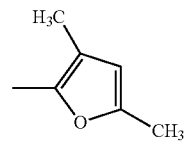
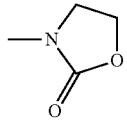
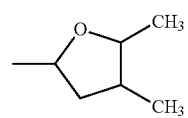
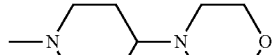
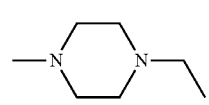
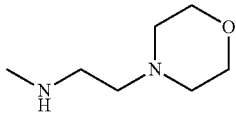
According to some embodiments, a is 1 and b is 0. According to some embodiments, a is 0 and b is 1. According to some embodiments, a and b are both 1.
According to some embodiments, each R² is —H.
According to some embodiments, each R³ is —H.

According to some embodiments, each $R^4$ is independently selected from —H, —$(C_1$-$C_6)$ alkyl and halogen, wherein the halogen is preferably selected from —F, —Cl and —Br. According to some embodiments, one $R^4$ is halogen and the other $R^4$ is —H. According to some embodiments, each $R^4$ is —H.

According to some embodiments, X is selected from —O—, —O—$(CHR^9)$—, —O—$(CHR^9)_2$—, —$(CHR^9)$—, —$(CHR^9)_2$— and —$CH_2(CHR^9)_2$—. According to some embodiments, X is selected from —O—, —$OCH_2$—, —O—$(CH_2)_2$—, —S—, —$SCH_2$—, —S—$(CH_2)_2$—, —$(CH_2)$—, —$(CH_2)_2$— and —$(CH_2)_3$—. According to some embodiments, X is selected from —$CH_2$—, —$(CH_2)_2$— and —$OCH_2$—. According to some embodiments, X is —$(CH_2)_2$—. According to some embodiments, X is —$OCH_2$—.

According to some embodiments, $R^5$ is selected from —H, —$C_1$-$C_6$ alkyl, benzyl, halogen, —$(C_1$-$C_3)$ haloalkyl, —$OR^{7a}$, —CN, —$NR^{7a}R^{8a}$, —$C(=O)NR^{7a}R^{8a}$, —$C(=O)OR^{7a}$, 5-6 membered heteroaryl and substituted 5-6 membered heteroaryl.

According to some embodiments, $R^5$ is selected from —H, —$C_1$-$C_6$ alkyl, benzyl, —$C_1$, —F, —Br, —$(C_1$-$C_3)$ haloalkyl, —$OC_1$-$C_6$ alkyl, —CN, —$NH(C_1$-$C_6)$alkyl, —$C(=O)NH(C_1$-$C_6)$alkyl, —$C(=O)OC_1$-$C_6$ alkyl, 5-6 membered heteroaryl and substituted 5-6 membered heteroaryl.

According to some embodiments, $R^5$ is selected from —H, —$C_1$-$C_6$ alkyl, —F, —$C_1$, —Br, —$OC_1$-$C_6$ alkyl, —CN, —$NH(C_1$-$C_6)$alkyl, —$C(=O)NH(C_1$-$C_6)$alkyl and —$C(=O)O(C_1$-$C_6)$alkyl. According to some embodiments, $R^5$ is selected from —H, —$C_1$-$C_6$ alkyl and halogen; wherein halogen is preferably selected from —F, —Cl and —Br. According to some embodiments, $R^5$ is —H.

According to some embodiments, $R^7$ is selected from —H and —$C_1$-$C_6$ alkyl. According to some embodiments, $R^7$ is —H. According to some embodiments, $R^7$ is —$C_1$-$C_6$ alkyl.

According to some embodiments, $R^8$ is selected from —H and —$C_1$-$C_6$ alkyl. According to some embodiments, $R^8$ is —H. According to some embodiments, $R^8$ is —$C_1$-$C_6$ alkyl. According to some embodiments, $R^7$ and $R^8$ are —H.

According to some embodiments, $R^{7a}$ is selected from —H and —$C_1$-$C_6$ alkyl. According to some embodiments, $R^{7a}$ is —H. According to some embodiments, $R^{7a}$ is —$C_1$-$C_6$ alkyl.

According to some embodiments, $R^{8a}$ is selected from —H and —$C_1$-$C_6$ alkyl. According to some embodiments, $R^{8a}$ is —H. According to some embodiments, $R^{8a}$ is —$C_1$-$C_6$ alkyl. According to some embodiments, $R^{7a}$ and $R^{8a}$ are —H.

According to some embodiments, $R^{8b}$ is —$C_1$-$C_6$ alkyl. According to some embodiments, $R^{8b}$ is —H.

According to some embodiments, each $R^9$ is selected from —H, —OH, —$(C_1$-$C_6)$ alkyl, —$O(C_1$-$C_6)$ alkyl, benzyl, —O-benzyl, —$C_1$ and —F and $R^{9a}$ is —H; or a geminal $R^9$ and $R^{9a}$ together form a carbonyl group. According to some embodiments, $R^9$ and $R^{9a}$ are —H.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —$(C_3$-$C_6)$ cycloalkyl, —$(C_1$-$C_3)$ haloalkyl, —$O(C_1$-$C_3)$ haloalkyl, 5-6 membered heterocyclyl, —OH, —$O(C_1$-$C_6)$ alkyl, —$O(CH_2)_r$-(5-6 membered heterocyclyl), —$O(CH_2)_r$— $O(C_1$-$C_6)$ alkyl, —$O(CH_2)_r$—$NH(C_1$-$C_6$ alkyl)$_2$, —$NH_2$, —CN, —$NH(C_1$-$C_6)$ alkyl, —$N(C_1$-$C_6$ alkyl)$_2$, —$NH(CH_2)_r$—$O(C_1$-$C_6)$alkyl, —$NH(CH_2)_r$—$N(C_1$-$C_6$ alkyl)$_2$, —$C(=O)NH_2$, —$C(=O)NH(C_1$-$C_6)$ alkyl and —$C(=O)N(C_1$-$C_6$ alkyl)$_2$; wherein r is an integer selected independently from 1, 2, 3 and 4.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —$(C_3$-$C_6)$ cycloalkyl, —$(C_1$-$C_3)$ haloalkyl, —$O(C_1$-$C_3)$ haloalkyl, 5-6 membered heterocyclyl, —OH, —$O(C_1$-$C_6)$ alkyl, —$NH_2$, —CN, —$NH(C_1$-$C_6)$ alkyl, —$N(C_1$-$C_6$ alkyl)$_2$, —$C(=O)NH_2$, —$C(=O)NH(C_1$-$C_6)$ alkyl and —$C(=O)N(C_1$-$C_6$ alkyl)$_2$.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —$(C_3$-$C_6)$ cycloalkyl, —$C(=O)(C_1$-$C_6)$alkyl, —OH and —$O(C_1$-$C_6)$ alkyl; wherein the halogen is preferably selected from —F, —Cl and —Br.

According to some embodiments, $R^6$ is selected from 9-10 membered bicyclic heteroaryl and substituted 9-10 membered bicyclic heteroaryl. According to some embodiments, $R^6$ is selected from:

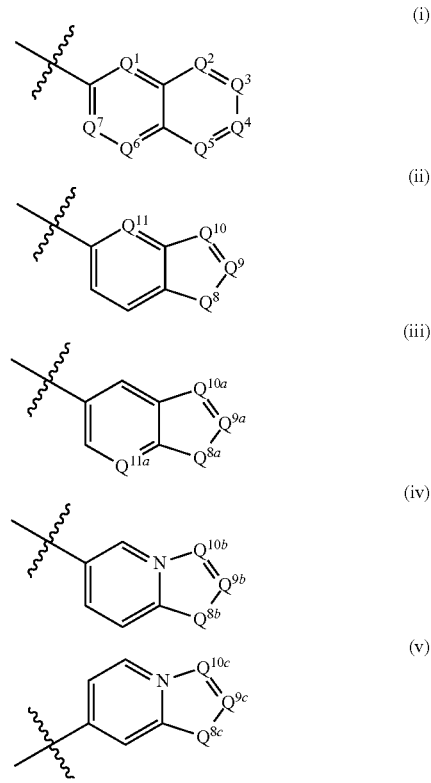

wherein, when $R^6$ is (i), $Q^1, Q^2, Q^3, Q^4, Q^5, Q^6$ and $Q^7$ are independently selected from N and C—$R^{10}$, provided that 0, 1, 2 or 3 of $Q^1, Q^2, Q^3, Q^4, Q^5, Q^6$ and $Q^7$ are N, and the remainder of $Q^1, Q^2, Q^3, Q^4, Q^4, Q^6$ and $Q^7$ are C—$R^{10}$;

when $R^6$ is (ii), $Q^8$ is selected from O, S and N—$R^{10n}$ and $Q^9, Q^{10}$ and $Q^{11}$ are independently selected from N and C—$R^{10}$;

when $R^6$ is (iii), $Q^{8a}$ is selected from O, S and N—$R^{10n}$, $Q^{9a}$, $Q^{10A}$ and $Q^{11a}$ are independently selected from N and C—$R^{10}$;

when $R^6$ is (iv), $Q^{8b}$ is selected from O, S and N—$R^{10n}$; and $Q^{9b}$ and $Q^{10b}$ are independently selected from N and C—$R^{10}$; and when $R^6$ is (v), $Q^{8a}$ is selected from O, S and N—$R^{10n}$; and $Q^{9c}$ and $Q^{10c}$ are independently selected from N and C—$R^{10}$;

and wherein each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH(CH$_2$)$_r$—O($C_1$-$C_6$)alkyl, —NH(CH$_2$)$_r$—N($C_1$-$C_6$ alkyl)$_2$, —C(O)O($C_1$-$C_6$alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, $R^6$ is selected from:

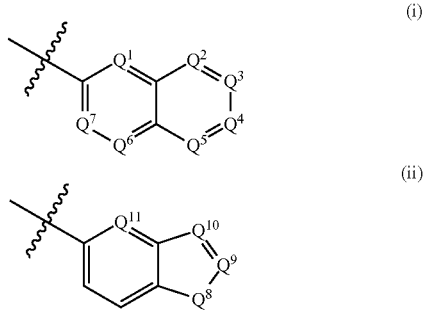

wherein $Q^1$ and $Q^{11}$ are C—$R^{10z}$;

$Q^2$, $Q^3$, $Q^4$, $Q^5$, $Q^6$, $Q^7$, $Q^9$, and $Q^{10}$ are independently selected from N and C—$R^{10}$, provided that 0, 1, 2 or 3 of $Q^2$, $Q^3$, $Q^4$, $Q^5$, $Q^6$ and $Q^7$ are N, and the remainder of $Q^2$, $Q^3$, $Q^4$, $Q^5$, $Q^6$ and $Q^7$ are C—$R^{10}$;

$Q^8$ is selected from O, S and N—$R^{10n}$;

and wherein each $R^{10z}$ is independently selected from halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH(CH$_2$)$_r$—O($C_1$-$C_6$)alkyl, —NH(CH$_2$)$_r$—N($C_1$-$C_6$ alkyl)$_2$, —C(O)O($C_1$-$C_6$alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4;

each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH ($C_1$-$C_6$) alkyl, —N($C_1$-$C_6$ alkyl)$_2$, —NH(CH$_2$)$_r$—O ($C_1$-$C_6$)alkyl, —NH(CH$_2$)$_r$—N($C_1$-$C_6$ alkyl)$_2$, —C(O) O($C_1$-$C_6$alkyl), —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, each $R^{10z}$ is independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, each $R^{10z}$ is independently selected from —$C_1$-$C_6$ alkyl, —($C_3$-$C_6$) cycloalkyl, and —O($C_1$-$C_6$) alkyl. According to some embodiments, each $R^{10z}$ is independently selected from —$C_1$-$C_6$ alkyl.

According to some embodiments, each $R^{10}$ is independently selected from —H, halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, $R^{10}$ is selected from —H and —$C_1$-$C_6$ alkyl. According to some embodiments, $R^{10}$ is —H. According to some embodiments, $R^{10}$ is —$C_1$-$C_6$ alkyl.

According to some embodiments, each $R^{10n}$ is independently selected from —H, —($C_1$-$C_6$)alkyl, substituted —($C_1$-$C_6$)alkyl, benzyl, substituted benzyl and t-butoxycarbonyl. According to some embodiments, $R^{10n}$ is selected from —H and —$C_1$-$C_6$ alkyl. According to some embodiments, $R^{10n}$ is —H. According to some embodiments, $R^{10n}$ is —$C_1$-$C_6$ alkyl.

According to some embodiments, $R^6$ may be selected from the ring systems shown in Table 2, wherein $R^{10n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 2 may be substituted by $R^{10}$ substituents as $R^{10}$ is defined herein.

TABLE 2

A selection of some suitable R6 moieties.

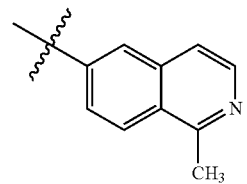 [SMILES: *c1ccc2c(C)nccc2c1]

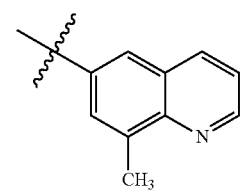 [SMILES: *c1cc(C)c2ncccc2c1]

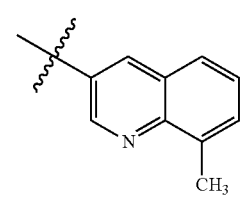 [SMILES: *c1cnc2c(C)cccc2c1]

TABLE 2-continued
A selection of some suitable R6 moieties.
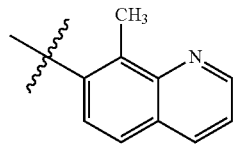
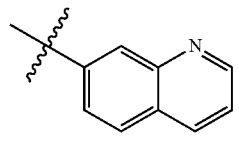 [SMILES: *c1ccc2cccnc2c1]
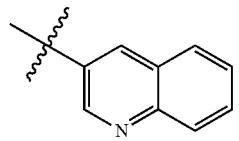 [SMILES: *c1cnc2ccccc2c1]
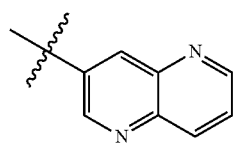 [SMILES: *c1cnc2cccnc2c1]
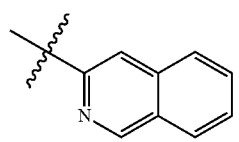 [SMILES: *c1cc2ccccc2cn1]
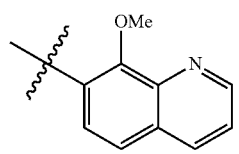 [SMILES: *c1ccc2cccnc2c1OC]
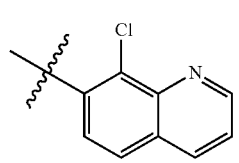 [SMILES: *c1ccc2cccnc2c1Cl]
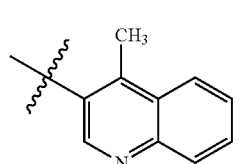
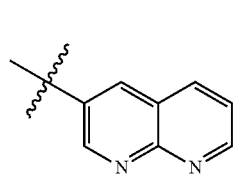 [SMILES: *c1cnc2ncccc2c1]
TABLE 2-continued
A selection of some suitable R6 moieties.
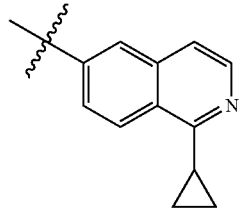 [SMILES: *c1ccc2c(C3CC3)nccc2c1]
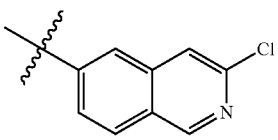 [SMILES: *c1ccc2cnc(Cl)cc2c1]
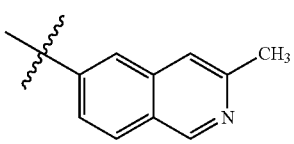 [SMILES: *c1ccc2cnc(C)cc2c1]
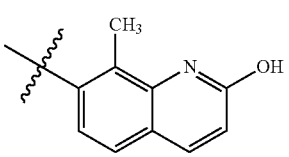 [SMILES: *c1ccc2ccc(O)nc2c1C]
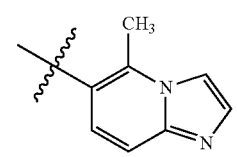 [SMILES: *c1ccc2nccn2c1C]
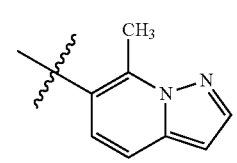 [SMILES: *c1ccc2ccnn2c1C]
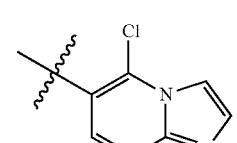
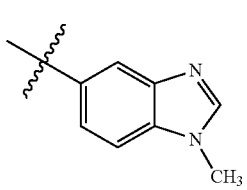 [SMILES: *c1ccc2c(c1)ncn2C]
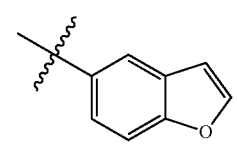 [SMILES: *c1ccc2occc2c1]

TABLE 2-continued

A selection of some suitable R6 moieties.

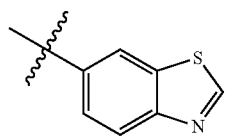 [SMILES: *c1ccc2ncsc2c1]

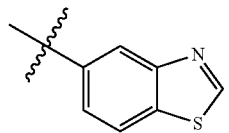

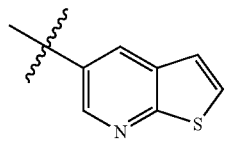 [SMILES: *c1cnc2sccc2c1]

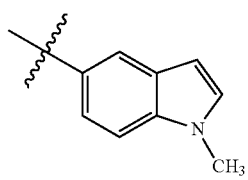 [SMILES: *c1ccc2c(ccn2C)c1]

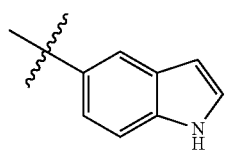 [SMILES: *c1ccc2[nH]ccc2c1]

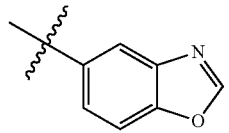

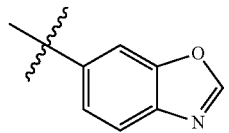 [SMILES: *c1ccc2ncoc2c1]

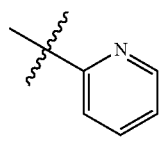 [SMILES: *c1ccccn1]

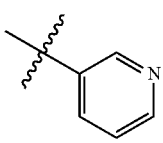 [SMILES: *c1cccnc1]

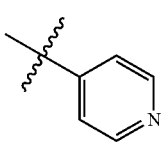 [SMILES: *c1ccncc1]

TABLE 2-continued

A selection of some suitable R6 moieties.

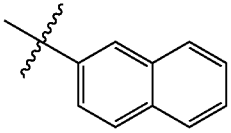 [SMILES: *c1ccc2ccccc2c1]

It will be understood that the non-bridgehead ring carbon ring atoms in (i), (ii), (iii), (iv) and (v) above (i.e., non-bridgehead ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —($C_1$-$C_3$) alkyl, —O($C_1$-$C_3$)alkyl and halogen.

According to some embodiments, one of these ring carbon ring atoms is substituted with a substituent selected from —OH, —$CH_3$, cyclopropyl, —$OCH_3$, —F and —Cl. According to some embodiments, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ to the core of the spiropiperidine molecule is on a 6-membered ring portion of the 9-membered bicyclic heteroaryl or substituted 9-membered bicyclic heteroaryl.

According to some embodiments, $R^6$ is:

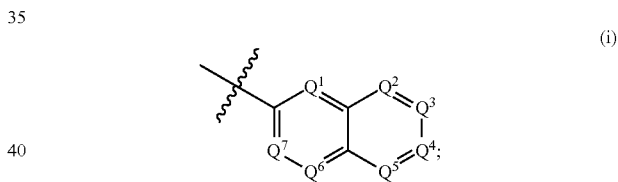

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{10}$. According to some embodiments, when $R^6$ is (i), $Q^2$ is N, and the remainder of $Q^1$, $Q^3$, $Q^4$, $Q^5$, $Q^6$ and $Q^7$ are C—$R^{10}$. According to some embodiments, when $R^6$ is (i), $Q^6$ is N, and $Q^1$, $Q^2$, $Q^3$, $Q^5$, $Q^5$ and $Q^7$ are C—$R^{10}$. According to some embodiments, when $R^6$ is (i), $Q^6$ is N, $Q^2$, $Q^3$, $Q^5$, $Q^5$ and $Q^7$ are CH, and $Q^1$ is C—$R^{10}$, wherein —$R^{10}$ is other than —H.

According to some embodiments, $R^6$ is:

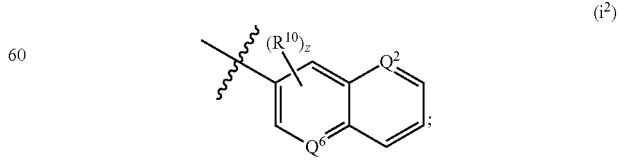

($i^2$)

wherein one of $Q^2$ and $Q^6$ is N, and the other of $Q^2$ and $Q^6$ is C—$R^{10}$, and z is an integer selected from 0, 1, 2 and 3. According to some embodiments of (i²), Q² is N, and Q⁶ is C—R¹⁰. According to some embodiments, Q⁶ is N, and Q² is C—R¹⁰. According to some embodiments, z is selected from 0, 1 and 2. According to some embodiments of (i²), z is 0 or 1. It will be understood that a z value of 0 is the equivalent of designating all R¹⁰ that are bonded to the (i²) bicyclic heteroaryl at other than Q² and Q⁶ as being —H.

According to some embodiments, R⁶ is:

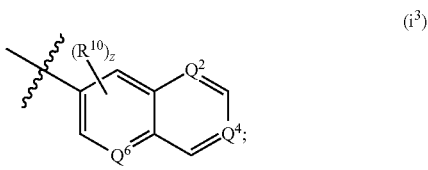

(i³)

wherein one or two of Q², Q⁴ and Q⁶ is N, and the remainder of Q², Q⁴ and Q⁶ are C—R¹⁰, and z is an integer selected from 0, 1, 2 and 3.

According to some embodiments of (i³), z is 0, 1 or 2. According to some embodiments, z is 0 or 1. It will be understood that a z value of 0 is the equivalent of designating all R¹⁰ that are bonded to the bicyclic heteroaryl moiety at other than Q², Q⁴ or Q⁶ as being —H.

According to some embodiments of (i³), Q² is N, and Q⁴ and Q⁶ are C—R¹⁰. According to some embodiments of (i³), Q⁶ is N, and Q² and Q⁴ are C—R¹⁰. According to some embodiments of (i³), Q⁴ is N, and Q² and Q⁶ are C—R¹⁰. According to some embodiments of (i³), Q² is C—R¹⁰, and Q⁴ and Q⁶ are N. According to some embodiments of (i³), Q⁶ is C—R¹⁰, and Q² and Q⁴ are N. According to some embodiments of (i³), Q⁴ is C—R¹⁰, and Q² and Q⁶ are N.

Another aspect of this application is directed to compounds of Formula IA:

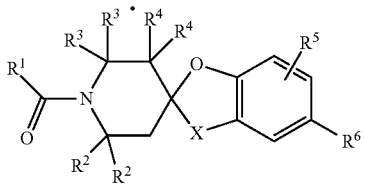

IA and salts thereof, e.g., pharmaceutically acceptable salts thereof, wherein:

R¹ is selected from —(C₁-C₇) hydrocarbyl, substituted —(C₁-C₇) hydrocarbyl, 3-7 membered heterocyclyl, —C(=O)(C₁-C₇) hydrocarbyl, —NR⁷R⁸, —SR⁷, —NR⁷(OR⁸) and —NR⁷(SR⁸);

each R² is independently selected from —H and —(C₁-C₄) alkyl;

each R³ is independently selected from —H and —(C₁-C₄) alkyl each R⁴ is independently selected from —H, —(C₁-C₆) alkyl, —OH, —O(C₁-C₆) alkyl, halogen, —CN, or the two geminal R⁴ groups may together form a carbonyl group;

wherein one of the R³ groups can optionally be structurally connected to one of the R² groups to form an alkylene bridge to produce a bicyclic ring; or one of the R³ groups can optionally be structurally connected to the R¹ group to form a 5 to 7 membered heterocyclyl ring fused to the 1-2 face of the piperidine ring; or one of the R³ groups can optionally be structurally connected to the R⁴ group to form a 5-7 membered carbocyclic or heterocyclic ring fused to the 2-3 face of the piperidine ring;

X is selected from —O(CH₂)_q(CR⁹R⁹ᵃ)_{p1}—, —S(CH₂)_q(CR⁹R⁹ᵃ)_{p2}—, —(CH₂)_q(CR⁹R⁹ᵃ)_{p3}— and —CH=CH—;

p1 is an integer selected from 0 and 1;
p2 is an integer selected from 0 and 1;
p3 is an integer selected from 1 and 2;
q is an integer selected from 0 and 1; R⁵ is selected from —H, —C₁-C₇ hydrocarbyl, halogen, —(C₁-C₃) haloalkyl, —OR⁷ᵃ, —CN, —NR⁷ᵃR⁸ᵃ, —O(CH₂)ₙNR⁷ᵃR⁸ᵃ, —O(CH₂)ₙOR⁸ᵃ, —NR⁸ᵃ(CH₂)ₙNR⁷ᵃR⁸ᵃ, —NR⁸ᵃ(CH₂)ₙOR⁸ᵃ, —C(=O)NR⁷ᵃR⁸ᵃ, —C(=O)OR⁷ᵃ, 5-6 membered heteroaryl, substituted 5-6 membered heteroaryl; wherein n is an integer selected from 2, 3 and 4;

R⁶ is selected from 9-10 membered bicyclic heteroaryl and substituted 9-10 membered bicyclic heteroaryl;

R⁷ is selected from —H, —(C₁-C₇) hydrocarbyl, substituted —(C₁-C₇) hydrocarbyl, —C(=O)Rᵇ, —(C₁-C₆) heteroalkyl, 6 membered aryl, 5-6 membered heteroaryl and 5-6 membered heterocyclyl, wherein R⁸ᵇ is selected from —H and —(C₁-C₆) alkyl;

R⁸ is selected from —H, 3-7 membered heterocycloalkyl, and —(C₁-C₆) alkyl, wherein R⁷ can optionally be structurally connected to R⁸ to form a 5 to 7 membered heterocyclyl ring;

R⁷ᵃ is selected from —H, —(C₁-C₇) hydrocarbyl, substituted —(C₁-C₇) hydrocarbyl, —C(=O)R⁸ᵇ and —(C₁-C₆) heteroalkyl, wherein R⁸ᵇ is selected from —H and —(C₁-C₆) alkyl;

R⁸ᵃ is selected from —H and —(C₁-C₆) alkyl, wherein R⁷ᵃ can optionally be structurally connected to R⁸ᵃ to form a 5 to 7 membered heterocyclyl ring;

each R⁹ is independently selected from —H, —OH, —(C₁-C₇) hydrocarbyl, —O(C₁-C₇) hydrocarbyl and halogen; and each R⁹ᵃ is —H, or a geminal R⁹ and R⁹ᵃ may together form a carbonyl group.

According to some embodiments, R¹ is selected from —(C₁-C₇) hydrocarbyl, substituted —(C₁-C₇) hydrocarbyl, 3-7 membered heterocyclyl, —NR⁷R⁸, —SR⁷, —NR⁷(OR⁸) and —NR⁷(SR⁸).

According to some embodiments, R¹ is selected from —(C₁-C₆) alkyl, substituted —(C₁-C₆) alkyl, —(C₃-C₆) cycloalkyl, substituted —(C₃-C₆)cycloalkyl, benzyl, substituted benzyl, 5-6 membered heterocyclyl, —C(=O)(C₁-C₆) alkyl, —SR⁷, —NR⁷R⁸ and —NR⁷(OR⁸).

According to some embodiments, R¹ is selected from —(C₁-C₆) alkyl, substituted —(C₁-C₆) alkyl, —(C₃-C₆) cycloalkyl, substituted —(C₃-C₆)cycloalkyl, benzyl, substituted benzyl, —SR⁷, —NR⁷R⁸ and —NR⁷(OR⁸). According to some embodiments, R¹ is selected from —NR⁷R⁸ and —NR⁷(OR⁸). According to some embodiments, R¹ is —NR⁷R⁸. According to some embodiments, R¹ is —NR⁷(OR⁸).

According to other embodiments, R¹ is selected from —CH₃, —CH₂CH₃, —(CH₂)₂CH₃, —(CH₂)₃CH₃, —(CH₂)₄CH₃, —CH(CH₃)₃, —C(CH₃)₃, cyclopropyl, substituted cyclopropyl, cyclobutyl, substituted cyclobutyl, cyclopentyl, —C(=O)CH₃, —C(=O)CH₂CH₃, —NH—OH, —NH—OCH₃, —NH—OCH₂CH₃, —N(CH₃)—

OCH$_3$, —NH$_2$, —NHCH$_3$, —NH—CH$_2$CH$_3$, —NH(CH$_2$)$_2$—CH$_3$, —NH(CH$_2$)$_3$—CH$_3$, —NH(CH$_2$)$_4$—CH$_3$, —NH(CH$_2$)$_5$—CH$_3$, —N(CH$_3$)$_2$, —N(Et)$_2$, —NH—CH(CH$_3$)$_2$, —NH—OCH$_2$CH$_3$, —NHSCH$_3$, —NHSCH$_2$CH$_3$, —SCH$_3$, —SCH$_2$CH$_3$, —SCH(CH$_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH$_2$—OCH$_3$, —(CH$_2$)$_2$—OCH$_3$ and —(CH$_2$)$_3$—OCH$_3$.

According to other embodiments, R$^1$ is selected from —CH$_3$, —CH$_2$CH$_3$, —(CH$_2$)$_2$CH$_3$, —(CH$_2$)$_3$CH$_3$, —(CH$_2$)$_4$CH$_3$, —CH(CH$_3$)$_3$, —C(CH$_3$)$_3$, cyclopropyl, substituted cyclopropyl, cyclobutyl, substituted cyclobutyl, cyclopentyl, —C(=O)CH$_3$, —C(=O)CH$_2$CH$_3$, —NH—OH, —NH—OCH$_3$, —NH—OCH$_2$CH$_3$, —N(CH$_3$)—OCH$_3$, —NH$_2$, —NHCH$_3$, —NH—CH$_2$CH$_3$, —NH(CH$_2$)$_2$—CH$_3$, —NH(CH$_2$)$_3$—CH$_3$, —NH(CH$_2$)$_4$—CH$_3$, —NH(CH$_2$)$_5$—CH$_3$, —N(CH$_3$)$_2$, —N(Et)$_2$, —NH—CH(CH$_3$)$_2$, —NH—OCH$_2$CH$_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH$_2$—OCH$_3$, —(CH$_2$)$_2$—OCH$_3$ and —(CH$_2$)$_3$—OCH$_3$.

According to some embodiments, when R$^1$ is substituted cyclopropyl, the cyclopropyl ring may be substituted with 1 or two substituents selected from —OH, —CH$_2$OH, —C(=O)NH$_2$, —NH$_2$, —CH$_3$, —CN and —CF$_3$.

According to some embodiments, when R$^1$ is tetrahydrofuranyl, it is tetrahydrofuran-2-yl or tetrahydrofuran-3-yl. According to some embodiments, when R$^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when R$^1$ is furanyl, it is 2-furanyl or 3-furanyl. According to some embodiments, when R$^1$ is substituted furanyl, it is 2-methylfuran-2-yl, 5-methylfuran-2-yl, or 2,5-dimethylfuran-2-yl.

According to some embodiments, when R$^1$ is dioxolanyl, it is 1,3-dioxolan-2-yl. According to some embodiments, when R$^1$ is substituted dioxolanyl it is 2-methyl-1,3-dioxolan-2-yl.

According to some embodiments, when R$^1$ is tetrahydroisoxazolidine, it is tetra-hydroisoxazolidin-2-yl. According to some embodiments, when R$^1$ is tetrahydropyrrolyl, it is tetrahydropyrrol-1-yl. According to some embodiments, when R$^1$ is morpholinyl, it is morpholin-1-yl. According to some embodiments, when R$^1$ is piperidinyl, it is piperidin-1-yl. According to some embodiments, when R$^1$ is furanyl, it is 2-furanyl or 3-furanyl. According to some embodiments, when R$^1$ is thiophenyl, it is 2-thiophenyl or 2-thiophenyl. According to some embodiments, when R$^1$ is tetrahydrothiophenyl, it is 2-tetrahydrothiophenyl or 2-tetrahydrothiophenyl. According to some embodiments, when R$^1$ is sulfolanyl, it is sulfolan-2-yl or sulfolan-3-yl. According to some embodiments, when R$^1$ is oxazolyl, it is oxazol-1-yl, oxazol-2-one-1-yl oxazol-2-yl or oxazol-5-yl. According to some embodiments, when R$^1$ is isoxazolyl, it is isoxazol-1-yl, isoxazol-3-yl or isoxazol-5-yl. According to some embodiments, when R$^1$ is imidazolyl, it is imidazol-2-yl or imidazol-5-yl. According to some embodiments, when R$^1$ is thiazolyl, it is thiazol-2-yl or thiazol-5-yl. According to some embodiments, when R$^1$ is isothiazolyl, it is isothiazol-3-yl or isothiazol-5-yl. According to some embodiments, when R$^1$ is pyridyl, it is 2-pyridyl, 3-pyridyl, or 4-pyridyl. According to some embodiments, when R$^1$ is substituted quinolyl, it is quinolin-1-yl, quinolin-2-yl or quinolin-3-yl. According to some embodiments, when R$^1$ is substituted phenyl, it is 2-methylphenyl, 3-methylphenyl, 4-methylphenyl, or 2,5-dimethylphenyl. According to some embodiments, R$^1$ is selected from the moieties depicted in Table 1 and Table 1a supra.

According to some embodiments, each R$^2$ is —H.

According to some embodiments, each R$^3$ is —H.

According to some embodiments, each R$^4$ is independently selected from —H, —(C$_1$-C$_6$) alkyl and halogen, wherein the halogen is preferably selected from —F, —Cl and —Br. According to some embodiments, one R$^4$ is halogen and the other R$^4$ is —H. According to some embodiments, each R$^4$ is —H.

According to some embodiments, X is selected from —O—, —O—(CHR$^9$)—, —O—(CHR$^9$)$_2$—, —(CHR$^9$)—, —(CHR$^9$)$_2$— and —CH$_2$(CHR$^9$)$_2$—. According to some embodiments, X is selected from —O—, —OCH$_2$—, —O—(CH$_2$)$_2$—, —S—, —SCH$_2$—, —S—(CH$_2$)$_2$—, —(CH$_2$)—, —(CH$_2$)$_2$— and —(CH$_2$)$_3$—. According to some embodiments, X is selected from —CH$_2$—, —(CH$_2$)$_2$— and —OCH$_2$—. According to some embodiments, X is —(CH$_2$)$_2$—.

According to some embodiments, R$^5$ is selected from —H, —C$_1$-C$_6$ alkyl, benzyl, halogen, —(C$_1$-C$_3$) haloalkyl, —OR$^{7a}$, —CN, —NR$^{7a}$R$^{8a}$, —C(=O)NR$^{7a}$R$^{8a}$, —C(=O)OR$^{7a}$, 5-6 membered heteroaryl and substituted 5-6 membered heteroaryl.

According to some embodiments, R$^5$ is selected from —H, —C$_1$-C$_6$ alkyl, benzyl, —C$_1$, —F, —Br, —(C$_1$-C$_3$) haloalkyl, —OC$_1$-C$_6$ alkyl, —CN, —NH(C$_1$-C$_6$)alkyl, —C(=O)NH(C$_1$-C$_6$)alkyl, —C(=O)OC$_1$-C$_6$ alkyl, 5-6 membered heteroaryl and substituted 5-6 membered heteroaryl.

According to some embodiments, R$^5$ is selected from —H, —C$_1$-C$_6$ alkyl, —F, —C$_1$, —Br, —OC$_1$-C$_6$ alkyl, —CN, —NH(C$_1$-C$_6$)alkyl, —C(=O)NH(C$_1$-C$_6$)alkyl and —C(=O)O(C$_1$—C$_6$)alkyl. According to some embodiments, R$^5$ is selected from —H, —C$_1$-C$_6$ alkyl and halogen; wherein halogen is preferably selected from —F, —Cl and —Br. According to some embodiments, R$^5$ is —H.

According to some embodiments, R$^7$ is selected from —H and —C$_1$-C$_6$ alkyl. According to some embodiments, R$^7$ is —H. According to some embodiments, R$^7$ is —C$_1$-C$_6$ alkyl.

According to some embodiments, R$^8$ is selected from —H and —C$_1$-C$_6$ alkyl. According to some embodiments, R$^8$ is —H. According to some embodiments, R$^8$ is —C$_1$-C$_6$ alkyl. According to some embodiments, R$^7$ and R$^8$ are —H.

According to some embodiments, R$^{7a}$ is selected from —H and —C$_1$-C$_6$ alkyl. According to some embodiments, R$^{7a}$ is —H. According to some embodiments, R$^{7a}$ is —C$_1$-C$_6$ alkyl.

According to some embodiments, R$^{8a}$ is selected from —H and —C$_1$-C$_6$ alkyl. According to some embodiments, R$^{8a}$ is —H. According to some embodiments, R$^{8a}$ is —C$_1$-C$_6$ alkyl. According to some embodiments, R$^{7a}$ and R$^{8a}$ are —H.

According to some embodiments, R$^{8b}$ is —C$_1$-C$_6$ alkyl. According to some embodiments, R$^{8b}$ is —H.

According to some embodiments, each R$^9$ is selected from —H, —OH, —(C$_1$-C$_6$) alkyl, —O(C$_1$-C$_6$) alkyl, benzyl, —O-benzyl, —C₁ and —F and $R^{9a}$ is —H; or a geminal $R^9$ and $R^{9a}$ together form a carbonyl group. According to some embodiments, $R^9$ and $R^{9a}$ are —H.

According to some embodiments, when $R^6$ is substituted bicyclic heteroaryl, the bicyclic heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —O(CH$_2$)$_r$-(5-6 membered heterocyclyl), —O(CH$_2$)$_r$— O($C_1$-$C_6$) alkyl, —O(CH$_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH(CH$_2$)$_r$—O($C_1$-$C_6$)alkyl, —NH(CH$_2$)$_r$—N($C_1$-$C_6$ alkyl)$_2$, —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4.

According to some embodiments, when $R^6$ is substituted bicyclic heteroaryl, the bicyclic heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —NH$_2$, —CN, —NH($C_1$-$C_6$) alkyl, —N($C_1$-$C_6$ alkyl)$_2$, —C(=O)NH$_2$, —C(=O)NH($C_1$-$C_6$) alkyl and —C(=O)N($C_1$-$C_6$ alkyl)$_2$.

According to some embodiments, when $R^6$ is substituted bicyclic heteroaryl, the bicyclic heteroaryl is substituted with 1, 2 or 3 substituents independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br.

According to some embodiments, $R^6$ is selected from 9-10 membered bicyclic heteroaryl and substituted 9-10 membered bicyclic heteroaryl. According to some embodiments, $R^6$ is selected from:

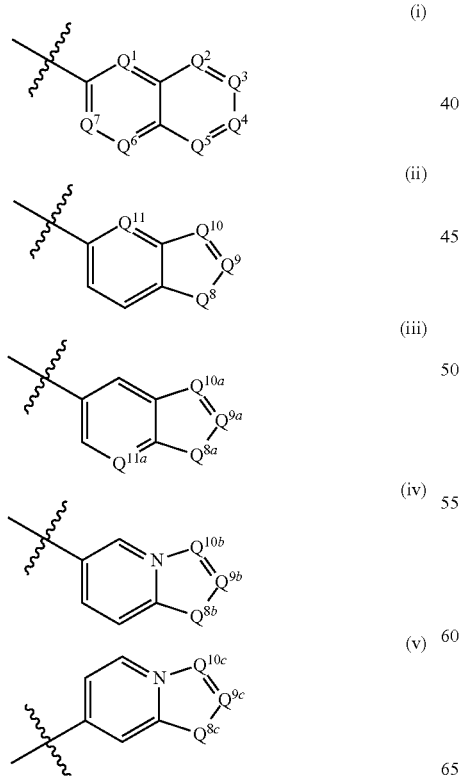

wherein, when $R^6$ is (i), $Q^1$, $Q^2$, $Q^3$, $Q^4$, $Q^5$, $Q^6$ and $Q^7$ are independently selected from N and C—$R^{10}$, provided that 0, 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$;

when $R^6$ is (ii), $Q^8$ is selected from O, S and N—$R^{10n}$ and $Q^9$, $Q^{10}$ and $Q^{11}$ are independently selected from N and C—$R^{10}$;

when $R^6$ is (iii), $Q^{8a}$ is selected from O, S and N—$R^{10n}$, $Q^{9a}$, $Q^{10A}$ and $Q^{11}a$ are independently selected from N and C—$R^{10}$;

when $R^6$ is (iv), $Q^{8b}$ is selected from O, S and N—$R^{10n}$; and $Q^{9b}$ and $Q^{10b}$ are independently selected from N and C—$R^{10}$; and when $R^6$ is (v), $Q^{8a}$ is selected from O, S and N—$R^{10n}$; and $Q^{9c}$ and $Q^{10c}$ are independently selected from N and C—$R^{10}$;

and wherein each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH(CH$_2$)$_r$—O($C_1$-$C_6$)alkyl, —NH(CH$_2$)$_r$—N($C_1$-$C_6$ alkyl)$_2$, —C(O)O($C_1$-$C_6$ alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, $R^6$ is selected from:

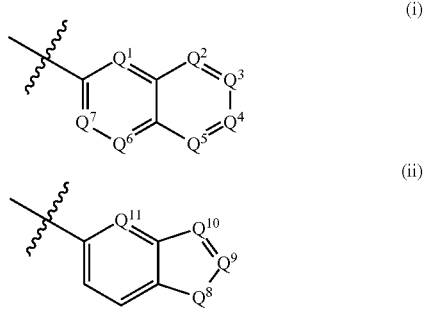

wherein
$Q^1$ and $Q^{11}$ are C—$R^{10z}$;
$Q^2$, $Q^3$, $Q^4$, $Q^5$, $Q^6$, $Q^7$, $Q^9$, and $Q^{10}$ are independently selected from N and C—$R^{10}$, provided that 0, 1, 2 or 3 of $Q^2$, $Q^3$, $Q^4$, $Q^5$, $Q^6$ and $Q^7$ are N, and the remainder of $Q^2$, $Q^3$, $Q^4$, $Q^5$, $Q^6$ and $Q^7$ are C—$R^{10}$;
$Q^8$ is selected from O, S and N—$R^{10n}$;
and wherein each $R^{10z}$ is independently selected from halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH(CH$_2$)$_r$—O($C_1$-$C_6$)alkyl, —NH(CH$_2$)$_r$—N($C_1$-$C_6$ alkyl)$_2$, —C(O)O($C_1$-$C_6$alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4;

each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O(CH$_2$)$_r$-(5-6 membered heterocyclyl), —O(CH$_2$)$_r$—O($C_1$-$C_6$)alkyl, —O(CH$_2$)$_r$—NH($C_1$-$C_6$ alkyl)$_2$, —NH$_2$, —CN, —NH ($C_1$-$C_6$) alkyl, —N($C_1$-$C_6$ alkyl)$_2$, —NH(CH$_2$)$_r$—O ($C_1$-$C_6$)alkyl, —NH(CH$_2$)$_r$—N($C_1$-$C_6$ alkyl)$_2$, —C(O) O($C_1$-$C_6$alkyl), —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, each $R^{10z}$ is independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, each $R^{10z}$ is independently selected from —$C_1$-$C_6$ alkyl, —($C_3$-$C_6$) cycloalkyl, and —O($C_1$-$C_6$) alkyl. According to some embodiments, each $R^{10z}$ is independently selected from —$C_1$-$C_6$ alkyl.

According to some embodiments, each $R^{10}$ is independently selected from —H, halogen, —($C_1$-$C_6$) alkyl, —($C_3$-$C_6$) cycloalkyl, —C(=O)($C_1$-$C_6$)alkyl, —C(=O)O($C_1$-$C_6$) alkyl, —OH and —O($C_1$-$C_6$) alkyl; wherein the halogen is preferably selected from —F, —Cl and —Br. According to some embodiments, $R^{10}$ is selected from —H and —$C_1$-$C_6$ alkyl. According to some embodiments, $R^{10}$ is —H. According to some embodiments, $R^{10}$ is —$C_1$-$C_6$ alkyl.

According to some embodiments, each $R^{10n}$ is independently selected from —H, —($C_1$-$C_6$)alkyl, substituted —($C_1$-$C_6$)alkyl, benzyl, substituted benzyl and t-butoxycarbonyl. According to some embodiments, $R^{10n}$ is selected from —H and —$C_1$-$C_6$ alkyl. According to some embodiments, $R^{10n}$ is —H. According to some embodiments, $R^{10n}$ is —$C_1$-$C_6$ alkyl.

According to some embodiments, $R^6$ may be selected from the ring systems shown in Table 2, wherein $R^{10n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 2 may be substituted by $R^{10}$ substituents as $R^{10}$ is defined herein.

Another aspect of this application is directed to compounds of Formula IB:

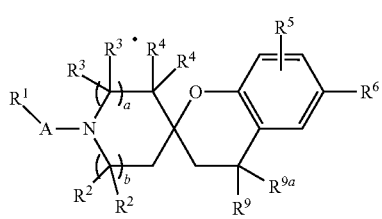

and salts thereof, e.g., pharmaceutically acceptable salts thereof, wherein:

A is selected from —C(=O)— and —SO$_2$—;

$R^1$ is selected from —($C_1$-$C_7$) hydrocarbyl, substituted —($C_1$-$C_7$) hydrocarbyl, 3-7 membered heterocyclyl, —C(=O)($C_1$-$C_7$) hydrocarbyl, —NR$^7$R$^8$, —OR$^7$, —SR$^7$, —N R$^7$(OR$^8$) and —N R$^7$(SR$^8$);

a and b are independently selected from 0 and 1;

each $R^2$ is independently selected from —H and —($C_1$-$C_4$) alkyl;

each $R^3$ is independently selected from —H and —($C_1$-$C_4$) alkyl;

each $R^4$ is independently selected from —H, —($C_1$-$C_6$) alkyl, —OH, —O($C_1$-$C_6$) alkyl, halogen, —CN, or the two geminal $R^4$ groups may together form a carbonyl group;

wherein one of the $R^3$ groups can optionally be structurally connected to one of the $R^2$ groups to form an alkylene bridge to produce a bicyclic ring; or one of the $R^3$ groups can optionally be structurally connected to the $R^1$ group to form a 5 to 7 membered heterocyclyl ring fused to the 1-2 face of the piperidine ring; or one of the $R^3$ groups can optionally be structurally connected to the $R^4$ group to form a 5-7 membered carbocyclic or heterocyclic ring fused to the 2-3 face of the piperidine ring;

$R^5$ is selected from —H, —$C_1$-$C_7$ hydrocarbyl, halogen, —($C_1$-$C_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl and substituted 5-6 membered heteroaryl;

$R^6$ is selected from naphthyl, substituted naphthyl, 6-membered heteroaryl, substituted 6-membered heteroaryl, 9-10 membered bicyclic heteroaryl and substituted 9-10 membered bicyclic heteroaryl;

$R^7$ is selected from —H, —($C_1$-$C_7$) hydrocarbyl, substituted —($C_1$-$C_7$) hydrocarbyl, —C(=O)R$^{8b}$, —($C_1$-$C_6$) heteroalkyl, 6 membered aryl, 5-6 membered heteroaryl and 5-6 membered heterocyclyl, wherein $R^{8b}$ is selected from —H and —($C_1$-$C_6$) alkyl;

$R^8$ is selected from —H, 3-7 membered heterocyloalkyl, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)R$^{8b}$ and —($C_1$-$C_6$) heteroalkyl, wherein $R^{8b}$ is selected from —H and —($C_1$-$C_6$) alkyl;

$R^{8a}$ is selected from —H and —($C_1$-$C_6$) alkyl, wherein $R^{7a}$ can optionally be structurally connected to $R^{8a}$ to form a 5 to 7 membered heterocyclyl ring; and $R^9$ is selected from —H, —OH, —($C_1$-$C_7$) hydrocarbyl, —O($C_1$-$C_7$) hydrocarbyl and halogen; and $R^{9a}$ is —H; or $R^9$ and $R^{9a}$ together form a carbonyl group.

According to some embodiments of compounds according to Formula IB, A is —C(=O)—. According to other embodiments, A is —SO$_2$—.

According to some embodiments, $R^1$ is selected from —($C_1$-$C_7$) hydrocarbyl, substituted —($C_1$-$C_7$) hydrocarbyl, 3-7 membered heterocyclyl, —NR$^7$R$^8$, —SR$^7$, —NR$^7$(OR$^8$) and —NR$^7$(SR$^8$).

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, benzyl, substituted benzyl, 5-6 membered heterocyclyl, —C(=O)($C_1$-$C_6$) alkyl, —SR$^7$, —NR$^7$R$^8$ and —NR$^7$(OR$^8$).

According to some embodiments, $R^1$ is selected from —($C_1$-$C_6$) alkyl, substituted —($C_1$-$C_6$)alkyl, —($C_3$-$C_6$) cycloalkyl, substituted —($C_3$-$C_6$)cycloalkyl, benzyl, substituted benzyl, —SR$^7$, —NR$^7$R$^8$ and —NR$^7$(OR$^8$). According to some embodiments, R$^1$ is selected from —NR$^7$R$^8$ and —NR$^7$(OR$^8$). According to some embodiments, R$^1$ is —NR$^7$R$^8$. According to some embodiments, R$^1$ is —NR$^7$(OR$^8$).

According to other embodiments, R$^1$ is selected from —CH$_3$, —CH$_2$CH$_3$, —(CH$_2$)$_2$CH$_3$, —(CH$_2$)$_3$CH$_3$, —(CH$_2$)$_4$CH$_3$, —CH(CH$_3$)$_3$, —C(CH$_3$)$_3$, cyclopropyl, substituted cyclopropyl, cyclobutyl, substituted cyclobutyl, cyclopentyl, —C(=O)CH$_3$, —C(=O)CH$_2$CH$_3$, —NH—OH, —NH—OCH$_3$, —NH—OCH$_2$CH$_3$, —N(CH$_3$)—OCH$_3$, —NH$_2$, —NHCH$_3$, —NH—CH$_2$CH$_3$, —NH(CH$_2$)$_2$—CH$_3$, —NH(CH$_2$)$_3$—CH$_3$, —NH(CH$_2$)$_4$—CH$_3$, —NH(CH$_2$)$_5$—CH$_3$, —N(CH$_3$)$_2$, —N(Et)$_2$, —NH—CH(CH$_3$)$_2$, —NH—OCH$_2$CH$_3$, —NHSCH$_3$, —NHSCH$_2$CH$_3$, —SCH$_3$, —SCH$_2$CH$_3$, —SCH(CH$_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH$_2$—OCH$_3$, —(CH$_2$)$_2$—OCH$_3$ and —(CH$_2$)$_3$—OCH$_3$.

According to other embodiments, R$^1$ is selected from —CH$_3$, —CH$_2$CH$_3$, —(CH$_2$)$_2$CH$_3$, —(CH$_2$)$_3$CH$_3$, —(CH$_2$)$_4$CH$_3$, —CH(CH$_3$)$_3$, —C(CH$_3$)$_3$, cyclopropyl, substituted cyclopropyl, cyclobutyl, substituted cyclobutyl, cyclopentyl, —C(=O)CH$_3$, —C(=O)CH$_2$CH$_3$, —NH—OH, —NH—OCH$_3$, —NH—OCH$_2$CH$_3$, —N(CH$_3$)—OCH$_3$, —NH$_2$, —NHCH$_3$, —NH—CH$_2$CH$_3$, —NH(CH$_2$)$_2$—CH$_3$, —NH(CH$_2$)$_3$—CH$_3$, —NH(CH$_2$)$_4$—CH$_3$, —NH(CH$_2$)$_5$—CH$_3$, —N(CH$_3$)$_2$, —N(Et)$_2$, —NH—CH(CH$_3$)$_2$, —NH—OCH$_2$CH$_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH$_2$—OCH$_3$, —(CH$_2$)$_2$—OCH$_3$ and —(CH$_2$)$_3$—OCH$_3$.

According to some embodiments, when R$^1$ is substituted cyclopropyl, the cyclopropyl ring may be substituted with 1 or two substituents selected from —OH, —CH$_2$OH, —C(=O)NH$_2$, —NH$_2$, —CH$_3$, —CN and —CF$_3$.

According to some embodiments, when R$^1$ is tetrahydrofuranyl, it is tetrahydrofuran-2-yl or tetrahydrofuran-3-yl. According to some embodiments, when R$^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when R$^1$ is furanyl, it is 2-furanyl or 3-furanyl. According to some embodiments, when R$^1$ is substituted furanyl, it is 2-methylfuran-2-yl, 5-methylfuran-2-yl, or 2,5-dimethylfuran-2-yl.

According to some embodiments, when R$^1$ is dioxolanyl, it is 1,3-dioxolan-2-yl. According to some embodiments, when R$^1$ is substituted dioxolanyl it is 2-methyl-1,3-dioxolan-2-yl.

According to some embodiments, when R$^1$ is tetrahydroisoxazolidine, it is tetra-hydroisoxazolidin-2-yl. According to some embodiments, when R$^1$ is tetrahydropyrrolyl, it is tetrahydropyrrol-1-yl. According to some embodiments, when R$^1$ is morpholinyl, it is morpholin-1-yl. According to some embodiments, when R$^1$ is piperidinyl, it is piperidin-1-yl. According to some embodiments, when R$^1$ is furanyl, it is 2-furanyl or 3-furanyl. According to some embodiments, when R$^1$ is thiophenyl, it is 2-thiophenyl or 2-thiophenyl. According to some embodiments, when R$^1$ is tetrahydrothiophenyl, it is 2-tetrahydrothiophenyl or 2-tetrahydrothiophenyl. According to some embodiments, when R$^1$ is sulfolanyl, it is sulfolan-2-yl or sulfolan-3-yl. According to some embodiments, when R$^1$ is oxazolyl, it is oxazol-1-yl, oxazol-2-one-1-yl oxazol-2-yl or oxazol-5-yl. According to some embodiments, when R$^1$ is isoxazolyl, it is isoxazol-1-yl, isoxazol-3-yl or isoxazol-5-yl. According to some embodiments, when R$^1$ is imidazolyl, it is imidazol-2-yl or imidazol-5-yl. According to some embodiments, when R$^1$ is thiazolyl, it is thiazol-2-yl or thiazol-5-yl. According to some embodiments, when R$^1$ is isothiazolyl, it is isothiazol-3-yl or isothiazol-5-yl. According to some embodiments, when R$^1$ is pyridyl, it is 2-pyridyl, 3-pyridyl, or 4-pyridyl. According to some embodiments, when R$^1$ is substituted quinolyl, it is quinolin-1-yl, quinolin-2-yl or quinolin-3-yl. According to some embodiments, when R$^1$ is substituted phenyl, it is 2-methylphenyl, 3-methylphenyl, 4-methylphenyl, or 2,5-dimethylphenyl. According to some embodiments, R$^1$ is selected from the moieties depicted in Table 1 and Table 1A, supra.

According to some embodiments, a is 1 and b is 0. According to some embodiments, a is 0 and b is 1. According to some embodiments, a and b are both 1.

According to some embodiments, each R$^2$ is —H.

According to some embodiments, each R$^3$ is —H.

According to some embodiments, each R$^4$ is independently selected from —H, —(C$_1$-C$_6$) alkyl and halogen, wherein the halogen is preferably selected from —F, —Cl and —Br. According to some embodiments, one R$^4$ is halogen and the other R$^4$ is —H. According to some embodiments, each R$^4$ is —H.

According to some embodiments, R$^5$ is selected from —H, —C$_1$-C$_6$ alkyl, benzyl, halogen, —(C$_1$-C$_3$) haloalkyl, —OR$^{7a}$, —CN, —NR$^{7a}$R$^{8a}$, —C(=O)NR$^{7a}$R$^{8a}$, —C(=O)OR$^{7a}$, 5-6 membered heteroaryl and substituted 5-6 membered heteroaryl.

According to some embodiments, R$^5$ is selected from —H, —C$_1$-C$_6$ alkyl, benzyl, —C$_1$, —F, —Br, —(C$_1$-C$_3$) haloalkyl, —OC$_1$-C$_6$ alkyl, —CN, —NHC$_1$-C$_6$ alkyl, —C(=O)NHC$_1$-C$_6$ alkyl, —C(=O)OC$_1$-C$_6$ alkyl, 5-6 membered heteroaryl and substituted 5-6 membered heteroaryl.

According to some embodiments, R$^5$ is selected from —H, —C$_1$-C$_6$ alkyl, —F, —C$_1$, —Br, —OC$_1$-C$_6$ alkyl, —CN, —NHC$_1$-C$_6$ alkyl, —C(=O)NHC$_1$-C$_6$ alkyl and —C(=O)OC$_1$-C$_6$ alkyl. According to some embodiments, R$^5$ is selected from —H, —C$_1$-C$_6$ alkyl and halogen; wherein halogen is preferably selected from —F, —Cl and —Br. According to some embodiments, R$^5$ is —H.

According to some embodiments, R$^7$ selected from —H and —C$_1$-C$_6$ alkyl. According to some embodiments, R$^7$ is —H. According to some embodiments, R$^7$ is —C$_1$-C$_6$ alkyl.

According to some embodiments, R$^8$ is selected from —H and —C$_1$-C$_6$ alkyl. According to some embodiments, R$^8$ is —H. According to some embodiments, R$^8$ is —C$_1$-C$_6$ alkyl. According to some embodiments, R$^7$ and R$^8$ are —H.

According to some embodiments, R$^{7a}$ is selected from —H and —C$_1$-C$_6$ alkyl. According to some embodiments, R$^{7a}$ is —H. According to some embodiments, R$^{7a}$ is —C$_1$-C$_6$ alkyl.

According to some embodiments, R$^{8a}$ is selected from —H and —C$_1$-C$_6$ alkyl. According to some embodiments, $R^{8a}$ is —H. According to some embodiments, $R^{8a}$ is —$C_1$-$C_6$ alkyl. According to some embodiments, $R^{7a}$ and $R^{8a}$ are —H.

According to some embodiments, $R^{8b}$ is —$C_1$-$C_6$ alkyl. According to some embodiments, $R^{8b}$ is —H.

According to some embodiments, $R^9$ is selected from —H, —OH, —($C_1$-$C_6$) alkyl, —O($C_1$-$C_6$) alkyl, benzyl, —O-benzyl, —$C_1$ and —F and $R^{9a}$ is —H, or the geminal $R^9$ and $R^{9a}$ together form a carbonyl group. According to some embodiments, $R^9$ and $R^{9a}$ are —H.

According to some embodiments, when $R^6$ is substituted naphthyl, 6-membered heteroaryl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —O($CH_2$)$_r$-(5-6 membered heterocyclyl), —O($CH_2$)$_r$— O($C_1$-$C_6$) alkyl, —O($CH_2$)$_r$—NH($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(=O)$NH_2$, —C(=O)NH($C_1$-$C_6$) alkyl and —C(=O)N($C_1$-$C_6$ alkyl)$_2$; wherein r is an integer selected independently from 1, 2, 3 and 4.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —$NH_2$, —CN, —NH($C_1$-$C_6$) alkyl, —N($C_1$-$C_6$ alkyl)$_2$, —C(=O)$NH_2$, —C(=O)NH($C_1$-$C_6$) alkyl and —C(=O)N($C_1$-$C_6$ alkyl)$_2$.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br.

According to some embodiments, $R^6$ is selected from 9-10 membered bicyclic heteroaryl and substituted 9-10 membered bicyclic heteroaryl. According to some embodiments, $R^6$ is selected from:

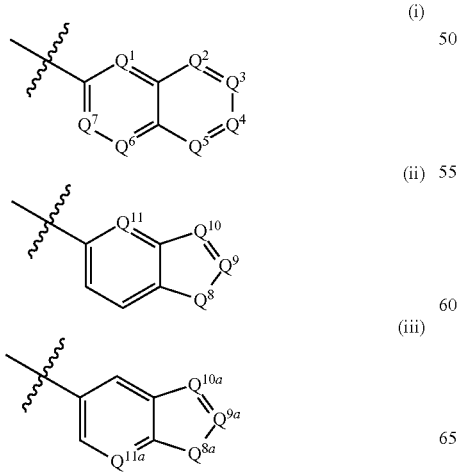

-continued

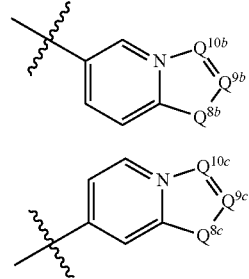

wherein, when $R^6$ is (i), $Q^1$, $Q^2$, $Q^3$, $Q^4$, $Q^5$, $Q^6$ and $Q^7$ are independently selected from N and C—$R^{10}$, provided that 0, 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$;

when $R^6$ is (ii), $Q^8$ is selected from O, S and N—$R^{10n}$ and $Q^9$, $Q^{10}$ and $Q^{11}$ are independently selected from N and C—$R^{10}$, when $R^6$ is (iii), $Q^{8a}$ is selected from O, S and N—$R^{10n}$, $Q^{9a}$, $Q^{10A}$ and $Q^{11}a$ are independently selected from N and C—$R^{10}$;

when $R^6$ is (iv), $Q^{8b}$ is selected from O, S and N—$R^{10n}$; and $Q^{9b}$ and $Q^{10b}$ are independently selected from N and C—$R^{10}$; and when $R^6$ is (v), $Q^{8c}$ is selected from O, S and N—$R^{10n}$; and $Q^{9C}$ and $Q^{10c}$ are independently selected from N and C—$R^{10}$;

and wherein each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —O($CH_2$)$_r$-(5-6 membered heterocyclyl), —O($CH_2$)$_r$— O($C_1$-$C_6$) alkyl, —O($CH_2$)$_r$—NH($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(=O)$NH_2$, —C(=O)O($C_1$-$C_6$) alkyl, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —$CO_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, $R^6$ is selected from:

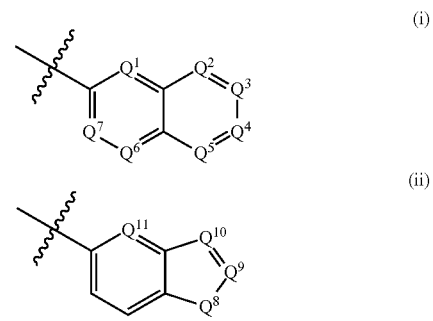

wherein $Q^1$ and $Q^{11}$ are C—$R^{10z}$;

$Q^2$, $Q^3$, $Q^4$, $Q^5$, $Q^6$, $Q^7$, $Q^9$, and $Q^{10}$ are independently selected from N and C—$R^{10}$; provided that 0, 1, 2 or 3 of $Q^2$, $Q^3$, $Q^4$, $Q^5$, $Q^6$ and $Q^7$ are N, and the remainder of $Q^2$, $Q^3$, $Q^4$, $Q^5$, $Q^6$ and $Q^7$ are C—$R^{10}$;

$Q^8$ is selected from O, S and N—$R^{10n}$;

and wherein each $R^{10z}$ is independently selected from halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(O)O($C_1$-$C_6$alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4;

each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(O)O($C_1$-$C_6$alkyl), —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, each $R^{10z}$ is independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, each $R^{10z}$ is independently selected from —$C_1$-$C_6$ alkyl, —($C_3$-$C_6$) cycloalkyl, and —O($C_1$-$C_6$) alkyl. According to some embodiments, each $R^{10z}$ is independently selected from —$C_1$-$C_6$ alkyl.

According to some embodiments, each $R^{10}$ is independently selected from —H, halogen, —($C_1$-$C_6$) alkyl, —($C_3$-$C_6$) cycloalkyl, —C(=O)($C_1$-$C_6$)alkyl, —C(=O)O($C_1$-$C_6$) alkyl, —OH and —O($C_1$-$C_6$) alkyl; wherein the halogen is preferably selected from —F, —Cl and —Br. According to some embodiments, $R^{10}$ is selected from —H and —$C_1$-$C_6$ alkyl. According to some embodiments, $R^{10}$ is —H. According to some embodiments, $R^{10}$ is —$C_1$-$C_6$ alkyl.

According to some embodiments, each $R^{10n}$ is independently selected from —H, —($C_1$-$C_6$)alkyl, substituted —($C_1$-$C_6$)alkyl, benzyl, substituted benzyl and t-butoxycarbonyl. According to some embodiments, $R^{10n}$ is selected from —H and —$C_1$-$C_6$ alkyl. According to some embodiments, $R^{10n}$ is —H. According to some embodiments, $R^{10n}$ is —$C_1$-$C_6$ alkyl.

According to some embodiments of Formula IB, $R^6$ may be selected from the ring systems shown in Table 2, supra, wherein $R^{10n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 2 may be substituted by $R^{10}$ substituents as $R^{10}$ is defined herein.

It will be understood that the non-bridgehead ring carbon ring atoms in (i), (ii), (iii), (iv) and (v) above (i.e., non-bridgehead ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —CH$_3$, cyclopropyl, —OCH$_3$, —F and —Cl.

According to some embodiments of compounds according to Formula IB, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ to the core of the spiropiperidine molecule is on a 6-membered ring portion of the 9-membered bicyclic heteroaryl or substituted 9-membered bicyclic heteroaryl.

According to some embodiments of compounds according to Formula IB, $R^6$ is:

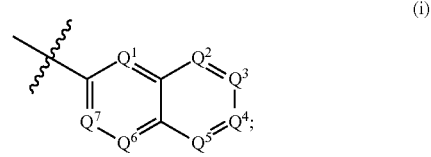

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{10}$. According to some embodiments, when $R^6$ is (i), $Q^2$ is N, and the remainder of $Q^1$, $Q^3$, $Q^4$, $Q^5$, $Q^6$ and $Q^7$ are C—$R^{10}$. According to some embodiments, when $R^6$ is (i), $Q^6$ is N, and $Q^1$, $Q^2$, $Q^3$, $Q^5$, $Q^5$ and $Q^7$ are C—$R^{10}$. According to some embodiments, when $R^6$ is (i), $Q^6$ is N, $Q^2$, $Q^3$, $Q^5$, $Q^5$ and $Q^7$ are CH, and $Q^1$ is C—$R^{10}$, wherein —$R^{10}$ is other than —H.

According to some embodiments of compounds according to Formula IB, $R^6$ is:

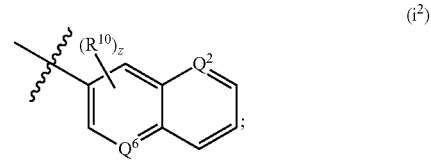

(i²)

wherein one of $Q^2$ and $Q^6$ is N, and the other of $Q^2$ and $Q^6$ is C—$R^{10}$, and z is an integer selected from 0, 1, 2 and 3. According to some embodiments of (i²), $Q^2$ is N, and $Q^6$ is C—$R^{10}$. According to some embodiments, $Q^6$ is N, and $Q^2$ is C—$R^{10}$. According to some embodiments, z is selected from 0, 1 and 2. According to some embodiments of (i²), z is 0 or 1. It will be understood that a z value of 0 is the equivalent of designating all $R^{10}$ that are bonded to the (i²) bicyclic heteroaryl at other than $Q^2$ and $Q^6$ as being —H.

According to some embodiments of compounds according to Formula IB, $R^6$ is:

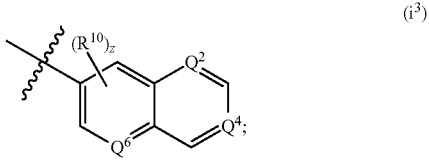
(i³)

wherein one or two of $Q^2$, $Q^4$ and $Q^6$ is N, and the remainder of $Q^2$, $Q^4$ and $Q^6$ are C—$R^1$, and z is an integer selected from 0, 1, 2 and 3.

According to some embodiments of (i³), z is 0, 1 or 2. According to some embodiments, z is 0 or 1. It will be understood that a z value of 0 is the equivalent of designating all $R^{10}$ that are bonded to the bicyclic heteroaryl moiety at other than $Q^2$, $Q^4$ or $Q^6$ as being —H.

According to some embodiments of (i³), $Q^2$ is N, and $Q^4$ and $Q^6$ are C—$R^{10}$. According to some embodiments of (i³), $Q^6$ is N, and $Q^2$ and $Q^4$ are C—$R^{10}$. According to some embodiments of (i³), $Q^4$ is N, and $Q^2$ and $Q^6$ are C—$R^{10}$. According to some embodiments of (i³), $Q^2$ is C—$R^{10}$, and $Q^4$ and $Q^6$ are N. According to some embodiments of (i³), $Q^6$ is C—$R^{10}$, and $Q^2$ and $Q^4$ are N. According to some embodiments of (i³), $Q^4$ is C—$R^{10}$, and $Q^2$ and $Q^6$ are N.

Another aspect of this application is directed to compounds of Formula IC:

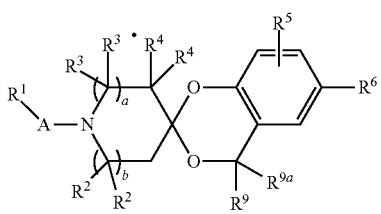
IC and salts thereof, e.g., pharmaceutically acceptable salts thereof, wherein:
A is selected from —C(=O)— and —SO$_2$—;
$R^1$ is selected from —(C$_1$-C$_7$) hydrocarbyl, substituted —(C$_1$-C$_7$) hydrocarbyl, 3-7 membered heterocyclyl, —C(=O)(C$_1$-C$_7$) hydrocarbyl, —NR$^7$R$^8$, —OR$^7$, —SR$^7$, —NR$^7$(OR$^8$) and —NR$^7$(SR$^8$);
a and b are independently selected from 0 and 1;
each $R^2$ is independently selected from —H and —(C$_1$-C$_4$) alkyl;
each $R^3$ is independently selected from —H and —(C$_1$-C$_4$) alkyl
each $R^4$ is independently selected from —H, —(C$_1$-C$_6$) alkyl, —OH, —O(C$_1$-C$_6$) alkyl, halogen, —CN, or the two geminal $R^4$ groups may together form a carbonyl group;
wherein one of the $R^3$ groups can optionally be structurally connected to one of the $R^2$ groups to form an alkylene bridge to produce a bicyclic ring; or
one of the $R^3$ groups can optionally be structurally connected to the $R^1$ group to form a 5 to 7 membered heterocyclyl ring fused to the 1-2 face of the piperidine ring; or
one of the $R^3$ groups can optionally be structurally connected to the $R^4$ group to form a 5-7 membered carbocyclic or heterocyclic ring fused to the 2-3 face of the piperidine ring;

$R^5$ is selected from —H, —C$_1$-C$_7$ hydrocarbyl, halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl and substituted 5-6 membered heteroaryl;
$R^6$ is selected from naphthyl, substituted naphthyl, 6-membered heteroaryl, substituted 6-membered heteroaryl, 9-10 membered bicyclic heteroaryl and substituted 9-10 membered bicyclic heteroaryl;
$R^7$ is selected from —H, —(C$_1$-C$_7$) hydrocarbyl, substituted —(C$_1$-C$_7$) hydrocarbyl, —C(=O)R$^b$, —(C$_1$-C$_6$) heteroalkyl, 6 membered aryl, 5-6 membered heteroaryl and 5-6 membered heterocyclyl, wherein R$^{8b}$ is selected from —H and —(C$_1$-C$_6$) alkyl;
$R^8$ is selected from —H and —(C$_1$-C$_6$) alkyl, wherein $R^7$ can optionally be structurally connected to $R^8$ to form a 5 to 7 membered heterocyclyl ring;
$R^{7a}$ is selected from —H, —(C$_1$-C$_7$) hydrocarbyl, substituted —(C$_1$-C$_7$) hydrocarbyl, C(=O)R$^{8b}$ and —(C$_1$-C$_6$) heteroalkyl, wherein R$^{8b}$ is selected from —H and —(C$_1$-C$_6$) alkyl;
$R^{8a}$ is selected from —H and —(C$_1$-C$_6$) alkyl, wherein $R^{7a}$ can optionally be structurally connected to $R^{8a}$ to form a 5 to 7 membered heterocyclyl ring; and
$R^9$ is selected from —H, —OH, —(C$_1$-C$_7$) hydrocarbyl, —O(C$_1$-C$_7$) hydrocarbyl and halogen; and
$R^{9a}$ is —H; or $R^9$ and $R^{9a}$ together form a carbonyl group.

According to some embodiments of compounds according to Formula IC, A is —C(=O)—. According to other embodiments, A is —SO$_2$—.

According to some embodiments, $R^1$ is selected from —(C$_1$-C$_7$) hydrocarbyl, substituted —(C$_1$-C$_7$) hydrocarbyl, 3-7 membered heterocyclyl, —NR$^7$R$^8$, —SR$^7$, —NR$^7$(OR$^8$) and —NR$^7$(SR$^8$).

According to some embodiments, $R^1$ is selected from —(C$_1$-C$_6$) alkyl, substituted —(C$_1$-C$_6$) alkyl, —(C$_3$-C$_6$) cycloalkyl, substituted —(C$_3$-C$_6$)cycloalkyl, benzyl, substituted benzyl, 5-6 membered heterocyclyl, —C(=O)(C$_1$-C$_6$) alkyl, —SR$^7$, —NR$^7$R$^8$ and —NR$^7$(OR$^8$).

According to some embodiments, $R^1$ is selected from —(C$_1$-C$_6$) alkyl, substituted —(C$_1$-C$_6$) alkyl, —(C$_3$-C$_6$) cycloalkyl, substituted —(C$_3$-C$_6$)cycloalkyl, benzyl, substituted benzyl, —SR$^7$, —NR$^7$R$^8$ and —NR$^7$(OR$^8$). According to some embodiments, $R^1$ is selected from —NR$^7$R$^8$ and —NR$^7$(OR$^8$). According to some embodiments, $R^1$ is —NR$^7$R$^8$. According to some embodiments, $R^1$ is —NR$^7$(OR$^8$).

According to other embodiments, $R^1$ is selected from —CH$_3$, —CH$_2$CH$_3$, —(CH$_2$)$_2$CH$_3$, —(CH$_2$)$_3$CH$_3$, —(CH$_2$)$_4$CH$_3$, —CH(CH$_3$)$_3$, —C(CH$_3$)$_3$, cyclopropyl, substituted cyclopropyl, cyclobutyl, substituted cyclobutyl, cyclopentyl, —C(=O)CH$_3$, —C(=O)CH$_2$CH$_3$, —NH—OH, —NH—OCH$_3$, —NH—OCH$_2$CH$_3$, —N(CH$_3$)—OCH$_3$, —NH$_2$, —NHCH$_3$, —NH—CH$_2$CH$_3$, —NH(CH$_2$)$_2$—CH$_3$, —NH(CH$_2$)$_3$—CH$_3$, —NH(CH$_2$)$_4$—CH$_3$, —NH(CH$_2$)$_5$—CH$_3$, —N(CH$_3$)$_2$, —N(Et)$_2$, —NH—CH(CH$_3$)$_2$, —NH—OCH$_2$CH$_3$, —NHSCH$_3$, —NHSCH$_2$CH$_3$, —SCH$_3$, —SCH$_2$CH$_3$, —SCH(CH$_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH$_2$—OCH$_3$, —(CH$_2$)$_2$—OCH$_3$ and —(CH$_2$)$_3$—OCH$_3$.

According to other embodiments, $R^1$ is selected from —$CH_3$, —$CH_2CH_3$, —$(CH_2)_2CH_3$, —$(CH_2)_3CH_3$, —$(CH_2)_4CH_3$, —$CH(CH_3)_2$, —$C(CH_3)_3$, cyclopropyl, substituted cyclopropyl, cyclobutyl, substituted cyclobutyl, cyclopentyl, —$C(=O)CH_3$, —$C(=O)CH_2CH_3$, —NH—OH, —NH—$OCH_3$, —NH—$OCH_2CH_3$, —$N(CH_3)$—$OCH_3$, —$NH_2$, —$NHCH_3$, —NH—$CH_2CH_3$, —NH$(CH_2)_2$—$CH_3$, —$NH(CH_2)_3$—$CH_3$, —$NH(CH_2)_4$—$CH_3$, —$NH(CH_2)_5$—$CH_3$, —$N(CH_3)_2$, —$N(Et)_2$, —NH—CH$(CH_3)_2$, —NH—$OCH_2CH_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —$(CH_2)_2$—$OCH_3$ and —$(CH_2)_3$—$OCH_3$.

According to some embodiments, when $R^1$ is substituted cyclopropyl, the cyclopropyl ring may be substituted with 1 or 2 substituents selected from —OH, —$CH_2OH$, —$C(=O)NH_2$, —$NH_2$, —$CH_3$, —CN and —$CF_3$.

According to some embodiments, when $R^1$ is tetrahydrofuranyl, it is tetrahydrofuran-2-yl or tetrahydrofuran-3-yl. According to some embodiments, when $R^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when $R^1$ is furanyl, it is 2-furanyl or 3-furanyl. According to some embodiments, when $R^1$ is substituted furanyl, it is 2-methylfuran-2-yl, 5-methylfuran-2-yl, or 2,5-dimethylfuran-2-yl.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetrahydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is furanyl, it is 2-furanyl or 3-furanyl. According to some embodiments, when $R^1$ is thiophenyl, it is 2-thiophenyl or 2-thiophenyl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl. According to some embodiments, when $R^1$ is oxazolyl, it is oxazol-1-yl, oxazol-2-one-1-yl oxazol-2-yl or oxazol-5-yl. According to some embodiments, when $R^1$ is isoxazolyl, it is isoxazol-1-yl, isoxazol-3-yl or isoxazol-5-yl. According to some embodiments, when $R^1$ is imidazolyl, it is imidazol-2-yl or imidazol-5-yl. According to some embodiments, when $R^1$ is thiazolyl, it is thiazol-2-yl or thiazol-5-yl. According to some embodiments, when $R^1$ is isothiazolyl, it is isothiazol-3-yl or isothiazol-5-yl. According to some embodiments, when $R^1$ is pyridyl, it is 2-pyridyl, 3-pyridyl, or 4-pyridyl. According to some embodiments, when $R^1$ is substituted quinolyl, it is quinolin-1-yl, quinolin-2-yl or quinolin-3-yl. According to some embodiments, when $R^1$ is substituted phenyl, it is 2-methylphenyl, 3-methylphenyl, 4-methylphenyl, or 2,5-dimethylphenyl. According to some embodiments, $R^1$ is selected from the moieties depicted in Table 1 and Table 1a, supra.

According to some embodiments, a is 1 and b is 0. According to some embodiments, a is 0 and b is 1. According to some embodiments, a and b are both 1.

According to some embodiments, each $R^2$ is —H.

According to some embodiments, each $R^3$ is —H.

According to some embodiments, each $R^4$ is independently selected from —H, —$(C_1-C_6)$ alkyl and halogen, wherein the halogen is preferably selected from —F, —Cl and —Br. According to some embodiments, one $R^4$ is halogen and the other $R^4$ is —H. According to some embodiments, each $R^4$ is —H.

According to some embodiments, $R^5$ is selected from —H, —$C_1-C_6$ alkyl, benzyl, halogen, —$(C_1-C_3)$ haloalkyl, —$OR^{7a}$, —CN, —$NR^{7a}R^{8a}$, —$C(=O)NR^{7a}R^{8a}$, —$C(=O)OR^{7a}$, 5-6 membered heteroaryl and substituted 5-6 membered heteroaryl.

According to some embodiments, $R^5$ is selected from —H, —$C_1-C_6$ alkyl, benzyl, —$C_1$, —F, —Br, —$(C_1-C_3)$ haloalkyl, —$OC_1-C_6$ alkyl, —CN, —$NHC_1-C_6$ alkyl, —$C(=O)NHC_1-C_6$ alkyl, —$C(=O)OC_1-C_6$ alkyl, 5-6 membered heteroaryl and substituted 5-6 membered heteroaryl.

According to some embodiments, $R^5$ is selected from —H, —$C_1-C_6$ alkyl, —F, —Cl, —Br, —$OC_1-C_6$ alkyl, —CN, —$NHC_1-C_6$ alkyl, —$C(=O)NHC_1-C_6$ alkyl and —$C(=O)OC_1-C_6$ alkyl. According to some embodiments, $R^5$ is selected from —H, —$C_1-C_6$ alkyl and halogen. According to some embodiments, $R^5$ is —H.

According to some embodiments, $R^7$ is selected from —H and —$C_1-C_6$ alkyl. According to some embodiments, $R^7$ is —H. According to some embodiments, $R^7$ is —$C_1-C_6$ alkyl.

According to some embodiments, $R^8$ is selected from —H and —$C_1-C_6$ alkyl. According to some embodiments, $R^8$ is —H. According to some embodiments, $R^8$ is —$C_1-C_6$ alkyl. According to some embodiments, $R^7$ and $R^8$ are —H.

According to some embodiments, $R^{7a}$ is selected from —H and —$C_1-C_6$ alkyl. According to some embodiments, $R^{7a}$ is —H. According to some embodiments, $R^{7a}$ is —$C_1-C_6$ alkyl.

According to some embodiments, $R^{8a}$ is selected from —H and —$C_1-C_6$ alkyl. According to some embodiments, $R^{8a}$ is —H. According to some embodiments, $R^{8a}$ is —$C_1-C_6$ alkyl. According to some embodiments, $R^{7a}$ and $R^{8a}$ are —H.

According to some embodiments, $R^{8b}$ is —$C_1-C_6$ alkyl. According to some embodiments, $R^{8b}$ is —H.

According to some embodiments, $R^9$ is selected from —H, —OH, —$(C_1-C_6)$ alkyl, —$O(C_1-C_6)$ alkyl, benzyl, —O-benzyl, —$C_1$ and —F and $R^{9a}$ is —H, or the geminal $R^9$ and $R^{9a}$ together form a carbonyl group. According to some embodiments, $R^9$ and $R^{9a}$ are —H.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1-C_6)$ alkyl, —$(C_3-C_6)$ cycloalkyl, —$(C_1-C_3)$ haloalkyl, —$O(C_1-C_3)$ haloalkyl, 5-6 membered heterocyclyl, —OH, —$O(C_1-C_6)$ alkyl, —$O(CH_2)_r$-(5-6 membered heterocyclyl), —$O(CH_2)_r$— $O(C_1-C_6)$ alkyl, —$O(CH_2)_r$—$NH(C_1-C_6$ alkyl$)_2$, —$NH_2$, —CN, —$NH(C_1-C_6)$ alkyl, —$N(C_1-C_6$ alkyl$)_2$, —$NH(CH_2)_r$—$O(C_1-C_6)$alkyl, —$NH(CH_2)_r$—$N(C_1-C_6$ alkyl$)_2$, —$C(=O)NH_2$, —$C(=O)NH(C_1-C_6)$ alkyl and —$C(=O)N(C_1-C_6$ alkyl$)_2$; wherein r is an integer selected independently from 1, 2, 3 and 4.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —$NH_2$, —CN, —NH($C_1$-$C_6$) alkyl, —N($C_1$-$C_6$ alkyl)$_2$, —C(=O)$NH_2$, —C(=O)NH($C_1$-$C_6$) alkyl and —C(=O)N($C_1$-$C_6$ alkyl)$_2$.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br.

According to some embodiments, $R^6$ is selected from 9-10 membered bicyclic heteroaryl and substituted 9-10 membered bicyclic heteroaryl. According to some embodiments, $R^6$ is selected from:

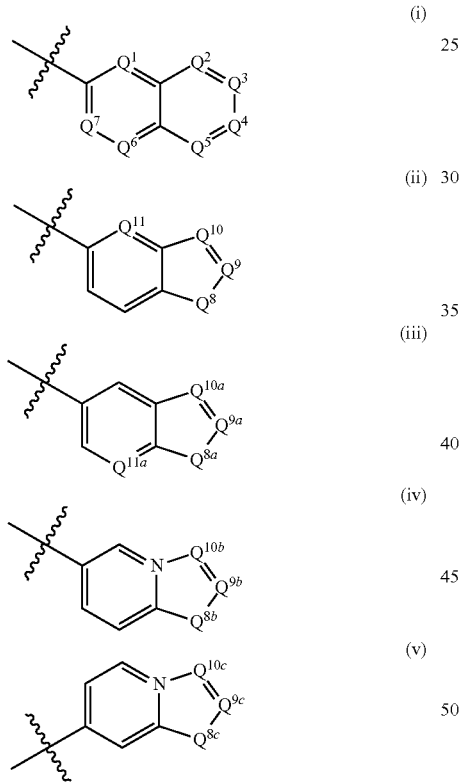

wherein, when $R^6$ is (i), $Q^1$, $Q^2$, $Q^3$, $Q^4$, $Q^5$, $Q^6$ and $Q^7$ are independently selected from N and C—$R^{10}$, provided that 0, 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$; when $R^6$ is (ii), $Q^8$ is selected from O, S and N—$R^{10n}$ and $Q^9$, $Q^{10}$ and $Q^{11}$ are independently selected from N and C—$R^{10}$;

when $R^6$ is (iii), $Q^{8a}$ is selected from O, S and N—$R^{10n}$, $Q^{9a}$, $Q^{10A}$ and $Q^{11a}$ are independently selected from N and C—$R^{10}$;

when $R^6$ is (iv), $Q^{8b}$ is selected from O, S and N—$R^{10n}$; and $Q^{9b}$ and $Q^{10b}$ are independently selected from N and C—$R^{10}$; and when $R^6$ is (v), $Q^{8a}$ is selected from O, S and N—$R^{10n}$; and $Q^{9C}$ and $Q^{10c}$ are independently selected from N and C—$R^{10}$;

and wherein each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$)haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —O($CH_2$)$_r$—NH($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)O($C_1$-$C_6$)alkyl, —C(=O)$NH_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —$CO_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, $R^6$ is selected from:

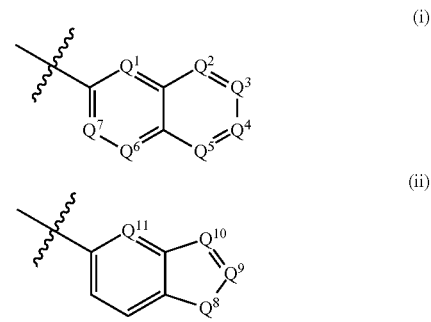

wherein
$Q^1$ and $Q^{11}$ are C—$R^{10n}$;
$Q^2$, $Q^3$, $Q^4$, $Q^5$, $Q^6$, $Q^7$, $Q^9$, and $Q^{10}$ are independently selected from N and C—$R^{10}$, provided that 0, 1, 2 or 3 of $Q^2$, $Q^3$, $Q^4$, $Q^5$, $Q^6$ and $Q^7$ are N, and the remainder of $Q^2$, $Q^3$, $Q^4$, $Q^5$, $Q^6$ and $Q^7$ are C—$R^{10}$;
$Q^8$ is selected from O, S and N—$R^{10n}$;
and wherein each $R^{10z}$ is independently selected from halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(O)O($C_1$-$C_6$alkyl), —C(=O)$NH_2$, —C(=O)NH($C_1$-$C_6$)alkyl and —C(=O)N($C_1$-$C_6$ alkyl)$_2$; wherein r is an integer selected independently from 1, 2, 3 and 4;

each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —$NH_2$, —CN, —NH ($C_1$-$C_6$) alkyl, —N($C_1$-$C_6$ alkyl)$_2$, —NH($CH_2$)$_r$—O ($C_1$-$C_6$)alkyl, —NH($CH_2$)$_r$—N($C_1$-$C_6$ alkyl)$_2$, —C(O) O($C_1$-$C_6$alkyl), —C(=O)$NH_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —$CO_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, each $R^{10z}$ is independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, each $R^{10z}$ is independently selected from —$C_1$-$C_6$ alkyl, —($C_3$-$C_6$) cycloalkyl, and —O($C_1$-$C_6$) alkyl. According to some embodiments, each $R^{10z}$ is independently selected from —$C_1$-$C_6$ alkyl.

According to some embodiments, each $R^{10}$ is independently selected from —H, halogen, —($C_1$-$C_6$) alkyl, —($C_3$-$C_6$) cycloalkyl, —C(=O)($C_1$-$C_6$)alkyl, —C(=O)O($C_1$-$C_6$) alkyl, —OH and —O($C_1$-$C_6$) alkyl; wherein the halogen is preferably selected from —F, —Cl and —Br. According to some embodiments, $R^{10}$ is selected from —H and —$C_1$-$C_6$ alkyl. According to some embodiments, $R^{10}$ is —H. According to some embodiments, $R^{10}$ is —$C_1$-$C_6$ alkyl.

According to some embodiments, each $R^{10n}$ is independently selected from —H, —($C_1$-$C_6$)alkyl, substituted —($C_1$-$C_6$)alkyl, benzyl, substituted benzyl and t-butoxycarbonyl. According to some embodiments, $R^{10n}$ is selected from —H and —$C_1$-$C_6$ alkyl. According to some embodiments, $R^{10n}$ is —H. According to some embodiments, $R^{10n}$ is —$C_1$-$C_6$ alkyl.

According to some embodiments of Formula IC, $R^6$ may be selected from the ring systems shown in Table 2, supra, wherein $R^{10n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 2 may be substituted by $R^{10}$ substituents as $R^{10}$ is defined herein.

It will be understood that the non-bridgehead ring carbon ring atoms in (i), (ii), (iii), (iv) and (v) above (i.e., non-bridgehead ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, cyclopropyl, —$OCH_3$, —F and —Cl.

According to some embodiments of compounds according to Formula IC, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ to the core of the spiropiperidine molecule is on a 6-membered ring portion of the 9-membered bicyclic heteroaryl or substituted 9-membered bicyclic heteroaryl.

According to some embodiments of compounds according to Formula IC, $R^6$ is:

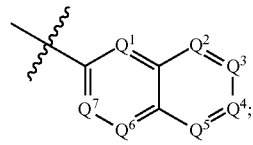

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{10}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{10}$. According to some embodiments, when $R^6$ is (i), $Q^2$ is N, and the remainder of $Q^1$, $Q^3$, $Q^4$, $Q^5$, $Q^6$ and $Q^7$ are C—$R^{10}$. According to some embodiments, when $R^6$ is (i), $Q^6$ is N, and $Q^1$, $Q^2$, $Q^3$, $Q^5$, $Q^5$ and $Q^7$ are C—$R^{10}$. According to some embodiments, when $R^6$ is (i), $Q^6$ is N, $Q^2$, $Q^3$, $Q^5$, $Q^5$ and $Q^7$ are CH, and $Q^1$ is C—$R^{10}$, wherein —$R^{10}$ is other than —H.

According to some embodiments of compounds according to Formula IC, $R^6$ is:

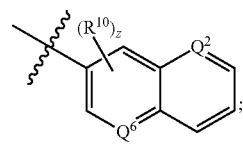

wherein one of $Q^2$ and $Q^6$ is N, and the other of $Q^2$ and $Q^6$ is C—$R^{10}$, and z is an integer selected from 0, 1, 2 and 3. According to some embodiments of ($i^2$), $Q^2$ is N, and $Q^6$ is C—$R^{10}$. According to some embodiments, $Q^6$ is N, and $Q^2$ is C—$R^{10}$. According to some embodiments, z is selected from 0, 1 and 2. According to some embodiments of ($i^2$), z is 0 or 1. It will be understood that a z value of 0 is the equivalent of designating all $R^{10}$ that are bonded to the ($i^2$) bicyclic heteroaryl at other than $Q^2$ and $Q^6$ as being —H.

According to some embodiments of compounds according to Formula IC, $R^6$ is:

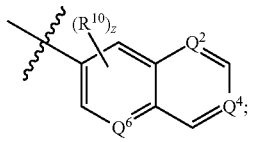

wherein one or two of $Q^2$, $Q^4$ and $Q^6$ is N, and the remainder of $Q^2$, $Q^4$ and $Q^6$ are C—$R^1$, and z is an integer selected from 0, 1, 2 and 3.

According to some embodiments of ($i^3$), z is 0, 1 or 2. According to some embodiments, z is 0 or 1. It will be understood that a z value of 0 is the equivalent of designating all $R^{10}$ that are bonded to the bicyclic heteroaryl moiety at other than $Q^2$, $Q^4$ or $Q^6$ as being —H.

According to some embodiments of ($i^3$), $Q^2$ is N, and $Q^4$ and $Q^6$ are C—$R^{10}$. According to some embodiments of ($i^3$), $Q^6$ is N, and $Q^2$ and $Q^4$ are C—$R^{10}$. According to some embodiments of ($i^3$), $Q^4$ is N, and $Q^2$ and $Q^6$ are C—$R^{10}$.

According to some embodiments of (i³), Q² is C—R¹⁰, and Q⁴ and Q⁶ are N. According to some embodiments of (i³), Q⁶ is C—R¹⁰, and Q² and Q⁴ are N. According to some embodiments of (i³), Q⁴ is C—R¹⁰, and Q² and Q⁶ are N.

Another aspect of this application is directed to compounds of Formula ID:

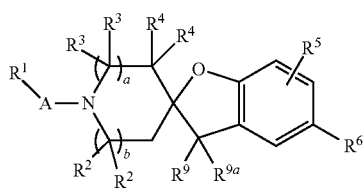

and salts thereof, e.g., pharmaceutically acceptable salts thereof, wherein:

A is selected from —C(=O)— and —SO₂—;

$R^1$ is selected from —($C_1$-$C_7$) hydrocarbyl, substituted —($C_1$-$C_7$) hydrocarbyl, 3-7 membered heterocyclyl, —C(=O)($C_1$-$C_7$) hydrocarbyl, —NR⁷R⁸, —OR⁷, —SR⁷, —N R⁷(OR⁸) and —N R⁷(SR⁸);

a and b are independently selected from 0 and 1;

each $R^2$ is independently selected from —H and —($C_1$-$C_4$) alkyl;

each $R^3$ is independently selected from —H and —($C_1$-$C_4$) alkyl each $R^4$ is independently selected from —H, —($C_1$-$C_6$) alkyl, —OH, —O($C_1$-$C_6$) alkyl, halogen, —CN, or the two geminal $R^4$ groups may together form a carbonyl group;

wherein one of the $R^3$ groups can optionally be structurally connected to one of the $R^2$ groups to form an alkylene bridge to produce a bicyclic ring; or one of the $R^3$ groups can optionally be structurally connected to the $R^1$ group to form a 5 to 7 membered heterocyclyl ring fused to the 1-2 face of the piperidine ring; or one of the $R^3$ groups can optionally be structurally connected to the $R^4$ group to form a 5-7 membered carbocyclic or heterocyclic ring fused to the 2-3 face of the piperidine ring;

$R^5$ is selected from —H, —$C_1$-$C_7$ hydrocarbyl, halogen, —($C_1$-$C_3$) haloalkyl, —OR⁷ᵃ, —CN, —NR⁷ᵃR⁸ᵃ, —O(CH₂)ₙNR⁷ᵃR⁸ᵃ, —O(CH₂)ₙOR⁸ᵃ, —NR⁸ᵃ(CH₂)ₙNR⁷ᵃR⁸ᵃ, —NR⁸ᵃ(CH₂)ₙOR⁸ᵃ, —C(=O)NR⁷ᵃR⁸ᵃ, —C(=O)OR⁷ᵃ, 5-6 membered heteroaryl and substituted 5-6 membered heteroaryl;

$R^6$ is selected from naphthyl, substituted naphthyl, 6-membered heteroaryl, substituted 6-membered heteroaryl, 9-10 membered bicyclic heteroaryl and substituted 9-10 membered bicyclic heteroaryl;

$R^7$ is selected from —H, —($C_1$-$C_7$) hydrocarbyl, substituted —($C_1$-$C_7$) hydrocarbyl, —C(=O)R⁸ᵇ, —($C_1$-$C_6$) heteroalkyl, 6 membered aryl, 5-6 membered heteroaryl and 5-6 membered heterocyclyl, wherein R⁸ᵇ is selected from —H and —($C_1$-$C_6$) alkyl;

$R^8$ is selected from —H, 3-7 membered heterocycloalkyl, and —($C_1$-$C_6$) alkyl, wherein R⁷ can optionally be structurally connected to R⁸ to form a 5 to 7 membered heterocyclyl ring;

$R^{7a}$ is selected from —H, —($C_1$-$C_7$) hydrocarbyl, substituted —($C_1$-$C_7$) hydrocarbyl, C(=O)R⁸ᵇ and —($C_1$-$C_6$) heteroalkyl, wherein R⁸ᵇ is selected from —H and —($C_1$-$C_6$) alkyl;

$R^{8a}$ is selected from —H and —($C_1$-$C_6$) alkyl, wherein R⁷ᵃ can optionally be structurally connected to R⁸ᵃ to form a 5 to 7 membered heterocyclyl ring; and $R^9$ is selected from —H, —OH, —($C_1$-$C_7$) hydrocarbyl, —O($C_1$-$C_7$) hydrocarbyl and halogen; and $R^{9a}$ is —H; or R⁹ and R⁹ᵃ together form a carbonyl group.

According to some embodiments of compounds according to Formula ID, A is —C(=O)—. According to other embodiments, A is —SO₂—.

According to some embodiments, $R^1$ is selected from —($C_1$-$C_7$) hydrocarbyl, substituted —($C_1$-$C_7$) hydrocarbyl, 3-7 membered heterocyclyl, —NR⁷R⁸, —SR⁷, —NR⁷(OR⁸) and —NR⁷(SR⁸).

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, benzyl, substituted benzyl, 5-6 membered heterocyclyl, —C(=O)($C_1$-$C_6$) alkyl, —SR⁷, —NR⁷R⁸ and —NR⁷(OR⁸).

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, benzyl, substituted benzyl, —SR⁷, —NR⁷R⁸ and —NR⁷(OR⁸). According to some embodiments, $R^1$ is selected from —NR⁷R⁸ and —NR⁷(OR⁸). According to some embodiments, $R^1$ is —NR⁷R⁸. According to some embodiments, $R^1$ is —NR⁷(OR⁸).

According to other embodiments, $R^1$ is selected from —CH₃, —CH₂CH₃, —(CH₂)₂CH₃, —(CH₂)₃CH₃, —(CH₂)₄CH₃, —CH(CH₃)₃, —C(CH₃)₃, cyclopropyl, substituted cyclopropyl, cyclobutyl, substituted cyclobutyl, cyclopentyl, —C(=O)CH₃, —C(=O)CH₂CH₃, —NH—OH, —NH—OCH₃, —NH—OCH₂CH₃, —N(CH₃)—OCH₃, —NH₂, —NHCH₃, —NH—CH₂CH₃, —NH(CH₂)₂—CH₃, —NH(CH₂)₃—CH₃, —NH(CH₂)₄—CH₃, —NH(CH₂)₅—CH₃, —N(CH₃)₂, —N(Et)₂, —NH—CH(CH₃)₂, —NH—OCH₂CH₃, —NHSCH₃, —NHSCH₂CH₃, —SCH₃, —SCH₂CH₃, —SCH(CH₃)₂, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH₂—OCH₃, —(CH₂)₂—OCH₃ and —(CH₂)₃—OCH₃.

According to other embodiments, $R^1$ is selected from —CH₃, —CH₂CH₃, —(CH₂)₂CH₃, —(CH₂)₃CH₃, —(CH₂)₄CH₃, —CH(CH₃)₃, —C(CH₃)₃, cyclopropyl, substituted cyclopropyl, cyclobutyl, substituted cyclobutyl, cyclopentyl, —C(=O)CH₃, —C(=O)CH₂CH₃, —NH—OH, —NH—OCH₃, —NH—OCH₂CH₃, —N(CH₃)—OCH₃, —NH₂, —NHCH₃, —NH—CH₂CH₃, —NH(CH₂)₂—CH₃, —NH(CH₂)₃—CH₃, —NH(CH₂)₄—CH₃, —NH(CH₂)₅—CH₃, —N(CH₃)₂, —N(Et)₂, —NH—CH(CH₃)₂, —NH—OCH₂CH₃, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH₂—OCH₃, —(CH₂)₂—OCH₃ and —(CH₂)₃—OCH₃.

According to some embodiments, when $R^1$ is substituted cyclopropyl, the cyclopropyl ring may be substituted with 1 or two substituents selected from —OH, —CH₂OH, —C(=O)NH₂, —NH₂, —CH₃, —CN and —CF₃.

According to some embodiments, when $R^1$ is tetrahydrofuranyl, it is tetrahydrofuran-2-yl or tetrahydrofuran-3-yl. According to some embodiments, when $R^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when $R^1$ is furanyl, it is 2-furanyl or 3-furanyl. According to some embodiments, when $R^1$ is substituted furanyl, it is 2-methylfuran-2-yl, 5-methylfuran-2-yl, or 2,5-dimethylfuran-2-yl.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetrahydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is furanyl, it is 2-furanyl or 3-furanyl. According to some embodiments, when $R^1$ is thiophenyl, it is 2-thiophenyl or 2-thiophenyl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl. According to some embodiments, when $R^1$ is oxazolyl, it is oxazol-1-yl, oxazol-2-one-1-yl oxazol-2-yl or oxazol-5-yl. According to some embodiments, when $R^1$ is isoxazolyl, it is isoxazol-1-yl, isoxazol-3-yl or isoxazol-5-yl. According to some embodiments, when $R^1$ is imidazolyl, it is imidazol-2-yl or imidazol-5-yl. According to some embodiments, when $R^1$ is thiazolyl, it is thiazol-2-yl or thiazol-5-yl. According to some embodiments, when $R^1$ is isothiazolyl, it is isothiazol-3-yl or isothiazol-5-yl. According to some embodiments, when $R^1$ is pyridyl, it is 2-pyridyl, 3-pyridyl, or 4-pyridyl. According to some embodiments, when $R^1$ is substituted quinolyl, it is quinolin-1-yl, quinolin-2-yl or quinolin-3-yl. According to some embodiments, when $R^1$ is substituted phenyl, it is 2-methylphenyl, 3-methylphenyl, 4-methylphenyl, or 2,5-dimethylphenyl. According to some embodiments, $R^1$ is selected from the moieties depicted in Table 1 and Table 1a, supra.

According to some embodiments, a is 1 and b is 0. According to some embodiments, a is 0 and b is 1. According to some embodiments, a and b are both 1.

According to some embodiments, each $R^2$ is —H.

According to some embodiments, each $R^3$ is —H.

According to some embodiments, each $R^4$ is independently selected from —H, —$(C_1$-$C_6)$ alkyl and halogen, wherein the halogen is preferably selected from —F, —Cl and —Br. According to some embodiments, one $R^4$ is halogen and the other $R^4$ is —H. According to some embodiments, each $R^4$ is —H.

According to some embodiments of compounds according to Formula ID, $R^5$ is selected from —H, —$C_1$-$C_7$ hydrocarbyl, halogen, —$(C_1$-$C_3)$ haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —$C(=O)NR^{7a}R^{8a}$, —$C(=O)OR^{7a}$, 5-6 membered heteroaryl and substituted 5-6 membered heteroaryl;

$R^5$ is selected from —H, —$C_1$-$C_6$ alkyl, benzyl, halogen, —$(C_1$-$C_3)$ haloalkyl, —$OR^{7a}$, —CN, —$NR^{7a}R^{8a}$, —$C(=O)NR^{7a}R^{8a}$, —$C(=O)OR^{7a}$, 5-6 membered heteroaryl and substituted 5-6 membered heteroaryl.

According to some embodiments, $R^5$ is selected from —H, —$C_1$-$C_6$ alkyl, benzyl, —$C_1$, —F, —Br, —$(C_1$-$C_3)$ haloalkyl, —$OC_1$-$C_6$ alkyl, —CN, —$NHC_1$-$C_6$ alkyl, —$C(=O)NHC_1$-$C_6$ alkyl, —$C(=O)OC_1$-$C_6$ alkyl, 5-6 membered heteroaryl and substituted 5-6 membered heteroaryl.

According to some embodiments, $R^5$ is selected from —H, —$C_1$-$C_6$ alkyl, —F, —Cl, —Br, —$OC_1$-$C_6$ alkyl, —CN, —$NHC_1$-$C_6$ alkyl, —$C(=O)NHC_1$-$C_6$ alkyl and —$C(=O)OC_1$-$C_6$ alkyl. According to some embodiments, $R^5$ is selected from —H, —$C_1$-$C_6$ alkyl and halogen. According to some embodiments, $R^5$ is —H.

According to some embodiments, $R^7$ is selected from —H and —$C_1$-$C_6$ alkyl. According to some embodiments, $R^7$ is —H. According to some embodiments, $R^7$ is —$C_1$-$C_6$ alkyl.

According to some embodiments, $R^8$ is selected from —H and —$C_1$-$C_6$ alkyl. According to some embodiments, $R^8$ is —H. According to some embodiments, $R^8$ is —$C_1$-$C_6$ alkyl. According to some embodiments, $R^7$ and $R^8$ are —H.

According to some embodiments, $R^{7a}$ is selected from —H and —$C_1$-$C_6$ alkyl. According to some embodiments, $R^{7a}$ is —H. According to some embodiments, $R^{7a}$ is —$C_1$-$C_6$ alkyl.

According to some embodiments, $R^{8a}$ is selected from —H and —$C_1$-$C_6$ alkyl. According to some embodiments, $R^{8a}$ is —H. According to some embodiments, $R^{8a}$ is —$C_1$-$C_6$ alkyl. According to some embodiments, $R^{7a}$ and $R^{8a}$ are —H.

According to some embodiments, $R^{8b}$ is —$C_1$-$C_6$ alkyl. According to some embodiments, $R^{8b}$ is —H.

According to some embodiments, $R^9$ is selected from —H, —OH, —$(C_1$-$C_6)$ alkyl, —$O(C_1$-$C_6)$ alkyl, benzyl, —O-benzyl, —$C_1$ and —F and $R^{9a}$ is —H, or the geminal $R^9$ and $R^{9a}$ together form a carbonyl group. According to some embodiments, $R^9$ and $R^{9a}$ are —H.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —$(C_3$-$C_6)$ cycloalkyl, —$(C_1$-$C_3)$ haloalkyl, —$O(C_1$-$C_3)$ haloalkyl, 5-6 membered heterocyclyl, —OH, —$O(C_1$-$C_6)$ alkyl, —$O(CH_2)_r$-(5-6 membered heterocyclyl), —$O(CH_2)_r$— $O(C_1$-$C_6)$ alkyl, —$O(CH_2)_r$—$NH(C_1$-$C_6$ alkyl)$_2$, —$NH_2$, —CN, —$NH(C_1$-$C_6)$ alkyl, —$N(C_1$-$C_6$ alkyl)$_2$, —$NH(CH_2)_r$—$O(C_1$-$C_6)$alkyl, —$NH(CH_2)_r$—$N(C_1$-$C_6$ alkyl)$_2$, —$C(=O)NH_2$, —$C(=O)NH(C_1$-$C_6)$ alkyl and —$C(=O)N(C_1$-$C_6$ alkyl)$_2$; wherein r is an integer selected independently from 1, 2, 3 and 4.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —$(C_3$-$C_6)$ cycloalkyl, —$(C_1$-$C_3)$ haloalkyl, —$O(C_1$-$C_3)$ haloalkyl, 5-6 membered heterocyclyl, —OH, —$O(C_1$-$C_6)$ alkyl, —$NH_2$, —CN, —$NH(C_1$-$C_6)$ alkyl, —$N(C_1$-$C_6$ alkyl)$_2$, —$C(=O)NH_2$, —$C(=O)NH(C_1$-$C_6)$ alkyl and —$C(=O)N(C_1$-$C_6$ alkyl)$_2$.

According to some embodiments, when $R^6$ is substituted naphthyl, substituted 6-membered heteroaryl or substituted bicyclic heteroaryl, the naphthyl or 6-membered heteroaryl or bicyclic heteroaryl is substituted with 1, 2 or 3 substituents independently selected from halogen, —$(C_1$-$C_6)$ alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br.

According to some embodiments, $R^6$ is selected from 9-10 membered bicyclic heteroaryl and substituted 9-10 membered bicyclic heteroaryl. According to some embodiments, $R^6$ is selected from:

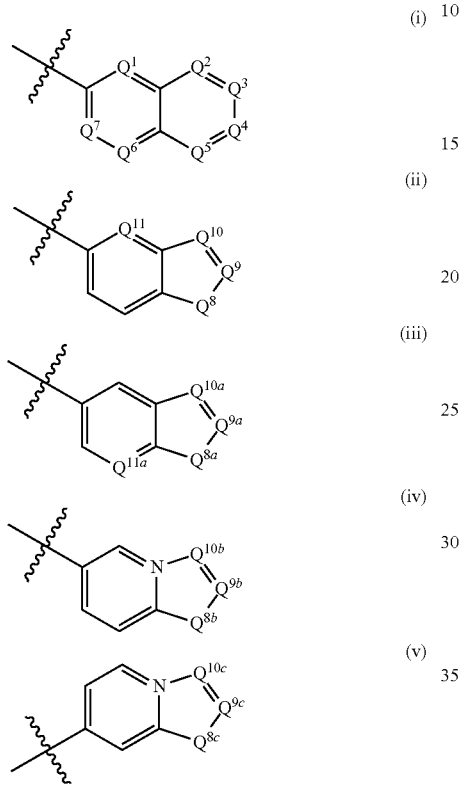

wherein, when $R^6$ is (i), $Q^1$, $Q^2$, $Q^3$, $Q^4$, $Q^5$, $Q^6$ and $Q^7$ are independently selected from N and C—$R^{10}$, provided that 0, 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^4$, $Q^6$ and $Q^7$ are C—$R^{10}$;

when $R^6$ is (ii), $Q^8$ is selected from O, S and N—$R^{10n}$ and $Q^9$, $Q^{10}$ and $Q^{11}$ are independently selected from N and C—$R^{10}$;

when $R^6$ is (iii), $Q^{8a}$ is selected from O, S and N—$R^{10n}$, $Q^{9a}$, $Q^{10A}$ and $Q^{11a}$ are independently selected from N and C—$R^{10}$;

when $R^6$ is (iv), $Q^{8b}$ is selected from O, S and N—$R^{10n}$; and $Q^{9b}$ and $Q^{10b}$ are independently selected from N and C—$R^{10}$; and when $R^6$ is (v), $Q^{8a}$ is selected from O, S and N—$R^{10n}$; and $Q^{9C}$ and $Q^{10c}$ are independently selected from N and C—$R^{10}$;

and wherein each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$)haloalkyl, -5-6 membered heterocyclyl, —OH, —O($C_1$-$C_6$) alkyl, —O($CH_2$)$_r$-(5-6 membered heterocyclyl), —O($CH_2$)$_r$— O($C_1$-$C_6$)alkyl, —O($CH_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)O($C_1$-$C_6$)alkyl, —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, $R^6$ is selected from:

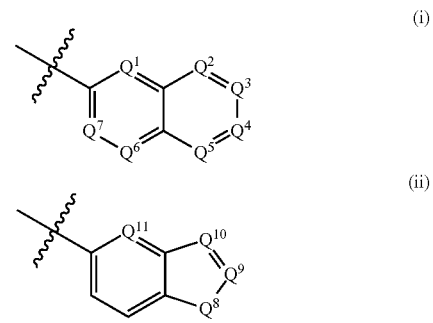

wherein $Q^1$ and $Q^{11}$ are C—$R^{10z}$;

$Q^2$, $Q^3$, $Q^4$, $Q^5$, $Q^6$, $Q^7$, $Q^9$, and $Q^{10}$ are independently selected from N and C—$R^{10}$, provided that 0, 1, 2 or 3 of $Q^2$, $Q^3$, $Q^4$, $Q^5$, $Q^6$ and $Q^7$ are N, and the remainder of $Q^2$, $Q^3$, $Q^4$, $Q^5$, $Q^6$ and $Q^7$ are C—$R^{10}$;

$Q^8$ is selected from O, S and N—$R^{10n}$;

and wherein each $R^{10z}$ is independently selected from halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(O)O($C_1$-$C_6$alkyl), —C(=O)NH$_2$, —C(=O)NH($C_1$-$C_6$)alkyl and —C(=O)N($C_1$-$C_6$ alkyl)$_2$; wherein r is an integer selected independently from 1, 2, 3 and 4;

each $R^{10}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$)alkyl, —O($CH_2$)$_r$—NH($C_1$-$C_6$ alkyl)$_2$, —NH$_2$, —CN, —NH($C_1$-$C_6$) alkyl, —N($C_1$-$C_6$ alkyl)$_2$, —NH($CH_2$)$_r$—O($C_1$-$C_6$)alkyl, —NH($CH_2$)$_r$—N($C_1$-$C_6$ alkyl)$_2$, —C(O)O($C_1$-$C_6$alkyl), —C(=O)NH$_2$, —C(=O)NH($C_1$-$C_6$) alkyl and —C(=O)N($C_1$-$C_6$ alkyl)$_2$; wherein r is an integer selected independently from 1, 2, 3 and 4; and each $R^{10n}$ is independently selected from —H, —($C_1$-$C_7$) hydrocarbyl, substituted —($C_1$-$C_7$) hydrocarbyl, —CO$_2$($C_1$-$C_7$) hydrocarbyl, —C(=O)($C_1$-$C_7$) hydrocarbyl and substituted —C(=O)($C_1$-$C_7$) hydrocarbyl.

According to some embodiments, each $R^{10z}$ is independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br. According to some embodiments, each $R^{10z}$ is independently selected from —$C_1$-$C_6$ alkyl, —($C_3$-$C_6$) cycloalkyl, and —O($C_1$-$C_6$) alkyl. According to some embodiments, each $R^{10z}$ is independently selected from —$C_1$-$C_6$ alkyl.

According to some embodiments, each $R^{10}$ is independently selected from —H, halogen, —$(C_1-C_6)$ alkyl, —$(C_3-C_6)$ cycloalkyl, —$C(=O)(C_1-C_6)$alkyl, —$C(=O)O(C_1-C_6)$ alkyl, —OH and —$O(C_1-C_6)$ alkyl; wherein the halogen is preferably selected from —F, —Cl and —Br. According to some embodiments, $R^{10}$ is selected from —H and —$C_1-C_6$ alkyl. According to some embodiments, $R^{10}$ is —H. According to some embodiments, $R^{10}$ is —$C_1-C_6$ alkyl.

According to some embodiments, each $R^{10n}$ is independently selected from —H, —$(C_1-C_6)$alkyl, substituted —$(C_1-C_6)$alkyl, benzyl, substituted benzyl and t-butoxycarbonyl. According to some embodiments, $R^{10n}$ is selected from —H and —$C_1-C_6$ alkyl. According to some embodiments, $R^{10n}$ is —H. According to some embodiments, $R^{10n}$ is —$C_1-C_6$ alkyl.

According to some embodiments of Formula ID, $R^6$ may be selected from the ring systems shown in Table 2, supra, wherein $R^{10n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 2 may be substituted by $R^{10}$ substituents as $R^{10}$ is defined herein.

It will be understood that the non-bridgehead ring carbon ring atoms in (i), (ii), (iii), (iv) and (v) above (i.e., non-bridgehead ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —$(C_1-C_3)$ alkyl, —$O(C_1-C_3)$alkyl and halogen. According to some embodiments, one of these ring carbon ring atoms is substituted with a substituent selected from —OH, —$CH_3$, cyclopropyl, —$OCH_3$, —F and —Cl.

According to some embodiments of compounds according to Formula ID, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ to the core of the spiropiperidine molecule is on a 6-membered ring portion of the 9-membered bicyclic heteroaryl or substituted 9-membered bicyclic heteroaryl.

According to some embodiments of compounds according to Formula ID, $R^6$ is:

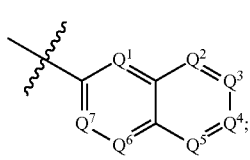

(i)

wherein 1 or 2 of $Q^1, Q^2, Q^3, Q^4, Q^5, Q^6$ and $Q^7$ are N, and the remainder of $Q^1, Q^2, Q^3, Q^4, Q^5, Q^6$ and $Q^7$ are C—$R^{10}$. According to some embodiments, when $R^6$ is (i), one of $Q^1, Q^2, Q^3, Q^4, Q^5, Q^6$ and $Q^7$ is N, and the remainder of $Q^1, Q^2, Q^3, Q^4, Q^5, Q^6$ and $Q^7$ are C—$R^{10}$. According to some embodiments, when $R^6$ is (i), $Q^2$ is N, and the remainder of $Q^1, Q^3, Q^4, Q^5, Q^6$ and $Q^7$ are C—$R^{10}$. According to some embodiments, when $R^6$ is (i), $Q^6$ is N, and $Q^1, Q^2, Q^3, Q, Q^5$ and $Q^7$ are C—$R^{10}$. According to some embodiments, when $R^6$ is (i), $Q^6$ is N, $Q^2, Q^3, Q^5, Q^5$ and $Q^7$ are CH, and $Q^1$ is C—$R^{10}$, wherein —$R^{10}$ is other than —H.

According to some embodiments of compounds according to Formula ID, $R^6$ is:

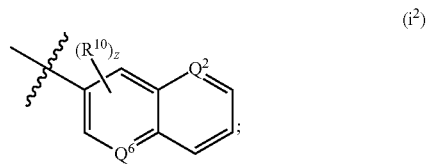

(i²)

wherein one of $Q^2$ and $Q^6$ is N, and the other of $Q^2$ and $Q^6$ is C—$R^{10}$, and z is an integer selected from 0, 1, 2 and 3. According to some embodiments of (i²), $Q^2$ is N, and $Q^6$ is C—$R^{10}$. According to some embodiments, $Q^6$ is N, and $Q^2$ is C—$R^{10}$. According to some embodiments, z is selected from 0, 1 and 2. According to some embodiments of (i²), z is 0 or 1. It will be understood that a z value of 0 is the equivalent of designating all $R^{10}$ that are bonded to the (i²) bicyclic heteroaryl at other than $Q^2$ and $Q^6$ as being —H.

According to some embodiments of compounds according to Formula ID, $R^6$ is:

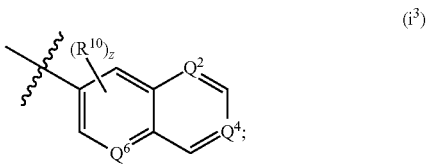

(i³)

wherein one or two of $Q^2, Q^4$ and $Q^6$ is N, and the remainder of $Q^2, Q^4$ and $Q^6$ are C—$R^{10}$, and z is an integer selected from 0, 1, 2 and 3.

According to some embodiments of (i³), z is 0, 1 or 2. According to some embodiments, z is 0 or 1. It will be understood that a z value of 0 is the equivalent of designating all $R^{10}$ that are bonded to the bicyclic heteroaryl moiety at other than $Q^2, Q^4$ or $Q^6$ as being —H.

According to some embodiments of (i³), $Q^2$ is N, and $Q^4$ and $Q^6$ are C—$R^{10}$. According to some embodiments of (i³), $Q^6$ is N, and $Q^2$ and $Q^4$ are C—$R^{10}$. According to some embodiments of (i³), $Q^4$ is N, and $Q^2$ and $Q^6$ are C—$R^{10}$. According to some embodiments of (i³), $Q^2$ is C—$R^{10}$, and $Q^4$ and $Q^6$ are N. According to some embodiments of (i³), $Q^6$ is C—$R^{10}$, and $Q^2$ and $Q^4$ are N. According to some embodiments of (i³), $Q^4$ is C—$R^{10}$, and $Q^2$ and $Q^6$ are N.

Another aspect of this application is directed to compounds of Formula IE:

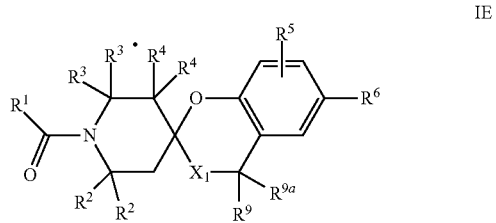

IE and salts thereof, e.g., pharmaceutically acceptable salts thereof, wherein:

R¹ is selected from —(C₁-C₇) hydrocarbyl, substituted —(C₁-C₇) hydrocarbyl, 3-7 membered heterocyclyl, —NR⁷R⁸, —SR⁷, —N R⁷(OR⁸) and —N R⁷(SR⁸);

each R² is independently selected from —H and —(C₁-C₄) alkyl;

each R³ is independently selected from —H and —(C₁-C₄) alkyl;

each R⁴ is independently selected from —H, —(C₁-C₆) alkyl, —OH, —O(C₁-C₆) alkyl, halogen, —CN, or the two geminal R⁴ groups may together form a carbonyl group;

wherein one of the R³ groups can optionally be structurally connected to one of the R² groups to form an alkylene bridge to produce a bicyclic ring; or one of the R³ groups can optionally be structurally connected to the R¹ group to form a 5 to 7 membered heterocyclyl ring fused to the 1-2 face of the piperidine ring; or one of the R³ groups can optionally be structurally connected to the R⁴ group to form a 5-7 membered carbocyclic or heterocyclic ring fused to the 2-3 face of the piperidine ring;

X₁ is selected from —O— and —S—;

R⁵ is selected from —H, —C₁-C₇ hydrocarbyl, halogen, —(C₁-C₃) haloalkyl, —OR⁷ᵃ, —CN, —NR⁷ᵃR⁸ᵃ, —O(CH₂)ₙNR⁷ᵃR⁸ᵃ, —O(CH₂)ₙOR⁸ᵃ, —NR⁸ᵃ(CH₂)ₙNR⁷ᵃR⁸ᵃ, —NR⁸ᵃ(CH₂)ₙOR⁸ᵃ, —C(=O)NR⁷ᵃR⁸ᵃ, —C(=O)OR⁷ᵃ, 5-6 membered heteroaryl and substituted 5-6 membered heteroaryl;

R⁶ is selected from naphthyl, substituted naphthyl, 6-membered heteroaryl and substituted 6-membered heteroaryl;

R⁷ is selected from —H, —(C₁-C₇) hydrocarbyl, substituted —(C₁-C₇) hydrocarbyl, —C(=O)R⁸ᵇ, —(C₁-C₆) heteroalkyl, 6 membered aryl, 5-6 membered heteroaryl and 5-6 membered heterocyclyl, wherein R⁸ᵇ is selected from —H and —(C₁-C₆) alkyl;

R⁸ is selected from —H and —(C₁-C₆) alkyl, wherein R⁷ can optionally be structurally connected to R⁸ to form a 5 to 7 membered heterocyclyl ring;

R⁷ᵃ is selected from —H, —(C₁-C₇) hydrocarbyl, substituted —(C₁-C₇) hydrocarbyl, —C(=O)R⁸ᵇ and —(C₁-C₆) heteroalkyl, wherein R⁸ᵇ is selected from —H and —(C₁-C₆) alkyl;

R⁸ᵃ is selected from —H and —(C₁-C₆) alkyl, wherein R⁷ᵃ can optionally be structurally connected to R⁸ᵃ to form a 5 to 7 membered heterocyclyl ring; and R⁹ is selected from —H, —OH, —(C₁-C₇) hydrocarbyl, —O(C₁-C₇) hydrocarbyl and halogen; and R⁹ᵃ is —H; or R⁹ and R⁹ᵃ together form a carbonyl group.

According to some embodiments of compounds according to Formula IE, R¹ is selected from —(C₁-C₇) hydrocarbyl, substituted —(C₁-C₇) hydrocarbyl and 3-7 membered heterocyclyl.

According to some embodiments, R¹ is selected from —(C₁-C₆) alkyl, substituted —(C₁-C₆)alkyl, —(C₃-C₆) cycloalkyl, substituted —(C₃-C₆)cycloalkyl, benzyl, substituted benzyl, —SR⁷, —NR⁷R⁸ and —NR⁷(OR⁸). According to some embodiments, R¹ is selected from —NR⁷R⁸ and —NR⁷(OR⁸). According to some embodiments, R¹ is —NR⁷R⁸. According to some embodiments, R¹ is —NR⁷(OR⁸).

According to some embodiments, R¹ is selected from —(C₁-C₆) alkyl, substituted —(C₁-C₆) alkyl, —(C₃-C₆) cycloalkyl, substituted —(C₃-C₆)cycloalkyl, benzyl, substituted benzyl and 5-6 membered heterocyclyl.

According to other embodiments, R¹ is selected from —CH₃, —CH₂CH₃, —(CH₂)₂CH₃, —(CH₂)₃CH₃, —(CH₂)₄CH₃, —CH(CH₃)₃, —C(CH₃)₃, cyclopropyl, substituted cyclopropyl, cyclobutyl, substituted cyclobutyl, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —CH₂—OCH₃, —(CH₂)₂—OCH₃ and —(CH₂)₃—OCH₃.

According to other embodiments, R¹ is selected from —CH₃, —CH₂CH₃, —(CH₂)₂CH₃, —(CH₂)₃CH₃, —(CH₂)₄CH₃, —CH(CH₃)₃, —C(CH₃)₃, cyclopropyl, substituted cyclopropyl, cyclobutyl, substituted cyclobutyl, tetrahydrofuranyl and substituted tetrahydrofuranyl.

According to some embodiments, when R¹ is substituted cyclopropyl, the cyclopropyl ring may be substituted with 1 or two substituents selected from —OH, —CH₂OH, —C(=O)NH₂, —NH₂, —CH₃, —CN and —CF₃. According to some embodiments, when R¹ is tetrahydrofuranyl, it is tetrahydrofuran-2-yl or tetrahydrofuran-3-yl. According to some embodiments, when R¹ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl. According to some embodiments, R¹ is selected from the moieties depicted in Table 1 and Table 1a, supra.

According to some embodiments, each R² is —H.

According to some embodiments, each R³ is —H.

According to some embodiments, each R⁴ is independently selected from —H, —(C₁-C₆) alkyl and halogen, wherein the halogen is preferably selected from —F, —Cl and —Br. According to some embodiments, one R⁴ is halogen and the other R⁴ is —H. According to some embodiments, each R⁴ is —H.

According to some embodiments, X₁ is —O—. According to some embodiments, X₁ is —S—.

According to some embodiments of compounds according to Formula IE, R⁵ is selected from —H, —C₁-C₇ hydrocarbyl, halogen, —(C₁-C₃) haloalkyl, —OR⁷ᵃ, —CN, —NR⁷ᵃR⁸ᵃ, —O(CH₂)ₙNR⁷ᵃR⁸ᵃ, —O(CH₂)ₙOR⁸ᵃ, —NR⁸ᵃ(CH₂)ₙNR⁷ᵃR⁸ᵃ, —NR⁸ᵃ(CH₂)ₙOR⁸ᵃ, —C(=O)NR⁷ᵃR⁸ᵃ, —C(=O)OR⁷ᵃ, 5-6 membered heteroaryl and substituted 5-6 membered heteroaryl.

According to some embodiments, R⁶ is naphthyl or substituted naphthyl. According to some embodiments, R⁶ is alpha-naphthyl or substituted alpha-naphthyl. According to other embodiments, R⁶ is beta-naphthyl or substituted beta-naphthyl.

According to some embodiments, R⁶ is 6-membered heteroaryl or substituted 6-membered heteroaryl. According to some embodiments, R⁶ is pyridylyl or substituted pyridylyl.

According to some embodiments, when R⁶ is substituted naphthyl or substituted 6-membered heteroaryl, the naphthyl or 6-membered heteroaryl is substituted with 1, 2 or 3 substituents independently selected from halogen, —(C₁-C₆) alkyl, —(C₃-C₆) cycloalkyl, —(C₁-C₃) haloalkyl, —O(C₁-C₃) haloalkyl, 5-6 membered heterocyclyl, —OH, —O(C₁-C₆) alkyl, —O(CH₂)ᵣ-(5-6 membered heterocyclyl), —O(CH₂)ᵣ— O(C₁-C₆) alkyl, —O(CH₂)ᵣ—NH(C₁-C₆ alkyl)₂, —NH₂, —CN, —NH(C₁-C₆) alkyl, —N(C₁-C₆ alkyl)₂, —NH(CH₂)ᵣ—O(C₁-C₆)alkyl, —NH(CH₂)ᵣ—N(C₁—C₆ alkyl)₂, —C(=O)NH₂, —C(=O)NH(C₁-C₆) alkyl and —C(=O)N(C₁-C₆ alkyl)₂; wherein r is an integer selected independently from 1, 2, 3 and 4.

According to some embodiments, when $R^6$ is substituted naphthyl or substituted 6-membered heteroaryl, the naphthyl or 6-membered heteroaryl is substituted with 1, 2 or 3 substituents independently selected from halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —$NH_2$, —CN, —NH($C_1$-$C_6$) alkyl, —N($C_1$-$C_6$ alkyl)$_2$, —C(=O)$NH_2$, —C(=O)NH($C_1$-$C_6$) alkyl and —C(=O)N($C_1$-$C_6$ alkyl)$_2$.

According to some embodiments, when $R^6$ is substituted naphthyl or substituted 6-membered heteroaryl, the naphthyl or 6-membered heteroaryl is substituted with 1, 2 or 3 substituents independently selected from halogen, —($C_1$-$C_6$) alkyl, —($C_3$-$C_6$) cycloalkyl, —C(=O)($C_1$-$C_6$)alkyl, —OH and —O($C_1$-$C_6$) alkyl; wherein the halogen is preferably selected from —F, —Cl and —Br.

According to some embodiments, $R^5$ is selected from —H, —$C_1$-$C_6$ alkyl, benzyl, halogen, —($C_1$-$C_3$) haloalkyl, —$OR^{7a}$, —CN, —$NR^{7a}R^{8a}$, —C(=O)$NR^{7a}R^{8a}$, —C(=O)$OR^{7a}$, 5-6 membered heteroaryl and substituted 5-6 membered heteroaryl.

According to some embodiments, $R^5$ is selected from —H, —$C_1$-$C_6$ alkyl, benzyl, —$C_1$, —F, —Br, —($C_1$-$C_3$) haloalkyl, —$OC_1$-$C_6$ alkyl, —CN, —NH$C_1$-$C_6$ alkyl, —C(=O)NH$C_1$-$C_6$ alkyl, —C(=O)$OC_1$-$C_6$ alkyl, 5-6 membered heteroaryl and substituted 5-6 membered heteroaryl.

According to some embodiments, $R^5$ is selected from —H, —$C_1$-$C_6$ alkyl, —F, —Cl, —Br, —$OC_1$-$C_6$ alkyl, —CN, —NH$C_1$-$C_6$ alkyl, —C(=O)NH$C_1$-$C_6$ alkyl and —C(=O)$OC_1$-$C_6$ alkyl. According to some embodiments, $R^5$ is selected from —H, —$C_1$-$C_6$ alkyl and halogen; wherein halogen is preferably selected from —F, —Cl and —Br. According to some embodiments, $R^5$ is —H.

According to some embodiments, $R^7$ is selected from —H and —$C_1$-$C_6$ alkyl. According to some embodiments, $R^7$ is —H. According to some embodiments, $R^7$ is —$C_1$-$C_6$ alkyl.

According to some embodiments, $R^8$ is selected from —H and —$C_1$-$C_6$ alkyl. According to some embodiments, $R^8$ is —H. According to some embodiments, $R^8$ is —$C_1$-$C_6$ alkyl. According to some embodiments, $R^7$ and $R^8$ are —H.

According to some embodiments, $R^{7a}$ is selected from —H and —$C_1$-$C_6$ alkyl. According to some embodiments, $R^{7a}$ is —H. According to some embodiments, $R^{7a}$ is —$C_1$-$C_6$ alkyl.

According to some embodiments, $R^{8a}$ is selected from —H and —$C_1$-$C_6$ alkyl. According to some embodiments, $R^{8a}$ is —H. According to some embodiments, $R^{8a}$ is —$C_1$-$C_6$ alkyl. According to some embodiments, $R^{7a}$ and $R^{8a}$ are —H.

According to some embodiments, $R^{8b}$ is —$C_1$-$C_6$ alkyl. According to some embodiments, $R^{8b}$ is —H.

According to some embodiments, $R^9$ is selected from —H, —OH, —($C_1$-$C_6$) alkyl, —O($C_1$-$C_6$) alkyl, benzyl, —O-benzyl, —$C_1$ and —F and $R^{9a}$ is —H, or the geminal $R^9$ and $R^{9a}$ together form a carbonyl group. According to some embodiments, $R^9$ and $R^{9a}$ are —H.

Compounds according to Formula I may include for example: [6-(1-methyl-6-isoquinolyl)spiro[chromane-2,4'-piperidine]-1'-yl]-[(2R)-tetrahydrofuran-2-yl]methanone; 1-[6-(4-methyl-3-quinolyl)spiro[chromane-2,4'-piperidine]-1'-yl]propan-1-one; cyclopropyl-[6-(4-methyl-3-quinolyl)spiro[chromane-2,4'-piperidine]-1'-yl]methanone; [6-(4-methyl-3-quinolyl)spiro[chromane-2,4'-piperidine]-1'-yl]-[(2R)-tetrahydrofuran-2-yl]methanone; [6-(1-cyclopropyl-6-isoquinolyl)spiro[chromane-2,4'-piperidine]-1'-yl]-[(2R)-tetrahydrofuran-2-yl]methanone; 1-[6-(8-methyl-7-quinolyl)spiro[chromane-2,4'-piperidine]-1'-yl]propan-1-one; cyclopropyl-[6-(8-methyl-7-quinolyl)spiro[chromane-2,4'-piperidine]-1'-yl]methanone; [6-(8-methyl-7-quinolyl)spiro[chromane-2,4'-piperidine]-1'-yl]-[(2R)-tetrahydrofuran-2-yl]methanone; 1-[6-(8-chloro-7-quinolyl)spiro[chromane-2,4'-piperidine]-1'-yl]propan-1-one; [6-(8-chloro-7-quinolyl)spiro[chromane-2,4'-piperidine]-1'-yl]-cyclopropylmethanone; [6-(8-chloro-7-quinolyl)spiro[chromane-2,4'-piperidine]-1'-yl]-[(2R)-tetrahydrofuran-2-yl]methanone; 1-[6-(8-methyl-3-quinolyl)spiro[chromane-2,4'-piperidine]-1'-yl]propan-1-one; cyclopropyl-[6-(8-methyl-3-quinolyl)spiro[chromane-2,4'-piperidine]-1'-yl]methanone; [6-(8-methyl-3-quinolyl)spiro[chromane-2,4'-piperidine]-1'-yl]-[(2R)-tetrahydrofuran-2-yl]methanone; cyclopropyl-[6-(8-methoxy-7-quinolyl)spiro[chromane-2,4'-piperidine]-1'-yl]methanone; [6-(8-methoxy-7-quinolyl)spiro[chromane-2,4'-piperidine]-1'-yl]-[(2R)-tetrahydrofuran-2-yl]methanone; 1-[6-(8-methyl-6-quinolyl)spiro[chromane-2,4'-piperidine]-1'-yl]propan-1-one; cyclopropyl-[6-(8-methyl-6-quinolyl)spiro[chromane-2,4'-piperidine]-1'-yl]methanone; 1-[6-(8-methoxy-7-quinolyl)spiro[chromane-2,4'-piperidine]-1'-yl]propan-1-one; [6-(8-methyl-6-quinolyl)spiro[chromane-2,4'-piperidine]-1'-yl]-[(2R)-tetrahydrofuran-2-yl]methanone; 1-[6-(1-methyl-6-isoquinolyl)spiro[4H-1,3-benzodioxine-2,4'-piperidine]-1'-yl]propan-1-one; cyclopropyl-[6-(1-methyl-6-isoquinolyl)spiro[4H-1,3-benzodioxine-2,4'-piperidine]-1'-yl]methanone; [6-(1-methyl-6-isoquinolyl)spiro[4H-1,3-benzodioxine-2,4'-piperidine]-1'-yl]-[(2R)-tetrahydrofuran-2-yl]methanone; 1-[6-(1-methyl-6-isoquinolyl)spiro[chromane-2,4'-piperidine]-1'-yl]propan-1-one; cyclopropyl-[6-(1-methyl-6-isoquinolyl)spiro[chromane-2,4'-piperidine]-1'-yl]methanone; 1-[6-(5-methylimidazo[1,2-a]pyridin-6-yl)spiro[chromane-2,4'-piperidine]-1'-yl]propan-1-one; cyclopropyl-[6-(5-methylimidazo[1,2-a]pyridin-6-yl)spiro[chromane-2,4'-piperidine]-1'-yl]methanone; [6-(5-methylimidazo[1,2-a]pyridin-6-yl)spiro[chromane-2,4'-piperidine]-1'-yl]-[(2R)-tetrahydrofuran-2-yl]methanone; 1-[6-(3-quinolyl)spiro[4H-1,3-benzodioxine-2,4'-piperidine]-1'-yl]propan-1-one; ethyl 6-(7-quinolyl)spiro[4H-1,3-benzodioxine-2,4'-piperidine]-1'-carboxylate; 2-methyl-1-[6-(7-quinolyl)spiro[4H-1,3-benzodioxine-2,4'-piperidine]-1'-yl]propan-1-one; cyclopropyl-[6-(7-quinolyl)spiro[4H-1,3-benzodioxine-2,4'-piperidine]-1'-yl]methanone; 1-[6-(3-quinolyl)spiro[4H-1,3-benzodioxine-2,4'-piperidine]-1'-yl]propan-1-one; 2-methyl-1-[6-(3-quinolyl)spiro[4H-1,3-benzodioxine-2,4'-piperidine]-1'-yl]propan-1-one; ethyl 6-(1,5-naphthyridin-3-yl)spiro[4H-1,3-benzodioxine-2,4'-piperidine]-1'-carboxylate; 1-[6-(1,5-naphthyridin-3-yl)spiro[4H-1,3-benzodioxine-2,4'-piperidine]-1'-yl]propan-1-one; cyclopropyl-[6-(1,5-naphthyridin-3-yl)spiro[4H-1,3-benzodioxine-2,4'-piperidine]-1'-yl]methanone; 1'-propanoyl-6-(3-quinolyl)spiro[chromane-2,4'-piperidine]-4-one; methyl 4-oxo-6-(3-quinolyl)spiro[chromane-2,4'-piperidine]-1'-carboxylate; cyclopropyl-[6-(3-quinolyl)spiro[4H-1,3-benzodioxine-2,4'-piperidine]-1'-yl]methanone; cyclobutyl-[6-(3-quinolyl)spiro[4H-1,3-benzodioxine-2,4'-piperidine]-1'-yl]methanone; 1-[4-hydroxy-6-(3-quinolyl)spiro[chromane-2,4'-piperidine]-1'-yl]propan-1-one; 1-[6-(3-quinolyl)spiro[chromene-2,4'-piperidine]-1'-yl]propan-1-one; cyclopropyl-[6-(3-quinolyl)spiro-[chromene-2,4'-piperidine]-1'-yl]methanone; cyclobutyl-[6-(3-quinolyl)spiro[chromene-2,4'-piperidine]-1'-yl]methanone; cyclopropyl-[4-hydroxy-6-(3-quinolyl)spiro[chromane-2,4'-piperidine]-1'-yl]methanone; 1-[6-(3-quinolyl)spiro[chromane-2,4'-piperidine]-1'-yl]propan-1-one; [6-(3-quinolyl)spiro[4H-1,3-benzodioxine-2,4'- piperidine]-1'-yl]-[(2R)-tetrahydrofuran-2-yl]methanone; cyclopropyl-[6-(8-methoxy-7-quinolyl)spiro[4H-1,3-benzodioxine-2,4'-piperidine]-1'-yl]methanone; [6-(8-methyl-7-quinolyl)spiro[4H-1,3-benzodioxine-2,4'-piperidine]-1'-yl]-[(2R)-tetrahydrofuran-2-yl]methanone; 6-(4-methyl-3-quinolyl)spiro[4H-1,3-benzodioxine-2,4'-piperidine]-1'-yl]-[(2R)-tetrahydrofuran-2-yl]methanone; 1-[6-(4-methyl-3-quinolyl)spiro[4H-1,3-benzodioxine-2,4'-piperidine]-1'-yl]propan-1-one; 1-[6-(8-methyl-7-quinolyl)spiro[4H-1,3-benzodioxine-2,4'-piperidine]-1'-yl]propan-1-one; cyclopropyl-[6-(8-methyl-7-quinolyl)spiro[4H-1,3-benzodioxine-2,4'-piperidine]-1'-yl]methanone; 1-[6-(8-methoxy-7-quinolyl)spiro[4H-1,3-benzodioxine-2,4'-piperidine]-1'-yl]propan-1-one; [6-(8-methoxy-7-quinolyl)spiro[4H-1,3-benzodioxine-2,4'-piperidine]-1'-yl]-[(2R)-tetrahydrofuran-2-yl]methanone; 1-[6-(8-chloro-7-quinolyl)spiro[4H-1,3-benzodioxine-2,4'-piperidine]-1'-yl]propan-1-one; [6-(8-chloro-7-quinolyl)spiro[4H-1,3-benzodioxine-2,4'-piperidine]-1'-yl]-cyclopropyl-methanone; [6-(8-chloro-7-quinolyl)spiro[4H-1,3-benzodioxine-2,4'-piperidine]-1'-yl]-[(2R)-tetrahydrofuran-2-yl]methanone; [2-[6-(8-methyl-7-quinolyl)spiro[4H-1,3-benzodioxine-2,4'-piperidine]-1'-yl]-2-oxo-ethyl]acetate; 2-hydroxy-1-[6-(8-methyl-7-quinolyl)spiro[chromane-2,4'-piperidine]-1'-yl]ethanone; 2-hydroxy-1-[6-(8-methyl-7-quinolyl)spiro[4H-1,3-benzodioxine-2,4'-piperidine]-1'-yl]ethanone; 6-(8-chloro-7-quinolyl)spiro[chromane-2,4'-piperidine]-1'-carboxamide; [2-[6-(8-chloro-7-quinolyl)spiro[chromane-2,4'-piperidine]-1'-yl]-2-oxo-ethyl]acetate; 6-(8-chloro-7-quinolyl)-N-tetrahydropyran-2-yloxy-spiro[chromane-2,4'-piperidine]-1'-carboxamide; 6-(8-chloro-7-quinolyl)-N-ethyl-spiro[chromane-2,4'-piperidine]-1'-carboxamide; 1-[6-(8-chloro-7-quinolyl)spiro[chromane-2,4'-piperidine]-1'-yl]-2-hydroxy-ethanone; 6-(8-chloro-7-quinolyl)spiro[chromane-2,4'-piperidine]-1'-carbohydroxamic acid; 6-(8-chloro-7-quinolyl)-N-ethoxy-spiro[chromane-2,4'-piperidine]-1'-carboxamide; 6-(8-chloro-7-quinolyl)-N-methoxy-spiro[chromane-2,4'-piperidine]-1'-carboxamide; ethyl 6-(8-chloro-7-quinolyl)spiro[chromane-2,4'-piperidine]-1'-carboxylate; 6-(3-quinolyl)spiro[chromane-2,4'-piperidine]-1'-carboxamide; 6-(benzofuran-5-yl)spiro[chromane-2,4'-piperidine]-1'-carboxamide; 6-(1,3-benzothiazol-6-yl)spiro[chromane-2,4'-piperidine]-1'-carboxamide; 6-(1-methylindol-5-yl)spiro[chromane-2,4'-piperidine]-1'-carboxamide; 6-(1H-indol-5-yl)spiro[chromane-2,4'-piperidine]-1'-carboxamide; 7-(8-methyl-7-quinolyl)spiro[4,5-dihydro-1,3-benzodioxepine-2,4'-piperidine]-1'-carboxamide; N-ethyl-7-(8-methyl-7-quinolyl)spiro[4,5-dihydro-1,3-benzodioxepine-2,4'-piperidine]-1'-carboxamide; N-ethoxy-7-(8-methyl-7-quinolyl)spiro[4,5-dihydro-1,3-benzodioxepine-2,4'-piperidine]-1'-carboxamide; N-methoxy-7-(8-methyl-7-quinolyl)spiro[4,5-dihydro-1,3-benzodioxepine-2,4'-piperidine]-1'-carboxamide; 6-(1-methylbenzimidazol-5-yl)spiro[chromane-2,4'-piperidine]-1'-carboxamide; 6-(1-methylbenzimidazol-5-yl)spiro[4H-1,3-benzodioxine-2,4'-piperidine]-1'-carboxamide; 6-(1,3-benzothiazol-5-yl)spiro[chromane-2,4'-piperidine]-1'-carboxamide; tert-butyl 6-thieno[2,3-b]pyridin-5-ylspiro[4H-1,3-benzodioxine-2,4'-piperidine]-1'-carboxylate; 6-thieno[2,3-b]pyridin-5-ylspiro[chromane-2,4'-piperidine]-1'-carboxamide; 6-(1,3-benzoxazol-5-yl)spiro[chromane-2,4'-piperidine]-1'-carboxamide; 6-(2-naphthyl)spiro[chromane-2,4'-piperidine]-1'-carboxamide; 6-(1,3-benzoxazol-6-yl)spiro[chromane-2,4'-piperidine]-1'-carboxamide; 6-thieno[2,3-b]pyridin-5-ylspiro[4H-1,3-benzodioxine-2,4'-piperidine]-1'-carboxamide; 6-(2-naphthyl)spiro[4H-1,3-benzodioxine-2,4'-piperidine]-1'-carboxamide; 6-(1,8-naphthyridin-3-yl)spiro[chromane-2,4'-piperidine]-1'-carboxamide; tert-butyl 6-(1-tert-butoxycarbonylindol-2-yl)spiro[4H-1,3-benzodioxine-2,4'-piperidine]-1'-carboxylate; tert-butyl 3-(1'-carbamoylspiro[chromane-2,4'-piperidine]-6-yl)indole-1-carboxylate; 6-(1H-indol-3-yl)spiro[chromane-2,4'-piperidine]-1'-carboxamide; 6-(1H-indol-3-yl)spiro[4H-1,3-benzodioxine-2,4'-piperidine]-1'-carboxamide; N-isobutyl-6-(8-methyl-7-quinolyl)spiro[chromane-2,4'-piperidine]-1'-carboxamide; N-ethyl-6-(8-methyl-7-quinolyl)spiro[chromane-2,4'-piperidine]-1'-carboxamide; N-isopropyl-6-(8-methyl-7-quinolyl)spiro[chromane-2,4'-piperidine]-1'-carboxamide; 6-(8-methyl-7-quinolyl)-N-propyl-spiro[chromane-2,4'-piperidine]-1'-carboxamide; N-(cyclopropylmethyl)-6-(8-methyl-7-quinolyl)spiro[chromane-2,4'-piperidine]-1'-carboxamide; N-ethoxy-6-(8-methyl-7-quinolyl)spiro[chromane-2,4'-piperidine]-1'-carboxamide; 6-(8-methyl-7-quinolyl)-N-propoxy-spiro[chromane-2,4'-piperidine]-1'-carboxamide; N-isopropoxy-6-(8-methyl-7-quinolyl)spiro[chromane-2,4'-piperidine]-1'-carboxamide; N-isobutoxy-6-(8-methyl-7-quinolyl)spiro-[chromane-2,4'-piperidine]-1'-carboxamide; 6-(8-methyl-7-quinolyl)spiro[chromane-2,4'-piperidine]-1'-carbohydroxamic acid; 6-(8-methyl-7-quinolyl)spiro[chromane-2,4'-piperidine]-1'-carboxamide; N-ethoxy-6-(5-methylimidazo[1,2-a]pyridin-6-yl)spiro[chromane-2,4'-piperidine]-1'-carboxamide; N-isopropoxy-6-(5-methylimidazo[1,2-a]pyridin-6-yl)spiro[chromane-2,4'-piperidine]-1'-carboxamide; 6-(5-methylimidazo[1,2-a]pyridin-6-yl)spiro[chromane-2,4'-piperidine]-1'-carboxamide; N-ethyl-6-(5-methylimidazo[1,2-a]pyridin-6-yl)spiro[chromane-2,4'-piperidine]-1'-carboxamide; N-isopropyl-6-(5-methylimidazo[1,2-a]pyridin-6-yl)spiro[chromane-2,4'-piperidine]-1'-carboxamide; N-ethyl-6-(7-methylpyrazolo[1,5-a]pyridin-6-yl)spiro[chromane-2,4'-piperidine]-1'-carboxamide; N-isopropyl-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carboxamide; N-ethoxy-6-(7-methylpyrazolo[1,5-a]pyridin-6-yl)spiro[chromane-2,4'-piperidine]-1'-carboxamide; N-isopropoxy-6-(7-methylpyrazolo[1,5-a]pyridin-6-yl)spiro[chromane-2,4'-piperidine]-1'-carboxamide; N-ethyl-6-(8-methyl-7-quinolyl)spiro[4H-1,3-benzodioxine-2,4'-piperidine]-1'-carboxamide; 6-(8-methyl-7-quinolyl)spiro[4H-1,3-benzodioxine-2,4'-piperidine]-1'-carboxamide; N-isopropyl-6-(8-methyl-7-quinolyl)spiro[4H-1,3-benzodioxine-2,4'-piperidine]-1'-carboxamide; N-methoxy-6-(8-methyl-7-quinolyl)spiro[chromane-2,4'-piperidine]-1'-carboxamide; N-ethoxy-6-(8-methyl-7-quinolyl)spiro[4H-1,3-benzodioxine-2,4'-piperidine]-1'-carboxamide; N-methoxy-6-(8-methyl-7-quinolyl)spiro[4H-1,3-benzodioxine-2,4'-piperidine]-1'-carboxamide; N-isopropoxy-6-(8-methyl-7-quinolyl)spiro[4H-1,3-benzodioxine-2,4'-piperidine]-1'-carboxamide; N-methoxy-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carbohydroxamic acid; N-ethyl-6-(7-methylpyrazolo[1,5-a]pyridin-6-yl)spiro[4H-1,3-benzodioxine-2,4'-piperidine]-1'-carboxamide; 6-(7-methylpyrazolo[1,5-a]pyridin-6-yl)spiro[4H-1,3-benzodioxine-2,4'-piperidine]-1'-carboxamide; N-methoxy-6-(7-methylpyrazolo[1,5-a]pyridin-6-yl)spiro[4H-1,3-benzodioxine-2,4'-piperidine]-1'-carboxamide; N-ethoxy-6-(7-methylpyrazolo[1,5-a]pyridin-6-yl)spiro[4H-1,3-benzodioxine-2,4'-piperidine]-1'-carboxamide; N-isopropoxy-6-(7-methylpyrazolo[1,5-a]pyridin-6-yl)spiro[4H-1,3-benzodioxine-2,4'-piperidine]-1'-carboxamide; 6-(8-chloro-7-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carboxamide; N-methoxy-6-(4-methyl-3-quinolyl)spiro[4H-1,3-benzodioxine-2,4'-piperidine]-1'-carboxamide; 6-(8-chloro-7-quinolyl)-N-methoxy-spiro[4H-1,3-benzodioxine-2,4'-piperidine]-1'-carboxamide; 6-(8-chloro-7-quinolyl)-N-ethoxy-spiro[4H-1,3-benzodioxine-2,4'-piperidine]-1'-carboxamide; 6-(8-chloro-7-quinolyl)spiro[4H-1,3-benzodioxine-2,4'-piperidine]-1'-carbohydroxamic acid; ethyl 6-(8-chloro-7-quinolyl)spiro[4H-1,3-benzodioxine-2,4'-piperidine]-1'-carboxylate; ethyl 6-(4-methyl-3-quinolyl)spiro[4H-1,3-benzodioxine-2,4'-piperidine]-1'-carboxylate; N-ethoxy-6-(4-methyl-3-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carbohydroxamic acid; 6-(5-methylimidazo[1,2-a]pyridin-6-yl)spiro[chromane-2,4'-piperidine]-1'-carbohydroxamic acid; 6-(3-isoquinolyl)spiro[4H-1,3-benzodioxine-2,4'-piperidine]-1'-carboxamide; 6-(3-isoquinolyl)spiro[chromane-2,4'-piperidine]-1'-carboxamide; 6-(3-isoquinolyl)-N-tetrahydropyran-2-yloxy-spiro[4H-1,3-benzodioxine-2,4'-piperidine]-1'-carboxamide; N-ethoxy-6-(3-isoquinolyl)spiro[4H-1,3-benzodioxine-2,4'-piperidine]-1'-carboxamide; 6-(3-isoquinolyl)-N-tetrahydropyran-2-yloxy-spiro[chromane-2,4'-piperidine]-1'-carboxamide; 6-(3-isoquinolyl)-N-methoxyspiro[4H-1,3-benzodioxine-2,4'-piperidine]-1'-carboxamide; 6-(3-isoquinolyl)-N-methoxyspiro[chromane-2,4'-piperidine]-1'-carboxamide; N-ethoxy-6-(3-isoquinolyl)spiro[chromane-2,4'-piperidine]-1'-carboxamide; 6-(3-isoquinolyl)spiro[4H-1,3-benzodioxine-2,4'-piperidine]-1'-carbohydroxamic acid; 6-(3-isoquinolyl)spiro[chromane-2,4'-piperidine]-1'-carbohydroxamic acid; 5-(8-methyl-7-quinolyl)spiro[3H-benzofuran-2,4'-piperidine]-1'-carboxamide; N-methoxy-5-(8-methyl-7-quinolyl)spiro[3H-benzofuran-2,4'-piperidine]-1'-carboxamide; N-ethoxy-5-(8-methyl-7-quinolyl)spiro[3H-benzofuran-2,4'-piperidine]-1'-carboxamide; 5-(8-methyl-7-quinolyl)spiro[3H-benzofuran-2,4'-piperidine]-1'-carbohydroxamic acid; N-ethyl-5-(8-methyl-7-quinolyl)spiro[3H-benzofuran-2,4'-piperidine]-1'-carboxamide; N-methoxy-5-(4-methyl-3-quinolyl)spiro[3H-benzofuran-2,4'-piperidine]-1'-carboxamide; N-ethoxy-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carboxamide; N-ethyl-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carbohydroxamic acid; 5-(8-methoxy-7-quinolyl)spiro[3H-benzofuran-2,4'-piperidine]-1'-carboxamide; N-ethyl-5-(8-methoxy-7-quinolyl)spiro[3H-benzofuran-2,4'-piperidine]-1'-carboxamide; 5-(7-methylpyrazolo[1,5-a]pyridin-6-yl)spiro[3H-benzofuran-2,4'-piperidine]-1'-carboxamide; N-ethyl-5-(7-methylpyrazolo[1,5-a]pyridin-6-yl)spiro[3H-benzofuran-2,4'-piperidine]-1'-carboxamide; N-methoxy-5-(8-methoxy-7-quinolyl)spiro[3H-benzofuran-2,4'-piperidine]-1'-carboxamide; N-ethoxy-5-(8-methoxy-7-quinolyl)spiro[3H-benzofuran-2,4'-piperidine]-1'-carboxamide; 5-(8-methoxy-7-quinolyl)-N-tetrahydropyran-2-yloxy-spiro[3H-benzofuran-2,4'-piperidine]-1'-carboxamide; N-ethoxy-5-(7-methylpyrazolo[1,5-a]pyridin-6-yl)spiro[3H-benzofuran-2,4'-piperidine]-1'-carboxamide; N-methoxy-5-(7-methylpyrazolo[1,5-a]pyridin-6-yl)spiro[3H-benzofuran-2,4'-piperidine]-1'-carboxamide; 5-(7-methylpyrazolo[1,5-a]pyridin-6-yl)-N-tetrahydropyran-2-yloxy-spiro[3H-benzofuran-2,4'-piperidine]-1'-carboxamide; 6-(8-methyl-2-oxo-1H-quinolin-7-yl)spiro[chromane-2,4'-piperidine]-1'-carboxamide; 5-(8-methoxy-7-quinolyl)spiro[3H-benzofuran-2,4'-piperidine]-1'-carbohydroxamic acid; 6-(8-methoxy-7-quinolyl)spiro[4H-1,3-benzodioxine-2,4'-piperidine]-1'-carboxamide; 6-(8-methoxy-7-quinolyl)spiro[chromane-2,4'-piperidine]-1'-carboxamide; ethyl 6-(8-methoxy-7-quinolyl)spiro[4H-1,3-benzodioxine-2,4'-piperidine]-1'-carboxylate; 6-(5-chloroimidazo[1,2-a]pyridin-6-yl)-N-isobutyl-spiro[chromane-2,4'-piperidine]-1'-carboxamide; N-isobutyl-6-(1-methyl-6-isoquinolyl)spiro[chromane-2,4'-piperidine]-1'-carboxamide; 6-(5-chloroimidazo[1,2-a]pyridin-6-yl)-N-isopropoxy-spiro[chromane-2,4'-piperidine]-1'-carboxamide; N-isopropoxy-6-(1-methyl-6-isoquinolyl)spiro[chromane-2,4'-piperidine]-1'-carboxamide; N-ethoxy-6-(4-methyl-3-quinolyl)spiro[chromane-2,4'-piperidine]-1'-carboxamide; N-isopropoxy-6-(1-methyl-6-isoquinolyl)spiro[4H-1,3-benzodioxine-2,4'-piperidine]-1'-carboxamide; 6-(1-methyl-6-isoquinolyl)spiro[chromane-2,4'-piperidine]-1'-carboxamide; N-methoxy-6-(1-methyl-6-isoquinolyl)spiro[chromane-2,4'-piperidine]-1'-carboxamide; N-ethoxy-6-(1-methyl-6-isoquinolyl)spiro[chromane-2,4'-piperidine]-1'-carboxamide; 6-(1-methyl-6-isoquinolyl)-N-propoxy-spiro[chromane-2,4'-piperidine]-1'-carboxamide; N-ethyl-6-(1-methyl-6-isoquinolyl)spiro[chromane-2,4'-piperidine]-1'-carboxamide; 6-(1-methyl-6-isoquinolyl)-N-propyl-spiro[chromane-2,4'-piperidine]-1'-carboxamide; 6-(1-methyl-6-isoquinolyl)spiro[chromane-2,4'-piperidine]-1'-carbohydroxamic acid; 6-(4-methyl-3-quinolyl)spiro[chromane-2,4'-piperidine]-1'-carboxamide; 6-(4-methyl-3-quinolyl)spiro[chromane-2,4'-piperidine]-1'-carbohydroxamic acid; N-methoxy-6-(4-methyl-3-quinolyl)spiro[chromane-2,4'-piperidine]-1'-carboxamide; N-isopropoxy-6-(4-methyl-3-quinolyl)spiro[chromane-2,4'-piperidine]-1'-carboxamide; 6-(1-methyl-6-isoquinolyl)spiro[4H-1,3-benzodioxine-2,4'-piperidine]-1'-carboxamide; N-methoxy-6-(1-methyl-6-isoquinolyl)spiro[4H-1,3-benzodioxine-2,4'-piperidine]-1'-carboxamide; N-ethoxy-6-(1-methyl-6-isoquinolyl)spiro[4H-1,3-benzodioxine-2,4'-piperidine]-1'-carboxamide; N-ethyl-6-(1-methyl-6-isoquinolyl)spiro[4H-1,3-benzodioxine-2,4'-piperidine]-1'-carboxamide; ethyl 6-(3-chloro-6-isoquinolyl)spiro[4H-1,3-benzodioxine-2,4'-piperidine]-1'-carboxylate; 6-(1-methyl-6-isoquinolyl)spiro[4H-1,3-benzodioxine-2,4'-piperidine]-1'-carbohydroxamic acid; ethyl 6-(3-methyl-6-isoquinolyl)spiro[4H-1,3-benzodioxine-2,4'-piperidine]-1'-carboxylate; 6-(3-methyl-6-isoquinolyl)spiro[4H-1,3-benzodioxine-2,4'-piperidine]-1'-carboxamide; N-ethyl-6-(3-methyl-6-isoquinolyl)spiro[4H-1,3-benzodioxine-2,4'-piperidine]-1'-carboxamide; N-ethoxy-6-(3-methyl-6-isoquinolyl)spiro[4H-1,3-benzodioxine-2,4'-piperidine]-1'-carboxamide; 6-(3-methyl-6-isoquinolyl)spiro[4H-1,3-benzodioxine-2,4'-piperidine]-1'-carbohydroxamic acid; N-methoxy-6-(3-methyl-6-isoquinolyl)spiro[4H-1,3-benzodioxine-2,4'-piperidine]-1'-carboxamide; 6-(3-methyl-6-isoquinolyl)spiro[chromane-2,4'-piperidine]-1'-carboxamide; N-ethoxy-6-(3-methyl-6-isoquinolyl)spiro[chromane-2,4'-piperidine]-1'-carboxamide; N-ethyl-6-(3-methyl-6-isoquinolyl)spiro[chromane-2,4'-piperidine]-1'-carboxamide; N-methoxy-6-(3-methyl-6-iso-quinolyl)spiro[chromane-2,4'-piperidine]-1'-carboxamide; N-methoxy-6-(8-methoxy-7-quinolyl)spiro[chromane-2,4'-piperidine]-1'-carboxamide; N-ethoxy-6-(8-methoxy-7-quinolyl)-spiro[chromane-2,4'-piperidine]-1'-carboxamide; 6-(8-methyl-7-quinolyl)-4-oxo-spiro[chromane-2,4'-piperidine]-1'-carboxamide; 4-hydroxy-6-(8-methyl-7-quinolyl)spiro-[chromane-2,4'-piperidine]-1'-carboxamide; 4-fluoro-6-(8-methyl-7- quinolyl)spiro[chromane-2,4'-piperidine]-1'-carboxamide; 1-[6-(2-pyridyl)spiro[chromane-2,4'-piperidine]-1'-yl]propan-1-one; cyclopropyl-[6-(2-pyridyl)spiro[chromane-2,4'-piperidine]-1'-yl]methanone; [6-(2-pyridyl)spiro[chromane-2,4'-piperidine]-1'-yl]-[(2R)-tetrahydrofuran-2-yl]methanone; 1-[6-(2-pyridyl)spiro[4H-1,3-benzodioxine-2,4'-piperidine]-1'-yl]propan-1-one; cyclopropyl-[6-(2-pyridyl)spiro[4H-1,3-benzodioxine-2,4'-piperidine]-1'-yl]methanone; [6-(2-pyridyl)spiro[4H-1,3-benzodioxine-2,4'-piperidine]-1'-yl]-[(2R)-tetrahydrofuran-2-yl]methanone; 1-[6-(3-pyridyl)spiro[chromane-2,4'-piperidine]-1'-yl]propan-1-one; cyclopropyl-[6-(3-pyridyl)spiro[chromane-2,4'-piperidine]-1'-yl]methanone; [6-(3-pyridyl)spiro[chromane-2,4'-piperidine]-1'-yl]-[(2R)-tetrahydrofuran-2-yl]methanone; 1-[6-(3-pyridyl)spiro[4H-1,3-benzodioxine-2,4'-piperidine]-1'-yl]propan-1-one; cyclopropyl-[6-(3-pyridyl)spiro[4H-1,3-benzodioxine-2,4'-piperidine]-1'-yl]methanone; 1-[6-(4-pyridyl)spiro[chromane-2,4'-piperidine]-1'-yl]propan-1-one; cyclopropyl-[6-(4-pyridyl)spiro[chromane-2,4'-piperidine]-1'-yl]methanone; [6-(4-pyridyl)spiro[chromane-2,4'-piperidine]-1'-yl]-[(2R)-tetrahydrofuran-2-yl]methanone; [6-(3-pyridyl)spiro[4H-1,3-benzodioxine-2,4'-piperidine]-1'-yl]-[(2R)-tetrahydrofuran-2-yl]methanone; cyclopropyl-[6-(4-pyridyl)spiro[4H-1,3-benzodioxine-2,4'-piperidine]-1'-yl]-methanone; [6-(4-pyridyl)spiro[4H-1,3-benzodioxine-2,4'-piperidine]-1'-yl]-[(2R)-tetrahydrofuran-2-yl]methanone; 1-[6-(4-pyridyl)spiro[4H-1,3-benzodioxine-2,4'-piperidine]-1'-yl]propan-1-one; 7-Fluoro-6-(1-methyl-6-isoquinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 6-(Benzofuran-2-yl)spiro[chromane-2,4'-piperidine]-1'-carboxamide; 6-(1H-Indol-2-yl)spiro[chromane-2,4'-piperidine]-1'-carboxamide; 8-Fluoro-6-(8-methyl-7-quinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(1-methyl-6-isoquinolyl)spiro[chromane-2,4'-piperidine]-1' carboxamide; 5-Methyl-6-(8-methyl-7-quinolyl)spiro[chromane-2,4'-piperidine]-1'-carboxamide; 5-methyl-6-(1-methyl-6-isoquinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(8-methyl-7-quinolyl)spiro[chromane-2,4'-piperidine]-1'-carboxamide; 7-Methyl-6-(8-methyl-7-quinolyl)spiro[chromane-2,4'-piperidine]-1'-carboxamide; N-methoxy-7-methyl-6-(8-methyl-7-quinolyl)spiro[chromane-2,4'-piperidine]-1'-carboxamide; N-Methoxy-7-methyl-6-(1-methyl-6-isoquinolyl)spiro[chromane-2,4'-piperidine]-1'-carboxamide; 8-Methoxy-6-(8-methyl-7-quinolyl)spiro[4H-1,3-benzodioxine-2,4'-piperidine]-1'-carboxamide; 8-Methoxy-6-(8-methyl-7-quinolyl)spiro[4H-1,3-benzodioxine-2,4'-piperidine]-1'-carboxamide; 8-chloro-6-(8-methyl-7-quinolyl)spiro[chromane-2,4'-piperidine]-1'-carboxamide; 8-Chloro-N-methoxy-6-(8-methyl-7-quinolyl)spiro[chromane-2,4'-piperidine]-1'-carboxamide; 6-(4-Hydroxy-8-methyl-7-quinolyl)spiro[chromane-2,4'-piperidine]-1'-carboxamide; and salts of such compounds, e.g., pharmaceutically acceptable salts.

Compounds according to Formula IA may include for example: [6-(1-methyl-6-isoquinolyl)spiro[chromane-2,4'-piperidine]-1'-yl]-[(2R)-tetrahydrofuran-2-yl]methanone; 1-[6-(4-methyl-3-quinolyl)spiro[chromane-2,4'-piperidine]-1'-yl]propan-1-one; cyclopropyl-[6-(4-methyl-3-quinolyl)spiro[chromane-2,4'-piperidine]-1'-yl]methanone; [6-(4-methyl-3-quinolyl)-spiro[chromane-2,4'-piperidine]-1'-yl]-[(2R)-tetrahydrofuran-2-yl]methanone; [6-(1-cyclopropyl-6-isoquinolyl)spiro[chromane-2,4'-piperidine]-1'-yl]-[(2R)-tetrahydrofuran-2-yl]methanone; 1-[6-(8-methyl-7-quinolyl)spiro[chromane-2,4'-piperidine]-1'-yl]propan-1-one; cyclopropyl-[6-(8-methyl-7-quinolyl)spiro[chromane-2,4'-piperidine]-1'-yl]methanone; [6-(8-methyl-7-quinolyl)spiro[chromane-2,4'-piperidine]-1'-yl]-[(2R)-tetrahydrofuran-2-yl]methanone; 1-[6-(8-chloro-7-quinolyl)spiro[chromane-2,4'-piperidine]-1'-yl]propan-1-one; [6-(8-chloro-7-quinolyl)spiro[chromane-2,4'-piperidine]-1'-yl]-cyclopropyl-methanone; [6-(8-chloro-7-quinolyl)spiro[chromane-2,4'-piperidine]-1'-yl]-[(2R)-tetrahydrofuran-2-yl]methanone; 1-[6-(8-methyl-3-quinolyl)spiro[chromane-2,4'-piperidine]-1'-yl]propan-1-one; cyclopropyl-[6-(8-methyl-3-quinolyl)spiro[chromane-2,4'-piperidine]-1'-yl]methanone; [6-(8-methyl-3-quinolyl)spiro[chromane-2,4'-piperidine]-1'-yl]-[(2R)-tetrahydrofuran-2-yl]methanone; cyclopropyl-[6-(8-methoxy-7-quinolyl)spiro[chromane-2,4'-piperidine]-1'-yl]methanone; [6-(8-methoxy-7-quinolyl)spiro[chromane-2,4'-piperidine]-1'-yl]-[(2R)-tetrahydrofuran-2-yl]methanone; 1-[6-(8-methyl-6-quinolyl)spiro[chromane-2,4'-piperidine]-1'-yl]propan-1-one; cyclopropyl-[6-(8-methyl-6-quinolyl)spiro[chromane-2,4'-piperidine]-1'-yl]methanone; 1-[6-(8-methoxy-7-quinolyl)spiro[chromane-2,4'-piperidine]-1'-yl]propan-1-one; [6-(8-methyl-6-quinolyl)spiro[chromane-2,4'-piperidine]-1'-yl]-[(2R)-tetrahydrofuran-2-yl]methanone; 1-[6-(1-methyl-6-isoquinolyl)spiro[4H-1,3-benzodioxine-2,4'-piperidine]-1'-yl]propan-1-one; cyclopropyl-[6-(1-methyl-6-isoquinolyl)spiro[4H-1,3-benzodioxine-2,4'-piperidine]-1'-yl]methanone; [6-(1-methyl-6-isoquinolyl)spiro[4H-1,3-benzodioxine-2,4'-piperidine]-1'-yl]-[(2R)-tetrahydrofuran-2-yl]methanone; 1-[6-(1-methyl-6-isoquinolyl)spiro[chromane-2,4'-piperidine]-1'-yl]propan-1-one; cyclopropyl-[6-(1-methyl-6-isoquinolyl)spiro[chromane-2,4'-piperidine]-1'-yl]methanone; 1-[6-(5-methylimidazo[1,2-a]pyridin-6-yl)spiro[chromane-2,4'-piperidine]-1'-yl]propan-1-one; cyclopropyl-[6-(5-methylimidazo[1,2-a]pyridin-6-yl)spiro[chromane-2,4'-piperidine]-1'-yl]methanone; [6-(5-methylimidazo[1,2-a]pyridin-6-yl)spiro[chromane-2,4'-piperidine]-1'-yl]-[(2R)-tetrahydrofuran-2-yl]methanone; 1-[6-(3-quinolyl)spiro[4H-1,3-benzodioxine-2,4'-piperidine]-1'-yl]propan-1-one; 2-methyl-1-[6-(7-quinolyl)spiro[4H-1,3-benzodioxine-2,4'-piperidine]-1'-yl]propan-1-one; cyclopropyl-[6-(7-quinolyl)spiro[4H-1,3-benzodioxine-2,4'-piperidine]-1'-yl]methanone; 1-[6-(3-quinolyl)spiro[4H-1,3-benzodioxine-2,4'-piperidine]-1'-yl]propan-1-one; 2-methyl-1-[6-(3-quinolyl)spiro[4H-1,3-benzodioxine-2,4'-piperidine]-1'-yl]propan-1-one; 1-[6-(1,5-naphthyridin-3-yl)spiro[4H-1,3-benzodioxine-2,4'-piperidine]-1'-yl]propan-1-one; cyclopropyl-[6-(1,5-naphthyridin-3-yl)spiro[4H-1,3-benzodioxine-2,4'-piperidine]-1'-yl]methanone; 1'-propanoyl-6-(3-quinolyl)spiro[chromane-2,4'-piperidine]-4-one; cyclopropyl-[6-(3-quinolyl)spiro[4H-1,3-benzodioxine-2,4'-piperidine]-1'-yl]-methanone; cyclobutyl-[6-(3-quinolyl)spiro[4H-1,3-benzodioxine-2,4'-piperidine]-1'-yl]-methanone; 1-[4-hydroxy-6-(3-quinolyl)spiro[chromane-2,4'-piperidine]-1'-yl]propan-1-one; 1-[6-(3-quinolyl)spiro[chromene-2,4'-piperidine]-1'-yl]propan-1-one; cyclopropyl-[6-(3-quinolyl)spiro[chromene-2,4'-piperidine]-1'-yl]methanone; cyclobutyl-[6-(3-quinolyl)spiro-[chromene-2,4'-piperidine]-1'-yl]methanone; cyclopropyl-[4-hydroxy-6-(3-quinolyl)-spiro[chromane-2,4'-piperidine]-1'-yl]methanone; 1-[6-(3-quinolyl)spiro[chromane-2,4'-piperidine]-1'-yl]propan-1-one; [6-(3-quinolyl)spiro[4H-1,3-benzodioxine-2,4'-piperidine]-1'-yl]-[(2R)-tetrahydrofuran-2-yl]methanone; cyclopropyl-[6-(8-methoxy-7-quinolyl)spiro[4H-1,3-benzodioxine-2,4'- piperidine]-1'-yl]methanone; [6-(8-methyl-7-quinolyl)spiro[4H-1,3-benzodioxine-2,4'-piperidine]-1'-yl]-[(2R)-tetrahydrofuran-2-yl]methanone; 6-(4-methyl-3-quinolyl)spiro[4H-1,3-benzodioxine-2,4'-piperidine]-1'-yl]-[(2R)-tetrahydrofuran-2-yl]methanone; 1-[6-(4-methyl-3-quinolyl)spiro[4H-1,3-benzodioxine-2,4'-piperidine]-1'-yl]propan-1-one; 1-[6-(8-methyl-7-quinolyl)spiro[4H-1,3-benzodioxine-2,4'-piperidine]-1'-yl]propan-1-one; cyclopropyl-[6-(8-methyl-7-quinolyl)spiro[4H-1,3-benzodioxine-2,4'-piperidine]-1'-yl]methanone; 1-[6-(8-methoxy-7-quinolyl)spiro[4H-1,3-benzodioxine-2,4'-piperidine]-1'-yl]propan-1-one; [6-(8-methoxy-7-quinolyl)spiro[4H-1,3-benzodioxine-2,4'-piperidine]-1'-yl]-[(2R)-tetrahydrofuran-2-yl]methanone; 1-[6-(8-chloro-7-quinolyl)spiro[4H-1,3-benzodioxine-2,4'-piperidine]-1'-yl]propan-1-one; [6-(8-chloro-7-quinolyl)spiro[4H-1,3-benzodioxine-2,4'-piperidine]-1'-yl]-cyclopropyl-methanone; [6-(8-chloro-7-quinolyl)spiro[4H-1,3-benzodioxine-2,4'-piperidine]-1'-yl]-[(2R)-tetrahydrofuran-2-yl]methanone; [2-[6-(8-methyl-7-quinolyl)spiro[4H-1,3-benzodioxine-2,4'-piperidine]-1'-yl]-2-oxo-ethyl]acetate; 2-hydroxy-1-[6-(8-methyl-7-quinolyl)spiro[chromane-2,4'-piperidine]-1'-yl]ethanone; 2-hydroxy-1-[6-(8-methyl-7-quinolyl)spiro[4H-1,3-benzodioxine-2,4'-piperidine]-1'-yl]ethanone; 6-(8-chloro-7-quinolyl)spiro[chromane-2,4'-piperidine]-1'-carboxamide; [2-[6-(8-chloro-7-quinolyl)spiro[chromane-2,4'-piperidine]-1'-yl]-2-oxo-ethyl]acetate; 6-(8-chloro-7-quinolyl)-N-tetrahydropyran-2-yloxy-spiro[chromane-2,4'-piperidine]-1'-carboxamide; 6-(8-chloro-7-quinolyl)-N-ethyl-spiro[chromane-2,4'-piperidine]-1'-carboxamide; 1-[6-(8-chloro-7-quinolyl)spiro[chromane-2,4'-piperidine]-1'-yl]-2-hydroxy-ethanone; 6-(8-chloro-7-quinolyl)spiro[chromane-2,4'-piperidine]-1'-carbohydroxamic acid; 6-(8-chloro-7-quinolyl)-N-ethoxy-spiro[chromane-2,4'-piperidine]-1'-carboxamide; 6-(8-chloro-7-quinolyl)-N-methoxy-spiro[chromane-2,4'-piperidine]-1'-carboxamide; 6-(3-quinolyl)spiro[chromane-2,4'-piperidine]-1'-carboxamide; 6-(benzofuran-5-yl)spiro[chromane-2,4'-piperidine]-1'-carboxamide; 6-(1,3-benzothiazol-6-yl)spiro[chromane-2,4'-piperidine]-1'-carboxamide; 6-(1-methylindol-5-yl)spiro[chromane-2,4'-piperidine]-1'-carboxamide; 6-(1H-indol-5-yl)spiro[chromane-2,4'-piperidine]-1'-carboxamide; 7-(8-methyl-7-quinolyl)spiro[4,5-dihydro-1,3-benzodioxepine-2,4'-piperidine]-1'-carboxamide; N-ethyl-7-(8-methyl-7-quinolyl)spiro[4,5-dihydro-1,3-benzodioxepine-2,4'-piperidine]-1'-carboxamide; N-ethoxy-7-(8-methyl-7-quinolyl)spiro[4,5-dihydro-1,3-benzodioxepine-2,4'-piperidine]-1'-carboxamide; N-methoxy-7-(8-methyl-7-quinolyl)spiro[4,5-dihydro-1,3-benzodioxepine-2,4'-piperidine]-1'-carboxamide; 6-(1-methylbenzimidazol-5-yl)spiro[chromane-2,4'-piperidine]-1'-carboxamide; 6-(1-methylbenzimidazol-5-yl)spiro[4H-1,3-benzodioxine-2,4'-piperidine]-1'-carboxamide; 6-(1,3-benzothiazol-5-yl)spiro[chromane-2,4'-piperidine]-1'-carboxamide; 6-thieno[2,3-b]pyridin-5-ylspiro[chromane-2,4'-piperidine]-1'-carboxamide; 6-(1,3-benzoxazol-5-yl)spiro[chromane-2,4'-piperidine]-1'-carboxamide; 6-(1,3-benzoxazol-6-yl)spiro[chromane-2,4'-piperidine]-1'-carboxamide; 6-thieno[2,3-b]pyridin-5-ylspiro[4H-1,3-benzodioxine-2,4'-piperidine]-1'-carboxamide; 6-(1,8-naphthyridin-3-yl)spiro[chromane-2,4'-piperidine]-1'-carboxamide; tert-butyl 3-(1'-carbamoylspiro[chromane-2,4'-piperidine]-6-yl)indole-1-carboxylate; 6-(1H-indol-3-yl)spiro[chromane-2,4'-piperidine]-1'-carboxamide; 6-(1H-indol-3-yl)spiro[4H-1,3-benzodioxine-2,4'-piperidine]-1'-carboxamide; N-isobutyl-6-(8-methyl-7-quinolyl)spiro[chromane-2,4'-piperidine]-1'-carboxamide; N-ethyl-6-(8-methyl-7-quinolyl)spiro[chromane-2,4'-piperidine]-1'-carboxamide; N-isopropyl-6-(8-methyl-7-quinolyl)spiro[chromane-2,4'-piperidine]-1'-carboxamide; 6-(8-methyl-7-quinolyl)-N-propyl-spiro[chromane-2,4'-piperidine]-1'-carboxamide; N-(cyclopropylmethyl)-6-(8-methyl-7-quinolyl)spiro[chromane-2,4'-piperidine]-1'-carboxamide; N-ethoxy-6-(8-methyl-7-quinolyl)spiro[chromane-2,4'-piperidine]-1'-carboxamide; 6-(8-methyl-7-quinolyl)-N-propoxy-spiro[chromane-2,4'-piperidine]-1'-carboxamide; N-isopropoxy-6-(8-methyl-7-quinolyl)spiro-[chromane-2,4'-piperidine]-1'-carboxamide; N-isobutoxy-6-(8-methyl-7-quinolyl)spiro-[chromane-2,4'-piperidine]-1'-carboxamide; 6-(8-methyl-7-quinolyl)spiro[chromane-2,4'-piperidine]-1'-carbohydroxamic acid; 6-(8-methyl-7-quinolyl)spiro[chromane-2,4'-piperidine]-1'-carboxamide; N-ethoxy-6-(5-methylimidazo[1,2-a]pyridin-6-yl)spiro[chromane-2,4'-piperidine]-1'-carboxamide; N-isopropoxy-6-(5-methylimidazo[1,2-a]pyridin-6-yl)spiro[chromane-2,4'-piperidine]-1'-carboxamide; 6-(5-methylimidazo[1,2-a]pyridin-6-yl)spiro[chromane-2,4'-piperidine]-1'-carboxamide; N-ethyl-6-(5-methylimidazo[1,2-a]pyridin-6-yl)spiro[chromane-2,4'-piperidine]-1'-carboxamide; N-isopropyl-6-(5-methylimidazo[1,2-a]pyridin-6-yl)spiro[chromane-2,4'-piperidine]-1'-carboxamide; N-ethyl-6-(7-methylpyrazolo[1,5-a]pyridin-6-yl)spiro[chromane-2,4'-piperidine]-1'-carboxamide; N-isopropyl-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carboxamide; N-ethoxy-6-(7-methylpyrazolo[1,5-a]pyridin-6-yl)spiro[chromane-2,4'-piperidine]-1'-carboxamide; N-isopropoxy-6-(7-methylpyrazolo[1,5-a]pyridin-6-yl)spiro[chromane-2,4'-piperidine]-1'-carboxamide; N-ethyl-6-(8-methyl-7-quinolyl)spiro[4H-1,3-benzodioxine-2,4'-piperidine]-1'-carboxamide; 6-(8-methyl-7-quinolyl)spiro[4H-1,3-benzodioxine-2,4'-piperidine]-1'-carboxamide; N-isopropyl-6-(8-methyl-7-quinolyl)spiro[4H-1,3-benzodioxine-2,4'-piperidine]-1'-carboxamide; N-methoxy-6-(8-methyl-7-quinolyl)spiro[chromane-2,4'-piperidine]-1'-carboxamide; N-ethoxy-6-(8-methyl-7-quinolyl)spiro[4H-1,3-benzodioxine-2,4'-piperidine]-1'-carboxamide; N-methoxy-6-(8-methyl-7-quinolyl)spiro[4H-1,3-benzodioxine-2,4'-piperidine]-1'-carboxamide; N-isopropoxy-6-(8-methyl-7-quinolyl)spiro[4H-1,3-benzodioxine-2,4'-piperidine]-1'-carboxamide; N-methoxy-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carbohydroxamic acid; N-ethyl-6-(7-methylpyrazolo[1,5-a]pyridin-6-yl)spiro[4H-1,3-benzodioxine-2,4'-piperidine]-1'-carboxamide; 6-(7-methylpyrazolo[1,5-a]pyridin-6-yl)spiro[4H-1,3-benzodioxine-2,4'-piperidine]-1'-carboxamide; N-methoxy-6-(7-methylpyrazolo[1,5-a]pyridin-6-yl)spiro[4H-1,3-benzodioxine-2,4'-piperidine]-1'-carboxamide; N-ethoxy-6-(7-methylpyrazolo[1,5-a]pyridin-6-yl)spiro[4H-1,3-benzodioxine-2,4'-piperidine]-1'-carboxamide; N-isopropoxy-6-(7-methylpyrazolo[1,5-a]pyridin-6-yl)spiro[4H-1,3-benzodioxine-2,4'-piperidine]-1'-carboxamide; 6-(8-chloro-7-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carboxamide; N-methoxy-6-(4-methyl-3-quinolyl)spiro[4H-1,3-benzodioxine-2,4'-piperidine]-1'-carboxamide; 6-(8-chloro-7-quinolyl)-N-methoxy-spiro[4H-1,3-benzodioxine-2,4'-piperidine]-1'-carboxamide; 6-(8-chloro-7-quinolyl)-N-ethoxy-spiro[4H-1,3-benzodioxine-2,4'-piperidine]-1'-carboxamide; 6-(8-chloro-7-quinolyl)spiro[4H-1,3- benzodioxine-2,4'-piperidine]-1'-carbohydroxamic acid; N-ethoxy-6-(4-methyl-3-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carbohydroxamic acid; 6-(5-methylimidazo[1,2-a]pyridin-6-yl) spiro[chromane-2,4'-piperidine]-1'-carbohydroxamic acid; 6-(3-isoquinolyl)spiro[4H-1,3-benzodioxine-2,4'-piperidine]-1'-carboxamide; 6-(3-isoquinolyl)spiro[chromane-2,4'-piperidine]-1'-carboxamide; 6-(3-isoquinolyl)-N-tetrahydropyran-2-yloxy-spiro[4H-1,3-benzodioxine-2,4'-piperidine]-1'-carboxamide; N-ethoxy-6-(3-isoquinolyl)spiro[4H-1,3-benzodioxine-2,4'-piperidine]-1'-carboxamide; 6-(3-isoquinolyl)-N-tetrahydropyran-2-yloxy-spiro[chromane-2,4'-piperidine]-1'-carboxamide; 6-(3-isoquinolyl)-N-methoxy-spiro[4H-1,3-benzodioxine-2,4'-piperidine]-1'-carboxamide; 6-(3-isoquinolyl)-N-methoxy-spiro[chromane-2,4'-piperidine]-1'-carboxamide; N-ethoxy-6-(3-isoquinolyl)spiro[chromane-2,4'-piperidine]-1'-carboxamide; 6-(3-isoquinolyl)spiro-[4H-1,3-benzodioxine-2,4'-piperidine]-1'-carbohydroxamic acid; 6-(3-isoquinolyl)spiro-[chromane-2,4'-piperidine]-1'-carbohydroxamic acid; 5-(8-methyl-7-quinolyl)spiro[3H-benzofuran-2,4'-piperidine]-1'-carboxamide; N-methoxy-5-(8-methyl-7-quinolyl)spiro[3H-benzofuran-2,4'-piperidine]-1'-carboxamide; N-ethoxy-5-(8-methyl-7-quinolyl)spiro[3H-benzofuran-2,4'-piperidine]-1'-carboxamide; 5-(8-methyl-7-quinolyl)spiro[3H-benzofuran-2,4'-piperidine]-1'-carbohydroxamic acid; N-ethyl-5-(8-methyl-7-quinolyl)spiro[3H-benzofuran-2,4'-piperidine]-1'-carboxamide; N-methoxy-5-(4-methyl-3-quinolyl)spiro[3H-benzofuran-2,4'-piperidine]-1'-carboxamide; N-ethoxy-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carboxamide; N-ethyl-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carbohydroxamic acid; 5-(8-methoxy-7-quinolyl)spiro[3H-benzofuran-2,4'-piperidine]-1'-carboxamide; N-ethyl-5-(8-methoxy-7-quinolyl)spiro[3H-benzofuran-2,4'-piperidine]-1'-carboxamide; 5-(7-methylpyrazolo[1,5-a]pyridin-6-yl)spiro[3H-benzofuran-2,4'-piperidine]-1'-carboxamide; N-ethyl-5-(7-methylpyrazolo[1,5-a]pyridin-6-yl)spiro[3H-benzofuran-2,4'-piperidine]-1'-carboxamide; N-methoxy-5-(8-methoxy-7-quinolyl)spiro[3H-benzofuran-2,4'-piperidine]-1'-carboxamide; N-ethoxy-5-(8-methoxy-7-quinolyl)spiro[3H-benzofuran-2,4'-piperidine]-1'-carboxamide; 5-(8-methoxy-7-quinolyl)-N-tetrahydropyran-2-yloxy-spiro[3H-benzofuran-2,4'-piperidine]-1'-carboxamide; N-ethoxy-5-(7-methylpyrazolo[1,5-a]pyridin-6-yl)spiro[3H-benzofuran-2,4'-piperidine]-1'-carboxamide; N-methoxy-5-(7-methylpyrazolo[1,5-a]pyridin-6-yl)spiro[3H-benzofuran-2,4'-piperidine]-1'-carboxamide; 5-(7-methylpyrazolo[1,5-a]pyridin-6-yl)-N-tetrahydropyran-2-yloxy-spiro[3H-benzofuran-2,4'-piperidine]-1'-carboxamide; 6-(8-methyl-2-oxo-1H-quinolin-7-yl)spiro[chromane-2,4'-piperidine]-1'-carboxamide; 5-(8-methoxy-7-quinolyl)spiro[3H-benzofuran-2,4'-piperidine]-1'-carbohydroxamic acid; 6-(8-methoxy-7-quinolyl)spiro[4H-1,3-benzodioxine-2,4'-piperidine]-1'-carboxamide; 6-(8-methoxy-7-quinolyl)spiro[chromane-2,4'-piperidine]-1'-carboxamide; 6-(5-chloroimidazo[1,2-a]pyridin-6-yl)-N-isobutyl-spiro[chromane-2,4'-piperidine]-1'-carboxamide; N-isobutyl-6-(1-methyl-6-isoquinolyl)spiro[chromane-2,4'-piperidine]-1'-carboxamide; N-isopropoxy-6-(1-methyl-6-isoquinolyl)spiro[chromane-2,4'-piperidine]-1'-carboxamide; N-ethoxy-6-(4-methyl-3-quinolyl)spiro[chromane-2,4'-piperidine]-1'-carboxamide; N-isopropoxy-6-(1-methyl-6-isoquinolyl)spiro[4H-1,3-benzodioxine-2,4'-piperidine]-1'-carboxamide; 6-(1-methyl-6-isoquinolyl)spiro[chromane-2,4'-piperidine]-1'-carboxamide; N-methoxy-6-(1-methyl-6-isoquinolyl)spiro[chromane-2,4'-piperidine]-1'-carboxamide; N-ethoxy-6-(1-methyl-6-isoquinolyl)spiro[chromane-2,4'-piperidine]-1'-carboxamide; 6-(1-methyl-6-isoquinolyl)-N-propoxy-spiro[chromane-2,4'-piperidine]-1'-carboxamide; N-ethyl-6-(1-methyl-6-isoquinolyl)spiro[chromane-2,4'-piperidine]-1'-carboxamide; 6-(1-methyl-6-isoquinolyl)-N-propyl-spiro[chromane-2,4'-piperidine]-1'-carboxamide; 6-(1-methyl-6-iso-quinolyl)spiro[chromane-2,4'-piperidine]-1'-carbohydroxamic acid; 6-(4-methyl-3-quinolyl)-spiro[chromane-2,4'-piperidine]-1'-carboxamide; 6-(4-methyl-3-quinolyl)spiro[chromane-2,4'-piperidine]-1'-carbohydroxamic acid; N-methoxy-6-(4-methyl-3-quinolyl)spiro[chromane-2,4'-piperidine]-1'-carboxamide; N-isopropoxy-6-(4-methyl-3-quinolyl)spiro[chromane-2,4'-piperidine]-1'-carboxamide; 6-(1-methyl-6-isoquinolyl)spiro[4H-1,3-benzodioxine-2,4'-piperidine]-1'-carboxamide; N-methoxy-6-(1-methyl-6-isoquinolyl)spiro[4H-1,3-benzodioxine-2,4'-piperidine]-1'-carboxamide; N-ethoxy-6-(1-methyl-6-isoquinolyl)spiro[4H-1,3-benzodioxine-2,4'-piperidine]-1'-carboxamide; N-ethyl-6-(1-methyl-6-isoquinolyl)spiro[4H-1,3-benzodioxine-2,4'-piperidine]-1'-carboxamide; 6-(1-methyl-6-isoquinolyl)spiro[4H-1,3-benzodioxine-2,4'-piperidine]-1'-carbohydroxamic acid; 6-(3-methyl-6-isoquinolyl)spiro[4H-1,3-benzodioxine-2,4'-piperidine]-1'-carboxamide; N-ethyl-6-(3-methyl-6-isoquinolyl)spiro[4H-1,3-benzodioxine-2,4'-piperidine]-1'-carboxamide; N-ethoxy-6-(3-methyl-6-isoquinolyl)spiro[4H-1,3-benzodioxine-2,4'-piperidine]-1'-carboxamide; 6-(3-methyl-6-isoquinolyl)spiro[4H-1,3-benzodioxine-2,4'-piperidine]-1'-carbohydroxamic acid; N-methoxy-6-(3-methyl-6-isoquinolyl)spiro[4H-1,3-benzodioxine-2,4'-piperidine]-1'-carboxamide; 6-(3-methyl-6-isoquinolyl)spiro[chromane-2,4'-piperidine]-1'-carboxamide; N-ethoxy-6-(3-methyl-6-isoquinolyl)spiro[chromane-2,4'-piperidine]-1'-carboxamide; N-ethyl-6-(3-methyl-6-isoquinolyl)spiro[chromane-2,4'-piperidine]-1'-carboxamide; N-methoxy-6-(3-methyl-6-isoquinolyl)spiro[chromane-2,4'-piperidine]-1'-carboxamide; N-methoxy-6-(8-methoxy-7-quinolyl)spiro[chromane-2,4'-piperidine]-1'-carboxamide; N-ethoxy-6-(8-methoxy-7-quinolyl)spiro[chromane-2,4'-piperidine]-1'-carboxamide; 6-(8-methyl-7-quinolyl)-4-oxo-spiro[chromane-2,4'-piperidine]-1'-carboxamide; 4-hydroxy-6-(8-methyl-7-quinolyl)spiro[chromane-2,4'-piperidine]-1'-carboxamide; 4-fluoro-6-(8-methyl-7-quinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 6-(Benzofuran-2-yl)spiro[chromane-2,4'-piperidine]-1'-carboxamide; 6-(1H-Indol-2-yl)spiro[chromane-2,4'-piperidine]-1'-carboxamide; 8-Fluoro-6-(8-methyl-7-quinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(1-methyl-6-isoquinolyl)spiro[chromane-2,4'-piperidine]-1' carboxamide; 5-Methyl-6-(8-methyl-7-quinolyl)spiro[chromane-2,4'-piperidine]-1'-carboxamide; 5-methyl-6-(1-methyl-6-isoquinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(8-methyl-7-quinolyl)spiro[chromane-2,4'-piperidine]-1'-carboxamide; 7-Methyl-6-(8-methyl-7-quinolyl)spiro[chromane-2,4'-piperidine]-1'-carboxamide; N-methoxy-7- methyl-6-(8-methyl-7-quinolyl)spiro[chromane-2,4'-piperidine]-1'-carboxamide; N-Methoxy-7-methyl-6-(1-methyl-6-isoquinolyl)spiro[chromane-2,4'-piperidine]-1'-carboxamide; 8-chloro-6-(8-methyl-7-quinolyl)spiro[chromane-2,4'-piperidine]-1'-carboxamide; 8-Chloro-N-methoxy-6-(8-methyl-7-quinolyl)spiro[chromane-2,4'-piperidine]-1'-carboxamide; 6-(4-Hydroxy-8-methyl-7-quinolyl)spiro[chromane-2,4'-piperidine]-1'-carboxamide; and salts of such compounds, e.g., pharmaceutically acceptable salts.

Compounds according to Formula IB may include for example: [6-(1-methyl-6-isoquinolyl)spiro[chromane-2,4'-piperidine]-1'-yl]-[(2R)-tetrahydrofuran-2-yl]methanone; 1-[6-(4-methyl-3-quinolyl)spiro[chromane-2,4'-piperidine]-1'-yl]propan-1-one; cyclopropyl-[6-(4-methyl-3-quinolyl)spiro[chromane-2,4'-piperidine]-1'-yl]¬methanone; [6-(4-methyl-3-quinolyl)spiro[chromane-2,4'-piperidine]-1'-yl]-[(2R)-tetrahydrofuran-2-yl]methanone; [6-(1-cyclopropyl-6-isoquinolyl)spiro[chromane-2,4'-piperidine]-1'-yl]-[(2R)-tetrahydrofuran-2-yl]methanone; 1-[6-(8-methyl-7-quinolyl)spiro[chromane-2,4'-piperidine]-1'-yl]propan-1-one; cyclopropyl-[6-(8-methyl-7-quinolyl)spiro[chromane-2,4'-piperidine]-1'-yl]methanone; [6-(8-methyl-7-quinolyl)spiro[chromane-2,4'-piperidine]-1'-yl]-[(2R)-tetrahydrofuran-2-yl]methanone; 1-[6-(8-chloro-7-quinolyl)spiro[chromane-2,4'-piperidine]-1'-yl]propan-1-one; [6-(8-chloro-7-quinolyl)spiro[chromane-2,4'-piperidine]-1'-yl]-cyclopropylmethanone; [6-(8-chloro-7-quinolyl)spiro[chromane-2,4'-piperidine]-1'-yl]-[(2R)-tetrahydrofuran-2-yl]methanone; 1-[6-(8-methyl-3-quinolyl)spiro[chromane-2,4'-piperidine]-1'-yl]propan-1-one; cyclopropyl-[6-(8-methyl-3-quinolyl)spiro[chromane-2,4'-piperidine]-1'-yl]¬methanone; [6-(8-methyl-3-quinolyl)spiro[chromane-2,4'-piperidine]-1'-yl]-[(2R)-tetrahydrofuran-2-yl]methanone; cyclopropyl-[6-(8-methoxy-7-quinolyl)spiro[chromane-2,4'-piperidine]-1'-yl]methanone; [6-(8-methoxy-7-quinolyl)spiro[chromane-2,4'-piperidine]-1'-yl]-[(2R)-tetrahydrofuran-2-yl]methanone; 1-[6-(8-methyl-6-quinolyl)spiro[chromane-2,4'-piperidine]-1'-yl]propan-1-one; cyclopropyl-[6-(8-methyl-6-quinolyl)spiro[chromane-2,4'-piperidine]-1'-yl]methanone; 1-[6-(8-methoxy-7-quinolyl)spiro[chromane-2,4'-piperidine]-1'-yl]propan-1-one; [6-(8-methyl-6-quinolyl)spiro[chromane-2,4'-piperidine]-1'-yl]-[(2R)-tetrahydrofuran-2-yl]methanone; 1-[6-(1-methyl-6-isoquinolyl)spiro[chromane-2,4'-piperidine]-1'-yl]propan-1-one; cyclopropyl-[6-(1-methyl-6-isoquinolyl)spiro[chromane-2,4'-piperidine]-1'-yl]methanone; 1-[6-(5-methylimidazo[1,2-a]pyridin-6-yl)spiro[chromane-2,4'-piperidine]-1'-yl]propan-1-one; cyclopropyl-[6-(5-methylimidazo[1,2-a]pyridin-6-yl)spiro[chromane-2,4'-piperidine]-1'-yl]methanone; [6-(5-methylimidazo[1,2-a]pyridin-6-yl)spiro[chromane-2,4'-piperidine]-1'-yl]-[(2R)-tetrahydrofuran-2-yl]methanone; 1'-propanoyl-6-(3-quinolyl)spiro[chromane-2,4'-piperidine]-4-one; methyl 4-oxo-6-(3-quinolyl)spiro[chromane-2,4'-piperidine]-1'-carboxylate; 1-[4-hydroxy-6-(3-quinolyl)spiro[chromane-2,4'-piperidine]-1'-yl]propan-1-one; cyclopropyl-[4-hydroxy-6-(3-quinolyl)spiro[chromane-2,4'-piperidine]-1'-yl]methanone; 1-[6-(3-quinolyl)-spiro[chromane-2,4'-piperidine]-1'-yl]propan-1-one; 2-hydroxy-1-[6-(8-methyl-7-quinolyl)spiro[chromane-2,4'-piperidine]-1'-yl]-ethanone; 6-(8-chloro-7-quinolyl)spiro-[chromane-2,4'-piperidine]-1'-carboxamide; [2-[6-(8-chloro-7-quinolyl)spiro[chromane-2,4'-piperidine]-1'-yl]-2-oxo-ethyl]acetate; 6-(8-chloro-7-quinolyl)-N-tetrahydropyran-2-yloxy-spiro[chromane-2,4'-piperidine]-1'-carboxamide; 6-(8-chloro-7-quinolyl)-N-ethyl-spiro-[chromane-2,4'-piperidine]-1'-carboxamide; 1-[6-(8-chloro-7-quinolyl)spiro[chromane-2,4'-piperidine]-1'-yl]-2-hydroxy-ethanone; 6-(8-chloro-7-quinolyl)spiro[chromane-2,4'-piperidine]-1'-carbohydroxamic acid; 6-(8-chloro-7-quinolyl)-N-ethoxy-spiro[chromane-2,4'-piperidine]-1'-carboxamide; 6-(8-chloro-7-quinolyl)-N-methoxy-spiro[chromane-2,4'-piperidine]-1'-carboxamide; ethyl 6-(8-chloro-7-quinolyl)spiro[chromane-2,4'-piperidine]-1'-carboxylate; 6-(3-quinolyl)spiro[chromane-2,4'-piperidine]-1'-carboxamide; 6-(benzofuran-5-yl)spiro[chromane-2,4'-piperidine]-1'-carboxamide; 6-(1,3-benzothiazol-6-yl)spiro[chromane-2,4'-piperidine]-1'-carboxamide; 6-(1-methylindol-5-yl)spiro[chromane-2,4'-piperidine]-1'-carboxamide; 6-(1H-indol-5-yl)spiro[chromane-2,4'-piperidine]-1'-carboxamide; 6-(1-methylbenzimidazol-5-yl)spiro[chromane-2,4'-piperidine]-1'-carboxamide; 6-(1,3-benzothiazol-5-yl)spiro[chromane-2,4'-piperidine]-1'-carboxamide; 6-thieno[2,3-b]pyridin-5-ylspiro[chromane-2,4'-piperidine]-1'-carboxamide; 6-(1,3-benzoxazol-5-yl)spiro[chromane-2,4'-piperidine]-1'-carboxamide; 6-(2-naphthyl)spiro[chromane-2,4'-piperidine]-1'-carboxamide; 6-(1,3-benzoxazol-6-yl)spiro[chromane-2,4'-piperidine]-1'-carboxamide; 6-(1,8-naphthyridin-3-yl)spiro[chromane-2,4'-piperidine]-1'-carboxamide; tert-butyl 3-(1'-carbamoylspiro[chromane-2,4'-piperidine]-6-yl)indole-1-carboxylate; 6-(1H-indol-3-yl)spiro[chromane-2,4'-piperidine]-1'-carboxamide; N-isobutyl-6-(8-methyl-7-quinolyl)spiro[chromane-2,4'-piperidine]-1'-carboxamide; N-ethyl-6-(8-methyl-7-quinolyl)spiro[chromane-2,4'-piperidine]-1'-carboxamide; N-isopropyl-6-(8-methyl-7-quinolyl)spiro[chromane-2,4'-piperidine]-1'-carboxamide; 6-(8-methyl-7-quinolyl)-N-propyl-spiro[chromane-2,4'-piperidine]-1'-carboxamide; N-(cyclopropylmethyl)-6-(8-methyl-7-quinolyl)spiro[chromane-2,4'-piperidine]-1'-carboxamide; N-ethoxy-6-(8-methyl-7-quinolyl)spiro[chromane-2,4'-piperidine]-1'-carboxamide; 6-(8-methyl-7-quinolyl)-N-propoxy-spiro[chromane-2,4'-piperidine]-1'-carboxamide; N-isopropoxy-6-(8-methyl-7-quinolyl)spiro[chromane-2,4'-piperidine]-1'-carboxamide; N-isobutoxy-6-(8-methyl-7-quinolyl)spiro[chromane-2,4'-piperidine]-1'-carboxamide; 6-(8-methyl-7-quinolyl)spiro[chromane-2,4'-piperidine]-1'-carbohydroxamic acid; 6-(8-methyl-7-quinolyl)spiro[chromane-2,4'-piperidine]-1'-carboxamide; N-ethoxy-6-(5-methylimidazo[1,2-a]pyridin-6-yl)spiro[chromane-2,4'-piperidine]-1'-carboxamide; N-isopropoxy-6-(5-methylimidazo[1,2-a]pyridin-6-yl)spiro[chromane-2,4'-piperidine]-1'-carboxamide; 6-(5-methylimidazo[1,2-a]pyridin-6-yl)spiro[chromane-2,4'-piperidine]-1'-carboxamide; N-ethyl-6-(5-methylimidazo[1,2-a]pyridin-6-yl)spiro[chromane-2,4'-piperidine]-1'-carboxamide; N-isopropyl-6-(5-methylimidazo[1,2-a]pyridin-6-yl)spiro[chromane-2,4'-piperidine]-1'-carboxamide; N-ethyl-6-(7-methylpyrazolo[1,5-a]pyridin-6-yl)spiro[chromane-2,4'-piperidine]-1'-carboxamide; N-isopropyl-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carboxamide; N-ethoxy-6-(7-methylpyrazolo[1,5-a]pyridin-6-yl)spiro[chromane-2,4'-piperidine]-1'-carboxamide; N-isopropoxy-6-(7-methylpyrazolo[1,5-a]pyridin-6-yl)spiro[chromane-2,4'-piperidine]-1'-carboxamide; N-methoxy-6-(8-methyl-7-quinolyl)spiro[chromane-2,4'-piperidine]-1'-carboxamide; N-methoxy-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carbohydroxamic acid; 6-(5-methylimidazo[1,2-a]pyridin-6-yl)spiro[chromane-2,4'-piperidine]-1'-carbohydroxamic acid; 6-(3-isoquinolyl)spiro[chromane-2,4'-piperidine]-1'-carboxamide; 6-(3- isoquinolyl)-N-tetrahydropyran-2-yloxy-spiro[chromane-2,4'-piperidine]-1'-carboxamide; 6-(3-isoquinolyl)-N-methoxy-spiro[chromane-2,4'-piperidine]-1'-carboxamide; N-ethoxy-6-(3-isoquinolyl)spiro[chromane-2,4'-piperidine]-1'-carboxamide; 6-(3-isoquinolyl)spiro[chromane-2,4'-piperidine]-1'-carbohydroxamic acid; 6-(8-methyl-2-oxo-1H-quinolin-7-yl)spiro[chromane-2,4'-piperidine]-1'-carboxamide; 5-(8-methoxy-7-quinolyl)spiro[3H-benzofuran-2,4'-piperidine]-1'-carbohydroxamic acid; 6-(8-methoxy-7-quinolyl)spiro[chromane-2,4'-piperidine]-1'-carboxamide; 6-(5-chloroimidazo[1,2-a]pyridin-6-yl)-N-isobutyl-spiro[chromane-2,4'-piperidine]-1'-carboxamide; N-isobutyl-6-(1-methyl-6-isoquinolyl)spiro[chromane-2,4'-piperidine]-1'-carboxamide; 6-(5-chloroimidazo[1,2-a]pyridin-6-yl)-N-isopropoxy-spiro[chromane-2,4'-piperidine]-1'-carboxamide; N-isopropoxy-6-(1-methyl-6-iso-quinolyl)spiro[chromane-2,4'-piperidine]-1'-carboxamide; N-ethoxy-6-(4-methyl-3-quinolyl)spiro[chromane-2,4'-piperidine]-1'-carboxamide; 6-(1-methyl-6-isoquinolyl)spiro-[chromane-2,4'-piperidine]-1'-carboxamide; N-methoxy-6-(1-methyl-6-isoquinolyl)spiro-[chromane-2,4'-piperidine]-1'-carboxamide; N-ethoxy-6-(1-methyl-6-isoquinolyl)spiro-[chromane-2,4'-piperidine]-1'-carboxamide; 6-(1-methyl-6-isoquinolyl)-N-propoxy-spiro-[chromane-2,4'-piperidine]-1'-carboxamide; N-ethyl-6-(1-methyl-6-isoquinolyl)spiro[chromane-2,4'-piperidine]-1'-carboxamide; 6-(1-methyl-6-isoquinolyl)-N-propyl-spiro[chromane-2,4'-piperidine]-1'-carboxamide; 6-(1-methyl-6-isoquinolyl)spiro[chromane-2,4'-piperidine]-1'-carbohydroxamic acid; 6-(4-methyl-3-quinolyl)spiro[chromane-2,4'-piperidine]-1'-carboxamide; 6-(4-methyl-3-quinolyl)spiro[chromane-2,4'-piperidine]-1'-carbohydroxamic acid; N-methoxy-6-(4-methyl-3-quinolyl)spiro[chromane-2,4'-piperidine]-1'-carboxamide; N-isopropoxy-6-(4-methyl-3-quinolyl)spiro[chromane-2,4'-piperidine]-1'-carboxamide; 6-(3-methyl-6-isoquinolyl)spiro[chromane-2,4'-piperidine]-1'-carboxamide; N-ethoxy-6-(3-methyl-6-isoquinolyl)spiro[chromane-2,4'-piperidine]-1'-carboxamide; N-ethyl-6-(3-methyl-6-isoquinolyl)spiro[chromane-2,4'-piperidine]-1'-carboxamide; N-methoxy-6-(3-methyl-6-isoquinolyl)spiro[chromane-2,4'-piperidine]-1'-carboxamide; N-methoxy-6-(8-methoxy-7-quinolyl)spiro[chromane-2,4'-piperidine]-1'-carboxamide; N-ethoxy-6-(8-methoxy-7-quinolyl)spiro[chromane-2,4'-piperidine]-1'-carboxamide; 6-(8-methyl-7-quinolyl)-4-oxo-spiro[chromane-2,4'-piperidine]-1'-carboxamide; 4-hydroxy-6-(8-methyl-7-quinolyl)spiro[chromane-2,4'-piperidine]-1'-carboxamide; 4-fluoro-6-(8-methyl-7-quinolyl)spiro[chromane-2,4'-piperidine]-1'-carboxamide; 1-[6-(2-pyridyl)spiro[chromane-2,4'-piperidine]-1'-yl]propan-1-one; cyclopropyl-[6-(2-pyridyl)spiro[chromane-2,4'-piperidine]-1'-yl]-methanone; [6-(2-pyridyl)spiro[chromane-2,4'-piperidine]-1'-yl]-[(2R)-tetrahydrofuran-2-yl]methanone; 1-[6-(3-pyridyl)spiro[chromane-2,4'-piperidine]-1'-yl]propan-1-one; cyclopropyl-[6-(3-pyridyl)spiro[chromane-2,4'-piperidine]-1'-yl]methanone; [6-(3-pyridyl)spiro[chromane-2,4'-piperidine]-1'-yl]-[(2R)-tetrahydrofuran-2-yl]methanone; 1-[6-(4-pyridyl)spiro[chromane-2,4'-piperidine]-1'-yl]propan-1-one; cyclopropyl-[6-(4-pyridyl)spiro[chromane-2,4'-piperidine]-1'-yl]methanone; [6-(4-pyridyl)spiro[chromane-2,4'-piperidine]-1'-yl]-[(2R)-tetrahydrofuran-2-yl]methanone; 7-Fluoro-6-(1-methyl-6-isoquinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 6-(Benzofuran-2-yl)spiro[chromane-2,4'-piperidine]-1'-carboxamide; 6-(1H-Indol-2-yl)spiro[chromane-2,4'-piperidine]-1'-carboxamide; 8-Fluoro-6-(8-methyl-7-quinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(1-methyl-6-isoquinolyl)spiro[chromane-2,4'-piperidine]-1'-carboxamide; 5-Methyl-6-(8-methyl-7-quinolyl)spiro[chromane-2,4'-piperidine]-1'-carboxamide; 5-methyl-6-(1-methyl-6-isoquinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(8-methyl-7-quinolyl)spiro[chromane-2,4'-piperidine]-1'-carboxamide; 7-Methyl-6-(8-methyl-7-quinolyl)spiro[chromane-2,4'-piperidine]-1'-carboxamide; N-methoxy-7-methyl-6-(8-methyl-7-quinolyl)spiro[chromane-2,4'-piperidine]-1'-carboxamide; N-Methoxy-7-methyl-6-(1-methyl-6-isoquinolyl)spiro[chromane-2,4'-piperidine]-1'-carboxamide; 8-chloro-6-(8-methyl-7-quinolyl)spiro[chromane-2,4'-piperidine]-1'-carboxamide; 8-Chloro-N-methoxy-6-(8-methyl-7-quinolyl)spiro[chromane-2,4'-piperidine]-1'-carboxamide; 6-(4-Hydroxy-8-methyl-7-quinolyl)spiro[chromane-2,4'-piperidine]-1'-carboxamide; and salts of such compounds, e.g., pharmaceutically acceptable salts.

Compounds according to Formula IC may include for example: 1-[6-(1-methyl-6-isoquinolyl)spiro[4H-1,3-benzodioxine-2,4'-piperidine]-1'-yl]propan-1-one; cyclopropyl-[6-(1-methyl-6-isoquinolyl)spiro[4H-1,3-benzodioxine-2,4'-piperidine]-1'-yl]methanone; [6-(1-methyl-6-isoquinolyl)spiro[4H-1,3-benzodioxine-2,4'-piperidine]-1'-yl]-[(2R)-tetrahydrofuran-2-yl]methanone; 1-[6-(3-quinolyl)spiro[4H-1,3-benzodioxine-2,4'-piperidine]-1'-yl]propan-1-one; ethyl 6-(7-quinolyl)spiro[4H-1,3-benzodioxine-2,4'-piperidine]-1'-carboxylate; 2-methyl-1-[6-(7-quinolyl)spiro[4H-1,3-benzodioxine-2,4'-piperidine]-1'-yl]-propan-1-one; cyclopropyl-[6-(7-quinolyl)spiro[4H-1,3-benzodioxine-2,4'-piperidine]-1'-yl]-methanone; 1-[6-(3-quinolyl)spiro[4H-1,3-benzodioxine-2,4'-piperidine]-1'-yl]propan-1-one; 2-methyl-1-[6-(3-quinolyl)spiro[4H-1,3-benzodioxine-2,4'-piperidine]-1'-yl]propan-1-one; ethyl 6-(1,5-naphthyridin-3-yl)spiro[4H-1,3-benzodioxine-2,4'-piperidine]-1'-carboxylate; 1-[6-(1,5-naphthyridin-3-yl)spiro[4H-1,3-benzodioxine-2,4'-piperidine]-1'-yl]propan-1-one; cyclopropyl-[6-(1,5-naphthyridin-3-yl)spiro[4H-1,3-benzodioxine-2,4'-piperidine]-1'-yl]methanone; cyclopropyl-[6-(3-quinolyl)spiro[4H-1,3-benzodioxine-2,4'-piperidine]-1'-yl]methanone; cyclobutyl-[6-(3-quinolyl)spiro[4H-1,3-benzodioxine-2,4'-piperidine]-1'-yl]methanone; [6-(3-quinolyl)spiro[4H-1,3-benzodioxine-2,4'-piperidine]-1'-yl]-[(2R)-tetrahydrofuran-2-yl]methanone; cyclopropyl-[6-(8-methoxy-7-quinolyl)spiro[4H-1,3-benzodioxine-2,4'-piperidine]-1'-yl]methanone; [6-(8-methyl-7-quinolyl)spiro[4H-1,3-benzodioxine-2,4'-piperidine]-1'-yl]-[(2R)-tetrahydrofuran-2-yl]methanone; 6-(4-methyl-3-quinolyl)spiro[4H-1,3-benzodioxine-2,4'-piperidine]-1'-yl]-[(2R)-tetrahydrofuran-2-yl]methanone; 1-[6-(4-methyl-3-quinolyl)spiro[4H-1,3-benzodioxine-2,4'-piperidine]-1'-yl]propan-1-one; 1-[6-(8-methyl-7-quinolyl)spiro[4H-1,3-benzodioxine-2,4'-piperidine]-1'-yl]propan-1-one; cyclopropyl-[6-(8-methyl-7-quinolyl)spiro[4H-1,3-benzodioxine-2,4'-piperidine]-1'-yl]methanone; 1-[6-(8-methoxy-7-quinolyl)spiro[4H-1,3-benzodioxine-2,4'-piperidine]-1'-yl]propan-1-one; [6-(8-methoxy-7-quinolyl)spiro[4H-1,3-benzodioxine-2,4'-piperidine]-1'-yl]-[(2R)-tetrahydrofuran-2-yl]methanone; 1-[6-(8-chloro-7-quinolyl)spiro[4H-1,3-benzodioxine-2,4'-piperidine]-1'-yl]propan-1-one; [6-(8-chloro-7-quinolyl)spiro[4H-1,3-benzodioxine-2,4'-piperidine]-1'-yl]-cyclopropyl-methanone; [6-(8-chloro-7-quinolyl)spiro[4H-1,3-benzodioxine-2,4'-piperidine]-1'-yl]-

[(2R)-tetrahydrofuran-2-yl]methanone; [2-[6-(8-methyl-7-quinolyl)spiro[4H-1,3-benzo-dioxine-2,4'-piperidine]-1'-yl]-2-oxo-ethyl]acetate; 2-hydroxy-1-[6-(8-methyl-7-quinolyl)-spiro[4H-1,3-benzodioxine-2,4'-piperidine]-1'-yl]ethanone; 6-(1-methylbenzimidazol-5-yl)-spiro[4H-1,3-benzodioxine-2,4'-piperidine]-1'-carboxamide; tert-butyl 6-thieno[2,3-b]pyridin-5-ylspiro[4H-1,3-benzodioxine-2,4'-piperidine]-1'-carboxylate; 6-thieno[2,3-b]pyridin-5-ylspiro[4H-1,3-benzodioxine-2,4'-piperidine]-1'-carboxamide; 6-(2-naphthyl)spiro[4H-1,3-benzodioxine-2,4'-piperidine]-1'-carboxamide; tert-butyl 6-(1-tert-butoxycarbonylindol-2-yl)spiro[4H-1,3-benzodioxine-2,4'-piperidine]-1'-carboxylate; 6-(1H-indol-3-yl)spiro[4H-1,3-benzodioxine-2,4'-piperidine]-1'-carboxamide; N-ethyl-6-(8-methyl-7-quinolyl)spiro[4H-1,3-benzodioxine-2,4'-piperidine]-1'-carboxamide; 6-(8-methyl-7-quinolyl)spiro[4H-1,3-benzodioxine-2,4'-piperidine]-1'-carboxamide; N-isopropyl-6-(8-methyl-7-quinolyl)spiro[4H-1,3-benzodioxine-2,4'-piperidine]-1'-carboxamide; N-ethoxy-6-(8-methyl-7-quinolyl)spiro[4H-1,3-benzodioxine-2,4'-piperidine]-1'-carboxamide; N-methoxy-6-(8-methyl-7-quinolyl)spiro[4H-1,3-benzodioxine-2,4'-piperidine]-1'-carboxamide; N-isopropoxy-6-(8-methyl-7-quinolyl)spiro[4H-1,3-benzodioxine-2,4'-piperidine]-1'-carboxamide; N-ethyl-6-(7-methylpyrazolo[1,5-a]pyridin-6-yl)spiro[4H-1,3-benzo-dioxine-2,4'-piperidine]-1'-carboxamide; 6-(7-methylpyrazolo[1,5-a]pyridin-6-yl)spiro[4H-1,3-benzodioxine-2,4'-piperidine]-1'-carboxamide; N-methoxy-6-(7-methylpyrazolo[1,5-a]pyridin-6-yl)spiro[4H-1,3-benzodioxine-2,4'-piperidine]-1'-carboxamide; N-ethoxy-6-(7-methylpyrazolo[1,5-a]pyridin-6-yl)spiro[4H-1,3-benzodioxine-2,4'-piperidine]-1'-carboxamide; N-isopropoxy-6-(7-methylpyrazolo[1,5-a]pyridin-6-yl)spiro[4H-1,3-benzodioxine-2,4'-piperidine]-1'-carboxamide; 6-(8-chloro-7-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carboxamide; N-methoxy-6-(4-methyl-3-quinolyl)spiro[4H-1,3-benzodioxine-2,4'-piperidine]-1'-carboxamide; 6-(8-chloro-7-quinolyl)-N-methoxy-spiro[4H-1,3-benzodioxine-2,4'-piperidine]-1'-carboxamide; 6-(8-chloro-7-quinolyl)-N-ethoxy-spiro[4H-1,3-benzodioxine-2,4'-piperidine]-1'-carboxamide; 6-(8-chloro-7-quinolyl)spiro[4H-1,3-benzodioxine-2,4'-piperidine]-1'-carbohydroxamic acid; ethyl 6-(8-chloro-7-quinolyl)spiro[4H-1,3-benzodioxine-2,4'-piperidine]-1'-carboxylate; ethyl 6-(4-methyl-3-quinolyl)spiro[4H-1,3-benzodioxine-2,4'-piperidine]-1'-carboxylate; N-ethoxy-6-(4-methyl-3-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carbohydroxamic acid; 6-(3-isoquinolyl)spiro[4H-1,3-benzodioxine-2,4'-piperidine]-1'-carboxamide; 6-(3-isoquinolyl)-N-tetrahydropyran-2-yloxy-spiro[4H-1,3-benzodioxine-2,4'-piperidine]-1'-carboxamide; N-ethoxy-6-(3-isoquinolyl)spiro[4H-1,3-benzodioxine-2,4'-piperidine]-1'-carboxamide; 6-(3-isoquinolyl)-N-methoxy-spiro[4H-1,3-benzodioxine-2,4'-piperidine]-1'-carboxamide; 6-(3-isoquinolyl)spiro-[4H-1,3-benzodioxine-2,4'-piperidine]-1'-carbohydroxamic acid; 6-(8-methoxy-7-quinolyl)-spiro[4H-1,3-benzodioxine-2,4'-piperidine]-1'-carboxamide; ethyl 6-(8-methoxy-7-quinolyl)spiro[4H-1,3-benzodioxine-2,4'-piperidine]-1'-carboxylate; N-isopropoxy-6-(1-methyl-6-isoquinolyl)spiro[4H-1,3-benzodioxine-2,4'-piperidine]-1'-carboxamide; 6-(1-methyl-6-isoquinolyl)spiro[4H-1,3-benzodioxine-2,4'-piperidine]-1'-carboxamide; N-methoxy-6-(1-methyl-6-isoquinolyl)spiro[4H-1,3-benzodioxine-2,4'-piperidine]-1'-carboxamide; N-ethyl-6-(1-methyl-6-isoquinolyl)spiro[4H-1,3-benzodioxine-2,4'-piperidine]-1'-carboxamide; N-ethyl-6-(1-methyl-6-isoquinolyl)spiro[4H-1,3-benzodioxine-2,4'-piperidine]-1'-carboxamide; ethyl 6-(3-chloro-6-isoquinolyl)spiro[4H-1,3-benzodioxine-2,4'-piperidine]-1'-carboxylate; 6-(1-methyl-6-isoquinolyl)spiro[4H-1,3-benzodioxine-2,4'-piperidine]-1'-carbohydroxamic acid; ethyl 6-(3-methyl-6-isoquinolyl)spiro[4H-1,3-benzo-dioxine-2,4'-piperidine]-1'-carboxylate; 6-(3-methyl-6-isoquinolyl)spiro[4H-1,3-benzodioxine-2,4'-piperidine]-1'-carboxamide; N-ethyl-6-(3-methyl-6-isoquinolyl)spiro[4H-1,3-benzodioxine-2,4'-piperidine]-1'-carboxamide; N-ethoxy-6-(3-methyl-6-isoquinolyl)spiro[4H-1,3-benzodioxine-2,4'-piperidine]-1'-carboxamide; 6-(3-methyl-6-isoquinolyl)spiro[4H-1,3-benzodioxine-2,4'-piperidine]-1'-carbohydroxamic acid; N-methoxy-6-(3-methyl-6-isoquinolyl)spiro[4H-1,3-benzodioxine-2,4'-piperidine]-1'-carboxamide; 1-[6-(2-pyridyl)spiro[4H-1,3-benzodioxine-2,4'-piperidine]-1'-yl]propan-1-one; cyclopropyl-[6-(2-pyridyl)spiro[4H-1,3-benzodioxine-2,4'-piperidine]-1'-yl]methanone; [6-(2-pyridyl)spiro[4H-1,3-benzodioxine-2,4'-piperidine]-1'-yl]-[(2R)-tetrahydrofuran-2-yl]methanone; 1-[6-(3-pyridyl)spiro[4H-1,3-benzodioxine-2,4'-piperidine]-1'-yl]propan-1-one; cyclopropyl-[6-(3-pyridyl)spiro[4H-1,3-benzodioxine-2,4'-piperidine]-1'-yl]methanone; [6-(3-pyridyl)spiro[4H-1,3-benzodioxine-2,4'-piperidine]-1'-yl]-[(2R)-tetrahydrofuran-2-yl]methanone; cyclopropyl-[6-(4-pyridyl)spiro[4H-1,3-benzodioxine-2,4'-piperidine]-1'-yl]methanone; [6-(4-pyridyl)spiro[4H-1,3-benzodioxine-2,4'-piperidine]-1'-yl]-[(2R)-tetrahydrofuran-2-yl]methanone; 1-[6-(4-pyridyl)spiro[4H-1,3-benzodioxine-2,4'-piperidine]-1'-yl]propan-1-one; 8-Methoxy-6-(8-methyl-7-quinolyl)spiro[4H-1,3-benzodioxine-2,4'-piperidine]-1'-carboxamide; 8-Methoxy-6-(8-methyl-7-quinolyl)spiro[4H-1,3-benzodioxine-2,4'-piperidine]-1'-carboxamide; and salts of such compounds, e.g., pharmaceutically acceptable salts.

Compounds according to Formula ID may include for example: 5-(8-methyl-7-quinolyl)spiro[3H-benzofuran-2,4'-piperidine]-1'-carboxamide; N-methoxy-5-(8-methyl-7-quinolyl)spiro[3H-benzofuran-2,4'-piperidine]-1'-carboxamide; N-ethoxy-5-(8-methyl-7-quinolyl)spiro[3H-benzofuran-2,4'-piperidine]-1'-carboxamide; 5-(8-methyl-7-quinolyl)-spiro[3H-benzofuran-2,4'-piperidine]-1'-carbohydroxamic acid; N-ethyl-5-(8-methyl-7-quinolyl)spiro[3H-benzofuran-2,4'-piperidine]-1'-carboxamide; N-methoxy-5-(4-methyl-3-quinolyl)spiro[3H-benzofuran-2,4'-piperidine]-1'-carboxamide; N-ethoxy-5-(4-methyl-3-quinolyl)spiro[3H-benzofuran-2,4'-piperidine]-1'-carboxamide; 5-(4-methyl-3-quinolyl)spiro-[3H-benzofuran-2,4'-piperidine]-1'-carboxamide; N-ethyl-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carbohydroxamic acid; 5-(8-methoxy-7-quinolyl)spiro[3H-benzofuran-2,4'-piperidine]-1'-carboxamide; N-ethyl-5-(8-methoxy-7-quinolyl)spiro[3H-benzofuran-2,4'-piperidine]-1'-carboxamide; 5-(7-methylpyrazolo[1,5-a]pyridin-6-yl)spiro[3H-benzofuran-2,4'-piperidine]-1'-carboxamide; N-ethyl-5-(7-methylpyrazolo[1,5-a]pyridin-6-yl)spiro[3H-benzofuran-2,4'-piperidine]-1'-carboxamide; N-methoxy-5-(8-methoxy-7-quinolyl)spiro[3H-benzofuran-2,4'-piperidine]-1'-carboxamide; N-ethoxy-5-(8-methoxy-7-quinolyl)spiro[3H-benzofuran-2,4'-piperidine]-1'-carboxamide; 5-(8-methoxy-7-quinolyl)-N-tetrahydropyran-2-yloxy-spiro[3H-benzofuran-2,4'-piperidine]-1'-carboxamide; N-ethoxy-5-(7-methylpyrazolo[1,5-a]pyridin-6-yl)spiro[3H-benzofuran-2,4'-piperidine]-1'-carboxamide; N-methoxy-5-(7-methylpyrazolo[1,5-a]pyridin-6-yl)spiro[3H- benzofuran-2,4'-piperidine]-1'-carboxamide; 5-(7-methylpyrazolo[1,5-a]pyridin-6-yl)-N-tetrahydropyran-2-yloxy-spiro[3H-benzofuran-2,4'-piperidine]-1'-carboxamide; and salts of such compounds, e.g., pharmaceutically acceptable salts.

Compounds according to Formula IE may include for example: 6-(2-naphthyl)spiro[4H-1,3-benzodioxine-2,4'-piperidine]-1'-carboxamide; 1-[6-(2-pyridyl)spiro-[chromane-2,4'-piperidine]-1'-yl]propan-1-one; cyclopropyl-[6-(2-pyridyl)spiro[chromane-2,4'-piperidine]-1'-yl]methanone; [6-(2-pyridyl)spiro[chromane-2,4'-piperidine]-1'-yl]-[(2R)-tetrahydrofuran-2-yl]methanone; 1-[6-(2-Pyridyl)spiro[4H-1,3-benzodioxine-2,4'-piperidine]-1'-yl]propan-1-one; cyclopropyl-[6-(2-pyridyl)spiro[4H-1,3-benzodioxine-2,4'-piperidine]-1'-yl]methanone; [6-(2-pyridyl)spiro[4H-1,3-benzodioxine-2,4'-piperidine]-1'-yl]-[(2R)-tetrahydrofuran-2-yl]methanone; 1-[6-(3-pyridyl)spiro[chromane-2,4'-piperidine]-1'-yl]propan-1-one; cyclopropyl-[6-(3-pyridyl)spiro[chromane-2,4'-piperidine]-1'-yl]methanone; [6-(3-pyridyl)spiro[chromane-2,4'-piperidine]-1'-yl]-[(2R)-tetrahydrofuran-2-yl]methanone; 1-[6-(3-pyridyl)spiro[4H-1,3-benzodioxine-2,4'-piperidine]-1'-yl]propan-1-one; cyclopropyl-[6-(3-pyridyl)spiro[4H-1,3-benzodioxine-2,4'-piperidine]-1'-yl]methanone; 1-[6-(4-pyridyl)spiro[chromane-2,4'-piperidine]-1'-yl]propan-1-one; cyclopropyl-[6-(4-pyridyl)spiro[chromane-2,4'-piperidine]-1'-yl] methanone; [6-(4-pyridyl)spiro[chromane-2,4'-piperidine]-1'-yl]-[(2R)-tetrahydrofuran-2-yl]methanone; [6-(3-pyridyl)spiro[4H-1,3-benzodioxine-2,4'-piperidine]-1'-yl]-[(2R)-tetrahydrofuran-2-yl]methanone; cyclopropyl-[6-(4-pyridyl)spiro[4H-1,3-benzodioxine-2,4'-piperidine]-1'-yl]methanone; [6-(4-pyridyl)spiro[4H-1,3-benzodioxine-2,4'-piperidine]-1'-yl]-[(2R)-tetrahydrofuran-2-yl]methanone; 1-[6-(4-pyridyl)spiro[4H-1,3-benzodioxine-2,4'-piperidine]-1'-yl]propan-1-one; and salts of such compounds, e.g., pharmaceutically acceptable salts.

The following terms and expressions have meanings as discussed below.

As used herein, the term "about" refers to a range of values from ±10% of a specified value. For example, the phrase "about 50" would be understood to include ±10% of 50, or from 45 to 55. The phrase "from about 10 to 100" includes ±10% of 10 and ±10% of 100, or from 9 to 110.

As used herein, a range of integer values in the form "x-y" or "x to y", or "x through y", includes the integers x and y, and includes all of the integers between x and y. For example, the expressions "1-6", or "1 to 6" or "1 through 6" are intended to include the integers 1, 2, 3, 4, 5 and 6. Preferred embodiments include each individual integer in the range, as well as any subcombination of integers. For example, preferred integers for the expression "1-6" can include 1, 2, 3, 4, 5, 6, 1-2, 1-3, 1-4, 1-5, 2-3, 2-4, 2-5, 2-6, etc.

The term "acyl" means a radical of the general formula —C(=O)—R, wherein —R is hydrogen or hydrocarbyl. Examples include, acetyl (—C(=O)CH$_3$), propionyl (—C(=O)CH$_2$CH$_3$), benzoyl (—C(=O)C$_6$H$_5$) and phenylacetyl (—C(=O)CH$_2$C$_6$H$_5$).

The term "alkyl", by itself or as part of another substituent means, a straight, branched or cyclic chain hydrocarbon radical, including di- and multi-radicals, having the number of carbon atoms designated (i.e. C$_1$-C$_6$ designates an alkyl group having from one to six carbons), and includes straight, branched chain or cyclic groups. Examples of alkyl groups include: methyl, ethyl, propyl, isopropyl, butyl, isobutyl, tert-butyl, pentyl, neopentyl, hexyl, cyclohexyl and cyclopropylmethyl.

The term "alkylene," by itself or as part of another substituent means a divalent straight, branched or cyclic chain hydrocarbon radical having the stated number of carbon atoms.

For example, —(C$_1$-C$_3$)-alkylene-CO$_2$H, would include, e.g., —CH$_2$CH$_2$CH$_2$—CO$_2$H, —CH$_2$CH(CH$_3$)—CO$_2$H, —C(CH$_3$)$_2$— CO$_2$H, -cyclopropyl-CO$_2$H and —CH(CH$_3$)—CH$_2$—CO$_2$H.

The term "alkoxy," employed alone or in combination with other terms means an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers.

The term "alkenyl," employed alone or in combination with other terms, means a stable monounsaturated or di-unsaturated hydrocarbon radical straight chain, branched chain or cyclic hydrocarbon group having the stated number of carbon atoms. Examples include vinyl, propenyl(allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

The term "amine" or "amino" refers to radicals of the general formula —NRR', wherein R and R' are independently selected from hydrogen and a hydrocarbyl radical, or wherein R and R' combined form a heterocyle. Examples of amino groups include: —NH$_2$, methylamino, diethylamino, anilino, benzylamino, piperidin-1-yl, piperazin-1-yl and indolin-1-yl.

The term "carbamyl" means the group —C(=O)NRR', wherein R and R' are independently selected from hydrogen and a hydrocarbyl radical, or wherein R and R' combined form a heterocyle. Examples of carbamyl groups include: —C(=O)NH$_2$ and —C(=O)N(CH$_3$)$_2$.

The term "cycloalkyl" refers to alkyl radicals that contain one or more rings, for example C$_3$ to C$_{10}$ cycloalkyl groups, e.g., cyclopropyl, cyclobutyl, cyclopentyl, cyclohexyl, cycloheptyl, norbornyl and octahydro-1H-indenyl. Though there is overlap in the scope of the terms "cycloalkyl" and "alkyl" as defined above, the two terms are often both employed to insure inclusion of cycloalkyl groups in various jurisdictions.

The term "heteroalkyl" by itself or in combination with another term, means a stable straight or branched chain radical consisting of the stated number of carbon atoms and one or two heteroatoms selected from O, N and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$ (wherein either or both of the two consecutive heteroatoms may also be oxidized S (SO or SO$_2$) or oxidized N (NO)).

The term "heteroalkenyl," by itself or in combination with another term, means a stable straight or branched chain mono- or di-unsaturated hydrocarbon radical consisting of the stated number of carbon atoms and one or two heteroatoms selected from O, N and S, and wherein the nitrogen and sulfur atoms may optionally be oxidized and the nitrogen heteroatom may optionally be quaternized. Up to two heteroatoms may be placed consecutively. Examples include —CH=CH—O—CH₃, —CH=CH—CH₂—OH, —CH₂—CH=N—OCH₃, —CH=CH—N(CH₃)—CH₃ and —CH₂—CH=CH—CH₂—SH.

The term "hydroxyalkyl" refers to a subset of heteroalkyl groups that is an alkyl radical wherein one or more of the carbon atoms is substituted with hydroxy. Examples include —CH₂CH(OH)CH₃ and —CH₂CH₂OH.

The terms "halo" or "halogen" by themselves or as part of another substituent mean, a fluorine, chlorine, bromine, or iodine atom.

The term "haloalkyl" refers to a $C_1$-$C_6$ alkyl group in which one or more of the carbon atoms is substituted with one or more halogen atoms. Preferred haloalkyl groups are $C_1$-$C_4$ alkyl groups in which one or more of the carbon atoms is substituted with one or more halogen atoms. The alkyl group may be a straight, branched or cyclic alkyl group. The halogen atom is one or more of fluorine, chlorine, bromine and iodine. Examples of haloalkyl groups include, trifluoromethyl, 2,2,2-trifluoroethyl, 2,2,2-trichloroethyl and 2-chloroethyl.

The term "sulfamyl" means the group —SO₂NRR', wherein R and R' are independently selected from hydrogen or a hydrocarbyl radical, or wherein R and R' combined form a heterocycle. Examples of sulfamyl groups include: —SO₂NH₂, —SO₂N(CH₃)₂, —SO₂(pyrrol-1-yl) and —SO₂NH(C₆H₅).

The term "aromatic" refers to a carbocycle or heterocycle having one or more polyunsaturated rings having aromatic character (4n+2) delocalized π (pi) electrons).

The term "aryl," employed alone or in combination with other terms, means a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "heterocycle" or "heterocyclyl" or "heterocyclic," by itself or as part of another substituent means, an unsubstituted or substituted, stable, mono- or multicyclic heterocyclic ring system which consists of carbon atoms and at least one heteroatom selected from N, O and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

As used herein "stable structure" or "stable compound" refers to a compound that is sufficiently robust to survive isolation to a useful degree of purity from a reaction mixture. The compounds according to the present invention are stable compounds.

The term "heteroaryl" or "heteroaromatic" refers to a heterocycle having aromatic character.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: bicyclic heterocycles, such as, Indolyl, particularly 3-, 4-, 5-, 6- and 7-indolyl, indolinyl, quinolyl, tetrahydroquinolyl, isoquinolyl, particularly 1- and 5-isoquinolyl, tetrahydroisoquinolyl, cinnolinyl, quinoxalinyl, particularly 2- and 5-quinoxalinyl, quinazolinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl and quinolizidinyl. Polycyclic heterocycles also include tricyclic and other polycyclic heterocycles such as dibenzofuran and benzofuro[2,3-b]pyridine.

The aforementioned listing of heterocyclyl and heteroaryl moieties is intended to be representative, not limiting.

The term "hydrocarbyl" refers to any moiety comprising only hydrogen and carbon atoms. For example, the term ($C_1$-$C_7$)hydrocarbyl would include hydrocarbon groups such as ($C_1$-$C_7$)alkyl groups and cycloalkyl, ($C_1$-$C_7$)alkenyl and cycloalkenyl groups, ($C_1$-$C_7$)alkynyl and cycloalkynyl groups, and aryl, e.g., benzyl and tolyl groups.

As used herein, the term "substituted" refers in general to any one or more hydrogen atoms on the indicated atom (preferably a carbon atom) being replaced with a selected group referred to herein as a "substituent", provided that the substituted atom's valency is not exceeded, and that the substitution results in a stable compound. A substituted group has from 1 to 5, preferably 1 to 3, and more preferably 1 independently selected substituents. Possible substituents include, but are not limited to halogens, —OH, —OR, —NR₂, —NHOH, —NO₂, —CN, —CF₃, —CF₂CF₃, —$C_1$-$C_7$ hydrocarbyl, —$C_1$-$C_6$ alkoxy, 3-7-membered heterocyclyl, 3-7-membered heteroaryl, =O, =S, —C(=O)R, —COOH, —CO₂R, —O—C(=O)R, —C(=O)NRR', —NRC(=O)R', —NRCO₂R', —OC(=O)NRR', —NRC(=O)NRR', —NRC(=S)NRR' and —SO₂NRR', wherein R and R' are each independently —H, —$C_1$-$C_7$ hydrocarbyl (e.g., —$C_1$-$C_6$ alkyl, —$C_2$-$C_6$ alkenyl —$C_3$-$C_6$ cycloalkyl, benzyl, or phenyl) or ($C_1$-$C_7$)acyl. According to some embodiments, substituents may be selected from halogens, —OH, —OR, —NR₂, —NHOH, —NO₂, —CN, —CF₃, —CF₂CF₃, —$C_1$-$C_6$ alkyl, benzyl, —$C_1$-$C_6$ alkoxy, 3-7-membered heterocyclyl, 3-7-membered heteroaryl, =O, =S, —C(=O)R, —COOH, —CO₂R, —O—C(=O)R, —C(=O)NRR', —NRC(=O)R', —NRCO₂R', —OC(=O)NRR', —NRC(=O)NRR', —NRC(=S)NRR' and —SO₂NRR', wherein R and R' are each independently selected from —H, —$C_1$-$C_6$ alkyl, —$C_3$-$C_6$ cycloalkyl, benzyl or phenyl.

Where a substituent is an alkyl or alkoxy group, the carbon chain may be branched, straight or cyclic, with straight being preferred.

Accordingly, the term "substituted hydrocarbyl" refers to: a hydrocarbyl group as defined above, having 1, 2, 3, 4 or 5 substituents, independently selected from the selection provided in the definition of the term "substituent" herein. Similarly, the expressions "substituted alkyl," "substituted cycloalkyl," "substituted alkenyl," "substituted alkynyl," "substituted aryl," "substituted benzyl," etc. refer to the specified (e.g., alkyl) group as defined herein, having 1, 2, 3, 4 or 5 substituents, independently selected from the selection provided in the definition of the term "substituent" herein.

Similarly, substituted naphthyl refers to naphthyl having 1, 2 or 3 substituents; substituted 6-membered heteroaryl refers to 6-membered heteroaryl having 1, 2 or 3 substituents; and substituted 9-10 membered bicyclic heteroaryl refers to 9-10 membered bicyclic heteroaryl having 1, 2 or three substituents. Substituents on aromatic rings will be understood to be singly bonded substituents, i.e., would generally not include the =O and =S substituents.

As used herein, the expression "FASN-mediated disorder" refers to a disease, disorder or condition which is treatable by inhibition of FASN activity. FASN-mediated disorders include, but are not limited to, cancers, viral disorders (wherein FASN inhibition correlates inhibition of viral replication), obesity related disorders, eating disorders, metabolic diseases (e.g., fatty liver disease, non-alcoholic hepatic steatosis and Type 2 diabetes), drug induced body weight gain; e.g. atypical antipsychotic-induced weight gain, cardiovascular diseases, gastrointestinal disorders and dermatological disorders; and complications of such diseases, disorders or conditions.

As used herein, the term "subject" refers to a warm blooded animal such as a mammal, preferably a human, which is afflicted with, or has the potential to be afflicted with one or more diseases and conditions described herein.

As used herein, a "therapeutically effective amount" refers to an amount of a compound of the present invention that is effective to treat or prevent the symptoms of a particular disorder. Such disorders include, but are not limited to; those pathological and neurological disorders associated with the aberrant activity of the receptors described herein, wherein the treatment or prevention comprises inhibiting the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable salt" refers to salts of compounds of the present invention that may be derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, trifluoroacetic, tartaric, glutamic, salicylic, oxalic, methanesulfonic, benzenesulfonic, para-toluenesulfonic, succinic and benzoic acid, and related inorganic and organic acids.

Base addition salts include those derived from inorganic bases such as ammonium and alkali and alkaline earth metal hydroxides, carbonates and bicarbonates, as well as salts derived from basic organic amines such as aliphatic and aromatic amines, aliphatic diamines and hydroxy alkamines. Such bases useful in preparing the salts of this invention thus include, for example, ammonium hydroxide, potassium carbonate, sodium bicarbonate, calcium hydroxide, methylamine, diethylamine, ethylenediamine, cyclohexylamine, diisopropylethyl amine (DIPEA), ethanolamine.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and THF. Mixtures of such solvates can also be prepared. The source of such solvate can be from the solvent of crystallization, inherent in the solvent of preparation or crystallization, or adventitious to such solvent. Such solvates are within the scope of the present invention.

It will be understood that compounds of the present invention may exist in various stereoisomeric forms. For example, compounds of the invention may be asymetrically substituted on the piperidine ring, e.g. a prophetic example such as (2R)-3'-methyl-6-(quinolin-6-yl)spiro[chromane-2, 4'-piperidine]-1'-carboxamide (structure below).

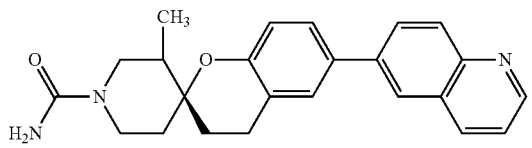

As such, the compounds of the present invention include both diastereomers and enantiomers. The compounds may be prepared as racemates and can conveniently be used as such. However, individual enantiomers can be isolated by resolution or chiral separation of a racemate, or may be synthesized by conventional techniques if so desired. Such racemates and individual enantiomers and mixtures thereof form part of the present invention.

It is known in the art how to prepare and isolate such optically active forms.

Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. Stereochemistry of Organic Compounds; Wiley: New York, 1994, and Jacques, J, et al. Enantiomers, Racemates, and Resolutions; Wiley: New York, 1981.

It is further recognized that functional groups present on intermediates used for the synthesis of the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), methoxybenzyl and dimethoxy (e.g., 2-4-dimethoxy) benzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

The compounds described herein are also intended to include such compounds wherein the molecular structures include isotopes of atoms in the chemical structure, e.g., carbon, hydrogen, nitrogen sulfur and other atoms occurring on those structures. Isotopes include those atoms having the same atomic number but different mass numbers. For example, isotopes of hydrogen include deuterium; isotopes of carbon include $^{13}C$; isotopes of nitrogen include $^{15}N$; and isotopes of sulfur include $^{33}S$.

Accordingly, within the chemical structure of any compound that is taught in this application:
- any hydrogen atom or group of hydrogen atoms, e.g., in a hydrocarbyl, heteroalkyl, aryl, heteroaryl, heterocyclyl or carbocyclyl group, could suitably be replaced by an isotope of hydrogen, i.e., deuterium;
- any carbon atom or group of carbon atoms, e.g., in a hydrocarbyl, heteroalkyl, aryl, heteroaryl, heterocyclyl or carbocyclyl group, could suitably be replaced by an isotope of carbon, e.g., $^{13}C$;
- any nitrogen atom or group of nitrogen atoms, e.g., in a heteroalkyl, heteroaryl, or heterocyclyl group, could suitably be replaced by an isotope of nitrogen, e.g., $^{15}N$; and
- any sulfur atom or group of sulfur atoms, e.g., in a heteroalkyl, heteroaryl, or heterocyclyl group, could suitably be replaced by an isotope of sulfur, e.g., $^{33}S$.

As used herein, a compound that is termed "isotopically-enriched" means that the abundance, e.g., of deuterium, $^{13}C$, or $^{15}N$ or $^{33}S$ at any relevant site of the compound is substantially more than the abundance of deuterium, $^{13}C$, or $^{15}N$ or $^{33}S$ naturally occurring at that site in an amount of the compound. A relevant site in a compound as used above is a site which would be designated as "H" or "C" or "N" or "S" in a chemical structure representation of the compound when not enriched. Relevant sites in the chemical structure of compounds taught herein for isotopic replacement an atom or atoms can include any site that is synthetically accessible for such isotopic replacement. The expression, "naturally occurring," as used above refers to the abundance of the particular atom which would be present at a relevant site in a compound if the compound was prepared without any affirmative synthesis step to enrich the abundance of a different isotope.

Thus, for example in a "deuterium-enriched" compound, the abundance of deuterium at any relevant site in the chemical structure can range from an amount that is substantially more than the natural abundance of deuterium (about 0.0115%) up to 100%, for example, from about 1% to about 100%, or from about 10% to about 100%, or from about 50% to about 100%, or from about 90% to about 100%.

Similarly, for a "$^{13}C$-enriched" compound, the abundance of $^{13}C$ at any relevant site in the chemical structure of the compound can range from an amount that is substantially more than the natural abundance of $^{13}C$ (about 1.109%) all the way up to 100%, for example, from about 5% to about 100%, or from about 10% to about 100%, or from about 50% to about 100%, or from about 90% to about 100%. Similarly for a "$^{15}N$-enriched" compound, the abundance of $^{15}N$ at any relevant site in the chemical structure of the compound can range from an amount that is substantially more than the natural abundance of $^{15}N$ (about 0.364%) all the way up to 100%, for example, from about 1% to about 100%, or from about 10% to about 100%, or from about 50% to about 100%, or from about 90% to about 100%.

Isotopically-enriched compounds can generally be prepared by conventional techniques known to those skilled in the art. Such isotopically-enriched compounds can also be prepared by adapting conventional processes as described in the scientific literature for synthesis of compounds disclosed herein, and using an appropriate isotopically-substituted reagent (or reagents) in place of the corresponding non isotopically-substituted reagent(s) employed in the conventional synthesis of the non isotopically-enriched compounds. Examples of ways to obtain a deuterium-enriched compound include exchanging hydrogen with deuterium or synthesizing the compound with deuterium-enriched starting materials.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described herein.

All other terms that are used herein in the description of the present invention will be understood to have meanings such as would be understood and accepted in the art.

For therapeutic purposes, the compounds that are described herein may be administered to a subject by any means that results in the contact of the active agent with the agent's site of action in the body of the subject. The compounds may be administered by any conventional means available for use in conjunction with pharmaceuticals, either as individual therapeutic agents, or in combination with other therapeutic agents. The compounds are preferably administered in therapeutically effective amounts for the treatment of the diseases and disorders described herein to a subject in need thereof.

A therapeutically effective amount of a compound as described herein may be readily determined by an attending diagnostician, as one skilled in the art, by the use of conventional techniques. The effective dose will vary depending upon a number of factors, including the type of disease or disorder treated, the extent of progression of the disease or disorder, the overall health status of the subject to be treated, the relative biological efficacy of the compound selected, the formulation of the active agent, and the route of administration used in treatment. Typically, the compounds are initially administered at lower dosage levels, with a gradual increase until the desired therapeutic effect is obtained.

Typical dose ranges may be from about 0.01 mg/kg to about 100 mg/kg of body weight per day, or from about 0.01 mg/kg to 10 mg/kg of body weight per day. Daily doses for adult humans may include about 25, 50, 100 and 200 mg, and an equivalent dose in a human child. The compounds may be administered in one or more unit dose forms. The unit dose may range from about 1 to about 500 mg administered one to four times a day, e.g., from about 10 mg to about 300 mg, administered two times a day. In an alternate method of describing an effective dose, an oral unit dose is one that is necessary to achieve a therapeutic blood serum level, e.g., a blood serum level of about 0.05 to 20 micrograms/mL in a subject, or about 1 to 20 micrograms/mL. The compounds described herein may be administered as the pure chemicals; however it is preferable to administer the active ingredient as a pharmaceutical composition.

Generally, compounds described herein may be administered to a patient alone or in combination with a pharmaceutically acceptable carrier. Accordingly, the compounds of the invention, for example, compounds of Formulae I-V, are preferably combined with a pharmaceutical carrier selected on the basis of the chosen route of administration and standard pharmaceutical practice—as described, for example, in Remington's Pharmaceutical Sciences (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the subject. The relative proportions of active ingredient and carrier may be determined, for example, by the solubility and chemical nature of the compounds, the chosen route of administration and standard pharmaceutical practice.

The compounds described herein may be formulated into pharmaceutical compositions by admixture with one or more pharmaceutically acceptable excipients. The excipients may be selected on the basis of the chosen route of administration and standard pharmaceutical practice, as described, for example, in Remington: The Science and Practice of Pharmacy, 20th ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations.

According to some embodiments of the invention, a pharmaceutical composition herein may contain both an amount of a FASN inhibitor having a chemical structure as described herein, and an amount of an antipsychotic agent. Suitable antipsychotic agents for such a dual API pharmaceutical composition include, for example, clozapine, risperidone, aripiprazole, olanzapine, quetiapine and ziprasidone. Such a dual API pharmaceutical composition may contain, for example, per dosage unit, from about 5 to about 1000 mg, or more, of a FASN inhibitor having a chemical structure as described herein, and from about 5 to about 1000 mg of an antipsychoric agent. In such embodiment, it is not necessary that each single dosage unit include an effective amount so long as the total amount of drug administered to a patient is an effective amount of each. Therefore, for example, a patient may require two or more single dosage units to receive effective amounts of both agents. The dosage may be adjusted appropriately to achieve desired drug levels, locally or systemically of both drugs.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders.

For oral administration, e.g., tablets, pills, powders, capsules, and troches, formulations can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the excipients as listed above, and may additionally contain a semi-solid or liquid carrier, such as a polyethylene glycol. Solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include, for example, mixtures of alcohols and water, and buffered media. Nonaqueous solvents include, for example, alcohols and glycols, such as ethanol, and polyethylene glycols; oils, such as vegetable oils; fatty acids and fatty acid esters. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; and antibacterial agents, such as chlorobutanol, or phenol; buffers. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

Pharmaceutical kits may comprise a therapeutically effective amount of a therapeutic compound as described herein, in one or more sterile containers are also within the ambit of the present invention. Sterilization of the container may be carried out using conventional sterilization methodology well known to those skilled in the art. The sterile containers of materials may comprise separate containers, or one or more multi-part containers. The compound as described herein may be separate, or may be combined into a single dosage form as described above. Such kits may further include, if desired, one or more of various conventional pharmaceutical kit components, e.g., one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in such a kit.

The compounds of the present invention may be used in methods for treating a condition or disorder associated with increased FASN expression and/or activity.

Such disorders include, for example:
obesity,
eating disorders
drug induced body weight gain; e.g. atypical antipsychotic-induced weight gain
cardiovascular diseases,
gastrointestinal disorders,
dermatological disorders,
metabolic diseases (e.g., non-alcoholic hepatic steatosis (NASH)) and Type 2 diabetes. (NASH is a serious liver disease for which the pathogenesis and prognosis have not been clearly determined. It is generally believed that abnormal fatty acid metabolism may be involved in the pathogenesis of NASH, with triacylglycerols and their fatty acid precursors likely possibly accumulating in the hepatocyte.)
viral disorders wherein FASN inhibition correlates inhibition of viral replication, and
cancers and/or cancer metastasis (e.g., human breast, ovarian, prostate, colon, lung, bladder, stomach and kidney cancers).

Accordingly, provided herein is a method of inhibiting fatty acid synthase (FASN) in a subject, wherein the subject has a FASN-mediated disorder. According to some embodiments, the FASN-mediated disorder is selected from cancers, viral disorders (wherein FASN inhibition correlates inhibition of viral replication), obesity related disorders, eating disorders, metabolic diseases (e.g., fatty liver disease, non-alcoholic hepatic steatosis and Type 2 diabetes), drug induced body weight gain; e.g. atypical antipsychotic-induced weight gain, cardiovascular diseases, gastrointestinal disorders and dermatological disorders, the method comprising administering to a subject a therapeutically effective amount of a compound of Formula I, IA, IB, IC, ID or IE. Also provided herein is a method for treating, preventing and/or managing a FASN-mediated disorder, disease or condition, the method comprising administering to a subject suffering from a FASN-mediated disorder a therapeutically or prophylactically effective amount of at least one compound of Formula I, IA, IB, IC, ID, or IE, or a pharmaceutically acceptable salt thereof, or a pharmaceutical composition comprising said at least one compound pharmaceutically acceptable salt thereof.

The methods of treatment provided herein comprise administering to a subject in need of such treatment a therapeutically effective amount of a compound of the invention, preferably a compound of Formulae I-IE. Accordingly, the invention includes a method of treatment of a subject suffering from a disorder mediated by fatty acid synthase, the method comprising administering to the subject a therapeutically effective amount of a compound according to Formulae I, IA, IB, IC, ID, and IE; or a therapeutically effective amount of a pharmaceutical composition comprising a compound according to Formulae I, IB, IC and ID. The invention also includes a method of treating a subject who is suffering from obesity, weight gain, or weight gain, or weight gain associated with drug therapy, e.g., drug therapy with an antipsychotic agent, e.g., clozapine, risperidone, aripiprazole, olanzapine, quetiapine and ziprasidone. The method comprises administering to the subject a therapeutically effective amount of a compound according to Formulae I, IA, IB, IC, ID, or IE; or a therapeutically effective amount of a pharmaceutical composition comprising a compound according to Formulae I-IE.

The compounds of the present invention can be synthesized using the methods as described generally herein, and by methods that are described in the working examples that are provided herein, or variations thereon. The compounds of the invention may also be prepared by using other known synthetic methods, or variations thereon. Unless otherwise stated, starting compounds in the synthetic methods described herein are commercially available, or may be readily synthesized by known methods. The reactions are generally performed in solvents that are appropriate to the reagents and reaction conditions. The materials employed in the reactions are understood to be suitable for the transformations being effected, and the materials and methods employed in product isolation understood to be suitable for the product compounds. Also, in the description of the synthetic methods herein, it is to be understood that all proposed reaction conditions, including choice of solvent, reaction atmosphere, reaction temperature, duration of experiment and workup procedures are chosen to be conditions appropriate for that reaction as would be understood by one skilled in the art of organic synthesis. It is understood that the examples and embodiments described herein are provided for illustrative purposes only, and that various modifications or changes in light thereof will be clearly understood to be included within the scope of this application and the scope of the appended claims. Specific chemical transformations are listed in the schemes and working examples provided herein, and the skilled person will readily appreciate that a variety of different reagents may be used in place of those listed. Common replacements for such reagents can be found in, for example, in texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

Compounds of the invention may be prepared by organic syntheses utilizing known organic reactions. Spirocyclic piperidine intermediates may be synthesized as illustrated with the synthesis of intermediates 1-4. The synthesis of the spirocyclic piperidine examples with variations at $R^5$ and $R^6$ may be accomplished using the methods for intermediates 1-4, except starting with, for example, a substituted ($R^5$) 1-(5-bromo-2-hydroxyphenyl) or an ethan-1-one substituted ($R^5$) 4-bromo-2-(hydroxymethyl)phenol intermediate known in the literature. Further elaboration of the spirocyclic piperidines examples at $R^6$ using known methods is outlined in the general Scheme 1. For example, reaction with the spiropiperidine boronic acid or a spiropiperidine boranate ester intermediate of formula 1 as shown in Scheme 1, using a transition metal (e.g., palladium) catalyzed coupling reaction with an appropriate an $R^6$ heteroaryl halide can be used to produce an intermediate of formula 2. The intermediate of formula 2 can then be deprotected to remove the protecting group (PG), e.g., under acidic conditions if the PG is a Boc group, to give an intermediate amine of formula 3. The intermediate amine of formula 3 may then be reacted with reagents such as carboxylic acids, carboxylic acid halides, carboxylic acid anhydrides, isocyanates, or sulfonyl halides to produce compounds according to Formulae I. Alternatively, the above order of the steps may be reversed, i.e., the starting compound of formula 1a can be acylated first to produce an intermediate acylated amine. The intermediate amine then converted to a boronic acid intermediate and coupled, or the spirocyclic piperidine halide can be reacted with an appropriate R⁶ boronic acid or R⁶ organostannane reagent with transition metal (e.g., palladium) catalysis to produce compounds of Formulae I-IE. In addition, as shown in general Scheme 2, the coupling partners may be reverse such that a spirocyclic piperidine intermediate of formula 1b may be coupled with an R⁶ boronic acid or R⁶ organostannane to give intermediates of formula 2, which can be used to produce examples of Formulae I-V as previously described.

coumarin derivative CPM contains a thiol-reactive maleimide that becomes fluorescent upon interaction with the sulfhydryl group of CoA.

For the example compounds described herein, the reaction was performed in 384-well low volume non-binding plates (Coring, N.Y.) using recombinant human baculovirus-expressed GST-tagged FASN. The 20-μL assay mixture contained 50 mM HEPES (pH 7.5), 5 nM FASN, 150 μM NADPH (Sigma, St. Louis, Mo.), 10 μM acetyl-CoA (Sigma), 25 μM malonyl-CoA (Sigma) and test compound [diluted in dimethyl sulfoxide (DMSO); 0.5% DMSO final

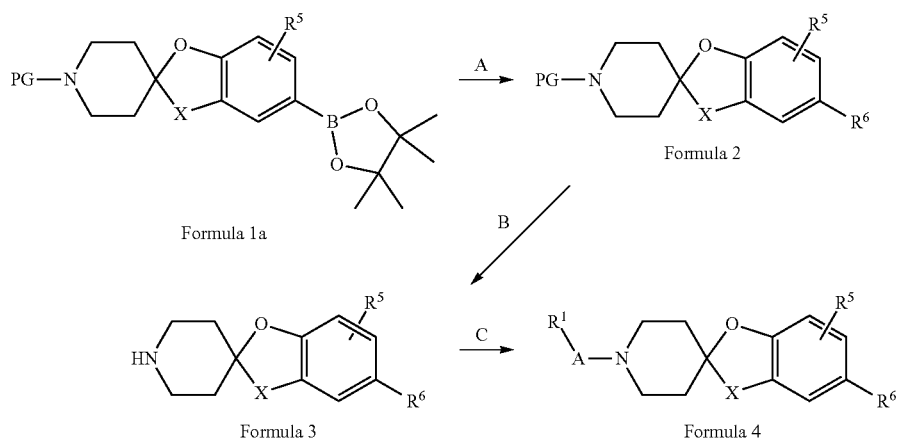

Scheme 1: Variation of R⁶ via Transition Metal Catalyzed Coupling

PG = Protecting Group;
A = transition metal catalyzed coupling step;
B = piperidine nitrogen deprotection step;
C = piperidine nitrogen acylation (or sulfonylation) step

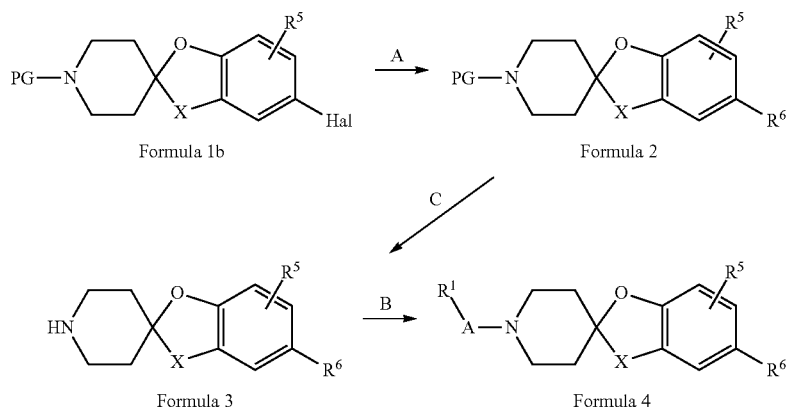

Scheme 2: Variation of R⁶ via Transition Metal Catalyzed Coupling

PG = Protecting Group; Hal = Br or I;
A = transition metal catalyzed coupling step;
B = piperidine nitrogen deprotection step;
C = piperidine nitrogen acylation (or sulfonylation) step FASN Enzyme activity may be determined by detecting coenzyme A (CoA), a product of FASN-catalyzed synthesis of palmitate from acetyl-CoA and malonyl-CoA with NADPH as a cofactor. The assay is fluorescence-based and measures the interaction of free CoA with 7-diethylamino-3-(4'-malemimidylphenyl)-4-methylcoumarin (CPM; Life Technologies, CA) as described in Chung et al (2008). The in assay after 100 nL addition]. See, Chung et al.; "A fluorescence-based thiol quantification assay for ultra-high-throughput screening for inhibitors of coenzyme A production," Assay Drug Dev Tech 2008; 6:361-374.

The reaction was initiated by adding malonyl-CoA, followed by incubation for 90 minutes at 250° C. A stock solution of the CPM reagent was prepared in DMSO at 66

μM and stored at −200° C. To detect CoA produced in the FASN reaction, the CPM stock was diluted to 50 μM in 70% ethanol and added at 4 μL/well to the assay plate. The reaction mixture was then incubated for 30 minutes. Fluorescence was measured using the EnVision™ 2102 multi-label plate reader (PerkinElmer, Waltham, Mass.) utilizing a general dual mirror, a 390 nM excitation filter and a 530 nM emission filter. Data analysis was performed using ActivityBase (IDBS, Guilford, UK). $IC_{50}$ values were calculated by plotting the percent inhibition versus log 10 of the concentration of the compound, and fitting to the nonlinear regression sigmoidal dose-response (variable slope) equation in XLFit (IDBS). The $IC_{50}$ data for the Examples described herein is provided in Table 3 below (A=1 to 99 nM; B=100 to 999 nM; C=1000-10,000 nM; N—not yet tested).

TABLE 3

| $IC_{50}$ data for Compounds of Formula I | |
|---|---|
| Example # | Activity |
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | B |
| 14 | A |
| 15 | A |
| 16 | A |
| 17 | B |
| 18 | B |
| 19 | A |
| 20 | A |
| 21 | A |
| 22 | A |
| 23 | A |
| 24 | A |
| 25 | B |
| 26 | B |
| 27 | B |
| 28 | A |
| 29 | A |
| 30 | A |
| 31 | A |
| 32 | A |
| 33 | A |
| 34 | A |
| 35 | C |
| 36 | C |
| 37 | C |
| 38 | B |
| 39 | C |
| 40 | A |
| 41 | A |
| 42 | B |
| 43 | A |
| 44 | A |
| 45 | A |
| 46 | B |
| 47 | A |
| 48 | A |
| 49 | A |
| 50 | A |
| 51 | A |
| 52 | A |
| 53 | A |
| 54 | A |
| 55 | A |

TABLE 3-continued

| $IC_{50}$ data for Compounds of Formula I | |
|---|---|
| Example # | Activity |
| 56 | A |
| 57 | A |
| 58 | A |
| 59 | A |
| 60 | B |
| 61 | B |
| 62 | B |
| 63 | A |
| 64 | B |
| 65 | A |
| 66 | A |
| 67 | C |
| 68 | B |
| 69 | A |
| 70 | A |
| 71 | C |
| 72 | B |
| 73 | C |
| 74 | C |
| 75 | B |
| 76 | B |
| 77 | B |
| 78 | B |
| 79 | A |
| 80 | A |
| 81 | B |
| 82 | B |
| 83 | B |
| 84 | C |
| 85 | C |
| 86 | C |
| 87 | N |
| 88 | N |
| 89 | C |
| 90 | N |
| 91 | N |
| 92 | N |
| 93 | N |
| 94 | N |
| 95 | N |
| 96 | N |
| 97 | A |
| 98 | B |
| 99 | A |
| 100 | A |
| 101 | A |
| 102 | A |
| 103 | A |
| 104 | B |
| 105 | B |
| 106 | A |
| 107 | A |
| 108 | A |
| 109 | B |
| 110 | A |
| 111 | B |
| 112 | A |
| 113 | B |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | C |
| 126 | A |
| 127 | B |
| 128 | A |
| 129 | A |
| 130 | A |
| 131 | B |

TABLE 3-continued

IC$_{50}$ data for Compounds of Formula I

| Example # | Activity |
|---|---|
| 132 | B |
| 133 | A |
| 134 | A |
| 135 | A |
| 136 | B |
| 137 | C |
| 138 | B |
| 139 | A |
| 140 | C |
| 141 | C |
| 142 | C |
| 143 | C |
| 144 | B |
| 145 | A |
| 146 | B |
| 147 | A |
| 148 | A |
| 149 | A |
| 150 | C |
| 151 | C |
| 152 | A |
| 153 | C |
| 154 | C |
| 155 | C |
| 156 | C |
| 157 | C |
| 158 | C |
| 159 | C |
| 160 | C |
| 161 | C |
| 162 | C |
| 163 | C |
| 164 | C |
| 165 | C |
| 166 | C |
| 167 | C |
| 168 | C |
| 169 | C |
| 170 | C |
| 171 | C |
| 172 | C |
| 173 | C |
| 174 | A |
| 175 | A |
| 176 | B |
| 177 | A |
| 178 | A |
| 179 | A |
| 180 | A |
| 181 | A |
| 182 | A |
| 183 | B |
| 184 | A |
| 185 | A |
| 186 | A |
| 187 | A |
| 188 | A |
| 189 | C |
| 190 | A |
| 191 | B |
| 192 | A |
| 193 | A |
| 194 | B |
| 195 | A |
| 196 | A |
| 197 | A |
| 198 | C |
| 199 | C |
| 200 | C |
| 201 | C |
| 202 | A |
| 203 | A |
| 204 | B |
| 205 | A |
| 206 | C |
| 207 | A |

TABLE 3-continued

IC$_{50}$ data for Compounds of Formula I

| Example # | Activity |
|---|---|
| 208 | B |
| 209 | A |
| 210 | A |
| 211 | A |
| 212 | B |
| 213 | B |
| 214 | N |
| 215 | C |
| 216 | C |
| 217 | C |
| 218 | C |
| 219 | C |
| 220 | B |
| 221 | C |
| 222 | C |
| 223 | B |
| 224 | C |
| 225 | C |
| 226 | C |
| 227 | C |
| 228 | B |
| 229 | B |
| 230 | C |
| 231 | B |
| 232 | C |
| 233 | B |
| 234 | C |
| 235 | C |
| 236 | C |
| 237 | A |
| 238 | A |
| 239 | C |
| 240 | C |
| 241 | C |
| 242 | A |
| 243 | B |
| 244 | C |
| 245 | B |
| 246 | B |
| 247 | C |
| 248 | C |
| 249 | C |
| 250 | B |
| 251 | C |

EXAMPLES

Intermediate 1. Ethyl 6-(4,4,5,5-tetramethyl-1,3,2-dioxaborolan-2-yl)-4H-spiro[benzo[d][1,3]-dioxine-2,4'-piperidine]-1'-carboxylate

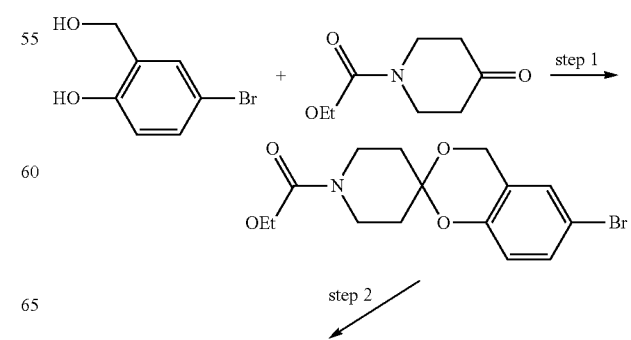

-continued

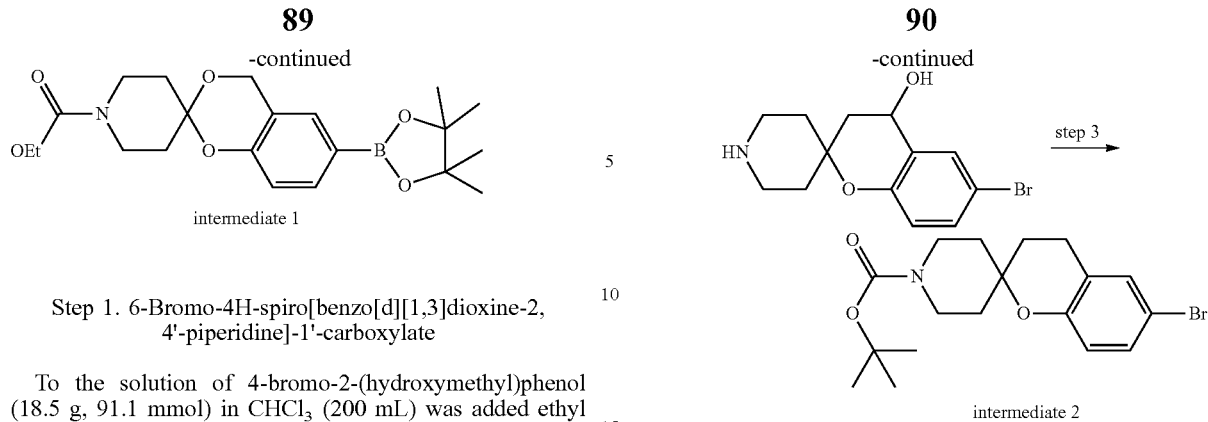

intermediate 1

Step 1. 6-Bromo-4H-spiro[benzo[d][1,3]dioxine-2,4'-piperidine]-1'-carboxylate To the solution of 4-bromo-2-(hydroxymethyl)phenol (18.5 g, 91.1 mmol) in CHCl$_3$ (200 mL) was added ethyl 4-oxopiperidine-1-carboxylate (18.13 g, 105.7 mmol), followed by toluenesulfonic acid (TsOH) (1.5 g). The resulting solution was heated to reflux with a Dean-Stark trap under argon overnight. The solvent was removed and the residue dissolved in t-butylmethyl ether (TBME) (250 mL) and washed with 2N NaOH (100 ml), water (100 mL), and brine (100 mL). The organic phase was dried (MgSO$_4$), filtered and concentrated to yield crude product as a gum. The product was purified by silica gel column chromatography (EtOAc/hexanes 10-30%) to give ethyl 6-bromo-4H-spiro[benzo[d][1,3]dioxine-2,4'-piperidine]-1'-carboxylate as a white solid (27.3 g, 84%).

Step 2. Ethyl 6-(4,4,5,5-tetramethyl-1,3,2-dioxaborolan-2-yl)-4H-spiro[benzo[d][1,3]-dioxine-2,4'-piperidine]-1'-carboxylate A suspension of ethyl 6-bromo-4H-spiro[benzo[d][1,3]dioxine-2,4'-piperidine]-1'-carboxylate (22 g, 61.8 mmol), 4,4,4',4',5,5,5',5'-octamethyl-2,2'-bi(1,3,2-dioxaborolane) (23.5 g, 92.6 mmol), Pd(DPPF)$_2$Cl$_2$ (2.5 g, 3.4 mmol), and potassium acetate (KOAc) (17.8 g, 181.6 mmol) in N,N-dimethylformamide (DMF) (150 mL) was degassed with argon for 10 min. The resulting suspension was heated at 90° C. for 5 h until completion by LC/MS. After cooling to room temperature (RT), brine (500 mL) and TBME (300 mL) were added, the layers separated and the organics again washed with brine (200 mL). The organic phase was dried (MgSO$_4$), filtered and concentrated to yield a crude product as a gum. The product was purified by silica gel column chromatography (5-15% EtOAc/hexanes) to give ethyl 6-(4,4,5,5-tetramethyl-1,3,2-dioxaborolan-2-yl)-4H-spiro[benzo[d][1,3]dioxine-2,4'-piperidine]-1'-carboxylate (21 g, 84%) obtained as a gum.

Intermediate 2. 6-Bromo-4-hydroxyspiro[chromane-2,4'-piperidine]-1'-carboxylate

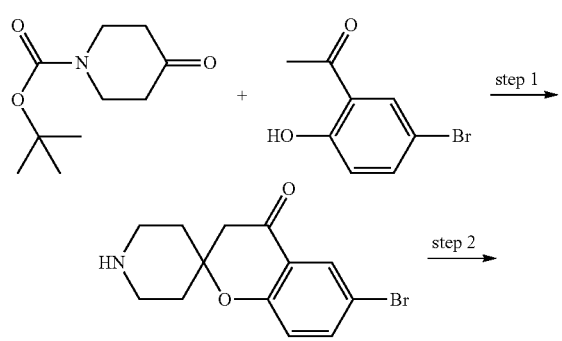

intermediate 2

Step 1. A solution of tert-butyl 4-oxopiperidine-1-carboxylate (21.5 g, 100 mmol), 1-(5-bromo-2-hydroxyphenyl)ethan-1-one (20.0 g, 100 mmol), and pyrrolidine (20 mL, 270 mmol) in methanol (200 mL) was heated at reflux for 4 h until completion was confirmed by LC/MS. The methanol was concentrated, the residue was dissolved in TBME (250 mL) and washed with washed with 1N HCl (200 mL), saturated NaHCO$_3$ solution (200 mL) and brine (200 mL). The organic phase was dried (MgSO$_4$), filtered and concentrated to yield a gum. The crude product was dissolved in hexanes (500 mL) and stirred at RT overnight to give a yellow solid, which was collected by filtration and further washed with hexanes. After drying, tert-butyl 6-bromo-4-oxospiro[chromane-2,4'-piperidine]-1'-carboxylate was obtained as a yellow solid (42.2 g).

Step 2. To the solution of tert-butyl 6-bromo-4-oxospiro[chromane-2,4'-piperidine]-1'-carboxylate (39.6 g, 100 mmol) in tetrahydrofuran (THF) (50 mL) and methanol (100 mL) was added NaBH$_4$ (4.16 g, 110 mmol) at 10 to 20° C. in portions over 10 min. The reaction was continued at 20° C. for 1 h until LC/MS indicated completion. The reaction mixture was poured into ice water (500 mL) and 3N HCl was slowly added until pH-7 (~35 mL). The organic solvents were removed and the aqueous phase extracted with EtOAc (100 mL×2). The combined organic phases were dried (MgSO$_4$), filtered and concentrated to yield tert-butyl 6-bromo-4-hydroxyspiro[chromane-2,4'-piperidine]-1'-carboxylate (40 g) as a gum, which was used directly to next step.

Step 3. The solution of tert-butyl 6-bromo-4-hydroxyspiro[chromane-2,4'-piperidine]-1'-carboxylate (~40 g) in dichloromethane (DCM) (~30 mL) was slowly added to a stirring trifluoroacetic acid (TFA) (100 mL) over 20 min at RT. At the end of addition, the mixture was stirred for additional 20 min and Et$_3$SiH (55 mL) was added at RT. The resulting orange solution was heated at reflux for 2 days until a sample of reaction was confirmed complete by $^1$H NMR. The solvents were removed and TBME (~500 mL) was added to allow the product to fully precipitate out, which was then collected by filtration to give the product (TFA salt) as a white solid. The white solid was suspended in DCM (100 mL) and saturated NaHCO$_3$(100 mL) was added slowly at 0° C. and followed by addition of di-tert-butylcarbonate (Boc$_2$O) (24 g, 120 mmol). After stirring at RT for 5 h, the layers were separated. The aqueous layer was extracted again with DCM (50 mL). The combined organic phases were dried (MgSO$_4$), filtered and concentrated to yield tert-butyl 6-bromospiro[chromane-2,4'-piperidine]-1'-carboxylate as an off-white solid, which was triturated with hexanes to yield 27 g of 6-bromo-4-hydroxyspiro[chromane-2,4'-piperidine]-1'-carboxylate.

Intermediate 3. tert-Butyl 6-(4,4,5,5-tetramethyl-1,3,2-dioxaborolan-2-yl)spiro[chromane-2,4'-piperidine]-1'-carboxylate

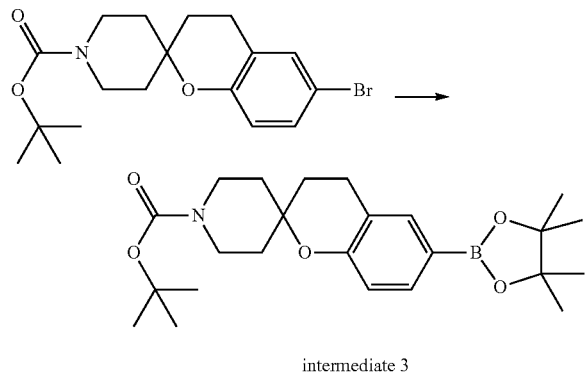

intermediate 3

A suspension of tert-butyl 6-bromospiro[chromane-2,4'-piperidine]-1'-carboxylate (intermediate 2; 23 g, 61 mmol), 4,4,4',4',5,5,5',5'-octamethyl-2,2'-bi(1,3,2-dioxaborolane) (24 g, 93 mmol), Pd(DPPF)$_2$Cl$_2$ (2.5 g, 3.4 mmol), and KOAc (18 g, 182 mmol) in DMF (150 mL) was degassed with argon for 10 min. The resulting suspension was heated at 90° C. for 5 h until competition confirmed by LC/MS. After cooling to RT, brine (500 mL) and TBME (300 mL) were added, the layers separated and the organic layer washed again with brine (200 mL). The organic phase was dried (MgSO$_4$), filtered and concentrated to yield (28 g) of crude product as a solid. The product was purified by silica gel column chromatography (10-25% EtOAc/hexanes) to give tert-butyl 6-(4,4,5,5-tetramethyl-1,3,2-dioxaborolan-2-yl)spiro[chromane-2,4'-piperidine]-1'-carboxylate as a white solid (22 g, 84%).

Intermediate 4. tert-Butyl 5-(4,4,5,5-tetramethyl-1,3,2-dioxaborolan-2-yl)-3H-spiro[benzo-furan-2,4'-piperidine]-1'-carboxylate

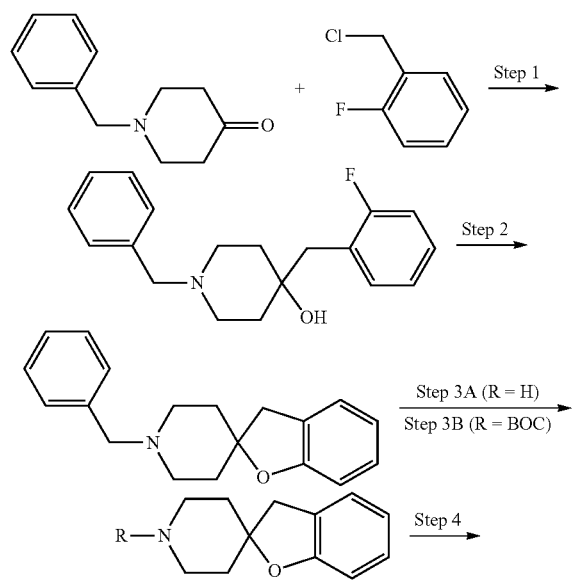

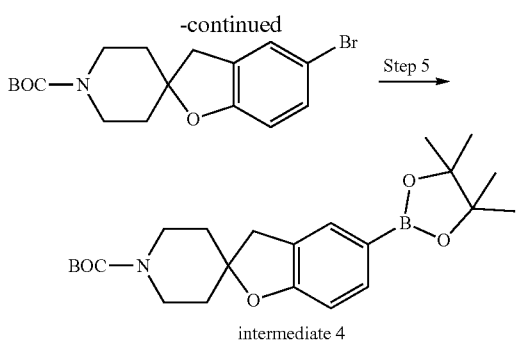

intermediate 4

Step 1. A solution of 1-(chloromethyl)-2-fluorobenzene (25 g, 173 mmol) in ether (50 mL) was slowly added to a stirred suspension of Mg (8.4 g, 346 mmol) in ether (100 mL) over 20 min at RT with the addition of I2 (100 mg). The speed of addition was such to maintain gentle reflux. At the end of the addition, the suspension was refluxed for 2 h, then cooled to 0° C. (ice bath temperature), followed by addition of 1-benzyl-4-(2-fluorobenzyl)piperidin-4-ol (29 g, 156 mmol) in ether (50 mL) over 5 min. The reaction was warm up to RT and stirred overnight. Saturated NH$_4$Cl (100 mL) and TBME (300 mL) were added and the layers separated. The organic layer was washed again with brine (200 mL) and was dried (MgSO$_4$), filtered and concentrated to obtain the crude product. The product was purified by silica gel column chromatography (20-80% EtOAc/hexanes). To give 1'-benzyl-3H-spiro[benzofuran-2,4'-piperidine] (32 g).

Step 2. A solution of 1'-benzyl-3H-spiro[benzofuran-2,4'-piperidine] in DMF (50 mL) was added dropwise to a suspension of NaH (60% dispersion; 21 g, 535 mmol) in DMF (150 mL) and toluene (50 mL) over 5 min. The reaction mixture was heated to reflux for 3 h until LC/MS confirmed completion. After cooling to RT, brine (500 mL) and TBME (300 mL) were added and the layers separated. The organic layer was washed with brine (200 mL), dried (MgSO$_4$), filtered and concentrated to yield 40 g of crude product as an oil. The product was purified by silica gel column chromatography (20-80% EtOAc/hexanes) to give 3H-spiro[benzofuran-2,4'-piperidine] as a light yellow oil (17.5 g).

Step 3A. To the solution of 3H-spiro[benzofuran-2,4'-piperidine] (17.5 g, 62.5 mmol) in methanol (100 mL) was added 5.0 g of 10% Pd/C and 1 mL formic acid. The suspension was hydrogenated at 60 PSI for 12 h at 60° C. After cooling to RT, the catalyst was removed by filtration and washed with methanol (10 mL×2). The combined filtrate was concentrated to give 11.5 g of 3H-spiro[benzofuran-2,4'-piperidine] as an oil.

Step 3B. The oil was suspended in DCM (100 mL) and sat. NaHCO$_3$(100 mL) at 0° C. followed by addition of Boc$_2$O (17.6 g, 80 mmol). After stirring at RT for 5 h, the layers were separated, the aqueous layer back extracted with DCM (50 mL) and the combined organic phases were dried (MgSO$_4$), filtered and concentrated to yield tert-butyl 3H-spiro[benzofuran-2,4'-piperidine]-1'-carboxylate as an off-white solid. Trituration with hexanes gave 13.5 g of desired product.

Step 4. To the solution of tert-butyl 3H-spiro[benzofuran-2,4'-piperidine]-1'-carboxylate (13.5 g, 46.7 mmol) in THF (50 mL) and methanol (50 mL) was added NBS (8.7 g, 49.0 mmol) at 10 to 20° C. in small portions over 10 min. The reaction was maintained at RT for 3 h until LC/MS indicated completion. The reaction mixture was poured into water (500 mL) and the organic solvent was separated. The aqueous layer was extracted with EtOAc (2×100 mL) and the combined organic layers were dried (MgSO₄), filtered and concentrated to yield tert-butyl 5-bromo-3H-spiro[benzofuran-2,4'-piperidine]-1'-carboxylate (17 g) as an off-white solid. trituration with hexanes yielded 16.5 g of the desired product.

Step 5. A suspension of tert-butyl 5-bromo-3H-spiro[benzofuran-2,4'-piperidine]-1'-carboxylate (15 g, 40.5 mmol), 4,4,4',4',5,5,5',5'-octamethyl-2,2'-bi(1,3,2-dioxaborolane)(16 g, 62 mmol), Pd(DPPF)₂Cl₂ (2.0 g, 2.7 mmol), and KOAc (15 g, 150 mmol) in DMF (100 mL) was degassed with argon for 10 min. The resulting suspension was heated at 90° C. for 5 h until completion confirmed by LC/MS. After cooling to RT, brine (500 mL) and TBME (300 mL) were added and the layers separated. The organic phase was dried (MgSO₄), filtered and concentrated to yield a crude product as a solid. The product was purified by silica gel column chromatography (10-35% EtOAc/hexane). To give tert-butyl 5-(4,4,5,5-tetramethyl-1,3,2-dioxaborolan-2-yl)-3H-spiro[benzofuran-2,4'-piperidine]-1'-carboxylate as a white solid (14.5 g).

Example 1. [6-(1-Methyl-6-isoquinolyl)spiro[chromane-2,4'-piperidine]-1'-yl]-[(2R)-tetrahydrofuran-2-yl]methanone, HCl

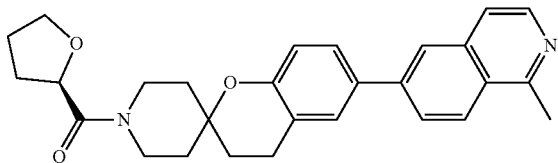 [SMILES: Cc1nccc2cc(-c3ccc4c(c3)CCC3(CCN(C(=O)[C@H]5CCCO5)CC3)O4)ccc12]

Step 1. To a Schlenk flask was added 6-(4,4,5,5-tetramethyl-1,3,2-dioxaborolan)-3,4-di-hydrospiro(chromene-2,4-piperidine)-1-carboxylic acid tert-butyl ester (0.5 g, 1.16 mmol), 6-bromo-1-chloro-isoquinoline (0.28 g, 1.16 mmol), tetrakis(triphenylphosphine)-palladium(0) (0.13 g, 0.12 mmol), 1M Na₂CO₃ (3.5 mL, 3.5 mmol), and 1,4-dioxane (7 mL). The flask was degassed under an atmosphere of argon for 5 min and then heated at 80° C. overnight. The reaction was cooled to RT, filtered through a pad of diatomaceous earth (celite), washed with 1N Na₂CO₃, water and brine, then dried over Na₂SO₄ and concentrated. The product was purified by ISCO silica gel chromatography (10-20% ethyl acetate/hexanes). The fractions containing product were concentrated to give 6-(1-chloro-isoquinoline)-3,4-dihydrospiro(chromene-2,4-piperidine)-1-carboxylic acid tert-butyl ester was isolated as a solid (0.22 g, 41%); LCMS m/z=465 (M+1).

Step 2. To a Schlenk flask under an atmosphere of argon was added 6-(1-chloro-isoquinoline)-3,4-dihydrospiro(chromene-2,4-piperidine)-1-carboxylic acid tert-butyl ester (0.22 g, 0.48 mmol), methylboronic acid (144 mg, 2.40 mmol), [1,1'-bis(diphenylphosphino)-ferrocene]dichloropalladium(II), complex with DCM (1:1) (78 mg, 0.09 mmol), potassium phosphate (0.51 g, 2.40 mmol) and 1,4-dioxane (8 mL). The flask was degassed under an atmosphere of argon for 5 min and heated at 99° C. for 1 h. The reaction was cooled, filtered through a pad of celite, washed with 1N Na₂CO₃, water and brine, then dried over Na₂SO₄ and concentrated. The product was purified via ISCO silica gel chromatography (20-50% ethyl acetate/hexanes) to give 6-(1-Methyl-isoquinoline)-3,4-dihydrospiro(chromene-2,4-piperidine)-1-carboxylic acid tert-butyl ester was isolated as a solid (0.14 g, 68%). LCMS m/z=445 (M+1).

Step 3. 6-(1-Methyl-isoquinoline)-3,4-dihydrospiro(chromene-2,4-piperidine)-1-carboxylic acid tert-butyl ester was in DCM (4 mL) was added TFA (1 mL) dropwise. The reaction was stirred at RT for 1 h and concentrated. The residue was partitioned between DCM and 1N Na₂CO₃, washed with brine and dried over Na₂SO₄ to give 6-(methyl-isoquinoline)-3,4-dihydrospiro(chromene-2,4-piperidine) (0.11 g, 100%). LCMS m/z=345 (M+1).

Step 4 A mixture of (1-[bis(dimethylamino)methylene]-1H-1,2,3-triazolo[4,5-b]pyridinium 3-oxid hexafluorophosphate) (HATU) (138 mg, 0.36 mmol), (R)-tetrahydrofuran-2-carboxylic acid (0.03 mL, 0.36 mmol), and N,N-diisopropylethylamine (DIPEA) (0.17 mL) in DCM (5 mL) was stirred for 15 min at rt. Then 6-(methylisoquinoline)-3,4-dihydrospiro(chromene-2,4-piperidine) (114 mg, 0.33 mmol) was added and the reaction was stirred for an additional 20 min at RT. The solution was washed with 1N Na₂CO₃ and brine, then dried over Na₂SO₄ and concentrated. The product was purified using Gilson (0.1% TFA in water/0.1% TFA in acetonitrile (ACN) 30-100%). The fractions with product were combined and diluted with DCM, washed with 1N Na₂CO₃ and brine, then dried over Na₂SO₄ and concentrated. The HCl salt was synthesized by adding 2M of hydrogen chloride in diethyl ether (0.17 mL, 0.33 mmol) to the base in DCM. The mixture was concentrated and the solid collected and dried sample at 65° C. under high vacuum overnight to give [6-(1-methyl-6-isoquinolyl)spiro[chromane-2,4'-piperidine]-1'-yl]-[(2R)-tetrahydrofuran-2-yl]methanone hydrochloride (0.05 g, 32%). LCMS m/z=443 (M+1). ¹H NMR (DMSO-d6) δ: 8.51-8.62 (m, 2H), 8.45 (d, 1H, J=6.5 Hz), 8.30-8.36 (m, 1H), 8.27 (s, 1H), 7.70-7.81 (m, 2H), 7.02 (d, 1H, J=8.5 Hz), 4.63-4.74 (m, 1H), 4.02-4.16 (m, 1H), 3.69-3.90 (m, 3H), 3.33-3.66 (m, 2H), 3.19 (s, 3H), 3.02-3.15 (m, 1H), 2.88 (m, 2H), 1.95-2.12 (m, 2H), 1.88 (m, 6H), 1.61-1.72 (m, 1H), 1.50-1.60 (m, 1H).

Example 2. 1-[6-(4-Methyl-3-quinolyl)spiro[chromane-2,4'-piperidine]-1'-yl]propan-1-one, HCl

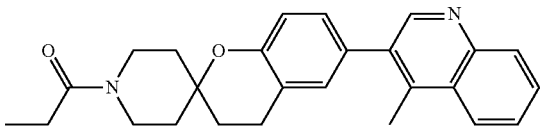

Step 1. tert-Butyl 6-(4-methyl-3-quinolyl)spiro[chromane-2,4'-piperidine]-1'-carboxylate was synthesized from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 3-bromo-4-methylquinoline (0.31 g, 1.40 mmol) using the procedure for example 1 step 1 (0.46 g, 89%). LCMS m/z=445 (M+1).

Step 2. tert-Butyl 6-(4-methyl-3-quinolyl)spiro[chromane-2,4'-piperidine]-1'-carboxylate was dissolved in DCM (6 mL), TFA (2 mL) was added dropwise and stirred at RT for 2 h and concentrated. The product was partitioned between DCM and 1N Na₂CO₃, washed with brine, dried over Na₂SO₄ and concentrated. The residue was dissolved in DCM, 2M of hydrogen chloride in diethyl ether (0.58 mL, 1.16 mmol) was added and was concentrated to give 6-(4-methyl-3-quinolyl)spiro[chromane-2,4'-piperidine] 2HCl (420 mg, 98%). LCMS m/z=345 (M+1).

Step 3. To 6-(4-methyl-3-quinolyl)spiro[chromane-2,4'-piperidine] 2HCl (90 mg, 0.2 mmol) in DCM (4 mL) was added triethylamine (TEA) (0.8 mL, 5 mmol), followed by propanoyl chloride (30 uL, 0.4 mmol) dropwise. The reaction was stirred at RT for 20 min, diluted with DCM, and washed with 1N Na$_2$CO$_3$, water and brine. The DCM was dried over Na$_2$SO$_4$ and concentrated. The product was purified by Gilson chromatography (0.1% TFA in water/ 0.1% TFA in ACN gradient). The pure fractions were combined and diluted with DCM, then washed with 1N Na$_2$CO$_3$ and brine, dried over Na$_2$SO$_4$, and concentrated. The HCL salt was synthesized by adding 2M hydrogen chloride in diethyl ether (0.11 mL, 0.22 mmol) to a DCM solution of base, the DCM solution was concentrated and the solid collected to give 1-[6-(4-methyl-3-quinolyl)spiro[chromane-2,4'-piperidine]-1'-yl]propan-1-one HCl as a white solid (0.04 g, 40%). Analysis: LCMS m/z=401 (M+1). $^1$H NMR (DMSO-d$_6$) δ: 9.03 (s, 1H), 8.40 (d, 1H, J=8.3 Hz), 8.23 (d, 1H, J=8.3 Hz), 8.00 (m, 1H), 7.88 (m, 1H), 7.30 (m, 2H), 6.99 (d, 1H, J=8.3 Hz), 4.03-4.20 (m, 1H), 3.63-3.78 (m, 1H), 3.27-3.52 (m, 1H), 2.99-3.18 (m, 1H), 2.82-2.90 (m, 2H), 2.79 (s, 3H), 2.36 (d, 2H, J=7.5 Hz), 1.72-1.92 (m, 4H), 1.62-1.71 (m, 1H), 1.49-1.61 (m, 1H), 1.01 (t, 3H, J=7.4 Hz).

Example 3. Cyclopropyl-[6-(4-methyl-3-quinolyl)spiro[chromane-2,4'-piperidine]-1'-yl]-methanone HCl

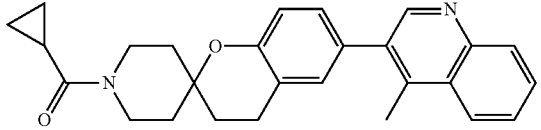 [SMILES: Cc1c(-c2ccc3c(c2)CCC2(CCN(C(=O)C4CC4)CC2)O3)cnc2ccccc12]

This compound was synthesized from 6-(4-methyl-3-quinolyl)spiro[chromane-2,4'-piperidine]2HCl (90 mg, 0.2 mmol) and cyclopropanecarbonyl chloride (30 uL, 0.4 mmol) using the procedure for Example 2 (0.05 g, 50%). Analysis: LCMS m/z=413 (M+1). $^1$H NMR (DMSO-d$_6$) δ: 9.05 (s, 1H), 8.38-8.43 (m, 1H), 8.17-8.28 (m, 1H), 7.97-8.08 (m, 1H), 7.83-7.92 (m, 1H), 7.23-7.32 (m, 2H), 6.93-7.05 (m, 1H), 4.00-4.19 (m, 2H), 3.45-3.65 (m, 1H), 3.04-3.21 (m, 1H), 2.85 (m, 2H), 2.80 (s, 3H), 1.98-2.07 (m, 2H), 1.89 (s, 2H), 1.44-1.84 (m, 4H), 0.63-0.83 (m, 4H).

Example 4. [6-(4-Methyl-3-quinolyl)spiro[chromane-2,4'-piperidine]-1'-yl]-[(2R)-tetrahydrofuran-2-yl]methanone, HCl

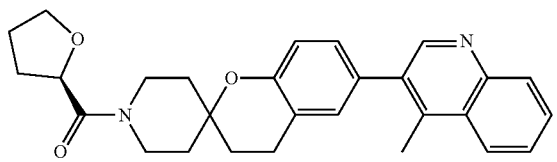 [SMILES: Cc1c(-c2ccc3c(c2)CCC2(CCN(C(=O)[C@H]4CCCO4)CC2)O3)cnc2ccccc12]

This compound was synthesized from 6-(4-methyl-3-quinolyl)spiro[chromane-2,4'-piperidine]2HCl (90 mg, 0.2 mmol) and (R)-tetrahydrofuran-2-carboxylic acid (23 μL, 0.24 mmol) in an analogous manner to Example 1 (0.07 g, 60%). Analysis: LCMS m/z=444 (M+1). $^1$H NMR (DMSO-d$_6$) δ: 9.06 (s, 1H), 8.42 (d, 1H, J=8.3 Hz), 8.27 (d, 1H, J=8.3 Hz), 7.95-8.06 (m, 1H), 7.84-7.94 (m, 1H), 7.23-7.35 (m, 2H), 6.93-7.04 (m, 1H), 4.63-4.74 (m, 1H), 4.04-4.19 (m, 1H), 3.69-3.91 (m, 3H), 3.33-3.55 (m, 1H), 3.00-3.21 (m, 1H), 2.82-2.88 (m, 2H), 2.81 (s, 3H), 1.95-2.15 (m, 2H), 1.73-1.92 (m, 6H), 1.63-1.73 (m, 1H), 1.50-1.62 (m, 1H).

Example 5. [6-(1-Cyclopropyl-6-isoquinolyl)spiro[chromane-2,4'-piperidine]-1'-yl]-[(2R)-tetrahydrofuran-2-yl]methanone

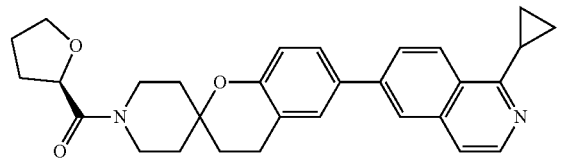 [SMILES: O=C([C@H]1CCCO1)N1CCC2(CCc3cc(-c4ccc5c(C6CC6)nccc5c4)ccc3O2)CC1]

Step 1. 6-(1-Chloroisoquinoline)-3,4-dihydrospiro(chromene-2,4-piperidine)-1-carboxylic acid tert-butyl ester was synthesized from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 6-bromo-1-chloroisoquinoline (0.28 g, 1.16 mmol) in an analogous manner to Example 1 step 1. Product isolated as a solid (0.18 g, 32%). LCMS m/z=465 (M+1).

Step 2. tert-Butyl 6-(1-cyclopropyl-6-isoquinolyl)spiro[chromane-2,4'-piperidine]-1'-carboxylate was prepared from 6-(1-chloroisoquinoline)-3,4-dihydrospiro(chromene-2,4-piperidine)-1-carboxylic acid tert-butyl ester (0.18 g, 0.38 mmol) and cyclopropyl boronic acid (0.16 g, 1.88 mmol) in an analogous manner to Example 1 step 2. Product isolated as a solid (0.12 g, 67%). LCMS m/z=471 (M+1).

Step 3. 6-(1-Cyclopropyl-6-isoquinolyl)spiro[chromane-2,4'-piperidine] was prepared from tert-butyl 6-(1-cyclopropyl-6-isoquinolyl)spiro[chromane-2,4'-piperidine]-1'-carboxylate (0.12 g, 0.25 mmol) and TFA (0.8 mL) in an analogous manner to Example 1 step 3. Product isolated as a solid (0.09 g, 97%). LCMS m/z=371 (M+1).

Step 4. A mixture of HATU (103 mg, 0.27 mmol), (R)-tetrahydrofuran-2-carboxylic acid (26 uL, 0.27 mmol), and DIPEA (128 uL, 0.74 mmol) in DCM (3 mL) was stirred for 15 min at RT. 6-(1-Cyclopropyl-6-isoquinolyl)spiro[chromane-2,4'-piperidine] (91 mg, 0.24 mmol) was added and the reaction was stirred for an additional 20 min. The solution was washed with 1N Na$_2$CO$_3$ and brine, then dried over Na$_2$SO$_4$, and concentrated. The product was purified using the Gilson (0.1% TFA in water/0.1% TFA in ACN gradient). Pure fractions were combined and diluted with DCM. The DCM solution was washed with 1N Na$_2$CO$_3$ and brine, dried over Na$_2$SO$_4$, and concentrated to give [6-(1-cyclopropyl-6-isoquinolyl)spiro[chromane-2,4'-piperidine]-1'-yl]-[(2R)-tetrahydrofuran-2-yl]methanone as a solid (0.05 g, 43%). LCMS m/z=469 (M+1). $^1$H NMR (DMSO-d$_6$) δ: 8.62 (d, 1H, J=8.5 Hz), 8.22-8.33 (m, 2H), 8.01-8.11 (m, 1H), 7.70-7.80 (m, 1H), 7.59-7.70 (m, 2H), 6.93-7.02 (m, 1H), 4.63-4.76 (m, 1H), 4.02-4.17 (m, 1H), 3.68-3.89 (m, 3H), 3.30-3.51 (m, 1H), 3.00-3.18 (m, 2H), 2.94 (m, 2H), 1.92-2.13 (m, 2H), 1.72-1.91 (m, 6H), 1.60-1.71 (m, 1H), 1.49-1.59 (m, 1H), 1.13-1.28 (m, 4H).

Example 6. 1-[6-(8-Methyl-7-quinolyl)spiro[chromane-2,4'-piperidine]-1'-yl]propan-1-one

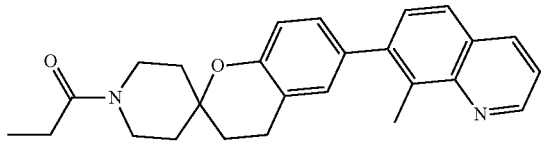 [SMILES: CCC(=O)N1CCC2(CCc3cc(-c4ccc5cccnc5c4C)ccc3O2)CC1]

Step 1. tert-Butyl 6-(8-methyl-7-quinolyl)spiro[chromane-2,4'-piperidine]-1'-carboxylate was prepared from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 7-bromo-8-methylquinoline (0.31 g, 1.4 mmol) in an analogous manner to Example 1a. Product isolated as a solid (0.46 g, 89%). LCMS m/z=445 (M+1).

Step 2. 6-(8-methyl-7-quinolyl)spiro[chromane-2,4'-piperidine] dihydrochloride was prepared from tert-butyl 6-(8-methyl-7-quinolyl)spiro[chromane-2,4'-piperidine]-1'-carboxylate (0.46 g, 1.03 mmol) and trifluoroacetic acid (2 mL) in an analogous manner to Example 2b. Product isolated as a solid (0.42 g, 97%). LCMS m/z=345 (M+1).

Step 3. To 6-(8-methyl-7-quinolyl)spiro[chromane-2,4'-piperidine] 2HCl (90 mg, 0.2 mmol) in DCM (4 mL) was added TEA (0.8 mL, 5 mmol), followed by propanoyl chloride (30 uL) dropwise and the reaction was stirred at rt for 20 min. The reaction was diluted with DCM, washed with 1N $Na_2CO_3$/water/brine, dried over $Na_2SO_4$, and concentrated. The product was purified using the Gilson (0.1% TFA in water/0.1% TFA in ACN gradient), diluted clean fractions with DCM, washed with 1N $Na_2CO_3$/brine, dried over $Na_2SO_4$, and concentrated. 1-[6-(8-Methyl-7-quinolyl)spiro[chromane-2,4'-piperidine]-1'-yl]propan-1-one was isolated as a solid (0.03 g, 40%). Analysis: LCMS m/z=401 (M+1); $^1$H NMR (DMSO-$d_6$) δ: 8.97 (m, 1H), 8.32-8.42 (m, 1H), 7.84 (d, 1H, J=8.5 Hz), 7.55 (m, 1H), 7.48 (d, 1H, J=8.5 Hz), 7.10-7.21 (m, 2H), 6.84-6.94 (m, 1H), 4.07-4.21 (m, 1H), 3.59-3.75 (m, 1H), 3.32-3.46 (m, 1H), 3.00-3.14 (m, 1H), 2.82 (m, 2H), 2.69 (s, 3H), 2.35 (m, 2H), 1.70-1.85 (br m, 4H), 1.58-1.70 (m, 1H), 1.47-1.58 (m, 1H), 1.01 (t, 3H, J=7.4 Hz).

Example 7. Cyclopropyl-[6-(8-methyl-7-quinolyl)spiro[chromane-2,4'-piperidine]-1'-yl]methanone, HCl

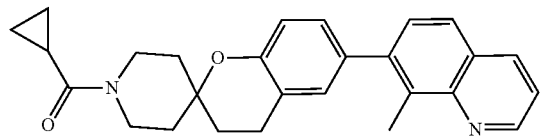 [SMILES: Cc1c(-c2ccc3c(c2)CCC2(CCN(C(=O)C4CC4)CC2)O3)ccc2cccnc12]

This compound was synthesized from 6-(8-methyl-7-quinolyl)spiro[chromane-2,4'-piperidine]2HCl (90 mg, 0.2 mmol) and cyclopropanecarbonyl chloride (30 uL, 0.4 mmol) in an analogous manner to Example 6 to give a solid (0.06 g, 60%). Analysis: LCMS m/z=413 (M+1); $^1$H NMR (DMSO-$d_6$) δ: 9.09 (d, 1H, J=3.3 Hz), 8.66-8.80 (m, 1H), 8.01 (m, 1H), 7.71-7.85 (m, 1H), 7.66 (m, 1H), 7.16-7.26 (m, 2H), 6.96 (d, 1H, J=8.3 Hz), 4.01-4.16 (m, 2H), 3.48-3.61 (m, 1H), 3.02-3.19 (m, 1H), 2.84 (m, 2H), 2.72 (s, 3H), 1.96-2.07 (m, 1H), 1.50-1.92 (br m, 6H), 0.62-0.78 (m, 4H).

Example 8. [6-(8-Methyl-7-quinolyl)spiro[chromane-2,4'-piperidine]-1'-yl]-[(2R)-tetrahydrofuran-2-yl]methanone, HCl

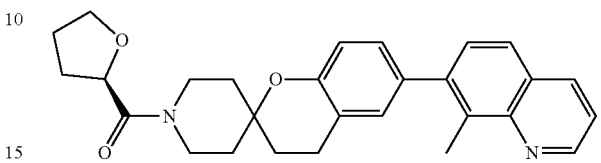

This compound was synthesized from 6-(8-methyl-7-quinolyl)spiro[chromane-2,4'-piperidine]2HCl (90 mg, 0.2 mmol) and (R)-tetrahydrofuran-2-carboxylic acid (23 uL, 0.24 mmol) in an analogous manner to Example 6 (0.05 g, 50%). Analysis: LCMS m/z=443 (M+1); $^1$H NMR (DMSO-$d_6$) δ: 9.08 (d, 1H, J=3.3 Hz), 8.65-8.76 (m, 1H), 7.96-8.06 (m, 1H), 7.72-7.83 (m, 1H), 7.56-7.67 (m, 1H), 7.21 (m, 2H), 6.90-6.98 (m, 1H), 4.62-4.74 (m, 1H), 4.02-4.16 (m, 1H), 3.76 (m, 3H), 3.34-3.53 (m, 1H), 3.01-3.19 (m, 1H), 2.83 (m, 2H), 2.72 (s, 3H), 1.95-2.14 (m, 2H), 1.73-1.90 (m, 6H), 1.62-1.73 (m, 1H), 1.49-1.60 (m, 1H).

Example 9. 1-[6-(8-chloro-7-quinolyl)spiro[chromane-2,4'-piperidine]-1'-yl]propan-1-one

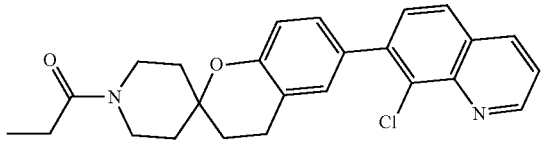 [SMILES: CCC(=O)N1CCC2(CCc3cc(-c4ccc5cccnc5c4Cl)ccc3O2)CC1]

Step 1. tert-Buty 6-(8-chloro-7-quinolyl)spiro[chromane-2,4'-piperidine]-1'-carboxylate was prepared from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 7-bromo-8-chloroquinoline (0.3 g, 1.22 mmol) in an analogous manner to Example 2 (0.4 g, 74%). LCMS m/z=465 (M+1).

Step 2. 6-(8-Chloro-7-quinolyl)spiro[chromane-2,4'-piperidine] dihydrochloride was prepared from tert-butyl 6-(8-chloro-7-quinolyl)spiro[chromane-2,4'-piperidine]-1'-carboxylate (0.4 g, 0.86 mmol) and TFA (2 mL) in an analogous manner to Example 2 step 2. Product isolated as a solid (0.39 g, 100%). LCMS m/z=365 (M+1).

Step 3. 1-[6-(8-Chloro-7-quinolyl)spiro[chromane-2,4'-piperidine]-1'-yl]propan-1-one was prepared from 6-(8-chloro-7-quinolyl)spiro[chromane-2,4'-piperidine] dihydrochloride (90 mg, 0.2 mmol) and propanoyl chloride (30 uL, 0.4 mmol) in an analogous manner to Example 6 (0.04 g, 40%). Analysis: LCMS m/z=421 (M+1); $^1$H NMR (DMSO-$d_6$) δ: 9.05 (dd, 1H, J=4.0, 1.8 Hz), 8.49 (dd, 1H, J=8.3, 1.8 Hz), 8.01 (d, 1H, J=8.8 Hz), 7.58-7.71 (m, 2H), 7.26-7.35 (m, 2H), 6.94 (d, 1H, J=9.0 Hz), 4.05-4.20 (m, 1H), 3.68 (br m, 1H), 3.34-3.48 (m, 1H), 3.00-3.17 (m, 1H), 2.83 (m, 2H), 2.35 (m, 2H), 1.70-1.91 (m, 4H), 1.60-1.70 (m, 1H), 1.46-1.57 (m, 1H), 1.01 (t, 3H, J=7.4 Hz).

Example 10. [6-(8-Chloro-7-quinolyl)spiro[chromane-2,4'-piperidine]-1'-yl]-cyclopropyl-methanone, HCl

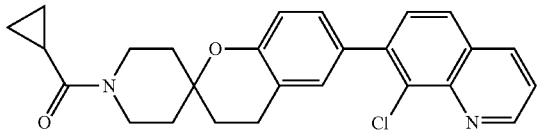 [SMILES: O=C(C1CC1)N1CCC2(CCc3cc(-c4ccc5cccnc5c4Cl)ccc3O2)CC1]

This compound was synthesized from 6-(8-chloro-7-quinolyl)spiro[chromane-2,4'-piperidine]2HCl (90 mg, 0.2 mmol) and cyclopropanecarbonyl chloride (30 uL, 0.4 mmol) in an analogous manner to Example 9 (0.05 g, 40%). Analysis: LCMS m/z=433 (M+1); $^1$H NMR (DMSO-d$_6$) δ: 9.06 (dd, 1H, J=4.1, 1.6 Hz), 8.50 (dd, 1H, J=8.3, 1.5 Hz), 8.02 (d, 1H, J=8.8 Hz), 7.63 (m, 2H), 7.31 (m, 2H), 6.95 (d, 1H, J=9.0 Hz), 5.04-5.35 (br m, 1H), 3.95-4.22 (m, 2H), 3.42-3.64 (m, 1H), 3.02-3.19 (m, 1H), 2.83 (m, 2H), 1.95-2.08 (m, 1H), 1.61-1.92 (m, 5H), 1.49-1.61 (m, 1H), 0.62-0.80 (m, 4H).

Example 11. [6-(8-Chloro-7-quinolyl)spiro[chromane-2,4'-piperidine]-1'-yl]-[(2R)-tetrahydrofuran-2-yl]methanone, HCl

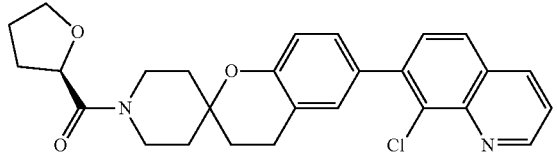 [SMILES: O=C([C@H]1CCCO1)N1CCC2(CCc3cc(-c4ccc5cccnc5c4Cl)ccc3O2)CC1]

This compound was synthesized from 6-(8-chloro-7-quinolyl)spiro[chromane-2,4'-piperidine]2HCl (90 mg, 0.2 mmol) and (R)-tetrahydrofuran-2-carboxylic acid (23 uL, 0.24 mmol) in an analogous manner to Example 1 (0.06 g, 50%). Analysis: LCMS m/z=464 (M+1); $^1$H NMR (DMSO-d$_6$) δ: 9.06 (dd, 1H, J=4.1, 1.6 Hz), 8.46-8.54 (m, 1H), 8.02 (d, 1H, J=8.5 Hz), 7.58-7.70 (m, 2H), 7.31 (m, 2H), 6.87-6.99 (m, 1H), 4.74-4.97 (br m, 1H), 4.61-4.75 (m, 1H), 4.01-4.18 (m, 1H), 3.76 (m, 3H), 3.29-3.53 (m, 1H), 3.01-3.19 (m, 1H), 2.83 (m, 2H), 1.94-2.17 (m, 2H), 1.87 (m, 6H), 1.62-1.70 (m, 1H), 1.49-1.62 (m, 1H).

Example 12. 1-[6-(8-Methyl-3-quinolyl)spiro[chromane-2,4'-piperidine]-1'-yl]propan-1-one

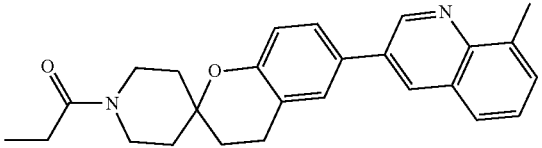 [SMILES: CCC(=O)N1CCC2(CCc3cc(-c4cnc5c(C)cccc5c4)ccc3O2)CC1]

Step 1. tert-Butyl 6-(8-methyl-3-quinolyl)spiro[chromane-2,4'-piperidine]-1'-carboxylate was prepared from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 3-bromo-8-methylquinoline (0.31 g, 1.40 mmol) in an analogous manner to Example 1 0.41 g, 79%). LCMS m/z=445 (M+1).

Step 2. 6-(8-Methyl-3-quinolyl)spiro[chromane-2,4'-piperidine] 2HCl was prepared from tert-butyl 6-(8-methyl-3-quinolyl)spiro[chromane-2,4'-piperidine]-1'-carboxylate (0.41 g, 0.92 mmol) and TFA (2 mL) in an analogous manner to Example 2 step 2 (0.35 g, 90%). LCMS m/z=345 (M+1).

Step 3. 1-[6-(8-Methyl-3-quinolyl)spiro[chromane-2,4'-piperidine]-1'-yl]propan-1-one was prepared from 6-(8-methyl-3-quinolyl)spiro[chromane-2,4'-piperidine] 2HCl (90 mg, 0.2 mmol) and propanoyl chloride (30 uL, 0.4 mmol) in an analogous manner to Example 6 (0.03 g, 30%). Analysis: LCMS m/z=401 (M+1); $^1$H NMR (DMSO-d$_6$) δ: 9.15 (d, 1H, J=2.5 Hz), 8.39-8.51 (m, 1H), 7.88-7.95 (m, 1H), 7.77-7.84 (m, 1H), 7.55-7.66 (m, 2H), 7.42-7.50 (m, 1H), 6.91-7.00 (m, 1H), 4.08-4.15 (m, 1H), 3.64-3.73 (m, 1H), 3.35-3.43 (m, 1H), 3.00-3.11 (m, 1H), 2.80-2.92 (m, 2H), 2.54 (s, 3H), 2.25-2.39 (m, 2H), 1.83-1.89 (m, 2H), 1.70-1.81 (m, 2H), 1.60-1.68 (m, 1H), 1.47-1.57 (m, 1H), 1.00 (t, 3H, J=7.4 Hz).

Example 13. Cyclopropyl-[6-(8-methyl-3-quinolyl)spiro[chromane-2,4'-piperidine]-1'-yl]-methanone, HCl

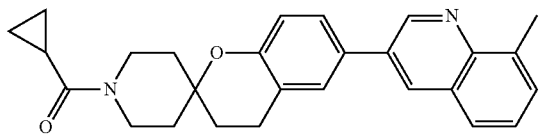

This compound was synthesized from 6-(8-methyl-3-quinolyl)spiro[chromane-2,4'-piperidine]2HCl (90 mg, 0.2 mmol) and cyclopropanecarbonyl chloride (30 uL, 0.4 mmol) in an analogous manner to Example 2 step 3 (0.07 g, 70%). Analysis: LCMS m/z=413 (M+1); $^1$H NMR (DMSO-d$_6$) δ: (d, 1H, J=1.8 Hz), 9.13 (br s, 1H), 8.15 (d, 1H, J=8.5 Hz), 8.04 (s, 1H), 7.66-7.80 (m, 3H), 7.02 (d, 1H, J=8.5 Hz), 3.98-4.18 (m, 2H), 3.47-3.60 (m, 1H), 3.02-3.16 (m, 1H), 2.88 (t, 2H, J=6.7 Hz), 2.61 (s, 3H), 1.96-2.07 (m, 1H), 1.89 (s, 2H), 1.62-1.85 (m, 3H), 1.46-1.61 (m, 1H), 0.68-0.76 (m, 4H).

Example 14. [6-(8-Methyl-3-quinolyl)spiro[chromane-2,4'-piperidine]-1'-yl]-[(2R)-tetrahydrofuran-2-yl]methanone, HCl

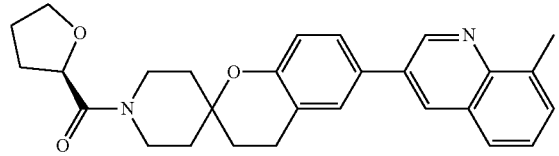 [SMILES: Cc1cccc2cc(-c3ccc4c(c3)CCC3(CCN(C(=O)[C@H]5CCCO5)CC3)O4)cnc12]

This compound was synthesized from 6-(8-methyl-3-quinolyl)spiro[chromane-2,4'-piperidine]2HCl (90 mg, 0.2 mmol) and (R)-tetrahydrofuran-2-carboxylic acid (23 uL, 0.24 mmol) in an analogous manner to Example 1 (0.05 g, 50%). Analysis: LCMS m/z=443 (M+1); $^1$H NMR (DMSO-d$_6$) δ: 9.44 (d, 1H, J=2.0 Hz), 9.13 (br s, 1H), 8.15 (d, 1H, J=8.3 Hz), 8.05 (s, 1H), 7.65-7.80 (m, 3H), 7.02 (dd, 1H, J=8.5, 1.8 Hz), 4.69 (m, 1H), 4.02-4.17 (m, 1H), 3.70-3.89

(m, 3H), 3.33-3.53 (m, 1H), 3.01-3.16 (m, 1H), 2.87 (m, 2H), 2.61 (s, 3H), 1.94-2.12 (m, 2H), 1.71-1.91 (m, 6H), 1.61-1.69 (m, 1H), 1.50-1.59 (m, 1H).

Example 15. Cyclopropyl-[6-(8-methoxy-7-quinolyl)spiro[chromane-2,4'-piperidine]-1'-yl]-methanone, HCl

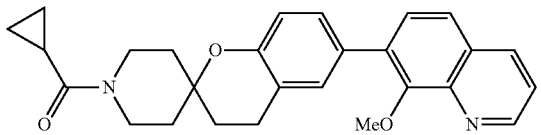

Step 1. tert-Butyl 6-(8-methoxy-7-quinolyl)spiro[chromane-2,4'-piperidine]-1'-carboxylate was prepared from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 7-bromo-8-methoxyquinoline (0.33 g, 1.40 mmol) in an analogous manner to Example 1 (0.44 g, 82%). LCMS m/z=461 (M+1).

Step 2. 6-(8-Methoxy-7-quinolyl)spiro[chromane-2,4'-piperidine] was prepared from tert-butyl 6-(8-methoxy-7-quinolyl)spiro[chromane-2,4'-piperidine]-1'-carboxylate (0.44 g, 0.96 mmol) and TFA (2 mL) in an analogous manner to Example 1 step 3 (0.32 g, 93%). LCMS m/z=361 (M+1).

Step 3. Cyclopropyl-[6-(8-methoxy-7-quinolyl)spiro[chromane-2,4'-piperidine]-1'-yl]methanone HCl was prepared from 6-(8-methoxy-7-quinolyl)spiro[chromane-2,4'-piperidine] (90 mg, 0.2 mmol) and cyclopropanecarbonyl chloride (40 uL, 0.4 mmol) in an analogous manner to Example 2 step 3 (0.07 g, 60%). Analysis: LCMS m/z=429 (M+1); $^1$H NMR (DMSO-$d_6$) δ: 9.12 (d, 1H, J=4.0 Hz), 8.84-8.96 (m, 1H), 8.01 (m, 1H), 7.85 (d, 2H, J=8.5 Hz), 7.39-7.54 (m, 2H), 6.99 (d, 1H, J=8.0 Hz), 3.95-4.18 (m, 2H), 3.77 (s, 3H), 3.50-3.61 (m, 1H), 3.06-3.20 (m, 1H), 2.86 (m, 2H), 1.97-2.08 (m, 1H), 1.89 (m, 3H), 1.64-1.79 (m, 2H), 1.47-1.62 (m, 1H), 0.64-0.81 (m, 4H).

Example 16. [6-(8-Methoxy-7-quinolyl)spiro[chromane-2,4'-piperidine]-1'-yl]-[(2R)-tetrahydrofuran-2-yl]methanone HCl

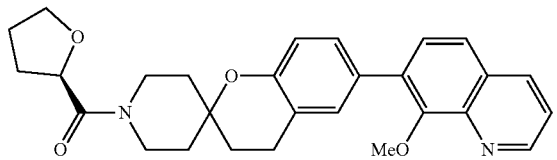 [SMILES: COc1c(-c2ccc3c(c2)CCC2(CCN(C(=O)[C@H]4CCCO4)CC2)O3)ccc2cccnc12]

This compound was synthesized from 6-(8-methoxy-7-quinolyl)spiro[chromane-2,4'-piperidine](90 mg, 0.2 mmol) and (R)-tetrahydrofuran-2-carboxylic acid (27 uL, 0.28 mmol) in an analogous manner to Example 1 step 4 (0.07 g, 60%). Analysis: LCMS m/z=459 (M+1); $^1$H NMR (DMSO-$d_6$) δ: 9.16 (d, 1H, J=3.8 Hz), 8.97-9.05 (m, 1H), 8.06 (m, 1H), 7.93-7.99 (m, 1H), 7.91 (m, 1H), 7.52 (m, 2H), 6.91-7.02 (m, 1H), 4.66-4.74 (m, 1H), 4.02-4.18 (m, 1H), 3.75-3.91 (m, 3H), 3.74 (s, 3H), 3.36-3.50 (m, 1H), 3.05-3.20 (m, 1H), 2.82-2.93 (m, 2H), 1.96-2.14 (m, 2H), 1.74-1.93 (m, 6H), 1.62-1.74 (m, 1H), 1.50-1.62 (m, 1H).

Example 17. 1-[6-(8-Methyl-6-quinolyl)spiro[chromane-2,4'-piperidine]-1'-yl]propan-1-one, HCl

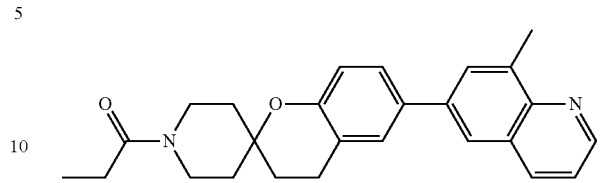

Step 1. tert-Butyl 6-(8-methyl-6-quinolyl)spiro[chromane-2,4'-piperidine]-1'-carboxylate was prepared from 6-(4,4,5,5-tetramethyl-1,3,2-dioxaborolan)-3,4-dihydrospiro(chromene-2,4-piperidine)-1-carboxylic acid tert-butyl ester (0.5 g, 1.16 mmol) and 6-bromo-8-methylquinoline (0.31 g, 1.40 mmol) in an analogous manner to Example 1 step 1(0.41 g, 78%). LCMS m/z=445 (M+1).

Step 2. 6-(8-Methyl-6-quinolyl)spiro[chromane-2,4'-piperidine] dihydrochloride was prepared from tert-butyl 6-(8-methyl-6-quinolyl)spiro[chromane-2,4'-piperidine]-1'-carboxylate (0.41 g, 0.91 mmol) in an analogous manner to Example 2 step 2 (0.36 g, 96%). LCMS m/z=345 (M+1).

Step 3. This compound was synthesized from 6-(8-methyl-6-quinolyl)spiro[chromane-2,4'-piperidine] 2HCl (90 mg, 0.2 mmol) and propanoyl chloride (30 uL, 0.4 mmol) in an analogous manner to Example 2 step 3 (0.05 g, 50%). Analysis: LCMS m/z=401 (M+1); $^1$H NMR (DMSO-$d_6$) δ: 9.04 (dd, 1H, J=4.8, 1.3 Hz), 8.75-8.83 (m, 1H), 8.25 (s, 1H), 8.17 (s, 1H), 7.79-7.90 (m, 1H), 7.57-7.68 (m, 2H), 6.98 (m, 1H), 4.05-4.21 (m, 1H), 3.54-3.77 (m, 1H), 3.34-3.45 (m, 1H), 2.99-3.14 (m, 1H), 2.86-2.93 (m, 2H), 2.84 (s, 3H), 2.28-2.41 (m, 2H), 1.84-1.91 (m, 2H), 1.71-1.82 (m, 2H), 1.59-1.70 (m, 1H), 1.49-1.58 (m, 1H), 1.00 (t, 3H, J=7.4 Hz).

Example 18. Cyclopropyl-[6-(8-methyl-6-quinolyl)spiro[chromane-2,4'-piperidine]-1'-yl]methanone HCl

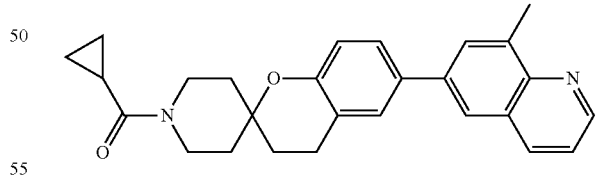

This compound was synthesized from 6-(8-methyl-6-quinolyl)spiro[chromane-2,4'-piperidine]2HCl (90 mg, 0.2 mmol) and cyclopropanecarbonyl chloride (30 uL, 0.4 mmol) in an analogous manner to Example 2 (0.06 g, 60%). Analysis: LCMS m/z=413 (M+1); $^1$H NMR (DMSO-$d_6$) δ: 9.05 (dd, 1H, J=4.8, 1.3 Hz), 8.77-8.85 (m, 1H), 8.26 (s, 1H), 8.18 (s, 1H), 7.80-7.89 (m, 1H), 7.56-7.68 (m, 2H), 6.98 (d, 1H, J=8.5 Hz), 4.09 (m, 2H), 3.46-3.60 (m, 1H), 3.02-3.18 (m, 1H), 2.87 (m, 2H), 2.85 (s, 3H), 1.97-2.10 (m, 1H), 1.62-1.88 (br m, 5H), 1.44-1.61 (m, 1H), 0.63-0.76 (m, 4H).

Example 19. 1-[6-(8-Methoxy-7-quinolyl)spiro[chromane-2,4'-piperidine]-1'-yl]propan-1-one

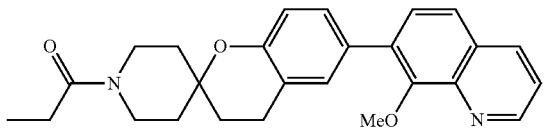

This compound was synthesized from 6-(8-methoxy-7-quinolyl)spiro[chromane-2,4'-piperidine](90 mg, 0.2 mmol) and propanoyl chloride (40 uL, 0.4 mmol) in an analogous manner to Example 15 (0.04 g, 30%). Analysis: LCMS m/z=417 (M+1); $^1$H NMR (DMSO-d$_6$) δ: 8.94 (dd, 1H, J=4.3, 1.8 Hz), 8.35-8.42 (m, 1H), 7.69-7.81 (m, 1H), 7.48-7.62 (m, 2H), 7.30-7.45 (m, 2H), 6.79-6.97 (m, 1H), 4.07-4.26 (m, 1H), 3.93 (s, 3H), 3.64-3.75 (m, 1H), 3.36-3.45 (m, 1H), 2.98-3.12 (m, 1H), 2.76-2.90 (m, 2H), 2.28-2.40 (m, 2H), 1.82-1.90 (m, 2H), 1.71-1.82 (m, 2H), 1.46-1.70 (br m, 2H), 1.01 (t, 3H, J=7.4 Hz).

Example 20. [6-(8-Methyl-6-quinolyl)spiro[chromane-2,4'-piperidine]-1'-yl]-[(2R)-tetrahydrofuran-2-yl]methanone, HCl

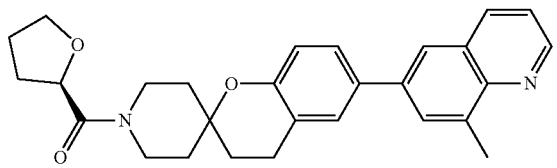

This compound was synthesized from 6-(8-methyl-6-quinolyl)spiro[chromane-2,4'-piperidine]2HCl (90 mg, 0.2 mmol) and (R)-tetrahydrofuran-2-carboxylic acid (23 uL, 0.24 mmol) in an analogous manner to Example 1 (0.06 g, 60%). Analysis: LCMS m/z=443 (M+1); $^1$H NMR (DMSO-d$_6$) δ: 9.03 (dd, 1H, J=4.5, 1.3 Hz), 8.71-8.82 (m, 1H), 8.25 (s, 1H), 8.16 (s, 1H), 7.76-7.87 (m, 1H), 7.65 (m, 2H), 6.97 (d, 1H, J=8.3 Hz), 4.64-4.77 (m, 1H), 3.99-4.16 (m, 1H), 3.67-3.90 (m, 3H), 3.33-3.49 (m, 1H), 2.97-3.16 (m, 1H), 2.86 (m, 2H), 2.84 (s, 3H), 1.94-2.14 (m, 2H), 1.86 (m, 6H), 1.50-1.71 (br m, 2H).

Example 21. 1-[6-(1-Methyl-6-isoquinolyl)spiro[4H-1,3-benzodioxine-2,4'-piperidine]-1'-yl]propan-1-one, HCl

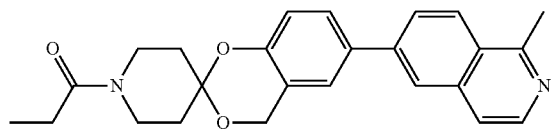

Step 1. To a Schlenk flask was added ethyl 6-(4,4,5,5-tetramethyl-1,3,2-dioxaborolan-2-yl)spiro[4H-1,3-benzodioxine-2,4'-piperidine]-1'-carboxylate (0.5 g, 1.24 mmol), 6-bromo-1-methyl-isoquinoline (0.33 g, 1.49 mmol), tetrakis(triphenylphosphine)-palladium(0) (0.14 g, 0.12 mmol), 1N Na$_2$CO$_3$ (3.72 mL, 3.72 mmol), and 1,4-dioxane (9 mL). The flask was degassed under an atmosphere of argon for 5 min and then heated at 99° C. overnight. The reaction was cooled to RT, filtered through a pad of celite, and washed with 1N Na$_2$CO$_3$ solution, water and brine. The solution was dried over Na$_2$SO$_4$ and concentrated. The product was purified by ISCO silica gel chromatography (100% ethyl acetate) to give the product as a solid (0.52 g, 100%). LCMS m/z=418 (M+1).

Step 2. Ethyl 6-(1-methyl-6-isoquinolyl)spiro[4H-1,3-benzodioxine-2,4'-piperidine]-1'-carboxylate was dissolved in a combination of ethanol (10 mL) and 6N NaOH (5 mL) and stirred at 80° C. overnight. After cooling to RT, the solution was partitioned between DCM and water, then washed with brine, dried over Na$_2$SO$_4$ and concentrated. The compound was dissolved in DCM, 2M of hydrogen chloride in diethyl ether (0.62 mL, 1.24 mmol) was added and was concentrated. 6-(1-Methyl-6-isoquinolyl)spiro[4H-1,3-benzodioxine-2,4'-piperidine] 2HCl was isolated as a dark solid (456 mg, 87%). LCMS m/z=347 (M+1).

Step 3. 1-[6-(1-Methyl-6-isoquinolyl)spiro[4H-1,3-benzodioxine-2,4'-piperidine]-1'-yl]propan-1-one HCl was prepared from 6-(1-methyl-6-isoquinolyl)spiro[4H-1,3-benzodioxine-2,4'-piperidine] dihydrochloride (90 mg, 0.2 mmol) and propanoyl chloride (30 uL, 0.4 mmol) in an analogous manner to Example 2 step 3 (0.04 g, 40%). Analysis: LCMS m/z=403 (M+1); $^1$H NMR (DMSO-d$_6$) δ: 8.60 (d, 1H, J=9.0 Hz), 8.54 (d, 1H, J=1.5 Hz), 8.47 (d, 1H, J=6.5 Hz), 8.31 (dd, 1H, J=9.0, 1.5 Hz), 8.25 (d, 1H, J=6.3 Hz), 7.84 (dd, 1H, J=8.7, 2.4 Hz), 7.78 (d, 1H, J=2.0 Hz), 7.08 (d, 1H, J=8.5 Hz), 5.01 (s, 2H), 3.55 (br m, 5H), 3.18 (s, 3H), 2.31-2.44 (m, 2H), 1.77-2.01 (br m, 4H), 1.00 (t, 3H, J=7.4 Hz).

Example 22. Cyclopropyl-[6-(1-methyl-6-isoquinolyl)spiro[4H-1,3-benzodioxine-2,4'-piperidine]-1'-yl]methanone, HCl

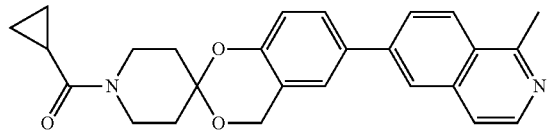 [SMILES: Cc1nccc2cc(-c3ccc4c(c3)COC3(CCN(C(=O)C5CC5)CC3)O4)ccc12]

This compound was synthesized from 6-(1-methyl-6-isoquinolyl)spiro[4H-1,3-benzodioxine-2,4'-piperidine] 2HCl (90 mg, 0.2 mmol) and cyclopropanecarbonyl chloride (39 uL, 0.43 mmol) in an analogous manner to Example 2 (0.03 g, 26%). Analysis: LCMS m/z=415 (M+1); $^1$H NMR (DMSO-d$_6$) δ: 8.59 (d, 1H, J=8.8 Hz), 8.53 (m, 1H), 8.47 (d, 1H, J=6.5 Hz), 8.28-8.33 (m, 1H), 8.16-8.25 (m, 1H), 7.81-7.87 (m, 1H), 7.78 (d, 1H, J=2.0 Hz), 7.09 (d, 1H, J=8.5 Hz), 5.02 (s, 2H), 3.70-3.85 (m, 2H), 3.51-3.69 (m, 3H), 3.16 (s, 3H), 1.77-2.07 (m, 5H), 0.67-0.81 (m, 4H).

Example 23. [6-(1-Methyl-6-isoquinolyl)spiro[4H-1,3-benzodioxine-2,4'-piperidine]-1'-yl]-[(2R)-tetrahydrofuran-2-yl]methanone, HCl

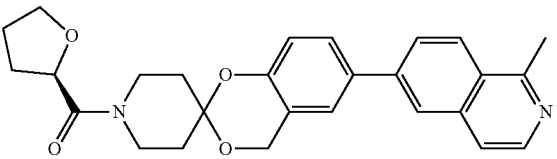 [SMILES: Cc1nccc2cc(-c3ccc4c(c3)COC3(CCN(C(=O)[C@H]5CCCO5)CC3)O4)ccc12]

This compound was synthesized from 6-(1-methyl-6-isoquinolyl)spiro[4H-1,3-benzodioxine-2,4'-piperidine] 2HCl (90 mg, 0.2 mmol) and (R)-tetrahydrofuran-2-carboxylic acid (23 uL, 0.24 mmol) in an analogous manner to Example 1. Product isolated as a solid (0.04 g, 30%). Analysis: LCMS m/z=445 (M+1); $^1$H NMR (DMSO-d$_6$) δ: 8.60 (d, 1H, J=8.8 Hz), 8.54 (d, 1H, J=1.5 Hz), 8.46 (d, 1H, J=6.5 Hz), 8.31 (dd, 1H, J=9.0, 1.8 Hz), 8.25 (d, 1H, J=6.5 Hz), 7.84 (dd, 1H, J=8.7, 2.4 Hz), 7.78 (d, 1H, J=2.0 Hz), 7.08 (d, 1H, J=8.5 Hz), 5.01 (s, 2H), 4.71 (m, 1H), 3.76 (m, 2H), 3.44-3.71 (m, 5H), 3.19 (s, 3H), 1.85 (br m, 8H).

Example 24. 1-[6-(1-Methyl-6-isoquinolyl)spiro[chromane-2,4'-piperidine]-1'-yl]propan-1-one, HCl

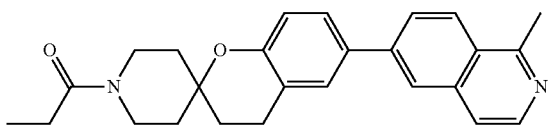

This compound was synthesized from 6-(1-methyl-6-isoquinolyl)spiro[chromane-2,4'-piperidine]2HCl (90 mg, 0.2 mmol) and propanoyl chloride (30 uL, 0.4 mmol) in an analogous manner to Example 2 (0.04 g, 40%). Analysis: LCMS m/z=401 (M+1); $^1$H NMR (DMSO-d$_6$) δ: 8.51-8.60 (m, 2H), 8.45 (d, 1H, J=6.5 Hz), 8.32 (dd, 1H, J=9.0, 1.8 Hz), 8.24 (d, 1H, J=6.5 Hz), 7.68-7.81 (m, 2H), 7.02 (d, 1H, J=8.5 Hz), 4.13 (m, 1H), 3.70 (m, 1H), 3.30-3.63 (br m, 2H), 3.19 (s, 3H), 3.06 m, (1H), 2.88 (m, 2H), 2.35 (m, 2H), 1.88 (m, 2H), 1.47-1.82 (m, 4H), 1.01 (t, 3H, J=7.4 Hz).

Example 25. Cyclopropyl-[6-(1-methyl-6-isoquinolyl)spiro[chromane-2,4'-piperidine]-1'-yl]methanone, HCl

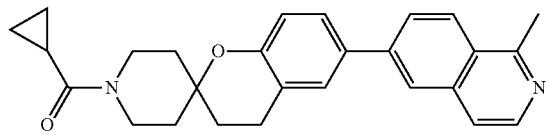 [SMILES: Cc1nccc2cc(-c3ccc4c(c3)CCC3(CCN(C(=O)C5CC5)CC3)O4)ccc12]

This compound was synthesized from 6-(1-methyl-6-isoquinolyl)spiro[chromane-2,4'-piperidine]2HCl (90 mg, 0.2 mmol) and cyclopropanecarbonyl chloride (30 uL, 0.4 mmol) in an analogous manner to Example 24 (0.04 g, 40%). Analysis: LCMS m/z=401 (M+1). $^1$H NMR (DMSO-d$_6$) δ: 8.51-8.62 (m, 2H), 8.45 (d, 1H, J=6.8 Hz), 8.33 (dd, 1H, J=9.0, 1.8 Hz), 8.26 (d, 1H, J=6.5 Hz), 7.72-7.83 (m, 2H), 7.03 (d, 1H, J=8.5 Hz), 4.09 (m, 2H), 3.52 (m, 3H), 3.19 (s, 2H), 3.10 (m, 1H), 2.89 (m, 2H), 2.06 (m, 1H), 1.62-1.90 (br m, 5H), 1.56 (m, 1H), 0.57-0.81 (m, 4H).

Example 26. 1-[6-(5-methylimidazo[1,2-a]pyridin-6-yl)spiro[chromane-2,4'-piperidine]-1'-yl]propan-1-one, HCL

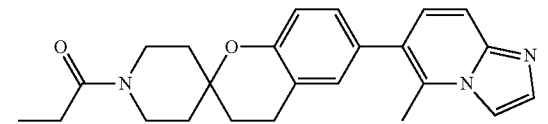 [SMILES: CCC(=O)N1CCC2(CCc3cc(-c4ccc5nccn5c4C)ccc3O2)CC1]

Step 1. tert-Butyl 6-(5-methylimidazo[1,2-a]pyridin-6-yl)spiro[chromane-2,4'-piperidine]-1'-carboxylate was prepared from 6-(4,4,5,5-tetramethyl-1,3,2-dioxaborolan)-3,4-dihydrospiro-(chromene-2,4-piperidine)-1-carboxylic acid tert-butyl ester (0.5 g, 1.16 mmol) and 6-bromo-5-methylimidazo[1,2-a]pyridine (0.3 g, 1.40 mmol) in an analogous manner to Example 1. LCMS m/z=434 (M+1).

Step 2. 6-(5-Methylimidazo[1,2-a]pyridin-6-yl)spiro[chromane-2,4'-piperidine] was prepared from tert-butyl 6-(5-methylimidazo[1,2-a]pyridin-6-yl)spiro[chromane-2,4'-piperidine]-1'-carboxylate and TFA (2 mL) in an analogous manner to Example 2 step 2. Analysis: LCMS m/z=334 (M+1); $^1$H NMR (DMSO-d$_6$) δ: 7.90 (s, 1H), 7.65 (m, 1H), 7.52 (m, 1H), 7.18 (m, 1H), 7.10 (m, 2H), 6.85 (m, 1H), 2.90 (m, 2H), 2.82 (m, 4H), 2.54 (s, 3H), 1.80 (m, 2H), 1.70 (m, 2H), 1.55 (m, 2H).

Step 3. 1-[6-(5-methylimidazo[1,2-a]pyridin-6-yl)spiro[chromane-2,4'-piperidine]-1'-yl]propan-1-one HCl was prepared from 6-(5-methylimidazo[1,2-a]pyridin-6-yl)spiro[chromane-2,4'-piperidine] (0.07 g, 0.21 mmol) and propanoyl chloride (0.04 mL, 0.4 mmol) in an analogous manner to Example 2 step 3 (0.04 g, 40%). Analysis: LCMS m/z=390 (M+1); $^1$H NMR (DMSO-d$_6$) δ: 8.40 (s, 1H), 8.30 (s, 1H), 7.86 (m, 2H), 7.18 (m, 2H), 6.96 (d, J=8.1 Hz, 1H), 4.14 (m, 1H), 3.67 (m, 1H), 3.40 (m, 1H), 3.06 (m, 1H), 2.82 (t, J=6.7 Hz, 2H), 2.70 (s, 3H), 2.32 (m, 2H), 1.85 (m, 2H), 1.49-1.79 (br m, 4H), 1.00 (t, J=7.4 Hz, 3H).

Example 27. Cyclopropyl-[6-(5-methylimidazo[1,2-a]pyridin-6-yl)spiro[chromane-2,4'-piperidine]-1'-yl]methanone, HCl

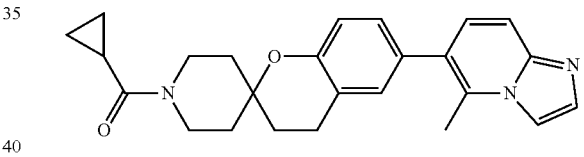

This compound was synthesized from 6-(5-methylimidazo[1,2-a]pyridin-6-yl)spiro[chromane-2,4'-piperidine] (0.07 g, 0.21 mmol) and cyclopropanecarbonyl chloride (0.04 g, 0.41 mmol) in an analogous manner to Example 2 step 3 (0.04 g, 45%). Analysis: LCMS m/z=402 (M+1); $^1$H NMR (DMSO-d$_6$) δ: 8.40 (s, 1H), 8.30 (s, 1H), 7.86 (m, 2H), 7.18 (m, 2H), 6.96 (d, J=8.1 Hz, 1H), 4.05 (m, 2H), 3.52 (m, 1H), 3.10 (m, 1H), 2.83 (m, 2H), 2.70 (s, 3H), 2.00 (m, 1H), 1.50-1.79 (br m, 6H), 0.75 (m, 4H).

Example 28. [6-(5-Methylimidazo[1,2-a]pyridin-6-yl)spiro[chromane-2,4'-piperidine]-1'-yl]-[(2R)-tetrahydrofuran-2-yl]methanone, HCl

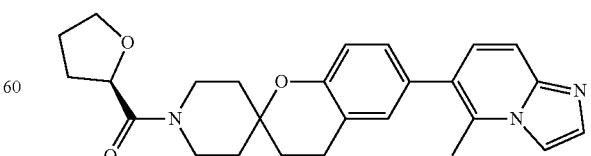

This compound was synthesized from 6-(5-methylimidazo[1,2-a]pyridin-6-yl)spiro[chromane-2,4'-piperidine] (0.07 g, 0.21 mmol) and (R)-tetrahydrofuran-2-carboxylic acid (0.02 mL, 0.23 mmol) an analogous manner to Example 1 step 4 (0.05 g, 52%). Analysis: LCMS m/z=432 (M+1); $^1$H NMR (DMSO-d$_6$) δ: 8.40 (s, 1H), 8.30 (s, 1H), 7.86 (m, 2H), 7.18 (m, 2H), 6.96 (d, J=8.1 Hz, 1H), 4.69 (m, 1H), 4.10 (m, 1H), 3.75 (m, 3H), 3.38 (m, 3H), 3.09 (m, 1H), 2.83 (m, 2H), 2.70 (s, 3H), 2.05 (m, 2H), 1.49-1.90 (br m, 6H).

The following examples were synthesized using procedures described for examples 1-28.

Example 29. 1-[6-(3-quinolyl)spiro[4H-1,3-benzodioxine-2,4'-piperidine]-1'-yl]propan-1-one

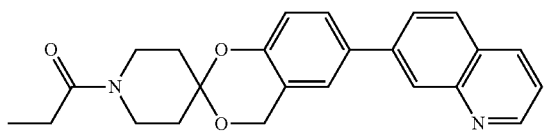

Analysis: LCMS m/z=389 (M+1); 1H NMR (DMSO-d$_6$): 9.2 (d, 1H, J=4 Hz), 8.96 (d, 1H, J=8 Hz), 8.43 (s, 1H), 8.33 (d, 1H, J=8.5 Hz), 8.18 (d, 1H, J=8.5 Hz), 7.90 (dd, 1H, J=4, 8 Hz), 7.72 (dd, 1H, J=2, 8 Hz), 7.67 (s, 1H), 7.07 (d, 1H, J=8.5 Hz), 5.00 (s, 2H), 3.61 (m, 1H), 3.54 (b, 3H), 2.38 (q, 2H, J=7.5 Hz), 1.92 (b, 2H), 1.83 (b, 2H), 1.00 (t, 3H, J=7.5 Hz).

Example 30. Ethyl 6-(7-quinolyl)spiro[4H-1,3-benzodioxine-2,4'-piperidine]-1'-carboxylate, HCl

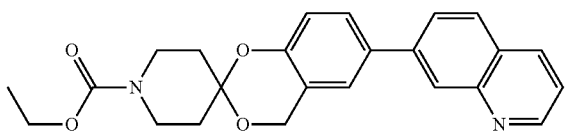

Analysis: LCMS m/z=405 (M+1); $^1$H NMR (DMSO-d$_6$) δ: 9.20 (d, 1H, J=4 Hz), 8.95 (d, 1H, J=8.4 Hz), 8.42 (s, 1H), 8.32 (d, 1H, J=8 Hz), 8.17 (d, 1H, J=8 Hz), 7.90 (dd, 1H, J=4, 8 Hz), 7.72 (d, 1H, J=8.4 Hz), 7.67 (s, 1H), 7.04 (d, 1H, J=9 Hz), 5.00 (s, 2H), 4.06 (q, 2H, J=7.4 Hz), 3.45-3.56 (m, 4H), 1.88 (b, 4H), 1.19 (t, 3H, J=7.2 Hz).

Example 31. 2-Methyl-1-[6-(7-quinolyl)spiro[4H-1,3-benzodioxine-2,4'-piperidine]-1'-yl]propan-1-one. HCl

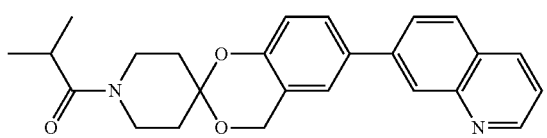

Analysis: LCMS=403 (M+1); $^1$H NMR (DMSO-d$_6$) δ: 9.16 (d, 1H, J=4 Hz), 8.88 (d, 1H, J=8 Hz), 8.37 (s, 1H), 8.29 (d, 1H, J=8 Hz), 8.15 (d, 1H, J=8 Hz), 7.86 (dd, 1H, J=4, 8 Hz), 7.72 (dd, 1H, j=2, 8 Hz), 7.67 (s, 1H), 7.06 (d, 1H, J=8.5 Hz), 5.00 (s, 2H), 3.52-3.66 (m, 4H), 2.92 (q, 1H, J=7 Hz), 1.92 (b, 2H), 1.84 (b, 2H), 1.03 (d, 6H, J=7 Hz).

Example 32. Cyclopropyl-[6-(7-quinolyl)spiro[4H-1,3-benzodioxine-2,4'-piperidine]-1'-yl]methanone, HCl

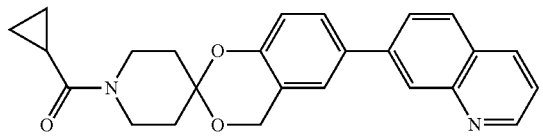 [SMILES: O=C(C1CC1)N1CCC2(CC1)OCc1cc(-c3ccc4cccnc4c3)ccc1O2]

Analysis: LCMS m/z=401 (M+1); 1H NMR (DMSO-d$_6$) δ: 9.16 (d, 1H, J=4 Hz), 8.87 9 d, 1H, J=8 Hz), 8.37 (s, 1H), 8.29 (d, 1H, J=8.5 Hz), 8.14 (d, 1H, j=8.5 Hz), 7.86 (dd, 1H, J=4.8 Hz), 7.73 (dd, 1H, J=2.8 Hz), 7.67 (b, 1H), 7.07 (d, 1H, J=8.5 Hz), 5.01 (s, 2H), 3.79 (b, 2H), 3.57 (b, 2H), 2.0-2.04 (m, 1H), 1.95 (b, 2H), 1.84 (b, 2H), 0.71-0.75 (m, 4H).

Example 33. 1-[6-(3-Quinolyl)spiro[4H-1,3-benzodioxine-2,4'-piperidine]-1'-yl]propan-1-one, HCl

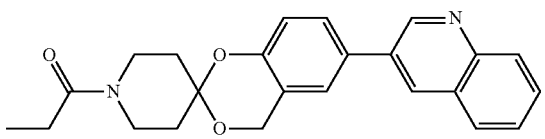

Analysis: LCMS m/z=389 (M+1); $^1$H NMR (DMSO-d$_6$) δ: 9.48 (s, 1H), 9.11 (s, 1H), 8.21-8.27 (m, 2H), 7.97 (t, 1H, J=8 Hz), 7.81-7.85 (m, 2H), 7.78 (s, 1H), 7.08 (d, 1H, J=8 Hz), 5.00 (s, 2H), 3.60-3.64 (m, 1H), 3.55 (b, 2H), 2.37 (q, 2H, J=7 Hz), 1.92 (b, 2H), 1.84 (b, 2H), 1.00 (t, 3H, J=7 Hz).

Example 34. 2-Methyl-1-[6-(3-quinolyl)spiro[4H-1,3-benzodioxine-2,4'-piperidine]-1'-yl]propan-1-one, HCl

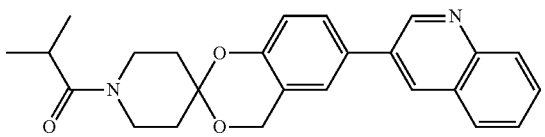 [SMILES: CC(C)C(=O)N1CCC2(CC1)OCc1cc(-c3cnc4ccccc4c3)ccc1O2]

Analysis: LCMS m/z=403 (M+1); $^1$H NMR (DMSO-d$_6$) δ:9.49 (s, 1H), 9.12 (s, 1H), 8.22-8.28 (m, 2H), 7.98 (t, 1H, J=8 Hz), 7.82-7.86 (m, 2H), 7.78 (s, 1H), 7.08 (d, 1H, J=8.5 Hz), 5.00 (s, 2H), 3.60 (b, 4H), 2.92 (q, 1H, J=7 Hz), 1.92 (b, 2H), 1.84 (b, 2H), 1.00 (d, 6H, J=7 Hz).

Example 35. Ethyl 6-(1,5-naphthyridin-3-yl)spiro[4H-1,3-benzodioxine-2,4'-piperidine]-1'-carboxylate, HCl

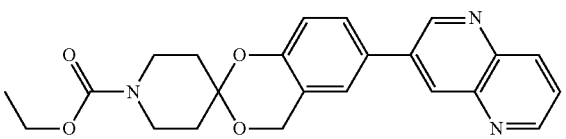

Analysis: LCMS m/z=406 (M+1); $^1$H NMR (DMSO-d$_6$) δ: 9.39 (d, 1H, J=2 Hz), 9.09 (dd, 1H, J=2, 4 Hz), 8.65 (d, 1H, J=2 Hz), 8.54 (d, 1H, J=8.5 Hz), 7.77-7.87 (m, 3H), 7.05 (d, 1H, J=8.5 Hz), 4.99 (s, 2H), 4.06 (q, 2H, J=7 Hz), 3.47-3.53 (m, 4H), 1.88 (b, 4H), 1.19 (t, 3H, J=7 Hz).

Example 36. 1-[6-(1,5-Naphthyridin-3-yl)spiro[4H-1,3-benzodioxine-2,4'-piperidine]-1'-yl]propan-1-one, HCl

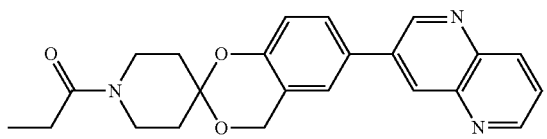 [SMILES: CCC(=O)N1CCC2(CC1)OCc1cc(-c3cnc4cccnc4c3)ccc1O2]

Analysis: LCMS m/z=390 (M+1); $^1$H NMR (DMSO-d$_6$) δ: 9.39 (d, 1H, J=2 Hz), 9.08 (dd, 1H, J=2.4 Hz), 8.64 (d, 1H, j=2 Hz), 8.53 (d, 1H, J=8.5 Hz), 7.80-7.85 (m, 2H), 7.77 (s, 1H), 7.05 (d, 1H, J=8.5 Hz), 4.99 (s, 2H), 3.60-3.64 (m, 1H), 3.52-3.58 (m, 2H), 2.36 (q, 2H, J=7 Hz), 1.92 (m, 2H), 1.82 (m, 2H), 1.00)t, 3H, J=7 Hz).

Example 37. Cyclopropyl-[6-(1,5-naphthyridin-3-yl)spiro[4H-1,3-benzodioxine-2,4'-piperidine]-1'-yl]methanone, HCl

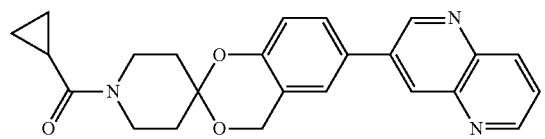

Analysis: LCMS m/z=402 (M+1); $^1$H NMR (DMSO-d$_6$) δ: 9.40 (d, 1H, j=2 Hz), 9.09 (dd, 1H, J=2.4 Hz), 8.66 (d, 1H, J=2 Hz), 8.55 (d, 1H, J=8.5 Hz), 7.81-7.87 (m, 2H), 7.78 (s, 1H), 7.06 (d, 1H, J=8.5 Hz), 5.01 (s, 2H), 3.77 (b, 2H), 3.58 (b, 2H), 1.99-2.05 (m, 1H), 1.95 (b, 2H), 1.84 (b, 2H), 0.71-0.75 (m, 4H).

Example 38. 1'-Propanoyl-6-(3-quinolyl)spiro[chromane-2,4'-piperidine]-4-one, HCl

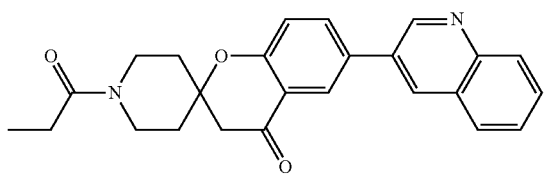 [SMILES: CCC(=O)N1CCC2(CC1)CC(=O)c1cc(-c3cnc4ccccc4c3)ccc1O2]

Analysis: LCMS m/z=401 (M+1); $^1$H NMR (DMSO-d$_6$) δ: 9.51 (s, 1H), 9.16 (s, 1H), 8.20-8.29 (m, 4H), 7.97 (t, 1H, J=8 Hz), 7.83 (t, 1H, J=8 Hz), 7.34 (d, 1H, J=8 Hz), 4.15 (d, 1H, J=13 Hz), 3.70 (d, 1H, J=13 Hz), 3.40 (t, 1H, J=12 Hz), 3.04 (t, 1H, J=12 Hz), 2.95 (s, 2H), 2.33 (q, 2H, J=7 Hz), 1.97 (t, 2H, J=12 Hz), 1.74-1.79 (m, 1H), 1.61-1.67 (m, 1H), 0.99 (t, 3H, J=7 Hz).

Example 39. Methyl 4-oxo-6-(3-quinolyl)spiro[chromane-2,4'-piperidine]-1'-carboxylate, HCl

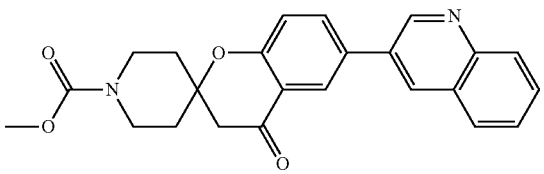 [SMILES: COC(=O)N1CCC2(CC1)CC(=O)c1cc(-c3cnc4ccccc4c3)ccc1O2]

Analysis: LCMS m/z=403 (M+1); $^1$H NMR (DMSO-d$_6$) δ: 9.40 (s, 1H), 8.95 (s, 1H), 8.24 (d, 1H, J=2 Hz), 8.12-8.19 (m, 3H), 7.89 (t, 1H, j=7 Hz), 7.75 (t, 1H, J=7 Hz), 7.31 (d, 1H, J=8.5 Hz), 3.79 (b, 2H), 3.47 (s, 3H), 3.23 (b, 2H), 2.94 (s, 2H), 1.95 (d, 2H, J=12 Hz), 1.68-1.75 9 m, 2H).

Example 40. Cyclopropyl-[6-(3-quinolyl)spiro[4H-1,3-benzodioxine-2,4'-piperidine]-1'-yl]methanone, HCl

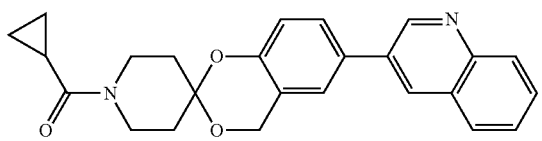

Analysis: LCMS m/z=401 (M+1); $^1$H NMR (DMSO-d$_6$) δ: 9.47 (s, 1H), 9.09 (s, 1H), 8.23 (m, 2H), 7.96 (t, 1H, J=8 Hz), 7.83 (m, 2H), 7.77 (s, 1H), 7.08 (d, 1H, J=7.5 Hz), 5.01 (s, 2H), 3.79 (b, 2H), 3.60 (b, 2H), 1.99-2.05 (m, 1H), 1.95 (b, 2H), 1.84 (b, 2H), 0.71-0.75 (m, 4H).

Example 41. Cyclobutyl-[6-(3-quinolyl)spiro[4H-1,3-benzodioxine-2,4'-piperidine]-1'-yl]methanone, HCl

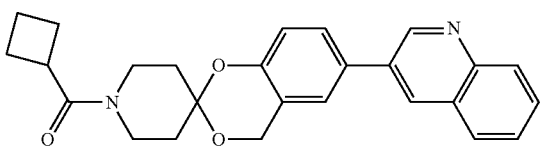

Analysis: LCMS m/z=415 (M+1): $^1$H NMR (DMSO-d$_6$) δ: 9.50 (s, 1H), 9.16 (s, 1H), 8.28 (d, 1H, J=8 Hz), 8.23 (d, 1H, J=8 Hz), 7.99 (t, 1H, J=8 Hz), 7.82-7.87 (m, 2H), 7.78 (s, 1H), 7.08 (d, 1H, J=8 Hz), 4.99 (s, 2H), 3.52-3.63 (m, 2H), 3.36-3.42 (m, 3H), 2.08-2.23 (m, 4H), 1.78-1.93 (m, 6H).

Example 42. 1-[4-Hydroxy-6-(3-quinolyl)spiro[chromane-2,4'-piperidine]-1'-yl]propan-1-one, HCl

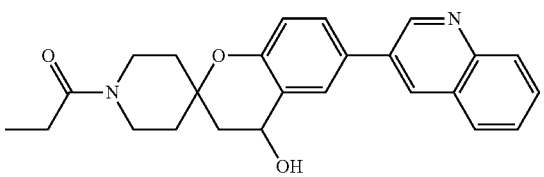

Example 38 (0.075 g, 0.19 mmol) in ethanol (3 mL) was added sodium borohydride (NaBH$_4$) (0.023 g, 0.60 mmol) followed by stirring at RT overnight. The mixture was then concentrated, dissolved in EtOAc and washed with 1N Na$_2$CO$_3$, and brine. The product was purified by ISCO silica gel chromatography (5-15% MeOH/DCM) to give an oil. The HCl salt was prepared by adding 1N HCl-ether to a DCM solution of base. The salt was recrystallized from DCM-ether and dried at 45° C. under vacuum. Analysis: LCMS m/z=403 (M+1); $^1$H NMR (DMSO-d$_6$) δ: 9.50 (s, 1H), 9.17 (s, 1H), 8.26-8.29 (m, 2H), 8.06 (m, 1H), 8.00 (t, 1H), J=8 Hz), 7.86 (t, 1H, J=8 Hz), 7.78 (dd, 1H, J=2, 8 Hz), 7.02 (d, 1H, J=8 Hz), 4.83 (t, 1H, J=7.5 Hz), 4.10 (t, 1H, J=12 Hz), 3.67 (t, 1H, J=12 Hz), 3.32-3.47 (m, 1H), 2.98-3.14 (m, 1H), 2.34 (q, 2H, J=7 Hz), 2.17-2.20 (m, 1H), 1.55-1.88 (m, 5H), 1.00 (t, 3H, J=7 Hz).

Example 43. 1-[6-(3-Quinolyl)spiro[chromene-2,4'-piperidine]-1'-yl]propan-1-one, HCl

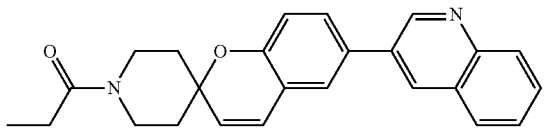 [SMILES: CCC(=O)N1CCC2(C=Cc3cc(-c4cnc5ccccc5c4)ccc3O2)CC1]

Step 1. Tert-Butyl 6-bromo-4-oxo-3,4-dihydro-1'H-spiro[chromene-2,4'-piperidine]-1'-carboxylate (5.00 g, 12.6 mmol) and sodium borohydride (1.19 g, 31.5 mmol) in ethanol (80 mL) were stirred for 4 h and concentrated, washed with water and dried. This material was heated in 4N HCl at 70° C. to give 6-bromo-spiro[chromene-2,4'-piperidine. LCMS m/z=281 (M+1). $^1$H NMR (CHLOROFORM-d) δ 7.26 (d, J=1.0 Hz, 1H), 7.16-7.23 (m, 1H), 7.10 (d, J=1.8 Hz, 1H), 6.72 (d, J=8.5 Hz, 1H), 6.29 (d, J=9.8 Hz, 2H), 5.65 (d, J=9.8 Hz, 1H), 3.01-3.16 (m, 4H), 2.85 (d, J=12.3 Hz, 4H), 1.95 (d, J=13.3 Hz, 2H).

Step 2. Palladium Acetate (0.020 g, 0.0892 mmol) and triphenylphosphine (0.0936 g, 0.357 mmol) were stirred 15 min under an atmosphere of nitrogen. 6-bromo-spiro[chromene-2,4'-piperidine (0.50 g, 1.78 mmol), 3-quinolineboronic acid (0.340 g, 1.96 mmol), N,N-dimethylformamide (7 mL) and 1 M of sodium carbonate (7.14 mL) were added and heated at 80° C. for 17 h. The mixture was concentrated, was dissolved in EtOAc, washed with 1N Na$_2$CO$_3$, water and brine, then dried (MgSO$_4$). The product was purified by ISCO (silica gel, 40 g 25-70% EtOAc/hexanes) to give 6-(3-quinolyl)spiro[chromene-2,4'-piperidine] (950 mg, 85%) as a white solid. LCMS m/z=329 (M+1).

Step 3. 6-(3-Quinolyl)spiro[chromene-2,4'-piperidine] (0.050 g, 0.15 mmol) and DIPEA (0.0796 mL, 0.457 mmol) in DCM (2 mL) was added propanoyl chloride (0.0265 mL, 0.304 mmol). After 2 h stirring at RT the mixture was concentrated, dissolved in EtOAc and washed with 1N Na$_2$CO$_3$ and brine. After drying over MgSO$_4$ the product was purified by ISCO silica gel chromatography (0-5% MeOH/DCM) to give an oil. The HCl salt was prepared by adding 1N HCl-ether to a DCM solution of base. The salt was recrystallized from DCM-ether and dried at 45° C. under vacuum to give a yellow solid. Analysis: LCMS m/z=385 (M+1); $^1$H NMR (DMSO-d$_6$) δ: 9.36 (s, 1H), 8.86 (s, 1H), 8.11 (d, 1H, j=9 Hz), 7.87 (t, 1H, J=7.5 Hz), 7.72-7.76 (m, 3H), 7.05 (d, 1H, J=8 Hz), 6.62 (d, 1H, J=10 Hz), 5.87 (d, 1H, J=10 Hz), 4.10 (d, 2H, J=12 Hz), 3.67 (d, H, J=12 Hz), 3.46 (t, 1H, J=12 Hz), 3.13 (t, 1H, J=14 Hz), 2.35 (q, 2H, J=7 Hz), 1.90 (t, 2H, J=14 Hz), 1.75 (t, 1H, J=12 Hz), 1.63 (t, 1H, J=12 Hz), 1.00 (t, 3H, J=7 Hz).

Example 44. Cyclopropyl-[6-(3-quinolyl)spiro[chromene-2,4'-piperidine]-1'-yl]methanone, HCl

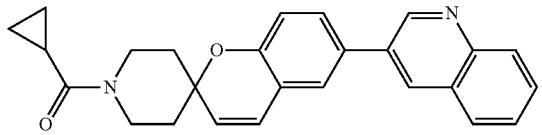

This compound was synthesized using the procedure for example 43 and cyclopropanecarbonyl chloride. Analysis: LCMS m/z=397 (M+1); $^1$H NMR (DMSO-d$_6$) δ: 9.47 (s, 1H), 9.07 (s, 1H), 8.22 (t, 1H, J=8 Hz), 7.95 (t, 1H, J=8 Hz), 7.76-7.84 (m, 3H), 7.08 (d, 1H, J=8 Hz), 6.62 (d, 1H, J=10 Hz), 5.90 (d, 1H, J=10 Hz), 4.08 (b, 2H), 3.60 (b, 1H), 3.18 (b, 1H), 1.87-2.04 (m, 3H), 1.78 (b, 1H), 1.64 (b, 1H), 0.70-0.74 (m, 4H).

Example 45. Cyclobutyl-[6-(3-quinolyl)spiro[chromene-2,4'-piperidine]-1'-yl]methanone, HCl

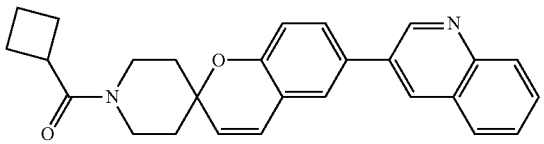 [SMILES: O=C(C1CCC1)N1CCC2(C=Cc3cc(-c4cnc5ccccc5c4)ccc3O2)CC1]

This example was synthesized using 6-(3-quinolyl)spiro[chromene-2,4'-piperidine] and cyclobutylcarbonyl chloride by the procedure for example 43. Analysis: LCMS m/z=411 (M+1); $^1$H NMR (DMSO-d$_6$) δ: 9.4 (s, 1H), 9.02 (s, 1H), 8.18-8.21 (m, 2H), 7.93 (t, 1H, J=7.5 Hz), 7.74-7.82 (m, 3H), 7.07 (d, 1H, J=8 Hz), 6.61 (d, 1H, J=8 Hz), 5.87 (d, 1H, J=8 Hz), 4.08 (d, 1H, J=14 Hz), 3.52 (d, 1H, J=14 Hz), 3.35-3.42 (m, 2H), 3.14 (t, 1H, J=12 Hz), 2.06-2.25 (m, 4H), 1.86-1.93 (m, 3H), 1.60-1.77 (m, 3H).

Example 46. Cyclopropyl-[4-hydroxy-6-(3-quinolyl)spiro[chromane-2,4'-piperidine]-1'-yl]methanone, HCl

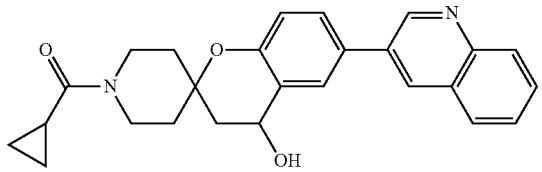 [SMILES: O=C(C1CC1)N1CCC2(CC1)CC(O)c1cc(-c3cnc4ccccc4c3)ccc1O2]

Analysis: LCMS m/z=415 (M+1); $^1$H NMR (DMSO-d$_6$) δ: 9.38 (s, 1H), 8.89 (s, 1H), 8.13-8.19 (m, 2H), 8.00 (s, 1H), 7.87-7.90 (m, 1H), 7.75 (m, 2H), 7.02 (d, 1H, J=8 Hz), 4.83 (m, 1H), 3.57 (m, 1H), 3.46 (m, 1H), 3.04-3.16 (m, 1H), 2.17-2.22 (m, 2H), 1.99 (b, 2H), 1.66-1.84 (m, 5H), 0.69-0.73 (m, 4H).

Example 47. 1-[6-(3-Quinolyl)spiro[chromane-2,4'-piperidine]-1'-yl]propan-1-one, HCl

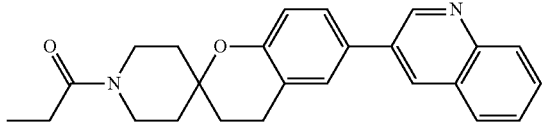 [SMILES: CCC(=O)N1CCC2(CCc3cc(-c4cnc5ccccc5c4)ccc3O2)CC1]

Analysis: LCMS m/z=387 (M+1); $^1$H NMR (DMSO-$d_6$) δ: 9.44 (s, 1H), 9.02 (s, 1H), 8.18 (d, 2H, J=7 Hz), 7.93 (m, 1H), 7.80 (m, 1H), 7.70-7.74 (m, 2H), 7.00 (d, 1H, J=8 Hz), 4.11 (m, 1H), 3.68 (m, 1H), 3.39 (m, 1H), 3.05 (m, 0.6), 2.86 (m, 1.4), 2.34 (m, 3H, J=7 Hz), 1.87 (m, 2H), 1.72-1.80 (m, 2H), 1.65 (m, 1H), 1.53 (m, 1H), 1.00 (t, 3H, J=7 Hz).

Examples 48-59 were synthesized using intermediate 1, the appropriate bromo-quinoline or isoquinoline, and the required R1 carboxylic acid or carbonyl chloride using methods described herein.

Example 48. [6-(3-Quinolyl)spiro[4H-1,3-benzodioxine-2,4'-piperidine]-1'-yl]-[(2R)-tetrahydrofuran-2-yl] methanone, HCl

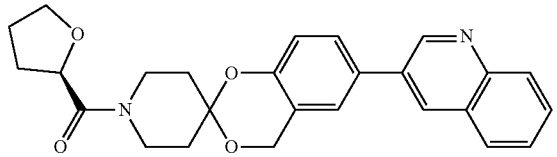 [SMILES: O=C([C@H]1CCCO1)N1CCC2(CC1)OCc1cc(-c3cnc4ccccc4c3)ccc1O2]

Analysis: LCMS m/z=431 (M+1); $^1$H NMR (DMSO-$d_6$) δ: 9.40 (s, 1H), 8.95 (s, 1H), 8.15 (d, 2H, J=8 Hz), 7.91 (m, 1H), 7.74-7.81 (m, 3H), 7.06 (d, 1H, J=8.5 Hz), 5.00 (s, 2H), 4.71 (m, 1H), 3.73-3.78 (m, 3H), 3.16 (m, 2H), 2.06 (m, 1H), 1.93-2.01 (m, 3H), 1.81-1.87 (m, 4H), 1.24-1.29 (m, 1H).

Example 49. Cyclopropyl-[6-(8-methoxy-7-quinolyl)spiro[4H-1,3-benzodioxine-2,4'-piperidine]-1'-yl]methanone, HCl

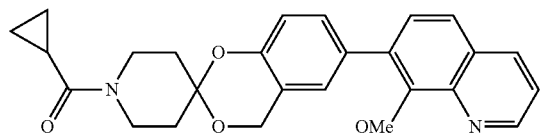 [SMILES: COc1c(-c2ccc3c(c2)COC2(CCN(C(=O)C4CC4)CC2)O3)ccc2cccnc12]

Analysis: LCMS m/z=431 (M+1); $^1$H NMR (400 MHz, DMSO-$d_6$) δ: 9.11 (1H, d, J=4.0 Hz), 8.85 (1H, br. s.), 8.01 (1H, d, J=8.5 Hz), 7.78-7.91 (2H, m), 7.58 (1H, dd, J=8.5, 2.0 Hz), 7.44-7.52 (3H, m), 7.11 (2H, d, J=7.8 Hz), 7.04 (1H, d, J=8.5 Hz), 4.99 (2H, s), 3.79 (4H, s), 3.53-3.69 (2H, m), 2.29 (3H, s), 1.82-1.99 (4H, m), 0.67-0.82 (4H, m).

Example 50. [6-(8-Methyl-7-quinolyl)spiro[4H-1,3-benzodioxine-2,4'-piperidine]-1'-yl]-[(2R)-tetrahydrofuran-2-yl] methanone, HCl

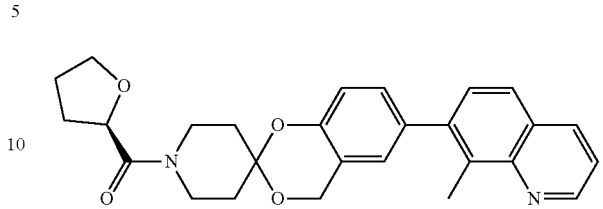

Analysis: LCMS m/z=445 (M+1); $^1$H NMR (400 MHz, DCCl$_3$) δ: 8.99 (dd, J=4.1, 1.6 Hz, 1H), 8.16 (dd, J=8.2, 1.6 Hz, 1H), 7.70 (d, J=8.5 Hz, 1H), 7.49-7.38 (m, 2H), 7.23 (s, 1H), 7.03 (s, 1H), 6.97 (d, J=8.3 Hz, 1H), 5.02-4.88 (m, 2H), 4.69 (br s, 1H), 4.07-3.52 (m, 6H), 2.76 (s, 3H), 2.30 (br s, 1H), 2.13-1.90 (m, 7H).

Example 51. 6-(4-Methyl-3-quinolyl)spiro[4H-1,3-benzodioxine-2,4'-piperidine]-1'-yl]-[(2R)-tetrahydrofuran-2-yl] methanone, HCl

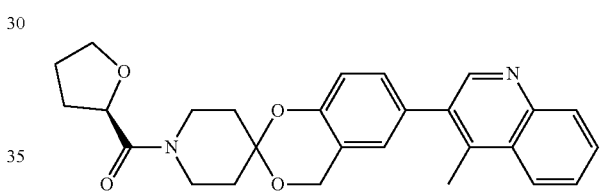

Analysis: LCMS m/z=445 (M+1); $^1$H NMR (400 MHz, DCCl$_3$) δ: 8.83 (s, 1H), 8.23 (t, J=8.8 Hz, 2H), 7.90 (br t, J=7.7 Hz, 1H), 7.84-7.73 (m, 1H), 7.21 (br d, J=8.3 Hz, 1H), 7.08-6.95 (m, 2H), 5.02-4.91 (m, 2H), 4.77-4.64 (m, 1H), 4.05-3.61 (m, 6H), 2.79 (s, 3H), 2.31 (br d, J=5.8 Hz, 1H), 2.06-2.02 (m, 2H), 1.54-1.43 (m, 3H).

Example 52. 1-[6-(4-Methyl-3-quinolyl)spiro[4H-1,3-benzodioxine-2,4'-piperidine]-1'-yl]propan-1-one, HCl

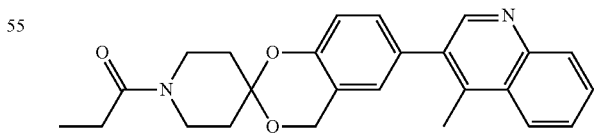

Analysis: LCMS m/z=403 (M+1); $^1$H NMR (400 MHz, DCCl$_3$) δ: 8.77 (s, 1H), 8.11 (dd, J=19.7, 8.2 Hz, 2H), 7.79-7.69 (m, 1H), 7.67-7.58 (m, 1H), 7.21 (dd, J=8.3, 2.0 Hz, 1H), 7.05-6.96 (m, 2H), 5.02-4.88 (m, 2H), 3.95-3.85 (m, 1H), 3.73-3.60 (m, 3H), 2.65 (s, 3H), 2.41 (q, J=7.5 Hz, 2H), 2.11-1.88 (m, 4H), 1.23-1.17 (m, 3H).

Example 53. 1-[6-(8-Methyl-7-quinolyl)spiro[4H-1,3-benzodioxine-2,4'-piperidine]-1'-yl]propan-1-one, HCl

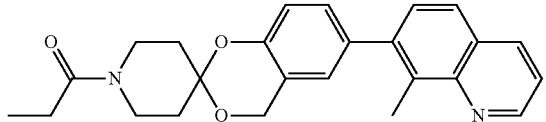 [SMILES: CCC(=O)N1CCC2(CC1)OCc1cc(-c3ccc4cccnc4c3C)ccc1O2]

Analysis: LCMS m/z=403 (M+1); $^1$H NMR (400 MHz, DCCl$_3$) δ: 9.00 (dd, J=4.3, 1.8 Hz, 1H), 8.16 (dd, J=8.3, 1.8 Hz, 1H), 7.73-7.67 (m, 1H), 7.45-7.38 (m, 2H), 7.25-7.22 (m, 1H), 7.03 (d, J=2.0 Hz, 1H), 6.97 (d, J=8.3 Hz, 1H), 5.02-4.89 (m, 2H), 3.97-3.85 (m, 1H), 3.74-3.58 (m, 3H), 2.76 (s, 3H), 2.47-2.35 (m, 2H), 2.11-1.91 (m, 4H), 1.19 (t, J=7.4 Hz, 3H).

Example 54. Cyclopropyl-[6-(8-methyl-7-quinolyl)spiro[4H-1,3-benzodioxine-2,4'-piperidine]-1'-yl]methanone, HCl

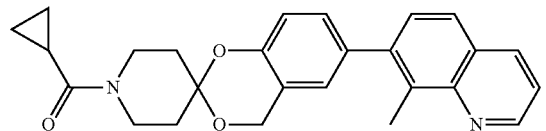

Analysis: LCMS m/z=415 (M+1); $^1$H NMR (400 MHz, DCCl$_3$) δ: 9.00 (dd, J=4.3, 1.8 Hz, 1H), 8.16 (dd, J=8.2, 1.9 Hz, 1H), 7.70 (d, J=8.3 Hz, 1H), 7.47-7.40 (m, 2H), 7.26-7.22 (m, 1H), 7.03 (d, J=2.0 Hz, 1H), 6.98 (d, J=8.3 Hz, 1H), 4.95 (br d, J=4.8 Hz, 2H), 3.97-3.85 (m, 2H), 3.82 (br s, 1H), 3.67 (br s, 1H), 2.76 (s, 3H), 2.14-1.94 (m, 4H), 1.85-1.78 (m, 1H), 1.05-0.99 (m, 2H), 0.84-0.77 (m, 2H).

Example 55. 1-[6-(8-Methoxy-7-quinolyl)spiro[4H-1,3-benzodioxine-2,4'-piperidine]-1'-yl]propan-1-one, HCl

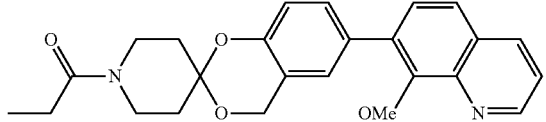 [SMILES: CCC(=O)N1CCC2(CC1)OCc1cc(-c3ccc4cccnc4c3OC)ccc1O2]

Analysis: LCMS m/z=419 (M+1); $^1$H NMR (400 MHz, DCCl$_3$) δ: 8.98 (dd, J=4.3, 1.8 Hz, 1H), 8.17 (dd, J=8.3, 1.8 Hz, 1H), 7.64-7.59 (m, 1H), 7.58-7.49 (m, 2H), 7.42 (dd, J=8.3, 4.3 Hz, 1H), 7.36 (d, J=2.0 Hz, 1H), 6.98 (d, J=8.5 Hz, 1H), 4.96 (d, J=6.8 Hz, 2H), 3.92-3.84 (m, 4H), 3.74-3.55 (m, 3H), 2.41 (q, J=7.4 Hz, 2H), 2.09-1.90 (m, 4H), 1.18 (t, J=7.5 Hz, 3H).

Example 56. [6-(8-Methoxy-7-quinolyl)spiro[4H-1,3-benzodioxine-2,4'-piperidine]-1'-yl]-[(2R)-tetrahydrofuran-2-yl] methanone, HCl

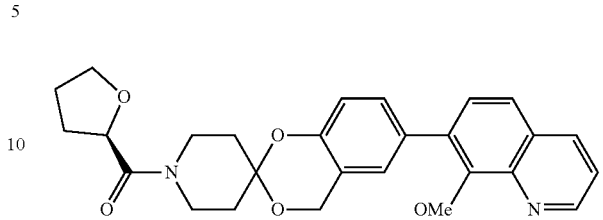

Analysis: LCMS m/z=461 (M+1); H NMR (400 MHz, DCCl$_3$) δ: 9.01 (dd, J=4.3, 1.8 Hz, 1H), 8.19 (dd, J=8.3, 1.8 Hz, 1H), 7.67-7.60 (m, 1H), 7.54 (d, J=8.3 Hz, 2H), 7.44 (dd, J=8.2, 4.1 Hz, 1H), 7.36 (s, 1H), 6.98 (d, J=8.5 Hz, 1H), 4.96 (d, J=2.5 Hz, 2H), 4.67 (dd, J=7.3, 5.8 Hz, 1H), 4.52 (dd, J=8.7, 5.6 Hz, 1H), 4.13-4.03 (m, 1H), 4.04-3.86 (m, 2H), 3.85 (d, J=1.3 Hz, 3H), 3.81-3.73 (m, 2H), 3.71-3.51 (m, 2H), 2.38-2.29 (m, 1H), 2.12-1.98 (m, 5H).

Example 57. 1-[6-(8-Chloro-7-quinolyl)spiro[4H-1,3-benzodioxine-2,4'-piperidine]-1'-yl]propan-1-one, HCl

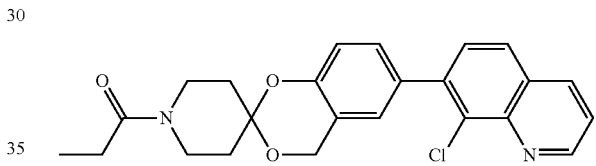

Analysis: LCMS m/z=423 (M+1); $^1$H NMR (400 MHz, DCCl$_3$) δ: 9.10 (dd, J=4.3, 1.8 Hz, 1H), 8.22 (dd, J=8.3, 1.8 Hz, 1H), 7.79 (d, J=8.5 Hz, 1H), 7.59-7.47 (m, 2H), 7.40 (dd, J=8.5, 2.3 Hz, 1H), 7.21 (d, J=2.0 Hz, 1H), 6.99 (d, J=8.3 Hz, 1H), 4.96 (d, J=5.0 Hz, 2H), 3.95-3.85 (m, 1H), 3.73-3.55 (m, 3H), 2.46-2.37 (m, 2H), 2.11-1.91 (m, 4H), 1.21-1.16 (m, 3H).

Example 58. [6-(8-Chloro-7-quinolyl)spiro[4H-1,3-benzodioxine-2,4'-piperidine]-1'-yl]-cyclopropyl-methanone, HCl

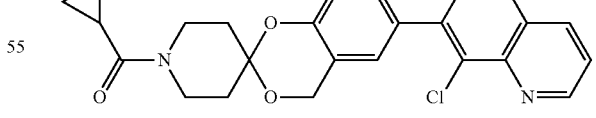

Analysis: LCMS m/z=435 (M+1); $^1$H NMR (400 MHz, DCCl$_3$) δ: 9.11 (dd, J=4.1, 1.6 Hz, 1H), 8.22 (dd, J=8.3, 1.5 Hz, 1H), 7.79 (d, J=8.3 Hz, 1H), 7.56-7.47 (m, 2H), 7.40 (dd, J=8.3, 2.3 Hz, 1H), 7.21 (d, J=2.0 Hz, 1H), 7.00 (d, J=8.5 Hz, 1H), 4.97 (d, J=3.0 Hz, 2H), 4.00-3.85 (m, 2H), 3.81 (br s, 1H), 3.73-3.62 (m, 1H), 2.17 (br d, J=4.3 Hz, 2H), 2.01 (br s, 2H), 1.26 (d, J=6.5 Hz, 1H), 1.07-0.98 (m, 3H), 0.83-0.76 (m, 2H).

Example 59. [6-(8-Chloro-7-quinolyl)spiro[4H-1,3-benzodioxine-2,4'-piperidine]-1'-yl]-[(2R)-tetrahydrofuran-2-yl] methanone, HCl

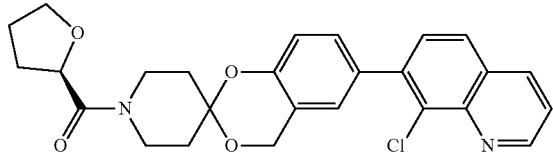 [SMILES: O=C([C@H]1CCCO1)N1CCC2(CC1)OCc1cc(-c3ccc4cccnc4c3Cl)ccc1O2]

Analysis: LCMS m/z=465 (M+1); $^1$H NMR (400 MHz, DCCl$_3$) δ: 9.10 (dd, J=4.1, 1.6 Hz, 1H), 8.22 (dd, J=8.3, 1.8 Hz, 1H), 7.79 (d, J=8.5 Hz, 1H), 7.57-7.49 (m, 2H), 7.40 (br d, J=8.5 Hz, 1H), 7.21 (d, J=2.0 Hz, 1H), 6.99 (d, J=8.5 Hz, 1H), 4.96 (s, 2H), 4.67 (t, J=6.3 Hz, 1H), 4.06-3.82 (m, 3H), 3.81-3.52 (m, 3H), 2.40-2.28 (m, 1H), 2.13-1.91 (m, 7H).

Example 60. [2-[6-(8-methyl-7-quinolyl)spiro[4H-1,3-benzodioxine-2,4'-piperidine]-1'-yl]-2-oxo-ethyl] acetate

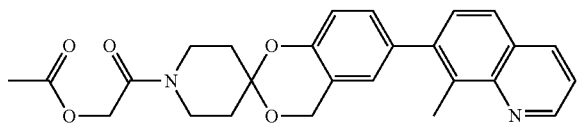 [SMILES: CC(=O)OCC(=O)N1CCC2(CC1)OCc1cc(-c3ccc4cccnc4c3C)ccc1O2]

To a solution of 6-(8-methyl-7-quinolyl)spiro[4H-1,3-benzodioxine-2,4'-piperidine] (0.060 g, 0.17 mmol) and DIPEA (0.060 mL, 0.045 g, 0.35 mmol) in anhydrous DCM (2.00 mL) at RT under N$_2$ was added (2-chloro-2-oxo-ethyl) acetate (0.024 mL, 0.031 g, 0.23 mmol) dropwise.

The mixture was stirred at RT 3 days. The reaction was partitioned between ethyl acetate and saturated aqueous NH$_4$Cl solution and the layers separated. The organic layer was washed with 15 mL of water, saturated aqueous NaHCO$_3$ solution, and brine, then dried over Na$_2$SO$_4$, filtered, concentrated, and dried under vacuum to yield a clear, colorless oil. ISCO silica gel chromatography (0 to 100% EtOAc-100 to 0% hexanes; 24 g column) yielded the compound as a clear, colorless oil (0.073 g, 94%). Analysis: LCMS m/z=447 (M+1); $^1$H NMR (400 MHz, DMSO-d$_6$) δ 8.97 (dd, J=4.1, 1.9 Hz, 1H), 8.37 (dd, J=8.3, 1.8 Hz, 1H), 7.85 (d, J=8.3 Hz, 1H), 7.55 (dd, J=8.2, 4.1 Hz, 1H), 7.47 (d, J=8.5 Hz, 1H), 7.27 (dd, J=8.4, 2.1 Hz, 1H), 7.19 (d, J=2.0 Hz, 1H), 6.99 (d, J=8.3 Hz, 1H), 4.96 (s, 2H), 4.83 (d, J=0.8 Hz, 2H), 3.68-3.58 (m, 1H), 3.57-3.42 (m, 3H), 2.68 (s, 3H), 2.09 (s, 3H), 1.96 (t, J=4.8 Hz, 2H), 1.92-1.79 (m, 2H).

Example 61. 2-Hydroxy-1-[6-(8-methyl-7-quinolyl)spiro[chromane-2,4'-piperidine]-1'-yl]-ethanone

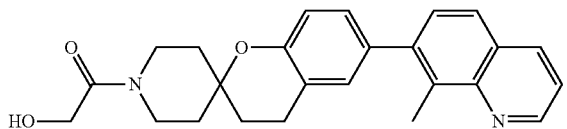

To a solution of [2-[6-(8-methyl-7-quinolyl)spiro[chromane-2,4'-piperidine]-1'-yl]-2-oxo-ethyl]acetate (0.048 g, 0.11 mmol) in methanol (2 mL) at RT under N$_2$ was added 1.0 N aqueous LiOH solution (0.16 mL, 0.16 mmol). The mixture was stirred at RT for several hours, then placed in the refrigerator overnight. Then, 1.0 N aqueous HCl solution (0.16 mL, 0.16 mmol) was added before partially concentrating to remove the MeOH. The residue was partitioned between 150 mL of ethyl acetate and 15 mL of saturated aqueous NH$_4$Cl solution and the layers separated. The organic layer was washed with 15 mL of water, saturated aqueous NaHCO$_3$ solution, and brine, then dried over Na$_2$SO$_4$, filtered, concentrated, and dried under vacuum at 50° C. overnight to yield the desired compound as an off-white solid (0.0414 g, 95%). Analysis: LCMS m/z=403 (M+1); $^1$H NMR (400 MHz, DMSO-d$_6$) δ 8.96 (dd, J=4.3, 1.8 Hz, 1H), 8.36 (dd, J=8.3, 2.0 Hz, 1H), 7.84 (d, J=8.3 Hz, 1H), 7.54 (dd, J=8.3, 4.3 Hz, 1H), 7.47 (d, J=8.3 Hz, 1H), 7.21-7.14 (m, 2H), 6.95-6.88 (m, J=8.5 Hz, 1H), 4.56-4.51 (m, 1H), 4.18-4.07 (m, J=5.4, 3.1 Hz, 3H), 3.55 (d, J=13.8 Hz, 1H), 3.40-3.35 (m, 1H), 3.13 (t, J=11.5 Hz, 1H), 2.82 (t, J=6.8 Hz, 2H), 2.68 (s, 3H), 1.86 (t, J=6.8 Hz, 2H), 1.79 (d, J=13.6 Hz, 2H), 1.74-1.62 (m, 1H), 1.62-1.50 (m, 1H).

Example 62. 2-Hydroxy-1-[6-(8-methyl-7-quinolyl)spiro[4H-1,3-benzodioxine-2,4'-piperidine]-1'-yl]ethanone

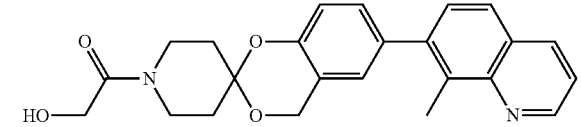

To a solution of [2-[6-(8-methyl-7-quinolyl)spiro[4H-1,3-benzodioxine-2,4'-piperidine]-1'-yl]-2-oxo-ethyl] acetate (0.067 g, 0.15 mmol) in methanol (2 mL) in a scintillation vial at RT under N$_2$ was added 1.0 N aqueous LiOH solution (0.23 mL, 0.23 mmol). The mixture was stirred at RT for several hours. In order to neutralize the mixture, 1.0 N aqueous HCl solution (0.23 mL, 0.23 mmol) was added before partially concentrating to remove the MeOH. The residue was partitioned between 150 mL of ethyl acetate and 15 mL of saturated aqueous NH$_4$Cl solution and separated. The organic layer was washed with 15 mL of water, saturated aqueous NaHCO$_3$ solution, and brine, then dried over Na$_2$SO$_4$, filtered, concentrated, and dried under vacuum at 50° C. overnight to yield the desired compound as a white solid (0.0572 g, 94%). Analysis: LCMS m/z=405 (M+1); $^1$H NMR (400 MHz, DMSO-d$_6$) δ 8.97 (dd, J=4.3, 1.8 Hz, 1H), 8.37 (dd, J=8.3, 1.8 Hz, 1H), 7.85 (d, J=8.5 Hz, 1H), 7.55 (dd, J=8.3, 4.3 Hz, 1H), 7.47 (d, J=8.5 Hz, 1H), 7.27 (dd, J=8.4, 2.1 Hz, 1H), 7.19 (d, J=2.0 Hz, 1H), 6.98 (d, J=8.3 Hz, 1H), 4.96 (s, 2H), 4.63-4.57 (m, 1H), 4.14 (d, J=5.5 Hz, 2H), 3.72-3.61 (m, 1H), 3.57 (d, J=4.8 Hz, 1H), 3.51-3.41 (m, J=7.0 Hz, 2H), 2.68 (s, 3H), 1.98-1.81 (m, 4H).

Example 63. 6-(8-Chloro-7-quinolyl)spiro[chromane-2,4'-piperidine]-1'-carboxamide

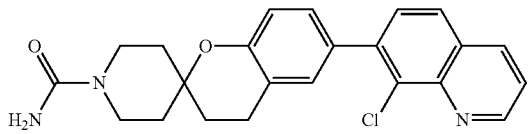

To a solution of 6-(8-chloro-7-quinolyl)spiro[chromane-2,4'-piperidine] (0.060 g, 0.16 mmol) and DIPEA (0.057 mL, 2.0 eq.) in DCM (2.0 mL) at RT under Ar was added isocyanato(trimethyl)silane (0.033 mL, 0.028 g, 0.25 mmol) dropwise. After stirring about 60 min at RT, additional isocyanato(trimethyl)silane (0.033 mL, 0.028 g, 0.25 mmol) was added, followed by a second portion (0.066 mL, 0.50 mmol) approximately 90 min later. The mixture was partitioned between 150 mL of EtOAc and 15 mL of saturated aqueous $NH_4Cl$ solution and separated. The organic layer was washed with 15 mL of water, saturated aqueous $NaHCO_3$ solution, and brine, then dried over $Na_2SO_4$, filtered, concentrated, and dried under vacuum to yield a clear, colorless oil. ISCO silica gel chromatography (0 to 100% (10% 20:1:1 $EtOH:NH_4OH:H_2O$—90% EtOAc)—100 to 0% hexanes; 24 g column) yielded the desired compound as a white solid (0.0400 g, 60%). Analysis: LCMS m/z=408 (M+1); $^1H$ NMR (400 MHz, DMSO-$d_6$) δ 9.05 (dd, J=4.1, 1.6 Hz, 1H), 8.48 (dd, J=8.4, 1.6 Hz, 1H), 8.01 (d, J=8.5 Hz, 1H), 7.66 (dd, J=8.3, 4.3 Hz, 1H), 7.62 (d, J=8.3 Hz, 1H), 7.34-7.27 (m, 2H), 6.96-6.89 (m, 1H), 5.97 (s, 2H), 3.70 (d, J=13.3 Hz, 2H), 3.22-3.11 (m, 2H), 2.82 (t, J=6.7 Hz, 2H), 1.85 (t, J=6.8 Hz, 2H), 1.75-1.66 (m, 2H), 1.62-1.50 (m, 2H).

Example 64. [2-[6-(8-chloro-7-quinolyl)spiro[chromane-2,4'-piperidine]-1'-yl]-2-oxo-ethyl]acetate

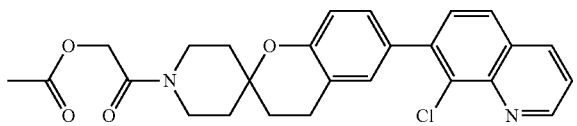

To a solution of 6-(8-chloro-7-quinolyl)spiro[chromane-2,4'-piperidine] (0.060 g, 0.16 mmol) and DIPEA (0.057 mL, 0.043 g, 0.33 mmol) in anhydrous DCM (2.00 mL) at RT under $N_2$ was added (2-chloro-2-oxo-ethyl) acetate (0.023 mL, 0.029 g, 0.21 mmol) dropwise. After stirring at RT for approximately 30 min, the mixture was partitioned between 150 mL of EtOAc and 15 mL of saturated aqueous $NH_4Cl$ solution and separated. The organic layer was washed with 15 mL of water, saturated aqueous $NaHCO_3$ solution, and brine, then dried over $Na_2SO_4$, filtered, concentrated, and dried under vacuum to yield a clear, colorless oil. ISCO silica gel chromatography ISCO (0 to 100% (10% 20:1:1 $EtOH:NH_4OH:H_2O$—90% EtOAc)—100 to 0% hexanes; 24 g column) yielded the desired compound as a white foam (0.054 g, 71%). Analysis: LCMS m/z=465 (M+1); $^1H$ NMR (400 MHz, DMSO-$d_6$) δ 9.05 (dd, J=4.1, 1.6 Hz, 1H), 8.48 (dd, J=8.3, 1.8 Hz, 1H), 8.01 (d, J=8.5 Hz, 1H), 7.68-7.64 (m, 1H), 7.62 (d, J=8.5 Hz, 1H), 7.35-7.29 (m, 2H), 6.98-6.92 (m, 1H), 4.82 (s, 2H), 4.06 (d, J=12.8 Hz, 1H), 3.59 (d, J=13.6 Hz, 1H), 3.45-3.35 (m, 2H), 3.11 (t, J=11.0 Hz, 1H), 2.83 (t, J=6.7 Hz, 2H), 2.09 (s, 3H), 1.87 (t, J=6.8 Hz, 2H), 1.84-1.75 (m, 2H), 1.75-1.65 (m, 1H), 1.62-1.49 (m, 1H).

Example 65. 6-(8-Chloro-7-quinolyl)-N-tetrahydropyran-2-yloxy-spiro[chromane-2,4'-piperidine]-1'-carboxamide

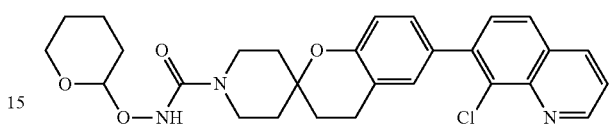

To a solution of 1,1'-carbonyldiimidazole (0.047 g, 0.29 mmol) in DCM (2.0 mL) at RT under $N_2$ was added O-tetrahydropyran-2-ylhydroxylamine (0.036 g, 0.31 mmol). The solution was stirred at RT for two h before adding DIPEA (0.074 mL, 0.055 g, 0.42 mmol) followed by 6-(8-chloro-7-quinolyl)spiro[chromane-2,4'-piperidine] (0.070 g, 0.19 mmol). After stirring at RT overnight the mixture was partitioned between 150 mL of EtOAc and 20 mL of saturated aqueous $NH_4Cl$ solution and separated. The organic layer was washed with 15 mL of water, saturated aqueous $NaHCO_3$ solution, and brine, then dried over $Na_2SO_4$, filtered, and concentrated to yield a clear, colorless oil. ISCO silica gel chromatography (0 to 100% (10% 20:1:1 $EtOH:NH_4OH:H_2O$—90% EtOAc)—100 to 0% hexanes; 24 g column) yielded 6-(8-chloro-7-quinolyl)-N-tetrahydropyran-2-yloxy-spiro[chromane-2,4'-piperidine]-1'-carboxamide (0.068 g, 70%) as a white foam. Analysis: LCMS m/z=508 (M+1); $^1H$ NMR (400 MHz, DMSO-$d_6$) δ 9.68 (s, 1H), 9.05 (dd, J=4.1, 1.6 Hz, 1H), 8.48 (dd, J=8.3, 1.8 Hz, 1H), 8.01 (d, J=8.5 Hz, 1H), 7.68-7.64 (m, 1H), 7.62 (d, J=8.3 Hz, 1H), 7.35-7.27 (m, 2H), 6.97-6.90 (m, 1H), 4.75 (t, J=3.0 Hz, 1H), 4.01-3.93 (m, 1H), 3.68 (d, J=13.6 Hz, 2H), 3.52-3.43 (m, 1H), 3.22-3.11 (m, J=11.0, 11.0 Hz, 2H), 2.82 (t, J=6.5 Hz, 2H), 1.85 (t, J=6.7 Hz, 2H), 1.78-1.44 (m, 10H).

Example 66. 6-(8-chloro-7-quinolyl)-N-ethyl-spiro[chromane-2,4'-piperidine]-1'-carboxamide

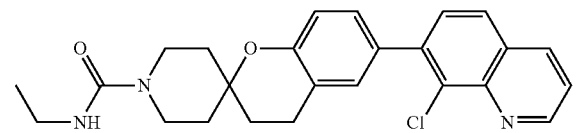

To a solution of 6-(8-chloro-7-quinolyl)spiro[chromane-2,4'-piperidine] (0.060 g, 0.16 mmol) in DCM (2.0 mL) at RT under Ar was added isocyanatoethane (0.020 mL, 0.018 g, 0.25 mmol).

The mixture was stirred at RT overnight. Additional portions of isocyanatoethane (0.020 mL, 0.018 g, 0.25 mmol) and DIPEA (0.057 mL, 0.320 mmol) were added, and the reaction continued to stir until the starting material was consumed. The mixture was partitioned between 150 mL of EtOAc and 15 mL of saturated aqueous $NH_4Cl$ solution and separated. The organic layer was washed with 15 mL of water, saturated aqueous $NaHCO_3$ solution, and brine, then dried over $Na_2SO_4$, filtered, concentrated, and dried under vacuum to yield a clear, colorless oil. The residue was purified by preparative HPLC on the Gilson (10 to 55% MeCN—90 to 45% water (both with 0.1% TFA) over 15 min.; 10 mL fractions; Phenomenex Gemini 5 μm NX-C18 110 Å 150×30 mm column). The clean fractions were combined and partitioned between 100 mL of DCM and 30 mL of saturated aqueous NaHCO₃ solution and then separated. The aqueous layer was back extracted with 40 mL of DCM. The organic layers were combined and washed with 15 mL of saturated aqueous NaHCO₃ solution, brine, then dried with Na₂SO₄, filtered, and concentrated to yield the desired compound as a white foam (0.0402 g, 56%). Analysis: LCMS m/z=436 (M+1); ¹H NMR (400 MHz, DMSO-d₆) δ 9.05 (dd, J=4.3, 1.8 Hz, 1H), 8.48 (dd, J=8.3, 1.8 Hz, 1H), 8.01 (d, J=8.5 Hz, 1H), 7.68-7.64 (m, 1H), 7.62 (d, J=8.5 Hz, 1H), 7.34-7.28 (m, 2H), 6.95-6.89 (m, 1H), 6.51 (t, J=5.4 Hz, 1H), 3.76-3.66 (m, J=13.3 Hz, 2H), 3.21-3.11 (m, J=10.9, 10.9 Hz, 2H), 3.10-3.01 (m, 2H), 2.82 (t, J=6.5 Hz, 2H), 1.85 (t, J=6.8 Hz, 2H), 1.76-1.65 (m, 2H), 1.61-1.49 (m, 2H), 1.02 (t, J=7.0 Hz, 3H).

Example 67. 1-[6-(8-chloro-7-quinolyl)spiro[chromane-2,4'-piperidine]-1'-yl]-2-hydroxy-ethanone

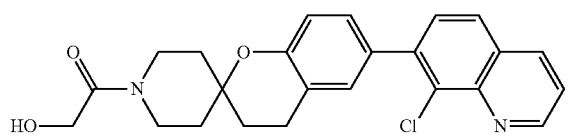 [SMILES: Cc1c(-c2ccc3c(c2)CCC2(CCN(C(=O)CO)CC2)O3)ccc2cccnc12]

To a solution of [2-[6-(8-chloro-7-quinolyl)spiro[chromane-2,4'-piperidine]-1'-yl]-2-oxo-ethyl]acetate (0.050 g, 0.11 mmol) in methanol (2 mL) at RT under N₂ was added 1.0 N aqueous LiOH solution (0.16 mL, 0.16 mmol). The mixture was stirred at RT for several h, then 1.0 N HCl solution (0.16 mL, 0.16 mmol) was added and the reaction concentrated. The residue was partitioned between 150 mL of EtOAc and 15 mL of saturated aqueous NH₄Cl solution and separated. The organic layer was washed with 15 mL of water, saturated aqueous NaHCO₃ solution, and brine, then dried over Na₂SO₄, filtered, and concentrated to yield the desired compound as a white foam (0.0407 g, 89%). Analysis: LCMS m/z=423 (M+1); ¹H NMR (400 MHz, DMSO-d₆) δ: 9.05 (dd, J=4.3, 1.8 Hz, 1H), 8.48 (dd, J=8.3, 1.8 Hz, 1H), 8.01 (d, J=8.5 Hz, 1H), 7.66 (dd, J=8.3, 4.3 Hz, 1H), 7.62 (d, J=8.5 Hz, 1H), 7.34-7.29 (m, 2H), 6.98-6.91 (m, 1H), 4.54 (t, J=5.4 Hz, 1H), 4.13 (dd, J=5.3, 3.3 Hz, 3H), 3.56 (d, J=13.6 Hz, 1H), 3.13 (t, J=11.8 Hz, 1H), 2.83 (t, J=6.8 Hz, 2H), 1.86 (t, J=6.8 Hz, 2H), 1.79 (d, J=13.6 Hz, 2H), 1.74-1.63 (m, 1H), 1.62-1.50 (m, 1H).

Example 68. 6-(8-Chloro-7-quinolyl)spiro[chromane-2,4'-piperidine]-1'-carbohydroxamic acid

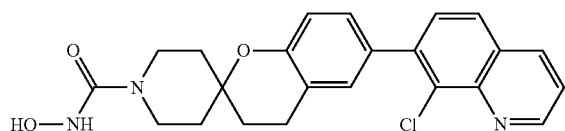

To a solution of 6-(8-chloro-7-quinolyl)-N-tetrahydropyran-2-yloxy-spiro[chromane-2,4'-piperidine]-1'-carboxamide (0.063 g, 0.12 mmol) in anhydrous DCM (2.0 mL) at RT under Ar was added hydrogen chloride (4 mol/L) in 1,4-dioxane solution (1.0 mL, 4.0 mmol) dropwise. The yellow suspension was stirred at RT for 90 min and then was concentrated. The residue was partitioned between 100 mL of DCM and 30 mL of saturated aqueous NaHCO₃ solution and then separated. The aqueous layer was back extracted with DCM, the organic layers combined and washed with 15 mL of saturated aqueous NaHCO₃ solution, and brine, then dried with Na₂SO₄, filtered, concentrated, and dried under vacuum to yield a white foam. The compound was dissolved in methanol and loaded onto a Phenomenex Strata-X-C 33u Polymeric Strong Cation 1 g/12 mL Giga Tube, washed with methanol, then eluted using 2.0 M ammonia in methanol. The eluent was concentrated. The residue was partitioned between 150 mL of EtOAc and 15 mL of saturated aqueous NH₄Cl solution and separated. The organic layer was washed with 15 mL of water, saturated aqueous NaHCO₃ solution, and brine, then dried over Na₂SO₄, filtered, concentrated, and dried under vacuum to yield the desired compound as a white foam (0.0430 g, 53%). Analysis: LCMS m/z=424 (M+1); ¹H NMR (400 MHz, DMSO-d₆) δ 9.08 (d, J=1.5 Hz, 1H), 9.05 (dd, J=4.3, 1.8 Hz, 1H), 8.48 (dd, J=8.3, 1.8 Hz, 1H), 8.01 (d, J=8.5 Hz, 1H), 7.99 (d, J=1.8 Hz, 1H), 7.69-7.64 (m, 1H), 7.62 (d, J=8.3 Hz, 1H), 7.34-7.28 (m, 2H), 6.96-6.90 (m, 1H), 3.67 (dt, J=13.4, 3.6 Hz, 2H), 3.22-3.11 (m, 2H), 2.82 (t, J=6.7 Hz, 2H), 1.85 (t, J=6.7 Hz, 2H), 1.72 (d, J=13.8 Hz, 2H), 1.63-1.50 (m, 2H).

Example 69. 6-(8-chloro-7-quinolyl)-N-ethoxy-spiro[chromane-2,4'-piperidine]-1'-carboxamide

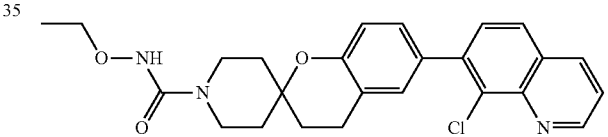

To a solution of 1,1'-carbonyldiimidazole (CDI)(0.040 g, 0.25 mmol) in anhydrous DCM (2.0 mL) in a scintillation vial at RT under N₂ was added DIPEA (0.063 mL, 0.047 g, 0.36 mmol) followed by O-ethylhydroxylamine HCl (0.026 g, 0.26 mmol). The solution was stirred at RT for 2 h before adding additional DIPEA (0.032 mL, 0.18 mmol) followed by 6-(8-chloro-7-quinolyl)spiro[chromane-2,4'-piperidine] (0.060 g, 0.16 mmol) and continuing to stir at RT overnight. The mixture was partitioned between 150 mL of EtOAc and 20 mL of saturated aqueous NH₄Cl solution and separated. The organic layer was washed with 15 mL of water, saturated aqueous NaHCO₃ solution, and brine, then dried over Na₂SO₄, filtered, and concentrated to yield a clear, colorless oil. ISCO silica gel chromatography (0 to 100% (10% 20:1:1 EtOH:NH₄OH:H₂O—90% EtOAc)—100 to 0% hexanes; 24 g column) yielded the desired compound as a white foam (0.0528 g, 71%). Analysis: LCMS m/z=452 (M+1); ¹H NMR (400 MHz, DMSO-d₆) δ 9.64 (s, 1H), 9.05 (dd, J=4.3, 1.8 Hz, 1H), 8.48 (dd, J=8.3, 1.5 Hz, 1H), 8.01 (d, J=8.8 Hz, 1H), 7.66 (dd, J=8.3, 4.3 Hz, 1H), 7.62 (d, J=8.5 Hz, 1H), 7.34-7.27 (m, 2H), 6.96-6.89 (m, 1H), 3.75 (q, J=7.0 Hz, 2H), 3.66 (br. s., 1H), 3.70-3.60 (m, J=13.6 Hz, 2H), 3.21-3.09 (m, 2H), 2.82 (t, J=6.7 Hz, 2H), 1.85 (t, J=6.7 Hz, 2H), 1.78-1.66 (m, 2H), 1.64-1.51 (m, 2H), 1.13 (t, J=7.0 Hz, 3H).

Example 70. 6-(8-chloro-7-quinolyl)-N-methoxy-spiro[chromane-2,4'-piperidine]-1'-carboxamide

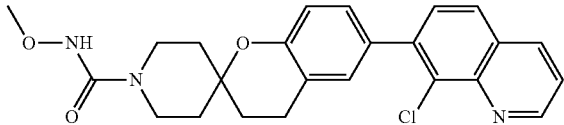 [SMILES: CONC(=O)N1CCC2(CCc3cc(-c4ccc5cccnc5c4Cl)ccc3O2)CC1]

This compound was synthesized using O-methylhydroxylamine HCl (0.022 g, 0.26 mmol) and 6-(8-chloro-7-quinolyl)spiro[chromane-2,4'-piperidine] (0.060 g, 0.16 mmol) by the method for example 69 to yield the desired compound as a white foam (0.0413 g, 57%). Analysis: LCMS m/z=438 (M+1); $^1$H NMR (400 MHz, DMSO-$d_6$) δ 9.74 (s, 1H), 9.05 (dd, J=4.0, 1.8 Hz, 1H), 8.48 (dd, J=8.3, 1.8 Hz, 1H), 8.01 (d, J=8.5 Hz, 1H), 7.68-7.63 (m, 1H), 7.62 (d, J=8.5 Hz, 1H), 7.34-7.27 (m, 2H), 6.96-6.89 (m, 1H), 3.70-3.60 (m, 2H), 3.55 (s, 3H), 3.21-3.09 (m, 2H), 2.82 (t, J=6.7 Hz, 2H), 1.85 (t, J=6.8 Hz, 2H), 1.78-1.67 (m, 2H), 1.64-1.52 (m, 2H).

Example 71. Ethyl 6-(8-chloro-7-quinolyl)spiro[chromane-2,4'-piperidine]-1'-carboxylate

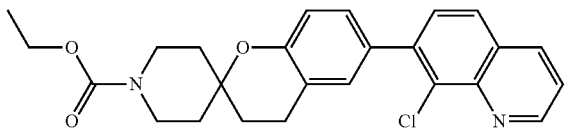 [SMILES: CCOC(=O)N1CCC2(CCc3cc(-c4ccc5cccnc5c4Cl)ccc3O2)CC1]

To a solution of 6-(8-chloro-7-quinolyl)spiro[chromane-2,4'-piperidine] (0.060 g, 0.16 mmol) and DIPEA (0.086 mL, 0.064 g, 0.49 mmol) in DCM (2.00 mL) at RT under $N_2$ was added ethyl carbonochloridate (0.024 mL, 0.027 g, 0.25 mmol) dropwise. The reaction was stirred at RT overnight, partitioned between 150 mL of EtOAc and 15 mL of saturated aqueous NH$_4$Cl solution and separated. The organic layer was washed with 15 mL of water, saturated aqueous NaHCO$_3$ solution, and brine, then dried over Na$_2$SO$_4$, filtered, concentrated, and dried under vacuum to yield a clear, colorless oil. Silica gel chromatography on the ISCO (0 to 100% EtOAc—100 to 0% hexanes; 24 g column) yielded the desired compound as a white foam (0.0566 g, 79%). Analysis: LCMS m/z=437 (M+1); $^1$H NMR (400 MHz, DMSO-$d_6$) δ 9.05 (dd, J=4.3, 1.8 Hz, 1H), 8.48 (dd, J=8.3, 1.5 Hz, 1H), 8.01 (d, J=8.5 Hz, 1H), 7.69-7.64 (m, 1H), 7.62 (d, J=8.3 Hz, 1H), 7.35-7.28 (m, 2H), 6.96-6.90 (m, 1H), 4.06 (q, J=7.0 Hz, 2H), 3.79 (d, J=12.8 Hz, 2H), 3.30-3.14 (m, 2H), 2.82 (t, J=6.5 Hz, 2H), 1.86 (t, J=6.8 Hz, 2H), 1.76 (d, J=13.3 Hz, 2H), 1.66-1.53 (m, 2H), 1.20 (t, J=7.0 Hz, 3H).

Example 72. 6-(3-Quinolyl)spiro[chromane-2,4'-piperidine]-1'-carboxamide

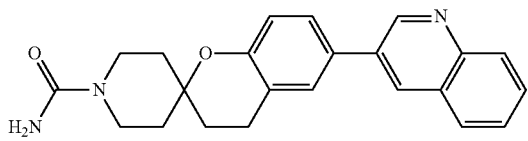 [SMILES: NC(=O)N1CCC2(CCc3cc(-c4cnc5ccccc5c4)ccc3O2)CC1]

Step 1. 6-bromospiro[chromane-2,4'-piperidine]-1'-carboxamide. To a solution of 6-bromo-spiro[chromane-2,4'-piperidine] TFA salt (0.50 g, 1.26 mmol) in DCM (6.31 mL) was added DIPEA (0.440 mL, 2.52 mmol) at 0° C. under N2 followed by isocyanato(trimethyl)silane (0.342 mL, 2.52 mmol). The ice bath was removed, and the mixture warmed allowed to stir at RT overnight. Additional isocyanato(trimethyl)silane and DIPEA were added 2×. After the reaction reached completion, it was partitioned between DCM and saturated NH$_4$Cl solution and the layers separated. The organic layer was washed with water, saturated aqueous NaHCO$_3$ solution, and brine, then dried over Na$_2$SO$_4$, filtered, and concentrated. The product was purified by ISCO silica gel chromatography (0 to 100% (20% 20:1:1 EtOH: NH$_4$OH:H$_2$O—80% EtOAc)—100 to 0% DCM) to give 6-bromospiro[chromane-2,4'-piperidine]-1'-carboxamide (0.39 g, 97%) as an off-white solid. Analysis: LCMS m/z=325/327 (M+1); 1H NMR (400 MHz, DMSO-$d_6$) δ 7.27 (d, J=2.5 Hz, 1H), 7.21 (dd, J=8.5, 2.5 Hz, 1H), 6.75 (d, J=8.8 Hz, 1H), 5.95 (s, 2H), 3.65 (d, J=13.3 Hz, 2H), 3.14-3.03 (m, 2H), 2.73 (t, J=6.7 Hz, 2H), 1.77 (t, J=6.8 Hz, 2H), 1.67-1.57 (m, 2H), 1.56-1.44 (m, 2H). This material was used directly in the next step.

Step 2. 6-(3-Quinolyl)spiro[chromane-2,4'-piperidine]-1'-carboxamide. A solution of 6-bromospiro[chromane-2,4'-piperidine]-1'-carboxamide (0.060 g, 0.18 mmol), 3-quinolylboronic acid (0.056 g, 0.32 mmol), tetrakis(triphenylphosphine)-palladium(0) (0.043 g, 0.037 mmol), and 1 M aqueous Na$_2$CO$_3$ solution (0.65 mL, 0.65 mmol) in 1,4-dioxane (3.0 mL) under nitrogen was heated at 80° C. for two h. The mixture was cooled, partitioned between EtOAc and saturated NH$_4$Cl solution and separated. The organic layer was washed with water, saturated NaHCO$_3$ solution, and brine, then dried over Na$_2$SO$_4$, filtered, and concentrated to yield a clear, colorless oil. Silica gel chromatography on the ISCO (0 to 100% (20% 20:1:1 EtOH: NH$_4$OH:H$_2$O—90% EtOAc)—100 to 0% hexanes; 40 g column) yielded the desired compound as a white solid (0.0466 g, 68%). Analysis: LCMS m/z=374 (M+1); $^1$H NMR (400 MHz, DMSO-$d_6$) δ 9.21 (d, J=2.3 Hz, 1H), 8.55 (d, J=2.3 Hz, 1H), 8.06-7.98 (m, 2H), 7.74 (ddd, J=8.3, 6.8, 1.4 Hz, 1H), 7.68-7.58 (m, 3H), 6.96 (d, J=8.3 Hz, 1H), 5.97 (s, 2H), 3.75-3.64 (m, J=13.3 Hz, 2H), 3.21-3.10 (m, 2H), 2.86 (t, J=6.8 Hz, 2H), 1.85 (t, J=6.8 Hz, 2H), 1.75-1.65 (m, 2H), 1.61-1.50 (m, 2H).

Example 73. 6-(Benzofuran-5-yl)spiro[chromane-2,4'-piperidine]-1'-carboxamide

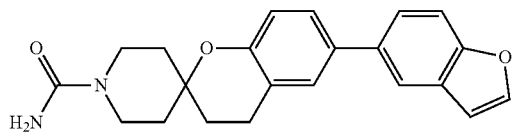 [SMILES: NC(=O)N1CCC2(CCc3cc(-c4ccc5occc5c4)ccc3O2)CC1]

This compound was synthesized using 6-bromospiro[chromane-2,4'-piperidine]-1'-carboxamide (0.060 g, 0.18 mmol) and benzofuran-5-ylboronic acid (0.052 g, 0.32 mmol), by the procedure for example 72 to give the desired compound as a white solid (0.0379 g, 57%). Analysis: LCMS m/z=363 (M+1); $^1$H NMR (400 MHz, DMSO-$d_6$) δ 8.00 (d, J=2.3 Hz, 1H), 7.83 (d, J=1.5 Hz, 1H), 7.62 (d, J=8.5 Hz, 1H), 7.52 (dd, J=8.5, 2.0 Hz, 1H), 7.42-7.36 (m, 2H), 6.97 (dd, J=2.1, 0.9 Hz, 1H), 6.87 (d, J=8.3 Hz, 1H), 5.95 (s, 2H), 3.68 (d, J=13.6 Hz, 2H), 3.19-3.09 (m, 2H), 2.82 (t, J=6.7 Hz, 2H), 1.82 (t, J=6.8 Hz, 2H), 1.72-1.63 (m, 2H), 1.59-1.48 (m, 2H).

Example 74. 6-(1,3-benzothiazol-6-yl)spiro[chromane-2,4'-piperidine]-1'-carboxamide

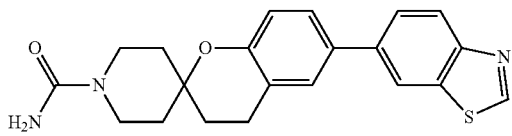 [SMILES: NC(=O)N1CCC2(CCc3cc(-c4ccc5ncsc5c4)ccc3O2)CC1]

This compound was synthesized using 6-bromospiro[chromane-2,4'-piperidine]-1'-carboxamide (0.060 g, 0.18 mmol) and 1,3-benzothiazol-6-ylboronic acid (0.058 g, 0.32 mmol) by the procedure for example 72 to give the desired compound as a white solid (0.0250 g, 36%). Analysis: LCMS m/z=380 (M+1); $^1$H NMR (400 MHz, DMSO-$d_6$) δ 9.36 (s, 1H), 8.39 (d, J=1.3 Hz, 1H), 8.10 (d, J=8.5 Hz, 1H), 7.78 (dd, J=8.7, 1.6 Hz, 1H), 7.54-7.45 (m, 2H), 6.91 (d, J=8.5 Hz, 1H), 5.96 (s, 2H), 3.69 (d, J=13.3 Hz, 2H), 3.20-3.08 (m, J=11.0, 11.0 Hz, 2H), 2.83 (t, J=6.7 Hz, 2H), 1.84 (t, J=6.7 Hz, 2H), 1.74-1.63 (m, 2H), 1.61-1.48 (m, 2H).

Example 75. 6-(1-Methylindol-5-yl)spiro[chromane-2,4'-piperidine]-1'-carboxamide

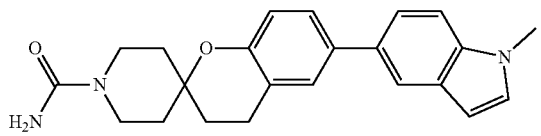 [SMILES: Cn1ccc2cc(-c3ccc4c(c3)CCC3(CCN(C(N)=O)CC3)O4)ccc21]

This compound was synthesized using 6-bromospiro[chromane-2,4'-piperidine]-1'-carboxamide (0.066 g, 0.20 mmol) and (1-methylindol-5-yl)boronic acid (0.062 g, 0.36 mmol by the procedure for example 72 to yield a white solid (0.040 g, 52%). Analysis: LCMS m/z=409 (M+1); $^1$H NMR (400 MHz, DMSO-$d_6$) δ 7.72 (d, J=1.0 Hz, 1H), 7.48-7.43 (m, 1H), 7.41-7.34 (m, 3H), 7.32 (d, J=3.0 Hz, 1H), 6.87-6.81 (m, 1H), 6.44 (dd, J=3.0, 0.8 Hz, 1H), 5.94 (s, 2H), 3.80 (s, 3H), 3.68 (d, J=13.3 Hz, 2H), 3.19-3.08 (m, 2H), 2.81 (t, J=6.7 Hz, 2H), 1.82 (t, J=6.8 Hz, 2H), 1.68 (d, J=13.6 Hz, 2H), 1.59-1.47 (m, 2H).

Example 76. 6-(1H-Indol-5-yl)spiro[chromane-2,4'-piperidine]-1'-carboxamide

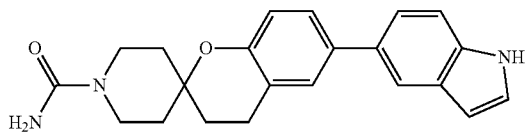 [SMILES: NC(=O)N1CCC2(CCc3cc(-c4ccc5[nH]ccc5c4)ccc3O2)CC1]

This compound was synthesized using 6-bromospiro[chromane-2,4'-piperidine]-1'-carboxamide (0.060 g, 0.18 mmol) and 1H-indol-5-ylboronic acid (0.052 g, 0.32 mmol), by the procedure for example 72 to give the desired compound as an off-white solid (0.0342 g, 51%). Analysis: LCMS m/z=362 (M+1); $^1$H NMR (400 MHz, DMSO-$d_6$) δ 11.07 (br. s., 1H), 7.71 (d, J=1.0 Hz, 1H), 7.41 (d, J=8.3 Hz, 1H), 7.38-7.28 (m, 4H), 6.84 (d, J=8.8 Hz, 1H), 6.44 (dt, J=1.9, 1.2 Hz, 1H), 5.95 (s, 2H), 3.68 (d, J=13.3 Hz, 2H), 3.20-3.07 (m, 2H), 2.81 (t, J=6.7 Hz, 2H), 1.82 (t, J=6.8 Hz, 2H), 1.73-1.63 (m, 2H), 1.59-1.46 (m, 2H).

Example 77. 7-(8-methyl-7-quinolyl)spiro[4,5-dihydro-1,3-benzodioxepine-2,4'-piperidine]-1'-carboxamide

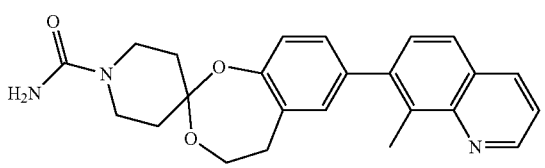 [SMILES: Cc1c(-c2ccc3c(c2)CCOC2(CCN(C(N)=O)CC2)O3)ccc2cccnc12]

Step 1. Ethyl 7-bromospiro[4,5-dihydro-1,3-benzodioxepine-2,4'-piperidine]-1'-carboxylate. A mixture of 4-bromo-2-(2-hydroxyethyl)phenol (2.50 g, 11.5 mmol), ethyl 4-oxopiperidine-1-carboxylate (1.82 mL, 2.07 g, 12.1 mmol), and p-toluenesulfonic acid monohydrate (0.219 g, 1.15 mmol) in benzene (58 mL) was heated at reflux with a Dean-Stark trap for 48 h. The reaction was cooled to RT and partitioned between 300 mL of EtOAc and 30 mL of saturated aqueous NH$_4$Cl solution and separated. The organic layer was washed with 30 mL of water, saturated aqueous NaHCO$_3$ solution, and brine, then dried over Na$_2$SO$_4$, filtered, and concentrated to yield a clear, brownish oil. ISCO chromatography (EtOAc/hexanes 0-75%; 80 g column) yielded the desired product as a white foam (3.38 g, 79%). Analysis: LCMS m/z=370/372 (M+1); $^1$H NMR (400 MHz, DMSO-$d_6$) δ 7.42 (d, J=2.5 Hz, 1H), 7.34 (dd, J=8.5, 2.5 Hz, 1H), 6.98 (d, J=8.3 Hz, 1H), 4.03 (q, J=7.0 Hz, 2H), 3.86 (t, J=5.6 Hz, 2H), 3.50-3.34 (m, 4H), 2.93 (t, J=5.5 Hz, 2H), 1.84-1.74 (m, 2H), 1.73-1.63 (m, 2H), 1.17 (t, J=7.0 Hz, 3H).

Step 2. Nitrogen was bubbled through a solution of ethyl 7-(4,4,5,5-tetramethyl-1,3,2-dioxaborolan-2-yl)spiro[4,5-dihydro-1,3-benzodioxepine-2,4'-piperidine]-1'-carboxylate. A solution of ethyl 7-bromospiro[4,5-dihydro-1,3-benzodioxepine-2,4'-piperidine]-1'-carboxylate (0.750 g, 2.03 mmol), 4,4,5,5-tetramethyl-2-(4,4,5,5-tetramethyl-1,3,2-dioxaborolan-2-yl)-1,3,2-dioxaborolane (0.772 g, 3.04 mmol) and potassium acetate (0.398 g, 4.05 mmol) in 1,4-dioxane (10.1 mL) for several min. Bis(tricyclohexyl-phosphine)palladium(0) (0.135 g, 0.203 mmol) was added and the reaction heated at 80° C. for 4 h. The mixture was partitioned between EtOAc and saturated aqueous NH$_4$Cl solution and separated. The organic layer was washed with water, saturated aqueous NaHCO$_3$ solution, and brine, then dried over Na$_2$SO$_4$, filtered through Celite, and concentrated to yield a dark oil. ISCO silica gel chromatography (EtOAc/hexanes 0-60%; 80 g column) yielded the desired compound as a foam (0.73 g, 86%). Analysis: LCMS m/z=418 (M+1); $^1$H NMR (400 MHz, DMSO-$d_6$) δ 7.51 (s, 1H), 7.48 (d, J=8.0 Hz, 1H), 7.01 (d, J=7.8 Hz, 1H), 4.03 (q, J=7.0 Hz, 2H), 3.86 (t, J=5.4 Hz, 2H), 3.41 (t, J=4.8 Hz, 4H), 2.95 (t, J=5.4 Hz, 2H), 1.85-1.74 (m, 2H), 1.73-1.61 (m, 2H), 1.28 (s, 12H), 1.17 (t, J=7.2 Hz, 3H).

Step 3. Ethyl 7-(8-methyl-7-quinolyl)spiro[4,5-dihydro-1,3-benzodioxepine-2,4'-piperidine]-1'-carboxylate. A solution of ethyl 7-(4,4,5,5-tetramethyl-1,3,2-dioxaborolan-2-yl)spiro[4,5-dihydro-1,3-benzodioxepine-2,4'-piperidine]-1'-carboxylate (0.725 g, 1.74 mmol), 7-bromo-8-methylquinoline (0.502 g, 2.26 mmol), triphenylphosphine (0.0911 g, 0.347 mmol), palladium(II) acetate (0.0195 g, 0.0869 mmol), in 1,4-dioxane (6.0 mL) was added 1 M aqueous $Na_2CO_3$ solution (5.21 mL). The reaction was heated at 80° C. overnight. The mixture cooled to RT, partitioned between EtOAc and $NH_4Cl$ solution and separated. The organic layer was washed with water, saturated aqueous $NaHCO_3$ solution, and brine, then dried over $Na_2SO_4$, filtered, concentrated to yield a clear, yellowish oil. ISCO silica gel chromatography (EtOAc-hexanes 0-60%; 80 g column) yielded the desired compound as an off-white oil (0.819 g, 100%). Analysis: LCMS m/z=433 (M+1); $^1$H NMR (400 MHz, DMSO-$d_6$) δ 8.97 (dd, J=4.3, 1.8 Hz, 1H), 8.37 (dd, J=8.3, 1.8 Hz, 1H), 7.86 (d, J=8.3 Hz, 1H), 7.56 (dd, J=8.2, 4.1 Hz, 1H), 7.49 (d, J=8.5 Hz, 1H), 7.29 (d, J=2.0 Hz, 1H), 7.27-7.23 (m, 1H), 7.13 (d, J=8.0 Hz, 1H), 4.05 (q, J=7.4 Hz, 2H), 3.97-3.89 (m, 3H), 3.58-3.47 (m, 2H), 3.47-3.38 (m, 2H), 3.03 (t, J=5.5 Hz, 2H), 2.68 (s, 3H), 1.92-1.81 (m, 2H), 1.81-1.69 (m, 2H), 1.19 (t, J=7.0 Hz, 4H).

Step 4. 7-(8-Methyl-7-quinolyl)spiro[4,5-dihydro-1,3-benzodioxepine-2,4'-piperidine]. To a suspension of ethyl 7-(8-methyl-7-quinolyl)spiro[4,5-dihydro-1,3-benzodioxepine-2,4'-piperidine]-1'-carboxylate (0.750 g, 1.73 mmol) and 6 N aqueous NaOH solution (4.0 mL, 24 mmol in ethanol (4.0 mL) was heated to 100° C. overnight. Additional 6 N NaOH (8.0 mL) and ethanol were added, and heating was continued 24 h. The mixture was cooled to RT, partitioned between EtOAc and $NaHCO_3$ solution and separated. The organic layer was washed with water, and brine, then dried over $Na_2SO_4$, filtered, and concentrated to yield a yellowish oil. ISCO silica gel chromatography (30% 20:1:1 EtOH:$NH_4OH$:$H_2O$—70% EtOAc; 0-100%) yielded the desired compound as an off-white solid (0.406 g, 65%). Analysis: LCMS m/z=361 (M+1); $^1$H NMR (400 MHz, DMSO-$d_6$) δ 8.97 (dd, J=4.1, 1.9 Hz, 1H), 8.37 (dd, J=8.3, 1.8 Hz, 1H), 7.86 (d, J=8.3 Hz, 1H), 7.59-7.52 (m, 1H), 7.49 (d, J=8.5 Hz, 1H), 7.27 (d, J=2.0 Hz, 1H), 7.26-7.20 (m, 1H), 7.06 (d, J=8.0 Hz, 1H), 3.91 (t, J=5.5 Hz, 2H), 3.00 (t, J=5.4 Hz, 2H), 2.87-2.77 (m, 2H), 2.76-2.68 (m, 2H), 2.67 (s, 3H), 1.86-1.75 (m, J=5.8 Hz, 1H), 1.86-1.75 (m, 2H), 1.73-1.63 (m, 2H).

Step 5. 7-(8-Methyl-7-quinolyl)spiro[4,5-dihydro-1,3-benzodioxepine-2,4'-piperidine]-1'-carboxamide. To a solution of 7-(8-methyl-7-quinolyl)spiro[4,5-dihydro-1,3-benzodioxepine-2,4'-piperidine] (0.050 g, 0.14 mmol) in DCM (2.0 mL) at 0° C. under $N_2$ was added isocyanato(trimethyl) silane (0.038 mL, 0.032 g, 0.28 mmol) dropwise. The ice bath warmed to RT and the reaction was stirred overnight. LC-MS showed a small amount of unreacted starting material. Additional isocyanato(trimethyl)silane (0.038 mL, 0.28 mmol) was added, and the reaction was stirred at RT for several more hours. The mixture was partitioned between EtOAc and saturated $NH_4Cl$ solution and separated. The organic layer was washed with water, saturated aqueous $NaHCO_3$ solution, and brine, then dried over $Na_2SO_4$, filtered, and concentrated to yield a white film. ISCO silica gel chromatography (20% (20:1:1 EtOH:$NH_4OH$:$H_2O$)—80% EtOAc; 0-100%)—100 to % DCM; 40 g column) yielded the desired compound as a white solid (0.046 g, 82%). Analysis: LCMS m/z=404 (M+1); $^1$H NMR (400 MHz, DMSO-$d^6$) δ 8.97 (dd, J=4.3, 1.8 Hz, 1H), 8.37 (dd, J=8.3, 1.8 Hz, 1H), 7.86 (d, J=8.5 Hz, 1H), 7.60-7.53 (m, 1H), 7.49 (d, J=8.5 Hz, 1H), 7.29 (d, J=2.3 Hz, 1H), 7.27-7.21 (m, 1H), 7.12 (d, J=8.3 Hz, 1H), 6.00 (s, 2H), 3.93 (t, J=5.5 Hz, 2H), 3.46-3.36 (m, 4H), 3.02 (t, J=5.4 Hz, 2H), 2.68 (s, 3H), 1.87-1.76 (m, 2H), 1.74-1.64 (m, 2H).

Example 78. N-Ethyl-7-(8-methyl-7-quinolyl)spiro[4,5-dihydro-1,3-benzodioxepine-2,4'-piperidine]-1'-carboxamide

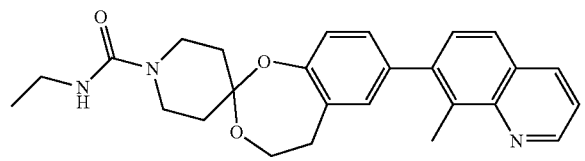

To a solution of 7-(8-methyl-7-quinolyl)spiro[4,5-dihydro-1,3-benzodioxepine-2,4'-piperidine](0.050 g, 0.14 mmol) in DCM (2.0 mL) under Ar was added isocyanatoethane (0.019 mL, 0.017 g, 0.24 mmol). The mixture was stirred at RT overnight, partitioned between EtOAc and saturated $NH_4Cl$ solution and separated. The organic layer was washed with water, saturated aqueous $NaHCO_3$ solution, and brine, then dried over $Na_2SO_4$, filtered, concentrated, and dried under vacuum to yield a clear, colorless oil. ISCO silica gel chromatography (0 to 100% (10% 20:1:1 EtOH:$NH_4OH$:$H_2O$—90% EtOAc)—100 to 0% hexanes; 40 g column) yielded the desired compound as a white foam (0.0426 g, 71%). Analysis: LCMS m/z=432 (M+1); $^1$H NMR (400 MHz, DMSO-$d_6$) δ 8.97 (dd, J=4.0, 1.8 Hz, 1H), 8.37 (dd, J=8.3, 1.8 Hz, 1H), 7.86 (d, J=8.3 Hz, 1H), 7.56 (dd, J=8.2, 4.1 Hz, 1H), 7.49 (d, J=8.3 Hz, 1H), 7.29 (d, J=2.0 Hz, 1H), 7.27-7.21 (m, 1H), 7.12 (d, J=8.0 Hz, 1H), 6.53 (t, J=5.3 Hz, 1H), 3.93 (t, J=5.4 Hz, 2H), 3.45-3.36 (m, 4H), 3.10-2.97 (m, 4H), 2.68 (s, 3H), 1.87-1.76 (m, 2H), 1.75-1.63 (m, 2H), 1.01 (t, J=7.2 Hz, 3H).

Example 79. N-Ethoxy-7-(8-methyl-7-quinolyl)spiro[4,5-dihydro-1,3-benzodioxepine-2,4'-piperidine]-1'-carboxamide

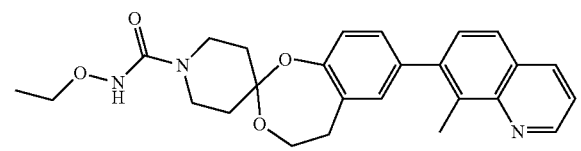

To a solution of CDI (0.034 g, 0.21 mmol) in DCM (2 mL) was added DIPEA (0.073 mL, 0.054 g, 0.42 mmol) followed by O-ethylhydroxylamine HCl (0.022 g, 0.22 mmol). The solution was stirred at RT for 2 h then 7-(8-methyl-7-quinolyl)spiro[4,5-dihydro-1,3-benzodioxepine-2,4'-piperidine] (0.050 g, 0.14 mmol) was added. After stirring at RT overnight the mixture was partitioned between EtOAc and saturated $NH_4Cl$ solution and separated. The organic layer was washed with water, saturated aqueous $NaHCO_3$ solution, and brine, then dried over $Na_2SO_4$, filtered, and concentrated to yield a clear, colorless oil. ISCO silica gel chromatography (0 to 100% (20% 20:1:1 EtOH:$NH_4OH$:

H₂O—80% EtOAc)—100 to 0% hexanes; 40 g column) yielded the desired compound as a white foam (0.0585 g, 94%). Analysis: LCMS m/z=448 (M+1); ¹H NMR (400 MHz, DMSO-d₆) δ 9.68 (s, 1H), 8.97 (dd, J=4.3, 1.8 Hz, 1H), 8.37 (dd, J=8.3, 1.8 Hz, 1H), 7.86 (d, J=8.3 Hz, 1H), 7.56 (dd, J=8.3, 4.3 Hz, 1H), 7.49 (d, J=8.3 Hz, 1H), 7.29 (d, J=2.0 Hz, 1H), 7.27-7.21 (m, 1H), 7.12 (d, J=8.0 Hz, 1H), 3.93 (t, J=5.5 Hz, 2H), 3.75 (q, J=7.0 Hz, 2H), 3.43-3.34 (m, 4H), 3.02 (t, J=5.4 Hz, 2H), 2.68 (s, 3H), 1.89-1.78 (m, 2H), 1.77-1.66 (m, 2H), 1.12 (t, J=7.0 Hz, 3H).

Example 80. N-Methoxy-7-(8-methyl-7-quinolyl)spiro[4,5-dihydro-1,3-benzodioxepine-2,4'-piperidine]-1'-carboxamide

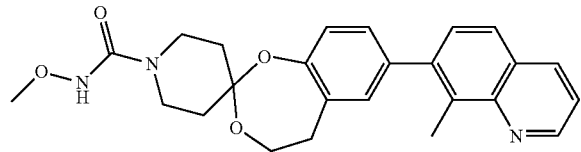 [SMILES: CCNC(=O)N1CCC2(CC1)OCCc1cc(-c3ccc4cccnc4c3C)ccc1O2]

This compound was synthesized using O-methylhydroxylamine HCl (0.024 g, 0.28 mmol) and 7-(8-methyl-7-quinolyl)spiro[4,5-dihydro-1,3-benzodioxepine-2,4'-piperidine] (0.060 g, 0.17 mmol) by the procedure for example 79 to give the desired compound as a white foam (0.0475 g, 66%). Analysis: LCMS m/z=434 (M+1); ¹H NMR (400 MHz, DMSO-d₆) δ 9.77 (s, 1H), 8.97 (dd, J=4.3, 1.8 Hz, 1H), 8.37 (dd, J=8.3, 1.8 Hz, 1H), 7.86 (d, J=8.5 Hz, 1H), 7.56 (dd, J=8.2, 4.1 Hz, 1H), 7.49 (d, J=8.3 Hz, 1H), 7.29 (d, J=2.3 Hz, 1H), 7.27-7.22 (m, 1H), 7.12 (d, J=8.0 Hz, 1H), 3.93 (t, J=5.5 Hz, 2H), 3.54 (s, 3H), 3.45-3.35 (m, 4H), 3.02 (t, J=5.5 Hz, 2H), 2.68 (s, 3H), 1.89-1.78 (m, 2H), 1.77-1.66 (m, 2H).

Example 81. 6-(1-Methylbenzimidazol-5-yl)spiro[chromane-2,4'-piperidine]-1'-carboxamide

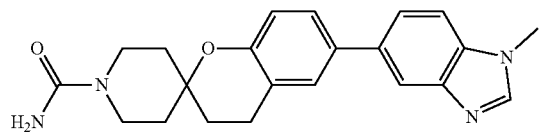 [SMILES: Cn1cnc2cc(-c3ccc4c(c3)CCC3(CCN(C(N)=O)CC3)O4)ccc21]

This compound was synthesized using 6-bromospiro[chromane-2,4'-piperidine]-1'-carboxamide (0.050 g, 0.15 mmol) and 1-methyl-5-(4,4,5,5-tetramethyl-1,3,2-dioxaborolan-2-yl)-benzimidazole (0.063 g, 0.25 mmol), by the procedure for example 72 to yield the desired compound as a white solid (0.0192 g, 33%). Analysis: LCMS m/z=377 (M+1); 1H NMR (400 MHz, DMSO-d₆) δ 8.18 (s, 1H), 7.81 (d, J=1.3 Hz, 1H), 7.61-7.57 (m, 1H), 7.53-7.49 (m, 1H), 7.44-7.38 (m, 2H), 6.86 (d, J=8.3 Hz, 1H), 5.96 (s, 2H), 3.85 (s, 3H), 3.68 (d, J=13.3 Hz, 2H), 3.19-3.08 (m, 2H), 2.82 (t, J=6.8 Hz, 2H), 1.82 (t, J=6.7 Hz, 2H), 1.73-1.63 (m, 2H), 1.59-1.47 (m, 2H).

Example 82. 6-(1-Methylbenzimidazol-5-yl)spiro[4H-1,3-benzodioxine-2,4'-piperidine]-1'-carboxamide

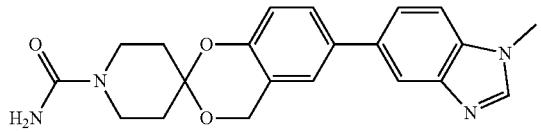

To a solution of 6-(1-methylbenzimidazol-5-yl)spiro[4H-1,3-benzodioxine-2,4'-piperidine (0.060 g, 0.18 mmol) in anhydrous DCM (2.0 mL) in a scintillation vial at RT under Ar was added isocyanato(trimethyl)silane (0.048 mL, 0.041 g, 0.36 mmol) dropwise. The reaction was stirred over a weekend. The white suspension was diluted with ether. The solid collected, was washed with ether, then dried under vacuum to yield the desired compound as a white solid (0.0638 g, 94%). Analysis: LCMS m/z=379 (M+1); ¹H NMR (400 MHz, DMSO-d₆) δ 8.22 (s, 1H), 7.84 (d, J=0.8 Hz, 1H), 7.66-7.59 (m, 1H), 7.57-7.48 (m, 2H), 7.44 (d, J=2.0 Hz, 1H), 6.93 (d, J=8.3 Hz, 1H), 6.04 (s, 2H), 4.94 (s, 2H), 3.86 (s, 3H), 1.87-1.73 (m, 4H).

Example 83. 6-(1,3-Benzothiazol-5-yl)spiro[chromane-2,4'-piperidine]-1'-carboxamide

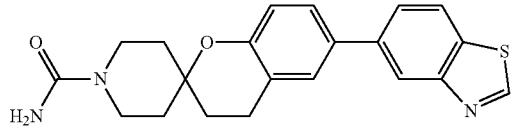

This compound was synthesized using 6-bromospiro[chromane-2,4'-piperidine]-1'-carboxamide (0.070 g, 0.22 mmol) and 5-(4,4,5,5-tetramethyl-1,3,2-dioxaborolan-2-yl)-1,3-benzothiazole (0.084 g, 0.32 mmol) to give the desired compound as an off-white solid (0.0467 g, 57%). Analysis: LCMS m/z=380 (M+1); ¹H NMR (400 MHz, DMSO-d₆) δ 9.41 (s, 1H), 8.27 (d, J=1.5 Hz, 1H), 8.19 (d, J=8.5 Hz, 1H), 7.74 (dd, J=8.4, 1.6 Hz, 1H), 7.56-7.48 (m, 2H), 6.90 (d, J=8.3 Hz, 1H), 5.96 (s, 2H), 3.69 (d, J=13.3 Hz, 2H), 3.20-3.08 (m, 2H), 2.84 (t, J=6.7 Hz, 2H), 1.84 (t, J=6.8 Hz, 2H), 1.74-1.63 (m, 2H), 1.60-1.48 (m, 2H).

Example 84. tert-Butyl 6-thieno[2,3-b]pyridin-5-ylspiro[4H-1,3-benzodioxine-2,4'-piperidine]-1'-carboxylate

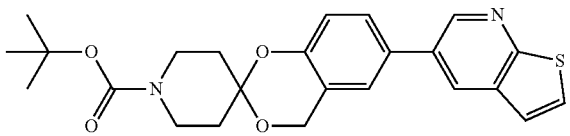 [SMILES: CC(C)(C)OC(=O)N1CCC2(CC1)OCc1cc(-c3cnc4sccc4c3)ccc1O2]

This compound was synthesized using tert-butyl 6-bromospiro[4H-1,3-benzodioxine-2,4'-piperidine]-1'-carboxylate (0.150 g, 0.390 mmol) and 5-(4,4,5,5-tetramethyl-1,3,2-dioxaborolan-2-yl)thieno[2,3-b]pyridine (0.153 g, 0.585 mmol) by the procedure for example 72 to yield the desired compound as an off-white solid (0.148 g, 87%). Analysis: LCMS m/z=439 (M+1); $^1$H NMR (400 MHz, DMSO-d$_6$) δ 8.83 (d, J=2.3 Hz, 1H), 8.48 (d, J=2.3 Hz, 1H), 7.92 (d, J=5.8 Hz, 1H), 7.62 (dd, J=8.5, 2.3 Hz, 1H), 7.55 (d, J=2.0 Hz, 1H), 7.48 (d, J=6.0 Hz, 1H), 7.00 (d, J=8.5 Hz, 1H), 4.95 (s, 2H), 3.53-3.39 (m, 4H), 1.91-1.77 (m, 4H), 1.42 (s, 9H).

Example 85. 6-Thieno[2,3-b]pyridin-5-ylspiro[chromane-2,4'-piperidine]-1'-carboxamide

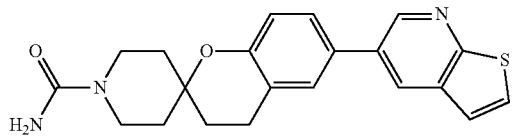 [SMILES: NC(=O)N1CCC2(CCc3cc(-c4cnc5sccc5c4)ccc3O2)CC1]

To a solution of 6-thieno[2,3-b]pyridin-5-ylspiro[chromane-2,4'-piperidine] (0.060 g, 0.18 mmol) in DCM (2.0 mL) was added isocyanato(trimethyl)silane (0.048 mL, 0.041 g, 0.36 mmol) dropwise. Additional DIEA (0.16 mL, 0.12 g, 0.89 mmol) and isocyanato(trimethyl)silane (0.024 mL, 0.021 g, 0.18 mmol) were added. After stirring several days the white suspension was diluted with of ether, and precipitate collected. The solid was washed with ether, then dried under vacuum to yield the desired compound as a white solid (0.0442 g, 65%). Analysis: LCMS m/z=380 (M+1); $^1$H NMR (400 MHz, DMSO-d$_6$) δ 8.82 (d, J=2.3 Hz, 1H), 8.46 (d, J=2.3 Hz, 1H), 7.91 (d, J=6.0 Hz, 1H), 7.54 (d, J=2.3 Hz, 1H), 7.53-7.49 (m, 1H), 7.47 (d, J=6.0 Hz, 1H), 6.93 (d, J=8.3 Hz, 1H), 5.96 (s, 2H), 3.69 (d, J=13.6 Hz, 2H), 3.20-3.09 (m, J=11.0, 11.0 Hz, 2H), 2.84 (t, J=6.8 Hz, 2H), 1.84 (t, J=6.8 Hz, 2H), 1.74-1.63 (m, 2H), 1.61-1.48 (m, 2H).

Example 86. 6-(1,3-Benzoxazol-5-yl)spiro[chromane-2,4'-piperidine]-1'-carboxamide

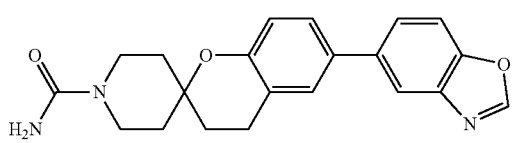

This compound was synthesized using 6-bromospiro[chromane-2,4'-piperidine]-1'-carboxamide (0.060 g, 0.18 mmol) and 5-(4,4,5,5-tetramethyl-1,3,2-dioxaborolan-2-yl)-1,3-benzoxazole (0.068 g, 0.28 mmol by the procedure for example 72 to yield the desired compound as an off-white solid (0.0226 g, 34%). Analysis: LCMS m/z=364 (M+1); $^1$H NMR (400 MHz, DMSO-d$_6$) δ 8.76 (s, 1H), 7.97 (d, J=1.5 Hz, 1H), 7.80 (d, J=8.5 Hz, 1H), 7.66 (dd, J=8.5, 1.8 Hz, 1H), 7.48-7.41 (m, 2H), 6.88 (d, J=8.3 Hz, 1H), 5.96 (s, 2H), 3.68 (d, J=13.3 Hz, 2H), 3.20-3.08 (m, 2H), 2.82 (t, J=6.8 Hz, 2H), 1.83 (t, J=6.8 Hz, 2H), 1.73-1.62 (m, 2H), 1.60-1.47 (m, 2H).

Example 87. 6-(2-Naphthyl)spiro[chromane-2,4'-piperidine]-1'-carboxamide

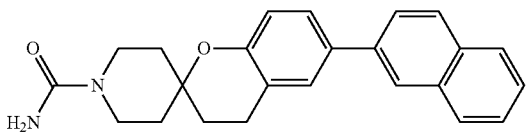

This compound was synthesized using 6-bromospiro[chromane-2,4'-piperidine]-1'-carboxamide (0.060 g, 0.18 mmol) and 2-naphthylboronic acid (0.048 g, 0.28 mmol) to give the desired compound as a white solid (0.035 g, 51%). Analysis: LCMS m/z=373 (M+1); $^1$H NMR (400 MHz, DMSO-d$_6$) δ 8.13 (d, J=1.3 Hz, 1H), 7.96 (d, J=8.8 Hz, 2H), 7.91 (d, J=7.5 Hz, 1H), 7.80 (dd, J=8.5, 1.8 Hz, 1H), 7.59-7.45 (m, 4H), 6.92 (d, J=8.3 Hz, 1H), 5.96 (s, 2H), 3.69 (d, J=13.6 Hz, 2H), 3.20-3.09 (m, 2H), 2.85 (t, J=6.7 Hz, 2H), 1.84 (t, J=6.8 Hz, 2H), 1.74-1.64 (m, 2H), 1.60-1.49 (m, 2H).

Example 88. 6-(1,3-Benzoxazol-6-yl)spiro[chromane-2,4'-piperidine]-1'-carboxamide

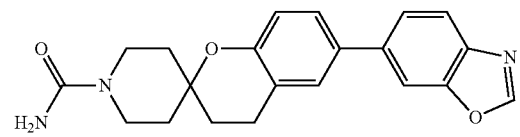 [SMILES: NC(=O)N1CCC2(CCc3cc(-c4ccc5ncoc5c4)ccc3O2)CC1]

This compound was synthesized using 6-bromospiro[chromane-2,4'-piperidine]-1'-carboxamide (0.075 g, 0.23 mmol) and 6-(4,4,5,5-tetramethyl-1,3,2-dioxaborolan-2-yl)-1,3-benzoxazole (0.099 g, 0.40 mmol) to yield the desired product as an off-white solid (0.0230 g, 27%). Analysis: LCMS m/z=364 (M+1); $^1$H NMR (400 MHz, DMSO-d$_6$) δ 8.73 (s, 1H), 7.98 (d, J=1.3 Hz, 1H), 7.81 (d, J=8.3 Hz, 1H), 7.64 (dd, J=8.4, 1.6 Hz, 1H), 7.51-7.44 (m, 2H), 6.89 (d, J=8.3 Hz, 1H), 5.96 (s, 2H), 3.68 (d, J=13.3 Hz, 2H), 3.19-3.08 (m, 2H), 2.83 (t, J=6.5 Hz, 2H), 1.83 (t, J=6.7 Hz, 2H), 1.73-1.63 (m, 2H), 1.59-1.48 (m, 2H).

Example 89. 6-thieno[2,3-b]pyridin-5-ylspiro[4H-1,3-benzodioxine-2,4'-piperidine]-1'-carboxamide

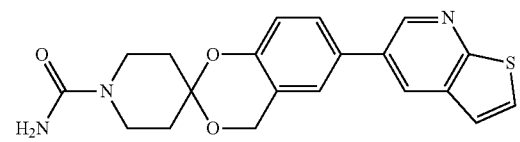 [SMILES: NC(=O)N1CCC2(CC1)OCc1cc(-c3cnc4sccc4c3)ccc1O2]

To a solution of 6-thieno[2,3-b]pyridin-5-ylspiro[4H-1,3-benzodioxine-2,4'-piperidine] 2HCl (0.133 g, 0.324 mmol) and DIPEA (0.339 mL, 0.251 g, 1.94 mmol) in DCM (2.0 mL) was added isocyanato(trimethyl)silane (0.0877 mL, 0.0747 g, 0.648 mmol) dropwise. After 24 h the reaction was concentrated, triturated with ether and dried to yield the desired compound as an off-white solid (0.0920 g, 74%). Analysis: LCMS m/z=382 (M+1); 1H NMR (400 MHz, DMSO-d$_6$) δ 8.83 (d, J=2.3 Hz, 1H), 8.48 (d, J=2.3 Hz, 1H), 7.92 (d, J=6.0 Hz, 1H), 7.62 (dd, J=8.5, 2.3 Hz, 1H), 7.55 (d, J=2.3 Hz, 1H), 7.48 (d, J=6.0 Hz, 1H), 7.00 (d, J=8.5 Hz, 1H), 6.04 (s, 2H), 4.96 (s, 2H), 3.49-3.38 (m, 4H), 1.87-1.74 (m, 4H).

Example 90. 6-(2-Naphthyl)spiro[4H-1,3-benzodioxine-2,4'-piperidine]-1'-carboxamide

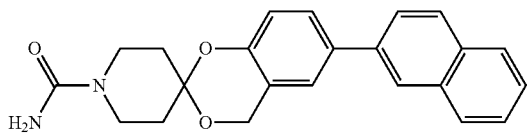

To a solution of 6-(2-naphthyl)spiro[4H-1,3-benzodioxine-2,4'-piperidine] HCl (0.075 g, 0.20 mmol) and DIPEA (0.18 mL, 0.13 g, 1.0 mmol) in DCM (2.0 mL) was added isocyanato-(trimethyl)silane (0.069 mL, 0.059 g, 0.51 mmol) dropwise. Additional portions of isocyanato(trimethyl)silane (0.069 mL, 0.059 g, 0.51 mmol) and DIPEA (0.18 mL, 0.13 g, 1.0 mmol) were added until the starting material was gone. The mixture was partitioned between EtOAc and saturated aqueous NH$_4$Cl solution and separated. The organic layer was washed with water, saturated NaHCO$_3$ solution, and brine, then dried over Na$_2$SO$_4$, filtered, concentrated, and dried under vacuum to yield a yellowish solid. This residue was suspended in 10 mL of ether and stirred for 30 min. The solid was collect, washed with ether, then dried under vacuum to yield the desired compound as a white solid (0.065 g, 85%). Analysis: LCMS m/z=375 (M+1); $^1$H NMR (400 MHz, DMSO-d$_6$) δ 8.15 (d, J=1.3 Hz, 1H), 7.97 (t, J=7.5 Hz, 2H), 7.92 (d, J=7.5 Hz, 1H), 7.81 (dd, J=8.7, 1.9, 1H), 7.65 (dd, J=8.5, 2.3 Hz, 1H), 7.57 (d, J=2.3 Hz, 1H), 7.56-7.46 (m, 2H), 6.99 (d, J=8.5 Hz, 1H), 6.05 (s, 2H), 4.97 (s, 2H), 3.50-3.37 (m, 4H), 1.88-1.74 (m, 4H).

Example 91. 6-(1,8-Naphthyridin-3-yl)spiro[chromane-2,4'-piperidine]-1'-carboxamide

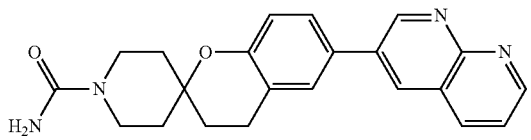 [SMILES: NC(=O)N1CCC2(CCc3cc(-c4cnc5ncccc5c4)ccc3O2)CC1]

To a solution of 6-(1,8-naphthyridin-3-yl)spiro[chromane-2,4'-piperidine] dihydrochloride (0.073 g, 0.18 mmol) and DIPEA (0.16 mL, 0.12 g, 0.90 mmol) in DMF (3.0 mL) was added isocyanato(trimethyl)silane (0.061 mL, 0.052 g, 0.45 mmol) dropwise. The reaction was stirred overnight, partitioned between EtOAc and saturated aqueous NH$_4$Cl solution and separated. The organic layer was washed with water, saturated aqueous NaHCO$_3$ solution, and brine, then dried over Na$_2$SO$_4$, filtered, concentrated, and dried under vacuum to yield a yellowish solid. The residue was purified by preparative HPLC on the Gilson (5 to 40% MeCN—95 to 60% water (both with 0.1% TFA) over 20 min.; 10 mL fractions; Phenomenex Gemini 5 μm NX-C18 110 Å 150×30 mm column). The clean fractions were combined and partitioned between DCM and saturated aqueous NaHCO$_3$ solution. The aqueous layer was back extracted with DCM, organic layers were washed with saturated NaHCO$_3$ solution, brine, dried with Na$_2$SO$_4$, filtered, and concentrated to yield the desired compound as an off-white solid (0.0317 g, 47%). Analysis: LCMS m/z=375 (M+1); $^1$H NMR (400 MHz, DMSO-d$_6$) δ 9.40 (d, J=2.8 Hz, 1H), 9.05 (dd, J=4.3, 2.0 Hz, 1H), 8.66 (d, J=2.5 Hz, 1H), 8.49 (dd, J=8.3, 1.8 Hz, 1H), 7.70-7.64 (m, 3H), 6.98 (d, J=8.3 Hz, 1H), 5.97 (s, 2H), 3.70 (d, J=13.3 Hz, 2H), 3.21-3.10 (m, 2H), 2.87 (t, J=6.7 Hz, 2H), 1.86 (t, J=6.8 Hz, 2H), 1.75-1.65 (m, 2H), 1.62-1.50 (m, 2H).

Example 92. tert-Butyl 6-(1-tert-butoxycarbonylindol-2-yl)spiro[4H-1,3-benzodioxine-2,4'-piperidine]-1'-carboxylate

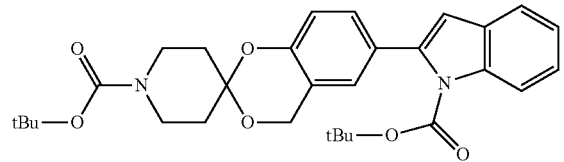 [SMILES: CC(C)(C)OC(=O)N1CCC2(CC1)OCc1cc(-c3cc4ccccc4n3C(=O)OC(C)(C)C)ccc1O2]

This compound was synthesized using tert-butyl 6-bromospiro[4H-1,3-benzodioxine-2,4'-piperidine]-1'-carboxylate (0.100 g, 0.260 mmol) and (1-tert-butoxycarbonylindol-2-yl)boronic acid (0.102 g, 0.390 mmol) to yield the desired compound as an off-white foam (0.082 g, 61%). Analysis: LCMS m/z=521 (M+1); $^1$H NMR (400 MHz, DMSO-d$_6$) δ 8.11-8.04 (m, 1H), 7.59 (d, J=7.3 Hz, 1H), 7.36-7.28 (m, 1H), 7.28-7.21 (m, 2H), 7.19 (d, J=2.0 Hz, 1H), 6.93 (d, J=8.3 Hz, 1H), 6.65 (s, 1H), 4.90 (s, 2H), 3.53-3.38 (m, 4H), 1.90-1.75 (m, 4H), 1.42 (s, 9H), 1.29 (s, 9H).

Example 93. tert-Butyl 3-(1'-carbamoylspiro[chromane-2,4'-piperidine]-6-yl)indole-1-carboxylate

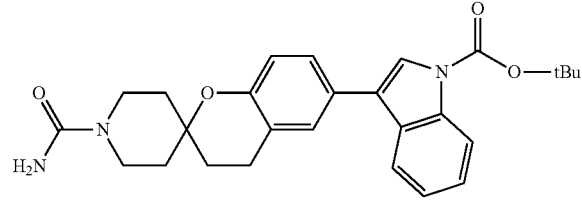 [SMILES: CC(C)(C)OC(=O)n1cc(-c2ccc3c(c2)CCC2(CCN(C(N)=O)CC2)O3)c2ccccc21]

This compound was synthesized using 6-bromospiro[chromane-2,4'-piperidine]-1'-carboxamide (0.068 g, 0.21 mmol) and (1-tert-butoxycarbonylindol-3-yl)boronic acid (0.082 g, 0.31 mmol) to yield the desired compound as an off-white solid (0.076 g, 79%). Analysis: LCMS m/z=462 (M+1); $^1$H NMR (400 MHz, DMSO-d$_6$) δ 8.14 (d, J=8.3 Hz, 1H), 7.83 (d, J=7.8 Hz, 1H), 7.76 (s, 1H), 7.45-7.36 (m, 3H), 7.35-7.28 (m, 1H), 6.91 (d, J=8.3 Hz, 1H), 5.96 (s, 2H), 3.69 (d, J=13.3 Hz, 2H), 3.20-3.08 (m, J=10.9, 10.9 Hz, 2H), 2.83 (t, J=6.7 Hz, 2H), 1.83 (t, J=6.8 Hz, 2H), 1.74-1.67 (m, 2H), 1.65 (s, 9H), 1.60-1.48 (m, 2H).

Example 94. 6-(1H-Indol-3-yl)spiro[chromane-2,4'-piperidine]-1'-carboxamide

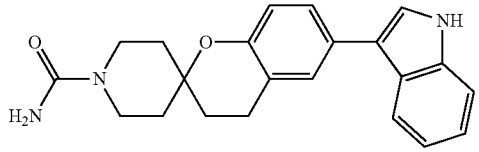 [SMILES: NC(=O)N1CCC2(CCc3cc(-c4c[nH]c5ccccc45)ccc3O2)CC1]

To a solution of tert-butyl 3-(1'-carbamoylspiro[chromane-2,4'-piperidine]-6-yl)indole-1-carboxylate (0.072 g, 0.16 mmol) in DCM (2 mL) was added hydrogen chloride (4 mol/L) in 1,4-dioxane (2.0 mL, 8.0 mmol) dropwise. The reaction was stirred overnight, concentrated, then dried under vacuum. Silica gel chromatography on the ISCO (0 to 100% (25% 20:1:1 EtOH:NH$_4$OH:H$_2$O—75% EtOAc)—100 to 0% hexanes; 40 g column) yielded the desired compound as an off-white solid (0.0330 g, 59%). Analysis: LCMS m/z=362 (M+1); $^1$H NMR (400 MHz, DMSO-d$_6$) δ: 11.20 (d, J=1.5 Hz, 1H), 7.81 (d, J=8.0 Hz, 1H), 7.52 (d, J=2.5 Hz, 1H), 7.41 (d, J=8.0 Hz, 1H), 7.39-7.34 (m, 2H), 7.16-7.09 (m, 1H), 7.09-7.02 (m, 1H), 6.88-6.81 (m, 1H), 5.95 (s, 2H), 3.69 (d, J=13.3 Hz, 2H), 3.20-3.09 (m, 2H), 2.81 (t, J=6.7 Hz, 2H), 1.82 (t, J=6.8 Hz, 2H), 1.69 (d, J=13.6 Hz, 2H), 1.59-1.47 (m, 2H).

Example 95. 6-(1H-Indol-3-yl)spiro[4H-1,3-benzodioxine-2,4'-piperidine]-1'-carboxamide

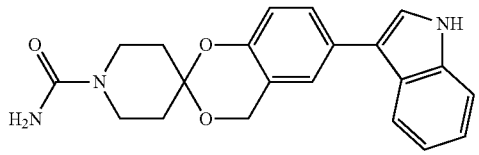

To a suspension of 6-(1H-indol-3-yl)spiro[4H-1,3-benzodioxine-2,4'-piperidine] (0.085 g, 0.27 mmol) in DCM (3 mL) was added isocyanato(trimethyl)silane (0.018 mL, 0.015 g, 0.13 mmol) dropwise. DMF (1 mL) and additional isocyanato(trimethyl)silane (0.018 mL, 0.015 g, 0.13 mmol) were added and the mixture was stirred for 2 h. The reaction was quenched with 1 mL of water, partitioned between EtOAc and saturated aqueous NH$_4$Cl solution and separated. The organic layer was washed with water, saturated aqueous NaHCO$_3$ solution, and brine, then dried over Na$_2$SO$_4$, filtered, concentrated, and dried under vacuum to yield a brownish film. ISCO silica gel chromatography (0 to 100% (25% 20:1:1 EtOH:NH$_4$OH:H$_2$O—75% EtOAc)—100 to 0% hexanes; 40 g column) yielded the desired compound as a tan solid (0.0382 g, 40%). Analysis: LCMS m/z=364 (M+1); $^1$H NMR (400 MHz, DMSO-d$_6$) δ 11.25 (d, J=1.5 Hz, 1H), 7.83 (d, J=7.8 Hz, 1H), 7.57 (d, J=2.5 Hz, 1H), 7.47 (dd, J=8.5, 2.3 Hz, 1H), 7.42 (d, J=8.0 Hz, 1H), 7.38 (d, J=2.0 Hz, 1H), 7.13 (td, J=7.5, 1.0 Hz, 1H), 7.10-7.03 (m, 1H), 6.91 (d, J=8.3 Hz, 1H), 6.03 (s, 2H), 4.94 (s, 2H), 3.48-3.38 (m, 4H), 1.86-1.73 (m, 4H).

Example 96. N-Isobutyl-6-(8-methyl-7-quinolyl)spiro[chromane-2,4'-piperidine]-1'-carboxamide

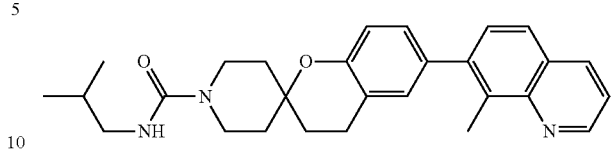

Step 1. tert-butyl 6-(8-methyl-7-quinolyl)spiro[chromane-2,4'-piperidine]-1'-carboxylate. A solution of palladium(II) acetate (0.26 g, 0.12 mmol), X-PHOS (0.23 g, 0.47 mmol), 7-bromo-8-methylquinoline (0.66 g, 3.0 mmol), tert-butyl 6-(4,4,5,5-tetramethyl-1,3,2-dioxaborolan-2-yl)spiro[chromane-2,4'-piperidine]-1'-carboxylate (1.0 g, 2.3 mmol) in dioxane (40 mL) and 1 M Na$_2$CO$_3$ (9.3 mL) was heated at 60° C. for 4 h. The reaction was cooled to RT, concentrated, and then partitioned between EtOAc and water. The organic layer was separated, washed with brine, dried over MgSO$_4$, filtered and concentrated. The product was purified by ISCO silica gel chromatography (80 g column, 0-25% EtOAc/hexanes) to yield product (0.652 g, 63%). 1H NMR (400 MHz, DMSO-d$_6$) δ 8.96 (dd, J=4.1, 1.9 Hz, 1H), 8.35 (dd, J=8.3, 1.8 Hz, 1H), 7.83 (d, J=8.5 Hz, 1H), 7.54 (dd, J=8.3, 4.3 Hz, 1H), 7.47 (d, J=8.3 Hz, 1H), 7.22-7.13 (m, 2H), 6.94-6.88 (m, 1H), 3.73 (br d, J=13.3 Hz, 2H), 3.20 (br s, 2H), 2.82 (t, J=6.7 Hz, 2H), 2.68 (s, 3H), 1.85 (t, J=6.8 Hz, 2H), 1.74 (br d, J=13.3 Hz, 2H), 1.64-1.52 (m, 2H), 1.42 (s, 9H).

Step 2. 6-(8-methyl-7-quinolyl)spiro[chromane-2,4'-piperidine] dihydrochloride. Tert-butyl 6-(8-methyl-7-quinolyl)spiro[chromane-2,4'-piperidine]-1'-carboxylate (630 mg, 1.4 mmol) in dioxane (20 mL) at 0° C., was added 2 M HCl in dioxane (9.45 mL). After stirring 18 h, the solids were collected and dried to give the product as the dihydrochloride salt (0.468 g, 79%). $^1$H NMR (400 MHz, DMSO-d$_6$) δ: 9.43-9.21 (m, 2H), 9.18 (dd, J=4.9, 1.4 Hz, 1H), 8.96 (br d, J=7.5 Hz, 1H), 8.21-8.07 (m, 1H), 7.94 (br dd, J=8.0, 5.0 Hz, 1H), 7.72 (d, J=8.5 Hz, 1H), 7.28-7.19 (m, 2H), 7.00 (d, J=8.3 Hz, 1H), 3.27-3.04 (m, 4H), 2.86 (br t, J=6.7 Hz, 2H), 2.76 (s, 3H), 2.02-1.82 (m, 6H).

Step 3. N-isobutyl-6-(8-methyl-7-quinolyl)spiro[chromane-2,4'-piperidine]-1'-carboxamide. 6-(8-Methyl-7-quinolyl)spiro[chromane-2,4'-piperidine] 2HCl (100 mg, 0.24 mmol), 1-isocyanato-2-methylpropane (48 mg, 0.48 mmol) in DCM (2 mL) was added DIPEA (0.084 mL, 0.48 mmol) at RT. After stirring at RT for 1 h, the mixture was partitioned between DCM and 1 M Na$_2$CO$_3$, and the layers separated and dried. The DCM layer was concentrated and the product purified by Gilson HPLC reverse phase chromatography, (5-55% acetonitrile in H$_2$O with 0.1% TFA). The clean fractions were concentrated and the freebase generated using a strong cation exchange column to yield N-isobutyl-6-(8-methyl-7-quinolyl)spiro[chromane-2,4'-piperidine]-1'-carboxamide (43 mg, 41%). Analysis: LCMS m/z=444 (M+1); $^1$H NMR (400 MHz, DMSO-d$_6$) δ: 8.96 (1H, dd, J=4.1, 1.9 Hz), 8.36 (1H, dd, J=8.3, 1.8 Hz), 7.84 (1H, d, J=8.3 Hz), 7.54 (1H, dd, J=8.3, 4.3 Hz), 7.47 (1H, d, J=8.3 Hz), 7.10-7.21 (2H, m), 6.87-6.94 (1H, m), 6.53 (1H, t, J=5.6 Hz), 3.72 (2H, br d, J=13.3 Hz), 3.09-3.26 (2H, m), 2.76-2.91 (4H, m), 2.69 (3H, s), 1.84 (2H, t, J=6.8 Hz), 1.65-1.77 (3H, m), 1.50-1.62 (2H, m), 0.83 (6H, d, J=6.8 Hz).

Example 97. N-Ethyl-6-(8-methyl-7-quinolyl)spiro[chromane-2,4'-piperidine]-1'-carboxamide

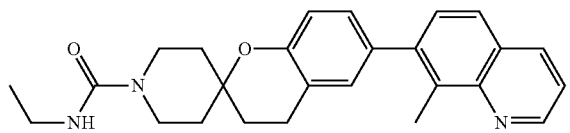 [SMILES: CCNC(=O)N1CCC2(CCc3cc(-c4ccc5cccnc5c4C)ccc3O2)CC1]

This compound was synthesized from 6-(8-methyl-7-quinolyl)spiro[chromane-2,4'-piperidine]2HCl (100 mg, 0.24 mmol) and ethyl isocyanate (35 mg, 0.4826 mmol) using the method for example 96 to yield N-ethyl-6-(8-methyl-7-quinolyl)spiro[chromane-2,4'-piperidine]-1'-carboxamide (84 mg, 84%) Analysis: LCMS m/z=416 (M+1); $^1$H NMR (400 MHz, DMSO-d$_6$) δ: 8.96 (1H, dd, J=4.1, 1.9 Hz), 8.36 (1H, dd, J=8.3, 1.8 Hz), 7.84 (1H, d, J=8.3 Hz), 7.50-7.60 (1H, m), 7.47 (1H, d, J=8.5 Hz), 7.07-7.22 (2H, m), 6.83-6.95 (1H, m), 6.50 (1H, t, J=5.3 Hz), 3.64-3.76 (2H, m), 3.11-3.24 (2H, m), 3.01-3.11 (2H, m), 2.81 (2H, t, J=6.7 Hz), 2.69 (3H, s), 1.84 (2H, t, J=6.7 Hz), 1.71 (2H, br d, J=13.6 Hz), 1.50-1.61 (2H, m), 1.02 (3H, t, J=7.0 Hz).

Example 98. N-Isopropyl-6-(8-methyl-7-quinolyl)spiro[chromane-2,4'-piperidine]-1'-carboxamide

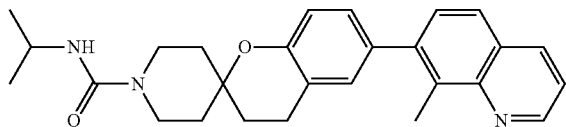

This compound was synthesized from 6-(8-methyl-7-quinolyl)spiro[chromane-2,4'-piperidine]2HCl and isopropyl isocyanate by the procedure for example 96. Analysis: LCMS m/z=430 (M+1); $^1$H NMR (400 MHz, DMSO-d$_6$) δ: 8.96 (dd, J=4.1, 1.9 Hz, 1H), 8.36 (dd, J=8.3, 1.8 Hz, 1H), 7.84 (d, J=8.3 Hz, 1H), 7.61-7.51 (m, 1H), 7.47 (d, J=8.5 Hz, 1H), 7.22-7.11 (m, 2H), 6.96-6.84 (m, 1H), 6.19 (d, J=7.5 Hz, 1H), 3.71 (br d, J=13.3 Hz, 3H), 3.15 (br s, 2H), 2.82 (s, 2H), 2.69 (s, 3H), 1.84 (t, J=6.8 Hz, 2H), 1.70 (br d, J=13.6 Hz, 2H), 1.54 (br s, 2H), 1.13-0.96 (m, 6H).

Example 99. 6-(8-Methyl-7-quinolyl)-N-propyl-spiro[chromane-2,4'-piperidine]-1'-carboxamide

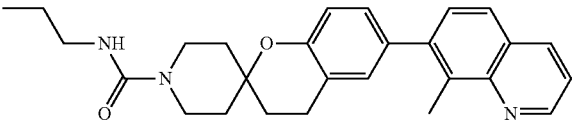 [SMILES: CCCNC(=O)N1CCC2(CCc3cc(-c4ccc5cccnc5c4C)ccc3O2)CC1]

This compound was synthesized from 6-(8-methyl-7-quinolyl)spiro[chromane-2,4'-piperidine]2HCl and propyl isocyanate by the procedure for example 96. Analysis: LCMS m/z=430 (M+1); $^1$H NMR (400 MHz, DMSO-d$_6$) δ: 8.96 (dd, J=4.0, 1.8 Hz, 1H), 8.36 (dd, J=8.3, 1.8 Hz, 1H), 7.84 (d, J=8.3 Hz, 1H), 7.58-7.51 (m, 1H), 7.47 (d, J=8.3 Hz, 1H), 7.22-7.13 (m, 2H), 6.94-6.86 (m, 1H), 6.51 (t, J=5.4 Hz, 1H), 3.71 (br d, J=13.3 Hz, 2H), 3.23-3.11 (m, 2H), 3.04-2.93 (m, 2H), 2.81 (br t, J=6.7 Hz, 2H), 2.69 (s, 3H), 1.84 (t, J=6.8 Hz, 2H), 1.71 (br d, J=13.6 Hz, 2H), 1.62-1.50 (m, 2H), 1.42 (sxt, J=7.3 Hz, 2H), 0.84 (t, J=7.4 Hz, 3H).

Example 100. N-(Cyclopropylmethyl)-6-(8-methyl-7-quinolyl)spiro[chromane-2,4'-piperidine]-1'-carboxamide

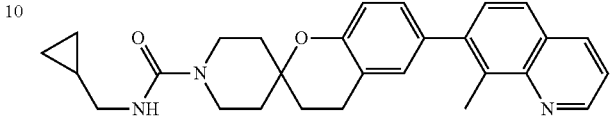

This compound was synthesized from 6-(8-methyl-7-quinolyl)spiro[chromane-2,4'-piperidine]2HCl and (isocyanatomethyl)cyclopropane by the procedure for example 96. Analysis: LCMS m/z=442 (M+1); $^1$H NMR (400 MHz, DMSO-d$_6$) δ: 8.96 (dd, J=4.1, 1.9 Hz, 1H), 8.36 (dd, J=8.3, 1.8 Hz, 1H), 7.84 (d, J=8.5 Hz, 1H), 7.54 (dd, J=8.3, 4.3 Hz, 1H), 7.47 (d, J=8.5 Hz, 1H), 7.23-7.13 (m, 2H), 6.94-6.88 (m, 1H), 6.60 (t, J=5.6 Hz, 1H), 3.79-3.66 (m, 2H), 3.24-3.11 (m, 2H), 2.92 (t, J=6.1 Hz, 2H), 2.82 (br t, J=6.7 Hz, 2H), 2.69 (s, 3H), 1.85 (t, J=6.8 Hz, 2H), 1.72 (br d, J=13.6 Hz, 2H), 1.63-1.51 (m, 2H), 1.01-0.87 (m, 1H), 0.43-0.32 (m, 2H), 0.20-0.12 (m, 2H).

Example 101. N-Ethoxy-6-(8-methyl-7-quinolyl)spiro[chromane-2,4'-piperidine]-1'-carboxamide

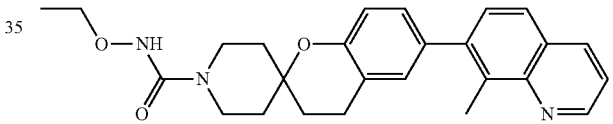

Step 1. A stirred solution of 6-(8-methyl-7-quinolyl)spiro[chromane-2,4'-piperidine] 2HCl (700 mg, 1.677 mmol) in DCM (20 mL) was added DIPEA (0.877 mL) and triphosgene (0.508 g, 1.68 mmol) a 0° C. The reaction was monitored by HPLC until completion, and then partitioned between DCM and brine. The organic layer was separated, dried (MgSO$_4$), concentrated to give 6-(8-methyl-7-quinolyl)spiro[chromane-2,4'-piperidine]-1'-carbonyl chloride that was used directly in the next step.

Step 2. A solution of 6-(8-methyl-7-quinolyl)spiro[chromane-2,4'-piperidine]-1'-carbonyl chloride (97 mg, 0.2384 mmol) in DCM (3 mL) was added DIPEA (0.125 mL) and then ethoxyamine HCl (47 mg, 0.4770 mmol). The reaction was heated to 70° C. for 24 h, and then cooled to RT. The mixture was diluted with DCM, and washed with water and brine. The layers were separated, dried and concentrated, and then the product purified by Gilson (0-50% ACN/water with 0.1% TFA). The pure fractions were concentrated and the freebase in DCM generated with a phemonex strong cation exchange column to give N-ethoxy-6-(8-methyl-7-quinolyl)spiro[chromane-2,4'-piperidine]-1'-carboxamide (30 mg, 29%). Analysis: LCMS m/z=432 (M+1); $^1$H NMR (400 MHz, DMSO-d$_6$) δ: 9.65 (s, 1H), 8.96 (dd, J=4.3, 1.8 Hz, 1H), 8.35 (dd, J=8.3, 1.8 Hz, 1H), 7.84 (d, J=8.3 Hz, 1H), 7.54 (dd, J=8.3, 4.3 Hz, 1H), 7.47 (d, J=8.3 Hz, 1H), 7.23-7.10 (m, 2H), 6.93-6.86 (m, 1H), 3.76 (q, J=7.0 Hz, 2H), 3.65 (br d, J=13.3 Hz, 2H), 3.23-3.10 (m, 2H), 2.81 (br t, J=6.5 Hz, 2H), 2.68 (s, 3H), 1.85 (t, J=6.8 Hz, 2H), 1.72 (br d, J=13.6 Hz, 2H), 1.65-1.47 (m, 2H), 1.13 (t, J=7.0 Hz, 3H)

Example 102. 6-(8-Methyl-7-quinolyl)-N-propoxy-spiro[chromane-2,4'-piperidine]-1'-carboxamide

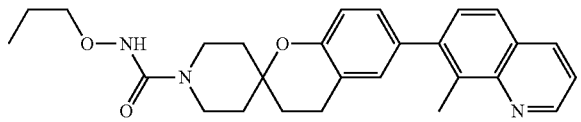 [SMILES: CCCONC(=O)N1CCC2(CCc3cc(-c4ccc5cccnc5c4C)ccc3O2)CC1]

This compound was synthesized from 6-(8-methyl-7-quinolyl)spiro[chromane-2,4'-piperidine]2HCl and 1-(ammoniooxy)propane chloride by the procedure for example 101. Analysis: LCMS m/z=446 (M+1); $^1$H NMR (400 MHz, DMSO-d$_6$) δ: 9.64 (s, 1H), 8.96 (dd, J=4.1, 1.9 Hz, 1H), 8.36 (dd, J=8.3, 1.8 Hz, 1H), 7.84 (d, J=8.3 Hz, 1H), 7.60-7.51 (m, 1H), 7.47 (d, J=8.5 Hz, 1H), 7.25-7.13 (m, 2H), 6.96-6.84 (m, 1H), 3.67 (t, J=6.7 Hz, 4H), 3.15 (br t, J=10.9 Hz, 2H), 2.81 (br t, J=6.7 Hz, 2H), 2.68 (s, 3H), 1.85 (t, J=6.8 Hz, 2H), 1.72 (br d, J=13.8 Hz, 2H), 1.63-1.40 (m, 4H), 0.90 (t, J=7.4 Hz, 3H).

Example 103. N-Isopropoxy-6-(8-methyl-7-quinolyl)spiro[chromane-2,4'-piperidine]-1'-carboxamide

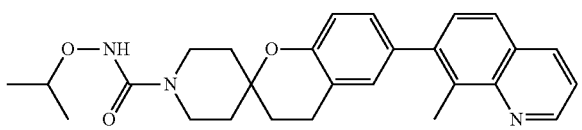

This compound was synthesized from 6-(8-methyl-7-quinolyl)spiro[chromane-2,4'-piperidine]2HCl and 2-(ammoniooxy)propane HCl by the procedure for example 101. Analysis: LCMS m/z=446 (M+1); $^1$H NMR (400 MHz, DMSO-d$_6$) δ: 9.49 (s, 1H), 8.96 (dd, J=4.1, 1.9 Hz, 1H), 8.36 (dd, J=8.3, 1.8 Hz, 1H), 7.84 (d, J=8.3 Hz, 1H), 7.54 (dd, J=8.3, 4.3 Hz, 1H), 7.47 (d, J=8.3 Hz, 1H), 7.23-7.11 (m, 2H), 6.95-6.85 (m, 1H), 3.88 (dquin, J=12.4, 6.2 Hz, 1H), 3.66 (br d, J=13.6 Hz, 2H), 3.16 (br t, J=10.9 Hz, 2H), 2.82 (br t, J=6.7 Hz, 2H), 2.68 (s, 3H), 1.85 (br t, J=6.7 Hz, 2H), 1.72 (br d, J=13.3 Hz, 2H), 1.66-1.49 (m, 2H), 1.12 (d, J=6.3 Hz, 6H).

Example 104. N-Isobutoxy-6-(8-methyl-7-quinolyl)spiro[chromane-2,4'-piperidine]-1'-carboxamide

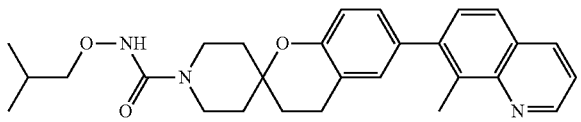

This compound was synthesized from 6-(8-methyl-7-quinolyl)spiro[chromane-2,4'-piperidine]2HCl and O-isobutylhydroxylamine HCl by the procedure for example 102. Analysis: LCMS m/z=460 (M+1); $^1$H NMR (400 MHz, DMSO-d$_6$) δ: 9.65 (s, 1H), 8.96 (dd, J=4.3, 1.8 Hz, 1H), 8.35 (dd, J=8.3, 1.8 Hz, 1H), 7.84 (d, J=8.3 Hz, 1H), 7.54 (dd, J=8.3, 4.3 Hz, 1H), 7.47 (d, J=8.5 Hz, 1H), 7.21-7.14 (m, 2H), 6.95-6.83 (m, 1H), 3.71-3.59 (m, 2H), 3.49 (d, J=6.8 Hz, 2H), 3.23-3.05 (m, 2H), 2.81 (br t, J=6.7 Hz, 2H), 2.68 (s, 3H), 1.95-1.81 (m, 3H), 1.72 (br d, J=13.8 Hz, 2H), 1.64-1.51 (m, 2H), 0.90 (d, J=6.8 Hz, 6H).

Example 105. 6-(8-methyl-7-quinolyl)spiro[chromane-2,4'-piperidine]-1'-carbohydroxamic acid

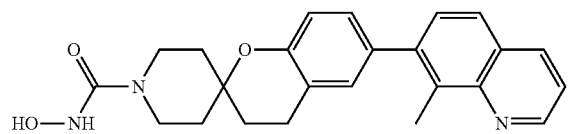

This compound was synthesized from 6-(8-methyl-7-quinolyl)spiro[chromane-2,4'-piperidine]2HCl and hydroxylamine HCl by the procedure for example 102. Analysis: LCMS m/z=404 (M+1); $^1$H NMR (400 MHz, DMSO-d$_6$) δ: 9.08 (s, 1H), 8.96 (dd, J=4.3, 1.8 Hz, 1H), 8.36 (dd, J=8.2, 1.9 Hz, 1H), 8.11-7.93 (m, 1H), 7.84 (d, J=8.3 Hz, 1H), 7.54 (dd, J=8.2, 4.1 Hz, 1H), 7.47 (d, J=8.3 Hz, 1H), 7.22-7.09 (m, 2H), 6.97-6.83 (m, 1H), 3.74-3.60 (m, 2H), 3.24-3.09 (m, 2H), 2.82 (br t, J=6.7 Hz, 2H), 2.68 (s, 3H), 1.84 (t, J=6.8 Hz, 2H), 1.72 (br d, J=13.6 Hz, 2H), 1.63-1.48 (m, 2H).

Example 106. 6-(8-Methyl-7-quinolyl)spiro[chromane-2,4'-piperidine]-1'-carboxamide

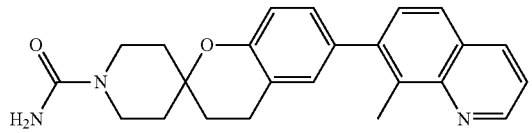

This compound was synthesized from 6-(8-methyl-7-quinolyl)spiro[chromane-2,4'-piperidine]2HCl and trimethylsilyl isocyanate by the procedure for example 101. Analysis: LCMS m/z=388 (M+1); $^1$H NMR (400 MHz, DMSO-d$_6$) δ: 8.96 (dd, J=4.1, 1.9 Hz, 1H), 8.35 (dd, J=8.3, 1.8 Hz, 1H), 7.84 (d, J=8.3 Hz, 1H), 7.54 (dd, J=8.3, 4.3 Hz, 1H), 7.47 (d, J=8.3 Hz, 1H), 7.23-7.08 (m, 2H), 6.99-6.84 (m, 1H), 5.96 (s, 2H), 3.70 (br d, J=13.3 Hz, 2H), 3.26-3.10 (m, 2H), 2.82 (br t, J=6.7 Hz, 2H), 2.69 (s, 3H), 1.85 (t, J=6.7 Hz, 2H), 1.77-1.65 (m, 2H), 1.61-1.47 (m, 2H)

Example 107. N-Ethoxy-6-(5-methylimidazo[1,2-a]pyridin-6-yl)spiro[chromane-2,4'-piperidine]-1'-carboxamide

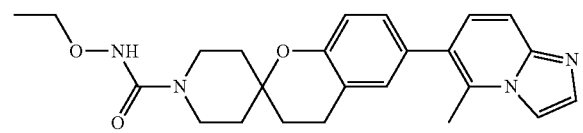

Step 1. tert-Butyl 6-(5-methylimidazo[1,2-a]pyridin-6-yl)spiro[chromane-2,4'-piperidine]-1'-carboxylate was synthesized from tert-butyl 6-(4,4,5,5-tetramethyl-1,3,2-dioxaborolan-2-yl)spiro[chromane-2,4'-piperidine]-1'-carboxylate and 6-bromo-5-methylimidazo[1,2-a]pyridine by the procedure for example 96, step 1. Analysis: LCMS m/z=434 (M+1); ¹H NMR (400 MHz, DMSO-$d_6$) δ: 7.88 (s, 1H), 7.67 (d, J=1.0 Hz, 1H), 7.51 (d, J=9.3 Hz, 1H), 7.19 (d, J=9.3 Hz, 1H), 7.16-7.08 (m, 2H), 6.89 (d, J=8.3 Hz, 1H), 3.72 (br d, J=12.5 Hz, 2H), 3.27-3.10 (m, 2H), 2.80 (br t, J=6.7 Hz, 2H), 2.54 (s, 3H), 1.84 (t, J=6.8 Hz, 2H), 1.73 (br d, J=13.3 Hz, 2H), 1.64-1.50 (m, 2H), 1.42 (s, 9H)

Step 2. 6-(5-Methylimidazo[1,2-a]pyridin-6-yl)spiro[chromane-2,4'-piperidine] 2HCl was synthesized from tert-butyl 6-(5-methylimidazo[1,2-a]pyridin-6-yl)spiro[chromane-2,4'-piperidine]-1'-carboxylate using the procedure for example 96 step. ¹H NMR (400 MHz, DMSO-$d_6$) δ 9.85-9.51 (m, 2H), 8.53-8.24 (m, 2H), 8.04-7.81 (m, 2H), 7.73-7.48 (m, 1H), 7.28-7.14 (m, 2H), 7.00 (d, J=8.3 Hz, 1H), 4.33 (br d, J=8.5 Hz, 2H), 3.56 (s, 5H), 3.30-3.00 (m, 4H), 2.96-2.80 (m, 2H), 2.74 (s, 3H), 2.12-1.80 (m, 6H).

Step 3. N-Ethoxy-6-(5-methylimidazo[1,2-a]pyridin-6-yl)spiro[chromane-2,4'-piperidine]-1'-carboxamide. To a solution of CDI (0.060 g, 0.37 mmol) in DCM (2 mL) and THF (0.50 mL) was added DIPEA (0.086 mL, 0.49 mmol) at RT under nitrogen, followed by ethoxyamine HCl (2.0 eq., 0.49 mmol). After 2 h, DIPEA (84 µL) and 6-(5-methylimidazo[1,2-a]pyridin-6-yl)spiro[chromane-2,4'-piperidine] 2HCl (0.10 g, 0.25 mmol) was added and stirred overnight. The mixture was diluted with DCM and washed with water and brine, separated, dried and concentrated. The product was purified by GILSON (Gemini-NX-5u, C18 110A 150× 30 mm 5 micron column), (10-50% ACN/$H_2O$ with 0.1% TFA) and the fractions combined and concentrated. The product was freebased in DCM using a strong cation exchange column, concentrated and dried under vacuum at 40° C. to yield N-ethoxy-6-(5-methylimidazo[1,2-a]pyridin-6-yl)spiro[chromane-2,4'-piperidine]-1'-carboxamide (0.054 g, 52%). Analysis: LCMS m/z=421 (M+1); ¹H NMR (400 MHz, DMSO-$d_6$) δ: 9.64 (s, 1H), 7.88 (d, J=0.8 Hz, 1H), 7.67 (d, J=1.3 Hz, 1H), 7.51 (d, J=9.3 Hz, 1H), 7.19 (d, J=9.3 Hz, 1H), 7.15-7.07 (m, 2H), 6.89 (d, J=8.5 Hz, 1H), 3.75 (q, J=7.1 Hz, 2H), 3.69-3.59 (m, 2H), 3.22-3.07 (m, 2H), 2.80 (br t, J=6.8 Hz, 2H), 2.55 (s, 3H), 1.83 (t, J=6.7 Hz, 2H), 1.77-1.65 (m, 2H), 1.63-1.49 (m, 2H), 1.13 (t, J=6.9 Hz, 3H).

Example 108. N-Isopropoxy-6-(5-methylimidazo[1,2-a]pyridin-6-yl)spiro[chromane-2,4'-piperidine]-1'-carboxamide

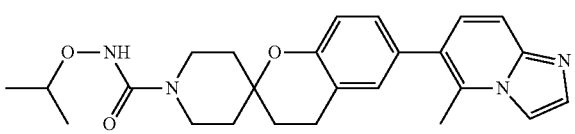 [SMILES: Cc1c(-c2ccc3c(c2)CCC2(CCN(C(=O)NOC(C)C)CC2)O3)ccc2nccn12]

This compound was synthesized from 6-(5-methylimidazo[1,2-a]pyridin-6-yl)spiro[chromane-2,4'-piperidine] 2HCl and 2-(ammoniooxy)propane HCl by the procedure for example 107. Analysis: LCMS m/z=435 (M+1); ¹H NMR (400 MHz, DMSO-$d_6$) δ: 9.49 (s, 1H), 7.88 (d, J=0.8 Hz, 1H), 7.67 (d, J=1.3 Hz, 1H), 7.51 (d, J=9.3 Hz, 1H), 7.19 (d, J=9.3 Hz, 1H), 7.15-7.09 (m, 2H), 6.89 (d, J=7.8 Hz, 1H), 3.87 (quin, J=6.2 Hz, 1H), 3.72-3.60 (m, 2H), 3.22-3.09 (m, 2H), 2.80 (br t, J=6.7 Hz, 2H), 2.55 (s, 3H), 1.83 (t, J=6.8 Hz, 2H), 1.76-1.66 (m, 2H), 1.62-1.50 (m, 2H), 1.12 (d, J=6.3 Hz, 6H).

Example 109. 6-(5-Methylimidazo[1,2-a]pyridin-6-yl)spiro[chromane-2,4'-piperidine]-1'-carboxamide

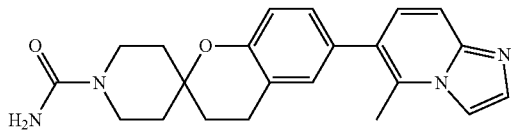 [SMILES: Cc1c(-c2ccc3c(c2)CCC2(CCN(C(N)=O)CC2)O3)ccc2nccn12]

This compound was synthesized from 6-(5-methylimidazo[1,2-a]pyridin-6-yl)spiro[chromane-2,4'-piperidine] dihydrochloride and trimethylsilyl isocyanate using the procedure for example 107. Analysis: LCMS m/z=377 (M+1); ¹H NMR (400 MHz, DMSO-$d_6$) δ: 7.88 (s, 1H), 7.67 (d, J=1.3 Hz, 1H), 7.51 (d, J=9.0 Hz, 1H), 7.20 (d, J=9.0 Hz, 1H), 7.16-7.04 (m, 2H), 6.89 (d, J=8.3 Hz, 1H), 5.96 (s, 2H), 3.69 (br d, J=13.3 Hz, 2H), 3.15 (br t, J=10.8 Hz, 2H), 2.80 (br t, J=6.7 Hz, 2H), 2.55 (s, 3H), 1.83 (br t, J=6.8 Hz, 2H), 1.73-1.64 (m, 2H), 1.60-1.44 (m, 2H).

Example 110. N-Ethyl-6-(5-methylimidazo[1,2-a]pyridin-6-yl)spiro[chromane-2,4'-piperidine]-1'-carboxamide

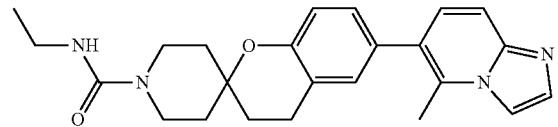

This compound was synthesized from 6-(5-methylimidazo[1,2-a]pyridin-6-yl)spiro[chromane-2,4'-piperidine] 2HCl and ethyl isocyanate using the procedure for example 107. Analysis: LCMS m/z=405 (M+1); ¹H NMR (400 MHz, DMSO-$d_6$) δ: 7.92-7.83 (m, 1H), 7.67 (d, J=1.3 Hz, 1H), 7.51 (d, J=9.3 Hz, 1H), 7.20 (d, J=9.3 Hz, 1H), 7.16-7.09 (m, 2H), 6.88 (d, J=8.5 Hz, 1H), 6.50 (t, J=5.4 Hz, 1H), 3.76-3.64 (m, 2H), 3.23-3.10 (m, 2H), 3.09-2.99 (m, 2H), 2.80 (t, J=6.7 Hz, 2H), 2.55 (s, 3H), 1.83 (t, J=6.8 Hz, 2H), 1.69 (br d, J=13.6 Hz, 2H), 1.62-1.49 (m, 2H), 1.02 (t, J=7.2 Hz, 3H).

Example 111. N-Isopropyl-6-(5-methylimidazo[1,2-a]pyridin-6-yl)spiro[chromane-2,4'-piperidine]-1'-carboxamide

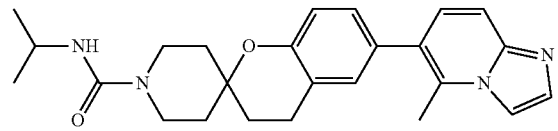 [SMILES: Cc1c(-c2ccc3c(c2)CCC2(CCN(C(=O)NC(C)C)CC2)O3)ccc2nccn12]

This compound was synthesized from 6-(5-methylimidazo[1,2-a]pyridin-6-yl)spiro[chromane-2,4'-piperidine] 2HCl and isopropyl isocyanate Analysis: LCMS m/z=419 (M+1); ¹H NMR (400 MHz, DMSO-$d_6$) δ: 7.89 (d, J=0.8

Hz, 1H), 7.67 (d, J=1.3 Hz, 1H), 7.51 (d, J=9.3 Hz, 1H), 7.20 (d, J=9.3 Hz, 1H), 7.16-7.10 (m, 2H), 6.88 (d, J=8.3 Hz, 1H), 6.19 (d, J=7.8 Hz, 1H), 3.85-3.65 (m, 3H), 3.14 (br t, J=10.9 Hz, 2H), 2.80 (br t, J=6.4 Hz, 2H), 2.55 (s, 3H), 1.83 (br t, J=6.7 Hz, 2H), 1.69 (br d, J=13.3 Hz, 2H), 1.61-1.47 (m, 2H), 1.06 (d, J=6.5 Hz, 6H).

Example 112. N-Ethyl-6-(7-methylpyrazolo[1,5-a]pyridin-6-yl)spiro[chromane-2,4'-piperidine]-1'-carboxamide

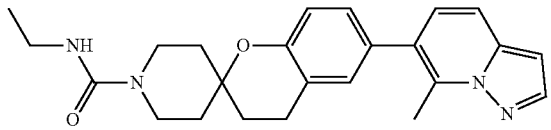

This compound was synthesized using tert-butyl 6-(4,4,5,5-tetramethyl-1,3,2-dioxaborolan-2-yl)spiro[chromane-2,4'-piperidine]-1'-carboxylate and 6-bromo-7-methyl-pyrazolo[1,5-a]pyridine using procedures previously described for example 96.

Step 1. tert-butyl 6-(7-methylpyrazolo[1,5-a]pyridin-6-yl) spiro[chromane-2,4'-piperidine]-1'-carboxylate. Analysis: LCMS m/z=434 (M+1), $^1$H NMR (400 MHz, DCCl$_3$) δ: 8.02 (d, J=2.3 Hz, 1H), 7.48 (d, J=8.8 Hz, 1H), 7.14-7.09 (m, 2H), 7.06 (d, J=2.0 Hz, 1H), 6.91 (d, J=8.3 Hz, 1H), 6.58 (d, J=2.5 Hz, 1H), 3.92 (br s, 2H), 3.27 (br s, 2H), 2.84 (t, J=6.8 Hz, 2H), 2.76 (s, 3H), 1.86 (t, J=6.8 Hz, 4H), 1.66-1.52 (m, 2H), 1.48 (s, 9H) Step 2. 6-(7-methylpyrazolo[1,5-a]pyridin-6-yl)spiro[chromane-2,4'-piperidine] 2HCl. Analysis: LCMS m/z=334 (M+1).

Step 3. N-ethyl-6-(7-methylpyrazolo[1,5-a]pyridin-6-yl) spiro[chromane-2,4'-piperidine]-1'-carboxamide. This compound was synthesized from 6-(7-methylpyrazolo[1,5-a]pyridin-6-yl)spiro[chromane-2,4'-piperidine] 2HCl and ethyl isocyanate. Analysis: LCMS m/z=405 (M+1); $^1$H NMR (400 MHz, DMSO-d$_6$) δ: 8.05 (d, J=2.3 Hz, 1H), 7.64 (d, J=9.0 Hz, 1H), 7.16 (t, J=4.5 Hz, 1H), 7.17-7.14 (m, J=2.5 Hz, 2H), 6.89 (d, J=8.0 Hz, 1H), 6.68 (d, J=2.3 Hz, 1H), 6.49 (t, J=5.4 Hz, 1H), 3.77-3.63 (m, 2H), 3.19-3.11 (m, 2H), 3.10-3.00 (m, 2H), 2.80 (br t, J=6.7 Hz, 2H), 2.66 (s, 3H), 1.83 (t, J=6.7 Hz, 2H), 1.74-1.62 (m, 2H), 1.61-1.42 (m, 2H), 1.02 (t, J=7.2 Hz, 3H).

Example 113. N-Isopropyl-6-(7-methylpyrazolo[1,5-a]pyridin-6-yl)spiro[chromane-2,4'-piperidine]-1'-carboxamide

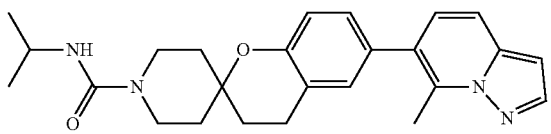 [SMILES: Cc1c(-c2ccc3c(c2)CCC2(CCN(C(=O)NC(C)C)CC2)O3)ccc2ccnn12]

This compound was synthesized from 6-(7-methylpyrazolo[1,5-a]pyridin-6-yl)spiro[chromane-2,4'-piperidine] 2HCl and isopropyl isocyanate. Analysis: LCMS m/z=419 (M+1); $^1$H NMR (400 MHz, DMSO-d$_6$) δ: 8.05 (d, J=2.3 Hz, 1H), 7.64 (d, J=8.8 Hz, 1H), 7.17 (t, J=4.5 Hz, 2H), 7.14 (br d, J=2.3 Hz, 1H), 6.89 (d, J=8.5 Hz, 1H), 6.68 (d, J=2.3 Hz, 1H), 6.18 (d, J=7.8 Hz, 1H), 3.82-3.73 (m, 1H), 3.74-3.67 (m, 2H), 3.20-3.05 (m, 2H), 2.80 (br t, J=6.8 Hz, 2H), 2.66 (s, 3H), 1.83 (t, J=6.8 Hz, 2H), 1.69 (br d, J=13.8 Hz, 2H), 1.61-1.44 (m, 2H), 1.06 (d, J=6.5 Hz, 6H).

Example 114. 6-(7-Methylpyrazolo[1,5-a]pyridin-6-yl)spiro[chromane-2,4'-piperidine]-1'-carboxamide

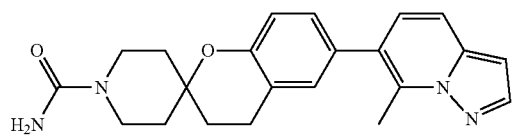

This compound was synthesized from 6-(7-methylpyrazolo[1,5-a]pyridin-6-yl)spiro[chromane-2,4'-piperidine] 2HCl and trimethylsilyl isocyanate Analysis: LCMS m/z=377 (M+1); $^1$H NMR (400 MHz, DMSO-d$_6$) δ: 8.05 (d, J=2.3 Hz, 1H), 7.64 (d, J=9.0 Hz, 1H), 7.17 (t, J=4.5 Hz, 2H), 7.17-7.13 (m, 1H), 6.89 (d, J=8.3 Hz, 1H), 6.68 (d, J=2.3 Hz, 1H), 5.96 (s, 2H), 3.78-3.62 (m, 2H), 3.22-3.10 (m, 2H), 2.80 (t, J=6.5 Hz, 2H), 2.66 (s, 3H), 1.84 (t, J=6.8 Hz, 2H), 1.75-1.62 (m, 2H), 1.62-1.48 (m, 2H).

Example 115. N-Ethoxy-6-(7-methylpyrazolo[1,5-a]pyridin-6-yl)spiro[chromane-2,4'-piperidine]-1'-carboxamide

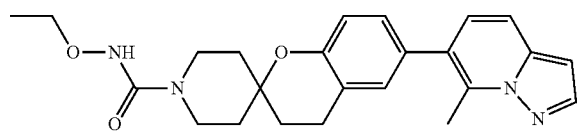 [SMILES: CCONC(=O)N1CCC2(CCc3cc(-c4ccc5ccnn5c4C)ccc3O2)CC1]

This compound was synthesized from 6-(7-methylpyrazolo[1,5-a]pyridin-6-yl)spiro[chromane-2,4'-piperidine] 2HCl (0.09 g, 0.2 mmol) using the procedure for example 107 to give a white solid (0.038 g, 40%). Analysis LCMS m/z=421 (M+1); $^1$H NMR (400 MHz, DMSO-d$_6$) δ: 9.64 (s, 1H), 8.05 (d, J=2.3 Hz, 1H), 7.64 (d, J=8.8 Hz, 1H), 7.20-7.06 (m, 3H), 6.89 (d, J=8.0 Hz, 1H), 6.68 (d, J=2.3 Hz, 1H), 3.75 (q, J=7.0 Hz, 2H), 3.70-3.58 (m, 2H), 3.21-3.07 (m, 2H), 2.80 (br t, J=6.7 Hz, 2H), 2.66 (s, 3H), 1.83 (t, J=6.8 Hz, 2H), 1.76-1.67 (m, 2H), 1.63-1.49 (m, 2H), 1.13 (t, J=7.0 Hz, 3H).

Example 116. N-Isopropoxy-6-(7-methylpyrazolo[1,5-a]pyridin-6-yl)spiro[chromane-2,4'-piperidine]-1'-carboxamide

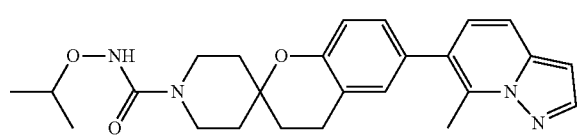

This compound was synthesized from 6-(7-methylpyrazolo[1,5-a]pyridin-6-yl)spiro[chromane-2,4'-piperidine] 2HCl (0.09 g, 0.2 mmol) and O-isopropylhydroxylamine HCl using the procedure for example 107. Analysis LCMS m/z=435 (M+1); $^1$H NMR (400 MHz, DMSO-d$_6$) δ: 9.48 (s, 1H), 8.05-7.95 (m, 1H), 7.64 (d, J=9.0 Hz, 1H), 7.21-7.10 (m, 3H), 6.89 (d, J=8.3 Hz, 1H), 6.68 (d, J=2.3 Hz, 1H), 3.87

(quin, J=6.1 Hz, 1H), 3.65 (br d, J=13.6 Hz, 2H), 3.22-3.06 (m, 2H), 2.80 (br t, J=6.5 Hz, 2H), 2.66 (s, 3H), 1.83 (t, J=6.8.

Example 117. N-Ethyl-6-(8-methyl-7-quinolyl)spiro[4H-1,3-benzodioxine-2,4'-piperidine]-1'-carboxamide

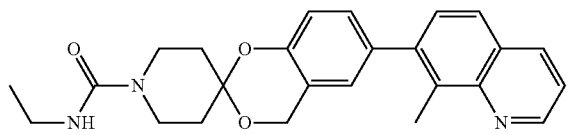 [SMILES: CCNC(=O)N1CCC2(CC1)OCc1cc(-c3ccc4cccnc4c3C)ccc1O2]

This compound was synthesized from ethyl 6-(4,4,5,5-tetramethyl-1,3,2-dioxaborolan-2-yl)spiro[4H-1,3-benzodioxine-2,4'-piperidine]-1'-carboxylate, 7-bromo-8-methylquinoline and ethyl isocyanate. Analysis: LCMS m/z=418 (M+1); $^1$H NMR (400 MHz, DMSO-$d_6$) δ: 8.97 (dd, J=4.0, 1.8 Hz, 1H), 8.36 (dd, J=8.3, 1.8 Hz, 1H), 7.85 (d, J=8.5 Hz, 1H), 7.62-7.51 (m, 1H), 7.47 (d, J=8.5 Hz, 1H), 7.26 (dd, J=8.4, 2.1 Hz, 1H), 7.18 (d, J=2.0 Hz, 1H), 6.97 (d, J=8.3 Hz, 1H), 6.58 (t, J=5.4 Hz, 1H), 4.94 (s, 2H), 3.54-3.36 (m, 4H), 3.06 (dd, J=7.0, 5.5 Hz, 2H), 2.68 (s, 3H), 1.82 (br s, 4H), 1.02 (t, J=7.2 Hz, 3H).

Example 118. 6-(8-Methyl-7-quinolyl)spiro[4H-1,3-benzodioxine-2,4'-piperidine]-1'-carboxamide

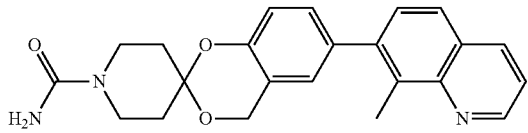

This compound was synthesized from 6-(8-methyl-7-quinolyl)spiro[4H-1,3-benzodioxine-2,4'-piperidine] and trimethylsilyl isocyanate. Analysis: LCMS m/z=390 (M+1); $^1$H NMR (400 MHz, DMSO-$d_6$) δ: 8.97 (dd, J=4.1, 1.9 Hz, 1H), 8.36 (dd, J=8.3, 1.8 Hz, 1H), 7.85 (d, J=8.3 Hz, 1H), 7.55 (dd, J=8.3, 4.3 Hz, 1H), 7.47 (d, J=8.5 Hz, 1H), 7.26 (dd, J=8.3, 2.3 Hz, 1H), 7.18 (d, J=2.0 Hz, 1H), 6.97 (d, J=8.3 Hz, 1H), 6.04 (s, 2H), 4.94 (s, 2H), 3.56-3.36 (m, 4H), 2.68 (s, 3H), 1.82 (br s, 4H).

Example 119. N-Isopropyl-6-(8-methyl-7-quinolyl)spiro[4H-1,3-benzodioxine-2,4'-piperidine]-1'-carboxamide

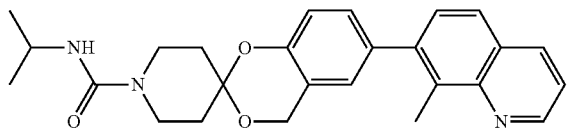

This compound was synthesized from 6-(8-methyl-7-quinolyl)spiro[4H-1,3-benzodioxine-2,4'-piperidine] and 2-isocyanatopropane. Analysis: LCMS m/z=432 (M+1); $^1$H NMR (400 MHz, DMSO-$d_6$) δ: 8.97 (dd, J=4.0, 1.8 Hz, 1H), 8.37 (dd, J=8.3, 1.8 Hz, 1H), 7.85 (d, J=8.3 Hz, 1H), 7.55 (dd, J=8.2, 4.1 Hz, 1H), 7.47 (d, J=8.3 Hz, 1H), 7.26 (dd, J=8.3, 2.3 Hz, 1H), 7.18 (d, J=2.0 Hz, 1H), 6.97 (d, J=8.5 Hz, 1H), 6.29 (d, J=7.5 Hz, 1H), 4.94 (s, 2H), 3.77 (dq, J=13.8, 6.7 Hz, 1H), 3.50-3.37 (m, 4H), 2.68 (s, 3H), 1.91-1.74 (m, 4H), 1.07 (d, J=6.5 Hz, 6H).

Example 120. N-Methoxy-6-(8-methyl-7-quinolyl)spiro[chromane-2,4'-piperidine]-1'-carboxamide

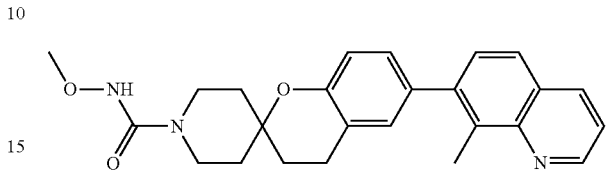

This compound was synthesized from 6-(8-methyl-7-quinolyl)spiro[chromane-2,4'-piperidine]2HCl and O-methylhydroxylamine HCl. Analysis: LCMS m/z=418 (M+1); $^1$H NMR (400 MHz, DMSO-$d_6$) δ: 9.74 (s, 1H), 8.96 (dd, J=4.1, 1.9 Hz, 1H), 8.36 (dd, J=8.2, 1.9 Hz, 1H), 7.84 (d, J=8.3 Hz, 1H), 7.54 (dd, J=8.2, 4.1 Hz, 1H), 7.47 (d, J=8.3 Hz, 1H), 7.21-7.07 (m, 2H), 6.96-6.84 (m, 1H), 3.71-3.59 (m, 2H), 3.55 (s, 3H), 3.23-3.08 (m, 2H), 2.81 (br t, J=6.7 Hz, 2H), 2.68 (s, 3H), 1.85 (t, J=6.8 Hz, 2H), 1.73 (br d, J=13.8 Hz, 2H), 1.65-1.49 (m, 2H).

Example 121. N-Ethoxy-6-(8-methyl-7-quinolyl)spiro[4H-1,3-benzodioxine-2,4'-piperidine]-1'-carboxamide

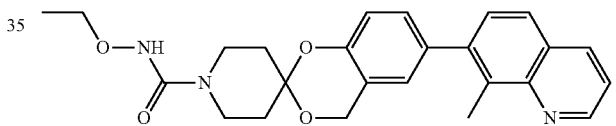

This compound was synthesized from 6-(8-methyl-7-quinolyl)spiro[4H-1,3-benzodioxine-2,4'-piperidine] and ethoxyamine HCl. Analysis: LCMS m/z=434 (M+1); $^1$H NMR (400 MHz, DMSO-$d_6$) δ: 9.73 (s, 1H), 8.97 (dd, J=4.1, 1.9 Hz, 1H), 8.37 (dd, J=8.3, 1.8 Hz, 1H), 7.85 (d, J=8.3 Hz, 1H), 7.59-7.51 (m, 1H), 7.47 (d, J=8.5 Hz, 1H), 7.26 (dd, J=8.3, 2.3 Hz, 1H), 7.18 (d, J=2.0 Hz, 1H), 6.97 (d, J=8.5 Hz, 1H), 4.94 (s, 2H), 3.76 (q, J=7.0 Hz, 2H), 3.53-3.33 (m, 4H), 2.68 (s, 3H), 2.00-1.74 (m, 4H), 1.13 (t, J=7.0 Hz, 3H).

Example 122. N-Methoxy-6-(8-methyl-7-quinolyl)spiro[4H-1,3-benzodioxine-2,4'-piperidine]-1'-carboxamide

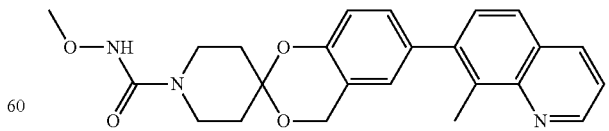

This compound was synthesized from 6-(8-methyl-7-quinolyl)spiro[4H-1,3-benzodioxine-2,4'-piperidine] and O-methylhydroxylamine HCl. Analysis: LCMS m/z=420 (M+1); $^1$H NMR (400 MHz, DMSO-$d_6$) δ: 9.82 (s, 1H), 8.97 (dd, J=4.1, 1.9 Hz, 1H), 8.37 (dd, J=8.3, 1.8 Hz, 1H), 7.85

(d, J=8.3 Hz, 1H), 7.55 (dd, J=8.2, 4.1 Hz, 1H), 7.47 (d, J=8.3 Hz, 1H), 7.26 (dd, J=8.5, 2.3 Hz, 1H), 7.18 (d, J=2.0 Hz, 1H), 6.97 (d, J=8.3 Hz, 1H), 4.94 (s, 2H), 3.55 (s, 3H), 3.49-3.33 (m, 4H), 2.68 (s, 3H), 1.95-1.78 (m, 4H).

Example 123. N-Isopropoxy-6-(8-methyl-7-quinolyl)spiro[4H-1,3-benzodioxine-2,4'-piperidine]-1'-carboxamide

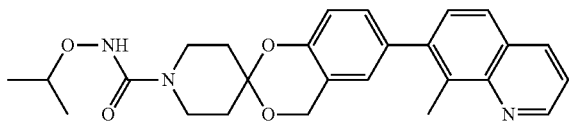

This compound was synthesized from 6-(8-methyl-7-quinolyl)spiro[4H-1,3-benzodioxine-2,4'-piperidine] and O-isopropylhydroxylamine HCl. Analysis: LCMS m/z=448 (M+1); $^1$H NMR (400 MHz, DMSO-$d_6$) δ: 9.58 (s, 1H), 8.97 (dd, J=4.1, 1.9 Hz, 1H), 8.37 (dd, J=8.3, 1.8 Hz, 1H), 7.85 (d, J=8.3 Hz, 1H), 7.55 (dd, J=8.2, 4.0 Hz, 1H), 7.47 (d, J=8.5 Hz, 1H), 7.26 (dd, J=8.4, 2.1 Hz, 1H), 7.18 (d, J=2.0 Hz, 1H), 6.97 (d, J=8.5 Hz, 1H), 4.99-4.85 (m, 2H), 3.88 (quin, J=6.1 Hz, 1H), 3.52-3.22 (m, 4H), 2.68 (s, 3H), 1.94-1.72 (m, 4H), 1.13 (d, J=6.3 Hz, 6H).

Example 124. N-Methoxy-6-(7-methylpyrazolo[1,5-a]pyridin-6-yl)spiro[chromane-2,4'-piperidine]-1'-carboxamide

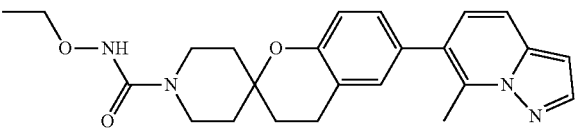 [SMILES: CCONC(=O)N1CCC2(CCc3cc(-c4ccc5ccnn5c4C)ccc3O2)CC1]

This compound was synthesized from 6-(7-methylpyrazolo[1,5-a]pyridin-6-yl)spiro[chromane-2,4'-piperidine] 2HCl, triphosgene and o-methylhydroxylamine HCl, by the procedure described for example 101. Analysis: LCMS m/z=407 (M+1); $^1$H NMR (400 MHz, DMSO-$d_6$) δ 9.73 (s, 1H), 8.05 (d, J=2.3 Hz, 1H), 7.64 (d, J=8.8 Hz, 1H), 7.22-7.07 (m, 3H), 6.89 (d, J=8.3 Hz, 1H), 6.68 (d, J=2.3 Hz, 1H), 3.63 (br d, J=13.1 Hz, 2H), 3.54 (s, 3H), 3.14 (brt, J=10.9 Hz, 2H), 2.80 (br t, J=6.7 Hz, 2H), 2.66 (s, 3H), 1.84 (t, J=6.8 Hz, 2H), 1.71 (br d, J=13.8 Hz, 2H), 1.62-1.50 (m, 2H)

Example 125. 6-(7-Methylpyrazolo[1,5-a]pyridin-6-yl)spiro[chromane-2,4'-piperidine]-1'-carbohydroxamic acid

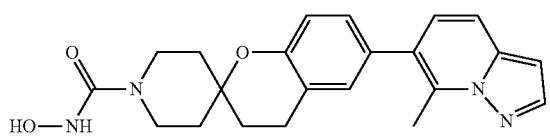 [SMILES: Cc1c(-c2ccc3c(c2)CCC2(CCN(C(=O)NO)CC2)O3)ccc2ccnn12]

This compound was synthesized from 6-(7-methylpyrazolo[1,5-a]pyridin-6-yl)spiro[chromane-2,4'-piperidine] 2HCl, triphosgene and hydroxylamine HCl. Analysis: LCMS m/z=393 (M+1); $^1$H NMR (400 MHz, DMSO-$d_6$) δ: 9.07 (s, 1H), 8.05 (d, J=2.3 Hz, 1H), 7.98 (br s, 1H), 7.64 (d, J=8.8 Hz, 1H), 7.21-7.10 (m, 3H), 6.89 (d, J=8.3 Hz, 1H), 6.68 (d, J=2.3 Hz, 1H), 3.65 (br d, J=13.3 Hz, 2H), 3.23-3.09 (m, 2H), 2.80 (br t, J=6.5 Hz, 2H), 2.66 (s, 3H), 1.83 (t, J=6.8 Hz, 2H), 1.71 (br d, J=13.6 Hz, 2H), 1.62-1.49 (m, 2H).

Example 126. N-Ethyl-6-(7-methylpyrazolo[1,5-a]pyridin-6-yl)spiro[4H-1,3-benzodioxine-2,4'-piperidine]-1'-carboxamide

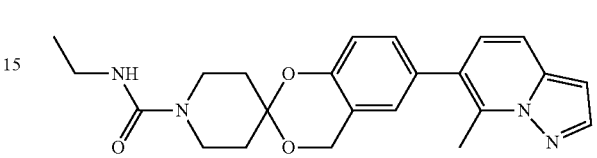

This compound was synthesized from 6-(7-methylpyrazolo[1,5-a]pyridin-6-yl)spiro[4H-1,3-benzodioxine-2,4'-piperidine] and ethyl isocyanate. Analysis: LCMS m/z=407 (M+1); $^1$H NMR (400 MHz, DMSO-$d_6$) δ: 8.06 (d, J=2.3 Hz, 1H), 7.66 (d, J=8.8 Hz, 1H), 7.26 (dd, J=8.3, 2.3 Hz, 1H), 7.19-7.13 (m, 2H), 6.96 (d, J=8.5 Hz, 1H), 6.69 (d, J=2.3 Hz, 1H), 6.58 (t, J=5.3 Hz, 1H), 4.93 (s, 2H), 3.52-3.34 (m, 4H), 3.06 (dd, J=7.2, 5.4 Hz, 2H), 2.66 (s, 3H), 1.81 (br s, 4H), 1.02 (t, J=7.2 Hz, 3H).

Example 127. 6-(7-Methylpyrazolo[1,5-a]pyridin-6-yl)spiro[4H-1,3-benzodioxine-2,4'-piperidine]-1'-carboxamide

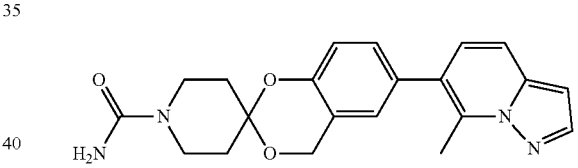

This compound was synthesized using 6-(7-methylpyrazolo[1,5-a]pyridin-6-yl)spiro[4H-1,3-benzodioxine-2,4'-piperidine] and trimethylsilyl isocyanate. Analysis: LCMS m/z=379 (M+1); $^1$H NMR (400 MHz, DMSO-$d_6$) δ: 8.06 (d, J=2.3 Hz, 1H), 7.66 (d, J=8.8 Hz, 1H), 7.26 (dd, J=8.3, 2.3 Hz, 1H), 7.19-7.12 (m, 2H), 6.96 (d, J=8.3 Hz, 1H), 6.69 (d, J=2.3 Hz, 1H), 6.04 (s, 2H), 4.93 (s, 2H), 3.42 (dt, J=10.2, 5.2 Hz, 4H), 2.66 (s, 3H), 1.81 (br s, 4H).

Example 128. N-Methoxy-6-(7-methylpyrazolo[1,5-a]pyridin-6-yl)spiro[4H-1,3-benzodioxine-2,4'-piperidine]-1'-carboxamide

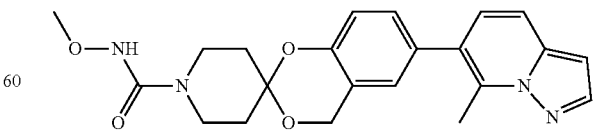

This compound was synthesized using 6-(7-methylpyrazolo[1,5-a]pyridin-6-yl)spiro[4H-1,3-benzodioxine-2,4'-piperidine] and O-methylhydroxylamine HCl. Analysis: LCMS m/z=409 (M+1); $^1$H NMR (400 MHz, DMSO-$d_6$) δ:

9.81 (s, 1H), 8.06 (d, J=2.3 Hz, 1H), 7.66 (d, J=8.8 Hz, 1H), 7.26 (dd, J=8.3, 2.3 Hz, 1H), 7.19-7.17 (m, 1H), 7.17 (d, J=8.8 Hz, 1H), 6.96 (d, J=8.3 Hz, 1H), 6.69 (d, J=2.3 Hz, 1H), 4.93 (s, 2H), 3.54 (s, 3H), 3.48-3.32 (m, 4H), 2.66 (s, 3H), 1.95-1.76 (m, 4H).

Example 129. N-Ethoxy-6-(7-methylpyrazolo[1,5-a]pyridin-6-yl)spiro[4H-1,3-benzodioxine-2,4'-piperidine]-1'-carboxamide

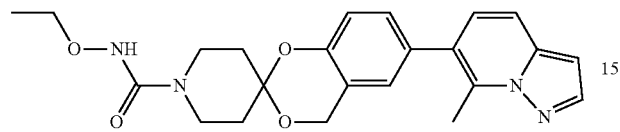

This compound was synthesized using 6-(7-methylpyrazolo[1,5-a]pyridin-6-yl)spiro[4H-1,3-benzodioxine-2,4'-piperidine] and O-ethylhydroxylamine HCl. Analysis: LCMS m/z=423 (M+1); $^1$H NMR (400 MHz, DMSO-d$_6$) δ: 9.72 (s, 1H), 8.06 (d, J=2.5 Hz, 1H), 7.66 (d, J=8.8 Hz, 1H), 7.26 (dd, J=8.3, 2.3 Hz, 1H), 7.20-7.11 (m, 2H), 6.96 (d, J=8.5 Hz, 1H), 6.69 (d, J=2.3 Hz, 1H), 4.93 (s, 2H), 3.75 (q, J=7.0 Hz, 2H), 3.50-3.22 (m, 4H), 2.66 (s, 3H), 1.92-1.75 (m, 4H), 1.13 (t, J=7.2 Hz, 3H).

Example 130. N-Isopropoxy-6-(7-methylpyrazolo[1,5-a]pyridin-6-yl)spiro[4H-1,3-benzodioxine-2,4'-piperidine]-1'-carboxamide

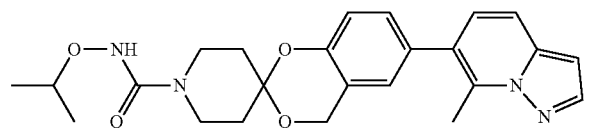

This compound was synthesized using 6-(7-methylpyrazolo[1,5-a]pyridin-6-yl)spiro[4H-1,3-benzodioxine-2,4'-piperidine] O-isopropylhydroxylamine HCl. Analysis: LCMS m/z=437 (M+1); $^1$H NMR (400 MHz, DMSO-d$_6$) δ: 9.57 (s, 1H), 8.06 (d, J=2.3 Hz, 1H), 7.66 (d, J=8.8 Hz, 1H), 7.26 (dd, J=8.3, 2.3 Hz, 1H), 7.19-7.09 (m, 2H), 6.96 (d, J=8.3 Hz, 1H), 6.69 (d, J=2.3 Hz, 1H), 4.93 (s, 2H), 3.88 (quin, J=6.1 Hz, 1H), 3.50-3.23 (m, 4H), 2.66 (s, 3H), 1.93-1.71 (m, 4H), 1.12 (d, J=6.0 Hz, 6H).

Example 131. 6-(8-Chloro-7-quinolyl)spiro[4H-1,3-benzodioxine-2,4'-piperidine]-1'-carboxamide

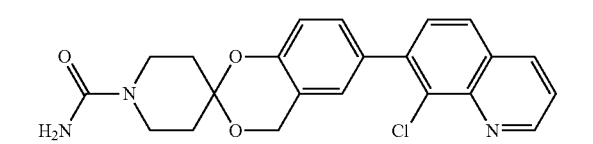 [SMILES: NC(=O)N1CCC2(CC1)OCc1cc(-c3ccc4cccnc4c3Cl)ccc1O2]

This compound was synthesized using 6-(8-chloro-7-quinolyl)spiro[4H-1,3-benzodioxine-2,4'-piperidine] and trimethylsilyl isocyanate. Analysis: LCMS m/z=410 (M+1); $^1$H NMR (400 MHz, DMSO-d$_6$) δ: 9.06 (dd, J=4.3, 1.8 Hz, 1H), 8.49 (dd, J=8.4, 1.6 Hz, 1H), 8.03 (d, J=8.8 Hz, 1H), 7.67 (dd, J=8.3, 4.3 Hz, 1H), 7.62 (d, J=8.5 Hz, 1H), 7.40 (dd, J=8.3, 2.3 Hz, 1H), 7.31 (d, J=2.3 Hz, 1H), 7.00 (d, J=8.5 Hz, 1H), 6.05 (s, 2H), 4.95 (s, 2H), 3.56-3.37 (m, 4H), 1.83 (br s, 4H).

Example 132. 6-(4-Methyl-3-quinolyl)spiro[4H-1,3-benzodioxine-2,4'-piperidine]-1'-carboxamide This compound was synthesized using 6-(4-methyl-3-quinolyl)spiro[4H-1,3-benzodioxine-2,4'-piperidine] and trimethylsilyl isocyanate. Analysis: LCMS m/z=390 (M+1); $^1$H NMR (400 MHz, DMSO-d$_6$) δ: 8.73 (s, 1H), 8.19 (dd, J=8.5, 0.8 Hz, 1H), 8.04 (dd, J=8.3, 1.0 Hz, 1H), 7.77 (ddd, J=8.3, 6.9, 1.4 Hz, 1H), 7.68 (ddd, J=8.4, 6.8, 1.4 Hz, 1H), 7.29 (dd, J=8.3, 2.3 Hz, 1H), 7.22 (d, J=2.3 Hz, 1H), 7.01 (d, J=8.3 Hz, 1H), 6.05 (s, 2H), 4.95 (s, 2H), 3.54-3.36 (m, 4H), 2.63 (s, 3H), 1.83 (br s, 4H).

Example 133. N-Methoxy-6-(4-methyl-3-quinolyl)spiro[4H-1,3-benzodioxine-2,4'-piperidine]-1'-carboxamide A suspension of N,N'-disuccinimidyl carbonate (85 mass %), o-methylhydroxylamine HCl (0.03198 g, 0.3753 mmol), and DIPEA (0.06790 g, 0.5254 mmol) in ACN (1 ml) was stirred at RT for 0.5 h. 6-(4-Methyl-3-quinolyl)spiro[4H-1,3-benzodioxine-2,4'-piperidine] (52 mg, 0.1501 mmol), and DIPEA (0.06790 g, 0.5254 mmol) were added and stirred 0.5 h. The reaction was then partitioned between EtOAc and water, separated and the organic layer back extracted with EtOAc. The combined organic layers were washed with brine, dried (MgSO$_4$), filtered and concentrated. The product was purified by Gilson (5-45% ACN in water with 0.1% TFA). The pure fractions were concentrated, freebased, and dried at 50° C. overnight to give a solid. Analysis: LCMS m/z=420 (M+1); $^1$H NMR (400 MHz, DMSO-d$_6$) δ: 9.82 (s, 1H), 8.72 (s, 1H), 8.19 (dd, J=8.4, 0.9 Hz, 1H), 8.04 (dd, J=8.5, 1.0 Hz, 1H), 7.77 (ddd, J=8.3, 6.9, 1.4 Hz, 1H), 7.72-7.64 (m, 1H), 7.29 (dd, J=8.3, 2.3 Hz, 1H), 7.22 (d, J=2.0 Hz, 1H), 7.01 (d, J=8.3 Hz, 1H), 4.95 (s, 2H), 3.55 (s, 3H), 3.49-3.34 (m, 4H), 2.63 (s, 3H), 1.92-1.78 (m, 4H).

Example 134. 6-(8-Chloro-7-quinolyl)-N-methoxy-spiro[4H-1,3-benzodioxine-2,4'-piperidine]-1'-carboxamide

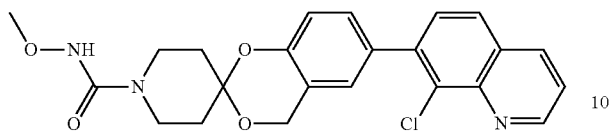

This compound was synthesized using 6-(8-chloro-7-quinolyl)spiro[4H-1,3-benzodioxine-2,4'-piperidine] and o-methylhydroxylamine HCl. Analysis: LCMS m/z=440 (M+1); $^1$H NMR (400 MHz, DMSO-d$_6$) δ: 9.82 (s, 1H), 9.06 (dd, J=4.3, 1.8 Hz, 1H), 8.50 (dd, J=8.3, 1.5 Hz, 1H), 8.03 (d, J=8.5 Hz, 1H), 7.67 (dd, J=8.3, 4.3 Hz, 1H), 7.62 (d, J=8.5 Hz, 1H), 7.40 (dd, J=8.4, 2.1 Hz, 1H), 7.31 (d, J=2.3 Hz, 1H), 7.00 (d, J=8.5 Hz, 1H), 4.95 (s, 2H), 3.55 (s, 3H), 3.50-3.34 (m, 4H), 1.85 (br d, J=6.3 Hz, 4H).

Example 135. 6-(8-Chloro-7-quinolyl)-N-ethoxy-spiro[4H-1,3-benzodioxine-2,4'-piperidine]-1'-carboxamide

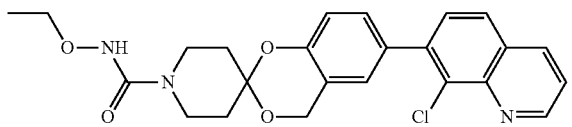

This compound was synthesized using 6-(8-chloro-7-quinolyl)spiro[4H-1,3-benzodioxine-2,4'-piperidine] and ethoxyamine HCl and 6-(8-chloro-7-quinolyl)spiro[4H-1,3-benzodioxine-2,4'-piperidine]. Analysis: LCMS m/z=454 (M+1); $^1$H NMR (400 MHz, DMSO-d$_6$) δ: 9.73 (s, 1H), 9.06 (dd, J=4.3, 1.8 Hz, 1H), 8.49 (dd, J=8.3, 1.8 Hz, 1H), 8.03 (d, J=8.5 Hz, 1H), 7.67 (dd, J=8.3, 4.3 Hz, 1H), 7.62 (d, J=8.5 Hz, 1H), 7.40 (dd, J=8.3, 2.3 Hz, 1H), 7.31 (d, J=2.0 Hz, 1H), 7.00 (d, J=8.5 Hz, 1H), 4.95 (s, 2H), 3.76 (q, J=7.0 Hz, 2H), 3.51-3.34 (m, 4H), 1.94-1.75 (m, 4H), 1.13 (t, J=7.0 Hz, 3H).

Example 136. 6-(8-Chloro-7-quinolyl)spiro[4H-1,3-benzodioxine-2,4'-piperidine]-1'-carbohydroxamic acid

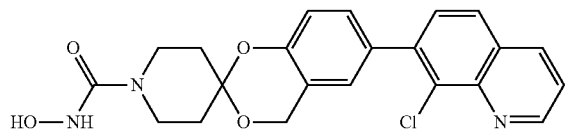 [SMILES: O=C(NO)N1CCC2(CC1)OCc1cc(-c3ccc4cccnc4c3Cl)ccc1O2]

This compound was synthesized using 6-(8-chloro-7-quinolyl)spiro[4H-1,3-benzodioxine-2,4'-piperidine] and O-(tetrahydro-2h-pyran-2-yl)hydroxylamine. 6-(8-Chloro-7-quinolyl)-N-tetrahydropyran-2-yloxy-spiro[4H-1,3-benzodioxine-2,4'-piperidine]-1'-carboxamide (0.125 g, 0.24 mmole) in DCM (5 mL) and TFA (2 mL) was stirred 2 h and concentrated. The product was purified by Gilson chromatography (5-45% ACN in water with 0.1% TFA). The pure fractions were concentrated, freebased and dried at 50° C. under vacuum. Analysis: LCMS m/z=426 (M+1); $^1$H NMR (400 MHz, DMSO-d$_6$) δ: 9.15 (s, 1H), 9.06 (dd, J=4.1, 1.6 Hz, 1H), 8.49 (dd, J=8.3, 1.5 Hz, 1H), 8.09-7.99 (m, J=8.8 Hz, 2H), 7.67 (dd, J=8.3, 4.3 Hz, 1H), 7.62 (d, J=8.5 Hz, 1H), 7.40 (dd, J=8.4, 2.1 Hz, 1H), 7.31 (d, J=2.0 Hz, 1H), 7.00 (d, J=8.5 Hz, 1H), 4.95 (s, 2H), 3.51-3.35 (m, 4H), 1.93-1.80 (m, 4H).

Example 137. Ethyl 6-(8-chloro-7-quinolyl)spiro[4H-1,3-benzodioxine-2,4'-piperidine]-1'-carboxylate

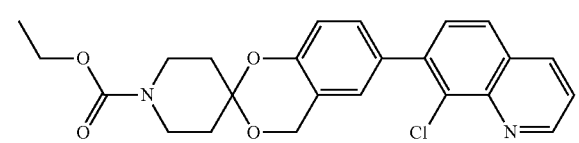

This compound was synthesized using 7-bromo-8-chloroquinoline and ethyl 6-(4,4,5,5-tetramethyl-1,3,2-dioxaborolan-2-yl)spiro[4H-1,3-benzodioxine-2,4'-piperidine]-1'-carboxylate. Analysis: LCMS m/z=439 (M+1); $^1$H NMR (400 MHz, DMSO-d$_6$) δ: 9.06 (dd, J=4.1, 1.6 Hz, 1H), 8.49 (dd, J=8.3, 1.8 Hz, 1H), 8.03 (d, J=8.5 Hz, 1H), 7.67 (dd, J=8.3, 4.3 Hz, 1H), 7.62 (d, J=8.5 Hz, 1H), 7.41 (dd, J=8.3, 2.3 Hz, 1H), 7.31 (d, J=2.0 Hz, 1H), 7.00 (d, J=8.3 Hz, 1H), 4.95 (s, 2H), 4.07 (q, J=7.0 Hz, 2H), 3.64-3.40 (m, 4H), 1.99-1.77 (m, 4H), 1.20 (t, J=7.0 Hz, 3H).

Example 138. Ethyl 6-(4-methyl-3-quinolyl)spiro[4H-1,3-benzodioxine-2,4'-piperidine]-1'-carboxylate

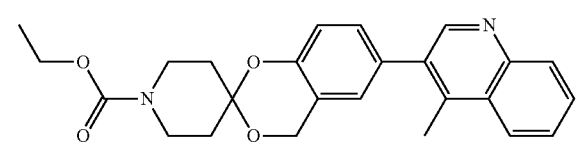 [SMILES: CCOC(=O)N1CCC2(CC1)OCc1cc(-c3cnc4ccccc4c3C)ccc1O2]

This compound was synthesized using 3-bromo-4-methylquinoline and ethyl 6-(4,4,5,5-tetramethyl-1,3,2-dioxaborolan-2-yl)spiro[4H-1,3-benzodioxine-2,4'-piperidine]-1'-carboxylate. Analysis LCMS m/z=419 (M+1); $^1$H NMR (400 MHz, DMSO-d$_6$) δ: 8.72 (s, 1H), 8.19 (dd, J=8.4, 0.9 Hz, 1H), 8.04 (dd, J=8.4, 0.9 Hz, 1H) 7.77 (ddd, J=8.3, 6.9, 1.4 Hz, 1H), 7.72-7.64 (m, 1H), 7.29 (dd, J=8.3, 2.3 Hz, 1H), 7.22 (d, J=2.0 Hz, 1H), 7.01 (d, J=8.3 Hz, 1H), 4.96 (s, 2H), 4.06 (quin, J=7.2 Hz, 2H), 3.64-3.40 (m, 4H), 2.63 (s, 3H), 1.95-1.81 (m, 4H), 1.20 (t, J=7.0 Hz, 3H).

Example 139. N-Ethoxy-6-(4-methyl-3-quinolyl)spiro[4H-1,3-benzodioxine-2,4'-piperidine]-1'-carboxamide

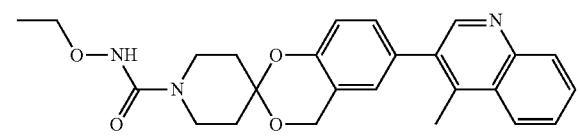

This compound was synthesized using 6-(4-methyl-3-quinolyl)spiro[4H-1,3-benzodioxine-2,4'-piperidine] and ethoxyamine HCl. Analysis: LCMS m/z=434 (M+1); ¹H NMR (400 MHz, DMSO-d₆) δ: 9.73 (s, 1H), 9.78-9.65 (m, 1H), 8.72 (s, 1H), 8.19 (dd, J=8.4, 0.9 Hz, 1H), 8.04 (dd, J=8.3, 1.0 Hz, 1H), 7.82-7.73 (m, 1H), 7.73-7.63 (m, 1H), 7.29 (dd, J=8.3, 2.3 Hz, 1H), 7.22 (d, J=2.0 Hz, 1H), 7.01 (d, J=8.3 Hz, 1H), 4.95 (s, 2H), 3.76 (q, J=7.0 Hz, 2H), 3.54-3.25 (m, 4H), 2.63 (s, 3H), 1.93-1.76 (m, 4H), 1.20-1.09 (m, 3H).

Example 140. 6-(4-Methyl-3-quinolyl)spiro[4H-1,3-benzodioxine-2,4'-piperidine]-1'-carbohydroxamic acid

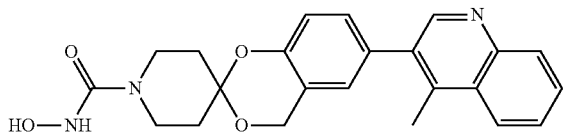 [SMILES: Cc1c(-c2ccc3c(c2)COC2(CCN(C(=O)NO)CC2)O3)cnc2ccccc12]

This compound was synthesized using O 6-(7-methylpyrazolo[1,5-a]pyridin-6-yl)spiro[4H-1,3-benzodioxine-2,4'-piperidine] and -(tetrahydro-2H-pyran-2-yl)hydroxylamine. 6-(4-Methyl-3-quinolyl)-N-tetrahydropyran-2-yloxy-spiro[4H-1,3-benzodioxine-2,4'-piperidine]-1'-carboxamide (0.066 g, 0.13 mmol), and 2 M HCl in dioxane (5 eq.) in ACN (5 mL) was stirred overnight at RT and concentrated. The product was purified by Gilson reverse phase chromatography (5-40% ACN in water with 0.1% TFA). The pure fractions were combined, concentrated, freebased and dried under vacuum at 50° C. to give 6-(4-methyl-3-quinolyl)spiro[4H-1,3-benzodioxine-2,4'-piperidine]-1'-carbohydroxamic acid (55 mg, 31%). Analysis: LCMS m/z=406 (M+1); ¹H NMR (400 MHz, DMSO-d₆) δ: 9.15 (s, 1H), 8.72 (s, 1H), 8.19 (d, J=7.5 Hz, 1H), 8.12-7.96 (m, 2H), 7.77 (ddd, J=8.2, 6.8, 1.5 Hz, 1H), 7.68 (td, J=7.6, 1.4 Hz, 1H), 7.29 (dd, J=8.4, 2.1 Hz, 1H), 7.22 (d, J=2.0 Hz, 1H), 7.01 (d, J=8.3 Hz, 1H), 4.95 (s, 2H), 3.55-3.21 (m, 4H), 2.63 (s, 3H), 1.94-1.76 (m, 4H).

Example 141. 6-(5-Methylimidazo[1,2-a]pyridin-6-yl)spiro[chromane-2,4'-piperidine]-1'-carbohydroxamic acid

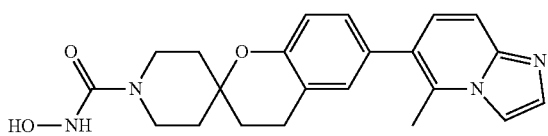 [SMILES: Cc1c(-c2ccc3c(c2)CCC2(CCN(C(=O)NO)CC2)O3)ccc2nccn12]

This compound was synthesized using O-(tetrahydro-2H-pyran-2-yl)hydroxylamine and 6-(5-methylimidazo[1,2-a]pyridin-6-yl)-N-tetrahydropyran-2-yloxy-spiro[chromane-2,4'-piperidine]-1'-carboxamide. 6-(5-Methylimidazo[1,2-a]pyridin-6-yl)-N-tetrahydropyran-2-yloxy-spiro[chromane-2,4'-piperidine]-1'-carboxamide Analysis: LCMS m/z=477 (M+1); ¹H NMR (400 MHz, CDCl₃) δ: 7.94 (d, J=10.0 Hz, 1H), 7.71 (s, 1H), 7.59-7.51 (m, 2H), 7.19 (d, J=9.3 Hz, 1H), 7.10-7.02 (m, 2H), 6.91 (d, J=8.3 Hz, 1H), 5.01-4.88 (m, 1H), 4.08-3.93 (m, 1H), 3.87 (br d, J=11.8 Hz, 2H), 3.68-3.58 (m, 1H), 3.33 (br t, J=12.9 Hz, 2H), 2.89-2.71 (m, 4H), 2.56 (s, 3H), 1.96-1.75 (m, 6H), 1.74-1.49 (m, 6H). 6-(5-Methylimidazo[1,2-a]pyridin-6-yl)spiro[chromane-2,4'-piperidine]-1'-carbohydroxamic acid Analysis: LCMS m/z=393 (M+1); ¹H NMR (400 MHz, DMSO-d₆) δ: 9.06 (s, 1H), 7.97 (s, 1H), 7.88 (s, 1H), 7.67 (d, J=1.3 Hz, 1H), 7.51 (d, J=9.0 Hz, 1H), 7.25-7.09 (m, 3H), 6.89 (d, J=8.3 Hz, 1H), 3.65 (br d, J=13.6 Hz, 2H), 3.15 (br t, J=10.7 Hz, 2H), 2.80 (br t, J=6.8 Hz, 2H), 2.55 (s, 3H), 1.83 (br t, J=6.8 Hz, 2H), 1.70 (br d, J=13.3 Hz, 2H), 1.61-1.48 (m, 2H).

Example 142. 6-(3-Isoquinolyl)spiro[4H-1,3-benzodioxine-2,4'-piperidine]-1'-carboxamide

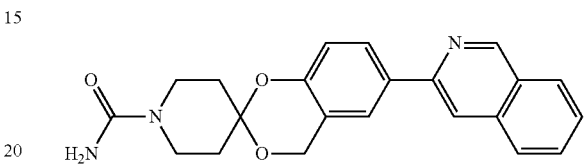

This compound was synthesized using trimethylsilyl isocyanate and 6-(3-isoquinolyl)spiro[4H-1,3-benzodioxine-2,4'-piperidine] TFA salt. Analysis: LCMS m/z=376 (M+1); ¹H NMR (400 MHz, DMSO-d₆) δ: 9.36 (s, 1H), 8.33 (s, 1H), 8.12 (d, J=7.5 Hz, 1H), 8.05 (dd, J=8.5, 2.3 Hz, 1H), 8.02-7.96 (m, 2H), 7.78 (ddd, J=8.2, 6.9, 1.3 Hz, 1H), 7.64 (ddd, J=8.1, 7.0, 1.3 Hz, 1H), 6.99 (d, J=8.5 Hz, 1H), 6.03 (s, 2H), 4.99 (s, 2H), 3.52-3.36 (m, 4H), 1.90-1.74 (m, 4H).

Example 143. 6-(3-Isoquinolyl)spiro[chromane-2,4'-piperidine]-1'-carboxamide

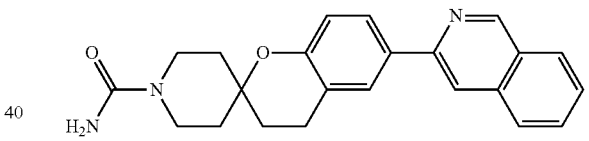

This compound was synthesized using trimethylsilyl isocyanate and 6-(3-isoquinolyl)-spiro[chromane-2,4'-piperidine] TFA salt. Analysis: LCMS m/z=374 (M+1); ¹H NMR (400 MHz, DMSO-d₆) δ: 9.35 (s, 1H), 8.29 (s, 1H), 8.10 (d, J=8.0 Hz, 1H), 8.03-7.91 (m, 2H), 7.76 (ddd, J=8.2, 6.9, 1.3 Hz, 1H), 7.62 (ddd, J=8.2, 6.9, 1.0 Hz, 1H), 7.25-7.24 (m, 1H), 6.99-6.87 (m, 1H), 5.95 (br s, 2H), 3.69 (br d, J=13.3 Hz, 2H), 3.25-3.08 (m, 2H), 2.86 (br t, J=6.7 Hz, 2H), 1.86 (t, J=6.8 Hz, 2H), 1.77-1.65 (m, 2H), 1.62-1.49 (m, 2H).

Example 144. 6-(3-Isoquinolyl)-N-tetrahydropyran-2-yloxy-spiro[4H-1,3-benzodioxine-2,4'-piperidine]-1'-carboxamide

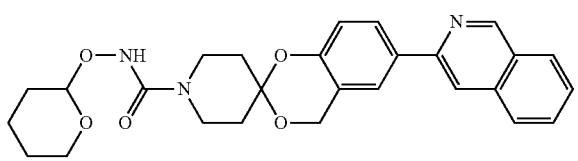 [SMILES: O=C(NOC1CCCCO1)N1CCC2(CC1)OCc1cc(-c3cc4ccccc4cn3)ccc1O2]

This compound was synthesized using O-(tetrahydro-2H-pyran-2-yl)hydroxylamine and 6-(3-isoquinolyl)spiro[4H-1, 3-benzodioxine-2,4'-piperidine] TFA salt. Analysis: LCMS m/z=476 (M+1); $^1$H NMR (400 MHz, CDCl$_3$) δ: 9.30 (s, 1H), 8.02-7.95 (m, 2H), 7.91 (dd, J=8.5, 2.3 Hz, 1H), 7.87-7.83 (m, 2H), 7.69 (ddd, J=8.1, 7.0, 1.3 Hz, 1H), 7.57 (ddd, J=8.2, 6.9, 1.0 Hz, 1H), 7.31 (s, 1H), 7.00 (d, J=8.5 Hz, 1H), 4.98 (s, 2H), 4.96-4.92 (m, 1H), 4.03-3.92 (m, 1H), 3.70-3.58 (m, 3H), 3.57-3.49 (m, 2H), 2.06-1.88 (m, 4H), 1.86-1.74 (m, 3H), 1.69-1.52 (m, 2H).

Example 145. N-Ethoxy-6-(3-isoquinolyl)spiro[4H-1,3-benzodioxine-2,4'-piperidine]-1'-carboxamide

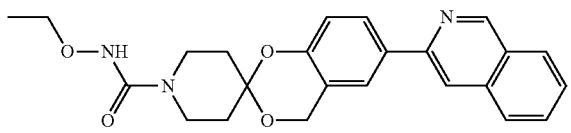

This compound was synthesized using ethoxyamine hydrochloride and 6-(3-isoquinolyl)-spiro[4H-1,3-benzodioxine-2,4'-piperidine] TFA salt. Analysis: LCMS m/z=420 (M+1); $^1$H NMR (400 MHz, DMSO-d$_6$) δ: 9.72 (s, 1H), 9.36 (s, 1H), 8.32 (s, 1H), 8.12 (d, J=8.0 Hz, 1H), 8.05 (dd, J=8.5, 2.3 Hz, 1H), 8.01-7.97 (m, 2H), 7.78 (ddd, J=8.2, 7.0, 1.1 Hz, 1H), 7.64 (ddd, J=8.2, 6.9, 1.0 Hz, 1H), 6.99 (d, J=8.5 Hz, 1H), 4.98 (s, 2H), 3.75 (q, J=7.0 Hz, 2H), 3.49-3.33 (m, 4H), 1.94-1.75 (m, 4H), 1.13 (t, J=7.0 Hz, 3H).

Example 146. 6-(3-Isoquinolyl)-N-tetrahydropyran-2-yloxy-spiro[chromane-2,4'-piperidine]-1'-carboxamide

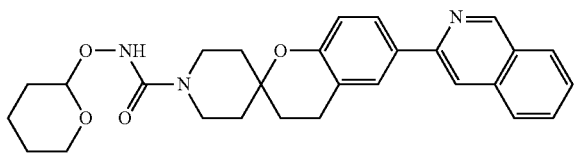 [SMILES: O=C(NOC1CCCCO1)N1CCC2(CCc3cc(-c4cc5ccccc5cn4)ccc3O2)CC1]

This compound was synthesized using CDI, O-(tetrahydro-2H-pyran-2-yl)hydroxylamine, and 6-(3-isoquinolyl) spiro[chromane-2,4'-piperidine] TFA salt. Analysis: LCMS m/z=474 (M+1); $^1$H NMR (400 MHz, CDCl$_3$) δ: 9.30 (s, 1H), 8.00-7.95 (m, 2H), 7.92 (d, J=2.3 Hz, 1H), 7.88-7.82 (m, 2H), 7.68 (td, J=7.6, 1.1 Hz, 1H), 7.58-7.52 (m, 1H), 7.30 (s, 1H), 6.97 (d, J=8.5 Hz, 1H), 5.01-4.84 (m, 1H), 4.02-3.91 (m, 1H), 3.90-3.78 (m, 2H), 3.71-3.57 (m, 1H), 3.41-3.26 (m, 2H), 2.91 (t, J=6.8 Hz, 2H), 1.95-1.76 (m, 7H), 1.71-1.53 (m, 5H).

Example 147. 6-(3-Isoquinolyl)-N-methoxy-spiro[4H-1,3-benzodioxine-2,4'-piperidine]-1'-carboxamide

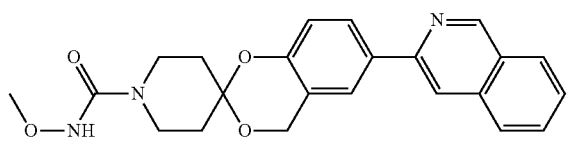 [SMILES: CONC(=O)N1CCC2(CC1)OCc1cc(-c3cc4ccccc4cn3)ccc1O2]

This compound was synthesized using O-methylhydroxylamine HCl and 6-(3-isoquinolyl)-spiro[4H-1,3-benzodioxine-2,4'-piperidine] TFA salt. Analysis: LCMS m/z=406 (M+1); $^1$H NMR (400 MHz, DMSO-d$_6$) δ: 9.81 (s, 1H), 9.36 (s, 1H), 8.33 (s, 1H), 8.12 (d, J=8.0 Hz, 1H), 8.05 (dd, J=8.5, 2.3 Hz, 1H), 8.02-7.97 (m, 2H), 7.78 (ddd, J=8.2, 6.9, 1.3 Hz, 1H), 7.64 (ddd, J=8.1, 7.0, 1.3 Hz, 1H), 6.99 (d, J=8.5 Hz, 1H), 4.98 (s, 2H), 3.55 (s, 3H), 3.47-3.34 (m, 4H), 1.94-1.76 (m, 4H).

Example 148. 6-(3-Isoquinolyl)-N-methoxy-spiro[chromane-2,4'-piperidine]-1'-carboxamide

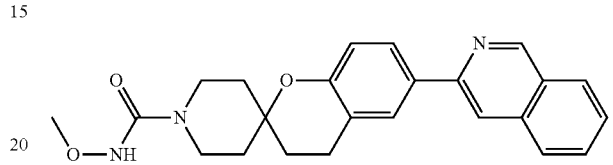

This compound was synthesized using o-methylhydroxylamine HCl and 6-(3-isoquinolyl)-spiro[chromane-2,4'-piperidine] TFA salt. Analysis: LCMS m/z=404 (M+1); $^1$H NMR (400 MHz, DMSO-d$_6$) δ: 9.73 (s, 1H), 9.35 (s, 1H), 8.29 (s, 1H), 8.10 (d, J=8.0 Hz, 1H), 8.04-7.91 (m, 3H), 7.76 (ddd, J=8.2, 7.0, 1.1 Hz, 1H), 7.62 (ddd, J=8.1, 7.0, 1.0 Hz, 1H), 6.92 (d, J=8.5 Hz, 1H), 3.69-3.59 (m, 2H), 3.54 (s, 3H), 3.20-3.09 (m, 2H), 2.86 (t, J=6.8 Hz, 2H), 1.86 (t, J=6.8 Hz, 2H), 1.72 (br d, J=13.6 Hz, 2H), 1.62-1.50 (m, 2H).

Example 149. N-Ethoxy-6-(3-isoquinolyl)spiro[chromane-2,4'-piperidine]-1'-carboxamide

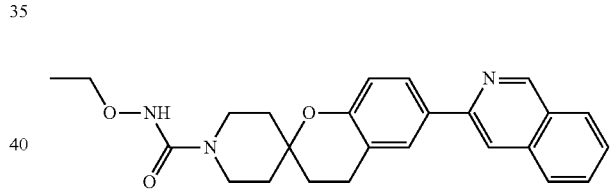

This compound was synthesized using ethoxyamine hydrochloride and 6-(3-isoquinolyl)spiro[chromane-2,4'-piperidine] TFA salt. Analysis: LCMS m/z=418 (M+1); $^1$H NMR (400 MHz, DMSO-d$_6$) δ: 9.64 (s, 1H), 9.35 (s, 1H), 8.29 (s, 1H), 8.10 (d, J=8.0 Hz, 1H), 8.02-7.88 (m, 3H), 7.76 (ddd, J=8.2, 6.8, 1.3 Hz, 1H), 7.62 (ddd, J=8.2, 6.9, 1.0 Hz, 1H), 6.92 (d, J=8.5 Hz, 1H), 3.75 (q, J=7.0 Hz, 2H), 3.64 (br d, J=13.6 Hz, 2H), 3.20-3.08 (m, 2H), 2.86 (br t, J=6.8 Hz, 2H), 1.85 (t, J=6.8 Hz, 2H), 1.72 (br d, J=13.6 Hz, 2H), 1.64-1.50 (m, 2H), 1.13 (t, J=7.0 Hz, 3H).

Example 150. 6-(3-Isoquinolyl)spiro[4H-1,3-benzodioxine-2,4'-piperidine]-1'-carbohydroxamic acid

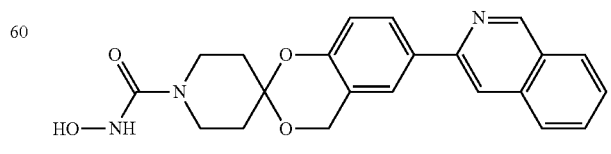

This compound was synthesized using 6-(3-isoquinolyl)-N-tetrahydropyran-2-yloxy-spiro[4H-1,3-benzodioxine-2, 4'-piperidine]-1'-carboxamide and TFA. Analysis: LCMS m/z=392 (M+1); $^1$H NMR (400 MHz, DMSO-$d_6$) δ: 9.36 (s, 1H), 9.14 (s, 1H), 8.33 (s, 1H), 8.12 (d, J=8.0 Hz, 1H), 8.05 (br dd, J=8.5, 2.3 Hz, 2H), 8.02-7.96 (m, 2H), 7.78 (ddd, J=8.2, 6.8, 1.3 Hz, 1H), 7.64 (td, J=7.5, 1.3 Hz, 1H), 6.99 (d, J=8.5 Hz, 1H), 4.98 (s, 2H), 3.56-3.33 (m, 4H), 1.83 (br d, J=5.3 Hz, 4H).

Example 151. 6-(3-Isoquinolyl)spiro[chromane-2,4'-piperidine]-1'-carbohydroxamic acid

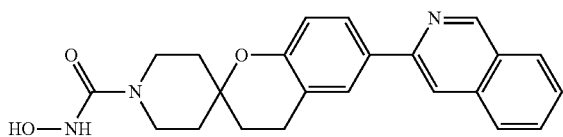

6-(3-Isoquinolyl)-N-tetrahydropyran-2-yloxy-spiro[chromane-2,4'-piperidine]-1'-carboxamide (0.041 g, 0.087 mmol), and TFA (10 eq.) in DCM (2 mL) was stirred at RT overnight. When the reaction was completed by HPLC it was then concentrated and the product purified by Gilson reverse phase chromatography (5-40% ACN in water with 0.1% TFA). The pure fractions were concentrated, and the product freebased using an ion exchange column eluting first with MeOH, then 2 N NH$_4$ in MeOH. The freebase was concentrated, dried at 50° C. under vacuum overnight. Analysis: LCMS m/z=390 (M+1); $^1$H NMR (400 MHz, DMSO-$d_6$) δ: 9.34 (s, 1H), 9.07 (s, 1H), 8.29 (s, 1H), 8.10 (d, J=8.3 Hz, 1H), 8.04-7.92 (m, 4H), 7.76 (ddd, J=8.3, 7.0, 1.3 Hz, 1H), 7.62 (ddd, J=8.1, 7.0, 1.3 Hz, 1H), 6.92 (d, J=8.5 Hz, 1H), 3.65 (br d, J=13.6 Hz, 2H), 3.15 (br t, J=10.8 Hz, 2H), 2.86 (br t, J=6.7 Hz, 2H), 1.85 (br t, J=6.8 Hz, 2H), 1.71 (br d, J=13.6 Hz, 2H), 1.62-1.49 (m, 2H).

Example 152. 5-(8-Methyl-7-quinolyl)spiro[3H-benzofuran-2,4'-piperidine]-1'-carboxamide

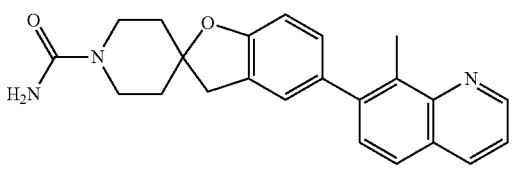 [SMILES: Cc1c(-c2ccc3c(c2)CC2(CCN(C(N)=O)CC2)O3)ccc2cccnc12]

This compound was synthesized using trimethylsilyl isocyanate and 5-(8-methyl-7-quinolyl)-spiro[3H-benzofuran-2,4'-piperidine] 2HCl. Analysis: LCMS m/z=374 (M+1); $^1$H NMR (400 MHz, DMSO-$d_6$) δ: 8.96 (dd, J=4.1, 1.9 Hz, 1H), 8.36 (dd, J=8.2, 1.9 Hz, 1H), 7.84 (d, J=8.3 Hz, 1H), 7.54 (dd, J=8.3, 4.3 Hz, 1H), 7.46 (d, J=8.5 Hz, 1H), 7.28 (d, J=1.5 Hz, 1H), 7.16 (dd, J=8.0, 2.0 Hz, 1H), 6.88 (d, J=8.3 Hz, 1H), 6.01 (s, 2H), 3.54-3.36 (m, 4H), 3.12 (s, 2H), 2.68 (s, 3H), 1.86-1.65 (m, 4H).

Example 153. N-Methoxy-5-(8-methyl-7-quinolyl)spiro[3H-benzofuran-2,4'-piperidine]-1'-carboxamide

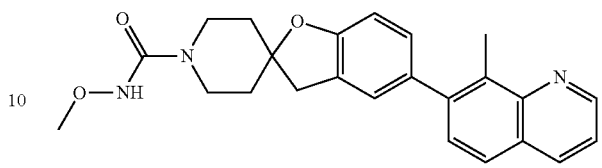

This compound was synthesized using O-methylhydroxylamine HCl, CDI and 5-(8-methyl-7-quinolyl)spiro[3H-benzofuran-2,4'-piperidine] 2HCl. Analysis: LCMS m/z=404 (M+1); $^1$H NMR (400 MHz, DMSO-$d_6$) δ: 9.79 (s, 1H), 8.96 (dd, J=4.1, 1.9 Hz, 1H), 8.36 (dd, J=8.3, 2.0 Hz, 1H), 7.84 (d, J=8.3 Hz, 1H), 7.54 (dd, J=8.2, 4.1 Hz, 1H), 7.46 (d, J=8.3 Hz, 1H), 7.28 (d, J=1.5 Hz, 1H), 7.16 (dd, J=8.2, 1.9 Hz, 1H), 6.88 (d, J=8.0 Hz, 1H), 3.55 (s, 3H), 3.52-3.42 (m, 2H), 3.42-3.34 (m, 2H), 3.11 (s, 2H), 2.67 (s, 3H), 1.90-1.69 (m, 4H).

Example 154. N-Ethoxy-5-(8-methyl-7-quinolyl)spiro[3H-benzofuran-2,4'-piperidine]-1'-carboxamide

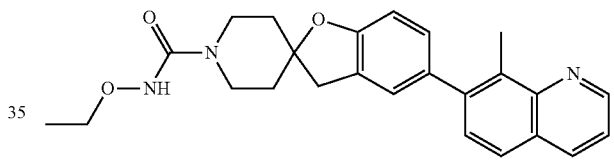

This compound was synthesized using ethoxyamine HCl, CDI and 5-(8-methyl-7-quinolyl)spiro[3H-benzofuran-2,4'-piperidine] 2HCl. Analysis: LCMS m/z=418 (M+1); $^1$H NMR (400 MHz, DMSO-$d_6$) δ: 9.70 (s, 1H), 8.96 (dd, J=4.1, 1.9 Hz, 1H), 8.36 (dd, J=8.3, 2.0 Hz, 1H), 7.84 (d, J=8.3 Hz, 1H), 7.54 (ddd, J=8.3, 4.2, 0.5 Hz, 1H), 7.46 (d, J=8.5 Hz, 1H), 7.28 (d, J=1.5 Hz, 1H), 7.16 (dd, J=8.2, 1.9 Hz, 1H), 6.88 (d, J=8.0 Hz, 1H), 3.76 (d, J=7.0 Hz, 2H), 3.55-3.43 (m, 2H), 3.39 (br dd, J=8.7, 3.9 Hz, 2H), 3.11 (s, 2H), 2.67 (s, 3H), 1.90-1.66 (m, 4H), 1.13 (t, J=7.0 Hz, 3H).

Example 155. 5-(8-Methyl-7-quinolyl)spiro[3H-benzofuran-2,4'-piperidine]-1'-carbohydroxamic acid

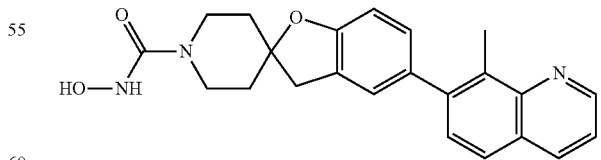

Step 1. tert-Butyl 5-(8-methyl-7-quinolyl)spiro[3H-benzofuran-2,4'-piperidine]-1'-carboxylate was synthesized using tert-butyl 5-(4,4,5,5-tetramethyl-1,3,2-dioxaborolan-2-yl)spiro[3H-benzofuran-2,4'-piperidine]-1'-carboxylate (1.5 g, 3.6 mmol) and 7-bromo-8-methylquinoline. Analysis: LCMS m/z=431 (M+1); $^1$H NMR (400 MHz, DMSO-d$_6$) δ: 8.96 (dd, J=4.0, 1.8 Hz, 1H), 8.35 (dd, J=8.3, 1.8 Hz, 1H), 7.83 (d, J=8.5 Hz, 1H), 7.54 (dd, J=8.2, 4.1 Hz, 1H), 7.46 (d, J=8.5 Hz, 1H), 7.28 (d, J=1.5 Hz, 1H), 7.16 (dd, J=8.2, 1.9 Hz, 1H), 6.88 (d, J=8.0 Hz, 1H), 3.63-3.50 (m, 2H), 3.42 (br s, 2H), 3.11 (s, 2H), 2.67 (s, 3H), 1.91-1.68 (m, 4H), 1.43 (s, 9H).

Step 2. 5-(8-Methyl-7-quinolyl)spiro[3H-benzofuran-2,4'-piperidine] 2HCl was synthesized from tert-butyl 5-(8-methyl-7-quinolyl)spiro[3H-benzofuran-2,4'-piperidine]-1'-carboxylate and 2 M HCl in dioxane. Analysis: LCMS m/z=330 (M+1); $^1$H NMR (400 MHz, DMSO-d$_6$) δ: 8.96 (dd, J=4.3, 1.8 Hz, 1H), 8.35 (dd, J=8.3, 1.8 Hz, 1H), 7.83 (d, J=8.3 Hz, 1H), 7.54 (dd, J=8.3, 4.3 Hz, 1H), 7.46 (d, J=8.5 Hz, 1H), 7.26 (d, J=1.3 Hz, 1H), 7.14 (dd, J=8.3, 2.0 Hz, 1H), 6.85 (d, J=8.3 Hz, 1H), 3.07 (s, 2H), 2.98-2.86 (m, 2H), 2.73-2.62 (m, 5H), 1.84-1.64 (m, 4H).

Step 3. 5-(8-Methyl-7-quinolyl)-N-tetrahydropyran-2-yloxy-spiro[3H-benzofuran-2,4'-piperidine]-1'-carboxamide was synthesized using o-(tetrahydro-2H-pyran-2-yl)hydroxylamine, CDI and 5-(8-methyl-7-quinolyl)spiro[3H-benzofuran-2,4'-piperidine] 2HCl. Hydrolysis using TFA gave 5-(8-methyl-7-quinolyl)spiro[3H-benzofuran-2,4'-piperidine]-1'-carbohydroxamic acid. Analysis: LCMS m/z=390 (M+1); $^1$H NMR (400 MHz, DMSO-d$_6$) δ: 9.13 (s, 1H), 8.96 (dd, J=4.0, 1.8 Hz, 1H), 8.36 (dd, J=8.3, 1.8 Hz, 1H), 8.02 (s, 1H), 7.84 (d, J=8.3 Hz, 1H), 7.58-7.51 (m, 1H), 7.46 (d, J=8.3 Hz, 1H), 7.28 (d, J=1.5 Hz, 1H), 7.16 (dd, J=8.3, 2.0 Hz, 1H), 6.88 (d, J=8.0 Hz, 1H), 3.53-3.35 (m, 4H), 3.11 (s, 2H), 2.68 (s, 3H), 1.88-1.68 (m, 4H).

Example 156. N-Ethyl-5-(8-methyl-7-quinolyl)spiro[3H-benzofuran-2,4'-piperidine]-1'-carboxamide

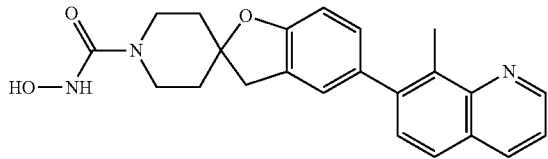 [SMILES: Cc1c(-c2ccc3c(c2)CC2(CCN(C(=O)NO)CC2)O3)ccc2cccnc12]

This compound was synthesized using 5-(4-methyl-3-quinolyl)spiro[3H-benzofuran-2,4'-piperidine] 2HCl and isocyanatoethane. Analysis: LCMS m/z=402 (M+1); $^1$H NMR (400 MHz, DMSO-d$_6$) δ: 8.96 (dd, J=4.3, 1.8 Hz, 1H), 8.36 (dd, J=8.3, 1.8 Hz, 1H), 7.84 (d, J=8.3 Hz, 1H), 7.54 (dd, J=8.2, 4.1 Hz, 1H), 7.46 (d, J=8.3 Hz, 1H), 7.28 (d, J=1.5 Hz, 1H), 7.16 (dd, J=8.2, 1.9 Hz, 1H), 6.87 (d, J=8.0 Hz, 1H), 6.55 (t, J=5.3 Hz, 1H), 3.55-3.36 (m, 4H), 3.11 (s, 2H), 3.10-3.02 (m, 2H), 2.68 (s, 3H), 1.89-1.65 (m, 4H), 1.02 (t, J=7.0 Hz, 3H).

Example 157. N-Methoxy-5-(4-methyl-3-quinolyl)spiro[3H-benzofuran-2,4'-piperidine]-1'-carboxamide

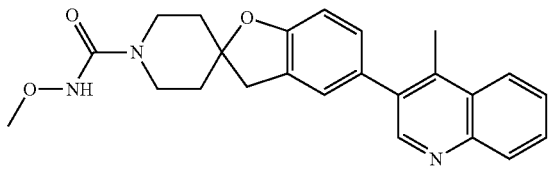 [SMILES: CONC(=O)N1CCC2(CC1)Cc1cc(-c3cnc4ccccc4c3C)ccc1O2]

This compound was synthesized using O-methylhydroxylamine HCl, CDI and 5-(4-methyl-3-quinolyl)spiro[3H-benzofuran-2,4'-piperidine] 2HCl. Analysis: LCMS m/z=404 (M+1); $^1$H NMR (400 MHz, DMSO-d$_6$) δ: 9.79 (s, 1H), 8.71 (s, 1H), 8.18 (dd, J=8.5, 1.0 Hz, 1H), 8.03 (dd, J=8.3, 1.0 Hz, 1H), 7.81-7.72 (m, 1H), 7.71-7.64 (m, 1H), 7.32 (d, J=1.5 Hz, 1H), 7.19 (dd, J=8.0, 2.0 Hz, 1H), 6.91 (d, J=8.3 Hz, 1H), 3.55 (s, 3H), 3.52-3.43 (m, 2H), 3.41-3.35 (m, 2H), 3.12 (s, 2H), 2.62 (s, 3H), 1.87-1.70 (m, 4H).

Example 158. N-ethoxy-5-(4-methyl-3-quinolyl)spiro[3H-benzofuran-2,4'-piperidine]-1'-carboxamide

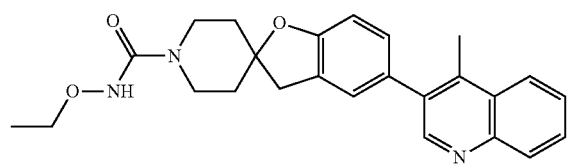 [SMILES: CCONC(=O)N1CCC2(CC1)Cc1cc(-c3cnc4ccccc4c3C)ccc1O2]

This compound was synthesized using ethoxyamine HCl, CDI and 5-(4-methyl-3-quinolyl)-spiro[3H-benzofuran-2,4'-piperidine] 2HCl. Analysis: LCMS m/z=418 (M+1); $^1$H NMR (400 MHz, DMSO-d$_6$) δ: 9.70 (s, 1H), 8.71 (s, 1H), 8.18 (dd, J=8.4, 0.9 Hz, 1H), 8.03 (dd, J=8.3, 1.0 Hz, 1H), 7.82-7.73 (m, 1H), 7.71-7.64 (m, 1H), 7.32 (d, J=1.5 Hz, 1H), 7.19 (dd, J=8.2, 1.9 Hz, 1H), 6.91 (d, J=8.0 Hz, 1H), 3.76 (q, J=7.0 Hz, 2H), 3.54-3.42 (m, 2H), 3.41-3.35 (m, 2H), 3.12 (s, 2H), 2.62 (s, 3H), 1.90-1.69 (m, 4H), 1.13 (t, J=7.0 Hz, 3H).

Example 159. 5-(4-Methyl-3-quinolyl)spiro[3H-benzofuran-2,4'-piperidine]-1'-carboxamide

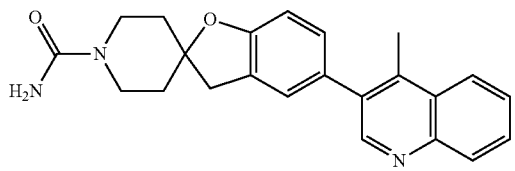 [SMILES: Cc1c(-c2ccc3c(c2)CC2(CCN(C(N)=O)CC2)O3)cnc2ccccc12]

This compound was synthesized using 5-(4-methyl-3-quinolyl)spiro[3H-benzofuran-2,4'-piperidine] 2HCl and trimethylsilyl isocyanate. Analysis: LCMS m/z=374 (M+1); $^1$H NMR (400 MHz, DMSO-d$_6$) δ: 8.71 (s, 1H), 8.18 (dd, J=8.5, 0.8 Hz, 1H), 8.03 (dd, J=8.3, 1.0 Hz, 1H), 7.76 (ddd, J=8.3, 6.8, 1.4 Hz, 1H), 7.70-7.63 (m, 1H), 7.32 (d, J=1.5 Hz, 1H), 7.19 (dd, J=8.2, 1.9 Hz, 1H), 6.91 (d, J=8.3 Hz, 1H), 6.01 (s, 2H), 3.55-3.38 (m, 4H), 3.13 (s, 2H), 2.63 (s, 3H), 1.88-1.65 (m, 4H).

Example 160. N-Ethyl-5-(4-methyl-3-quinolyl)spiro[3H-benzofuran-2,4'-piperidine]-1'-carboxamide

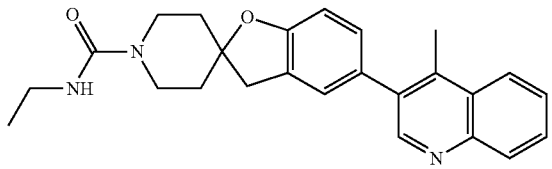 [SMILES: CCNC(=O)N1CCC2(CC1)Cc1cc(-c3cnc4ccccc4c3C)ccc1O2]

This compound was synthesized using 5-(4-methyl-3-quinolyl)spiro[3H-benzofuran-2,4'-piperidine] 2HCl and isocyanatoethane. Analysis: LCMS m/z=402 (M+1); $^1$H NMR (400 MHz, DMSO-d$_6$) δ: 8.71 (s, 1H), 8.18 (dd, J=8.4, 0.9 Hz, 1H), 8.03 (dd, J=8.3, 1.0 Hz, 1H), 7.76 (ddd, J=8.3, 6.9, 1.4 Hz, 1H), 7.67 (ddd, J=8.3, 6.9, 1.4 Hz, 1H), 7.32 (d, J=1.5 Hz, 1H), 7.19 (dd, J=8.0, 2.0 Hz, 1H), 6.91 (d, J=8.0 Hz, 1H), 6.55 (t, J=5.4 Hz, 1H), 3.55-3.36 (m, 4H), 3.12 (s, 2H), 3.10-3.02 (m, 2H), 2.63 (s, 3H), 1.87-1.66 (m, 4H), 1.02 (t, J=7.2 Hz, 3H).

Example 161. 5-(4-Methyl-3-quinolyl)spiro[3H-benzofuran-2,4'-piperidine]-1'-carbohydroxamic acid

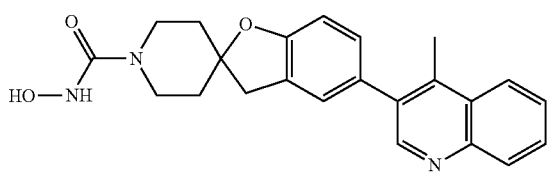 [SMILES: Cc1c(-c2ccc3c(c2)CC2(CCN(C(=O)NO)CC2)O3)cnc2ccccc12]

Step 1. tert-butyl 5-(4-methyl-3-quinolyl)spiro[3H-benzofuran-2,4'-piperidine]-1'-carboxylate was synthesized using tert-butyl 5-(4,4,5,5-tetramethyl-1,3,2-dioxaborolan-2-yl)spiro[3H-benzofuran-2,4'-piperidine]-1'-carboxylate and 3-bromo-4-methylquinoline Analysis: LCMS m/z=431 (M+1); $^1$H NMR (400 MHz, DMSO-d$_6$) δ: 8.71 (s, 1H), 8.18 (dd, J=8.4, 0.9 Hz, 1H), 8.03 (dd, J=8.3, 1.0 Hz, 1H), 7.76 (ddd, J=8.3, 6.9, 1.4 Hz, 1H), 7.71-7.64 (m, J=8.3, 6.5, 1.4 Hz, 1H), 7.32 (d, J=1.5 Hz, 1H), 7.19 (dd, J=8.3, 2.0 Hz, 1H), 6.91 (d, J=8.0 Hz, 1H), 3.62-3.50 (m, 2H), 3.48-3.36 (m, 2H), 3.13 (s, 2H), 2.62 (s, 3H), 1.91-1.68 (m, 4H), 1.43 (s, 9H).

Step 2. 5-(4-Methyl-3-quinolyl)spiro[3H-benzofuran-2,4'-piperidine] 2HCl was synthesized using tert-butyl 5-(4-methyl-3-quinolyl)spiro[3H-benzofuran-2,4'-piperidine]-1'-carboxylate and 2N HCL in dioxane. Analysis: LCMS m/z=331 (M+1); $^1$H NMR (400 MHz, DMSO-d$_6$) δ: 9.24 (br s, 1H), 9.06 (s, 1H), 8.45 (d, J=8.3 Hz, 1H), 8.35 (d, J=8.3 Hz, 1H), 8.13-8.03 (m, 1H), 7.97-7.88 (m, 1H), 7.44 (d, J=1.5 Hz, 1H), 7.32 (dd, J=8.3, 2.0 Hz, 1H), 7.00 (d, J=8.0 Hz, 1H), 3.22 (s, 6H), 2.81 (s, 3H), 2.14-2.02 (m, 4H).

Step 3. 5-(4-Methyl-3-quinolyl)-N-tetrahydropyran-2-yloxy-spiro[3H-benzofuran-2,4'-piperidine]-1'-carboxamide was synthesize using o-(tetrahydro-2H-pyran-2-yl)hydroxylamine and 5-(4-methyl-3-quinolyl)spiro[3H-benzofuran-2,4'-piperidine] 2HCl. LCMS m/z=474(M+1).

Step 4. 5-(4-Methyl-3-quinolyl)spiro[3H-benzofuran-2,4'-piperidine]-1'-carbohydroxamic acid was synthesized using 5-(4-methyl-3-quinolyl)-N-tetrahydropyran-2-yloxy-spiro[3H-benzofuran-2,4'-piperidine]-1'-carboxamide and TFA. Analysis: LCMS m/z=390 (M+1); $^1$H NMR (400 MHz, DMSO-d$_6$) δ: 9.13 (s, 1H), 8.71 (s, 1H), 8.18 (dd, J=8.5, 0.8 Hz, 1H), 8.03 (dd, J=8.3, 1.0 Hz, 2H), 7.76 (ddd, J=8.3, 6.9, 1.4 Hz, 1H), 7.71-7.63 (m, 1H), 7.31 (d, J=1.5 Hz, 1H), 7.19 (dd, J=8.2, 1.9 Hz, 1H), 6.91 (d, J=8.0 Hz, 1H), 3.53-3.38 (m, 4H), 3.13 (s, 2H), 2.62 (s, 3H), 1.87-1.69 (m, 4H).

Example 162. 5-(8-Methoxy-7-quinolyl)spiro[3H-benzofuran-2,4'-piperidine]-1'-carboxamide

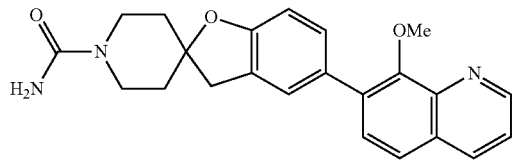 [SMILES: COc1c(-c2ccc3c(c2)CC2(CCN(C(N)=O)CC2)O3)ccc2cccnc12]

This compound was synthesized using 5-(8-methoxy-7-quinolyl)spiro[3H-benzofuran-2,4'-piperidine] 2HCl and trimethylsilyl isocyanate. Analysis: LCMS m/z=390 (M+1); $^1$H NMR (400 MHz, DMSO-d$_6$) δ: 8.94 (dd, J=4.0, 1.8 Hz, 1H), 8.38 (dd, J=8.3, 1.8 Hz, 1H), 7.75 (d, J=8.8 Hz, 1H), 7.59-7.52 (m, 2H), 7.47 (d, J=1.5 Hz, 1H), 7.38 (dd, J=8.3, 1.8 Hz, 1H), 6.88 (d, J=8.3 Hz, 1H), 6.01 (s, 2H), 3.91 (s, 3H), 3.56-3.37 (m, 4H), 3.12 (s, 2H), 1.86-1.64 (m, 4H).

Example 163. N-Ethyl-5-(8-methoxy-7-quinolyl)spiro[3H-benzofuran-2,4'-piperidine]-1'-carboxamide

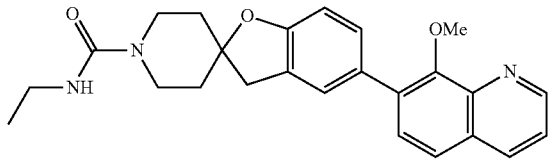

This compound was synthesized using 5-(8-methoxy-7-quinolyl)spiro[3H-benzofuran-2,4'-piperidine] 2HCl and isocyanatoethane. Analysis: LCMS m/z=418 (M+1); $^1$H NMR (400 MHz, DMSO-d$_6$) δ: 8.94 (dd, J=4.0, 1.8 Hz, 1H), 8.38 (dd, J=8.3, 1.8 Hz, 1H), 7.75 (d, J=8.5 Hz, 1H), 7.57 (d, J=8.5 Hz, 1H), 7.54 (dd, J=8.3, 4.2 Hz, 1H), 7.38 (dd, J=8.3, 2.0 Hz, 1H), 6.88 (d, J=8.0 Hz, 1H), 6.55 (t, J=5.3 Hz, 1H), 3.91 (s, 3H), 3.55-3.39 (m, 4H), 3.12 (s, 2H), 3.11-3.03 (m, 2H), 1.86-1.67 (m, 4H), 1.02 (t, J=7.2 Hz, 3H).

Example 164. 5-(7-Methylpyrazolo[1,5-a]pyridin-6-yl)spiro[3H-benzofuran-2,4'-piperidine]-1'-carboxamide

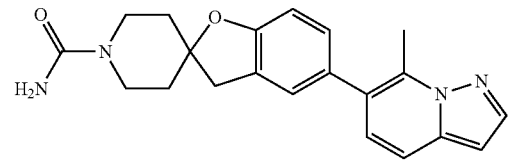 [SMILES: Cc1c(-c2ccc3c(c2)CC2(CCN(C(N)=O)CC2)O3)ccc2ccnn12]

Step 1. 5-(7-Methylpyrazolo[1,5-a]pyridin-6-yl)spiro[3H-benzofuran-2,4'-piperidine] 2HCl was synthesized using tert-butyl 5-(7-methylpyrazolo[1,5-a]pyridin-6-yl)spiro[3H-benzofuran-2,4'-piperidine]-1'-carboxylate and 4 M HCl in dioxane. Analysis: LCMS m/z=320 (M+1); $^1$H NMR (400 MHz, DMSO-d$_6$) δ: 8.94 (dd, J=4.0, 1.8 Hz, 1H), 8.38 (dd, J=8.3, 1.8 Hz, 1H), 7.75 (d, J=8.8 Hz, 1H), 7.57 (d, J=8.5 Hz, 1H), 7.55-7.52 (m, 1H), 7.47 (d, J=1.5 Hz, 1H), 7.38 (dd, J=8.3, 2.0 Hz, 1H), 6.88 (d, J=8.3 Hz, 1H), 6.01 (s, 2H), 3.91 (s, 3H), 3.57-3.39 (m, 4H), 3.12 (s, 2H), 1.86-1.67 (m, 4H).

Step 2. 5-(7-Methylpyrazolo[1,5-a]pyridin-6-yl)spiro[3H-benzofuran-2,4'-piperidine]-1'-carboxamide was synthesized using 5-(7-methylpyrazolo[1,5-a]pyridin-6-yl)spiro[3H-benzofuran-2,4'-piperidine] 2HCl and trimethylsilyl isocyanate. Analysis: LCMS m/z=363 (M+1); $^1$H NMR (400 MHz, DMSO-d$_6$) δ: 8.05 (d, J=2.3 Hz, 1H), 7.64 (d, J=8.8 Hz, 1H), 7.27 (d, J=1.5 Hz, 1H), 7.16 (d, J=8.8 Hz, 2H), 6.86 (d, J=8.3 Hz, 1H), 6.68 (d, J=2.3 Hz, 1H), 6.01 (s, 2H), 3.53-3.37 (m, 4H), 3.10 (s, 2H), 2.65 (s, 3H), 1.83-1.67 (m, 4H).

Example 165. N-Ethyl-5-(7-methylpyrazolo[1,5-a]pyridin-6-yl)spiro[3H-benzofuran-2,4'-piperidine]-1'-carboxamide

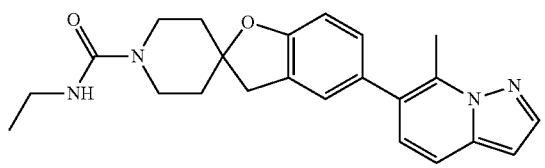 [SMILES: CCNC(=O)N1CCC2(CC1)Cc1cc(-c3ccc4ccnn4c3C)ccc1O2]

This compound was synthesized using 5-(7-methylpyrazolo[1,5-a]pyridin-6-yl)spiro[3H-benzofuran-2,4'-piperidine] 2HCl and isocyanatoethane. Analysis: LCMS m/z=391 (M+1); $^1$H NMR (400 MHz, DMSO-d$_6$) δ: 8.05 (d, J=2.3 Hz, 1H), 7.64 (d, J=8.8 Hz, 1H), 7.27 (d, J=1.5 Hz, 1H), 7.15 (d, J=9.0 Hz, 2H), 6.86 (d, J=8.0 Hz, 1H), 6.68 (d, J=2.3 Hz, 1H), 6.55 (t, J=5.4 Hz, 1H), 3.54-3.35 (m, 4H), 3.10 (s, 2H), 3.09-3.02 (m, 2H), 2.65 (s, 3H), 1.86-1.62 (m, 4H), 1.02 (t, J=7.2 Hz, 3H).

Example 166. N-Methoxy-5-(8-methoxy-7-quinolyl)spiro[3H-benzofuran-2,4'-piperidine]-1'-carboxamide

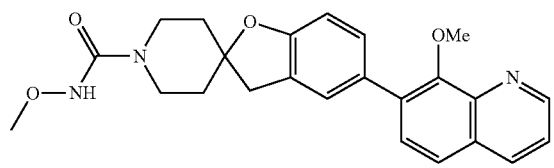

This compound was synthesized using 5-(8-methoxy-7-quinolyl)spiro[3H-benzofuran-2,4'-piperidine] 2HCl and O-methylhydroxylamine HCl Analysis: LCMS m/z=420 (M+1); $^1$H NMR (400 MHz, DMSO-d$_6$) δ: 9.79 (s, 1H), 8.94 (dd, J=4.1, 1.6 Hz, 1H), 8.38 (dd, J=8.3, 1.8 Hz, 1H), 7.75 (d, J=8.8 Hz, 1H), 7.57 (d, J=8.3 Hz, 1H), 7.54 (dd, J=8.3, 4.3 Hz, 1H), 7.47 (d, J=1.3 Hz, 1H), 7.38 (dd, J=8.3, 2.0 Hz, 1H), 6.88 (d, J=8.3 Hz, 1H), 3.91 (s, 3H), 3.55 (s, 3H), 3.52-3.42 (m, 2H), 3.41-3.34 (m, 2H), 3.12 (s, 2H), 1.88-1.66 (m, 4H).

Example 167. N-Ethoxy-5-(8-methoxy-7-quinolyl)spiro[3H-benzofuran-2,4'-piperidine]-1'-carboxamide

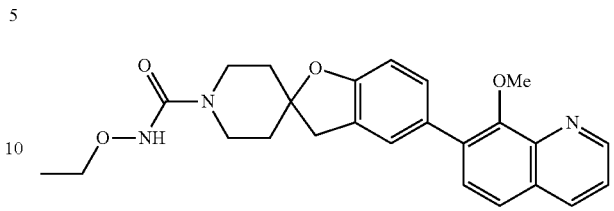

This compound was synthesized using 5-(8-methoxy-7-quinolyl)spiro[3H-benzofuran-2,4'-piperidine] 2HCl and ethoxyamine HCl. Analysis: LCMS m/z=434 (M+1); $^1$H NMR (400 MHz, DMSO-d$_6$) δ: 9.70 (s, 1H), 8.94 (dd, J=4.3, 1.8 Hz, 1H), 8.38 (dd, J=8.3, 1.8 Hz, 1H), 7.75 (d, J=8.8 Hz, 1H), 7.57 (d, J=8.3 Hz, 1H), 7.54 (dd, J=8.3, 4.3 Hz, 1H), 7.47 (d, J=1.3 Hz, 1H), 7.38 (dd, J=8.3, 2.0 Hz, 1H), 6.88 (d, J=8.3 Hz, 1H), 3.91 (s, 3H), 3.76 (q, J=6.9 Hz, 2H), 3.53-3.42 (m, 2H), 3.40-3.33 (m, 2H), 3.12 (s, 2H), 1.86-1.69 (m, 4H), 1.13 (t, J=7.0 Hz, 3H).

Example 168. 5-(8-Methoxy-7-quinolyl)-N-tetrahydropyran-2-yloxy-spiro[3H-benzofuran-2,4'-piperidine]-1'-carboxamide

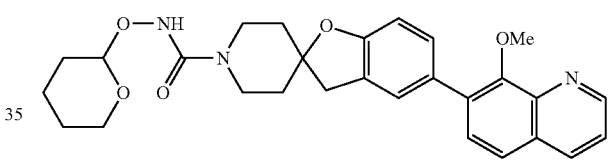

This compound was synthesized using 5-(8-methoxy-7-quinolyl)spiro[3H-benzofuran-2,4'-piperidine] 2HCl and O-(tetrahydro-2H-pyran-2-yl)hydroxylamine. Analysis: LCMS m/z=490 (M+1); $^1$H NMR (400 MHz, DMSO-d$_6$) δ: 9.73 (s, 1H), 8.94 (dd, J=4.3, 1.8 Hz, 1H), 8.38 (dd, J=8.3, 1.8 Hz, 1H), 7.75 (d, J=8.5 Hz, 1H), 7.57 (d, J=8.3 Hz, 1H), 7.54 (dd, J=8.3, 4.3 Hz, 1H), 7.47 (d, J=1.5 Hz, 1H), 7.38 (dd, J=8.3, 1.8 Hz, 1H), 6.88 (d, J=8.3 Hz, 1H), 4.76 (t, J=3.1 Hz, 1H), 4.02-3.95 (m, 1H), 3.91 (s, 3H), 3.53-3.44 (m, 3H), 3.43-3.34 (m, 2H), 3.12 (s, 2H), 1.89-1.43 (m, 10H).

Example 169. N-Ethoxy-5-(7-methylpyrazolo[1,5-a]pyridin-6-yl)spiro[3H-benzofuran-2,4'-piperidine]-1'-carboxamide

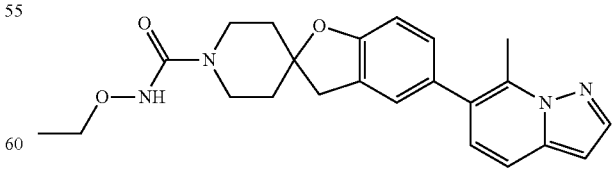

This compound was synthesized using 5-(7-methylpyrazolo[1,5-a]pyridin-6-yl)spiro[3H-benzofuran-2,4'-piperidine] HCl2 and ethoxyamine HCl. LCMS m/z=407(M+1); $^1$H NMR (400 MHz, DMSO-d$_6$) δ: 9.70 (s, 1H), 8.05 (d, J=2.3 Hz, 1H), 7.64 (d, J=8.8 Hz, 1H), 7.27 (d, J=1.5 Hz, 1H), 7.21-7.12 (m, 2H), 6.86 (d, J=8.0 Hz, 1H), 6.68 (d, J=2.3 Hz, 1H), 3.76 (q, J=7.0 Hz, 2H), 3.53-3.42 (m, 2H), 3.37 (dt, J=8.9, 4.3 Hz, 2H), 3.10 (s, 2H), 2.65 (s, 3H), 1.86-1.68 (m, 4H), 1.13 (t, J=7.0 Hz, 3H).

Example 170. N-Methoxy-5-(7-methylpyrazolo[1,5-a]pyridin-6-yl)spiro[3H-benzofuran-2,4'-piperidine]-1'-carboxamide

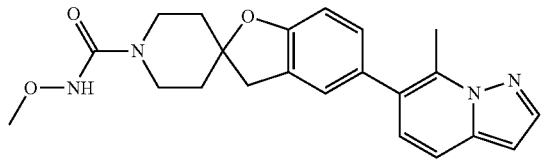 [SMILES: CONC(=O)N1CCC2(CC1)Cc1cc(-c3ccc4ccnn4c3C)ccc1O2]

This compound was synthesized using 5-(7-methylpyrazolo[1,5-a]pyridin-6-yl)spiro[3H-benzofuran-2,4'-piperidine] 2HCl and O-methylhydroxylamine HCl. Analysis: LCMS m/z=393 (M+1); $^1$H NMR (400 MHz, DMSO-d$_6$) δ: 9.79 (s, 1H), 8.05 (d, J=2.3 Hz, 1H), 7.64 (d, J=9.0 Hz, 1H), 7.27 (d, J=1.5 Hz, 1H), 7.20-7.11 (m, 2H), 6.86 (d, J=8.3 Hz, 1H), 6.68 (d, J=2.3 Hz, 1H), 3.55 (s, 3H), 3.51-3.42 (m, 2H), 3.40-3.34 (m, 2H), 3.10 (s, 2H), 2.65 (s, 3H), 1.87-1.69 (m, 4H).

Example 171. 5-(7-Methylpyrazolo[1,5-a]pyridin-6-yl)-N-tetrahydropyran-2-yloxy-spiro[3H-benzofuran-2,4'-piperidine]-1'-carboxamide

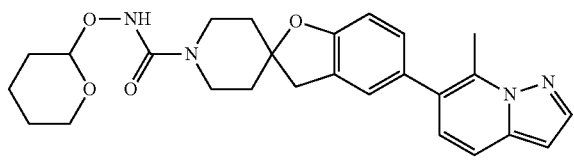 [SMILES: Cc1c(-c2ccc3c(c2)CC2(CCN(C(=O)NOC4CCCCO4)CC2)O3)ccc2ccnn12]

This compound was synthesized using 5-(7-methylpyrazolo[1,5-a]pyridin-6-yl)spiro[3H-benzofuran-2,4'-piperidine] 2HCl and O-(tetrahydro-2H-pyran-2-yl)hydroxylamine. Analysis: LCMS m/z=463 (M+1); $^1$H NMR (400 MHz, DMSO-d$_6$) δ 9.73 (s, 1H), 8.05 (d, J=2.3 Hz, 1H), 7.64 (d, J=8.8 Hz, 1H), 7.28 (d, J=1.5 Hz, 1H), 7.21-7.11 (m, 2H), 6.87 (d, J=8.3 Hz, 1H), 6.68 (d, J=2.3 Hz, 1H), 4.76 (t, J=3.0 Hz, 1H), 4.02-3.93 (m, 1H), 3.56-3.43 (m, 3H), 3.43-3.34 (m, 2H), 3.10 (s, 2H), 2.65 (s, 3H), 1.89-1.44 (m, 10H).

Example 172. 6-(8-Methyl-2-oxo-1H-quinolin-7-yl)spiro[chromane-2,4'-piperidine]-1'-carboxamide

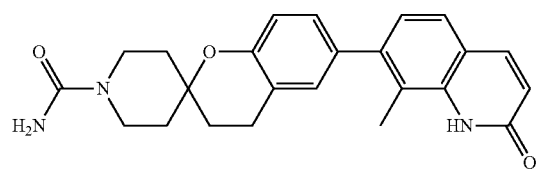 [SMILES: Cc1c(-c2ccc3c(c2)CCC2(CCN(C(N)=O)CC2)O3)ccc2ccc(=O)[nH]c12]

This example was synthesized using intermediate 3 and 7-bromo-8-methyl-1H-quinolin-2-one similar to the procedure for examples 101 and 106. Analysis: LCMS m/z=404 (M+1); $^1$H NMR (400 MHz, DMSO-d$_6$) δ:10.83 (s, 1H), 7.92 (d, J=9.5 Hz, 1H), 7.53 (d, J=8.0 Hz, 1H), 7.13-7.01 (m, 3H), 6.87 (d, J=8.3 Hz, 1H), 6.51 (d, J=9.3 Hz, 1H), 5.96 (s, 2H), 3.69 (br d, J=13.3 Hz, 2H), 3.15 (br t, J=10.8 Hz, 2H), 2.79 (br t, J=6.5 Hz, 2H), 2.32 (s, 3H), 1.83 (t, J=6.8 Hz, 2H), 1.69 (br d, J=13.8 Hz, 2H), 1.60-1.47 (m, 2H).

Example 173. 5-(8-Methoxy-7-quinolyl)spiro[3H-benzofuran-2,4'-piperidine]-1'-carbohydroxamic acid

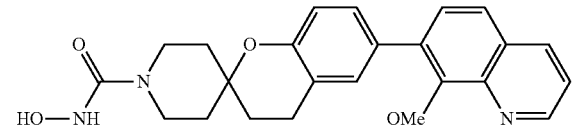 [SMILES: COc1c(-c2ccc3c(c2)CCC2(CCN(C(=O)NO)CC2)O3)ccc2cccnc12]

This compound was synthesized using 5-(8-methoxy-7-quinolyl)-N-tetrahydropyran-2-yloxy-spiro[3H-benzofuran-2,4'-piperidine]-1'-carboxamide and TFA. Analysis: LCMS m/z=406 (M+1); $^1$H NMR (400 MHz, DMSO-d$_6$) δ 9.13 (s, 1H), 8.94 (dd, J=4.3, 1.8 Hz, 1H), 8.38 (dd, J=8.3, 1.8 Hz, 1H), 8.03 (br s, 1H), 7.75 (d, J=8.5 Hz, 1H), 7.57 (d, J=8.5 Hz, 1H), 7.56-7.52 (m, 1H), 7.47 (d, J=1.5 Hz, 1H), 7.38 (dd, J=8.2, 1.9 Hz, 1H), 6.88 (d, J=8.3 Hz, 1H), 3.91 (s, 3H), 3.54-3.35 (m, 4H), 3.12 (s, 2H), 1.84-1.70 (m, 4H).

Example 174. 6-(8-Methoxy-7-quinolyl)spiro[4H-1,3-benzodioxine-2,4'-piperidine]-1'-carboxamide

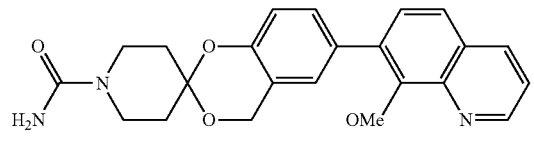

Step 1. tert-Butyl 6-(8-methoxy-7-quinolyl)spiro[4H-1,3-benzodioxine-2,4'-piperidine]-1'-carboxylate. tert-Butyl 6-(4,4,5,5-tetramethyl-1,3,2-dioxaborolan-2-yl)spiro[4H-1,3-benzo-dioxine-2,4'-piperidine]-1'-carboxylate (0.80 g, 1.9 mmol), 7-bromo-8-methoxy-quinoline (0.45 g, 1.9 mmol), palladium(II) acetate (0.024 g, 0.11 mmol) and triphenylphosphine (0.10 g, 0.38 mmol) in 1,4-dioxane (30 mL), DMF (50 mL) was added aq. Na$_2$CO$_3$ (0.5 M) (6.0 mL, 3.0 mmol). The mixture was vacuum degassed then heated at 85° C. overnight. The mixture was diluted with EtOAc (200 mL) and water (100 mL) and extracted. The aqueous extract was washed with EtOAc (50 mL) and the combined organics were dried over Na$_2$SO$_4$, filtered and concentrated. The residue was dissolved in DCM, applied to a silica gel loading cartridge (5 g) and purified on silica gel (80 g, 0-40% EtOAc:hexanes) to afford tert-butyl 6-(8-methoxy-7-quinolyl)spiro[4H-1,3-benzodioxine-2,4'-piperidine]-1'-carboxylate (0.38 g, 0.82 mmol, 43% Yield). LCMS m/z=463.

Step 2. 6-(8-Methoxy-7-quinolyl)spiro[4H-1,3-benzodioxine-2,4'-piperidine]. A mixture of tert-butyl 6-(8-methoxy-7-quinolyl)spiro[4H-1,3-benzodioxine-2,4'-piperidine]-1'-carboxylate (0.38 g, 0.82 mmol) and TFA (0.5 mL, 7 mmol) in DCM (10 mL) was stirred at RT for 24 h, then was diluted with DCM (20 mL) and NaOH (1M, 24 mL). The layers were separated and the aqueous phase was further extracted with DCM (2×20 mL). The combined organics were filtered through a phase separator, then dried over Na₂SO₄, filtered, and concentrated in vacuo to give a white foam. A small amount (50 mg) was purified by preparative HPLC to afford 6-(8-methoxy-7-quinolyl)spiro[4H-1,3-benzodioxine-2,4'-piperidine] TFA salt (20 mg). Analysis: LCMS m/z=363; ¹H NMR (400 MHz, DMSO-d₆) δ: 9.02 (dd, J=4.4, 1.6 Hz, 1H), 8.71 (br s, 2H), 8.57 (d, J=7.5 Hz, 1H), 7.87 (d, J=8.5 Hz, 1H), 7.71-7.64 (m, 2H), 7.54 (dd, J=8.5, 2.3 Hz, 1H), 7.43 (d, J=2.0 Hz, 1H), 7.03 (d, J=8.5 Hz, 1H), 5.00 (s, 2H), 3.88 (s, 3H), 3.29-3.16 (m, 4H), 2.19-2.06 (m, 4H). The remainder was used in the next step without further purification.

Step 3. 6-(8-Methoxy-7-quinolyl)spiro[4H-1,3-benzodioxine-2,4'-piperidine]-1'-carboxamide. A mixture of 6-(8-methoxy-7-quinolyl)spiro[4H-1,3-benzodioxine-2,4'-piperidine] (0.198 g, 0.546 mmol), trimethylsilyl isocyanate (0.30 mL, 1.9 mmol), DIPEA (0.50 mL, 2.9 mmol), and DCM (10.0 mL) was stirred overnight. The solution was concentrated and the resulting material was diluted with DCM an put on a 5 g preload silica gel. The material was purified on silica gel chromatography (24 g, 0-10% EtOAc: hexanes) to afford 6-(8-methoxy-7-quinolyl)spiro[4H-1,3-benzodioxine-2,4'-piperidine]-1'-carboxamide (0.183 g, 0.451 mmol, 83%) as an off-white solid. Analysis: LCMS m/z=406 (M+1); ¹H NMR (400 MHz, DMSO-d₆) δ 8.95 (dd, J=4.0, 1.8 Hz, 1H), 8.38 (dd, J=8.3, 1.8 Hz, 1H), 7.77 (d, J=8.5 Hz, 1H), 7.61-7.47 (m, 3H), 7.36 (d, J=2.3 Hz, 1H), 6.97 (d, J=8.5 Hz, 1H), 6.04 (s, 2H), 4.95 (s, 2H), 3.94 (s, 3H), 3.52-3.37 (m, 4H), 1.91-1.77 (m, 3H), 1.88-1.77 (m, 1H).

Example 175. 6-(8-Methoxy-7-quinolyl)spiro[chromane-2,4'-piperidine]-1'-carboxamide

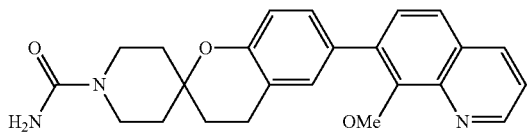

Step 1. tert-Butyl 6-(8-methoxy-7-quinolyl)spiro[chromane-2,4'-piperidine]-1'-carboxylate. A solution of tert-butyl 6-(4,4,5,5-tetramethyl-1,3,2-dioxaborolan-2-yl)spiro[chromane-2,4'-piperidine]-1'-carboxylate (0.90 g, 2.1 mmol), 7-bromo-8-methoxy-quinoline (0.50 g, 2.1 mmol), palladium(II) acetate (0.024 g, 0.11 mmol), triphenylphosphine (0.11 g, 0.42 mmol), 1,4-dioxane (30 mL), and DMF (50 mL) was added aq. Na₂CO₃ (0.5 M) (8.0 mL, 4.0 mmol). The mixture was vacuum degassed then heated at 85° C. overnight. The mixture was treated with water (120 mL) then cooled to RT and extracted with EtOAc (3×70 mL). The organic extract was washed with a mixture of water:brine (9:1, 100 mL) then with brine (100 mL), dried over Na₂SO₄, filtered and concentrated in vacuo. The residue was dried overnight under vacuum then the residue was dissolved in DCM, applied to a silica gel loading cartridge (25 g) and purified on silica gel (40 g, 0-40% ethyl acetate:hexane) to afford tert-butyl 6-(8-methoxy-7-quinolyl)-spiro[chromane-2,4'-piperidine]-1'-carboxylate as a white solid. Analysis: LCMS m/z 461 (M+1); ¹H NMR (400 MHz, DMSO-d₆) δ: 8.94 (dd, J=4.3, 1.8 Hz, 1H), 8.38 (dd, J=8.4, 1.6 Hz, 1H), 7.75 (d, J=8.5 Hz, 1H), 7.58 (d, J=8.5 Hz, 1H), 7.56-7.52 (m, 1H), 7.42-7.36 (m, 2H), 6.90 (d, J=8.3 Hz, 1H), 3.93 (s, 3H), 3.78-3.68 (m, 2H), 3.29-3.11 (m, 2H), 2.82 (t, J=6.7 Hz, 2H), 1.85 (t, J=6.8 Hz, 2H), 1.79-1.70 (m, 2H), 1.62-1.52 (m, 2H), 1.42 (s, 9H).

Step 2. 6-(8-Methoxy-7-quinolyl)spiro[chromane-2,4'-piperidine] 2HCl. tert-Butyl 6-(8-methoxy-7-quinolyl)spiro[chromane-2,4'-piperidine]-1'-carboxylate was dissolved in HCl (2M in 1,4-dioxane) (6.0 mL, 12 mmol) and after 5 min a precipitate formed. The reaction was diluted with ethanol (6.0 mL), stirred at RT overnight, then concentrated in vacuo to afford 6-(8-methoxy-7-quinolyl)spiro[chromane-2,4'-piperidine] 2HCl. Analysis: LCMS 361 (M+1); ¹H NMR (400 MHz, DMSO-d₆) δ: 9.16-9.02 (m, 2H), 9.00-8.89 (m, 1H), 8.87-8.77 (m, 1H), 7.98 (br d, J=8.8 Hz, 1H), 7.88-7.72 (m, 2H), 7.52-7.48 (m, 2H), 7.01 (d, J=8.3 Hz, 1H), 3.80 (s, 3H), 3.27-3.19 (m, 2H), 3.18-3.07 (m, 2H), 2.87 (br t, J=6.7 Hz, 2H), 2.00-1.86 (m, 6H).

Step 3. 6-(8-Methoxy-7-quinolyl)spiro[chromane-2,4'-piperidine]-1'-carboxamide. A suspension of 6-(8-methoxy-7-quinolyl)spiro[chromane-2,4'-piperidine] 2HCl (0.101 g, 0.233 mmol) in THF (2.0 mL) was treated with DIPEA (0.11 g, 0.15 mL, 0.86 mmol). After stirring for 2 min, a white precipitate formed. ACN (1.0 mL) was added, followed by DMF (2.0 mL) to give a homogenous solution. Trimethylsilyl isocyanate (0.085 g, 0.10 mL, 0.63 mmol) was then added to the mixture. After 90 min, water (11 mL) was added to the mixture and was aged at RT then at 4° C. overnight. The fine precipitate was collected on a Hirsch funnel, washed with water and dried under vacuum to afford crude product. The solids were dissolved in DMSO and purified by preparative HPLC (5-50% ACN: water, containing 0.1% TFA) to afford 6-(8-methoxy-7-quinolyl)spiro[chromane-2,4'-piperidine]-1'-carboxamide (0.064 g, 0.16 mmol, 68%). The pure fractions (freebased) treated with aq. Na₂CO₃ (10 mL) then extracted with DCM (2×30 mL), dried, concentrated and reconcentrated from ethanol and further dried. Analysis: LCMS 404 (M+1); ¹H NMR (400 MHz, DMSO-d₆) δ: 8.94 (dd, J=4.0, 1.8 Hz, 1H), 8.38 (dd, J=8.3, 1.8 Hz, 1H), 7.75 (d, J=8.5 Hz, 1H), 7.58 (d, J=8.5 Hz, 1H), 7.56-7.52 (m, 1H), 7.41-7.35 (m, 2H), 6.90 (d, J=8.3 Hz, 1H), 5.96 (s, 2H), 3.93 (s, 3H), 3.74-3.65 (m, 2H), 3.22-3.12 (m, 2H), 2.83 (t, J=6.7 Hz, 2H), 1.85 (t, J=6.8 Hz, 2H), 1.75-1.66 (m, 2H), 1.60-1.51 (m, 2H).

Example 176. Ethyl 6-(8-methoxy-7-quinolyl)spiro[4H-1,3-benzodioxine-2,4'-piperidine]-1'-carboxylate

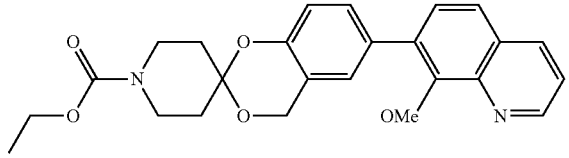 [SMILES: CCOC(=O)N1CCC2(CC1)OCc1cc(-c3ccc4cccnc4c3OC)ccc1O2]

A solution of ethyl 6-(4,4,5,5-tetramethyl-1,3,2-dioxaborolan-2-yl)spiro[4H-1,3-benzodioxine-2,4'-piperidine]-1'-carboxylate (0.78 g, 1.9 mmol), 7-bromo-8-methoxy-quinoline (0.45 g, 1.9 mmol), palladium(II) acetate (0.024 g, 0.11 mmol), triphenylphosphine (0.10 g, 0.38 mmol), 1,4-dioxane (30 mL), and DMF (50 mL) was added aq. Na₂CO₃ (0.5 M) (6.0 mL, 3.0 mmol). The mixture was vacuum degassed then heated at 85° C. overnight. The mixture was treated with water (120 mL) then cooled to RT and extracted with EtOAc (3×70 mL). The organic extract was washed with a mixture of water:brine (9:1, 100 mL) then with brine (100 mL), dried over Na₂SO₄, filtered and concentrated in vacuo. The residue was dried overnight under vacuum then the residue was dissolved in DCM, applied to a silica gel loading cartridge (25 g) and purified on silica gel (40 g, 0-40% EtOAc:hexanes) to afford ethyl 6-(8-methoxy-7-quinolyl)spiro[4H-1,3-benzodioxine-2,4'-piperidine]-1'-carboxylate (0.637 g, 1.47 mmol, 78%) as an off-white foam. Analysis: LCMS 435 (M+1); $^1$H NMR (400 MHz, DMSO-$d_6$) δ: 8.94 (dd, J=4.3, 1.8 Hz, 1H), 8.39 (dd, J=8.4, 1.6 Hz, 1H), 7.77 (d, J=8.8 Hz, 1H), 7.58 (d, J=8.5 Hz, 1H), 7.55 (dd, J=8.3, 4.0 Hz, 1H), 7.48 (dd, J=8.5, 2.3 Hz, 1H), 7.37 (d, J=2.0 Hz, 1H), 6.97 (d, J=8.3 Hz, 1H), 4.95 (s, 2H), 4.06 (q, J=7.0 Hz, 2H), 3.93 (s, 3H), 3.59-3.43 (m, 4H), 1.93-1.82 (m, 4H), 1.20 (t, J=7.2 Hz, 3H).

Example 177. 6-(5-Chloroimidazo[1,2-a]pyridin-6-yl)-N-isobutyl-spiro[chromane-2,4'-piperidine]-1'-carboxamide

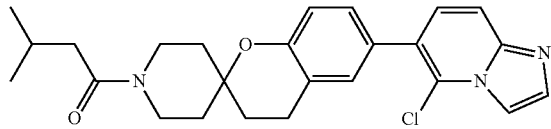

Step 1. A solution of tert-butyl 6-(5-chloroimidazo[1,2-a]pyridin-6-yl)spiro[chromane-2,4'-piperidine]-1'-carboxylate. 6-Bromo-5-chloroimidazo[1,2-a]pyridine (0.638 g, 2.76 mmol), tert-butyl 6-(4,4,5,5-tetramethyl-1,3,2-dioxaborolan-2-yl)spiro[chromane-2,4'-piperidine]-1'-carboxylate (1.213 g, 2.83 mmol), tetrakis(triphenylphosphine)palladium(0) (0.333 g, 0.288 mmol), Na$_2$CO$_3$ (1 M) (9 mL, 9 mmol) and 1,4-dioxane (18 g, 16 mL) were combined, purged with argon and heated at 100° C. under nitrogen for 17 h. The reaction was filtered through a pad of Celite and washed with DCM. The filtrate was concentrated and the residue dissolved in EtOAc, washed with 1 M aqueous Na$_2$CO$_3$, water and brine. Organic layer was dried over MgSO$_4$, filtered and concentrated. The residue was purified by ISCA silica gel chromatography (50-100% EtOAc/heptane) to afford a white solid (701 mg, 53%). LCMS m/z=454 (M+1); $^1$H NMR (400 MHz, DMSO-$d_6$) δ: 8.08 (s, 1H), 7.76 (d, 1H, J=1.2 Hz), 7.69 (d, 1H, J=9.2 Hz), 7.34 (d, 1H, J=9.2 Hz), 7.26 (m, 2H), 6.91 (m, 1H), 3.73 (m, 2H), 3.19 (m, 2H), 2.82-2.79 (m, 2H), 1.86-1.83 (m, 2H), 1.74-1.71 (m, 2H), 1.60-1.53 (m, 2H), 1.42 (s, 9H).

Step 2. 6-(5-Chloroimidazo[1,2-a]pyridin-6-yl)spiro[chromane-2,4'-piperidine] 2HCl. A solution of tert-butyl 6-(5-chloroimidazo[1,2-a]pyridin-6-yl)spiro[chromane-2,4'-piperidine]-1'-carboxylate (0.701 g, 1.54 mmol) in EtOAc (9.2 mL) was added 4M HCl in dioxane (4.4 mL). The reaction was stirred at RT for 17 h, and the resulting precipitate was collected by filtration and dried under high vacuum at 40° C. to afford an off-white solid (574 mg, 83%). Analysis: mp=310° C.; LCMS m/z=354 (M+1H); $^1$H NMR (400 MHz, DMSO-$d_6$) δ: 9.06 (br s, 1H), 8.93 (br s, 1H), 8.45 (s, 1H), 8.25 (s, 1H), 7.97 (d, 1H, J=9.0 Hz), 7.82 (d, 1H, J=9.6 Hz), 7.32 (m, 2H), 7.01 (d, 1H, J=9.0 Hz), 3.23 (m, 2H), 3.17-3.06 (m, 2H), 2.86-2.83 (m, 2H), 1.97-1.84 (m, 6H).

Step 3. 6-(5-Chloroimidazo[1,2-a]pyridin-6-yl)-N-isobutyl-spiro[chromane-2,4'-piperidine]-1'-carboxamide. To 6-(5-Chloroimidazo[1,2-a]pyridin-6-yl)spiro[chromane-2,4'-piperidine] 2HCl (0.088 g, 0.2062 mmol) and DIPEA (0.0906 g, 0.12 mL, 0.687 mmol) in DCM (2 mL) was added 1-isocyanato-2-methyl-propane (0.028 g, 0.2825 mmol). The reaction was stirred at RT for 20 h, then washed with 1 N Na$_2$CO$_3$ and brine. Organic layer was dried over MgSO$_4$, filtered and concentrated. The product was triturated with ether, filtered and dried under high vacuum at 40° C. to afford an off-white solid (52 mg, 55%). Analysis: mp 100° C.; LCMS m/z=354 (M+1); $^1$H NMR (400 MHz, DMSO-$d_6$) δ: 8.08 (s, 1H), 7.75 (d, 1H, J=1.2 Hz), 7.69 (d, 1H, J=9.1 Hz), 7.35 (d, 1H, J=9.2 Hz), 7.28-7.25 (m, 2H), 6.91 (m, 1H), 6.53 (m, 1H), 3.73-3.69 (m, 2H), 3.19-3.13 (m, 2H), 2.86-2.79 (m, 4H), 1.85-1.82 (m, 2H), 1.73-1.67 (m, 3H), 1.58-1.51 (m, 2H), 0.83 (d, 6H, J=6.7 Hz).

Example 178. N-Isobutyl-6-(1-methyl-6-isoquinolyl)spiro[chromane-2,4'-piperidine]-1'-carboxamide

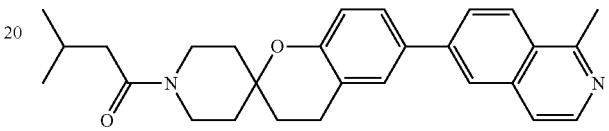

This compound was synthesized using 6-(methylisoquinoline)-3,4-dihydrospiro(chromene-2,4-piperidine) and 1-isocyanato-2-methyl-propane to give an off white solid (66%). Analysis: mp 198° C.; LCMS m/z=444 (M+1); $^1$H NMR (400 MHz, DMSO-$d_6$) δ: 8.33 (d, 1H, J=5.8 Hz), 8.23 (d, 1H, J=8.8 Hz), 8.15 (d, 1H, J=1.7 Hz), 7.97-7.94 (m, 1H), 7.68 (m, 1H), 7.62-7.58 (m, 2H), 6.94 (d, 1H, J=8.4 Hz), 6.53 (m, 1H), 3.73-3.70 (m, 2H), 3.18-3.12 (m, 2H), 2.89-2.83 (m, 7H), 1.86-1.83 (m, 2H), 1.73-1.68 (m, 3H), 1.58-1.51 (m, 2H), 0.83 (d, 6H, J=6.7 Hz).

Example 179. 6-(5-Chloroimidazo[1,2-a]pyridin-6-yl)-N-isopropoxy-spiro[chromane-2,4'-piperidine]-1'-carboxamide

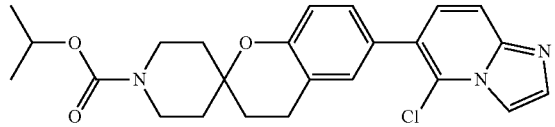 [SMILES: CC(C)OC(=O)N1CCC2(CCc3cc(-c4ccc5nccn5c4Cl)ccc3O2)CC1]

CDI (0.08 g, 0.49337 mmol), DCM (2.0 mL), THF (0.5 mL), 2-(aminooxy)propane HCl (0.052 g, 0.46608 mmol) and DIPEA (0.0815 g, 0.11 mL, 0.631 mmol) were combined and stirred at RT for 16 h. 6-(5-Chloroimidazo[1,2-a]pyridin-6-yl)spiro[chromane-2,4'-piperidine] 2HCl (0.112 g, 0.262 mmol) and DIPEA (0.15 mL, 0.860 mmol) were added and stirred for an additional 4 h. The reaction was diluted with EtOAc, washed with saturated ammonium chloride solution, water, saturated NaHCO$_3$ solution, and brine. The organic phase was dried over Na$_2$SO$_4$, filtered and concentrated. The residue was triturated with ether and dried under high vacuum at 40° C. to afford an off-white solid (59 mg, 49%). Analysis: mp 90° C.; LCMS: m/z=455 (M+1); $^1$H NMR (400 MHz, DMSO-$d_6$) δ: 9.49 (s, 1H), 8.08 (s, 1H), 7.75 (d, 1H, J=1.2 Hz), 7.69 (d, 1H, J=9.1 Hz), 7.35 (d, 1H, J=9.2 Hz), 7.26 (m, 2H), 6.91 (m, 1H), 3.90-3.84 (m, 1H), 3.67-3.63 (m, 2H), 3.17-3.12 (m, 2H), 2.82-2.79 (m, 2H), 1.85-1.82 (m, 2H), 1.72-1.69 (m, 2H), 1.60-1.53 (m, 2H), 1.12 (d, 6H, J=6.1 Hz).

Example 180. N-Isopropoxy-6-(1-methyl-6-isoquinolyl)spiro[chromane-2,4'-piperidine]-1'-carboxamide

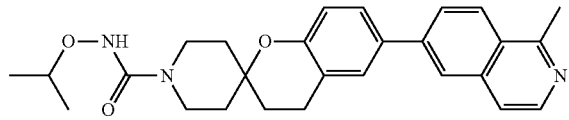

This compound was synthesized using 6-(methylisoquinoline)-3,4-dihydrospiro(chromene-2,4-piperidine) and 2-(ammoniooxy)propane HCl using the procedure for Example 179 as an off-white solid (43%). Analysis: mp 130° C.; LCMS m/z=446 (M+1); $^1$H NMR (400 MHz, DMSO-d$_6$) δ: 9.49 (s, 1H), 8.33 (d, 1H, J=5.7 Hz), 8.23 (d, 1H, J=8.8 Hz), 8.15 (d, 1H, J=1.8 Hz), 7.95 (m, 1H), 7.68 (m, 1H), 7.63-7.58 (m, 2H), 6.95 (d, 1H, J=8.4 Hz), 3.90-3.84 (m, 1H), 3.67-3.63 (m, 2H), 3.17-3.11 (m, 2H), 2.90-3.11 (m, 2H), 2.90-2.84 (m, 5H), 1.87-1.83 (m, 2H), 1.73-1.69 (m, 2H), 1.60-1.53 (m, 2H), 1.12 (d, 6H, J=6.2 Hz).

Example 181. N-Ethoxy-6-(4-methyl-3-quinolyl)spiro[chromane-2,4'-piperidine]-1'-carboxamide

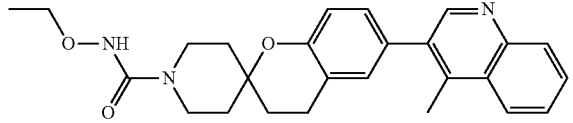 [SMILES: CCONC(=O)N1CCC2(CCc3cc(-c4cnc5ccccc5c4C)ccc3O2)CC1]

The title compound, a tan solid, was prepared in a manner similar to the procedure used to prepare Example 179 using intermediate 3 and O-ethylhydroxylamine HCl in 36% yield. Analysis: mp: 100° C.; LC-MS: m/z=345 (M+1); 1H NMR (400 MHz, DMSO-d$_6$) δ 9.64 (s, 1H), 8.72 (s, 1H), 8.18 (d, 1H, J=8.1 Hz), 8.03 (d, 1H, J=7.8 Hz), 7.78-7.74 (m, 1H), 7.69-7.65 (m, 1H), 7.21-7.17 (m, 2H), 6.94 (d, 1H, J=8.2 Hz), 3.78-3.73 (m, 2H), 3.67-3.63 (m, 2H), 3.18-3.13 (m, 2H), 2.84-2.81 (m, 2H), 2.63 (s, 3H), 1.87-1.84 (m, 2H), 1.74-1.71 (m, 2H), 1.61-1.54 (m, 2H), 1.15-1.11 (m, 3H)

Example 182. N-Isopropoxy-6-(1-methyl-6-isoquinolyl)spiro[4H-1,3-benzodioxine-2,4'-piperidine]-1'-carboxamide

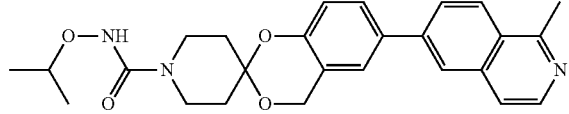 [SMILES: Cc1nccc2cc(-c3ccc4c(c3)COC3(CCN(C(=O)NOC(C)C)CC3)O4)ccc12]

A solution of CDI (0.073 g, 0.450 mmol), 2-(aminooxy)propane HCl (0.048 g, 0.43022 mmol), DCM (2.0 mL), THF (0.5 mL) and DIPEA (0.0741 g, 0.1 mL, 0.573 mmol) were stirred at RT for 1.5 h. 6-(1-Methyl-6-isoquinolyl)spiro[4H-1,3-benzodioxine-2,4'-piperidine] 2HCl (0.1 g, 0.2385 mmol) and DIPEA (0.0741 g, 0.1 mL, 0.573 mmol) were added and the reaction was stirred at RT for an additional 16 h. The reaction was diluted with DCM, washed with saturated ammonium chloride solution, water, saturated NaHCO$_3$ solution, then concentrated. The residue was purified by preparatory HPLC. The pure fractions were lyophilized, then was dissolved in EtOAc and washed with saturated aqueous NaHCO$_3$ solution, and water. The organic phase was dried over Na$_2$SO$_4$, filtered and concentrated to afford an off-white solid (16 mg, 15%). Analysis: mp 90° C.; LCMS: m/z=448 (M+1); $^1$H NMR (400 MHz, MeOD) δ: 8.25 (m, 1H), 8.24 (s, 1H), 8.05 (d, 1H, J=1.6 Hz), 7.93-7.90 (m, 1H), 7.68 (d, 1H, J=5.9 Hz), 7.62 (m, 1H), 7.49 (m, 1H), 6.98 (d, 1H, J=8.5 Hz), 4.97 (s, 2H), 3.99-3.93 (m, 1H), 3.54-3.51 (m, 4H), 2.93 (s, 3H), 1.95-1.92 (m, 4H), 1.21 (d, 6H, J=6.2 Hz).

Example 183. 6-(1-Methyl-6-isoquinolyl)spiro[chromane-2,4'-piperidine]-1'-carboxamide

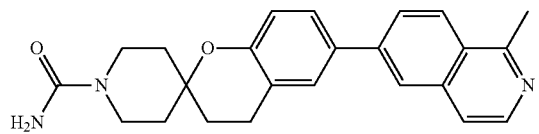 [SMILES: Cc1nccc2cc(-c3ccc4c(c3)CCC3(CCN(C(N)=O)CC3)O4)ccc12]

A solution of 6-(1-methyl-6-isoquinolyl)spiro[chromane-2,4'-piperidine] 2HCl (0.087 g, 0.2084 mmol), DIPEA (0.109 g, 0.145 mL, 0.830 mmol), and (trimethylsilyl) isocyanate (0.034 g, 0.04 mL, 0.295 mmol) in DCM (3 g, 2 mL, 40 mmol) were stirred at RT for 20 h. The reaction was diluted with DCM, washed with saturated aqueous NaHCO$_3$ solution, water, then brine. The organic phase was dried over Na$_2$SO$_4$, filtered and concentrated. The residue was triturated with ether and dried by high vacuum at 40° C. to afford a white solid (59 mg, 72%). Analysis: mp 208° C.; LCMS: m/z=388 (M+1); $^1$H NMR (400 MHz, DMSO-d$_6$) δ: 8.33 (d, 1H, J=5.8 Hz), 8.23 (d, 1H, J=8.8 Hz), 8.15 (d, 1H, J=1.7 Hz), 7.97-7.94 (m, 1H), 7.68 (d, 1H, J=5.8 Hz), 7.62-7.59 (m, 2H), 6.95 (d, 1H, J=8.4 Hz), 5.96 (s, 2H), 3.71-3.68 (m, 2H), 3.17-3.12 (m, 2H), 2.89-2.84 (m, 5H), 1.87-1.83 (m, 2H), 1.71-1.68 (m, 2H), 1.59-1.52 (m, 2H).

Example 184. N-methoxy-6-(1-methyl-6-isoquinolyl)spiro[chromane-2,4'-piperidine]-1'-carboxamide

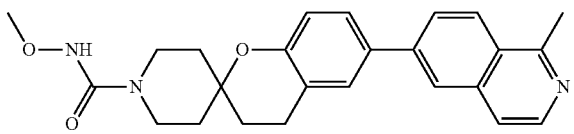

This compound was synthesized using 6-(1-methyl-6-isoquinolyl)spiro[chromane-2,4'-piperidine] 2HCl and methoxyamine HCl by the procedure for Example 182. Analysis: mp 240° C.; LCMS: m/z=418 (M+1); $^1$H NMR (400 MHz, DMSO-d$_6$) δ: 9.73 (s, 1H), 8.33 (d, 1H, J=5.7 Hz), 8.23 (d, 1H, J=8.8 Hz), 8.15 (d, 1H, J=1.6 Hz), 7.97-7.95 (m, 1H), 7.68 (d, 1H, J=5.7 Hz), 7.62-7.59 (m, 2H), 6.95 (d, 1H, J=8.4 Hz), 3.65-3.62 (m, 2H), 3.54 (s, 3H), 3.16-3.11 (m, 2H), 2.89-2.84 (m, 5H), 1.87-1.83 (m, 2H), 1.73-1.70 (m, 2H), 1.60-1.53 (m, 2H).

Example 185. N-ethoxy-6-(1-methyl-6-isoquinolyl)spiro[chromane-2,4'-piperidine]-1'-carboxamide

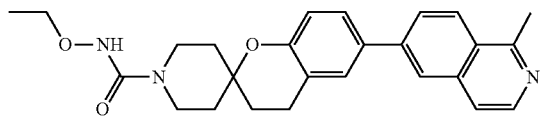

This compound was synthesized using 6-(1-methyl-6-isoquinolyl)spiro[chromane-2,4'-piperidine] 2HCl and ethoxyamine HCl by the procedure for Example 182. Analysis: mp: 100° C.; LCMS: m/z=432 (M+1); $^1$H NMR (400 MHz, DMSO-d$_6$) δ: 9.64 (s, 1H), 8.33 (d, 1H, J=4.9 Hz), 8.23 (d, 1H, J=8.8 Hz), 8.15 (d, 1H, J=1.7 Hz), 7.95 (m, 1H), 7.68 (d, 1H, J=5.8 Hz), 7.63-7.58 (m, 2H), 6.95 (d, 1H, J=8.4 Hz), 3.77-3.72 (m, 2H), 3.66-3.62 (m, 2H), 3.16-3.11 (m, 2H), 2.89-2.84 (m, 5H), 1.87-1.83 (m, 2H), 1.73-1.69 (m, 2H), 1.60-1.53 (m, 2H), 1.14-1.11 (m, 3H).

Example 186. 6-(1-Methyl-6-isoquinolyl)-N-propoxy-spiro[chromane-2,4'-piperidine]-1'-carboxamide

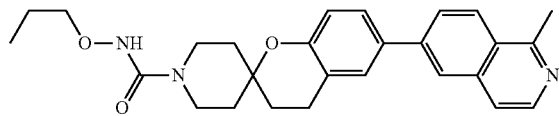 [SMILES: CCCONC(=O)N1CCC2(CCc3cc(-c4ccc5c(C)nccc5c4)ccc3O2)CC1]

This compound was synthesized using 6-(1-methyl-6-isoquinolyl)spiro[chromane-2,4'-piperidine] 2HCl and O-propylhydroxyamine HCl by the procedure for Example 182. Analysis: LCMS: m/z=446 (M+1); $^1$H NMR (400 MHz, DMSO-d$_6$) δ 9.63 (s, 1H), 8.33 (d, 1H, J=5.8 Hz), 8.23 (d, 1H, J=8.8 Hz), 8.15 (d, 1H, J=1.7 Hz), 7.97-7.94 (m, 1H), 7.68 (d, 1H, J=5.8 Hz), 7.62-7.58 (m, 2H), 6.95 (d, 1H, J=8.4 Hz), 3.68-3.62 (m, 4H), 3.16-3.11 (m, 2H), 2.89-2.84 (m, 5H), 1.87-1.83 (m, 2H), 1.73-1.69 (m, 2H), 1.60-1.51 (m, 4H), 0.92-0.88 (m, 3H).

Example 187. N-Ethyl-6-(1-methyl-6-isoquinolyl)spiro[chromane-2,4'-piperidine]-1'-carboxamide

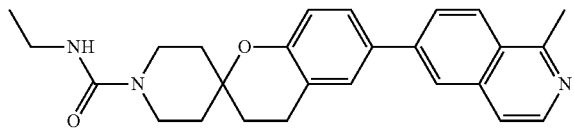

This compound was synthesized using 6-(1-methyl-6-isoquinolyl)spiro[chromane-2,4'-piperidine] 2HCl and ethylisocycanate in 64% yield. Analysis: mp 181° C.; LCMS m/z=416 (M+1); $^1$H NMR (400 MHz, DMSO-d$_6$) δ: 8.33 (d, 1H, J=5.7 Hz), 8.23 (d, 1H, J=8.8 Hz), 8.15 (d, 1H, J=1.6 Hz), 7.97-7.94 (m, 1H), 7.68 (d, 1H, J=5.8 Hz), 7.62-7.58 (m, 2H), 6.94 (d, 1H, J=8.4 Hz), 6.49 (m, 1H), 3.71-3.68 (m, 2H), 3.17-3.11 (m, 2H), 3.09-3.02 (m, 2H), 2.89-2.84 (m, 5H), 1.86-1.83 (m, 2H), 1.71-1.68 (m, 2H), 1.58-1.51 (m, 2H), 1.03-1.00 (m, 3H).

Example 188. 6-(1-methyl-6-isoquinolyl)-N-propyl-spiro[chromane-2,4'-piperidine]-1'-carboxamide

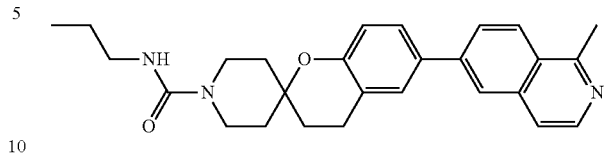

This compound was synthesized using 6-(1-methyl-6-isoquinolyl)spiro[chromane-2,4'-piperidine] 2HCl and propylisocycanate in 49% yield. Analysis: mp 178° C.; LCMS m/z=430 (M+1); $^1$H NMR (400 MHz, DMSO-d$_6$) δ: 8.33 (d, 1H, J=5.8 Hz), 8.23 (d, 1H, J=8.8 Hz), 8.15 (d, 1H, J=1.5 Hz), 7.97-7.94 (m, 1H), 7.68 (d, 1H, J=5.8 Hz), 7.62-7.58 (m, 2H), 6.94 (d, 1H, J=8.4 Hz), 6.50 (m, 1H), 3.70 (m, 2H), 3.17-3.12 (m, 2H), 3.01-2.96 (m, 2H), 2.89-2.84 (m, 5H), 1.85 (m, 2H), 1.71-1.68 (m, 2H), 1.58-1.51 (m, 2H), 1.46-1.37 (m, 2H), 0.85-0.81 (m, 3H).

Example 189. 6-(1-Methyl-6-isoquinolyl)spiro[chromane-2,4'-piperidine]-1'-carbohydroxamic acid

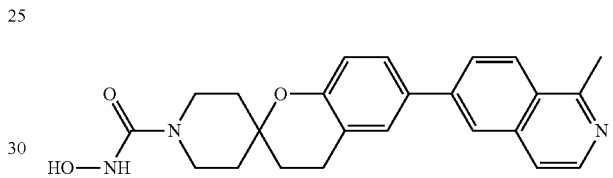

6-(1-Methyl-6-isoquinolyl)spiro[chromane-2,4'-piperidine] 2HCl (0.15 g, 0.3594 mmol) in DCM (5 mL) was added TEA (0.2 mL, 1.43 mmol) and triphosgene (0.136 g, 0.458 mmol). The reaction was stirred at RT for 2 h, concentrated and the residue was dissolved in DCE (8 mL). DIPEA (0.165 mL, 0.947 mmol) was then added, followed by hydroxylamine HCl (0.06 g, 0.8634 mmol). The reaction was heated at 70° C. under nitrogen for 4 h, then concentrated, diluted with EtOAc and washed with saturated aqueous NaHCO$_3$ solution, water, and brine. The organic layer was dried over Na$_2$SO$_4$, filtered and concentrated. The residue was purified by preparatory HPLC and the clean fractions lyophilized. The lyophilate was diluted with DCM, washed with aqueous NaHCO$_3$ solution, water, then brine. The organic layer was dried over Na$_2$SO$_4$, filtered and concentrated to afford an off-white solid (13 mg, 9%). Analysis: mp 230° C.; LCMS: m/z=404 (M+1); $^1$H NMR (400 MHz, DMSO-d$_6$) δ: 9.06 (s, 1H), 8.33 (d, 1H, J=5.7 Hz), 8.23 (d, 1H, J=8.8 Hz), 8.15 (d, 1H, J=1.7 Hz), 7.97-7.94 (m, 2H), 7.68 (d, 1H, J=5.8 Hz), 7.63-7.58 (m, 2H), 6.95 (d, 1H, J=8.4 Hz), 3.67-3.64 (m, 2H), 3.17-3.11 (m, 2H), 2.89-2.84 (m, 5H), 1.86-1.83 (m, 2H), 1.72-1.69 (m, 2H), 1.59-1.52 (m, 2H).

Example 190. 6-(4-methyl-3-quinolyl)spiro[chromane-2,4'-piperidine]-1'-carboxamide

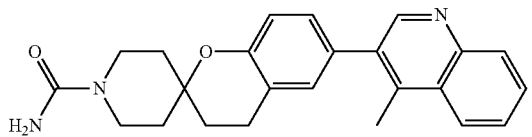

Step 1. 6-(4-methyl-3-quinolyl)spiro[chromane-2,4'-piperidine] 2HCl was synthesized using 6-(4,4,5,5-tetramethyl-1,3,2-dioxaborolan)-3,4-dihydrospiro(chromene-2,4-piperidine)-1-carboxylic acid tert-butyl ester and 3-bromo-4-methylquinoline in a manner similar to the procedure used to prepare Example 1. Analysis: mp 190° C.; LCMS m/z=345 (M+1); $^1$H NMR (400 MHz, DMSO-d$_6$) δ: 8.97 (m, 2H), 8.83 (m, 1H), 8.38 (d, 1H, J=8.4 Hz), 8.22 (d, 1H, J=8.4 Hz), 7.98 (m, 1H), 7.87 (m, 1H), 7.31-7.28 (m, 2H), 7.03 (d, 1H, J=8.3 Hz), 3.26-3.23 (m, 2H), 3.18-3.12 (m, 2H), 2.88-2.85 (m, 2H), 2.77 (s, 3H), 1.94-1.84 (m, 6H).

Step 2. 6-(4-Methyl-3-quinolyl)spiro[chromane-2,4'-piperidine]-1'-carboxamide was synthesized using 6-(4-methyl-3-quinolyl)spiro[chromane-2,4'-piperidine] 2HCl and (trimethylsilyl)isocyanate by the procedure to prepare Example 183 (40%). Analysis: mp 182° C.; LCMS: m/z=388 (M+1); $^1$H NMR (400 MHz, DMSO-d$_6$) δ: 8.72 (s, 1H), 8.19 (d, 1H, J=8.2 Hz), 8.03 (d, 1H, J=8.2 Hz), 7.78-7.74 (m, 1H), 7.69-7.65 (m, 1H), 7.21-7.18 (m, 2H), 6.94 (d, 1H, J=8.2 Hz), 5.97 (s, 2H), 3.72-3.68 (m, 2H), 3.19-3.14 (m, 2H), 2.85-2.81 (m, 2H), 2.63 (s, 3H), 1.87-1.84 (m, 2H), 1.73-1.69 (m, 2H), 1.60-1.54 (m, 2H).

Example 191. 6-(4-Methyl-3-quinolyl)spiro[chromane-2,4'-piperidine]-1'-carbohydroxamic acid

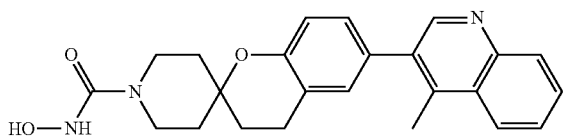

This compound was synthesized using 6-(4-methyl-3-quinolyl)spiro[chromane-2,4'-piperidine]2HCl and hydroxylamine HCl in a manner similar to the procedure used to prepare Example 189. Analysis: LCMS m/z=404 (M+1); $^1$H NMR (400 MHz, MeOD) δ: 8.65 (s, 1H), 8.19 (m, 1H), 8.03 (m, 1H), 7.78-7.74 (m, 1H), 7.69-7.65 (m, 1H), 7.15 (m, 2H), 6.96 (m, 1H), 5.49 (s, 1H), 3.81-3.78 (m, 2H), 3.33-3.26 (m, 2H), 2.91-2.88 (m, 2H), 2.68 (s, 3H), 1.90-1.84 (m, 4H), 1.69-1.61 (m, 2H).

Example 192. N-Methoxy-6-(4-methyl-3-quinolyl)spiro[chromane-2,4'-piperidine]-1'-carboxamide

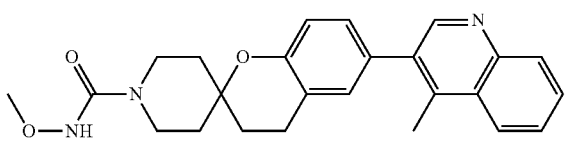 [SMILES: CONC(=O)N1CCC2(CCc3cc(-c4cnc5ccccc5c4C)ccc3O2)CC1]

Step 1. Ethyl 6-(1-methyl-6-isoquinolyl)spiro[4H-1,3-benzodioxine-2,4'-piperidine]-1'-carboxylate. 6-Bromo-1-methyl-isoquinoline (0.506 g, 2.2785 mmol), ethyl 6-(4,4,5,5-tetramethyl-1,3,2-dioxaborolan-2-yl)spiro[4H-1,3-benzodioxine-2,4'-piperidine]-1'-carboxylate (0.981 g, 2.43 mmol), tetrakis(triphenylphosphine)palladium(0) (0.263 g, 0.228 mmol), Na$_2$CO$_3$ in water (1 M) (7 mL) and 1,4-dioxane (14 g, 12 mL, 160 mmol) were combined in a flask. The reaction was purged with argon and heated at 100° C. under nitrogen for 18 h. The reaction was then cooled to RT, filtered through a pad of Celite, and washed with DCM. The filtrate was concentrated and residue was dissolved in EtOAc, washed with saturated aqueous NaHCO$_3$ solution, then brine. The organic layer was dried over MgSO$_4$, filtered and concentrated. The residue was purified by ISCO silica gel chromatography (50%-100% EtOAc/heptane) to give an off-white solid (966 mg, 96%). LCMS m/z=419 (M+1); $^1$H NMR (400 MHz, DMSO-d$_6$) δ: 8.34 (d, 1H, J=5.8 Hz), 8.25 (d, 1H, J=8.8 Hz), 8.17 (d, 1H, J=1.8 Hz), 7.96 (m, 1H), 7.72-7.68 (m, 2H), 7.54 (m, 1H), 7.02 (d, 1H, J=8.5 Hz), 4.98 (s, 2H), 4.09-4.02 (m, 2H), 3.57-3.41 (m, 4H), 2.89 (s, 3H), 1.89-1.83 (m, 4H), 1.22-1.17 (m, 3H).

Step 2. 6-(1-Methyl-6-isoquinolyl)spiro[4H-1,3-benzodioxine-2,4'-piperidine]. Ethyl 6-(1-methyl-6-isoquinolyl)spiro[4H-1,3-benzodioxine-2,4'-piperidine]-1'-carboxylate (0.966 g, 2.31 mmol), NaOH in water (6 M) (4.2 mL, 25 mmol) and ethanol (12 mL) were combined and heated at 90° C. for 23 h. The reaction was cooled to RT and concentrated, then diluted with water and extracted into EtOAc. The organic layer was washed with brine, dried over MgSO$_4$, filtered and concentrated. The residue was triturated with ether and dried by high vacuum to afford an orange solid. mp: 168° C.; LCMS: m/z=347 (M+1); $^1$H NMR (400 MHz, DMSO-d$_6$) δ: 8.34 (d, 1H, J=5.8 Hz), 8.24 (d, 1H, J=1.7 Hz), 8.16 (m, 1H), 7.97-7.94 (m, 1H), 7.68 (m, 2H), 7.68 (m, 2H), 7.60 (m, 1H), 6.99 (d, 1H, J=8.5 Hz), 4.94 (s, 2H), 2.89 (s, 3H), 2.76 (m, 4H), 1.78 (m, 4H).

Step 3. N-Methoxy-6-(4-methyl-3-quinolyl)spiro[chromane-2,4'-piperidine]-1'-carboxamide. This compound was synthesized using the procedure used to prepare Example 179 in 42% yield. Analysis: mp 193° C.; LCMS: m/z=418 (M+1); 1H NMR (400 MHz, DMSO-d$_6$) δ 9.74 (s, 1H), 8.72 (s, 1H), 8.18 (d, 1H, J=8.0 Hz), 8.03 (d, 1H, J=8.1 Hz), 7.78-7.74 (m, 1H), 7.69-7.65 (m, 1H), 7.19 (m, 2H), 6.94 (d, 1H, J=8.1 Hz), 3.65 (m, 2H), 3.54 (s, 3H), 3.18-3.13 (m, 2H), 2.84-2.81 (m, 2H), 2.63 (s, 3H), 1.87-1.84 (m, 2H), 1.75-1.71 (m, 2H), 1.61-1.55 (m, 2H).

Example 193. N-isopropoxy-6-(4-methyl-3-quinolyl)spiro[chromane-2,4'-piperidine]-1'-carboxamide

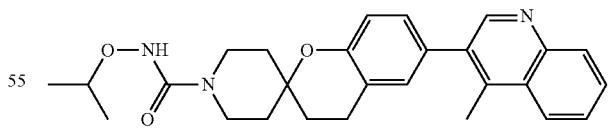

This compound was synthesized using the procedure to prepare Example 192 using intermediate 3 and O-isopropylhydroxylamine HCl in 18% yield. Analysis: mp: 91° C.; LCMS: m/z=446 (M+1); 1H NMR (400 MHz, MeOD) δ: 8.64 (s, 1H), 8.17 (d, 1H, J=8.2 Hz), 8.02 (d, 1H, J=8.2 Hz), 7.77-7.73 (m, 1H), 7.68-7.64 (m, 1H), 7.12 (m, 2H), 6.95 (m, 1H), 4.01-3.93 (m, 1H), 3.81-3.78 (m, 2H), 3.32-3.26 (m, 2H), 2.89-2.85 (m, 2H), 2.65 (s, 3H), 1.89-1.83 (m, 4H), 1.67-1.60 (m, 2H), 1.22 (d, 6H, J=6.2 Hz).

Example 194. 6-(1-Methyl-6-isoquinolyl)spiro[4H-1,3-benzodioxine-2,4'-piperidine]-1'-carboxamide

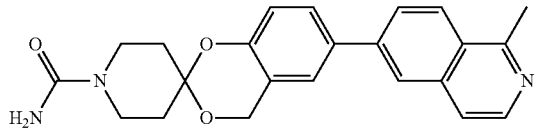 [SMILES: Cc1nccc2cc(-c3ccc4c(c3)COC3(CCN(C(N)=O)CC3)O4)ccc12]

This compound was synthesized using intermediate 1 and 6-bromo-1-methyl-isoquinoline by the procedure to prepare Example 183 in 56% yield. Analysis: mp: 218° C.; LCMS: m/z=390 (M+1); $^1$H NMR (400 MHz, DMSO-d$_6$) δ: 8.34 (d, 1H, J=5.7 Hz), 8.25 (d, 1H, J=8.8 Hz), 8.17 (d, 1H, J=1.7 Hz), 7.98-7.95 (m, 1H), 7.71-7.68 (m, 2H), 7.63 (m, 1H), 7.01 (d, 1H, J=8.5 Hz), 6.04 (s, 2H), 4.97 (s, 2H), 3.44-3.39 (m, 4H), 2.89 (s, 3H), 1.81 (m, 4H).

Example 195. N-methoxy-6-(1-methyl-6-isoquinolyl)spiro[4H-1,3-benzodioxine-2,4'-piperidine]-1'-carboxamide

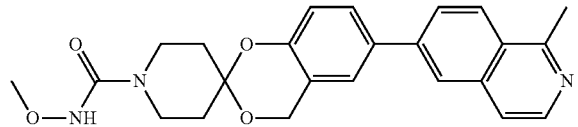

This compound was synthesized using intermediate 1, 6-bromo-1-methyl-isoquinoline and O-methylhydroxy amine HCl by the procedure to prepare Example 179 in 65% yield. Analysis: mp: 219° C.; LCMS: m/z=420 (M+1); $^1$H NMR (400 MHz, DMSO-d$_6$) δ: 9.81 (s, 1H), 8.34 (d, 1H, J=5.7 Hz), 8.25 (d, 1H, J=8.8 Hz), 8.17 (d, 1H, J=1.7 Hz), 7.96 (m, 1H), 7.71-7.68 (m, 2H), 7.62 (d, 1H, J=2.2 Hz), 7.01 (d, 1H, J=8.5 Hz), 4.97 (s, 2H), 3.54 (s, 3H), 3.43-3.37 (m, 4H), 2.89 (s, 3H), 1.86-1.82 (m, 4H).

Example 196. N-Ethoxy-6-(1-methyl-6-isoquinolyl)spiro[4H-1,3-benzodioxine-2,4'-piperidine]-1'-carboxamide

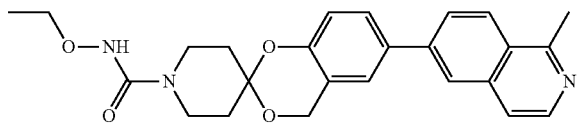 [SMILES: CCONC(=O)N1CCC2(CC1)OCc1cc(-c3ccc4c(C)nccc4c3)ccc1O2]

This compound was synthesized using intermediate 1, 6-bromo-1-methyl-isoquinoline and O-ethylhydroxy amine HCl by the procedure to prepare Example 179 in 63% yield. Analysis: mp: 179° C.; LCMS: m/z=434 (M+1); $^1$H NMR (400 MHz, DMSO-d$_6$) δ, 9.72 (s, 1H), 8.34 (d, 1H, J=5.7 Hz), 8.25 (d, 1H, J=8.8 Hz), 8.17 (d, 1H, J=1.7 Hz), 7.96 (m, 1H), 7.71-7.68 (m, 2H), 7.63 (m, 1H), 7.01 (d, 1H, J=8.5 Hz), 4.97 (s, 2H), 3.78-3.72 (m, 2H), 3.39 (m, 4H), 2.89 (s, 3H), 1.84-1.81 (m, 4H), 1.14-1.11 (m, 3H).

Example 197. N-ethyl-6-(1-methyl-6-isoquinolyl)spiro[4H-1,3-benzodioxine-2,4'-piperidine]-1'-carboxamide

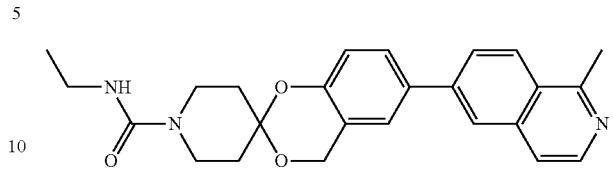

This compound was synthesized using intermediate 1, 6-bromo-1-methyl-isoquinoline and ethylisocyanate by the procedure to prepare Example 178 in 46% yield. Analysis: mp: 178° C.; LCMS: m/z=418 (M+1); $^1$H NMR (400 MHz, DMSO-d$_6$) δ, 9.72 (s, 1H), 8.34 (d, 1H, J=5.8 Hz), 8.25 (d, 1H, J=8.8 Hz), 8.17 (m, 1H), 7.96 (m, 1H), 7.71-7.68 (m, 2H), 7.63 (m, 1H), 7.01 (d, 1H, J=8.6 Hz), 6.59-6.56 (m, 1H), 4.97 (s, 2H), 3.43-3.40 (m, 4H), 3.09-3.02 (m, 2H), 2.89 (s, 3H), 1.81 (m, 4H), 1.03-1.00 (m, 3H).

Example 198. Ethyl 6-(3-chloro-6-isoquinolyl)spiro[4H-1,3-benzodioxine-2,4'-piperidine]-1'-carboxylate

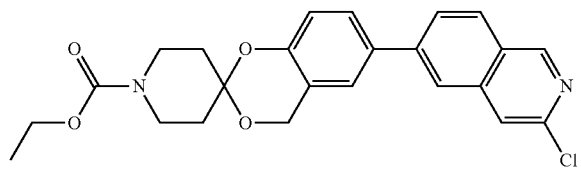 [SMILES: CCOC(=O)N1CCC2(CC1)OCc1cc(-c3ccc4cnc(Cl)cc4c3)ccc1O2]

6-Bromo-3-chloroisoquinoline (0.504 g, 2.0784 mmol), ethyl 6-(4,4,5,5-tetramethyl-1,3,2-dioxaborolan-2-yl)spiro[4H-1,3-benzodioxine-2,4'-piperidine]-1'-carboxylate (0.962 g, 2.385 mmol), tetrakis(triphenylphosphine)palladium(0) (0.242 g, 0.209 mmol), Na$_2$CO$_3$ in water (1 M) (7 mL, 7 mmol) and 1,4-dioxane (14 g, 12 mL, 160 mmol) were combined, purged with argon and heated at 100° C. under nitrogen for 20 h. The reaction was cooled to RT, filtered through a pad of Celite, and washed with DCM. The filtrate was concentrated, the residue was dissolved in EtOAc, and washed with saturated aqueous NaHCO$_3$ solution, then brine. The organic layer was dried over MgSO$_4$, filtered and concentrated. The residue was purified by ISCO silica gel chromatography (30-65% EtOAc/heptane) to give a white solid (649 mg, 68%). Analysis: mp: 92° C.; LCMS: m/z=439 (M+1); $^1$H NMR (400 MHz, DMSO-d$_6$) δ: 9.20 (s, 1H), 8.24-8.19 (m, 2H), 8.01 (m, 2H), 7.71-7.68 (m, 1H), 7.62 (m, 1H), 7.03 (d, 1H, J=8.5 Hz), 4.98 (s, 2H), 4.09-4.03 (m, 2H), 3.57-3.44 (m, 4H), 1.92-1.82 (m, 4H), 1.21-1.18 (m, 3H).

Example 199. 6-(1-Methyl-6-isoquinolyl)spiro[4H-1,3-benzodioxine-2,4'-piperidine]-1'-carbohydroxamic acid

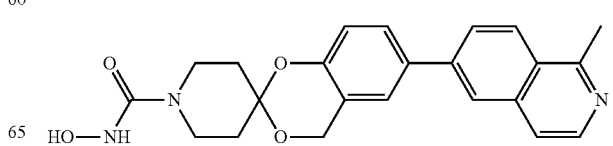

This compound was synthesized using intermediate 1, 6-bromo-1-methyl-isoquinoline and hydroxylamine by the procedure to prepare Example 189 in 6% yield. Analysis: mp: 193° C.; LCMS: m/z=406 (M+1); $^1$H NMR (400 MHz, MeOD) δ: 8.25-8.22 (m, 2H), 8.04 (s, 1H), 7.92-7.89 (m, 1H), 7.66 (d, 1H, J=5.9 Hz), 7.62-7.60 (m, 1H), 7.48 (m, 1H), 6.97 (d, 1H, J=8.5 Hz), 5.49 (s, 1H), 4.97 (s, 2H), 3.54-3.51 (m, 4H), 2.92 (s, 3H), 1.94-1.91 (m, 4H).

Example 200. Ethyl 6-(3-methyl-6-isoquinolyl)spiro[4H-1,3-benzodioxine-2,4'-piperidine]-1'-carboxylate

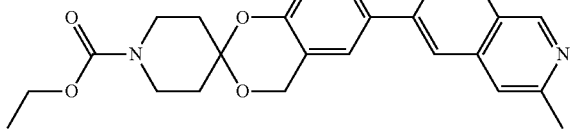

Ethyl 6-(3-chloro-6-isoquinolyl)spiro[4H-1,3-benzodioxine-2,4'-piperidine]-1'-carboxylate (0.638 g, 1.454 mmol), methylboronic acid (0.446 g, 7.45 mmol), bis(di-tert-butyl(4-dimethyl-aminophenyl)phosphine)dichloropalladium(II) (0.216 g, 0.289797 mmol), cesium carbonate (2.402 g, 7.37 mmol), water (1.9 g, 1.9 mL, 100 mmol) and 1,4-dioxane (80 g, 70 mL, 900 mmol) were combined, purged with argon and then heated at 100° C. under nitrogen for 19 h. The reaction was cooled to RT, filtered through a pad of Celite, and washed with DCM. The filtrate was concentrated, the residue dissolved in DCM, and washed with saturated aqueous NaHCO$_3$ solution, then brine. The organic layer was dried over Na$_2$CO$_3$, filtered and concentrated. The residue was purified by ISCO silica gel chromatography (50-100% EtOAc/heptane) to afford a yellow solid (303 mg, 47%). Analysis: LCMS: m/z=419 (M+1); $^1$H NMR (400 MHz, DMSO-d$_6$) δ: 9.21 (s, 1H), 8.11 (d, 1H, J=8.5 Hz), 8.06 (s, 1H), 7.87 (m, 1H), 7.68-7.65 (m, 2H), 7.60 (m, 1H), 7.00 (d, 1H, J=8.5 Hz), 4.97 (s, 2H), 4.09-4.02 (m, 2H), 3.55-3.45 (m, 4H), 2.61 (s, 3H), 1.87-1.83 (m, 4H), 1.22-1.18 (m, 3H).

Example 201. 6-(3-Methyl-6-isoquinolyl)spiro[4H-1,3-benzodioxine-2,4'-piperidine]-1'-carboxamide

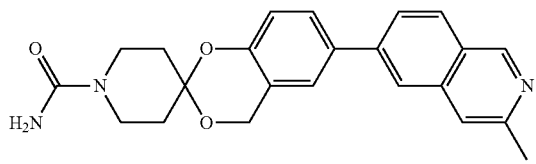

Step 1. Ethyl 6-(3-methyl-6-isoquinolyl)spiro[4H-1,3-benzodioxine-2,4'-piperidine]-1'-carboxylate (0.303 g, 0.724 mmol), NaOH in water (6 M) (1.3 mL, 7.9 mmol) and ethanol (3.8 mL) were combined and heated at 85° C. for 2 days. The reaction was cooled to RT and concentrated. The residue was diluted with water and EtOAc. The solid that formed was collected and dried under high vacuum at 40° C. overnight to yield a yellow solid (221 mg, 88%).

Step 2. 6-(3-Methyl-6-isoquinolyl)spiro[4H-1,3-benzodioxine-2,4'-piperidine]-1'-carboxamide. This compound was synthesized using the procedure to prepare Example 183 in 40% yield. Analysis: mp: 210° C.; LCMS: m/z=390 (M+1); $^1$H NMR (400 MHz, DMSO-d$_6$) δ: 8.21 (s, 1H), 8.11 (d, 1H, J=8.7 Hz), 8.06 (s, 1H), 7.89-7.86 (m, 1H), 7.69-7.65 (m, 2H), 7.59 (d, 1H, J=2.2 Hz), 7.00 (d, 1H, J=8.5 Hz), 6.04 (s, 2H), 4.97 (s, 2H), 3.44-3.40 (m, 4H), 2.61 (s, 3H), 1.81 (m, 4H).

Example 202. N-Ethyl-6-(3-methyl-6-isoquinolyl)spiro[4H-1,3-benzodioxine-2,4'-piperidine]-1'-carboxamide

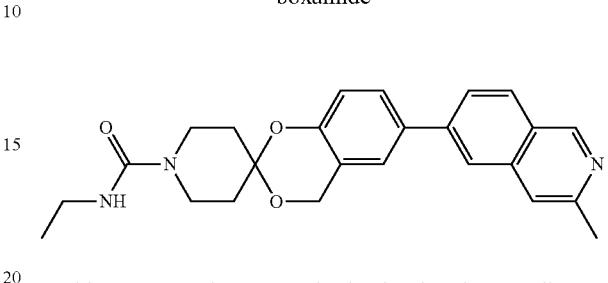

This compound was synthesized using intermediate 1, 6-bromo-3-methyl-isoquinoline and ethylisocyanate by the procedure to prepare Example 178 in 55% yield. Analysis: mp: 187° C.; LCMS: m/z=418 (M+1); $^1$H NMR (400 MHz, DMSO-d$_6$) δ: 9.21 (s, 1H), 8.21 (d, 1H, J=8.6 Hz), 8.07 (s, 1H), 7.89-7.86 (m, 1H), 7.68-7.65 (m, 2H), 7.59 (d, 1H, J=2.1 Hz), 7.00 (d, 1H, J=8.5 Hz), 6.60-6.57 (m, 1H), 4.97 (s, 2H), 3.42 (m, 4H), 3.09-3.02 (m, 2H), 2.61 (s, 3H), 1.81 (m, 4H), 1.03-1.00 (m, 3H).

Example 203. N-Ethoxy-6-(3-methyl-6-isoquinolyl)spiro[4H-1,3-benzodioxine-2,4'-piperidine]-1'-carboxamide

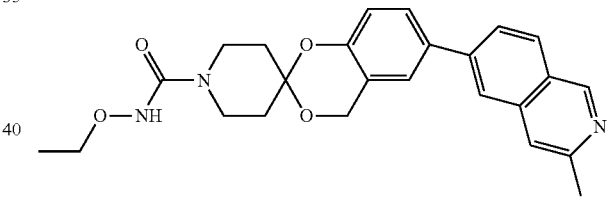

This compound was synthesized using intermediate 1, 6-bromo-3-methyl-isoquinoline and O-ethylhydroxylamine by the procedure to prepare Example 179 in 59% yield. Analysis: mp: 181° C.; LCMS: m/z=434 (M+1); $^1$H NMR (400 MHz, DMSO-d$_6$) δ: 9.72 (s, 1H), 9.21 (s, 1H), 8.12 (d, 1H, J=8.6 Hz), 8.06 (m, 1H), 7.89-7.86 (m, 1H), 7.69-7.65 (m, 2H), 7.60 (m, 1H), 7.01 (d, 1H, J=8.5 Hz), 4.96 (s, 2H), 3.78-3.72 (m, 2H), 3.40-3.36 (m, 4H), 2.61 (s, 3H), 1.84-1.81 (m, 4H), 1.14-1.11 (m, 3H).

Example 204. 6-(3-Methyl-6-isoquinolyl)spiro[4H-1,3-benzodioxine-2,4'-piperidine]-1'-carbohydroxamic acid

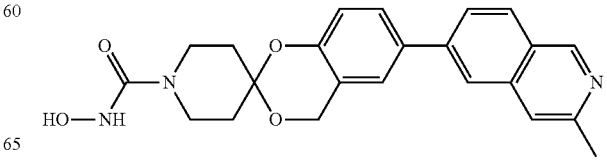

CDI (0.08 g, 0.49337 mmol), O-tetrahydropyran-2-ylhydroxylamine (0.066 g, 0.56338 mmol), DIPEA (0.16 mL, 0.917 mmol), DCM (2 mL) and THF (0.5 mL) were combined and stirred at RT for 2.5 h. 6-(3-Methyl-6-isoquinolyl)spiro[4H-1,3-benzodioxine-2,4'-piperidine] (0.109 g, 0.3147 mmol) in DCM (2 mL) was added and stirred for 24 h at RT. The reaction was diluted with DCM, washed with saturated ammonium chloride solution, saturated NaHCO₃ solution, then brine. The organic layer was dried over Na₂CO₃, filtered and concentrated. The product in DCM (3.0 mL) was added HCl in dioxane (4 M; 2.0 mL) and stirred for 1.5 h. The solution was concentrated, and the product purified by preparatory HPLC and lyophilized. The lyophilate was diluted with DCM, washed with saturated NaHCO₃ solution, then water, and brine. The organic phase was dried over Na₂SO₄, filtered and concentrated to afford a yellow solid (12 mg, 9%). Analysis: mp: 104° C.; LCMS: m/z=406 (M+H); ¹H NMR (400 MHz, MeOD) δ: 9.11 (s, 1H), 8.08 (d, 1H, J=8.6 Hz), 8.00 (m, 1H), 7.86 (m, 1H), 7.86 (m, 1H), 7.68 (s, 1H), 7.64-7.61 (m, 1H), 7.50 (d, 1H, J=2.1 Hz), 6.99 (d, 1H, J=8.6 Hz), 4.99 (s, 2H), 3.54-3.51 (m, 4H), 2.67 (s, 3H), 1.95-1.92 (m, 4H).

Example 205. N-Methoxy-6-(3-methyl-6-isoquinolyl)spiro[4H-1,3-benzodioxine-2,4'-piperidine]-1'-carboxamide

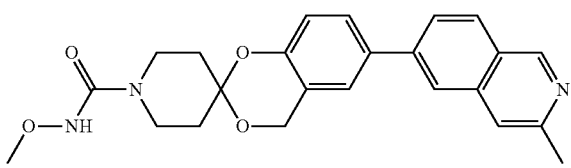 [SMILES: CCNC(=O)N1CCC2(CC1)OCc1cc(-c3ccc4cnc(C)cc4c3)ccc1O2]

This compound was synthesized using intermediate 1, 6-bromo-3-methyl-isoquinoline and O-methylhydroxylamine by the procedure to prepare Example 179 in 24% yield. Analysis: mp: 173° C.; LCMS: m/z=420 (M+1); ¹H NMR (400 MHz, DMSO-d₆) δ: 9.81 (s, 1H), 9.21 (s, 1H), 8.12 (d, 1H, J=8.6 Hz), 8.06 (m, 1H), 7.89-7.86 (m, 1H), 7.69-7.65 (m, 2H), 7.59 (m, 1H), 7.01 (d, 1H, J=8.5 Hz), 4.97 (s, 2H), 3.54 (s, 3H), 3.41-3.36 (m, 4H), 2.61 (s, 3H), 1.83 (m, 4H).

Example 206. 6-(3-Methyl-6-isoquinolyl)spiro[chromane-2,4'-piperidine]-1'-carboxamide

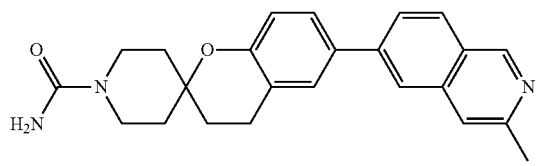 [SMILES: Cc1cc2cc(-c3ccc4c(c3)CCC3(CCN(C(N)=O)CC3)O4)ccc2cn1]

Step 1. 6-Bromo-3-chloroisoquinoline (2.015 g, 8.309 mmol), tert-butyl 6-(4,4,5,5-tetramethyl-1,3,2-dioxaborolan-2-yl)spiro[chromane-2,4'-piperidine]-1'-carboxylate (3.971 g, 9.248 mmol), tetrakis(triphenylphosphine)palladium(0) (1.031 g, 0.892 mmol), Na₂CO₃ in water (1 M) (30 mL, 30 mmol) and 1,4-dioxane (56 g, 50 mL, 630 mmol) were combined, purged with argon and heated at 100° C. under nitrogen for 4 days. The reaction was cooled to RT, filtered through a pad of Celite, and washed with DCM. The filtrate was concentrated and the residue was dissolved in DCM, washed with saturated aq. NaHCO₃, and then brine. The organic layer was dried over Na₂SO₄, filtered and concentrated. The residue was purified by ISCO silica gel chromatography (30% EtOAc/heptane) to afford a yellow solid (3.23 g, 79%). Analysis: LCMS: m/z=465 (M+1); ¹H NMR (400 MHz, DMSO-d₆) δ: 9.18 (s, 1H), 8.22-8.18 (m, 2H), 8.02-7.99 (m, 2H), 7.62-7.58 (m, 2H), 6.96 (d, 1H, J=8.4 Hz), 3.74-3.71 (m, 2H), 3.22-3.18 (m, 2H), 2.87-2.84 (m, 2H), 1.88-1.84 (m, 2H), 1.75-1.71 (m, 2H), 1.61-1.53 (m, 2H), 1.41 (s, 9H).

Step 2. tert-Butyl 6-(3-chloro-6-isoquinolyl)spiro[chromane-2,4'-piperidine]-1'-carboxylate (3.225 g, 6.935 mmol), methylboronic acid (2.12 g, 35.4 mmol), bis(di-tert-butyl(4-dimethylaminophenyl)phosphine)dichloropalladium(II) (1.005 g, 1.348 mmol), cesium carbonate (12.178 g, 37.4 mmol), water (9 g, 9 mL, 500 mmol) and 1,4-dioxane (400 g, 300 mL, 4000 mmol) were combined, purged with argon and heated at 100° C. under nitrogen for 19 h. The reaction was cooled to RT, then filtered through a pad of Celite, and washed with DCM. The filtrate was concentrated and the residue was dissolved in DCM, washed with saturated aq. NaHCO₃, then brine. The organic layer was dried over Na₂SO₄, filtered and concentrated. The residue was purified by ISCO silica gel chromatography (10-60% EtOAc/heptane) to give 1.38 g (42%). LCMS: m/z=445 (M+1); ¹H NMR (400 MHz, DMSO-d₆) δ: 9.19 (s, 1H), 8.09 (d, 1H, J=8.7 Hz), 8.04 (s, 1H), 7.87 (m, 1H), 7.65 (s, 1H), 7.59-7.56 (m, 2H), 6.94 (d, 1H, J=8.4 Hz), 3.74-3.71 (m, 2H), 3.23-3.18 (m, 2H), 2.87-2.83 (m, 2H), 2.61 (s, 3H), 1.87-1.84 (m, 2H), 1.75-1.71 (m, 2H), 1.60-1.53 (m, 2H), 1.41 (s, 9H).

Step 3. 6-(3-Methyl-6-isoquinolyl)spiro[chromane-2,4'-piperidine] 2HCl. tert-Butyl 6-(3-methyl-6-isoquinolyl)spiro[chromane-2,4'-piperidine]-1'-carboxylate (1.38 g, 3.10 mmol) and EtOAc (18 mL) were combined in a flask. HCl (4 M) in dioxane (9 mL, 36 mmol) was added and the reaction was stirred at RT for 24 h. The reaction was filtered and the isolated solid triturated with ether, then dried by high vacuum at 40° C. to afford a yellow solid (1.132 g, 83%). Analysis: mp>300° C.; LCMS: m/z=345 (M+1); ¹H NMR (400 MHz, DMSO-d₆) δ: 9.73 (s, 1H), 9.12 (m, 1H), 8.99 (m, 1H), 8.46 (d, 1H, J=8.8 Hz), 8.40 (s, 1H), 8.26-8.23 (m, 1H), 8.19 (s, 1H), 7.77-7.73 (m, 2H), 7.06 (d, 1H, J=8.4 Hz), 3.22 (m, 2H), 3.15-3.10 (m, 2H), 2.91-2.88 (m, 2H), 2.79 (s, 3H), 1.99-1.85 (m, 6H).

Step 4. 6-(3-Methyl-6-isoquinolyl)spiro[chromane-2,4'-piperidine]-1'-carboxamide. This compound was synthesized using the procedure to prepare Example 183 in 56% yield. Analysis: mp: 193° C.; LCMS: m/z=388 (M+1); ¹H NMR (400 MHz, DMSO-d₆) δ: 9.19 (s, 1H), 8.09 (d, 1H, J=8.6 Hz), 8.05 (s, 1H), 7.89-7.86 (m, 1H), 7.65 (s, 2H), 7.61-7.56 (m, 2H, J=2.2 Hz), 6.94 (d, 1H, J=8.4 Hz), 5.96 (s, 2H), 3.71-3.67 (m, 2H), 3.17-3.11 (m, 2H), 2.87-2.84 (m, 2H), 2.61 (s, 3H), 1.86-1.83 (m, 2H), 1.71-1.67 (m, 2H), 1.59-1.52 (m, 2H).

Example 207. N-Ethoxy-6-(3-methyl-6-isoquinolyl)spiro[chromane-2,4'-piperidine]-1'-carboxamide

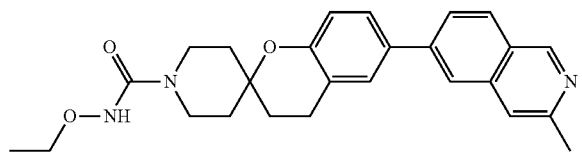 [SMILES: CCONC(=O)N1CCC2(CCc3cc(-c4ccc5cnc(C)cc5c4)ccc3O2)CC1]

This compound was synthesized using 6-(3-methyl-6-isoquinolyl)spiro[chromane-2,4'-piperidine] 2HCl and O-ethylhydroxylamine HCl by the procedure to prepare Example 179 in 67% yield. Analysis: mp 180° C.; LCMS: m/z=432 (M+1); $^1$H NMR (400 MHz, DMSO-$d_6$) δ: 9.64 (s, 1H), 9.19 (s, 1H), 8.09 (d, 1H, J=8.6 Hz), 8.04 (s, 1H), 7.88-7.86 (m, 1H), 7.65 (s, 1H), 7.59-7.56 (m, 2H), 6.94 (d, 1H, J=8.3 Hz), 3.77-3.72 (m, 2H), 3.66-3.62 (m, 2H), 3.16-3.11 (m, 2H), 2.86-2.83 (m, 2H), 2.61 (s, 3H), 1.86-1.83 (m, 2H), 1.73-1.69 (m, 2H), 1.60-1.53 (m, 2H), 1.14-1.11 (m, 3H).

Example 208. N-Ethyl-6-(3-methyl-6-isoquinolyl)spiro[chromane-2,4'-piperidine]-1'-carboxamide

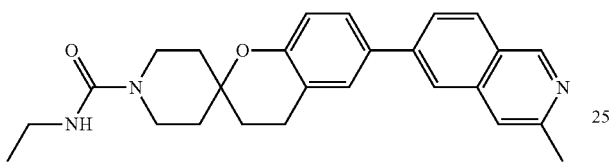

This compound was synthesized using 6-(3-methyl-6-isoquinolyl)spiro[chromane-2,4'-piperidine] 2HCl and ethylisocycante by the procedure to prepare Example 178 in 35% yield. Analysis: mp: 145° C.; LCMS: m/z=416 (M+1); $^1$H NMR (400 MHz, DMSO-$d_6$) δ: 9.19 (s, 1H), 8.09 (d, 1H, J=8.7 Hz), 8.04 (s, 1H), 7.87 (m, 1H), 7.65 (s, 1H), 7.59-7.56 (m, 2H), 6.93 (d, 1H, J=8.3 Hz), 6.49 (m, 1H), 3.71-3.68 (m, 2H), 3.17-3.11 (m, 2H), 3.09-3.02 (m, 2H), 2.87-2.83 (m, 2H), 2.61 (s, 3H), 1.86-1.83 (m, 2H), 1.71-1.68 (m, 2H), 1.57-1.52 (m, 2H), 1.03-1.00 (m, 3H).

Example 209. N-Methoxy-6-(3-methyl-6-isoquinolyl)spiro[chromane-2,4'-piperidine]-1'-carboxamide

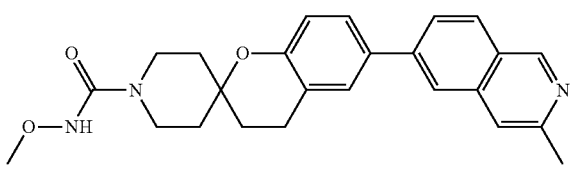

This compound was synthesized using 6-(3-methyl-6-isoquinolyl)spiro[chromane-2,4'-piperidine] 2HCl and O-methylhydroxylamine HCl by the procedure to prepare Example 179 in 51% yield. Analysis: mp: 139° C.; LCMS: m/z=418 (M+1); $^1$H NMR (400 MHz, DMSO-$d_6$) δ: 9.72 (s, 1H), 9.19 (s, 1H), 8.09 (d, 1H, J=8.6 Hz), 8.04 (s, 1H), 7.87 (m, 1H), 7.65 (s, 1H), 7.59-7.56 (m, 2H), 6.94 (d, 1H, J=8.3 Hz), 3.65-3.62 (m, 2H), 3.54 (s, 3H), 3.16-3.11 (m, 2H), 2.86-2.83 (m, 2H), 2.61 (s, 3H), 1.86-1.83 (m, 2H), 1.73-1.70 (m, 2H), 1.60-1.53 (m, 2H).

Example 210. N-Methoxy-6-(8-methoxy-7-quinolyl)spiro[chromane-2,4'-piperidine]-1'-carboxamide

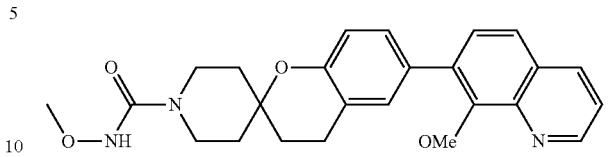

This compound was synthesized using 6-(8-methoxy-7-quinolyl)spiro[chromane-2,4'-piperidine]2HCl and O-methylhydroxylamine HCl by the procedure to prepare Example 179 in 31% yield. Analysis: mp: 76° C.; LCMS: m/z=434 (M+1); $^1$H NMR (400 MHz, DMSO-$d_6$) δ: 9.74 (s, 1H), 8.93 (m, 1H), 8.39-8.36 (m, 1H), 7.75 (d, 1H, J=8.6 Hz), 7.58 (d, 1H, J=8.5 Hz), 7.56-7.53 (m, 1H), 7.41-7.37 (m, 2H), 6.90 (d, 1H, J=8.3 Hz), 3.93 (s, 3H), 3.66-3.62 (m, 2H), 3.54 (s, 3H), 3.18-3.11 (m, 2H), 2.84-2.81 (m, 2H), 1.86-1.83 (m, 2H), 1.74-1.71 (m, 2H), 1.61-1.53 (m, 2H).

Example 211. N-Ethoxy-6-(8-methoxy-7-quinolyl)spiro[chromane-2,4'-piperidine]-1'-carboxamide

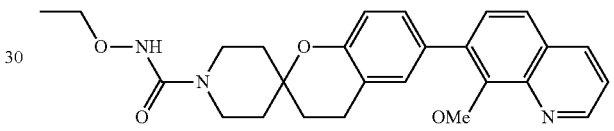

This compound was synthesized using 6-(8-methoxy-7-quinolyl)spiro[chromane-2,4'-piperidine]2HCl and O-ethylhydroxylamine HCl by the procedure to prepare Example 179 in 31% yield. Analysis: mp: 164° C.; LCMS: m/z=448 (M+1); $^1$H NMR (400 MHz, DMSO-$d_6$) δ: 9.65 (s, 1H), 8.93 (m, 1H), 8.39-8.36 (m, 1H), 7.75 (d, 1H, J=8.6 Hz), 7.58 (d, 1H, J=8.5 Hz), 7.56-7.53 (m, 1H), 7.41-7.37 (m, 2H), 6.90 (d, 1H, J=8.3 Hz), 3.93 (s, 3H), 3.78-3.73 (m, 2H), 3.66-3.63 (m, 2H), 3.18-3.12 (m, 2H), 2.84-2.80 (m, 2H), 1.86-1.83 (m, 2H), 1.74-1.70 (m, 2H), 1.60-1.53 (m, 2H), 1.14-1.11 (m, 3H).

Example 212. 6-(8-methyl-7-quinolyl)-4-oxo-spiro[chromane-2,4'-piperidine]-1'-carboxamide

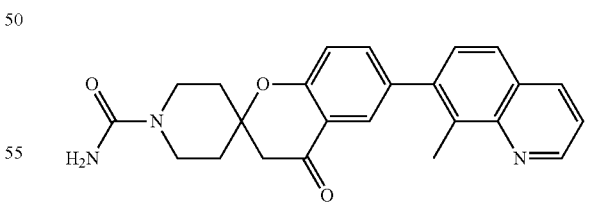

Step 1. tert-Butyl 6-(8-methyl-7-quinolyl)-4-oxo-spiro[chromane-2,4'-piperidine]-1'-carboxylate. tert-Butyl 6-bromo-4-oxo-spiro[chromane-2,4'-piperidine]-1'-carboxylate (1.221 g, 3.081 mmol), 8-methyl-7-(4,4,5,5-tetramethyl-1,3,2-dioxaborolan-2-yl)quinoline (0.815 g, 3.027 mmol), tetrakis(triphenylphosphine)palladium(0) (0.337 g, 0.292 mmol), Na$_2$CO$_3$ in water (1 M) (8.6 mL, 9 mmol) and 1,4-dioxane (17 g, 15 mL, 190 mmol) were combined, purged with argon and heated at 100° C. under nitrogen for 18 h. The reaction was cooled to RT, filtered through a pad of Celite, and washed with DCM. The filtrate was concentrated and the residue was dissolved in DCM, washed with saturated aq. NaHCO₃, then brine. The organic layer was dried over Na₂SO₄, filtered and concentrated. Residue was purified by ISCO silica gel chromatography (10-35% EtOAc/heptane) to afford a white solid (1.2 g, 81%). LCMS: m/z=459 (M+1); ¹H NMR (400 MHz, DMSO-d₆) δ: 8.98 (m, 1H), 8.40-8.37 (m, 1H), 7.88 (d, 1H, J=8.4 Hz), 7.74 (d, 1H, J=3.2 Hz), 7.72-7.69 (m, 1H), 7.59-7.56 (m, 1H), 7.49 (d, 1H, J=8.4 Hz), 7.22 (d, 1H, J=8.5 Hz), 3.77-3.74 (m, 2H), 3.18 (m, 2H), 2.93 (s, 2H), 2.67 (s, 3H), 1.97-1.94 (m, 2H), 1.72-1.65 (m, 2H), 1.41 (s, 9H).

Step 2. tert-Butyl 6-(8-methyl-7-quinolyl)-4-oxo-spiro[chromane-2,4'-piperidine]-1'-carboxylate (0.101 g, 0.2202 mmol) in EtOAc (2.0 mL) was added HCl (4 M) in dioxane (0.65 mL, 2.6 mmol) and was stirred at RT for 20 h. The precipitate was collected by filtration, triturated with ether and dried by high vacuum at 40° C. to afford a yellow solid (66 mg, 66%). mp: 278° C.; LCMS: m/z=360 (M+1); ¹H NMR (400 MHz, DMSO-d₆) δ: 9.04-9.02 (m, 1H), 8.95 (m, 1H), 8.77 (m, 1H), 8.51 (m, 1H), 7.95 (d, 1H, J=8.4 Hz), 7.78-7.74 (m, 2H), 7.67-7.64 (m, 1H), 7.54 (d, 1H, J=8.4 Hz), 7.29 (d, 1H, J=8.4 Hz), 3.23-3.12 (m, 4H), 3.01 (s, 2H), 2.68 (s, 3H), 2.20-2.18 (m, 2H), 1.99-1.91 (m, 2H).

Step 3. 6-(8-methyl-7-quinolyl)-4-oxo-spiro[chromane-2,4'-piperidine]-1'-carboxamide. This compound was synthesized using the procedure to prepare Example 183 in 41% yield. Analysis: mp: 213° C.; LCMS: m/z=402 (M+1); ¹H NMR (400 MHz, DMSO-d₆) δ: 8.98 (m, 1H), 8.40-8.37 (m, 1H), 7.88 (d, 1H, J=8.4 Hz), 7.74 (d, 1H, J=2.3 Hz), 7.71-7.69 (m, 1H), 7.59-7.56 (m, 1H), 7.50 (d, 1H, J=8.4 Hz), 7.22 (d, 1H, J=8.4 Hz), 6.00 (s, 2H), 3.74-3.71 (m, 2H), 3.19-3.13 (m, 2H), 2.92 (s, 2H), 2.67 (s, 3H), 1.93-1.89 (m, 2H), 1.70-1.63 (m, 2H).

Example 213. 4-Hydroxy-6-(8-methyl-7-quinolyl)spiro[chromane-2,4'-piperidine]-1'-carboxamide

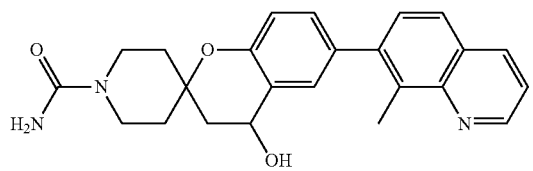 [SMILES: Cc1c(-c2ccc3c(c2)C(O)CC2(CCN(C(N)=O)CC2)O3)ccc2cccnc12]

Step 1. tert-Butyl 4-hydroxy-6-(8-methyl-7-quinolyl)spiro[chromane-2,4'-piperidine]-1'-carboxylate. NaBH₄ (0.047 g, 0.0497 mL, 1.24 mmol) was added to a solution of tert-butyl 6-(8-methyl-7-quinolyl)-4-oxo-spiro[chromane-2,4'-piperidine]-1'-carboxylate (0.558 g, 1.217 mmol) in methanol (12 mL) on an ice-water bath. The reaction was stirred at ice-bath temperature for 4.5 h, at which time an additional aliquot of NaBH₄ (35 mg) was added. The reaction was stirred an additional 2 h and quenched by dropwise addition of 1 N aqueous Na₂CO₃ solution. The reaction was concentrated, the residue dissolved in EtOAc, washed with saturated aq. NaHCO₃ and brine. The organic layer was dried over Na₂SO₄, filtered and concentrated, then purified by preparatory HPLC and lyophilized. The lyophilate was diluted with DCM, washed with saturated aq. NaHCO₃ solution, then brine. The organic phase was dried with Na₂SO₄, filtered and concentrated to afford a solid. LCMS: m/z=461 (M+1); 1H NMR (400 MHz, DMSO-d₆) δ; 8.97 (m, 1H), 8.38-8.35 (m, 1H), 7.86 (d, 1H, J=8.4 Hz), 7.56-7.53 (m, 1H), 7.50-7.47 (m, 2H), 7.24 (m, 1H), 6.91 (d, 1H, J=8.4 Hz), 5.47 (d, 1H, J=6.0 Hz), 4.81-4.76 (m, 1H), 3.74-3.71 (m, 2H), 3.15 (m, 2H), 2.70 (s, 3H), 2.18-2.13 (m, 1H), 1.86-1.55 (m, 5H), 1.42 (s, 9H).

Step 2. tert-Butyl 4-hydroxy-6-(8-methyl-7-quinolyl)spiro[chromane-2,4'-piperidine]-1'-carboxylate (0.12 g, 0.2605 mmol) in EtOAc (4 mL) was added HCl (4 M) in dioxane (0.8 mL, 3 mmol) and stirred at RT for 16 h. The reaction was concentrated and dried under high vacuum at 40° C. to afford a yellow solid (113 mg, 95%). mp>300° C.; LCMS: m/z=361 (M+1); ¹H NMR (400 MHz, DMSO-d₆) δ: 9.02 (m, 1H), 8.84 (m, 1H), 8.74-8.70 (m, 1H), 8.50 (m, 1H), 7.94 (m, 1H), 7.64 (m, 1H), 7.53-7.51 (m, 2H), 7.40-7.37 (m, 1H), 7.07 (d, 1H, J=8.4 Hz), 5.71-5.68 (m, 1H), 3.29-3.14 (m, 4H), 2.70 (s, 3H), 2.65-2.59 (m, 1H), 2.41-2.36 (m, 1H), 2.26-2.22 (m, 1H), 1.96 (m, 4H).

Step 3. 4-Hydroxy-6-(8-methyl-7-quinolyl)spiro[chromane-2,4'-piperidine]-1'-carboxamide. This compound was synthesized using the procedure to prepare Example 183 in 4% yield. LC-MS: m/z=404 (M+1); ¹H NMR (400 MHz, DMSO-d₆) δ: 8.97 (m, 1H), 8.36 (m, 1H), 7.85 (d, 1H, J=8.5 Hz), 7.56-7.53 (m, 1H), 7.50-7.47 (m, 2H), 7.24 (m, 1H), 6.90 (d, 1H, J=8.4 Hz), 5.96 (s, 2H), 5.45 (d, 1H, J=6.0 Hz), 5.79-4.76 (m, 1H), 3.71-3.65 (m, 3H), 3.28-3.19 (m, 1H), 3.23-3.06 (m, 1H), 2.70 (s, 3H), 2.17-2.13 (m, 1H), 1.84-1.78 (m, 2H), 1.74-1.64 (m, 1H), 1.59-1.56 (m, 1H).

Example 214. 4-Fluoro-6-(8-methyl-7-quinolyl)spiro[chromane-2,4'-piperidine]-1'-carboxamide TFA

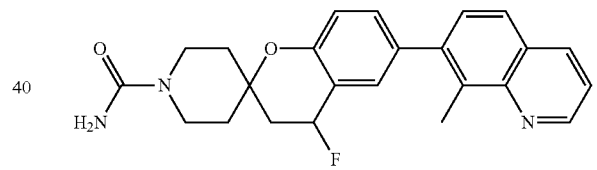

To deoxo-fluor (0.41 g, 0.34 mL, 1.8 mmol) and DCM (1.4 mL) in a Teflon bottle was added 4-hydroxy-6-(8-methyl-7-quinolyl)spiro[chromane-2,4'-piperidine]-1'-carboxamide (0.079 g, 0.1958 mmol) in DCM (3 mL). The reaction was stirred at RT for 2 h, then saturated aq. NaBH₄ solution was added dropwise to quench the reaction. The mixture was extracted with DCM, washed with brine, dried over Na₂SO₄, filtered and concentrated. The residue was purified by prep. HPLC and lyophilized to yield a yellow solid (19 mg, 19%). LCMS: m/z=406 (M+1); ¹H NMR (400 MHz, DMSO-d₆) δ: 9.03 (m, 1H), 8.53-8.50 (m, 1H), 7.94 (d, 1H, J=8.4 Hz), 7.67-7.64 (m, 1H), 7.55 (m, 1H), 7.48 (m, 1H), 7.43-7.40 (m, 1H), 7.05 (d, 1H, J=8.5 Hz), 5.85-5.70 (m, 1H), 3.76-3.63 (m, 2H), 3.30-3.21 (m, 1H), 3.12-3.06 (m, 1H), 2.70 (s, 3H), 2.37-2.29 (m, 1H), 2.27-2.13 (m, 1H), 1.95-1.91 (m, 1H), 1.75-1.70 (m, 2H), 1.67-1.60 (m, 1H).

The following examples were synthesized using spiro intermediate 1 or intermediate 3, the appropriate bromopyridine, and the corresponding R¹ carboxylic acid or carbonyl chloride by procedures described herein.

Example 215. 1-[6-(2-Pyridyl)spiro[chromane-2,4'-piperidine]-1'-yl]propan-1-one, HCl

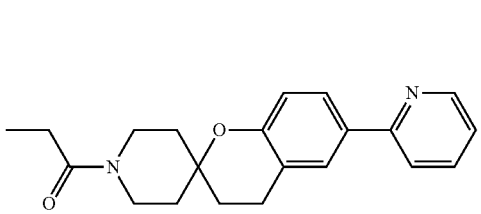 [SMILES: CCC(=O)N1CCC2(CCc3cc(-c4ccccn4)ccc3O2)CC1]

Analysis: LCMS m/z=337 (M+1). $^1$H NMR (DMSO-$d_6$) δ: 8.71 (dd, 1H, J=5.4, 0.9 Hz), 8.25-8.32 (m, 1H), 8.17 (d, 1H, J=8.3 Hz), 7.92 (d, 1H, J=2.3 Hz), 7.86 (dd, 1H, J=8.5, 2.5 Hz), 7.65 (t, 1H, J=6.3 Hz), 7.00 (d, 1H, J=8.8 Hz), 4.07-4.15 (m, 1H), 3.69 (m, 1H), 3.39 (m, 1H), 3.06 (m, 1H), 2.85 (m, 2H), 2.35 (m, 2H), 1.87 (m, 2H), 1.43-1.82 (br m, 4H), 1.00 (t, 3H, J=7.4 Hz).

Example 216. Cyclopropyl-[6-(2-pyridyl)spiro[chromane-2,4'-piperidine]-1'-yl]methanone, HCl

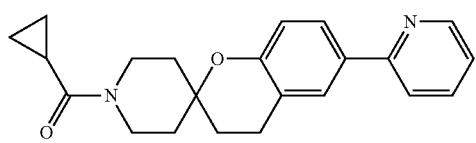

Analysis: LCMS m/z=349 (M+1). $^1$H NMR (DMSO-$d_6$) δ: 8.71 (dd, 1H, J=5.4, 0.9 Hz), 8.24 (d, 1H, J=7.3 Hz), 8.16 (d, 1H, J=8.0 Hz), 7.92 (d, 1H, J=2.3 Hz), 7.86 (dd, 1H, J=8.5, 2.5 Hz), 7.63 (t, 1H, J=6.3 Hz), 7.01 (d, 1H, J=8.8 Hz), 4.08 (br m, 2H), 3.44-3.58 (m, 1H), 3.05-3.18 (m, 1H), 2.85 (m, 2H), 1.96-2.10 (m, 1H), 1.89 (m, 2H), 1.48-1.83 (m, 4H), 0.59-0.83 (m, 4H).

Example 217. [6-(2-Pyridyl)spiro[chromane-2,4'-piperidine]-1'-yl]-[(2R)-tetrahydrofuran-2-yl]methanone, HCl

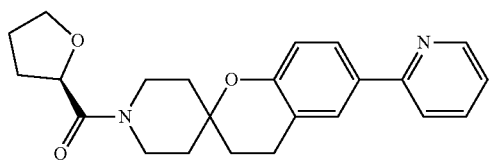 [SMILES: O=C([C@H]1CCCO1)N1CCC2(CCc3cc(-c4ccccn4)ccc3O2)CC1]

Analysis: LCMS m/z=379 (M+1). $^1$H NMR (DMSO-$d_6$) δ: 8.70 (d, 1H, J=5.0 Hz), 8.17-8.27 (m, 1H), 8.14 (d, 1H, J=8.0 Hz), 7.92 (m, 1H), 7.86 (dd, 1H, J=8.5, 2.0 Hz), 7.61 (m, 1H), 6.99 (d, 1H, J=8.3 Hz), 4.68 (m, 1H), 3.99-4.16 (m, 1H), 3.68-3.92 (m, 3H), 3.33-3.51 (m, 1H), 2.98-3.18 (m, 1H), 2.85 (m, 2H), 1.93-2.13 (m, 2H), 1.49-1.92 (br m, 9H).

Example 218. 1-[6-(2-Pyridyl)spiro[4H-1,3-benzodioxine-2,4'-piperidine]-1'-yl]propan-1-one, HCl

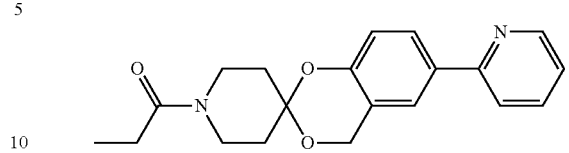

Analysis: LCMS m/z=339 (M+1). $^1$H NMR (DMSO-$d_6$) δ: 8.71 (d, 1H, J=4.5 Hz), 8.07-8.28 (m, 2H), 7.85-8.00 (m, 2H), 7.60 (m, 1H), 7.05 (d, 1H, J=8.5 Hz), 4.98 (s, 2H), 3.46-3.76 (m, 4H), 2.37 (m, 2H), 1.70-1.99 (m, 4H), 1.00 (t, 3H, J=7.3 Hz).

Example 219. Cyclopropyl-[6-(2-pyridyl)spiro[4H-1,3-benzodioxine-2,4'-piperidine]-1'-yl]methanone, HCl

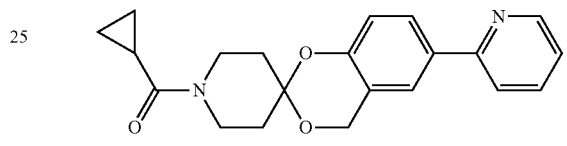

Analysis: LCMS m/z=351 (M+1). $^1$H NMR (DMSO-$d_6$) δ: 8.59-8.74 (m, 1H), 8.05-8.21 (m, 2H), 7.94 (dd, 1H, J=8.7, 2.4 Hz), 7.89 (d, 1H, J=2.0 Hz), 7.56 (d, 1H, J=6.0 Hz), 7.04 (d, 1H, J=8.5 Hz), 4.99 (s, 2H), 3.78 (br m, 4H), 1.74-2.09 (br m, 5H), 0.62-0.80 (m, 4H).

Example 220. [6-(2-Pyridyl)spiro[4H-1,3-benzodioxine-2,4'-piperidine]-1'-yl]-[(2R)-tetrahydrofuran-2-yl]methanone, HCl

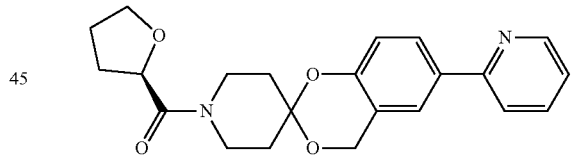

Analysis: LCMS m/z=381 (M+1). $^1$H NMR (DMSO-$d_6$) δ: 8.69 (d, 1H, J=4.3 Hz), 8.03-8.19 (m, 2H), 7.85-7.98 (m, 2H), 7.54 (m, 1H), 7.03 (d, 1H, J=8.5 Hz), 4.98 (s, 2H), 4.70 (m, 1H), 3.42-3.87 (br m, 6H), 1.74-2.16 (br m, 8H).

Example 221. 1-[6-(3-Pyridyl)spiro[chromane-2,4'-piperidine]-1'-yl]propan-1-one, HCl

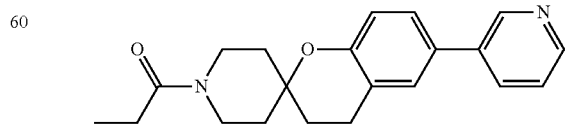

Analysis: LCMS m/z=337 (M+1). $^1$H NMR (DMSO-$d_6$) δ: 9.17 (s, 1H), 8.67-8.85 (m, 2H), 8.05 (dd, 1H, J=8.0, 5.5

Hz), 7.59-7.76 (m, 2H), 6.99 (d, 1H, J=8.5 Hz), 4.11 (m, 1H), 3.69 (m, 1H), 3.38 (m, 1H), 3.05 (m, 1H), 2.84 (m, 2H), 2.35 (m, 2H), 1.86 (m, 2H), 1.45-1.80 (m, 4H), 1.00 (t, 3H, J=7.4 Hz).

Example 222. Cyclopropyl-[6-(3-pyridyl)spiro[chromane-2,4'-piperidine]-1'-yl]methanone, HCl

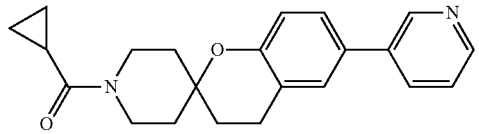 [SMILES: O=C(C1CC1)N1CCC2(CCc3cc(-c4cccnc4)ccc3O2)CC1]

Analysis: LCMS m/z=349 (M+1). $^1$H NMR (DMSO-d$_6$) δ: 9.14 (s, 1H), 8.65-8.81 (m, 2H), 7.98 (dd, 1H, J=8.3, 5.5 Hz), 7.57-7.71 (m, 2H), 7.00 (d, 1H, J=8.5 Hz), 4.08 (m, 2H), 3.45-3.60 (m, 1H), 3.04-3.14 (m, 1H), 2.85 (m, 2H), 2.00 (s, 1H), 1.63-1.94 (m, 5H), 1.54 (m, 1H), 0.59-0.83 (m, 4H).

Example 223. [6-(3-Pyridyl)spiro[chromane-2,4'-piperidine]-1'-yl]-[(2R)-tetrahydrofuran-2-yl]methanone, HCl

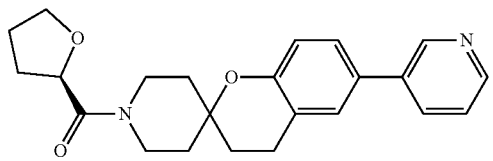 [SMILES: O=C([C@H]1CCCO1)N1CCC2(CCc3cc(-c4cccnc4)ccc3O2)CC1]

Analysis: LCMS m/z=379 (M+1). $^1$H NMR (DMSO-d$_6$) δ: 9.10 (s, 1H), 8.73 (d, 1H, J=4.8 Hz), 8.61 (d, 1H, J=8.5 Hz), 7.91 (dd, 1H, J=8.0, 5.3 Hz), 7.50-7.69 (m, 2H), 6.98 (dd, 1H, J=8.5, 1.8 Hz), 4.68 (m, 1H), 4.09 (s, 1H), 3.67-3.91 (m, 3H), 3.31-3.52 (m, 1H), 3.07 (m, 1H), 2.84 (m, 2H), 1.93-2.15 (m, 2H), 1.48-1.91 (m, 8H).

Example 224. 1-[6-(3-Pyridyl)spiro[4H-1,3-benzodioxine-2,4'-piperidine]-1'-yl]propan-1-one, HCl

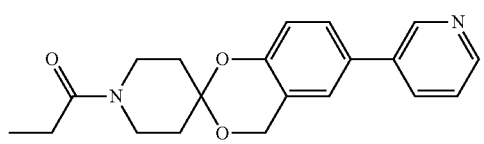 [SMILES: CCC(=O)N1CCC2(CC1)OCc1cc(-c3cccnc3)ccc1O2]

Analysis: LCMS m/z=339 (M+1). $^1$H NMR (DMSO-d$_6$) δ: 9.12 (s, 1H), 8.77 (d, 1H, J=5.0 Hz), 8.65 (d, 1H, J=8.0 Hz), 7.96 (dd, 1H, J=8.2, 5.4 Hz), 7.61-7.75 (m, 2H), 7.05 (d, 1H, J=8.5 Hz), 4.96 (s, 2H), 3.42-3.71 (m, 4H), 2.37 (m, 2H), 1.67-1.97 (m, 4H), 1.00 (t, 3H, J=7.4 Hz).

Example 225. Cyclopropyl-[6-(3-pyridyl)spiro[4H-1,3-benzodioxine-2,4'-piperidine]-1'-yl]methanone, HCl

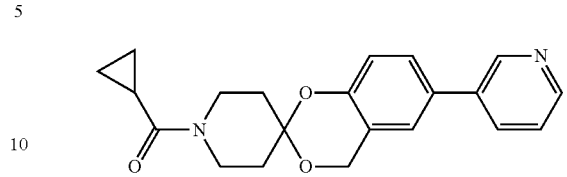

Analysis: LCMS m/z=351 (M+1). $^1$H NMR (DMSO-d$_6$) δ: 9.13 (s, 1H), 8.78 (d, 1H, J=5.0 Hz), 8.67 (d, 1H, J=8.5 Hz), 7.98 (dd, 1H, J=8.0, 5.5 Hz), 7.63-7.77 (m, 2H), 7.06 (d, 1H, J=8.5 Hz), 4.97 (s, 2H), 3.44-3.88 (m, 4H), 1.72-2.11 (m, 5H), 0.60-0.80 (m, 4H).

Example 226. 1-[6-(4-Pyridyl)spiro[chromane-2,4'-piperidine]-1'-yl]propan-1-one, HCl

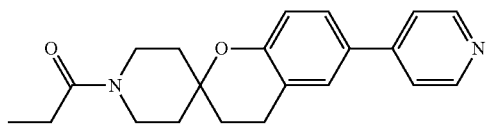 [SMILES: CCC(=O)N1CCC2(CCc3cc(-c4ccncc4)ccc3O2)CC1]

Analysis: LCMS m/z=337 (M+1). $^1$H NMR (DMSO-d$_6$) δ: 8.86 (d, 2H, J=6.5 Hz), 8.34 (d, 2H, J=6.8 Hz), 7.92 (d, 1H, J=2.3 Hz), 7.86 (dd, 1H, J=8.7, 2.4 Hz), 7.03 (d, 1H, J=8.5 Hz), 4.11 (m, 1H), 3.69 (m, 1H), 3.39 (m, 1H), 3.05 (m, 1H), 2.86 (m, 2H), 2.35 (m, 2H), 1.88 (m, 2H), 1.44-1.60 (m, 4H), 1.00 (t, 3H, J=7.4 Hz).

Example 227. Cyclopropyl-[6-(4-pyridyl)spiro[chromane-2,4'-piperidine]-1'-yl]methanone, HCl

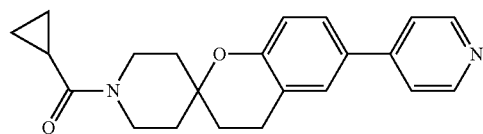 [SMILES: O=C(C1CC1)N1CCC2(CCc3cc(-c4ccncc4)ccc3O2)CC1]

Analysis: LCMS m/z=349 (M+1). $^1$H NMR (DMSO-d$_6$) δ: 8.82 (d, 2H, J=6.0 Hz), 8.25 (d, 2H, J=6.8 Hz), 7.88 (d, 1H, J=2.0 Hz), 7.82 (m, 1H), 7.03 (d, 1H, J=8.5 Hz), 4.08 (m, 2H), 3.43-3.63 (br m, 2H), 3.03-3.18 (m, 1H), 2.87 (m, 2H), 1.95-2.07 (m, 1H), 1.62-1.93 (m, 5H), 1.55 (m, 1H), 0.62-0.80 (m, 4H).

Example 228. [6-(4-Pyridyl)spiro[chromane-2,4'-piperidine]-1'-yl]-[(2R)-tetrahydrofuran-2-yl]methanone, HCl

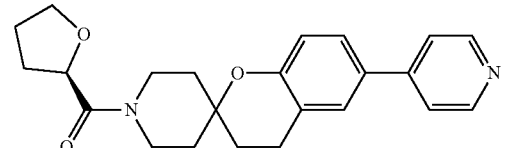

Analysis: LCMS m/z=379 (M+1). $^1$H NMR (DMSO-d$_6$) δ: 8.80 (d, 2H, J=6.0 Hz), 8.20 (d, 2H, J=6.5 Hz), 7.85 (d, 1H, J=2.3 Hz), 7.80 (dd, 1H, J=8.5, 2.5 Hz), 6.94-7.07 (m, 1H), 4.63-4.76 (m, 1H), 3.99-4.19 (m, 1H), 3.67-3.91 (m, 3H), 3.33-3.50 (br m, 3H), 3.00-3.18 (m, 1H), 2.86 (m, 2H), 1.48-2.16 (br m, 9H).

Example 229. [6-(3-Pyridyl)spiro[4H-1,3-benzodioxine-2,4'-piperidine]-1'-yl]-[(2R)-tetrahydrofuran-2-yl] methanone

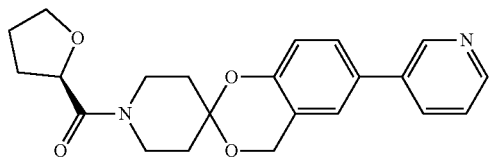

Analysis: LCMS m/z=381 (M+1). $^1$H NMR (DMSO-d$_6$) δ: 8.84 (dd, 1H, J=2.3, 0.8 Hz), 8.52 (dd, 1H, J=4.6, 1.6 Hz), 7.96-8.04 (m, 1H), 7.56 (dd, 1H, J=8.5, 2.3 Hz), 7.49 (d, 1H, J=2.3 Hz), 7.45 (m, 1H), 6.98 (d, 1H, J=8.5 Hz), 4.95 (s, 2H), 4.62-4.74 (m, 1H), 3.76 (m, 2H), 3.50-3.70 (br m, 3H), 1.75-2.12 (m, 9H).

Example 230. Cyclopropyl-[6-(4-pyridyl)spiro[4H-1,3-benzodioxine-2,4'-piperidine]-1'-yl]-methanone, HCl

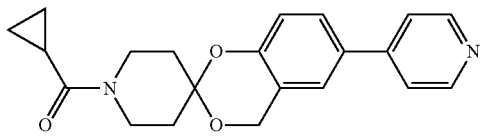 [SMILES: O=C(C1CC1)N1CCC2(CC1)OCc1cc(-c3ccncc3)ccc1O2]

Analysis: LCMS m/z=351 (M+1). $^1$H NMR (DMSO-d$_6$) δ: 8.86 (d, 2H, J=5.3 Hz), 8.26 (d, 2H, J=6.5 Hz), 7.83-7.96 (m, 2H), 7.10 (d, 1H, J=8.5 Hz), 5.00 (s, 2H), 3.78 (m, 5H), 1.74-2.16 (m, 5H), 0.62-0.85 (m, 4H).

Example 231. [6-(4-Pyridyl)spiro[4H-1,3-benzodioxine-2,4'-piperidine]-1'-yl]-[(2R)-tetrahydrofuran-2-yl]methanone, HCl

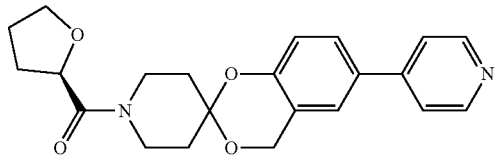 [SMILES: O=C([C@H]1CCCO1)N1CCC2(CC1)OCc1cc(-c3ccncc3)ccc1O2]

Analysis: LCMS m/z=381 (M+1). $^1$H NMR (DMSO-d$_6$) δ: 8.86 (m, 2H), 8.25 (d, 2H, J=6.3 Hz), 7.85-7.96 (m, 2H), 7.09 (d, 1H, J=8.5 Hz), 4.99 (s, 2H), 4.71 (m, 1H), 3.43-3.85 (m, 7H), 1.71-2.17 (m, 8H).

Example 232. 1-[6-(4-Pyridyl)spiro[4H-1,3-benzodioxine-2,4'-piperidine]-1'-yl]propan-1-one, HCl

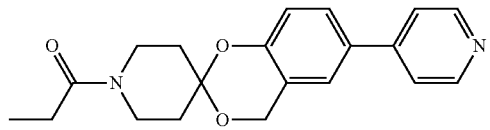

Analysis: LCMS m/z=339 (M+1). $^1$H NMR (DMSO-d$_6$) δ: 8.88 (d, 2H, J=5.5 Hz), 8.28 (d, 2H, J=6.5 Hz), 7.83-7.99 (m, 2H), 7.09 (d, 1H, J=8.5 Hz), 4.99 (s, 2H), 3.54 (m, 4H), 2.25-2.43 (m, 2H), 1.73-2.02 (m, 4H), 1.00 (t, 3H, J=7.4 Hz).

Example 233. 7-Fluoro-6-(1-methyl-6-isoquinolyl)spiro[chromane-2,4'-piperidine]-1'-carboxamide

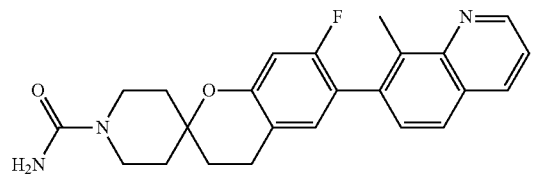

This example was synthesized using tert-butyl 6-bromo-7-fluoro-spiro[chromane-2,4'-piperidine]-1'-carboxylate from 1-(5-bromo-4-fluoro-2-hydroxy-phenyl)ethanone using the procedure for intermediate 2, and 8-methyl-7-(4,4,5,5-tetramethyl-1,3,2-dioxaborolan-2-yl)quinolone similar to example 106. Analysis: LCMS m/z=406 (M+1); $^1$H NMR (400 MHz, DMSO-d$_6$) δ 8.97 (dd, J=4.1, 1.9 Hz, 1H), 8.38 (dd, J=8.3, 1.8 Hz, 1H), 7.86 (d, J=8.3 Hz, 1H), 7.60-7.55 (m, 1H), 7.44 (d, J=8.3 Hz, 1H), 7.14 (d, J=8.8 Hz, 1H), 6.79 (d, J=11.3 Hz, 1H), 5.98 (s, 2H), 3.70 (br d, J=13.3 Hz, 2H), 3.17 (br t, J=10.8 Hz, 2H), 2.78 (br t, J=6.5 Hz, 2H), 2.58 (d, J=1.3 Hz, 3H), 1.85 (t, J=6.8 Hz, 2H), 1.75-1.66 (m, 2H), 1.62-1.51 (m, 2H); 19F NMR (377 MHz, DMSO-d$_6$) δ −116.74 (s, 1F).

Example 234. 7-Fluoro-6-(1-methyl-6-isoquinolyl)spiro[chromane-2,4'-piperidine]-1'-carboxamide

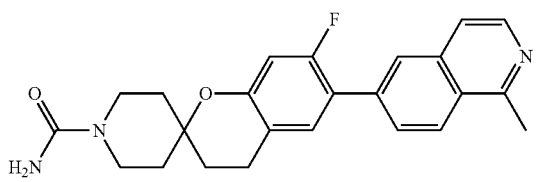

This example was synthesized using tert-butyl 6-bromo-7-fluoro-spiro[chromane-2,4'-piperidine]-1'-carboxylate and 1-methyl-6-(4,4,5,5-tetramethyl-1,3,2-dioxaborolan-2-yl)isoquinoline similar to example 233 and example 106. Analysis: LCMS m/z=406 (M+1); $^1$H NMR (400 MHz, DMSO-d$_6$) δ 8.36 (d, J=5.8 Hz, 1H), 8.25 (d, J=8.8 Hz, 1H), 8.05 (s, 1H), 7.81 (dt, J=8.7, 1.8 Hz, 1H), 7.70 (d, J=5.8 Hz, 1H), 7.44 (d, J=9.3 Hz, 1H), 6.83 (d, J=12.0 Hz, 1H), 5.98 (s, 2H), 3.69 (br d, J=13.3 Hz, 2H), 3.22-3.09 (m, 2H), 2.90

(s, 3H), 2.81 (br t, J=6.7 Hz, 2H), 1.85 (t, J=6.8 Hz, 2H), 1.74-1.63 (m, 2H), 1.62-1.50 (m, 2H); 19F NMR (377 MHz, DMSO-$d_6$) d-119.58 (s, 1F).

Example 235. 6-(Benzofuran-2-yl)spiro[chromane-2,4'-piperidine]-1'-carboxamide

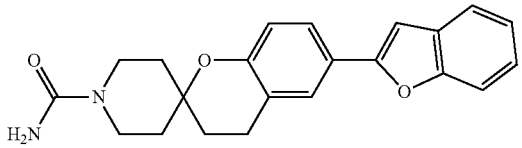

This example was synthesized using 6-bromospiro[chromane-2,4'-piperidine]-1'-carboxamide and benzofuran-2-yl-boronic acid similar to example 106. Analysis: LCMS m/z=363 (M+1); $^1$H NMR (400 MHz, DMSO-$d_6$) δ 7.68-7.55 (m, 4H), 7.30-7.20 (m, 3H), 6.91 (d, J=8.3 Hz, 1H), 5.96 (s, 2H), 3.68 (d, J=13.3 Hz, 2H), 3.19-3.08 (m, 2H), 2.83 (t, J=6.8 Hz, 2H), 1.84 (t, J=6.8 Hz, 2H), 1.73-1.63 (m, 2H), 1.60-1.48 (m, 2H).

Example 236. 6-(1H-Indol-2-yl)spiro[chromane-2,4'-piperidine]-1'-carboxamide

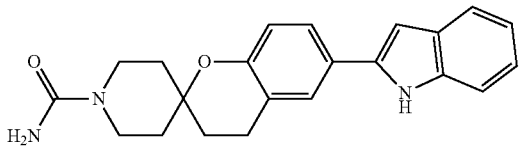

This example was synthesized using 6-bromospiro[chromane-2,4'-piperidine]-1'-carboxamide and indole-2-ylboronic acid similar to example 106. Analysis: LCMS m/z=362 (M+1); $^1$H NMR (400 MHz, DMSO-$d_6$) δ 11.35 (d, J=1.3 Hz, 1H), 7.62-7.54 (m, 2H), 7.47 (d, J=8.0 Hz, 1H), 7.35 (dd, J=8.0, 0.8 Hz, 1H), 7.04 (ddd, J=8.0, 7.0, 1.1 Hz, 1H), 6.96 (td, J=7.4, 1.0 Hz, 1H), 6.87 (d, J=8.3 Hz, 1H), 6.71 (d, J=1.3 Hz, 1H), 5.96 (s, 2H), 3.68 (d, J=13.6 Hz, 2H), 3.19-3.07 (m, J=10.9, 10.9 Hz, 2H), 2.82 (t, J=6.7 Hz, 2H), 1.84 (t, J=6.7 Hz, 2H), 1.73-1.62 (m, 2H), 1.59-1.47 (m, 2H).

Example 237. 8-Fluoro-6-(8-methyl-7-quinolyl)spiro[chromane-2,4'-piperidine]-1'-carboxamide

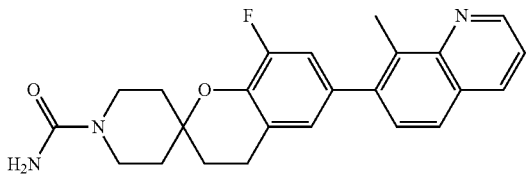

Step 1. 1-(5-bromo-3-fluoro-2-hydroxyphenyl)ethanone (1.008 g, 4.326 mmol), 1-boc-4-piperidone (0.906 g, 4.5471 mmol) pyrrolidine (0.3272 g, 0.384 mL, 4.60 mmol) and methanol (7.2 g, 9.1 mL, 220 mmol) were heated at 50° C. under nitrogen for 17 h. The reaction was cooled to room temperature, diluted with water and ethyl acetate, and the layers were separated. The aqueous phase was extracted with ethyl acetate and the combined organics were washed with 1M HCl, water, 1M NaOH, and brine. The combined organic layers were dried over sodium sulfate, filtered and concentrated in vacuo. The residue was purified by ISCO normal phase chromatography eluting 0% to 20% with ethyl acetate in heptane to give tert-butyl 6-bromo-8-fluoro-4-oxo-spiro[chromane-2,4'-piperidine]-1'-carboxylate (1.372 g, 77%). LCMS m/z=437 (M+1); $^1$H NMR (400 MHz, DMSO-$d_6$) δ 7.94-7.91 (m, 1H), 7.64-7.63 (m, 1H), 3.75-3.72 (m, 2H), 3.07 (m, 2H), 2.96 (s, 2H), 1.93-1.90 (m, 2H), 1.70-1.63 (m, 2H), 1.40 (s, 9H).

Step 2. Tert-butyl 6-bromo-8-fluoro-4-oxo-spiro[chromane-2,4'-piperidine]-1'-carboxylate (1.426 g, 3.442 mmol) and ethanol (20 g, 25 mL, 430 mmol) were combined in a flask and cooled on an ice bath. Sodium borohydride (0.289 g, 0.3058 mL, 7.64 mmol) was added and the reaction was stirred for 3.5 hours, warming to room temperature. The reaction was quenched by addition of 1 N aqueous sodium carbonate then the reaction was concentrated. The residue was dissolved in ethyl acetate and washed with saturated aqueous sodium bicarbonate solution, and brine. The organic layer was dried over sodium sulfate, filtered and concentrated to afford tert-butyl 6-bromo-8-fluoro-4-hydroxy-spiro[chromane-2,4'-piperidine]-1'-carboxylate, (1.319 g, 87%). LCMS m/z=439 (M+1); $^1$H NMR (400 MHz, DMSO-$d_6$) δ 7.42-7.38 (m, 2H), 5.67 (d, 1H, J=6.2 Hz), 4.74-4.68 (m, 1H), 3.72-3.65 (m, 2H), 3.16-3.03 (m, 2H), 2.18-2.13 (m, 1H), 1.83-1.53 (m, 5H), 1.40 (s, 9H).

Step 3. Tert-butyl 6-bromo-8-fluoro-4-hydroxy-spiro[chromane-2,4'-piperidine]-1'-carboxylate (1.319 g, 3.168 mmol), triethylsilane (1.6 g, 2.1 mL, 13 mmol) and dichloromethane (13 g, 9.9 mL, 150 mmol) were combined in a flask and cooled over an ice/water bath. TFA (3.7 g, 2.5 mL, 32 mmol) was added slowly and the reaction was stirred for 22 h, warming to room temperature. The reaction was concentrated, then TFA (2.5 mL) and triethylsilane (2.1 mL) were added. The reaction was heated at 50° C. for 24 h, then at 65° C. for 26 hours. The reaction was then cooled to room temperature and azeotroped four times with ethyl acetate. The residue was diluted with ethyl acetate, washed with saturated sodium bicarbonate solution, then brine. The organic layer was dried over sodium sulfate, filtered and concentrated. The residue was purified by Isco normal phase chromatography eluting with 0% to 10% methanol in DCM to afford a 3:1 mixture of 6-bromo-8-fluoro-spiro[chromane-2,4'-piperidine]: 6-bromo-8-fluoro-spiro[chromene-2,4'-piperidine].

Step 4. A 3:1 mixture of 6-bromo-8-fluoro-spiro[chromane-2,4'-piperidine]: 6-bromo-8-fluoro-spiro[chromene-2,4'-piperidine] (635 mg), N,N-diisopropylethylamine (0.593 g, 0.8 mL, 4.59 mmol) and DCM (11 mL) were combined in a round bottom flask. Di-tert-butyl dicarbonate (0.497 g, 2.2772 mmol) was added and the reaction was stirred at room temperature for 2 days. The reaction was diluted with water and DCM and the layers were separated. The aqueous layer was extracted with DCM; the combined organic layers were washed with brine, dried over sodium sulfate, filtered and concentrated. The residue was purified by Isco normal phase chromatography eluting 0% to 20% with ethyl acetate in heptane to afford a mixture of tert-butyl 6-bromo-8-fluoro-spiro[chromane-2,4'-piperidine]-1'-carboxylate and tert-butyl 6-bromo-8-fluoro-spiro[chromene-2,4'-piperidine]-1'-carboxylate.

Step 5. A mixture of tert-butyl 6-bromo-8-fluoro-spiro[chromane-2,4'-piperidine]-1'-carboxylate and tert-butyl 6-bromo-8-fluoro-spiro[chromene-2,4'-piperidine]-1'-carboxylate (0.53 g), bis(pinacolato)diboron (0.372 g, 1.46 mmol), [1,1'-bis(diphenylphosphino)ferrocene] dichloropalladium(II), complex with dichloromethane (1:1) (0.056 g, 0.0686 mmol), potassium acetate (0.404 g, 4.12 mmol) and 1,4-dioxane (6.8 g, 6.0 mL, 77 mmol) were combined in a round bottom flask. The reaction was purged with argon then heated at 90° C. under nitrogen for 17 h. The reaction was cooled to room temperature then filtered through a pad of silica gel rinsing with ethyl acetate. The filtrate was concentrated in vacuo; residue was purified by Isco normal phase chromatography eluting with 0% to 30% ethyl acetate in hexane to afford a mixture of tert-butyl 8-fluoro-6-(4,4,5,5-tetramethyl-1,3,2-dioxaborolan-2-yl)spiro[chromane-2,4'-piperidine]-1'-carboxylate and tert-butyl 8-fluoro-6-(4,4,5,5-tetramethyl-1,3,2-dioxaborolan-2-yl)spiro[chromene-2,4'-piperidine]-1'-carboxylate.

Step 6. A mixture of tert-butyl 8-fluoro-6-(4,4,5,5-tetramethyl-1,3,2-dioxaborolan-2-yl)spiro[chromane-2,4'-piperidine]-1'-carboxylate and tert-butyl 8-fluoro-6-(4,4,5,5-tetramethyl-1,3,2-dioxaborolan-2-yl)spiro[chromene-2,4'-piperidine]-1'-carboxylate (0.489 g) was dissolved in a mixture of ethanol (40 g, 50 mL, 860 mmol), DMF and methanol. The solution was passed through a Thales H-Cube hydrogenation reactor using a CatCart 20% Pd(OH)$_2$/C (20:80, Palladium hydroxide:carbon black) at 20° C. and 10 bar. The reaction solution was circulated through the reactor for 4 hours then concentrated to afford tert-butyl 8-fluoro-6-(4,4,5,5-tetramethyl-1,3,2-dioxaborolan-2-yl)spiro[chromane-2,4'-piperidine]-1'-carboxylate. LCMS m/z=470 (M+1); $^1$H NMR (400 MHz, Methanol-d$_4$) δ 7.27 (s, 1H), 7.21-7.18 (d, 1H, J=11.2 Hz), 3.89-3.86 (m, 2H), 3.24 (m, 2H), 2.85-2.81 (m, 2H), 1.89-1.85 (m, 2H), 1.82-1.79 (m, 2H), 1.64-1.56 (m, 2H), 1.46 (s, 9H), 1.32 (s, 12H).

Step 7. 7-bromo-8-methylquinoline (0.174 g, 0.78350 mmol), tert-butyl 8-fluoro-6-(4,4,5,5-tetramethyl-1,3,2-dioxaborolan-2-yl)spiro[chromane-2,4'-piperidine]-1'-carboxylate (0.306 g, 0.6840 mmol), tetrakis(triphenylphosphine)palladium(0) (0.076 g, 0.0658 mmol), sodium carbonate in water (1 M) (2 mL, 2 mmol) and 1,4-dioxane (4.1 g, 3.7 mL, 47 mmol) were combined in a flask. The reaction was purged with argon and heated at 100° C. under nitrogen for 23 hours. The reaction was cooled to room temperature then filtered through a pad of Celite, washing with DCM. The filtrate was concentrated and the residue was dissolved in DCM, washed with saturated aqueous sodium bicarbonate, then brine. The organic layer was dried over sodium sulfate, filtered and concentrated. The residue was purified by Isco normal phase chromatography eluting with 0% to 35% ethyl acetate in hexane to afford tert-butyl 8-fluoro-6-(8-methyl-7-quinolyl)spiro[chromane-2,4'-piperidine]-1'-carboxylate (231 mg, 69%). LCMS m/z=463 (M+1); $^1$H NMR (400 MHz, DMSO-d$_6$) δ 8.97 (m, 1H), 8.38-8.35 (m, 1H), 7.85 (d, 1H, J=8.4 Hz), 7.57-7.54 (m, 1H), 7.47 (d, 1H, J=8.5 Hz), 7.17-7.13 (m, 1H), 7.02 (m, 1H), 3.77-3.74 (m, 2H), 3.26-3.18 (m, 2H), 2.87-2.84 (m, 2H), 2.69 (s, 3H) 1.92-1.88 (m, 2H), 1.79-1.76 (m, 2H), 1.65-1.58 (m, 2H), 1.42 (s, 9H).

Step 8. Tert-butyl 8-fluoro-6-(8-methyl-7-quinolyl)spiro[chromane-2,4'-piperidine]-1'-carboxylate (0.231 g, 0.4994 mmol) and ethyl acetate (3.0 mL) were combined in a flask. Hydrogen chloride (4 M) in dioxane (1.5 mL, 6.0 mmol) was added and the reaction was stirred at room temperature for 18 hours. The reaction was concentrated and triturated with ether, then dried by high vacuum at 40° C. to afford 8-fluoro-6-(8-methyl-7-quinolyl)spiro[chromane-2,4'-piperidine] dihydrochloride (184 mg, 80%). LCMS m/z=363 (M+1); $^1$H NMR (400 MHz, DMSO-d$_6$) δ 9.04 (m, 1H), 8.91 (m, 2H), 8.57 (m, 1H), 7.95 (d, 1H, J=8.4 Hz), 7.71-7.68 (m, 1H), 7.55 (d, 1H, J=8.4 Hz), 7.23-7.19 (m, 1H), 7.07 (s, 1H), 3.38-3.24 (m, 2H), 3.09 (m, 2H), 2.91-2.87 (m, 2H), 2.71 (s, 3H) 2.03-1.86 (m, 6H).

Step 9. 8-fluoro-6-(8-methyl-7-quinolyl)spiro[chromane-2,4'-piperidine] dihydrochloride (0.07 g, 0.1608 mmol), N,N-diisopropylethylamine (0.0893 g, 0.118 mL, 0.677 mmol), (trimethylsilyl)isocyanate (0.026 g, 0.031 mL, 0.23 mmol) and dichloromethane (2 g, 2 mL, 30 mmol) were combined in a vial. The reaction was stirred at room temperature for 21 hours. The reaction was diluted with DCM, washed with saturated aq. sodium bicarbonate solution, then brine. The organic phase was dried over sodium sulfate, filtered and concentrated. The residue was triturated with ether and dried by high vacuum at 40° C. to afford the title compound, a white solid (20 mg, 31%). LCMS m/z=406 (M+1); $^1$H NMR (400 MHz, DMSO-d$_6$) δ 8.99 (m, 1H), 8.38 (m, 1H), 7.86 (d, 1H, J=8.4 Hz), 7.59-7.56 (m, 1H), 7.51-7.49 (d, 1H, J=8.4 Hz), 7.18-7.15 (m, 1H), 7.04 (s, 1H), 6.00 (s, 2H), 3.76-3.72 (m, 2H), 3.19-3.14 (m, 2H), 2.89-2.86 (m, 2H), 2.71 (s, 3H), 1.93-1.90 (m, 2H), 1.77-1.74 (m, 2H), 1.65-1.59 (m, 2H).

Example 238. 8-Fluoro-N-methoxy-6-(8-methyl-7-quinolyl)spiro[chromane-2,4'-piperidine]-1'-carboxamide

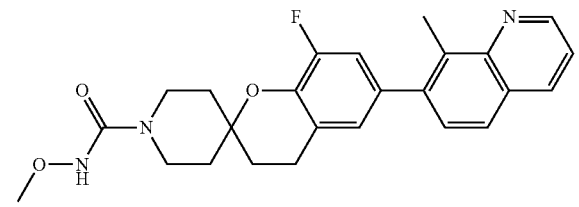

1,1'-Carbonyldiimidazole (0.094 g, 0.57971 mmol), DCM (2.0 mL) and O-methylhydroxylamine hydrochloride (0.047 g, 0.5627 mmol) and N,N-diisopropylethylamine (0.252 g, 0.341 mL, 1.95 mmol) were stirred at room temperature for 3 days. 8-fluoro-6-(8-methyl-7-quinolyl)spiro[chromane-2,4'-piperidine] dihydrochloride (0.082 g, 0.1883 mmol) was added and the reaction was stirred for 2 days. The reaction was diluted with DCM, washed with saturated ammonium chloride solution, then saturated sodium bicarbonate solution, then water, then brine. The organic phase was dried over sodium sulfate, filtered and concentrated. The residue was dried by high vacuum at 40° C. for 2 hours to afford the title compound, a tan solid (41 mg, 50%). LCMS m/z=436 (M+1); $^1$H NMR (400 MHz, DMSO-d$_6$) δ 9.78 (s, 1H), 8.99 (m, 1H), 8.40-8.37 (m, 1H), 7.86-7.88 (d, 1H, J=8.5 Hz), 7.59-7.56 (m, 1H), 7.49 (d, 1H, J=8.4 Hz), 7.19-7.15 (m, 1H), 7.04 (s, 1H), 3.70-3.67 (m, 2H), 3.57 (s, 3H), 3.20-3.12 (m, 2H), 2.71 (s, 3H), 1.94-1.90 (m, 2H), 1.80-1.77 (m, 2H), 1.67-1.59 (m, 2H).

Example 239. 5-Fluoro-6-(1-methyl-6-isoquinolyl)spiro[chromane-2,4'-piperidine]-1' carboxamide

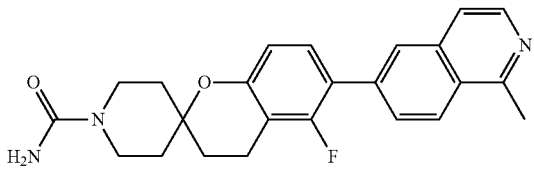

This example was synthesized using tert-butyl 6-bromo-5-fluoro-spiro[chromane-2,4'-piperidine]-1'-carboxylate and 1-methyl-6-(4,4,5,5-tetramethyl-1,3,2-dioxaborolan-2-yl)isoquinoline similar to example 233. Analysis: LCMS m/z=406 (M+1); $^1$H NMR (400 MHz, DMSO-d$_6$) δ 8.36 (d, J=5.8 Hz, 1H), 8.26 (d, J=8.8 Hz, 1H), 8.05 (s, 1H), 7.81 (d, J=8.8 Hz, 1H), 7.70 (d, J=6.0 Hz, 1H), 7.43 (t, J=8.8 Hz, 1H), 6.84 (d, J=8.5 Hz, 1H), 5.97 (s, 2H), 3.70 (br d, J=13.6 Hz, 2H), 3.14 (br t, J=10.8 Hz, 2H), 2.90 (s, 3H), 2.78 (br t, J=6.8 Hz, 2H), 1.87 (t, J=6.8 Hz, 2H), 1.77-1.66 (m, 2H), 1.63-1.50 (m, 2H); $^{19}$F NMR (377 MHz, DMSO-d$_6$) δ –121.15 (s, 1F).

Example 240. 5-Methyl-6-(8-methyl-7-quinolyl)spiro[chromane-2,4'-piperidine]-1'-carboxamide

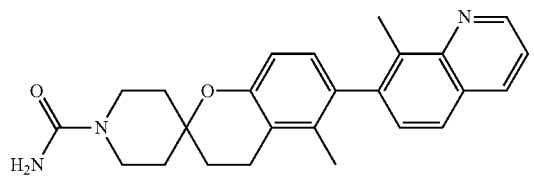 [SMILES: Cc1c(-c2ccc3cccnc3c2C)ccc2c1CCC1(CCN(C(N)=O)CC1)O2]

This example was synthesized using tert-butyl 6-bromo-5-methyl-spiro[chromane-2,4'-piperidine]-1'-carboxylate from 1-(3-bromo-6-hydroxy-2-methyl-phenyl)ethanone using the procedure for intermediate 2, and 8-methyl-7-(4,4,5,5-tetramethyl-1,3,2-dioxaborolan-2-yl)quinolone similar to example 106. Analysis: LCMS m/z=402 (M+1); $^1$H NMR (400 MHz, DMSO-d$_6$) δ 8.96 (dd, J=4.3, 1.8 Hz, 1H), 8.37 (dd, J=8.3, 2.0 Hz, 1H), 7.82 (d, J=8.3 Hz, 1H), 7.55 (dd, J=8.3, 4.3 Hz, 1H), 7.32 (d, J=8.3 Hz, 1H), 6.91 (d, J=8.3 Hz, 1H), 6.75 (d, J=8.3 Hz, 1H), 5.96 (s, 2H), 3.76-3.62 (m, 2H), 3.24-3.08 (m, 2H), 2.74-2.64 (m, 2H), 2.45 (s, 3H), 1.95-1.84 (m, 5H), 1.69 (br dd, J=13.4, 2.9 Hz, 2H), 1.62-1.48 (m, 2H).

Example 241. 5-methyl-6-(1-methyl-6-isoquinolyl)spiro[chromane-2,4'-piperidine]-1'-carboxamide

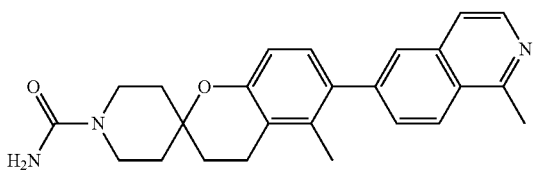 [SMILES: Cc1c(-c2ccc3c(C)nccc3c2)ccc2c1CCC1(CCN(C(N)=O)CC1)O2]

This example was synthesized using tert-butyl 6-bromo-5-methyl-spiro[chromane-2,4'-piperidine]-1'-carboxylate and 1-methyl-6-(4,4,5,5-tetramethyl-1,3,2-dioxaborolan-2-yl)isoquinoline similar to example 233. Analysis: LCMS m/z=402 (M+1); $^1$H NMR (400 MHz, DMSO-d$_6$) δ 8.36 (d, J=5.8 Hz, 1H), 8.24 (d, J=8.5 Hz, 1H), 7.82 (s, 1H), 7.69 (br d, J=6.0 Hz, 1H), 7.61 (dd, J=8.7, 1.6 Hz, 1H), 7.07 (d, J=8.3 Hz, 1H), 6.78 (d, J=8.3 Hz, 1H), 5.95 (s, 2H), 3.68 (br d, J=13.3 Hz, 2H), 3.14 (br t, J=10.8 Hz, 2H), 2.92 (s, 3H), 2.75-2.64 (m, 2H), 2.13 (s, 3H), 1.92-1.84 (m, 2H), 1.68 (br d, J=13.3 Hz, 1H), 1.60-1.47 (m, 2H).

Example 242. 8-Fluoro-N-methoxy-6-(8-methyl-7-quinolyl)spiro[chromane-2,4'-piperidine]-1'-carboxamide

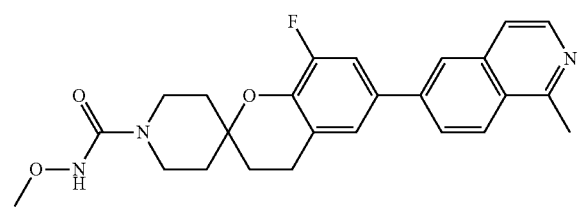

This compound was synthesized similar to example 238 instead using 1-methyl-6-(4,4,5,5-tetramethyl-1,3,2-dioxaborolan-2-yl)isoquinoline. Analysis: LCMS: m/z=436 (M+1); $^1$H NMR (400 MHz, DMSO-d$_6$) δ 9.76 (s, 1H), 8.36 (d, 1H, J=5.8 Hz), 8.27-8.23 (m, 2H), 8.00 (m, 1H), 7.70 (d, 1H, J=5.7 Hz), 7.63-7.60 (m, 1H), 7.51 (s, 1H), 3.69-3.66 (m, 2H), 3.56 (s, 3H), 3.16-3.10 (m, 2H), 2.90 (m, 5H), 1.93-1.90 (m, 2H), 1.78-1.75 (m, 2H), 1.66-1.59 (m, 2H).

Example 243. 5-Fluoro-6-(8-methyl-7-quinolyl)spiro[chromane-2,4'-piperidine]-1'-carboxamide

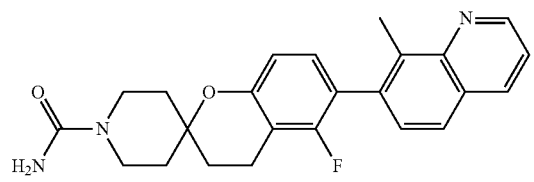

This example was synthesized using tert-butyl 6-bromo-5-fluoro-spiro[chromane-2,4'-piperidine]-1'-carboxylate and 8-methyl-7-(4,4,5,5-tetramethyl-1,3,2-dioxaborolan-2-yl)quinolone similar to example 233. Analysis: LCMS m/z=406 (M+1); $^1$H NMR (400 MHz, DMSO-d$_6$) δ 8.97 (dd, J=4.0, 1.8 Hz, 1H), 8.38 (dd, J=8.3, 1.8 Hz, 1H), 7.86 (d, J=8.3 Hz, 1H), 7.61-7.54 (m, 1H), 7.43 (d, J=8.5 Hz, 1H), 7.14 (t, J=8.7 Hz, 1H), 6.80 (d, J=8.5 Hz, 1H), 5.98 (s, 2H), 3.70 (br d, J=13.1 Hz, 2H), 3.16 (br t, J=10.8 Hz, 2H), 2.76 (brt, J=6.4 Hz, 2H), 2.58 (s, 3H), 1.93-1.82 (m, 2H), 1.79-1.67 (m, 2H), 1.66-1.49 (m, 2H).

Example 244. 7-Methyl-6-(8-methyl-7-quinolyl)spiro[chromane-2,4'-piperidine]-1'-carboxamide

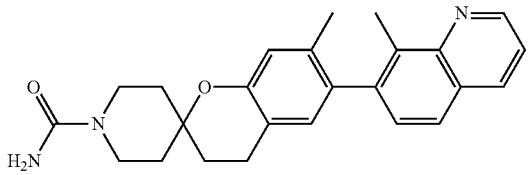 [SMILES: Cc1cc2c(cc1-c1ccc3cccnc3c1C)CCC1(CCN(C(N)=O)CC1)O2]

Step 1. 1-(5-bromo-2-hydroxy-4-methyl-phenyl)ethanone (2.015 g, 8.796 mmol), 1-boc-4-piperidone (1.840 g, 9.235 mmol), pyrrolidine (0.6518 g, 0.765 mL, 9.16 mmol) and methanol (14 g, 18 mL, 450 mmol) were heated at 50° C. under nitrogen for 17 h, then cooled to room temperature. The reaction was diluted with water and ethyl acetate and the layers were separated. The aqueous phase was extracted with ethyl acetate and the combined organics were washed with 1M HCl, water, 1M NaOH and brine. The organics were dried over sodium sulfate, filtered and concentrated in vacuo. The residue was purified by Isco normal phase chromatography eluting with 0% to 40% ethyl acetate in hexane to afford tert-butyl 6-bromo-7-methyl-4-oxo-spiro[chromane-2,4'-piperidine]-1'-carboxylate, a yellow solid (3.18 g, 88%). LCMS m/z=433 (M+23); $^1$H NMR (400 MHz, DMSO-d$_6$) δ 7.79 (s, 1H), 7.15 (m, 1H), 3.72 (m, 2H), 3.14-3.10 (m, 2H), 2.83 (s, 2H), 2.35 (s, 3H), 1.88-1.85 (m, 2H), 1.65-1.58 (m, 2H), 1.40 (s, 9H).

Step 2. Tert-butyl 6-bromo-7-methyl-4-oxo-spiro[chromane-2,4'-piperidine]-1'-carboxylate (3.18 g, 7.750 mmol) and ethanol (44 g, 56 mL, 970 mmol) were combined in a round bottom flask and cooled on an ice bath for 30 minutes. Sodium borohydride (0.655 g, 0.6931 mL, 17.3 mmol) was added and the reaction was stirred for 3 h warming to room temperature. The reaction was quenched by addition of 1 N aqueous sodium carbonate then concentrated. The residue was dissolved in ethyl acetate and washed with saturated aq. sodium bicarbonate solution, then brine. The organic phase was dried over sodium sulfate, filtered and concentrated to afford tert-butyl 6-bromo-4-hydroxy-7-methyl-spiro[chromane-2,4'-piperidine]-1'-carboxylate, an off-white solid (3.24 g, 96%). $^1$H NMR (400 MHz, DMSO-d$_6$) δ 7.55 (s, 1H), 6.83 (s, 1H), 5.48 (d, 1H, J=5.9 Hz), 4.70-4.65 (m, 1H), 3.72-3.65 (m, 2H), 3.20-3.06 (m, 2H), 2.27 (s, 3H), 2.12-2.07 (m, 1H), 1.80-1.64 (m, 4H), 1.42 (s, 9H).

Step 3. TFA (9.0 g, 6.1 mL, 79 mmol) was added slowly to tert-butyl 6-bromo-4-hydroxy-7-methyl-spiro[chromane-2,4'-piperidine]-1'-carboxylate (3.243 g, 7.866 mmol) in a round bottom flask. Triethylsilane (3.8 g, 5.3 mL, 33 mmol) was added to the reaction and heated at 50° C. for 4 h. The reaction was cooled to room temperature then ethyl acetate and saturated sodium bicarbonate solution were added slowly. The reaction was stirred until bubbling stopped. The layers were separated and the organic layer was washed with brine. The mixture was filtered to collect precipitate and the organic phase was dried over sodium sulfate, filtered and concentrated. Residue combined with precipitate was purified by Isco normal phase chromatography eluting with methanol/DCM to afford 6-bromo-7-methyl-spiro[chromane-2,4'-piperidine] (1.623 g, 70%). LCMS m/z=297 (M+1); $^1$H NMR (400 MHz, DMSO-d$_6$) δ 8.54 (br s, 1H), 7.33 (s, 1H), 6.86 (s, 1H), 3.23-3.20 (m, 2H), 3.12-3.05 (m, 2H), 2.76-2.72 (m, 2H), 2.26 (s, 3H), 1.90-1.73 (m, 6H).

Step 4. 6-bromo-7-methyl-spiro[chromane-2,4'-piperidine] (1.623 g, 5.479 mmol), N,N-diisopropylethylamine (1.52 g, 2.05 mL, 11.8 mmol) and DCM (29 mL) were combined in a round bottom flask. Di-tert-butyl dicarbonate (1.253 g, 5.741 mmol) was added and the reaction was stirred at room temperature for 3 hours. The reaction was diluted with water and DCM and the layers were separated. The aqueous layer was extracted once more with DCM; the combined organic layers were washed with brine, dried over sodium sulfate, filtered and concentrated. Residue was purified by Isco normal phase chromatography eluting with 0% to 30% ethyl acetate in heptane to afford tert-butyl 6-bromo-7-methyl-spiro[chromane-2,4'-piperidine]-1'-carboxylate (1.445 g, 67%). $^1$H NMR (400 MHz, DMSO-d$_6$) δ 7.29 (s, 1H), 6.81 (s, 1H), 3.72-3.69 (m, 2H), 3.20-3.13 (m, 2H), 2.73-2.69 (m, 2H), 2.25 (s, 3H), 1.79-1.76 (m, 2H), 1.68-1.65 (m, 2H), 1.56-1.49 (m, 2H), 1.42 (s, 9H).

Step 5. Tert-butyl 6-bromo-7-methyl-spiro[chromane-2,4'-piperidine]-1'-carboxylate (0.551 g, 1.390 mmol), 8-methyl-7-(4,4,5,5-tetramethyl-1,3,2-dioxaborolan-2-yl)quinoline (0.400 g, 1.49 mmol), tetrakis(triphenylphosphine)palladium(0) (0.111 g, 0.0961 mmol), sodium carbonate in water (1 M) (4.0 mL, 4 mmol) and 1,4-dioxane (6.8 g, 6.0 mL, 77 mmol) were combined in a round bottom flask. The reaction was purged with argon and heated at 100° C. under nitrogen for 20 h. The reaction was cooled to room temperature and filtered through a pad of Celite washing with ethyl acetate. The filtrate was concentrated and residue was dissolved in ethyl acetate, washed with saturated aq. sodium bicarbonate solution, then brine. The organic phase was dried over sodium sulfate, filtered and concentrated. Residue was purified by Isco normal phase chromatography eluting with 0% to 30% ethyl acetate in heptane to afford tert-butyl 7-methyl-6-(8-methyl-7-quinolyl)spiro[chromane-2,4'-piperidine]-1'-carboxylate (422 mg, 63%). LCMS m/z=459 (M+1); $^1$H NMR (400 MHz, DMSO-d$_6$) δ 9.01 (m, 1H), 8.42 (m, 1H), 7.88 (d, 1H, J=8.3 Hz), 7.63-7.60 (m, 1H), 6.93 (s, 1H), 6.84 (s, 1H), 3.80-3.05 (m, 2H), 3.33-3.25 (m, 2H), 2.81-2.77 (m, 2H), 2.52 (s, 3H), 1.99 (s, 3H), 1.90-1.86 (m, 2H), 1.81-1.77 (m, 2H), 1.67-1.56 (m, 2H), 1.48 (s, 9H).

Step 6. Tert-butyl 7-methyl-6-(8-methyl-7-quinolyl)spiro[chromane-2,4'-piperidine]-1'-carboxylate (0.422 g, 0.9202 mmol) and ethyl acetate (5.5 mL) were combined in a round bottom flask. Hydrogen chloride (4 M) in dioxane (2.8 mL, 11 mmol) was added and the reaction was stirred at room temperature for 24 hours. The reaction was concentrated, triturated with ether and dried by high vacuum at 40° C. to afford 7-methyl-6-(8-methyl-7-quinolyl)spiro[chromane-2,4'-piperidine] dihydrochloride (368 mg, 88%). LCMS m/z=359 (M+1); 1H NMR (400 MHz, DMSO-d$_6$) δ 9.06 (m, 1H), 8.92 (m, 1H), 8.78 (m, 1H), 8.62 (d, 1H, J=8.2 Hz), 7.96 (d, 1H, J=8.4 Hz), 7.74-7.71 (m, 1H), 7.43 (d, 1H, J=8.4 Hz), 6.93 (s, 1H), 6.86 (s, 1H), 3.24 (m, 2H), 3.12 (m, 2H), 2.80-2.76 (m, 2H), 2.50 (s, 3H), 1.99-1.93 (m, 5H), 1.91-1.81 (m, 4H).

Step 7. 7-Methyl-6-(8-methyl-7-quinolyl)spiro[chromane-2,4'-piperidine] dihydrochloride (0.074 g, 0.1715 mmol), N,N-diisopropylethylamine (0.0893 g, 0.118 mL, 0.677 mmol), (trimethylsilyl)isocyanate (0.026 g, 0.031 mL, 0.23 mmol) and dichloromethane (2 g, 2 mL, 30 mmol) were combined in a vial. The reaction was stirred at room temperature for 3 days. The reaction was diluted with DCM, washed with saturated aq. sodium bicarbonate solution, then brine. The organic phase was dried over sodium sulfate, filtered and concentrated. Residue was triturated with ether and dried by high vacuum at 40° C. to afford the title compound, an off-white solid (30 mg, 44%). Analysis: LCMS m/z=402 (M+1); $^1$H NMR (400 MHz, DMSO-d$_6$) δ 8.95 (m, 1H), 8.38-8.35 (m, 1H), 7.82 (d, 1H, J=8.3 Hz), 7.57-7.54 (m, 1H), 7.33 (d, 1H, J=8.4 Hz), 6.87 (s, 1H), 6.78 (s, 1H), 5.96 (s, 2H), 3.71-3.68 (m, 2H), 3.20-3.11 (m, 2H), 2.75-2.71 (m, 2H), 2.46 (s, 3H), 1.93 (s, 3H), 1.83-1.80 (m, 2H), 1.69 (m, 2H), 1.59-1.49 (m, 2H).

Example 245. N-methoxy-7-methyl-6-(8-methyl-7-quinolyl)spiro[chromane-2,4'-piperidine]-1'-carboxamide

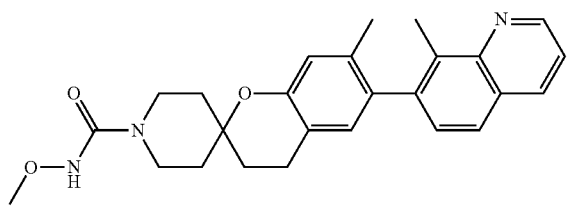 [SMILES: CONC(=O)N1CCC2(CCc3cc(-c4ccc5cccnc5c4C)c(C)cc3O2)CC1]

1,1'-Carbonyldiimidazole (0.1 g, 0.61671 mmol), DCM (2.1 mL) and O-methylhydroxylamine hydrochloride (0.051 g, 0.6106 mmol) and N,N-diisopropylethylamine (0.27 g, 0.365 mL, 2.09 mmol) were stirred at room temperature for 2 h. 7-methyl-6-(8-methyl-7-quinolyl)spiro[chromane-2,4'-piperidine] dihydrochloride (0.089 g, 0.2063 mmol) was added and the reaction was stirred for 4 days at room temperature. An additional solution of 1,1'-carbonyldiimidazole (98 mg), dichloromethane (2 mL) and O-methylhydroxylamine hydrochloride (50 mg) and N,N-diisopropylethylamine (0.365 mL) was added and the reaction was stirred for 26 hours. The reaction was diluted with DCM, washed with saturated ammonium chloride solution, then saturated sodium bicarbonate solution, then brine. The organic phase was dried over sodium sulfate, filtered and concentrated. The residue was purified by prep. HPLC reverse phase chromatography and lyophilized to afford a yellow solid. Analysis: LCMS m/z=432 (M+1); $^1$H NMR (400 MHz, DMSO-d$_6$) δ 9.73 (br s, 1H), 9.01 (m, 1H), 8.52 (m, 1H), 7.89 (d, 1H, J=10.4 Hz), 7.67-7.64 (m, 1H), 7.39 (d, 1H, J=8.4 Hz), 6.87 (s, 1H), 6.79 (s, 1H), 3.66-3.63 (m, 2H), 3.54 (s, 3H), 3.19-3.10 (m, 2H), 2.74-2.71 (m, 2H), 2.47 (s, 3H), 1.93 (s, 3H), 1.83-1.80 (m, 2H), 1.76-1.70 (m, 2H), 1.61-1.50 (m, 2H).

Example 246. N-Methoxy-7-methyl-6-(1-methyl-6-isoquinolyl)spiro[chromane-2,4'-piperidine]-1'-carboxamide

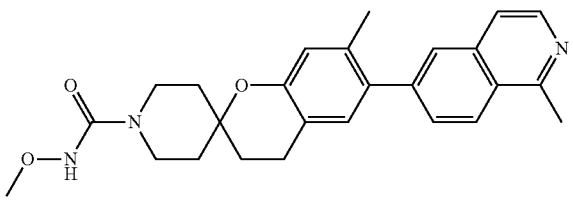

Step 1. 6-bromo-1-methyl-isoquinoline (3.002 g, 13.52 mmol), bis(pinacolato)diboron (3.564 g, 14.0 mmol), [1,1'-bis(diphenylphosphino)ferrocene]-dichloropalladium(II), complex with dichloromethane (1:1) (0.47 g, 0.576 mmol), potassium acetate (3.918 g, 39.9 mmol) and 1,4-dioxane (67.74 g, 60 mL, 769 mmol) were combined in a round bottom flask. The reaction was purged with argon then heated at 90° C. under nitrogen for 19 h. The reaction was cooled to room temperature, diluted with ethyl acetate then filtered through a pad of silica gel rinsing with ethyl acetate. The filtrate was concentrated in vacuo; residue was purified by Isco normal phase chromatography eluting with 0% to 70% ethyl acetate in heptane to yield 1-methyl-6-(4,4,5,5-tetramethyl-1,3,2-dioxaborolan-2-yl)isoquinoline, an off-white solid (2.809 g, 77%). $^1$H NMR (400 MHz, DMSO-d$_6$) δ 8.37 (d, 1H, J=5.7 Hz), 8.32 (m, 1H), 8.18 (d, 1H, J=8.4 Hz), 7.86 (m, 1H), 7.76 (d, 1H, J=5.7 Hz), 2.89 (s, 3H), 1.35 (s, 12H).

Step 2. Tert-butyl 6-bromo-7-methyl-spiro[chromane-2,4'-piperidine]-1'-carboxylate (0.201 g, 0.5072 mmol), 1-methyl-6-(4,4,5,5-tetramethyl-1,3,2-dioxaborolan-2-yl)isoquinoline (0.145 g, 0.539 mmol), tetrakis(triphenylphosphine)palladium(0) (0.043 g, 0.0372 mmol), sodium carbonate in water (1 M) (1.5 mL, 1 mmol) and 1,4-dioxane (2.5 g, 2.2 mL, 28 mmol) were combined in a round bottom flask. The reaction was purged with argon and heated at 100° C. under nitrogen for 21 h, then cooled to room temperature. The reaction was filtered through a pad of Celite, washing with ethyl acetate, then concentrated. The residue was dissolved in ethyl acetate and washed with saturated aqueous sodium bicarbonate solution, then brine. The organic phase was dried over sodium sulfate, filtered and concentrated. Residue was purified by Isco normal phase chromatography eluting with 0% to 45% ethyl acetate in heptane to afford tert-butyl 7-methyl-6-(1-methyl-6-isoquinolyl)spiro[chromane-2,4'-piperidine]-1'-carboxylate (134 mg, 55%). LCMS m/z=459 (M+1); $^1$H NMR (400 MHz, DMSO-d$_6$) δ 8.34 (d, 1H, J=5.7 Hz), 8.20 (d, 1H, J=8.6 Hz), 7.84 (d, 1H, J=1.4 Hz), 7.68-7.63 (m, 2H), 7.05 (s, 1H), 6.79 (s, 1H), 3.75-3.72 (m, 2H), 3.17-3.13 (m, 2H), 2.90 (s, 3H), 2.77-2.73 (m, 2H), 2.20 (s, 3H), 1.83-1.80 (m, 2H), 1.73-1.70 (m, 2H), 1.59-1.51 (m, 2H), 1.42 (s, 9H).

Step 3. Tert-butyl 7-methyl-6-(1-methyl-6-isoquinolyl)spiro[chromane-2,4'-piperidine]-1'-carboxylate (0.134 g, 0.2922 mmol) and ethyl acetate (2 mL) were combined in a flask. Hydrogen chloride (4 M) in dioxane (0.87 mL, 3.5 mmol) was added and the reaction was stirred at room temperature for 23 hours. The reaction was concentrated, triturated with ether and dried by high vacuum to afford 7-methyl-6-(1-methyl-6-isoquinolyl)spiro-[chromane-2,4'-piperidine]dihydrochloride, (122 mg, 92%). LC-MS: m/z=359 (M+H); 1H NMR (400 MHz, DMSO-d$_6$) δ 8.96 (m, 1H), 8.84-8.78 (m, 1H), 8.56 (d, 1H, J=8.7 Hz), 8.50 (d, 1H, J=6.5 Hz), 8.27 (m, 1H), 8.20 (s, 1H), 7.97 (d, 1H, J=8.6 Hz), 7.16 (s, 1H), 6.89 (s, 1H), 3.21-3.10 (m, 7H), 2.81-2.78 (m, 2H), 2.25 (s, 3H), 2.00-1.81 (m, 6H).

Step 4. This examples was synthesized using 7-methyl-6-(1-methyl-6-isoquinolyl)spiro-[chromane-2,4'-piperidine] dihydrochloride and O-methylhydroxylamine hydrochloride in a similar manner to examples 245. Analysis: LCMS: LCMS m/z=432 (M+1); $^1$H NMR (400 MHz, DMSO-d$_6$) δ 9.74 (br s, 1H), 8.58 (d, 1H, J=8.8 Hz), 8.52 (d, 1H, J=6.6 Hz), 8.29 (d, 1H, J=6.6 Hz), 8.22 (d, 1H, J=1.5 Hz), 8.01 (m, 1H), 7.14 (s, 1H), 6.85 (s, 1H), 3.67-3.63 (m, 2H), 3.54 (s, 3H), 3.18-3.09 (m, 5H), 2.78 (m, 2H), 2.25 (s, 3H), 1.84-1.81 (m, 2H), 1.72-1.69 (m, 2H), 1.60-1.53 (m, 2H).

Example 247. 8-Methoxy-6-(8-methyl-7-quinolyl)spiro[4H-1,3-benzodioxine-2,4'-piperidine]-1'-carboxamide

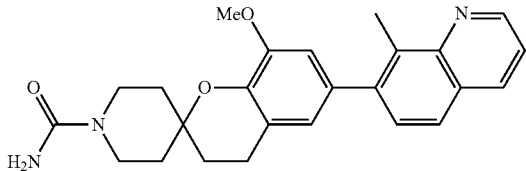

Step 1. 4-Bromo-2-(hydroxymethyl)-6-methoxy-phenol (0.500 g, 2.15 mmol), tert-butyl 4-oxopiperidine-1-carboxylate (0.581 g, 2.92 mmol), p-toluenesulfonic acid monohydrate (0.050 g, 0.26 mmol) and chloroform (10 g, 7.0 mL, 87 mmol) were combined in a flask. The reaction was heated at 90° C. while removing water with a Dean-Stark trap for 3 days. The reaction was cooled to room temperature and concentrated. The residue was dissolved in ethyl acetate, washed with saturated sodium bicarbonate solution then brine. The organic phase was dried with sodium sulfate, filtered and concentrated. The residue was purified by Isco normal phase chromatography eluting with 0 to 35% ethyl acetate in hexane to afford tert-butyl 6-bromo-8-methoxy-spiro[4H-1,3-benzodioxine-2,4'-piperidine]-1'-carboxylate (209 mg, 24%). $^1$H NMR (400 MHz, DMSO-$d_6$) δ 7.02 (d, 1H, J=2.2 Hz), 4.81 (s, 1H), 3.77 (s, 3H), 3.48-3.42 (m, 2H), 3.33 (m, 2H), 1.84-1.71 (m, 4H), 1.40 (s, 9H).

Step 2. Tert-butyl 6-bromo-8-methoxy-spiro[4H-1,3-benzodioxine-2,4'-piperidine]-1'-carboxylate (0.136 g, 0.3283 mmol), 8-methyl-7-(4,4,5,5-tetramethyl-1,3,2-dioxaborolan-2-yl)quinoline (0.11 g, 0.4086 mmol), tetrakis(triphenylphosphine)palladium(0) (0.029 g, 0.0251 mmol), sodium carbonate in water (1 M) (1.0 mL, 1 mmol) and 1,4-dioxane (2.258 g, 2 mL, 25.6 mmol) were combined in a round bottom flask. The reaction was purged with argon and heated at 100° C. under nitrogen for 17 h. The reaction was cooled to room temperature and filtered through a pad of Celite washing with ethyl acetate. The filtrate was concentrated, residue dissolved in ethyl acetate, washed with saturated aq. sodium bicarbonate solution, then brine. Organic phase was dried over sodium sulfate, filtered and concentrated. Residue was purified by Isco normal phase chromatography eluting with 0% to 30% ethyl acetate in heptane to afford tert-butyl 8-methoxy-6-(8-methyl-7-quinolyl)spiro[4H-1,3-benzodioxine-2,4'-piperidine]-1'-carboxylate, a white solid (114 mg, 69%). LCMS m/z=477 (M+1); $^1$H NMR (400 MHz, DMSO-$d_6$) δ 8.97 (m, 1H), 8.36 (m, 1H), 7.85 (d, 1H, J=8.4 Hz), 7.55 (m, 1H), 7.50 (d, 1H, J=8.4 Hz), 6.92 (d, 1H, J=1.8 Hz), 6.74 (d, 1H, J=1.8 Hz), 4.91 (s, 2H), 3.81 (s, 3H), 3.54-3.50 (m, 2H), 3.39 (m, 2H), 2.70 (s, 3H), 1.92-1.79 (m, 4H), 1.42 (s, 9H).

Step 3. Tert-butyl 8-methoxy-6-(8-methyl-7-quinolyl)spiro[4H-1,3-benzodioxine-2,4'-piperidine]-1'-carboxylate (0.114 g, 0.2392 mmol) and ethyl acetate (1.5 mL) were combined in a flask. Hydrogen chloride (4 M) in dioxane (0.74 mL, 3.0 mmol) was added and the reaction was stirred at room temperature. The reaction was concentrated, triturated with ether and dried on the high vacuum in the ChemDry apparatus at 40° C. to afford 8-methoxy-6-(8-methyl-7-quinolyl)spiro[4H-1,3-benzodioxine-2,4'-piperidine] dihydrochloride, a yellow solid (83 mg, 73%). LCMS m/z=377 (M+1); $^1$H NMR (400 MHz, DMSO-$d_6$) δ 9.02 (m, 1H), 8.86 (br s, 2H), 8.50 (m, 1H), 7.92 (d, 1H, J=8.5 Hz), 7.64 (m, 1H), 7.55 (d, 1H, J=8.5 Hz), 6.96 (d, 1H, J=1.8 Hz), 6.77 (d, 1H, J=1.8 Hz), 4.95 (s, 2H), 3.83 (s, 3H), 3.19 (m, 4H), 2.71 (s, 3H), 2.15-2.10 (m, 4H)

Step 4. 8-Methoxy-6-(8-methyl-7-quinolyl)spiro[4H-1,3-benzodioxine-2,4'-piperidine]dihydrochloride (0.083 g, 0.1847 mmol), N,N-diisopropylethylamine (0.102 g, 0.135 mL, 0.773 mmol), (trimethylsilyl)isocyanate (0.029 g, 0.034 mL, 0.25 mmol) and DCM (3 g, 2 mL, 30 mmol) were combined in a vial. The reaction was stirred at room temperature for 4 days, then diluted with DCM, washed with saturated aq. sodium bicarbonate solution, then brine. The organic phase was dried over sodium sulfate, filtered and concentrated. The residue was triturated with ether, then dried by high vacuum in the ChemDry apparatus at 40° C. to afford the title compound, an off-white solid Analysis: LCMS: m/z=420 (M+1); $^1$H NMR (400 MHz, DMSO-$d_6$) δ 8.97 (m, 1H), 8.38-8.35 (m, 1H), 7.85 (d, 1H, J=8.2 Hz), 7.57-7.54 (m, 1H), 7.50 (d, 1H, J=8.5 Hz), 6.92 (d, 1H, J=1.8 Hz), 6.74 (d, 1H, J=1.8 Hz), 6.04 (s, 2H), 4.91 (s, 2H), 3.81 (s, 3H), 3.50-3.44 (m, 2H), 2.70 (s, 3H), 1.87-1.79 (m, 4H), 1.24 (m, 2H).

Example 248. 8-Methoxy-6-(8-methyl-7-quinolyl)spiro[4H-1,3-benzodioxine-2,4'-piperidine]-1'-carboxamide

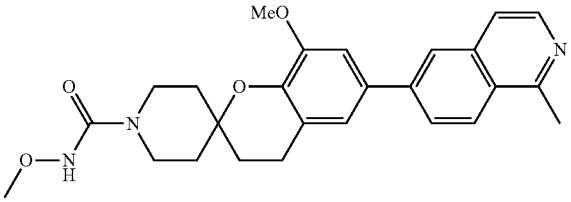

Step 1. Tert-butyl 6-bromo-8-methoxy-spiro[4H-1,3-benzodioxine-2,4'-piperidine]-1'-carboxylate (0.07 g, 0.1690 mmol), 1-methyl-6-(4,4,5,5-tetramethyl-1,3,2-dioxaborolan-2-yl)isoquinoline (0.057 g, 0.2117 mmol), tetrakis(triphenylphosphine)palladium(0) (0.014 g, 0.012 mmol), sodium carbonate in water (1 M) (0.51 mL, 0.5 mmol) and 1,4-dioxane (1.129 g, 1 mL, 12.8 mmol) were combined in a round bottom flask. The reaction was purged with argon and heated at 100° C. under nitrogen for 24 hours. The reaction was cooled to room temperature and filtered through a pad of Celite washing with ethyl acetate. The filtrate was concentrated, residue was dissolved in ethyl acetate, washed with saturated aq. sodium bicarbonate solution, then brine. The organic phase was dried over sodium sulfate, filtered and concentrated. Residue was purified by Isco normal phase chromatography eluting with 0% to 65% ethyl acetate in heptane to afford a white solid, tert-butyl 8-methoxy-6-(1-methyl-6-isoquinolyl)spiro[4H-1,3-benzodioxine-2,4'-piperidine]-1'-carboxylate (54 mg, 64%). LCMS m/z=477 (M+1); 1H NMR (400 MHz, DMSO-$d_6$) δ 8.34 (d, 1H, J=5.8 Hz), 8.24 (d, 1H, J=9.0 Hz), 8.21 (m, 1H), 7.99 (m, 1H), 7.69 (d, 1H, J=5.8 Hz), 7.33 (m, 1H), 7.19 (m, 1H), 4.94 (s, 2H), 3.91 (s, 3H), 3.52-3.47 (m, 2H), 3.38 (m, 2H), 2.90 (s, 3H), 1.90-1.81 (m, 4H), 1.42 (s, 9H).

Step 2. Tert-butyl 8-methoxy-6-(1-methyl-6-isoquinolyl)spiro[4H-1,3-benzodioxine-2,4'-piperidine]-1'-carboxylate (0.054 g, 0.1133 mmol) and ethyl acetate (1.0 mL) were combined in a flask. Hydrogen chloride (4 M) in dioxane (0.35 mL, 1.4 mmol) was added and the reaction was stirred at room temperature for 23 h. The reaction was concentrated to afford 8-methoxy-6-(1-methyl-6-isoquinolyl)spiro[4H-1,3-benzodioxine-2,4'-piperidine] dihydrochloride (40 mg, 75%). LCMS m/z=377 (M+1); $^1$H NMR (400 MHz, DMSO-d$_6$) δ 8.98-8.90 (m, 2H), 8.58-8.55 (m, 2H), 8.47 (d, 1H, J=6.5 Hz), 8.31 (m, 1H), 8.21 (m, 1H), 7.47 (m, 1H), 7.36 (m, 1H), 5.00 (s, 2H), 3.95 (s, 3H), 3.16 (m, 7H), 2.14 (m, 4H).

Step 3. 1,1'-Carbonyldiimidazole (0.092 g, 0.56738 mmol), 1,2-dichloroethane (2.0 mL, 2.5 g, 25 mmol) and O-methylhydroxylamine hydrochloride (0.047 g, 0.5627 mmol) and N,N-diisopropylethylamine (0.296 g, 0.4 mL, 2.29 mmol) were combined in a vial and stirred at 50° C. for 2.5 hours. The mixture was added to 8-methoxy-6-(1-methyl-6-isoquinolyl)spiro[4H-1,3-benzodioxine-2,4'-piperidine] dihydrochloride (0.04 g, 0.08901 mmol) and stirred at 50° C. for 18 hours. The reaction was diluted with DCM, washed with saturated aq. ammonium chloride solution, then saturated aq. sodium bicarbonate solution, then brine. The organic phase was dried over sodium sulfate, filtered and concentrated. The residue was purified by prep. HPLC and lyophilized to afford the title compound (17 mg, 34%). Analysis: LCMS m/z=450 (M+1); $^1$H NMR (400 MHz, DMSO-d$_6$) δ 9.83 (s, 1H), 8.61-8.57 (m, 2H), 8.50 (d, 1H, J=6.5 Hz), 8.36-8.33 (m, 1H), 8.25 (d, 1H, J=6.6 Hz), 7.46 (d, 1H, J=1.7 Hz), 7.35 (d, 1H, J=1.6 Hz), 4.96 (s, 2H), 3.94 (s, 3H), 3.55 (s, 3H), 3.47-3.42 (m, 2H), 3.35-3.30 (m, 2H), 3.16 (s, 3H), 1.90-1.78 (m, 4H).

Example 249. 8-chloro-6-(8-methyl-7-quinolyl)spiro[chromane-2,4'-piperidine]-1'-carboxamide

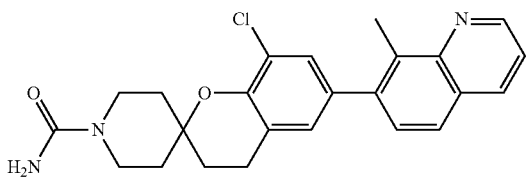 [SMILES: Cc1c(-c2cc(Cl)c3c(c2)CCC2(CCN(C(N)=O)CC2)O3)ccc2cccnc12]

Step 1. 1-(5-bromo-3-chloro-2-hydroxy-phenyl)ethanone (1.00 g, 4.01 mmol), 1-boc-4-piperidone (0.85 g, 4.2660 mmol) pyrrolidine (0.2982 g, 0.35 mL, 4.19 mmol) and methanol (7.1 g, 9.0 mL, 220 mmol) were combined in a flask and heated at 50° C. under nitrogen for 29 h. The reaction was cooled to room temperature, then diluted with water and ethyl acetate and the layers were separated. The aq. phase was further extracted with ethyl acetate and the combined organics were washed with 1M HCl, 1M NaOH then brine. The combined organic phases were dried over sodium sulfate, filtered and concentrated in vacuo. The residue was purified by Isco normal phase chromatography eluting with 0% to 30% ethyl acetate in heptane to afford tert-butyl 6-bromo-8-chloro-4-oxo-spiro[chromane-2,4'-piperidine]-1'-carboxylate (1.356 g, 79%). LCMS m/z=453 (M+Na); $^1$H NMR (400 MHz, DMSO-d$_6$) δ 8.05 (d, 1H, J=2.4 Hz), 7.76 (d, 1H, J=2.4 Hz), 3.82-3.79 (m, 2H), 3.05 (m, 2H), 2.95 (s, 2H), 1.93-1.90 (m, 2H), 1.69-1.61 (m, 2H), 1.40 (s, 9H).

Step 2. Tert-butyl 6-bromo-8-chloro-4-oxo-spiro[chromane-2,4'-piperidine]-1'-carboxylate (1.356 g, 3.148 mmol) and ethanol (19 g, 24 mL, 410 mmol) were combined in a flask and cooled over an ice/water bath. Sodium borohydride (0.275 g, 0.291 mL, 7.26 mmol) was added and the reaction was stirred for 3.5 hours warming to room temperature. The reaction was quenched by addition of 1 N aq. sodium carbonate then concentrated. The residue was dissolved in ethyl acetate, washed with saturated aq. sodium bicarbonate solution, then brine, dried over sodium sulfate, filtered and concentrated to afford an off-white solid, tert-butyl 6-bromo-8-chloro-4-hydroxy-spiro[chromane-2,4'-piperidine]-1'-carboxylate (1.15 g, 80%). $^1$H NMR (400 MHz, DMSO-d$_6$) δ 7.55-7.51 (m, 2H), 5.71 (m, 1H), 4.75-4.70 (m, 1H), 3.81-3.73 (m, 2H), 2.17-2.11 (m, 1H), 1.84-1.53 (m, 7H), 1.40 (s, 9H).

Step 3. Trifluoroacetic acid (3.2 g, 2.2 mL, 28 mmol) was added slowly to tert-butyl 6-bromo-8-chloro-4-hydroxy-spiro[chromane-2,4'-piperidine]-1'-carboxylate (1.150 g, 2.658 mmol) in a round bottom flask. Triethylsilane (1.4 g, 1.9 mL, 12 mmol) was added to the reaction and it was heated at 50° C. Over the course of 7 days, aliquots totaling 10 mL of triethylsilane and 10 mL of TFA were added while the reaction stirred at 50° C. The reaction was then cooled to room temperature. Ethyl acetate and saturated sodium bicarbonate solution were added slowly and the reaction was stirred until bubbling stopped. The layers were separated and the organic layer was washed with brine, dried over sodium sulfate, filtered and concentrated. The residue was purified by Isco normal phase chromatography eluting with 0% to 20% methanol in DCM to afford a 4:1 mixture of 6-bromo-8-chloro-spiro[chromane-2,4'-piperidine]: 6-bromo-8-chloro-spiro[chromene-2,4'-piperidine].

Step 4. A 4:1 mixture of 6-bromo-8-chloro-spiro[chromane-2,4'-piperidine]: 6-bromo-8-chloro-spiro[chromene-2,4'-piperidine] (1.05 g), N,N-diisopropylethylamine (0.982 g, 1.325 mL, 7.60 mmol), Di-tert-butyl dicarbonate (0.767 g, 3.5143 mmol) and dichloromethane (18 mL) were combined in a round bottom flask. The reaction was stirred at room temperature for 5 hours. The reaction was diluted with water and DCM and the layers were separated. The aqueous layer was extracted once more with DCM; the combined organic layers were washed with brine, dried over sodium sulfate, filtered and concentrated. The residue was purified by Isco eluting with 0% to 20% ethyl acetate in heptane to afford a 4:1 mixture of tert-butyl 6-bromo-8-chloro-spiro[chromane-2,4'-piperidine]-1'-carboxylate: tert-butyl 6-bromo-8-chloro-spiro[chromene-2,4'-piperidine]-1'-carboxylate (769 mg, 56%).

Step 5. A 4:1 mixture of tert-butyl 6-bromo-8-chloro-spiro[chromane-2,4'-piperidine]-1'-carboxylate: tert-butyl 6-bromo-8-chloro-spiro[chromene-2,4'-piperidine]-1'-carboxylate (769 mg) was dissolved in methanol (20 g, 20 mL, 500 mmol). The solution was hydrogenated on a Thales H-Cube hydrogenation reactor using a 5% Rh/C CatCart (5:95, Rhodium:carbon black) at room temperature (20° C.) and 10 bar (145 psi). The reaction was set up to recirculate the solution passed through the H-cube back into the reaction flask for 3 hours. The reaction was concentrated to afford tert-butyl 8-fluoro-6-(4,4,5,5-tetramethyl-1,3,2-dioxaborolan-2-yl)spiro[chromane-2,4'-piperidine]-1'-carboxylate (716 mg, 93%).

Step 6. Tert-butyl 6-bromo-8-chloro-spiro[chromane-2,4'-piperidine]-1'-carboxylate (0.442 g, 1.061 mmol), 8-methyl-7-(4,4,5,5-tetramethyl-1,3,2-dioxaborolan-2-yl)quinoline (0.276 g, 1.025 mmol), tetrakis(triphenylphosphine)palladium(0) (0.062 g, 0.0537 mmol), sodium carbonate in water (1 M) (3.2 mL, 3 mmol) and 1,4-dioxane (5.4 g, 4.8 mL, 62 mmol) were combined in a round bottom flask. The reaction was purged with argon and heated at 100° C. under nitrogen for 26 hours. The reaction was cooled to room temperature and filtered through a pad of Celite washing with ethyl acetate. The filtrate was concentrated, residue dissolved in ethyl acetate, washed with saturated aq. sodium bicarbonate solution, then brine. The organic phase was dried over sodium sulfate, filtered and concentrated. The residue was purified by Isco normal phase chromatography eluting with 0% to 25% ethyl acetate in heptane to afford tert-butyl 8-chloro-6-(8-methyl-7-quinolyl)spiro[chromane-2,4'-piperidine]-1'-carboxylate (275 mg, 53%). LCMS m/z=479 (M+1); $^1$H NMR (400 MHz, DMSO-$d_6$) δ 8.98 (m, 1H), 8.38 (m, 1H), 7.87 (d, 1H, J=8.5 Hz), 7.59-7.56 (m, 1H), 7.48 (d, 1H, J=8.4 Hz), 7.33 (d, 1H, J=2.1 Hz), 7.18 (d, 1H, J=2.0 Hz), 3.86-3.81 (m, 4H), 2.90-2.86 (m, 2H), 2.69 (s, 3H) 1.91-1.88 (m, 2H), 1.79-1.76 (m, 2H), 1.64-1.57 (m, 2H), 1.43 (s, 9H).

Step 7. Tert-butyl 8-chloro-6-(8-methyl-7-quinolyl)spiro[chromane-2,4'-piperidine]-1'-carboxylate (0.275 g, 0.5741 mmol) and ethyl acetate (3.6 mL) were combined in a flask. Hydrogen chloride (4 M) in dioxane (1.8 mL, 7.2 mmol) was added and the reaction was stirred at room temperature for 24 h. The reaction was concentrated to afford 8-chloro-6-(8-methyl-7-quinolyl)spiro[chromane-2,4'-piperidine] dihydrochloride (258 mg, 94%). LC-MS: m/z=379 (M+H); 1H NMR (400 MHz, DMSO-$d_6$) δ 8.99 (m, 1H), 8.78-8.59 (m, 2H), 8.42 (d, 1H, J=8.4 Hz), 7.88 (d, 1H, J=8.7 Hz), 7.61-7.58 (m, 1H), 7.48 (d, 1H, J=8.4 Hz), 7.36 (d, 1H, J=2.1 Hz), 7.21 (d, 1H, J=2.0 Hz), 3.32-3.29 (m, 2H), 3.13-3.10 (m, 2H), 2.92-2.88 (m, 2H), 2.68 (s, 3H) 2.03-1.84 (m, 6H).

Step 8. 8-chloro-6-(8-methyl-7-quinolyl)spiro[chromane-2,4'-piperidine] dihydrochloride (0.079 g, 0.1749 mmol), N,N-diisopropylethylamine (0.102 g, 0.135 mL, 0.774 mmol), (trimethylsilyl)isocyanate (0.030 g, 0.035 mL, 0.26 mmol) and dichloromethane (3 g, 2 mL, 30 mmol) were combined in a vial. The reaction was stirred at room temperature for 2 days. The reaction was diluted with DCM, washed with saturated aq. sodium bicarbonate solution, then brine. The organic phase was dried over sodium sulfate, filtered and concentrated. The residue was triturated with ether, transferred to a vial and dried on the high vac. in the ChemDry at 40° C. to afford the title compound, a white solid (12 mg, 16%). Analysis: LCMS m/z=422 (M+1); $^1$H NMR (400 MHz, DMSO-$d_6$) δ 8.97 (m, 1H), 8.37 (m, 1H), 7.85 (d, 1H, J=8.3 Hz), 7.57-7.54 (m, 1H), 7.48 (d, 1H, J=8.4 Hz), 7.32 (d, 1H, J=2.1 Hz), 7.17 (m, 1H), 5.99 (s, 2H), 3.81-3.78 (m, 2H), 3.15-3.10 (m, 2H), 2.89-2.85 (m, 2H), 2.69 (s, 3H), 1.90-1.87 (m, 2H), 1.74-1.71 (m, 2H), 1.61-1.55 (m, 2H).

Example 250. 8-Chloro-N-methoxy-6-(8-methyl-7-quinolyl)spiro[chromane-2,4'-piperidine]-1'-carboxamide

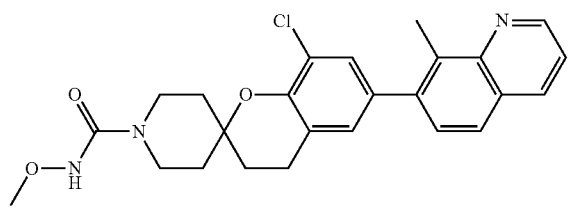 [SMILES: CONC(=O)N1CCC2(CCc3cc(-c4ccc5cccnc5c4C)cc(Cl)c3O2)CC1]

1,1'-Carbonyldiimidazole (0.114 g, 0.70305 mmol), DCM (2.4 mL), O-methylhydroxylamine hydrochloride (0.061 g, 0.7304 mmol) and N,N-diisopropylethylamine (0.308 g, 0.415 mL, 2.38 mmol) were combined and stirred at room temperature for 2.5 h. 8-Chloro-6-(8-methyl-7-quinolyl)spiro[chromane-2,4'-piperidine] dihydrochloride (0.101 g, 0.2236 mmol) was added and the reaction was stirred at room temperature for 6 days. The reaction was diluted with DCM, washed with saturated ammonium chloride solution, then saturated sodium bicarbonate solution, then water, then brine. The organic phase was dried over sodium sulfate, filtered and concentrated. The residue was triturated with ether then dried by high vacuum to afford the title compound, as an off-white solid Analysis: LCMS m/z=452 (M+1); $^1$H NMR (400 MHz, DMSO-$d_6$) δ 9.75 (s, 1H), 8.97 (m, 1H), 8.37 (m, 1H), 7.85 (d, 1H, J=8.4 Hz), 7.57-7.54 (m, 1H), 7.47 (d, 1H, J=8.4 Hz), 7.32 (d, 1H, J=2.1 Hz), 7.17 (d, 1H, J=2.0 Hz), 3.75-3.72 (m, 2H), 3.55 (s, 3H), 3.15-3.09 (m, 2H), 2.88-2.85 (m, 2H), 2.68 (s, 3H), 1.92-1.87 (m, 2H), 1.77-1.74 (m, 2H), 1.63-1.56 (m, 2H).

Example 251. 6-(4-Hydroxy-8-methyl-7-quinolyl)spiro[chromane-2,4'-piperidine]-1'-carboxamide

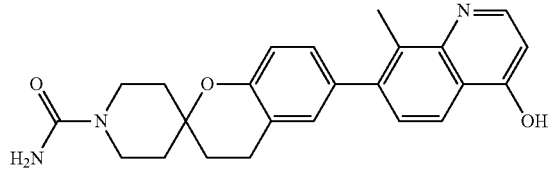 [SMILES: Cc1c(-c2ccc3c(c2)CCC2(CCN(C(N)=O)CC2)O3)ccc2c(O)ccnc12]

This example was synthesized using intermediate 3 and 7-bromo-8-methyl-quinolin-4-ol then following the procedure for example 106. Analysis: LCMS m/z=404 (M+1); $^1$H NMR (400 MHz, DMSO-$d_6$) δ 11.08 (br s, 1H), 7.97 (d, J=8.3 Hz, 1H), 7.84 (br s, 1H), 7.17 (br d, J=8.3 Hz, 1H), 7.13-7.06 (m, 2H), 6.88 (d, J=8.0 Hz, 1H), 6.07 (br d, J=7.5 Hz, 1H), 5.97 (s, 2H), 3.69 (br d, J=13.6 Hz, 2H), 3.17 (br d, J=5.3 Hz, 2H), 2.87-2.76 (m, 2H), 1.84 (br t, J=6.3 Hz, 2H), 1.69 (br d, J=13.6 Hz, 2H), 1.62-1.48 (m, 2H).

A number of embodiments of the invention have been described herein. Nevertheless, as those skilled in the art will appreciate, numerous modifications and variations of the present invention are possible in light of the above teachings; without departing from the scope of the invention that is disclosed herein. It is therefore understood that within the scope of the appended claims, the invention may be practiced otherwise than as specifically described herein, and the scope of the invention is intended to encompass all such variations.

What is claimed is:

1. A compound according to Formula I:

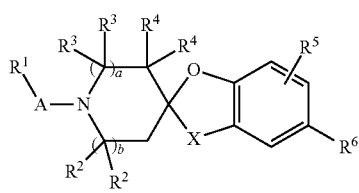

or a pharmaceutically acceptable salt thereof, wherein:
A is selected from —C(═O)— and —SO$_2$—:
$R^1$ is selected from —(C$_1$-C$_7$) hydrocarbyl, substituted —(C$_1$-C$_7$) hydrocarbyl, 3-7 membered heterocyclyl, —NR$^7$R$^8$, —SR$^7$, —NR$^7$(OR$^8$) and —NR$^7$(SR$^8$);
a and b are independently selected from 0 and 1;
each $R^2$ is independently selected from —H and —(C$_1$-C$_4$) alkyl;

each R³ is independently selected from —H and —(C₁-C₄) alkyl each R⁴ is independently selected from —H, —(C₁-C₆) alkyl, —OH, —O(C₁-C₆) alkyl, halogen, —CN, or the two geminal R⁴ groups may together form a carbonyl group;

wherein one of the R³ groups can optionally be structurally connected to one of the R² groups to form an alkylene bridge to produce a bicyclic ring; or one of the R³ groups can optionally be structurally connected to the R¹ group to form a 5 to 7 membered heterocyclyl ring fused to the 1-2 face of the piperidine ring; or one of the R³ groups can optionally be structurally connected to the R⁴ group to form a 5-7 membered carbocyclic or heterocyclic ring fused to the 2-3 face of the piperidine ring;

X is selected from —O(CH₂)_q(CR⁹R⁹ᵃ)_{p1}—, —S(CH₂)_q(CR⁹R⁹ᵃ)_{p2}—, —(CH₂)_q(CR⁹R⁹ᵃ)_{p3}— and —CH=CH—;

p1 is an integer selected from 0 and 1;
p2 is an integer selected from 0 and 1;
p3 is an integer selected from 1 and 2;
q is an integer selected from 0 and 1;

R⁵ is selected from —H, —C₁-C₇ hydrocarbyl, halogen, —(C₁-C₃) haloalkyl, —OR⁷ᵃ, —CN, NR⁷ᵃR⁸ᵃ, —(CH₂)_nNR⁷ᵃR⁸ᵃ, —O(CH₂)_nOR⁸ᵃ, —NR⁸ᵃ(CH₂)_nNR⁷ᵃR⁸ᵃ, —NR⁸ᵃ(CH₂)_nOR⁸ᵃ, C(=O)NR⁷ᵃR⁸ᵃ, C(=O)OR⁷ᵃ, 5-6 membered heteroaryl, substituted 5-6 membered heteroaryl; wherein n is an integer selected from 2, 3 and 4;

R⁶ is selected from naphthyl, substituted naphthyl, 9-10 membered bicyclic heteroaryl and substituted 9-10 membered bicyclic heteroaryl;

R⁷ is selected from —H, —(C₁-C₇) hydrocarbyl, substituted —(C₁-C₇) hydrocarbyl, —C(=O)R⁸ᵇ, —(C₁-C₆) heteroalkyl, 6 membered aryl, 5-6 membered heteroaryl and 5-6 membered heterocyclyl, wherein R⁸ᵇ is selected from —H and —(C₁-C₆) alkyl;

R⁸ is selected from —H, 3-7 membered heterocyclyl, and —(C₁-C₆) alkyl, wherein R⁷ can optionally be structurally connected to R⁸ to form a 5 to 7 membered heterocyclyl ring;

R⁷ᵃ is selected from —H, —(C₁-C₇) hydrocarbyl, substituted —(C₁-C₇) hydrocarbyl, —C(=O)R⁸ᵇ and —(C₁-C₆) heteroalkyl, wherein R⁸ᵇ is selected from —H and —(C₁-C₆) alkyl;

R⁸ᵇ is selected from —H, and —(C₁-C₆) alkyl, wherein R⁷ᵃ can optionally be structurally connected to R⁸ᵃ to form a 5 to 7 membered heterocyclyl ring;

each R⁹ is independently selected from —H, —OH, —(C₁-C₇) hydrocarbyl, —O(C₁-C₇) hydrocarbyl, and halogen; and each R⁹ᵃ is —H.

2. A compound according to claim 1, wherein R⁶ is selected from 9-10 membered bicyclic heteroaryl, and substituted 9-10 membered bicyclic heteroaryl.

3. A compound according to claim 2, wherein R⁶ is selected from:

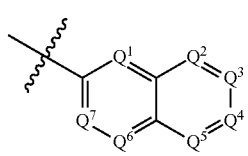
(i)

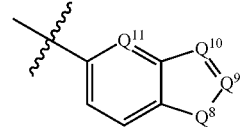
(ii)

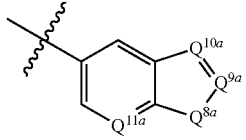
(iii)

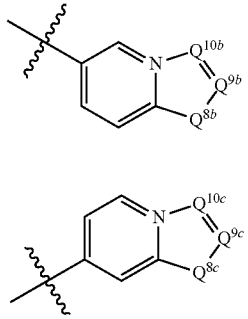
(iv)

(v)

wherein, when R⁶ is (i) Q¹, Q², Q³, Q⁴, Q⁵, Q⁶ and Q⁷ are independently selected from N and C—R¹⁰, provided that 0, 1, 2 or 3 of Q¹, Q², Q³, Q⁴, Q⁵, Q⁶ and Q⁷ are N, and the remainder of Q¹, Q², Q³, Q⁴, Q⁵, Q⁶ and Q⁷ are C—R¹⁰;

when R⁶ is (ii), Q⁸ is selected from O, S, and N—R¹⁰ᵐ and Q⁹, Q¹⁰ and Q¹¹ are independently selected from N and C—R¹⁰;

when R⁶ is (iii), Q⁸ᵃ is selected from O, S, and N-R¹⁰ⁿ, Q⁹ᵃ, Q¹⁰ᵃ and Q¹¹ᵃ are independently selected from N and C—R¹⁰;

when R⁶ is (iv), Q⁸ᵇ is selected from O, S, and N—R¹⁰ⁿ; and Q⁹ᵇ and Q¹⁰ᵇ are independently selected from N and C—R¹⁰; and when R⁶ is (v), Q⁸ᶜ is selected from O, S, and N—R¹⁰ⁿ; and Q⁹ᶜ and Q¹⁰ᶜ are independently selected from N and C—R¹⁰; wherein and wherein each R¹⁰ is independently selected from —H, halogen, —(C₁-C₆) alkyl, —(C₃-C₆) cycloalkyl, —(C₁-C₃) haloalkyl, —O(C₁-C₃) haloalkyl, -5-6 membered heterocyclyl, —OH, —O(C₁-C₆) alkyl, —O(CH₂)_r(5-6 membered heterocyclyl), —O(CH₂)_r—O(C₁-C₆)alkyl, —O(CH₂)_r—NH(C₁-C₆ alkyl)₂, —NH₂, —CN, —NH(C₁-C₆) alkyl, —N(C₁-C₆ alkyl)₂, —NH(CH₂)_r—O(C₁-C₆)alkyl, —NH(CH₂)_r—N(C₁-C₆ alkyl)₂, —C(=O)NH₂, —C(=O)NH(C₁-C₆)alkyl, and —C(=O)N(C₁-C₆ alkyl)₂; wherein r is an integer selected independently from 1, 2, 3, and 4; and each R¹⁰ⁿ is independently selected from —H, —(C₁-C₇) hydrocarbyl, substituted —(C₁-C₇) hydrocarbyl, —CO₂(C₁-C₇) hydrocarbyl, —C(=O)(C₁-C₇) hydrocarbyl and substituted —C(=O)(C₁-C₇) hydrocarbyl.

4. The compound according to claim 3, wherein $R^6$ is:

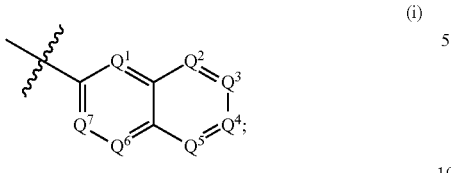

(i)

wherein 1 or 2 of Q1, Q2, Q3, Q4, Q5, Q6 and Q7 are N, and the remainder of $Q^1$, $Q^2$, $Q^3$, $Q^4$, $Q^5$, $Q^6$ and $Q^7$ are C—$R^{10}$.

5. The compound according to claim 3, wherein $R^6$ is:

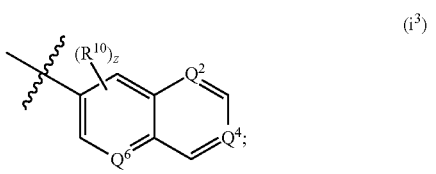

($i^3$)

wherein one or two of $Q^2$, $Q^4$ and $Q^6$ is N, and the remainder of $Q^2$, $Q^4$ and $Q^6$ are C—$R^{10}$, and z is an integer selected from 0, 1, 2 and 3.

6. The compound according to claim 1, wherein X is selected from —O—, —OCH$_2$—, —O-(CH$_2$)$_2$—, —S—, —S-(CH$_2$)$_2$—, —(CH$_2$)—, —(CH$_2$)$_2$—, and —(CH$_2$)$_3$.

7. The compound according to claim 6, wherein X is —(CH$_2$)$_2$—.

8. The compound according to claim 1, wherein $R^1$ is selected from —NR$^7$R$^8$ and —N(OR$^8$)R$^7$.

9. The compound according to claim 1, wherein a and b are 1.

10. The compound according to claim 1, wherein each $R^2$, $R^3$, and $R^4$ is H.

11. The compound according to claim 1, selected from:
[6-(1-methyl-6-isoquinolyl)spiro[chromane-2,4'-piperidine]-1'-yl]-[(2R)-tetrahydrofuran-2-yl]methanone; 1-[6-(4-methyl-3-quinolyl)spiro[chromane-2,4'-piperidine]-1'-yl]propan-1-one; cyclopropyl-[6-(4-methyl-3-quinolyl)spiro[chromane-2,4'-piperidine]-1'-yl]-methanone; [6-(4-methyl-3-quinolyl)spiro[chromane-2,4'-piperidine]-1'-yl]-[(2R)-tetrahydrofuran-2-yl]methanone; [6-(1-cyclopropyl-6-isoquinolyl)spiro[chromane-2,4'-piperidine]-1'-yl]-[(2R)-tetrahydrofuran-2-yl]methanone; 1-[6-(8-methyl-7-quinolyl)spiro[chromane-2,4'-piperidine]-1'-yl]propan-1-one; cyclopropyl-[6-(8-methyl-7-quinolyl)spiro[chromane-2,4'-piperidine]-1'-yl]methanone; [6-(8-methyl-7-quinolyl)spiro[chromane-2,4'-piperidine]-1'-yl]-[(2R)-tetrahydrofuran-2-yl]methanone; 1-[6-(8-chloro-7-quinolyl)spiro[chromane-2,4'-piperidine]-1'-yl]-propan-1-one; [6-(8-chloro-7-quinolyl)spiro[chromane-2,4'-piperidine]-1'-yl]-cyclo-propyl-methanone; [6-(8-chloro-7-quinolyl)spiro[chromane-2,4'-piperidine]-1'-yl]-[(2R)-tetrahydrofuran-2-yl]methanone; 1-[6-(8-methyl-3-quinolyl)spiro[chromane-2,4'-piperidine]-1'-yl]propan-1-one; cyclopropyl-[6-(8-methyl-3-quinolyl)spiro-[chromane-2,4'-piperidine]-1'-yl]methanone; [6-(8-methyl-3-quinolyl)spiro-[chromane-2,4'-piperidine]-1'-yl]-[(2R)-tetrahydrofuran-2-yl]methanone; cyclopropyl-[6-(8-methoxy-7-quinolyl)spiro[chromane-2,4'-piperidine]-1'-yl]methanone; [6-(8-methoxy-7-quinolyl)spiro[chromane-2,4'-piperidine]-1'-yl]-[(2R)-tetrahydrofuran-2-yl]methanone; 1-[6-(8-methyl-6-quinolyl)spiro[chromane-2,4'-piperidine]-1'-yl]propan-1-one; cyclopropyl-[6-(8-methyl-6-quinolyl)spiro[chromane-2,4'-piperidine]-1'-yl]methanone; 1-[6-(8-methoxy-7-quinolyl)spiro[chromane-2,4'-piperidine]-1'-yl]propan-1-one; [6-(8-methyl-6-quinolyl)spiro]chromane-2,4'-piperidine]-1'-yl]-[(2R)-tetrahydrofuran-2-yl]methanone; 1-[6-(1-methyl-6-isoquinolyl)spiro[4H-1,3-benzodioxine-2,4'-piperidine]-1'-yl]propan-1-one; cyclo-propyl-[6-(1-methyl-6-isoquinolyl)spiro[4H-1,3-benzodioxine-2,4'-piperidine]-1'-yl]-methanone; [6-(1-methyl-6-isoquinolyl)spiro[4H-1,3-benzodioxine-2,4'-piperidine]-1'-yl]-[(2R)-tetrahydrofuran-2-yl]methanone; 1-[6-(1-methyl-6-isoquinolyl)spiro[chromane-2,4'-piperidine]-1'-yl]propan-1-one; cyclopropyl-[6-(1-methyl-6-isoquinolyl)spiro[chromane-2,4'-piperidine]-1'-yl]methanone; 1-[6-(5-methylimidazo[1,2-a]pyridin-6-yl)spiro[chromane-2,4'-piperidine]-1'-yl]propan-1-one; cyclopropyl-[6-(5-methylimidazo[1,2-a]pyridin-6-yl)spiro[chromane-2,4'-piperidine]-1'-yl]methanone; [6-(5-methylimidazo[1,2-a]pyridin-6-yl)spiro[chromane-2,4'-piperidine]-1'-yl]-[(2R)-tetrahydrofuran-2-yl]methanone; 1-[6-(3-quinolyl)spiro[4H-1,3-benzodioxine-2,4'-piperidine]-1'-yl]propan-1-one; 2-methyl-1-]6-(7-quinolyl)spiro[4H-1,3-benzodioxine-2,4'-piperidine]-1'-yl]propan-1-one; cyclopropyl-[6-(7-quinolyl)spiro[4H-1,3-benzodioxine-2,4'-piperidine]-1'-yl]-methanone; 1-[6-(3-quinolyl)spiro[4H-1,3-benzodioxine-2,4'-piperidine]-1'-yl]propan-1-one; 2-methyl-1-[6-(3-quinolyl)spiro[4H-1,3-benzodioxine-2,4'-piperidine]-1'-yl]propan-1-one; 1-[6-(1,5-naphthyridin-3-yl)spiro[4H-1,3-benzo-dioxine-2,4'-piperidine]-1'-yl]propan-1-one; cyclopropyl-[6-(1,5-naphthyridin-3-yl)spiro[4H-1,3-benzodioxine-2,4'-piperidine]-1'-yl]methanone; cyclopropyl-[6-(3-quinolyl)spiro[4H-1,3-benzodioxine-2,4'-piperidine]-1'-yl]methanone; cyclobutyl-[6-(3-quinolyl)spiro[4H-1,3-benzodioxine-2,4'-piperidine]-1'-yl]methanone; 1-[4-hydroxy-6-(3-quinolyl)spiro[chromane-2,4'-piperidine]-1'-yl]propan-1-one; 1-[6-(3-quinolyl)spiro[chromene-2,4'-piperidine]-1'-yl]propan-1-one; cyclopropyl-[6-(3-quinolyl)spiro[chromene-2,4'-piperidine]-1'-yl]methanone; cyclobutyl-[6-(3-quinolyl)spiro[chromene-2,4'-piperidine]-1'-yl]methanone; cyclopropyl-[4-hydroxy-6-(3-quinolyl)spiro[chromane-2,4'-piperidine]-1'-yl]methanone; 1-[6-(3-quinolyl)spiro[chromane-2,4'-piperidine]-1'-yl]propan-1-one; [6-(3-quinolyl)spiro[4H-1,3-benzodioxine-2,4'-piperidine]-1'-yl]-[(2R)-tetrahydrofuran-2-yl]methanone; cyclopropyl-[6-(8-methoxy-7-quinolyl)spiro[4H-1,3-benzodioxine-2,4'-piperidine]-1'-yl]methanone; [6-(8-methyl-7-quinolyl)spiro[4H-1,3-benzo-dioxine-2,4'-piperidine]-1'-yl]-[(2R)-tetrahydrofuran-2-yl]methanone; 6-(4-methyl-3-quinolyl)spiro[4H-1,3-benzodioxine-2,4'-piperidine]-1'-yl]-[(2R)-tetrahydrofuran-2-yl]methanone; 1-[6-(4-methyl-3-quinolyl)spiro[4H-1,3-benzodioxine-2,4'-piperidine]-1'-yl]propan-1-one; 1-[6-(8-methyl-7-quinolyl)spiro[4H-1,3-benzodioxine-2,4'-piperidine]-1'-yl]propan-1-one; cyclopropyl-[6-(8-methyl-7-quinolyl)spiro[4H-1,3-benzodioxine-2,4'-piperidine]-1'-yl]methanone; 1-[6-(8-methoxy-7-quinolyl)-spiro[4H-1,3-benzodioxine-2,4'-piperidine]-1'-yl]propan-1-one; [6-(8-methoxy-7-quinolyl)spiro[4H-1,3-benzodioxine-2,4'-piperidine]-1'-yl]-[(2R)-tetrahydrofuran-2-yl]methanone; 1-[6-(8-chloro-7-quinolyl)spiro[4H-1,3-benzodioxine-2,4'-piperidine]-1'-yl]propan-1-one; [6-(8-chloro-7-quinolyl)spiro[4H-

1,3-benzodioxine-2,4'-piperidine]-1'-yl]-cyclopropyl-methanone; [6-(8-chloro-7-quinolyl)spiro[4H-1,3-benzodioxine-2,4'-piperidine]-1'-yl]-[(2R)-tetrahydrofuran-2-yl]methanone; [2-[6-(8-methyl-7-quinolyl)spiro[4H-1,3-benzodioxine-2,4'-piperidine]-1'-yl]-2-oxo-ethyl]-acetate; 2-hydroxy-1-[6-(8-methyl-7-quinolyl)spiro[chromane-2,4'-piperidine]-1'-yl]-ethanone, 2-hydroxy-1-[6-(8-methyl-7-quinolyl)spiro[4H-1,3-benzodioxine-2,4'-piperidine]-1'-yl]ethanone; 6-(8-chloro-7-quinolyl)spiro[chromane-2,4'-piperidine]-1'-carboxamide; [2-[6-(8-chloro-7-quinolyl)spiro[chromane-2,4'-piperidine]-1'-yl]-2-oxo-ethyl] acetate; 6-(8-chloro-7-quinolyl)-N-tetrahydropyran-2-yloxy-spiro[chromane-2, 4'-piperidine]-1'-carboxamide; 6-(8-chloro-7-quinolyl)-N-ethyl-spiro[chromane-2,4'-piperidine]-1'-carboxamide; 1-[6-(8-chloro-7-quinolyl)spiro[chromane-2,4'-piperidine]-1'-yl]-2-hydroxy-ethanone; 6-(8-chloro-7-quinolyl)spiro[chromane-2,4'-piperidine]-1'-carbohydroxamic acid; 6-(8-chloro-7-quinolyl)-N-ethoxy-spiro[chromane-2,4'-piperidine]-1'-carboxamide; 6-(8-chloro-7-quinolyl)-N-methoxy-spiro[chromane-2,4'-piperidine]-1'-carboxamide; 6-(3-quinolyl)spiro[chromane-2,4'-piperidine]-1'-carboxamide; 6-(benzofuran-5-yl)spiro[chromane-2,4'-piperidine]-1'-carboxamide; benzothiazol-6-yl)spiro[chromane-2,4'-piperidine]-1'-carboxamide; 6-(1-methylindol-5-yl)spiro[chromane-2,4'-piperidine]-1'-carboxamide; 6-(1H-indol-5-yl)spiro[chromane-2,4'-piperidine]-1'-carboxamide; 7-(8-methyl-7-quinolyl)spiro[4,5-dihydro-1,3-benzodioxepine-2,4'-piperidine]-1'-carboxamide; N-ethyl-7-(8-methyl-7-quinolyl)spiro[4,5-dihydro-1,3-benzodioxepine-2,4'-piperidine]-1'-carboxamide; N-ethoxy-7-(8-methyl-7-quinolyl)spiro[4,5-dihydro-1,3-benzodioxepine-2,4'-piperidine]-1'-carboxamide; N-methoxy-7-(8-methyl-7-quinolyl)spiro[4,5-dihydro-1,3-benzodioxepine-2,4'-piperidine]-1'-carboxamide; 6-(1-methylbenzimidazol-5-yl)spiro[chromane-2,4'-piperidine]-1'-carboxamide; 6-(1-methylbenzimidazol-5-yl)spiro[4H-1,3-benzodioxine-2,4'-piperidine]-1'-carboxamide; 6-(1,3-benzothiazol-5-yl)spiro[chromane-2,4'-piperidine]-1'-carboxamide; 6-thieno[2,3-b]pyridin-5-ylspiro[chromane-2,4'-piperidine]-1'-carboxamide; 6-1,3-benzoxazol-5-yl)spiro[chromane-2,4'-piperidine]-1'-carboxamide; 6-(1,3-benzoxazol-6-yl)spiro[chromane-2,4'-piperidine]-1'-carboxamide; 6-thieno[2,3-b]pyridin-5-ylspiro[4H-1,3-benzodioxine-2,4'-piperidine]-1'-carboxamide; 6-(1,8-naphthyridin-3-yl)spiro[chromane-2,4'-piperidine]-1'-carboxamide; tert-butyl 3-(1'-carbamoylspiro-[chromane-2,4'-piperidine]-6-yl)indole-1-carboxylate; 6-(1H-indol-3-yl)spiro[chromane-2,4'-piperidine]-1'-carboxamide; 6-(1H-indol-3-yl)spiro[4H-1,3-benzodioxine-2,4'-piperidine]-1'-carboxamide; N-isobutyl-6-(8-methyl-7-quinolyl)spiro[chromane-2,4'-piperidine]-1'-carboxamide; N-ethyl-6-(8-methyl-7-quinolyl)spiro[chromane-2,4'-piperidine]-1'-carboxamide; N-isopropyl-6-(8-methyl-7-quinolyl)spiro[chromane-2,4'-piperidine]-1'-carboxamide; 6-(8-methyl-7-quinolyl)-N-propyl-spiro[chromane-2,4'-piperidine]-1'-carboxamide; N-(cyclopropylmethyl)-6-(8-methyl-7-quinolyl)spiro[chromane-2,4'-piperidine]-1'-carboxamide; N-ethoxy-6-(8-methyl-7-quinolyl)spiro[chromane-2,4'-piperidine]-1'-carboxamide; 6-(8-methyl-7-quinolyl)-N-propoxy-spiro[chromane-2,4'-piperidine]-1'-carboxamide; N-isopropoxy-6-(8-methyl-7-quinolyl)spiro[chromane-2,4'-piperidine]-1'-carboxamide; N-isobutoxy-6-(8-methyl-7-quinolyl)spiro[chromane-2,4'-piperidine]-1'-carboxamide; 6-(8-methyl-7-quinolyl)spiro[chromane-2,4'-piperidine]-1'-carbohydroxamic acid; 6-(8-methyl-7-quinolyl)spiro[chromane-2,4'-piperidine]-1'-carboxamide; N-ethoxy-6-(5-methylimidazo[1,2-a]pyridin-6-yl)spiro[chromane-2,4'-piperidine]-1'-carboxamide; N-isopropoxy-6-(5-methylimidazo[1,2-a]pyridin-6-yl)spiro[chromane-2,4'-piperidine]-1'-carboxamide; 6-(5-methylimidazo[1,2-a]pyridin-6-yl)spiro[chromane-2,4'-piperidine]-1'-carboxamide; N-ethyl-6-(5-methylimidazo[1,2-a]pyridin-6-yl)spiro[chromane-2,4'-piperidine]-1'-carboxamide; N-isopropyl-6-(5-methylimidazo[1,2-a]pyridin-6-yl)spiro[chromane-2,4'-piperidine]-1'-carboxamide; N-ethyl-6-(7-methylpyrazolo[1,5-a]pyridin-6-yl)spiro[chromane-2,4'-piperidine]-1'-carboxamide; N-isopropyl-6-(7-methylpyrazolo[1,5-a]pyridin-6-yl)spiro[chromane-2,4'-piperidine]-1'-carboxamide; 6-(7-methylpyrazolo[1,5-a]pyridin-6-yl)spiro[chromane-2,4'-piperidine]-1'-carboxamide; N-ethoxy-6-(7-methylpyrazolo[1,5-a]pyridin-6-yl)spiro[chromane-2,4'-piperidine]-1'-carboxamide; N-isopropoxy-6-(7-methylpyrazolo[1,5-a]pyridin-6-yl)spiro[chromane-2,4'-piperidine]-1'-carboxamide; N-ethyl-6-(8-methyl-7-quinolyl)spiro[4H-1,3-benzodioxine-2,4'-piperidine]-1'-carboxamide; 6-(8-methyl-7-quinolyl)spiro[4H-1,3-benzodioxine-2,4'-piperidine]-1'-carboxamide; N-isopropyl-6-(8-methyl-7-quinolyl)spiro[4H-1,3-benzodioxine-2,4'-piperidine]-1'-carboxamide; N-methoxy-6-(8-methyl-7-quinolyl)spiro[chromane-2,4'-piperidine]-1'-carboxamide; N-ethoxy-6-(8-methyl-7-quinolyl)spiro[4H-1,3-benzodioxine-2,4'-piperidine]-1'-carboxamide; N-methoxy-6-(8-methyl-7-quinolyl)spiro[4H-1,3-benzodioxine-2,4'-piperidine]-1'-carboxamide; N-isopropoxy-6-(8-methyl-7-quinolyl)spiro[4H-1,3-benzodioxine-2,4'-piperidine]-1'-carboxamide; N-methoxy-6-(7-methylpyrazolo[1,5-a]pyridin-6-yl)-spiro[chromane-2,4'-piperidine]-1'-carboxamide; 6-(7-methylpyrazolo[1,5-a]pyridin-6-yl)spiro[chromane-2,4'-piperidine]-1'-carbohydroxamic acid; N-ethyl-6-(7-methyl-pyrazolo[1,5-a]pyridin-6-yl)spiro[4H-1,3-benzodioxine-2,4'-piperidine]-1'-carboxamide; 6-(7-methylpyrazolo[pyridin-6-yl)spiro[4H-1,3-benzodioxine-2,4'-piperidine]-1'-carboxamide; N-methoxy-6-(7-methylpyrazolo[1,5-a]pyridin-6-yl)spiro[4H-1,3-benzodioxine-2,4'-piperidine]-1'-carboxamide; N-ethoxy-6-(7-methylpyrazolo[1,5-a]pyridin-6-yl)spiro[4H-1,3-benzodioxine-2,4'-piperidine]-1'-carboxamide; N-isopropoxy-6-(7-methylpyrazolo[1,5-a]pyridin-6-yl)spiro[4H-1,3-benzodioxine-2,4'-piperidine]-1'-carboxamide; 6-(8-chloro-7-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carboxamide; N-methoxy-6-(4-methyl-3-quinolyl)spiro[4H-1,3-benzodioxine-2,4'-piperidine]-1'-carboxamide; 6-(8-chloro-7-quinolyl)-N-methoxy-spiro[4H-1,3-benzodioxine-2,4'-piperidine]-1'-carboxamide; 6-(8-chloro-7-quinolyl)-N-ethoxy-spiro[4H-1,3-benzodioxine-2,4'-piperidine]-1'-carboxamide; 6-(8-chloro-7-quinolyl)spiro[4H-1,3-benzodioxine-2,4'-piperidine]-1'-carbohydroxamic acid; N-ethoxy-6-(4-methyl-3-quinolyl)spiro[4H-1,3-benzodioxine-2,4'-piperidine]-1'-carboxamide; 6-(4-methyl-3-quinolyl)spiro[4H-1,3-benzodioxine-2,4'-piperidine]-1'-carbohydroxamic acid; 6-(5-methylimidazo[1,2-a]pyridin-6-yl)spiro

[chromane-2,4'-piperidine]-1'-carbohydroxamic acid; 6-(3-isoquinolyl)spiro[4H-1,3-benzodioxine-2,4'-piperidine]-1'-carboxamide; 6-(3-isoquinolyl)spiro[chromane-2,4'-piperidine]-1'-carboxamide; 6-(3-isoquinolyl)-N-tetrahydropyran-2-yloxy-spiro[4H-1,3-benzodioxine-2,4'-piperidine]-1'-carboxamide; N-ethoxy-6-(3-isoquinolyl)spiro[4H-1,3-benzodioxine-2,4'-piperidine]-1'-carboxamide; 6-(3-isoquinolyl)-N-tetrahydropyran-2-yloxy-spiro[chromane-2,4'-piperidine]-1'-carboxamide; 6-(3-soquinolyl)-N-methoxy-spiro[4H-1,3-benzodioxine-2,4'-piperidine]-1'-carboxamide; 6-(3-isoquinolyl)-N-methoxy-spiro[chromane-2,4'-piperidine]-1'-carboxamide; N-ethoxy-6-(3-isoquinolyl)spiro[chromane-2,4'-piperidine]-1'-carboxamide; 6-(3 soquinolyl)spiro-[4H-1,3-benzodioxine-2,4'-piperidine]-1'-carbohydroxamic acid; 6-(3-isoquinolyl)spiro[chromane-2,4'-piperidine]-1'-carbohydroxamic acid; 5-(8-methyl-7-quinolyl)spiro[3H-benzofuran-2,4'-piperidine]-1'-carboxamide; N-methoxy-5-(8-methyl-7-quinolyl)spiro[3H-benzofuran-2,4'-piperidine]-1'-carboxamide; N-ethoxy-5-(8-methyl-7-quinolyl)spiro[3H-benzofuran-2,4'-piperidine]-1'-carboxamide; 5-(8-methyl-7-quinolyl)spiro[3H-benzofuran-2,4'-piperidine]-1'-carbohydroxamic acid; N-ethyl-5-(8-methyl-7-quinolyl)spiro[3H-benzofuran-2,4'-piperidine]-1'-carboxamide; N-methoxy-5-(4-methyl-3-quinolyl)spiro[3H-benzofuran-2,4'-piperidine]-1'-carboxamide; N-ethoxy-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carboxamide; N-ethyl-5-(4-methyl-3-quinolyl)spiro[3H-benzofuran-2,4'-piperidine]-1'-carboxamide; 5-(4-methyl-3-quinolyl)spiro[3H-benzofuran-2,4'-piperidine]-1'-carbohydroxamic acid; 5-(8-methoxy-7-quinolyl)spiro[3H-benzofuran-2,4'-piperidine]-1'-carboxamide; N-ethyl-5-(8-methoxy-7-quinolyl)spiro[3H-benzofuran-2,4'-piperidine]-1'-carboxamide; 5-(7-methylpyrazolo[1,5-a]pyridin-6-yl)spiro[3H-benzofuran-2,4'-piperidine]-1'-carboxamide; N-ethyl-5-(7-methylpyrazolo[1,5-a]pyridin-6-yl)spiro[3H-benzofuran-2,4'-piperidine]-1'-carboxamide; N-methoxy-5-(8-methoxy-7-quinolyl)spiro[3H-benzofuran-2,4'-piperidine]-1'-carboxamide; N-ethoxy-5-(8-methoxy-7-quinolyl)spiro[3H-benzofuran-2,4'-piperidine]-1'-carboxamide; 5-(8-methoxy-7-quinolyl)-N-tetrahydropyran-2-yloxy-spiro[3H-benzofuran-2,4'-piperidine]-1'-carboxamide; N-ethoxy-5-(7-methylpyrazolo[1,5-a]pyridin-6-yl)spiro[3H-benzofuran-2,4'-piperidine]-1'-carboxamide; N-methoxy-5-(7-methylpyrazolo[1,5-a]pyridin-6-yl)spiro[3H-benzofuran-2,4'-piperidine]-1'-carboxamide; 5-(7-methylpyrazolo[1,5-a]pyridin-6-yl)-N-tetrahydropyran-2-yloxy-spiro[3H-benzofuran-2,4'-piperidine]-1'-carboxamide; 6-(8-methyl-2-oxo-1H-quinolin-7-yl)spiro[chromane-2,4'-piperidine]-1'-carboxamide; 5-(8-methoxy-7-quinolyl)spiro[3H-benzofuran-2,4'-piperidine]-1'-carbohydroxamic acid; 6-(8-methoxy-7-quinolyl)spiro[4H-1,3-benzodioxine-2,4'-piperidine]-1'-carboxamide; 6-(8-methoxy-7-quinolyl)spiro[chromane-2,4'-piperidine]-1'-carboxamide; 6-(5-chloroimidazo[1,2-a]pyridin-6-yl)-N-isobutylic-spiro[chromane-2,4'-piperidine]-1'-carboxamide; N-isobutyl-6-(1-methyl-6-isoquinolyl)-spiro[chromane-2,4'-piperidine]-1'-carboxamide; N-isopropoxy-6-(1-methyl-6-isoquinolyl)spiro[chromane-2,4'-piperidine]-1'-carboxamide; N-ethoxy-6-(4-methyl-3-quinolyl)spiro[chromane-2,4'-piperidine]-1'-carboxamide; N-isopropoxy-6-(1-methyl-6-isoquinolyl)spiro[4H-1,3-benzodioxine-2,4'-piperidine]-1'-carboxamide; 6-(1-methyl-6-isoquinolyl)spiro[chromane-2,4'-piperidine]-1'-carboxamide; N-methoxy-6-(1-methyl-6-isoquinolyl)spiro[chromane-2,4'-piperidine]-1'-carboxamide; N-ethoxy-6-(1-methyl-6-isoquinolyl)spiro[chromane-2,4'-piperidine]-1'-carboxamide; 6-(1-methyl-6-isoquinolyl)-N-propoxy-spiro[chromane-2,4'-piperidine]-1'-carboxamide; N-ethyl-6-(1-methyl-6-isoquinolyl)spiro[chromane-2,4'-piperidine]-1'-carboxamide; 6-(1-methyl-6-isoquinolyl)-N-propyl-spiro[chromane-2,4'-piperidine]-1'-carboxamide; 6-(1-methyl-6-isoquinolyl)spiro[chromane-2,4'-piperidine]-1'-carbohydroxamic acid; 6-(4-methyl-3-quinolyl)spiro[chromane-2,4'-piperidine]-1'-carboxamide; 6-(4-methyl-3-quinolyl)spiro[chromane-2,4'-piperidine]-1'-carbo-hydroxamic acid; N-methoxy-6-(4-methyl-3-quinolyl)spiro[chromane-2,4'-piperidine]-1'-carboxamide; N-isopropoxy-6-(4-methyl-3-quinolyl)spiro[chromane-2,4'-piperidine]-1'-carboxamide; 6-(1-methyl-6-isoquinolyl)spiro[4H-1,3-benzodioxine-2,4'-piperidine]-1'-carboxamide; N-methoxy-6-(1-methyl-6-isoquinolyl)spiro[4H-1,3-benzodioxine-2,4'-piperidine]-1'-carboxamide; N-ethoxy-6-(1-methyl-6-isoquinolyl)spiro[4H-1,3-benzodioxine-2,4'-piperidine]-1'-carboxamide; N-ethyl-6-(1-methyl-6-isoquinolyl)spiro[4H-1,3-benzodioxine-2,4'-piperidine]-1'-carboxamide; 6-(1-methyl-6-isoquinolyl)spiro[4H-1,3-benzodioxine-2,4'-piperidine]-1'-carbohydroxamic acid; 6-(3-methyl-6-isoquinolyl)spiro[4H-1,3-benzodioxine-2,4'-piperidine]-1'-carboxamide; N-ethyl-6-(3-methyl-6-isoquinolyl)spiro[4H-1,3-benzodioxine-2,4'-piperidine]-1'-carboxamide; N-ethoxy-6-(3-methyl-6-isoquinolyl)spiro[4H-1,3-benzodioxine-2,4'-piperidine]-1'-carboxamide; 6-(3-methyl-6-isoquinolyl)spiro[4H-1,3-benzodioxine-2,4'-piperidine]-1'-carbohydroxamic acid; N-methoxy-6-(3-methyl-6-isoquinolyl)spiro[4H-1,3-benzodioxine-2,4'-piperidine]-1'-carboxamide; 6-(3-methyl-6-isoquinolyl)spiro[chromane-2,4'-piperidine]-1'-carboxamide; N-ethoxy-6-(3-methyl-6-isoquinolyl)spiro[chromane-2,4'-piperidine]-1'-carboxamide; N-ethyl-6-(3-methyl-6-isoquinolyl)spiro[chromane-2,4'-piperidine]-1'-carboxamide; N-methoxy-6-(3-methyl-6-soquinolyl)spiro[chromane-2,4'-piperidine]-1'-carboxamide; N-methoxy-6-(8-methoxy-7-quinolyl)spiro[chromane-2,4'-piperidine]-1'-carboxamide; N-ethoxy-6-(8-methoxy-7-quinolyl)spiro[chromane-2,4'-piperidine]-1'-carboxamide; 6-(8-methyl-7-quinolyl)-4-oxo-Spiro[chromane-2,4'-piperidine]-1'-carboxamide; 4-hydroxy-6-(8-methyl-7-quinolyl)spiro[chromane-2,4'-piperidine]-1'-carboxamide; 4-fluoro-6-(8-methyl-7-quinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 7-Fluoro-6-(1-methyl-6-isoquinolyl)spiro[chromane-2,4'-piperidine]-1'-carboxamide; 6-(Benzofuran-2-yl)spiro[chromane-2,4'-piperidine]-1'-carboxamide; 6-(1H-Indol-2-yl)spiro[chromane-2,4'-piperidine]-1'-carboxamide; 8-Fluoro-6-(8-methyl-7-quinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(1-methyl-6-isoquinolyl)spiro[chromane-2,4'-piperidine]-1' carboxamide;

5-Methyl-6-(8-methyl-7-quinolyl)spiro[chromane-2,4'-piperidine]-1'-carboxamide; 5-methyl-6-(1-methyl-6-isoquinolyl)spiro[chromane-2,4'-piperidine]-1'-carboxamide; 8-Fluoro-N-methoxy-6-(8-methyl-7-quinolyl)spiro[chromane-2,4'-piperidine]-1'-carboxamide; 5-Fluoro-6-(8-methyl-7-quinolyl)spiro[chromane-2,4'-piperidine]-1'-carboxamide; 7-Methyl-6-(8-methyl-7-quinolyl)spiro[chromane-2,4'-piperidine]-1'-carboxamide; N-methoxy-7-methyl-6-(8-methyl-7-quinolyl)spiro[chromane-2,4'-piperidine]-1'-carboxamide; N-Methoxy-7-methyl-6-(1-methyl-6-isoquinolyl)spiro[chromane-2,4'-piperidine]-1'-carboxamide; 8-Methoxy-6-(8-methyl-7-quinolyl)spiro[4H-1,3-benzodioxine-2,4'-piperidine]-1'-carboxamide; 8-Methoxy-6-(8-methyl-7-quinolyl)spiro[4H-1,3-benzodioxine-2,4'-piperidine]-1'-carboxamide; 8-chloro-6-(8-methyl-7-quinolyl)spiro[chromane-2,4'-piperidine]-1'-carboxamide; 8-Chloro-N-methoxy-6-(8-methyl-7-quinolyl)spiro[chromane-2,4'-piperidine]-1'-carboxamide; 6-(4-Hydroxy-8-methyl-7-quinolyl)spiro[chromane-2,4'-piperidine]-1'-carboxamide; and pharmaceutically acceptable salts of such compounds.

12. A pharmaceutical composition comprising at least one compound according to claim 1, and at least one pharmaceutically acceptable excipient.

13. A method of treating a subject suffering from a disorder mediated by fatty acid synthase, comprising administering to the subject a therapeutically effective amount of a compound according to claim 1.

14. A method of treating a subject suffering from a disorder mediated by fatty acid synthase, comprising administering to the subject a therapeutically effective amount of a pharmaceutical composition according to claim 12.

15. A method of treating a subject who is suffering from weight gain associated with drug therapy with an antipsychotic agent, said method comprising administering a compound according to claim 1.

16. The method of claim 15, wherein the antipsychotic agent is selected from clozapine, risperidone, aripiprazole, olanzapine, quetiapine, ziprasidone, and combinations thereof.

* * * * *